United States Patent
Ma et al.

(10) Patent No.: US 12,334,190 B2
(45) Date of Patent: *Jun. 17, 2025

(54) MULTI-OMIC ASSESSMENT USING PROTEINS AND NUCLEIC ACIDS

(71) Applicant: PrognomIQ, Inc., San Mateo, CA (US)

(72) Inventors: Philip Ma, San Jose, CA (US); Bruce Wilcox, Keezletown, CA (US); Francois Collin, Berkeley, CA (US); Chinmay Belthangady, San Jose, CA (US); Mi Yang, Belmont, CA (US); Manoj Khadka, Belmont, CA (US); Manway Liu, Burlingame, CA (US); John Blume, Bellingham, WA (US); Robert S. Langer, Jr., Newton, MA (US); Ehdieh Khaledian, Belmont, CA (US)

(73) Assignee: PROGNOMIQ, INC., San Mateo, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 17/709,185

(22) Filed: Mar. 30, 2022

(65) Prior Publication Data

US 2022/0328129 A1  Oct. 13, 2022

Related U.S. Application Data

(60) Provisional application No. 63/322,149, filed on Mar. 21, 2022, provisional application No. 63/312,455, filed on Feb. 22, 2022, provisional application No. 63/288,825, filed on Dec. 13, 2021, provisional application No. 63/288,827, filed on Dec. 13, 2021, provisional application No. 63/278,637, filed on Nov. 12, 2021, provisional application No. 63/256,482, filed on Oct. 15, 2021, provisional application No. 63/229,232, filed on Aug. 4, 2021, provisional application No. 63/229,242, filed on Aug. 4, 2021, provisional application No. 63/228,533, filed on Aug. 2, 2021, provisional application No. 63/228,543, filed on Aug. 2, 2021, provisional application No. 63/184,498, filed on May 5, 2021, provisional application No. 63/183,816, filed on May 4, 2021, provisional application No. 63/183,852, filed on May 4, 2021, provisional application No. 63/183,844, filed on May 4, 2021, provisional application No. 63/183,829, filed on May 4, 2021, provisional application No. 63/168,594, filed on Mar. 31, 2021, provisional application No. 63/168,634, filed on Mar. 31, 2021.

(51) Int. Cl.
| | | |
|---|---|---|
| G16B 20/00 | (2019.01) | |
| G01N 33/574 | (2006.01) | |
| G01N 33/58 | (2006.01) | |
| G01N 33/68 | (2006.01) | |
| G01N 33/92 | (2006.01) | |
| G16B 25/10 | (2019.01) | |
| G16B 30/00 | (2019.01) | |
| G16B 40/20 | (2019.01) | |
| G16B 40/30 | (2019.01) | |
| G16H 20/40 | (2018.01) | |
| G16H 50/20 | (2018.01) | |

(52) U.S. Cl.
CPC ....... *G16B 20/00* (2019.02); *G01N 33/57484* (2013.01); *G01N 33/587* (2013.01); *G01N 33/6848* (2013.01); *G01N 33/92* (2013.01); *G16B 25/10* (2019.02); *G16B 30/00* (2019.02); *G16B 40/20* (2019.02); *G16B 40/30* (2019.02); *G16H 20/40* (2018.01); *G16H 50/20* (2018.01); *G01N 2570/00* (2013.01)

(58) Field of Classification Search
CPC ........ G16B 40/00–40/30; G06N 20/00–20/20; G16H 50/70; G16H 50/00
See application file for complete search history.

(56) References Cited

U.S. PATENT DOCUMENTS

| | | |
|---|---|---|
| 7,632,686 B2 | 12/2009 | Anderson |
| 7,749,299 B2 | 7/2010 | Vanheusden et al. |
| 7,906,758 B2 | 3/2011 | Stults et al. |
| 9,002,652 B1 | 4/2015 | Hood et al. |
| 9,005,994 B2 | 4/2015 | Huo |
| 9,234,895 B2 | 1/2016 | Hood et al. |

(Continued)

FOREIGN PATENT DOCUMENTS

| | | |
|---|---|---|
| CA | 2787201 A1 | 7/2011 |
| CA | 3126990 A1 | 8/2020 |

(Continued)

OTHER PUBLICATIONS

Ocaña, A., Pandiella, A. "Personalized therapies in the cancer omics era", Mol Cancer 9, 202 (2010), p. 1-12. (Year: 2010).*

(Continued)

*Primary Examiner* — G. Steven Vanni
(74) *Attorney, Agent, or Firm* — WILSON SONSINI GOODRICH & ROSATI

(57) ABSTRACT

Described herein are methods such as multi-omic methods for assessing a disease such as cancer. The multi-omic methods may integrate proteomic, transcriptomic, genomic, lipidomic, or metabolomic data. The method screening diseases or disease states. Also described herein are methods for screening for diseases or disease states from biological samples. The methods may include assessing whether a nodule, mass, or cyst is cancerous.

31 Claims, 162 Drawing Sheets

(56) References Cited

U.S. PATENT DOCUMENTS

| | | |
|---|---|---|
| 9,394,332 B2 | 7/2016 | Markert-Hahn et al. |
| 9,445,994 B2 | 9/2016 | Irvine et al. |
| 9,549,901 B2 | 1/2017 | Shi et al. |
| 9,589,374 B1 | 3/2017 | Gao et al. |
| 9,868,756 B2 | 1/2018 | Markert-Hahn et al. |
| 9,984,201 B2 | 5/2018 | Zhang et al. |
| 10,466,230 B2 | 11/2019 | Stults et al. |
| 10,829,816 B2 | 11/2020 | Staker et al. |
| 10,866,242 B2 | 12/2020 | Farokhzad et al. |
| 11,085,931 B2 | 8/2021 | Warthoe |
| 12,007,397 B2 | 6/2024 | Wilcox et al. |
| 12,087,405 B2 | 9/2024 | Blume et al. |
| 2004/0213446 A1 | 10/2004 | Shams et al. |
| 2005/0048489 A1 | 3/2005 | Thompson et al. |
| 2005/0221314 A1 | 10/2005 | Berlin et al. |
| 2006/0008618 A1 | 1/2006 | Wang et al. |
| 2007/0259363 A1 | 11/2007 | Amri et al. |
| 2008/0187207 A1 | 8/2008 | Bhanot et al. |
| 2008/0291122 A1 | 11/2008 | Smith et al. |
| 2009/0090855 A1* | 4/2009 | Kobold .............. B01D 15/325 250/282 |
| 2009/0176228 A1 | 7/2009 | Birse et al. |
| 2010/0042329 A1 | 2/2010 | Hood et al. |
| 2010/0188075 A1 | 7/2010 | Litvinov et al. |
| 2011/0117582 A1 | 5/2011 | Malima et al. |
| 2011/0171323 A1 | 7/2011 | Weiss |
| 2011/0215237 A1 | 9/2011 | Bateman |
| 2012/0046184 A1 | 2/2012 | Dawson et al. |
| 2013/0080073 A1 | 3/2013 | De Corral |
| 2013/0217057 A1 | 8/2013 | Kearney et al. |
| 2014/0063009 A1 | 3/2014 | Buehler et al. |
| 2014/0106976 A1 | 4/2014 | Sachs et al. |
| 2015/0105276 A1 | 4/2015 | Hofmann et al. |
| 2015/0253341 A1 | 9/2015 | McAvoy et al. |
| 2016/0032395 A1* | 2/2016 | Davicioni .............. G16B 25/10 435/6.12 |
| 2016/0047820 A1 | 2/2016 | Kearney et al. |
| 2016/0054300 A1 | 2/2016 | Winther et al. |
| 2016/0154006 A1* | 6/2016 | Hermanson .......... H01J 49/0027 250/288 |
| 2016/0260594 A1 | 9/2016 | Hendricks |
| 2017/0024641 A1 | 1/2017 | Wierzynski |
| 2017/0051073 A1* | 2/2017 | Hynes .............. A61K 51/1063 |
| 2017/0076195 A1 | 3/2017 | Yang et al. |
| 2017/0220734 A1 | 8/2017 | Colavin et al. |
| 2017/0277844 A1 | 9/2017 | Apte et al. |
| 2018/0067119 A1 | 3/2018 | Kearney et al. |
| 2018/0068083 A1 | 3/2018 | Cohen et al. |
| 2018/0086713 A1 | 3/2018 | Elkon et al. |
| 2018/0172694 A1 | 6/2018 | Farokhzad et al. |
| 2018/0274039 A1 | 9/2018 | Zhang et al. |
| 2018/0275143 A1 | 9/2018 | Wilcox et al. |
| 2019/0018019 A1 | 1/2019 | Shan et al. |
| 2019/0147983 A1 | 5/2019 | Shan et al. |
| 2019/0256924 A1 | 8/2019 | Vogelstein et al. |
| 2019/0328837 A1 | 10/2019 | Kim et al. |
| 2020/0002375 A1 | 1/2020 | Chowdhury |
| 2020/0025765 A1 | 1/2020 | Agorreta Arrazubi et al. |
| 2020/0025766 A1 | 1/2020 | Hanash et al. |
| 2020/0381083 A1 | 12/2020 | Chen |
| 2021/0000965 A1 | 1/2021 | Wang et al. |
| 2021/0005327 A1 | 1/2021 | Anwar et al. |
| 2021/0017598 A1 | 1/2021 | Jain et al. |
| 2021/0031166 A1 | 2/2021 | Porter et al. |
| 2021/0072255 A1 | 3/2021 | Farokhzad et al. |
| 2021/0098083 A1 | 4/2021 | Ma et al. |
| 2021/0104321 A1 | 4/2021 | Lipsky et al. |
| 2021/0132071 A1 | 5/2021 | Kostarelos et al. |
| 2021/0174958 A1* | 6/2021 | Drake .................. G16H 50/70 |
| 2021/0302416 A1 | 9/2021 | Soldo et al. |
| 2021/0375604 A1 | 12/2021 | Gajadhar et al. |
| 2022/0148680 A1 | 5/2022 | Blume et al. |
| 2022/0259202 A1 | 8/2022 | Meimetis |
| 2022/0260559 A1 | 8/2022 | Blume et al. |
| 2022/0299527 A1 | 9/2022 | Bateman et al. |
| 2022/0317014 A1 | 10/2022 | Peterman et al. |
| 2023/0145645 A1 | 5/2023 | Wilcox et al. |
| 2023/0266328 A1 | 8/2023 | Hadjidemetriou et al. |
| 2024/0395362 A1 | 11/2024 | Blume et al. |

FOREIGN PATENT DOCUMENTS

| | | | |
|---|---|---|---|
| CN | 102985819 | A | 3/2013 |
| CN | 109416926 | A | 3/2019 |
| CN | 109470859 | A | 3/2019 |
| EP | 1342794 | B1 | 12/2005 |
| EP | 1394173 | B1 | 10/2007 |
| EP | 2124051 | A1 | 11/2009 |
| EP | 2524219 | A2 | 11/2012 |
| EP | 2921858 | A1 | 9/2015 |
| EP | 3510402 | A1 | 7/2019 |
| EP | 3554681 | A1 | 10/2019 |
| EP | 4096694 | A1 | 12/2022 |
| GB | 2603051 | A | 7/2022 |
| JP | 2010539486 | A | 12/2010 |
| JP | 2011527414 | A | 10/2011 |
| JP | 2020502514 | A | 1/2020 |
| WO | WO-0063683 | A1 | 10/2000 |
| WO | WO-2005019477 | A2 | 3/2005 |
| WO | WO-2005036180 | A1 | 4/2005 |
| WO | WO-2008114917 | A1 | 9/2008 |
| WO | WO-2010097785 | A1 | 9/2010 |
| WO | WO-2013025759 | A1 | 2/2013 |
| WO | WO-2013152989 | A2 | 10/2013 |
| WO | WO-2014078855 | A1 | 5/2014 |
| WO | WO-2015116837 | A1 | 8/2015 |
| WO | WO-2015159293 | A2 | 10/2015 |
| WO | WO-2016008451 | A1 | 1/2016 |
| WO | WO-2016207391 | A1 | 12/2016 |
| WO | WO-2017106481 | A1 | 6/2017 |
| WO | WO-2017192965 | A2 | 11/2017 |
| WO | WO-2017212428 | A1 | 12/2017 |
| WO | WO-2018046542 | A1 | 3/2018 |
| WO | WO-2018112460 | A1 | 6/2018 |
| WO | WO-2018119216 | A1 | 6/2018 |
| WO | WO-2018161031 | A1 | 9/2018 |
| WO | WO-2018170518 | A1 | 9/2018 |
| WO | WO-2019050966 | A2 | 3/2019 |
| WO | WO-2019067092 | A1 | 4/2019 |
| WO | WO-2019182885 | A1 | 9/2019 |
| WO | WO-2019200410 | A1 | 10/2019 |
| WO | WO-2019209888 | A1 | 10/2019 |
| WO | WO-2020096631 | A2 | 5/2020 |
| WO | WO-2020198209 | A1 | 10/2020 |
| WO | WO-2021026172 | A1 | 2/2021 |
| WO | WO-2021087407 | A1 | 5/2021 |
| WO | WO-2021154893 | A1 | 8/2021 |
| WO | WO-2022020272 | A1 | 1/2022 |
| WO | WO-2022072471 | A1 | 4/2022 |
| WO | WO-2022182989 | A1 | 9/2022 |
| WO | WO-2022212583 | A1 | 10/2022 |
| WO | WO-2023019148 | A1 | 2/2023 |
| WO | WO-2023039479 | | 3/2023 |
| WO | WO-2023039579 | | 3/2023 |
| WO | WO-2023164697 | | 8/2023 |
| WO | WO-2023240046 | A2 | 12/2023 |
| WO | WO-2024054946 | A1 | 3/2024 |

OTHER PUBLICATIONS

Günther, O.P. et al. A computational pipeline for the development of multi-marker bio-signature panels and ensemble classifiers. BMC Bioinformatics 13, 326 (2012), p. 1-17. (Year: 2012).*

Lin, E., Lane, HY. "Machine learning and systems genomics approaches for multi-omics data." Biomark Res 5, 2 (2017), p. 1-6 (Year: 2017).*

Li, L. et al; "Data mining techniques for cancer detection using serum proteomic profiling", Artificial Intelligence in Medicine, vol. 32, Issue 2, 2004, pp. 71-83 (Year: 2004).*

Song, M. et al; "A Review of Integrative Imputation for Multi-Omics Datasets" Front. Genet. vol. 11, article 570255, Oct. 15, 2020, p. 1-15 (Year: 2020).*

(56) References Cited

OTHER PUBLICATIONS

Unger, Klaus K., et al. "Liquid chromatography-its development and key role in life science applications." Angewandte Chemie International Edition 49.13 (2010): 2300-2312 (Year: 2010).*

Bronsema, K. J. et al; "Internal standards in the quantitative determination of protein biopharmaceuticals using liquid chromatography coupled to mass spectrometry", Journal of Chromatography B, vols. 893-894, 2012, pp. 1-14. (Year: 2012).*

Havliš, Jan, and Andrej Shevchenko. "Absolute quantification of proteins in solutions and in polyacrylamide gels by mass spectrometry." Analytical chemistry 76.11 (2004): 3029-3036. (Year: 2004).*

Hasin, Yehudit, Marcus Seldin, and Aldons Lusis. "Multi-omics approaches to disease." Genome biology 18.1 (2017): 1-15. (Year: 2017).*

Pearson, Ryan M., Vanessa V. Juettner, and Seungpyo Hong. "Biomolecular corona on nanoparticles: a survey of recent literature and its implications in targeted drug delivery." Frontiers in chemistry 2 (2014): 108.*

Acharjee et al. Integration of metabolomics, lipidomics and clinical data using a machine learning method. BMC Bioinformatics. 2016; 17(Suppl 15): 37-49.

"Adalsteinsson, V.A., Ha, G., Freeman, S.S. et al. Scalable whole-exome sequencing of cell-free DNA reveals high concordance with metastatic tumors. Nat Commun 8, 1324 (2017). https://doi.org/10.1038/s41467-017-00965-y".

Altobelli et al. HtrA1: Its future potential as a novel biomarker for cancer. Oncology Reports, 2015, 34:555-566.

Arroyo et al. Expression-based, consistent biomarkers for prognosis and diagnosis in lung cancerClin Transl Oncol, 2020; 22(10):1867-1874.

Bell et al. A HUPO test sample study reveals common problems in mass spectrometry-based proteomics. Nat Methods. Jun. 2009; 6(6): 423-430.

Benjamini e al. Controlling the false discovery rate: a practical and powerful approach to multiple testing. Journal of the Royal Statistical Society. Series B (Methodological). pp. 289-300 (1995).

Blume, et al., Rapid, deep and precise profiling of the plasma proteome with multi-nanoparticle protein corona. Nature Communications, 2020; 11(3662): 1-14.

Bresnick et al. S100 proteins in cancer. Nature Reviews Cancer, 2015, 15:96-109.

"Butler et al., Lipids and Cancer: Emerging roles in pathogenesis, diagnosis and therapeutic intervention. Advanced Drug Delivery Review. 2020; 159:245-293".

Caracciolo, et al., Disease-specific protein corona sensor arrays may have disease detection capacity, 2019, Nanoscale Horiz., 4, p. 1063-1076. (Year:2019).

Carbone et al. Angiopoietin-Like proteins in Angiogenesis, Inflammation and cancer. Int J Mol Sci. Feb. 2018; 19(2): 431 (1-22).

"Chantada-Vazquez, et al., Identification of a Profile of Neutrophil-Derived Granule Proteins in the Surface of Gold Nanoparticles after Their Interaction with Human Breast Cancer Sera. Nanomaterials (Basel, Switzerland), 2020; 10(1223): 1-18. https://doi.org/10.3390/nano10061223".

Chen et al. Network analysis of differentially expressed smoking-associated mRNAs, lncRNAs and miRNAs reveals key regulators in smoking-associated lung cancer. Exp. Ther. Med., 2018;16: 4991-5002.

Cho et al. Serum amyloid A is elevated in the serum of lung cancer patients with poor prognosis. Br J Cancer. 2010, 102(12): 1731-1735.

"Choi, et al., DUX4 recruits p300/CBP through its C-terminus and induces global H3K27 acetylation changes. Nucleic Acids Research, 2016. vol. 44m No. 11, 5161-5173.".

"Schwenk, et al., The Human plasma proteome draft of 2017: Building on the human plasma peptideatlas from mass spectrometry and complementary assays. Journal Proteome Research, Dec. 2017; 16(12): 4299-4310.".

Co-pending U.S. Appl. No. 17/585,303, inventors Blumejohn; E. et al., filed Jan. 26, 2022.

Co-pending U.S. Appl. No. 17/709,202, inventors Maphilip et al., filed Mar. 30, 2022.

Co-pending U.S. Appl. No. 17/720,197, inventors Blumejohn; E. et al., filed Apr. 13, 2022.

"Corley, et al., Adenoma Detection Rate and Risk of Colorectal Cancer and Death. New Engl J Med Apr. 2014; 370:1298-1306.".

Domenico, et al., Nanoparticle-biomolecular corona: A new approach for the early detection of non-small-cell lung cancer, 2019, J Cell Physiol., 234, p. 9378-9386. (Year:2019).

Dougan et al. Proteomics-Metabolomics Combined Approach Identifies Peroxidasin as a Protector against Metabolic and Oxidative Stress in Prostate Cancer. Int. J. Mol. Sci., 2019, 20(12):3046.

Epelbaum et al. Haptoglobin-related protein as a Serum marker in Malignant Lymphoma. Pathology Oncology Research, 1998, 4(4):271-276.

Falahati et al., A health concern regarding the protein corona, aggregation and disaggregation, 2019, BBA-General Subjects, 1863, p. 971-991 (Year:2019).

Fan et al. Intelligence Algorithms for Protein Classification by Mass Spectrometry. BioMed Research International, vol. 2018, Article ID 2862458, 11 pages, 2018.

"Fredolini, et al., Shotgun proteomics coupled tonanoparticle-based biomarker enrichment reveals a novel panel of extracellular matrix proteins as candidate serum protein biomarkers for early-stage breast cancer detection. Breast Cancer Research (2020) 22:135https://doi.org/10.1186/s13058-020-01373-9".

"Gao, et al., Evaluation of Serum CEA, CA19-9, CA72-4, CA125 and Ferritin as Diagnostic markers and factors of clinical parameters for colorectal cancer. Science Reports, 2018; 8:2732.".

Geary et al. Identification of a Biomarker Panel for Early Detection of Lung Cancer patients. J. Proteome Res. 2019, 18, 9, 3369-3382.

Gould et al. Recent trends in the identification of incidental pulmonary nodules. Am J Respir Crit Care Med. Nov. 15, 2015;192(10):1208-14.

Graham et al. ST6GAL1: A key player in Cancer (Review). Oncol Lett. Aug. 2019; 18(2): 983-989.

"Guinney, et al., The Consensus Molecular subtypes of colorectal cancer. Nat. Med. Nov. 2015; 21(11): 1350-1356.".

Guler et al. Detection of Early Stage Pancreatic Cancer Using 5-Hydroxymethylcytosine Signatures in Circulating Cell Free DNA. Nature Communications 11(1):5270 (Dec. 2020).

Guo et al. Deep multiple instance learning classifies subtissue locations in mass spectrometry images from tissue-level annotations. Bioinformatics, vol. 36, Issue Supplement_1, Jul. 2020, pp. i300-i308.

"Gupta, et al., Recommendations for follow-up after colonoscopy and polypectomy: a consensus update by the US multi-society task force on colorectal cancer. Gastrointest Endosc. Mar. 2020; 91(3): 463-485.".

Hadjidemetriou, et al., A novel scavenging tool for cancer biomarker discovery based on the blood-circulating nanoparticle protein corona. Biomaterials. Jan. 2019; vol. 188: pp. 118-129.

Hanahan et al. Hallmarks of cancer: the next generation. Cell 144:646-674 (2011).

"Hasan, et al., Advances in pancreatic cancer biomarkers. Oncol Rev. Jan. 2019; 13(410): 69-76.".

Havel et al. The evolving landscape of biomarkers for checkpoint inhibitor immunotherapy. Nat Rev Cancer 19(3):133-150 (2019).

"Haynes, et al., Empowering multi-cohort gene expression analysis to increase reproducibility. Pac Symp Biocomput. 2016; 22: 144-153.".

"Huang, et al., Emerging trends and research foci in gastrointestinal microbiome. J Transl. Med. 2019; 17(67): 1-11.".

"Siegel, et al., Cancer Statistics, 2021. CA: A Cancer Journal for Clinicians. Jan. 2021; vol. 71 Issue 1: 7-33.".

"Silvestri GA, Tanner NT, Kearney P, Vachani A, Massion PP, Porter A, Springmeyer SC, Fang KC, Midthun D, Mazzone PJ; PANOPTIC Trial Team. Assessment of Plasma Proteomics Biomarker's Ability to Distinguish Benign From Malignant Lung Nodules: Results of the PANOPTIC (Pulmonary Nodule Plasma Proteomic Classifier) Trial. Chest. Sep. 2018;154(3):491-500. doi: 10.1016/j.chest.2018.02.012. Epub Mar. 1, 2018. PMID: 29496499; PMCID: PMC6689113.".

(56) References Cited

OTHER PUBLICATIONS

"Imperiale, et al., Multitarget stool DNA testing for colorectal-cancer screening. N Engl J Med. Apr. 2014; 370:1287-1297.".

Jong et al. Selecting a classification function for class prediction with gene expression data. Bioinformatics, vol. 32, Issue 12, Jun. 15, 2016, pp. 1814-1822.

"Kampf C et al., The human liver-specific proteome defined by transcriptomics and antibody-based profiling. FASEB J. (2014) PubMed: 24648543 DOI: 10.1096/fj.14-250555".

Keshishian, et al., Multiplexed, Quantitative Workflow for Sensitive Biomarker Discovery in Plasma Yields Novel Candidates for Early Myocardial Injury. Mol Cell Proteomics. Sep. 2015;14(9):2375-93. doi: 10.1074/mcp.M114.046813. Epub Feb. 27, 2015.

Keshishian, et al., Quantitative, multiplexed workflow for deep analysis of human blood plasma and biomarker discovery by mass spectrometry. Nat Protoc. Aug. 2017;12(8):1683-1701. doi:10.1038/nprot.2017.054. Epub Jul. 27, 2017.

"Klein, et al., Clinical validation of a targeted methylation-based multi-cancer early detection test using an independent validation set. Annals of Oncology, 2021; vol. 32 Issue 9: 1167-1177.".

Koh, H.M., et al., Prognostic Role of S100A8 and S100A9 Protein expressions in non-small cell carcinoma of the lung. Journal of pathology and translational medicine, 2019; 53:13-22.

"Koizumi, et al., Salivary cytokine panel indicative of non-small cell lung cancer. J Int Med Res. 2018; vol. 46(9): 3570-3582.".

"Li et al., PGAM1, regulated by miR-3614-5p, functions as an oncogene by activating transforming growth factor-B (TGF-B) signaling in the progression of non-small cell lung carcinoma. Cell death and Disease, 2011; 11(710): 1-16.".

Liu et al. High expression of NFAT2 contributes to carboplatin resistance in lung cancer. Experimental and Molecular Pathology, 2019; 110:104290.

Liu, et al., Human plasma N-glycoproteome analysis by immunoaffinity subtraction, hydrazide chemistry, and mass spectrometry. J Proteome Res. Nov.-Dec. 2005;4(6):2070-80. doi: 10.1021/pr0502065.

"Liu, et al., Sensitive and specific multi-cancer detection and localization using methylation signatures in cell-free DNA. Ann Oncol. Jun. 2020; 31(6): 745-759.".

"Lock, et al., Joint and individual variation explained (JIVE) for integrated analysis of multiple data types. Ann Appl Stat. Mar. 1, 2013;7(1):523-542. doi: 10.1214/12-AOAS597.".

"Luz-Crawford et al., Mesenchymal Stem Cell-Derived Interleukin 1 Receptor Antagonist Promotes Macrophage Polarization and Inhibits B Cell Differentiation. Stem Cells. Feb. 2016;34(2):483-92. doi: 10.1002/stem.2254. Epub Dec. 31, 2015. PMID: 26661518.".

Maples, et al., A highly accurate noninvasive multi-omics diagnostic test for nash. DiscernDx, Inc. Nash-Tag conference Abstract Book, Mar. 2021, p. 14.

"Massion P.P. and Walker R.C. Indeterminate pulmonary nodules: Risk for having or for developing lung cancer. Cancer Prev. Res. 2014; 7(12): 1173-1178.".

"Mathios, D., Johansen, J.S., Cristiano, S. et al. Detection and characterization of lung cancer using cell-free DNA fragmentomes. Nat Commun 12, 5060 (2021). https://doi.org/10.1038/s41467-021-24994-w".

McDonald et al. Suspected cancer symptoms and blood test results in primary care before a diagnosis of lung cancer: a case-control study. Future Oncol. (2019) 15(33), 3755-3762.

"McGuigan A, Kelly P, Turkington RC, Jones C, Coleman HG, McCain RS. Pancreatic cancer: A review of clinical diagnosis, epidemiology, treatment and outcomes. World J Gastroenterol. Nov. 21, 2018;24(43):4846-4861. doi: 10.3748/wjg.v24.i43.4846. PMID: 30487695; PMCID: PMC6250924.".

"Meester RG, Doubeni CA, Lansdorp-Vogelaar I, Goede SL, Levin TR, Quinn VP, Ballegooijen Mv, Corley DA, Zauber AG. Colorectal cancer deaths attributable to nonuse of screening in the United States. Ann Epidemiol. Mar. 2015;25(3):208-213.e1. doi: 10.1016/j.annepidem.2014.11.011. Epub Dec. 5, 2014. PMID: 25721748; PMCID: PMC4554530.".

"Murakami M, Naraba H, Tanioka T, Semmyo N, Nakatani Y, Kojima F, Ikeda T, Fueki M, Ueno A, Oh S, Kudo I. Regulation of prostaglandin E2 biosynthesis by inducible membrane-associated prostaglandin E2 synthase that acts in concert with cyclooxygenase-2. J Biol Chem. Oct. 20, 2000;275(42):32783-92. doi: 10.1074/jbc.M003505200. PMID: 10869354.".

"Nakao, et al., Oncological problems in pancreatic cancer surgery. World J Gastroenterol 2006; 12(28): 4466-4472 [PMID: 16874856 DOI: 10.3748/wjg.v12.i28.4466]".

"Song, et al., Diagnostic and prognostic significance of serum apolipoprotein C—I in triple-negative breast cancer based on mass spectrometry. Cancer Biology & Therapy, 2016; 17(6): 635-647.".

Parimon et al. Syndecan-1 Controls Lung Tumorigenesis by Regulating miRNAs Packaged in Exosomes. Am J Pathol. 2018; 188(4): 1094-1103.

PCT/US2021/015339 International Search Report and Written Opinion dated Apr. 13, 2021.

"Pereira, S. P., Oldfield, L., Ney, A., Hart, P. A., Keane, M. G., Pandol, S. J., Li, D., Greenhalf, W., Jeon, C. Y., Koay, E. J., Almario, C. V., Halloran, C., Lennon, A. M., & Costello, E. (2020). Early detection of pancreatic cancer. The lancet. Gastroenterology & hepatology, 5(7), 698-710. https://doi.org/10.1016/S2468-1253(19)30416-9".

Polasky, et al., Fast and comprehensive N- and O-glycoproteomics analysis with MSFragger-Glyco. Nat Methods. Nov. 2020;17(11):1125-1132. doi: 10.1038/s41592-020-0967-9. Epub Oct. 5, 2020.

"Qu Wq, Liu L, Yu Z. Clinical value of microRNA-23a upregulation in non-small cell lung cancer. Int J Clin Exp Med. Aug. 15, 2015;8(8):13598-603. PMID: 26550300; PMCID: PMC4612985.".

"Robinson, et al., A Systematic Investigation of the Malignant Functions and Diagnostic Potential of the Cancer Secretome. Cell Rep. Mar. 5, 2019; 26(10):2622-2635.e5. doi: 10.1016/j.celrep.2019.02.025.".

Roushan, et al., Peak Filtering, Peak Annotation, and Wildcard Search for Glycoproteomics. Mol Cell Proteomics. 2021;20:100011. doi: 10.1074/mcp.RA120.002260. Epub Dec. 8, 2020.

"Ruan H., Hu S., Zhang H., Du G., Li X., Li X., Li X. Upregulated SOX9 expression indicates worse prognosis in solid tumors: a systematic review and meta-analysis. Oncotarget. 2017; 8: 113163-113173. Retrieved from https://www.oncotarget.com/article/22635/text/".

Telenti, A. et al. Deep sequencing of 10,000 human genomes. Proc. Natl. Acad. Sci. USA 113(42):11901-11906 (Oct. 18, 2016).

Tenzer, S., et al. Nanoparticle size is a critical physicochemical determinant of the human blood plasma corona: a comprehensive quantitative proteomic analysis. ACS Nano 5, 7155-7167 (2011).

"The 1000 Genomes Project Consortium. A global reference for human genetic variation. Nature 526, 68-74 (2015). https://doi.org/10.1038/nature15393".

"Uhlen, M. et al., A Pathology atlas of the human cancer transcriptome. Science. 2017. PubMed: 28818916 DOI: 10.1126/science.aan2507".

U.S. Appl. No. 17/585,303 Office Action dated Apr. 25, 2022.

"Voronov, Elena et al. "Unique Versus Redundant Functions of IL-1α and IL-1β in the Tumor Microenvironment." Frontiers in immunology vol. 4 177. Jul. 8, 2013, doi:10.3389/fimmu.2013.00177".

Wang et al. MOGONET integrates multi-omics data using graph convolutional networks allowing patient classification and biomarker identification. Nature Communications, 2021; 12:3445.

Weinstein, et al. The cancer genome atlas pan-cancer analysis project. Nature genetics 45.10 (2013): 1113-1120.

"White A, Thompson TD, White MC, et al. Cancer Screening Test Use—United States, 2015. MMWR Morb Mortal Wkly Rep Mar. 2017;66(8):201-206. DOI: http://dx.doi.org/10.15585/mmwr.mm6608a1".

Xu et al. Calpain-2 Enhances non-small cell lung cancer progresion and Chemoresistance to paclitaxel via EGFR-pAKT pathway. Int J Biol Sci. 2019; 15(1): 127-137.

"Yigit M, Değirmencioğlu S, Ugurlu E, Yaren A. Effect of serum interleukin-1 receptor antagonist level on survival of patients with non-small cell lung cancer. Mol Clin Oncol. May 2017;6(5):708-

(56) References Cited

OTHER PUBLICATIONS 712. doi: 10.3892/mco.2017.1195. Epub Mar. 15, 2017. PMID: 28515924; PMCID: PMC5431311.".

Yoon et al. NOTUM Is Involved in the Progression of Colorectal Cancer Cancer Genomics & Proteomics, 2018; 15:485-497.

Yu et al. Prognostic and clinicopathological significance of Cacna2d1 expression in epithelial ovarian cancers: a retrospective study. Am J Cancer Res 2016;6(9):2088-2097.

Yuan et al. Modification of α2, 6-sialylation mediates the invasiveness and tumorigenicity of non-small cell lung cancer cells in vitro and in vivo via Notch 1/Hes1/MMPs pathway. Int J Cancer. 2018; 143(9):2319-2330.

Zhang et al. Identification of Apolipoprotein C—I as a Potential Wilms' Tumor Marker after Excluding inflammatory factors. Int. J. Mol. Sci. 2014, 15(9), 16186-16195.

Zhang et al. SMC4, which is essentially involved in lung development, is associated with lung adenocarcinoma progression. Scientific Reports, 2016, 6:34508.

"Zhang L, Zheng J, Ahmed R, Huang G, Reid J, Mandal R, Maksymuik A, Sitar DS, Tappia PS, Ramjiawan B, Joubert P, Russo A, Rolfo CD, Wishart DS. A High-Performing Plasma Metabolite Panel for Early-Stage Lung Cancer Detection. Cancers (Basel). Mar. 7, 2020;12(3):622. doi: 10.3390/cancers12030622. PMID: 32156060; PMCID: PMC7139410.".

"Zhang S., Che D., Yang F., Chi C., Meng H., Shen J., Qi L., Liu F., Lv L., Li Y., Meng Q., Liu J., Shang L., et al Tumor-associated macrophages promote tumor metastasis via the TGF-β/SOX9 axis in non-small cell lung cancer. Oncotarget. 2017; 8: 99801-99815. Retrieved from https://www.oncotarget.com/article/21068/text/".

Albers, et al., Dating genomic variants and shared ancestry in population-scale sequencing data. PLOS Biology, Jan. 2020, 18(1): 19 Pages. https://doi.org/10.1371/journal.pbio.3000586.

Alcalá et al. The Anthrax Toxin receptor 1 (ANTXR1) Is enriched in pancreatic cancer stem cells derived from primary tumor cultures. Stem Cells International, 2019, Article ID:1378639, 1-13 pages.

Andreeva, A.V., and Kutuzov, M.A. Cadherin 13 in cancer. Genes Chromosomes Cancer, 2010, 49(9):775-90.

Armagan, et al., Generalized Beta Mixtures of Gaussians. Advances in neutral information processing systems. Mar. 13, 2012; 1-9 Pages.

Bludau, I., Aebersold, R. Proteomic and interactomic insights into the molecular basis of cell functional diversity. Nat Rev Mol Cell Biol 2020;21: 327-340. https://doi.org/10.1038/s41580-020-0231-2.

Capriotti et al.: Analytical methods for characterizing the nanoparticle-protein corona. Chromatographia 77(11-12):755-769 DOI:10.1007/s10337-014-2677-x (2014).

Chantada-Vazquez, et al., Proteomic analysis of the bio-corona formed on the surface of (Au, Ag, Pt)-nanoparticles in human serum. Colloids Surf B Biointerfaces. May 1, 2019;177:141-148. doi: 10.1016/j.colsurfb.2019.01.056. Epub Jan. 29, 2019. PMID: 30721790.

Chantada-Vazquez et al., Proteomic investigation on bio-corona of Au, Ag and Fe nanoparticles for the discovery of triple negative breast cancer serum protein biomarkers. J Proteomics. Feb. 10, 2020;212:103581. doi: 10.1016/j.jprot.2019.103581. Epub Nov. 12, 2019. PMID: 31731051.

Chen, et al., Glycoproteomics analysis of human liver tissue by combination of multiple enzyme digestion and hydrazide chemistry. J Proteome Res. Feb. 2009;8(2):651-61. doi: 10.1021/pr8008012.

Chen, T., Kornblith, S., Norouzi, M. et al. A Simple Framework for Contrastive Learning of Visual Representations. Proceedings of the 37 th International Conference on Machine Learning, Vienna, Austria, PMLR 119, 2020.

Cohen, et al., Detection and localization of surgically resectable cancers with a multi-analyte blood test. Science Feb. 23, 2018: vol. 359, Issue 6378, pp. 926-930. DOI: 10.1126/science.aar3247.

Co-pending U.S. Appl. No. 17/930,663, inventors Liu; Manway et al., filed Sep. 8, 2022.

Co-pending U.S. Appl. No. 17/931,469, inventors Wilcox; Bruce et al., filed Sep. 12, 2022.

Corbo, et al., Analysis of the Human Plasma Proteome Using Multi-Nanoparticle Protein Corona for Detection of Alzheimer's Disease. Adv. Healthcare Mater. 2021, 10, 2000948. https://doi.org/10.1002/adhm.202000948.

Cox, et al., MaxQuant enables high peptide identification rates, individualized p.p.b.-range mass accuracies and proteome-wide protein quantification. Nat Biotechnol. Dec. 2008;26(12):1367-72. doi: 10.1038/nbt.1511. Epub Nov. 30, 2008.

Datta, S. et al., Statistical Analysis of Proteomics, Metabolomics, and Lipidomics Data Using Mass Spectrometry. Springer Cham, 2017; 295 Pages.

Demichev et al.: DIA-NN: neural networks and interference correction enable deep proteome coverage in high throughput. Nature Methods 17(1):41-44 DOI:10.1038/s41592-019-0638 (2020).

Gao, et al., "A latent factor model with a mixture of sparse and dense factors to model gene expression data with confounding effects." arXiv preprint arXiv:1310.4792 (Oct. 17, 2013) 1-28 Pages.

GB2205544.6 Examination Report dated Jun. 14, 2022.

Hadjidemetriou, Liposome protein corona in vivo: from fundamental principles to a tool for cancer biomarker discovery, 2017, University of Manchester, p. 1-233 (Year: 2017).

Hamm et al. Frequent expression loss of Inter-alpha-trypsin inhibitor heavy chain (ITIH) genes in multiple human solid tumors: A systematic expression analysis. BMC Cancer, Jan. 28, 2008, 8:25; 1-15 Pages.

Hammerschmidt et al., Lung Cancer: Current Diagnosis and Treatment, 2009, Dtsch Arztebl, 106(49), p. 809-820 (Year: 2009).

Haque, IS et al., Challenges in using ctDNA to achieve early detection of cancer. bioRxiv; Dec. 2017. 20 Pages; DOI: 10.1101/237578.

Haug U, Knudsen AB, Lansdorp-Vogelaar I, Kuntz KM. Development of new non-invasive tests for colorectal cancer screening: the relevance of information on adenoma detection. Int J Cancer. Jun. 15, 2015;136(12):2864-74. doi: 10.1002/ijc.29343. Epub Dec. 3, 2014. PMID: 25403937; PMCID: PMC4397119.

Heitzer, E. et al., Current and future perspectives of liquid biopsies in genomics-driven oncology. Nat Rev Genet 20, 71-88 (2019). https://doi.org/10.1038/s41576-018-0071-5.

Jensen, M., and Berthold, F. Targeting the neural cell adhesion molecule in cancer. Cancer Lett., Dec. 2007., 258(1):9-21.

John, et al., "Predicting gene expression from plasma cell-free DNA using both the fragment length and fragment position." AACR Annual Meeting; Mar. 29-Apr. 3, 2019; 1 Page.

Kim, et al., A chemical with proven clinical safety rescues down-syndrome-related phenotypes in through DYRK1A inhibition. Disease Models & Mechanisms (2016) 9, 839-848.

Liu et al., Spatial co-fragmentation pattern of cell-free DNA recapitulates in vivo chromatin organization and identifies tissues-of-origin. AACR. 2019; 1 Page.

Lu, et al., The crucial role of multiomic approach in cancer research and clinically relevant outcomes. EPMA Journal (2018) 9; 77-102: https://doi.org/10.1007/s13167-018-0128-8.

Lu, J., and Gu, J. Significance of β-Galactoside α2,6 Sialyltranferase 1 in Cancers. Molecules, 2015, 20, 7509-7527.

Ludwig C, Gillet L, Rosenberger G, Amon S, Collins BC, Aebersold R. Data-independent acquisition-based SWATH-MS for quantitative proteomics: a tutorial. Mol Syst Biol. Aug. 13, 2018;14(8):e8126. doi: 10.15252/msb.20178126. PMID: 30104418; PMCID: PMC6088389.

Mazzaschi G, Facchinetti F, Missale G, Canetti D, Madeddu D, Zecca A, Veneziani M, Gelsomino F, Goldoni M, Buti S, Bordi P, Aversa F, Ardizzoni A, Quaini F, Tiseo M. The circulating pool of functionally competent NK and CD8+ cells predicts the outcome of anti-PD1 treatment in advanced NSCLC. Lung Cancer. Jan. 2019;127:153-163. doi: 10.1016/j.lungcan.2018.11.038. Epub Nov. 29, 2018. PMID: 30642544.

Muller et al. Community-integrated omics links dominance of a microbial generalist to fine-tuned resource usage. Nature Communications vol. 5, Article No. 5603 (2014); 1-10 Pages.

(56) References Cited

OTHER PUBLICATIONS

PCT/US2022/022654 International Search Report and Written Opinion dated Aug. 15, 2022.

Pirinen et al. Versican in nonsmall cell lung cancer: Relation to hyaluronan, clinicopathologic factors, and prognosis. Human Pathlogy, 2004; 36(1):44-50.

Ponzi, et al., Integrative, multi-omics, analysis of blood samples improves model predictions: applications to cance. BMC Bioinformatics, 2021; 22:395 https://doi.org/10.1186/s12859-021-04296-0.

Putcha, et al., Blood-based detection of early-stage colorectal cancer using multiomics and machine learning. Journal of clinical oncology, 2020; 38(4): 66.

Ramos-Esquivel et al., Anti-PD-1/anti-PD-L1 immunotherapy versus docetaxel for previously treated advanced non-small cell lung cancer: a systematic review and meta-analysis of randomised clinical trials. ESMO Open 2017;2:e000236; 1-11 Pages. doi:10.1136/esmoopen-2017-000236.

Reel PS, Reel S, Pearson E, Trucco E, Jefferson E. Using machine learning approaches for multi-omics data analysis: A review. Biotechnol Adv. Jul.-Aug. 2021;49:107739. doi: 10.1016/j.biotechadv.2021.107739. Epub Mar. 29, 2021. PMID: 33794304.

Roy et al. Multiomics data collection visualization and utilization for guiding metabolic engineering. Frontiers in bioengineering and biotechnology, 2021, 9, Article 612983; 1-13 Pages.

Rubio, et al., Multi-omic analysis unveilsvbiological pathways in peripheral immune system associated to minimal hepatic encephalopathy appearance in cirrhotic patients. Scientific Reports, 2021; 11:1907.https://doi.org/10.1038/s41598-020-80941-7.

Skyarysz, A., Alkhalifah, Y., Darnley, K., Eddleston, M., McLaren, D., Nailon, W. H., Salman, D., Sykora, M., Thomas, P., & Soltoggio, A., Convolutional neural networks for automated targeted analysis of raw gas chromatography-mass spectrometry data. In Proceedings of the International Joint Conference on Neural Networks (IJCNN 2018) At: Rio de Janeiro, Brazil; 2018: 9 Pages. https://doi.org/10.1109/IJCNN.2018.8489539.

St. John et al., Predicting gene expression from plasma cell-free DNA using both the fragment length and fragment position. AACR. 2019; 1 Page.

Stelzer, et al., The GeneCards Suite: From Gene Data Mining to Disease Genome Sequence Analyses. Curr Protoc Bioinformatics. Jun. 20, 2016;54:1.30.1-1.30.33. doi: 10.1002/cpbi.5.

Ulz, et al., Inference of transcription factor binding from cellfree DNA enables tumor subtype prediction and early detection. Nature Communications, (2019) 10:4666; https://doi.org/10.1038/s41467-019-12714-4, www.nature.com/naturecommunications.

U.S. Appl. No. 17/585,303 Office Action dated Jul. 18, 2022.

U.S. Appl. No. 17/720,197 Office Action dated Oct. 14, 2022.

Wainberg, et al., Multiomic blood correlates of genetic risk identify presymptomatic disease alterations. PNAS, Sep. 2020; vol. 117, No. 35: 21813-21820.

Wan, et al., Machine learning enables detection of early-stage colorectal cancer by whole-genome sequencing of plasma cell-free DNA. BMC Cancer (2019) 19:832 https://doi.org/10.1186/s12885-019-6003-8.

Zhang et al., Deep Learning-Based Multi-Omics Data Integration Reveals Two Prognostic Subtypes in High-Risk Neuroblastoma. Front. Genet., Oct. 18, 2018 https://doi.org/10.3389/fgene.2018.00477.

Zhang, et al., Phenotype Prediction using a Tensor Representation and Deep Learning from Data Independent Acquisition Mass Spectrometry. bioRxiv 2020.03.05.978635; doi: https://doi.org/10.1101/2020.03.05.978635.

Zhu et al., Apolipoprotein M promotes proliferation and invasion in non-small cell lung cancers via upregulating S1PR1 and activating the ERK1/2 and PI3K/AKT signaling pathways. Biochemical and Biophysical Research Communications, 2018, 501(2):520-526.

Agajanian, et al., Integration of Random forest classifiers and deep convolutional neural networks for classification and Biomolecular modeling of cancer driver mutations. Frontiers in molecular biosciences 6 (2019): 44. Jun. 11, 2019, Retrieved on Oct. 30, 2022. From https://www.frontiersin.org/articles/10.3389/fmolb.2019.00044/full entire document.

Bakry et al. Protein profiling for cancer biomarker discovery using matrix-assisted laser desorption/ionization time-of-flight mass spectrometry and infrared imaging: A review. Analytica Chimica Acta 2011, vol. 690, pp. 26-34 (Year: 2011).

Cohen, et al., Combined circulating tumor DNA and protein biomarker-based liquid biopsy for the earlier detection of pancreatic cancers. PNAS, Sep. 5, 2017; 114 (38) 10202-10207, https://doi.org/10.1073/pnas.1704961114.

Co-pending U.S. Appl. No. 18/150,390, inventors Ma; Philip et al., filed Jan. 5, 2023.

Co-pending U.S. Appl. No. 18/164,446, inventors Ma; Philip et al., filed Feb. 3, 2023.

Correia, et al., Machine learning modeling of blood lipid biomarkers in familial hypercholesterolaemia versus polygenic/environmental dyslipidaemia. Nature portfolio, Scientific Reports (2021) 11:3801; 9 Pages.

Grossi et al. Prognostic role of the VeriStrate test in first line patients with non-small cell lung cancer treated with platinum-based chemotherapy. Lung Cancer 2018, vol. 117, pp. 64-69 (Year: 2018).

Jiang et al. "Surface-Enhanced Raman Nanoprobes with Embedded Standards for Quantitative Cholesterol Detection" small methods, vol. 2 Issue 11 (Nov. 13, 2018): pp. 1-14; entire document.

Katzke, et al., Blood lipids and lipoproteins in relation to incidence and mortality risks for CVD and cancer in the prospective EPIC-Heidelberg cohort, BMC Medicine (2017) 15:218; 13 Pages.

Khlebtsov et al. "Gap-enhanced Raman tags: fabrication, optical properties, and theranostic applications" Theranostics, vol. 10 Issue 5 (2020): pp. 2067-2094; entire document.

Leal et al. Prognostic performance of proteomic testing in advanced non-small cell lung cancer: a systematic literature review and meta-analysis. Current Medical Research and Opinion 2020, vol. 36, No. 9, pp. 1497-1505 (Year: 2020).

Lee et al. The clinical role of VeriStrat testing in patients with advanced non-small cell lung cancer considered unfit for first-line platinum-based chemotherapy. European Journal of Cancer 2019, vol. 120, pp. 86-96 (Year: 2019).

Lemjabbar-Alaoui et al. Lung Cancer: Biology and Treatment options. Biochimica et Biophysica Acta 2015, 1856, pp. 189-210 (Year: 2015).

Liu, et al., Machine Learning Protocols in Early Cancer Detection Based on Liquid Biopsy: A Survey. Life 2021, 11, 638,39 Pages. https://doi.org/ 10.3390/life11070638.

Nguyen, et al., Protein corona: a new approach for nanomedicine design, International Journal of Nanomedicine 2017:12; 3137-3151.

PCT/US2022/076125 International Search Report and Written Opinion dated Jan. 12, 2023.

PCT/US2022/076297 International Search Report and Written Opinion dated Nov. 30, 2022.

Qian et al. Screening for early stage lung cancer and its correlation with lung nodule detection. J Thorac Dis 2018, 1 0(Suppl 7): S846-859 (Year: 2018).

Ritz, et al.,, Protein Corona of Nanoparticles: Distinct Proteins Regulate the Cellular Uptake, Biomacromolecules 2015:16(4); 1311-1321 DOI: 10.1021/acs.biomac.5b00108.

Trivedi et al. Risk assessment for indeterminate pulmonary nodules using a novel, plasma-protein based biomarker assay. Biomed Res Clin Pract 2018, 3(4), pp. 1-17 (Year: 2018).

U.S. Appl. No. 17/709,202 Office Action dated Jan. 26, 2023.

U.S. Appl. No. 17/709,202 Office Action dated Nov. 23, 2022.

U.S. Appl. No. 17/720,197 Office Action dated Jan. 5, 2023.

U.S. Appl. No. 17/931,469 Office Action dated Dec. 28, 2022.

Yuan et al. "Antimicrobial peptide based magnetic recognition elements and Au@Ag-GO SERS tags with stable internal standards: a three in one biosensor for isolation, discrimination andkilling of multiple bacteria in whole blood" Chemical Science, vol. 9 (Nov. 2, 2018): pp. 8781-8795; entire document.

Zhang et al., Phenotype Classification using Proteome Data in a Data-Independent Acquisition Tensor Format. J Am Soc Mass Spectrom. Nov. 4, 2020;31(11):2296-2304. doi: 10.1021/jasms.0c00254. Epub Oct. 26, 2020. PMID: 33104352.

(56) References Cited

OTHER PUBLICATIONS

Brinkmann et al., Oral squamous cell carcinoma detection by salivary biomarkers in a Serbian population, Oral Oncology, vol. 47(1), 2011: pp. 51-55.
Co-pending U.S. Appl. No. 18/165,264, inventor Manway; Liu, filed Feb. 6, 2023.
"Seer, Inc. Form 10-Q For Quarterly period ended Jun. 30, 2021." Edgar. Securities and Exchange Commission, 2021, https://www.sec.gov/ix?doc=/Archives/edgar/data/0001726445/000162828021016865/seer-20210630.htm.
GB2205374.8 Examination Report dated Apr. 19, 2023.
Kopac. Protein corona, understanding the nanoparticle-protein interactions and future perspectives. International Journal of Biological Macromolecules 2021, vol. 169, pp. 290-301, published online Dec. 21, 2020 (Year: 2020).
Kuang, M. et al., Proteomic analysis of plasma exosomes to differentiate malignant from benign pulmonary nodules. Clin Proteom 16, 5 (2019). https://doi.org/10.1186/s12014-019-9225-5.
Li, Xiao-jun et al., A Blood-Based Proteomic Classifier for the Molecular Characterization of Pulmonary Nodules. Sci Transl Med. Oct. 16, 2013; 5(207): 207ra142. doi:10.1126/scitranslmed.3007013.
Melone. Seer debuts with proprietary proteomics platform to enable early detection of cancer and neurological diseases. Businesswire 2018, pp. 1-5 (Year: 2018).
Mishra et al. Biological effects of formation of protein corona onto nanoparticles. International Journal of Biological Macromolecules 2021, vol. 175, pp. 1-18, published on line Jan. 21, 2021 (Year: 2021).
Shriwash et al., Identification of differentially expressed genes in small and non-small cell lung cancer based on meta-analysis of mRNA, 2019, Heliyon, 5, p. 1-9 (Year: 2019).
U.S. Appl. No. 17/585,303 Office Action dated Mar. 6, 2023.
U.S. Appl. No. 17/709,202 Office Action dated May 10, 2023.
U.S. Appl. No. 17/931,469 Office Action dated Apr. 3, 2023.
U.S. Appl. No. 18/095,422 Office Action dated Apr. 14, 2023.
Walkey et al. ("Protein Corona Fingerprinting Predicts the Cellular Interaction of Gold and Silver Nanoparticles," ACS Nano, vol. 8, No. 3, pp. 2439-2455, published 2014) (Year: 2014).
Wan et al. ("Highly Specific Electrochemical Analysis of Cancer Cells using Multi-Nanoparticle Labeling," Angew. Chem. Int. Ed. 2014, vol. 53, pp. 13145-13149) (Year: 2014).
Zeng et al., Integrative Models of Histopathological Image Features and Omics Data Predict Survival inHead and Neck Squamous Cell Carcinoma, Frontiers in Cell and Development Biology, 2020; vol. 8: p. 55309, Available online at: https://www.frontiersin.org/articles/10.3389/fcell.2020.553099/full [accessed Apr. 14, 2023].
Cruz et al., Applications of Machine learning in cancer prediction and prognosis (Cancer Informatics, 2006, vol. 2, pp. 59-77).
Hsu, T. et al., Plasma-based detection of pancreatic cancer: A multiomics approach. Poster presented at the 2021 AACR virtual special conference: Pancreatic cancer, Sep. 29-30, 2021; 10 Pages.
Lennon, A. M. et al., Feasibility of blood testing combined with PET-CT to screen for cancer and guide intervention. Science 369, eabb9601 (2020). DOI: 10.1126/science. abb9601.
Lin, C. J. et al., Evaluation of a sensitive blood test for the detection of colorectal advanced adenomas in a prospective cohort using a multiomics approach. Poster Presented at the 2021 Gastrointestinal Cancers Symposium. 1 Page.
PCT/US2023/063358 International Search Report and Written Opinion dated Aug. 1, 2023.
Putcha, G. et al., Blood-based detection of early-stage colorectal cancer using multiomics and machine learning. Poster presented at American Society of Clinical Oncology. 2020, 1 Page.
Tanigawa et al. Upregulation of ANGPTL6 in mouse keratinocytes enhances susceptibility to psoriasis. Sci Rep. Oct. 4, 2016;6:34690. doi: 10.1038/srep34690. PMID.
U.S. Appl. No. 17/585,303 Notice of Allowance dated Apr. 26, 2023.
U.S. Appl. No. 17/720,197 Office Action dated Aug. 11, 2023.
U.S. Appl. No. 17/931,469 Office Action dated May 25, 2023.
U.S. Appl. No. 17/931,469 Office Action dated Sep. 19, 2023.
U.S. Appl. No. 18/095,422 Office Action dated Jun. 13, 2023.
U.S. Appl. No. 18/150,390 Office Action dated Jul. 5, 2023.
U.S. Appl. No. 18/164,446 Office Action dated Jul. 19, 2023.
U.S. Appl. No. 18/165,264 Office Action dated Aug. 11, 2023.
U.S. Appl. No. 17/585,303 Notice of Allowance dated Apr. 14, 2023.
Paschke, C. et al. Mirion—a software package for automatic processing of mass spectrometric images. Journal of the American Society for Mass Spectrometry 24(8):1296-1306 (2013).
U.S. Appl. No. 18/164,446 Office Action dated Feb. 15, 2024.
U.S. Appl. No. 18/164,446 Office Action dated Oct. 1, 2024.
U.S. Appl. No. 18/165,264 Office Action dated Sep. 5, 2024.
Waks, Adrienne G, and Eric P. Winer. Breast cancer treatment: a review. Jama 321(3):288-300 (2019).
Co-pending U.S. Appl. No. 18/643,947, inventors Wilcox; Bruce et al., filed Apr. 23, 2024.
Co-pending U.S. Appl. No. 18/815,648, inventors Wilcox; Bruce et al., filed Aug. 26, 2024.
Huo, Qun. et al. A facile nanoparticle immunoassay for cancer biomarker discovery. Journal of nanobiotechnology 9(20):1-12 (2011).
U.S. Appl. No. 18/643,947 Office Action dated Feb. 5, 2025.
Blume, J.E. et al., Validated Pancreatic Ductal Adeno Carcinoma Classifier Based on a Panel of Proteins Measured in Plasma with a Targeted Mass Spectrometry Assay in a Case-Control Study of 182 Subjects, Patent Application Disclosure Memo, PrognomiQ, Inc., 33 pages (Aug. 31, 2022).
Haan, T.J. et al., A repeat pattern of founder events for SARS-CoV-2 variants in Alaska, medRxiv, The Preprint Server for Health Sciences, 5 pages (2022).
Hua, S. et al., Site-specific protein glycosylation analysis with glycan isomer differentiation, Anal Bioanal Chem 403:1291-1302 (2012).
Husi, H. et al., Identification of diagnostic upper gastrointestinal cancer tissue type-specific urinary biomarkers, Biomedical Reports 10:165-174 (2019).
Jin, Y. et al., Alpha-1-antichymotrypsin as a novel biomarker for diagnosis, prognosis, and therapy prediction in human diseases, Cancer Cell International 22(156), 12 pages (2022).
Nie, S. et al. Glycoprotein biomarker panel for pancreatic cancer discovered by quantitative proteomics analysis. Journal of proteome research 13, 1873-1884 (2014).
Nie, S. et al., Quantitative Analysis of Single Amino Acid Variant Peptides Associated with Pancreatic Cancer in Serum by an Isobaric Labeling Quantitative Method, Journal of Proteome Research 13:6058-6066 (2014).
PCT/US2023/067945 International Search Report and Written Opinion dated Dec. 20, 2023.
PCT/US2023/073688 International Search Report and Written Opinion dated Dec. 15, 2023.
PubChem CID 155887589. Create Date: Apr. 22, 2021, https://pubchem.ncbi.nlm.nih.gov/compound/155887589 Date Accessed: Nov. 28, 2022 (Nov. 28, 2022), p. 2.
Roberts, A.S. et al., Identification of Potential Prognostic Biomarkers in Patients With Untreated, Advanced Pancreatic Cancer From a Phase 3 Trial (Cancer and Leukemia Group B 80303), Cancer 118:571-578 (2012).
Wu, W. et al., Solid Serous Cystadenoma of the Pancreas: A Case Report of 2 Patients Revealing Vimentin, beta-Catenin, alpha-1 Antitrypsin, and alpha-1 Antichymotrypsin as New Immunohistochemistry Staining Markers, Medicine 94(12):1-4 (Mar. 2015).
Yang et al. Cleavable Trifunctional Biotin Reagents for Protein Labelling, Capture and Release. Chemical Communications. vol. 49 (2013): 3 pages.
Zacharias L .G et al.,"HILIC and ERLIC Enrichment of Glycopeptides Derived from Breast and Brain Cancer Cells", Journal of proteome research, vol. 15(10), 2016, pp. 3624-3634.
Zhu, H. et al., A LC-MS All-in-One Workflow for Site-Specific Location, Identification and Quantification of N-/O-Glycosylation

(56) References Cited

OTHER PUBLICATIONS in Human Chorionic Gonadotropin Drug Products, The AAPS Journal, 10 pages (2017).

* cited by examiner

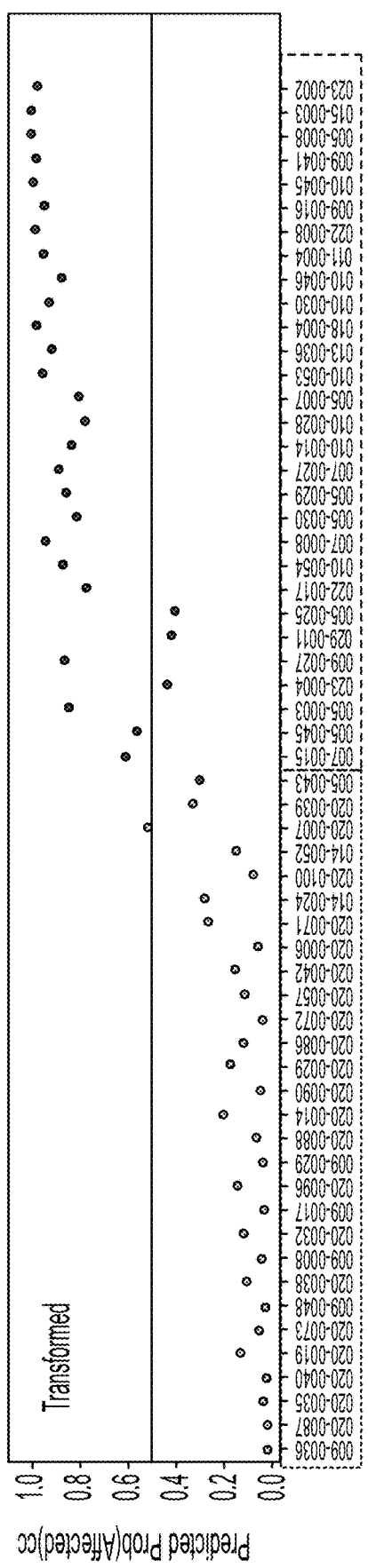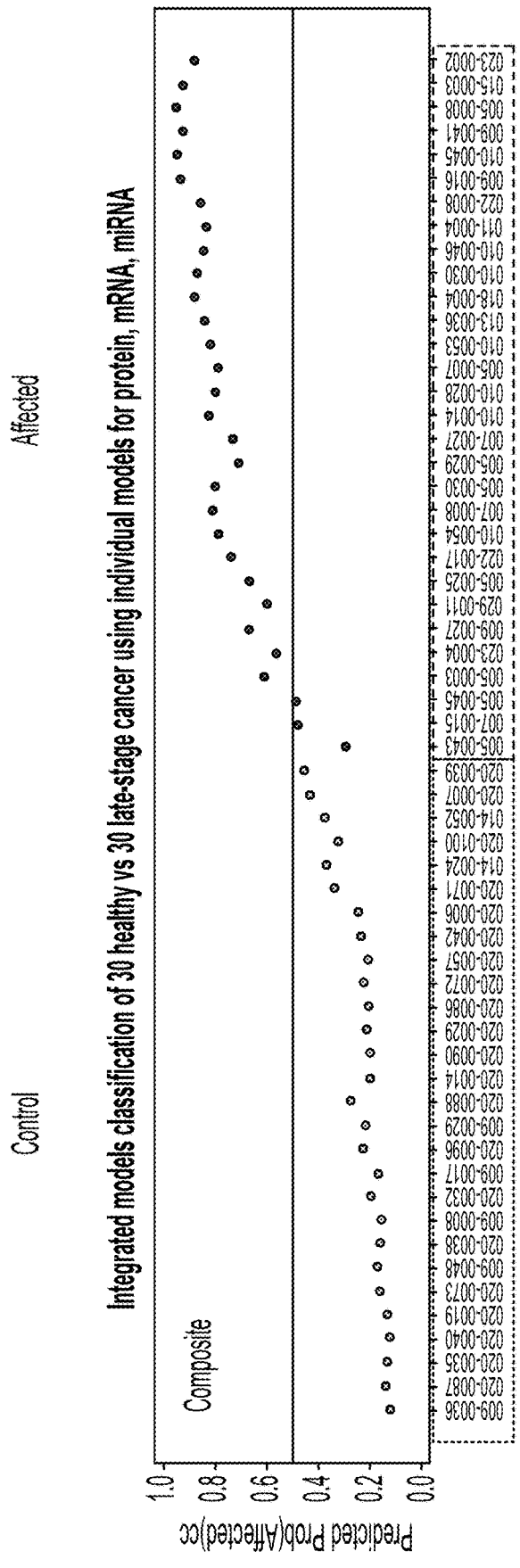
FIG. 16

|  | Sensitivity at 99.5% specificity | Sensitivity at 90% specificity |
|---|---|---|
| Protein (20) | 0.47 | 0.57 |
| Lipid (633) | 0.32 | 0.57 |
| Protein + lipid | 0.48 | 0.61 |

Fig. 23

| Indication | Sample | Isolation Method | QC | Sequencing Depth |
|---|---|---|---|---|
| cfDNA Methylation | Streck Plasma | Apostle Minimax | Fragment analysis by Caliper High-sensitivity chip | 100M PE |
| mRNA (Blood) | PAXgene Blood | Qiagen pAXgene total RNA | RNA Quantitation by ribgree, integrity assay by fragment analyzer | 100M PE |
| miRNA (Blood) | PAXgene Blood | Qiagen pAXgene total RNA | RNA Quantitation by ribgree, integrity assay by fragment analyzer | 100M PE |
| cf-miRNA | EDTA Plasma | miRNeasy SP Advanced kit | RNA Quantitation by ribgree, integrity assay by fragment analyzer | 25M SE |
| Whole Exome Sequencing | PBMC | Qiagen DSP Midi kit | DNA quantitation by picogreen, integrity assay by gel | 10Gb/sample |

Fig. 25

| | Intended use population | Value proposition of test |
|---|---|---|
| Lung cancer screening test | Higher-risk patients (as defined by USPSTF and other bodies) who are candidates for but have not received CT scan for lung cancer screening | • Informs physician on the probability of lung cancer, and therefore, of urgency/importance of having a CT scan of further workup<br>• Addresses higher-risk patients non-compliant to CT screening<br>• Improves selection and compliance of patients for CT imaging and biopsy |
| Lung cancer patient selection test for therapy response | Patients under consideration for treatment with Immune checkpoint inhibitors (ICI) | • Test identifies patients most likely to respond to ICI treatment and avoids use of ICI in patients unlikely to benefit from ICI. |
| Lung cancer recurrence monitoring | Patients with potentially resectable lung cancer | • Detects cancer recurrence before CT or other imaging scan |

Fig. 26A

| Protein | OT Score | Description |
|---|---|---|
| C9 | 0.23 | Involved in immune response; has been used in clinical practice and is being studied as biomarker for various cancers, including colon cancer |
| S100A8 | 0.20 | Calcium-binding protein which plays a prominent role in the regulation of inflammatory processes and immune response, and which has been studied as a biomarker in multiple cancers including colon and ovarian. |
| HPR | 0.18 | Protein associated with apolipoproteins to mediate immune response, and which has been studied as a biomarker for breast cancer. |
| CRP | 0.11 | Key protein associated with acute phase response; used in clinical practice to monitor progression of multiple cancers |
| CDH13 | 0.10 | Cell adhesion molecule, being studied as biomarker for multiple cancers, including breast cancer |
| FGL1 | 0.08 | Immune suppressive molecule that inhibits antigen-specific T-cell activation by acting as a major ligand of LAG3, and which is being studied as potential immune checkpoint inhibitor for cancer treatment |
| HTRA1 | 0.07 | Serine protease involved in modulation of growth factor systems, and hypothesized to play a role in tumorgenesis |
| CCL18 | 0.07 | Chemokine involved in pathways associated with cell migration and metastasis in cancer |

Fig. 26B

| Protein | OT Score | Description |
|---|---|---|
| S100A9 | 0.06 | Calcium- and zinc-binding protein involved in inflammatory events and initial development of the cancer cell |
| SAA1 | 0.03 | Major acute phase protein, studied as biomarker for multiple cancers, including lung cancer |
| APOC1 | 0.02 | Apolipoprotein involved in metabolism of high-density lipoprotein (HDL) and very low-density lipoprotein (VLDL) receptor; hypothesized to play a role in progression of tumors |
| ANTXR1 | 0.01 | Trans-membrane protein which modulates signaling of several pathways including vascular endothelial growth factor (VEGF); hypothesized to play a role in tumor angiogenesis |
| CLEC3B | 0.01 | Plasminogen-binding protein located in cell plasma, extracellular matrix and exosomes; hypothesized to play a role in tumor invasion and metastasis |
| ITIH2 | - | Protease inhibitor involved in stabilizing the extracellular matrix; hypothesized to potentially play a role in inhibiting metastatic cancer progression |
| C1QTNF3 | - | C1Q tumor necrosis related factor 3 is an adipokine involved in inflammation |

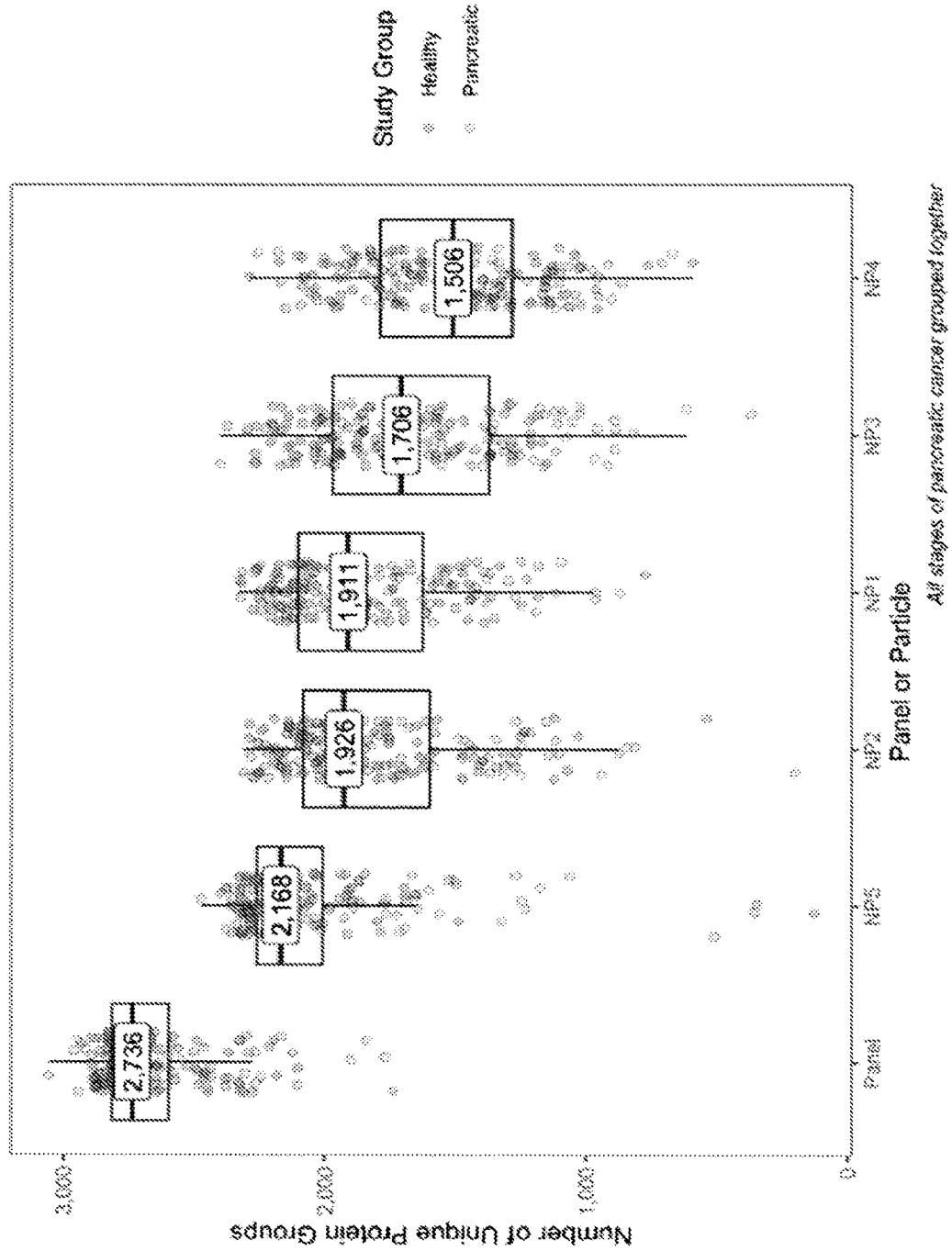

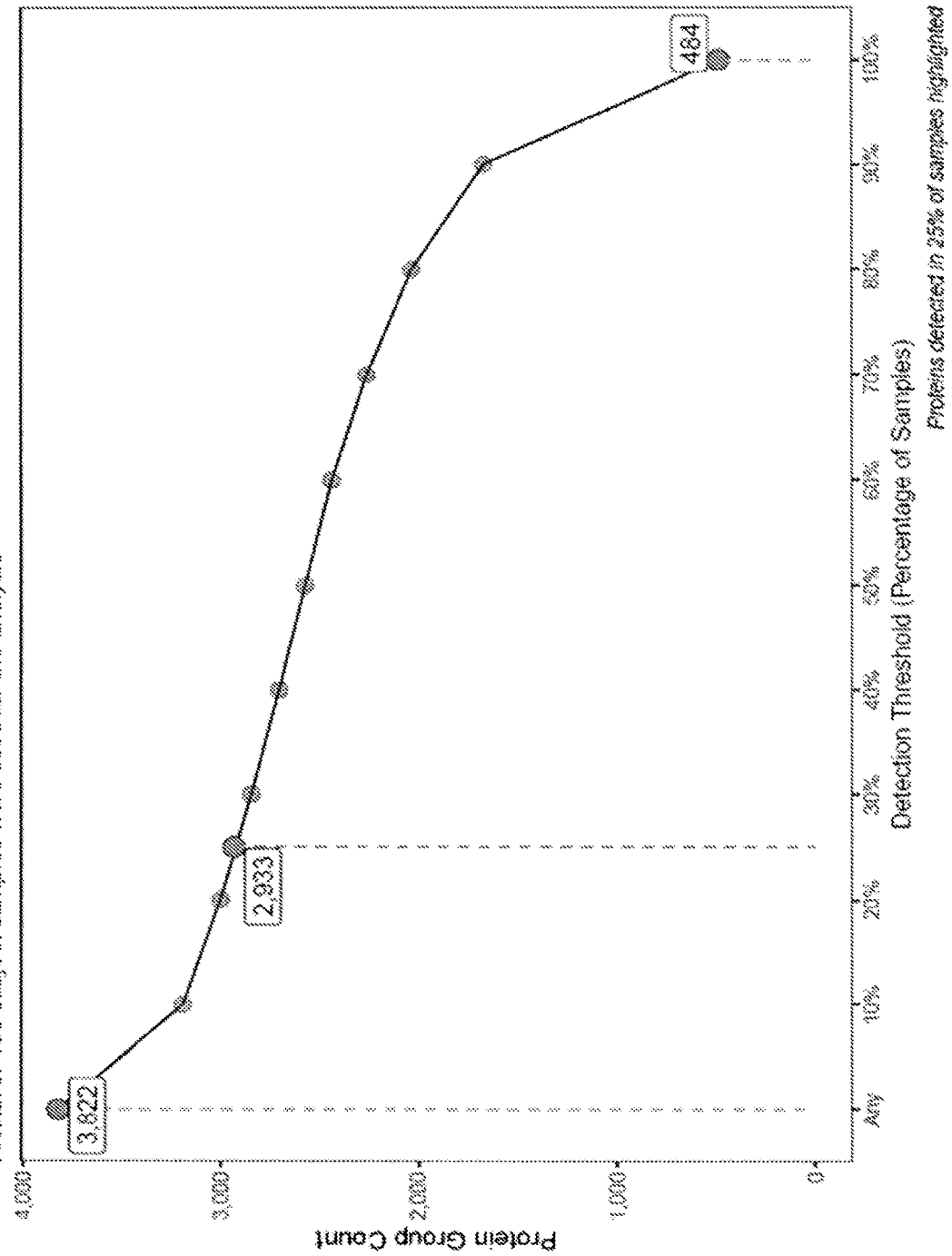

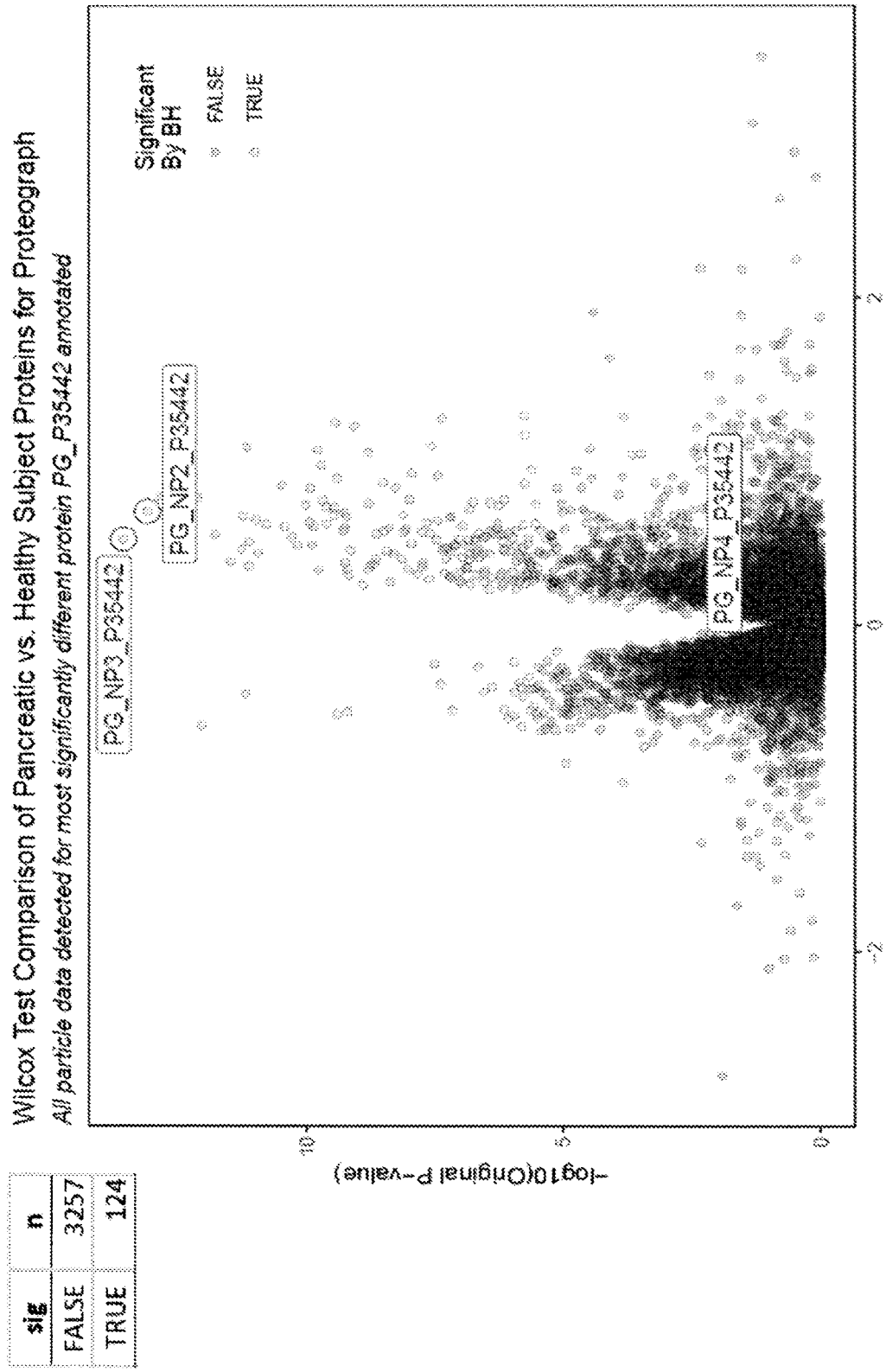

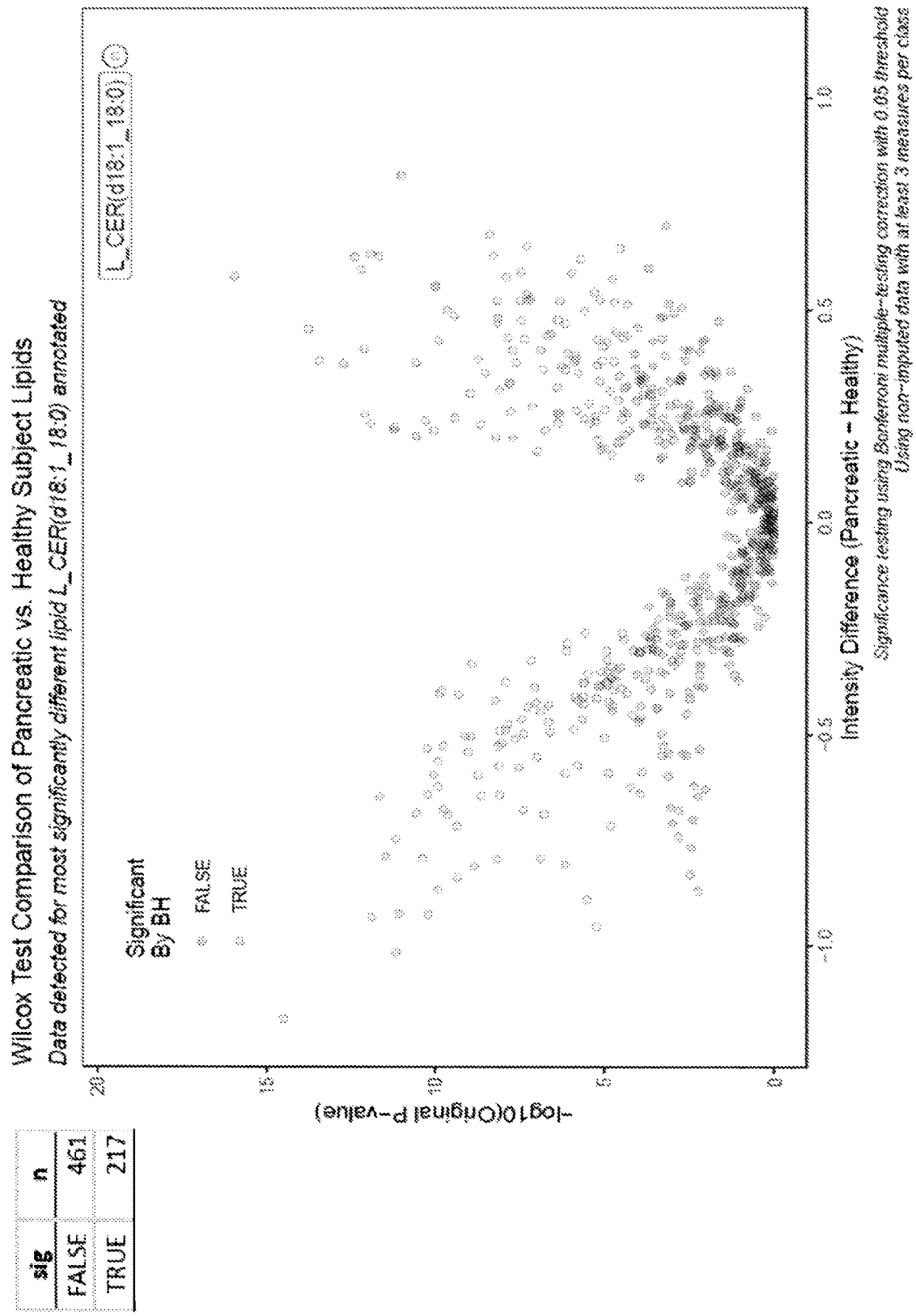

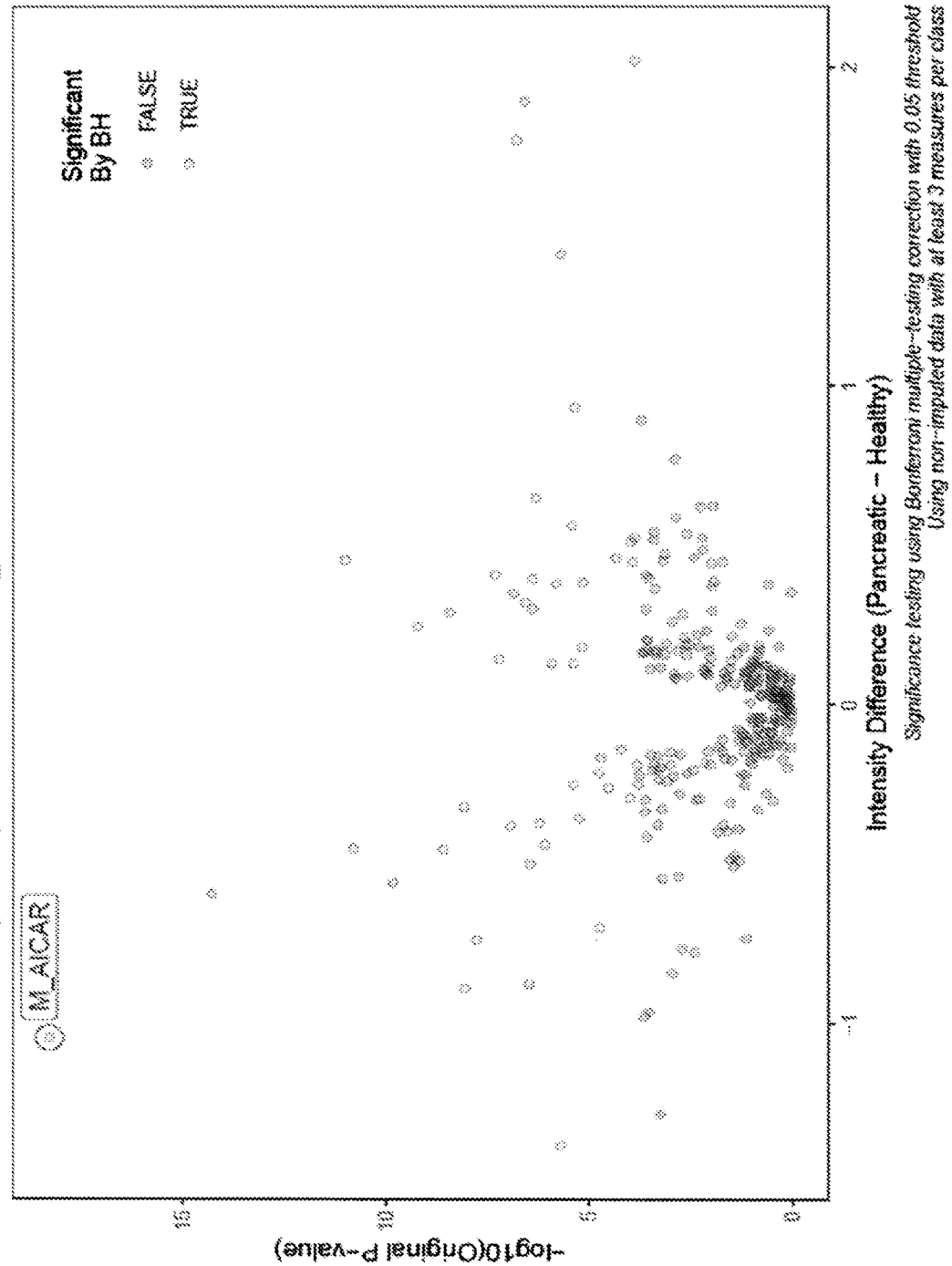

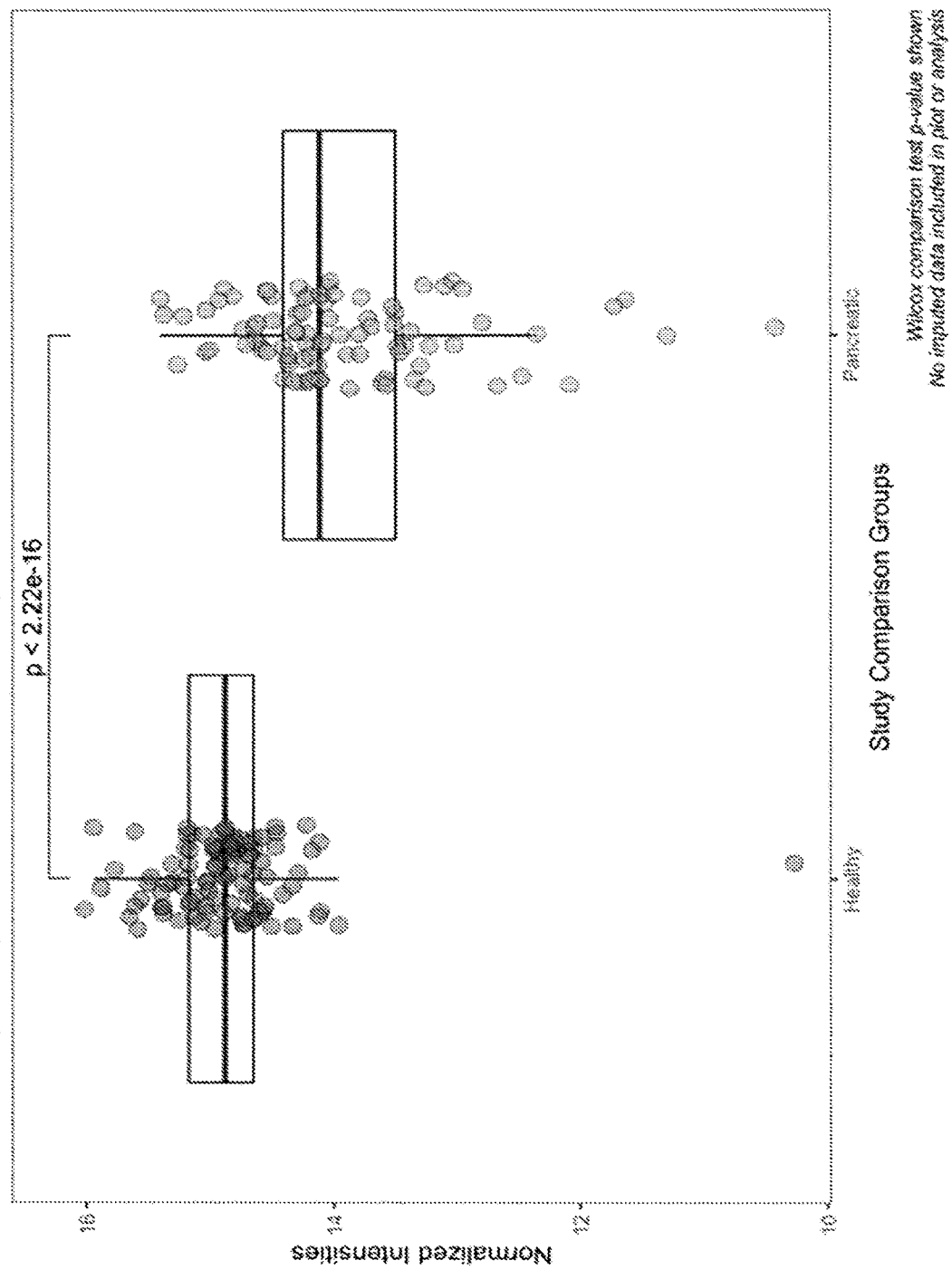

Fig. 39A
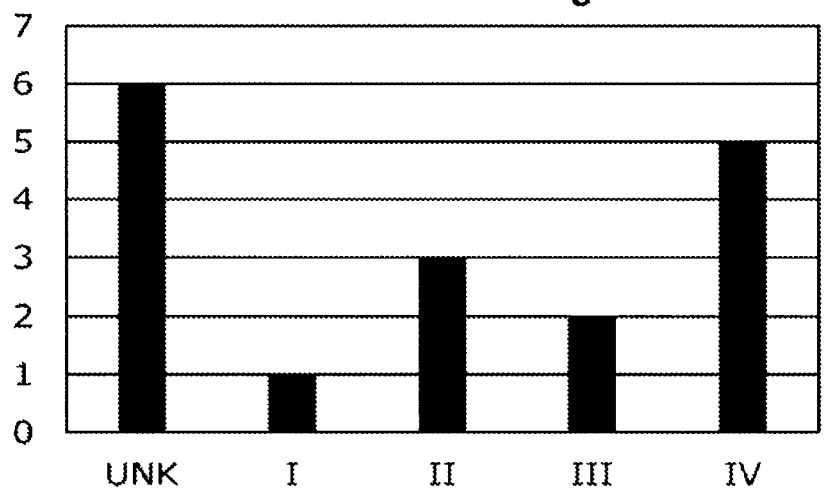
Fig. 39B
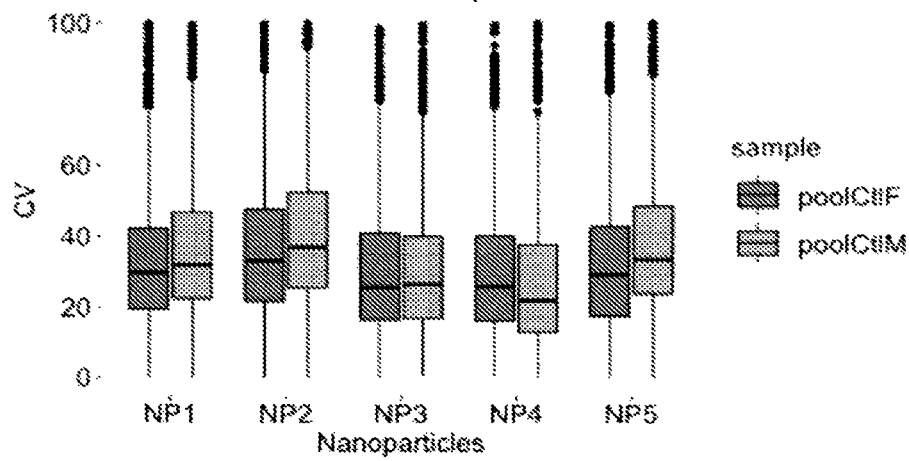
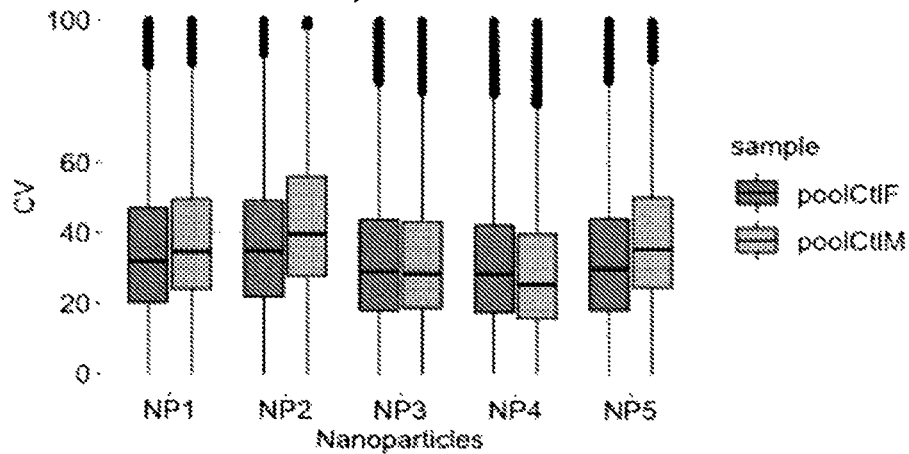

Cohorts

Sample iteration AUC 0.53 ± 0.03

Comparison Group

Fig. 54

| Protein | Function | Linkage to cancer |
|---|---|---|
| ANGPTL6 | Secreted glycoprotein, involved in angiogenesis | • Glioblastoma<br>• Colorectal cancer<br>• Gastric cancer |
| ANTXR2 | Secreted cell adhesion molecular involved in capillary morphogenesis | • Gliomas<br>• Gastric cancer<br>• Head and neck cancers |
| CCL18 | Secreted protein involved in chemotactic responses and immune function | Involved in tumor microenvironment for multiple cancers, including breast, bladder, pancreas, lung and oral cancers |
| HTRA1 | Secreted protein, involved in regulation of TGF-beta signaling, apoptosis, and EGFR/AKT pathway | Involved in mediating anti-tumor efficacy, including correlation of over-expression with cisplatin-resistance in NSCLC |
| TUBA1A | Structural protein and component of tubulin, the major constituent of microtubules | Drug target for cancer drugs paclitaxel and vinflunine |

Fig. 59
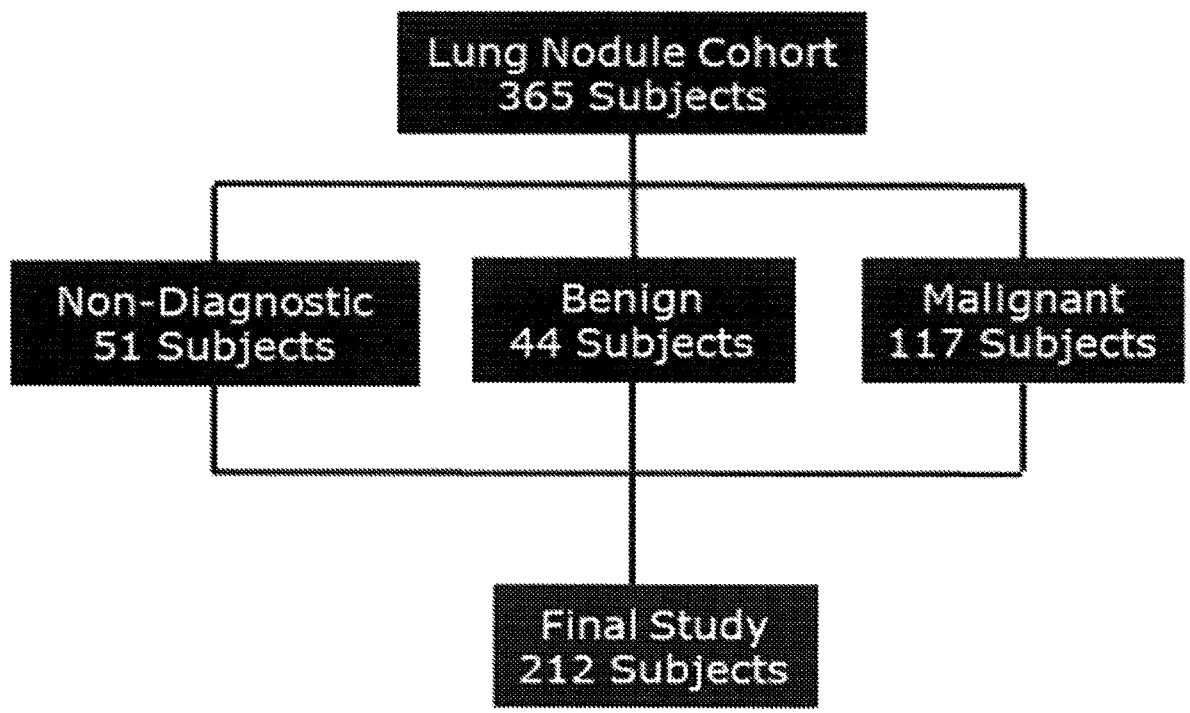
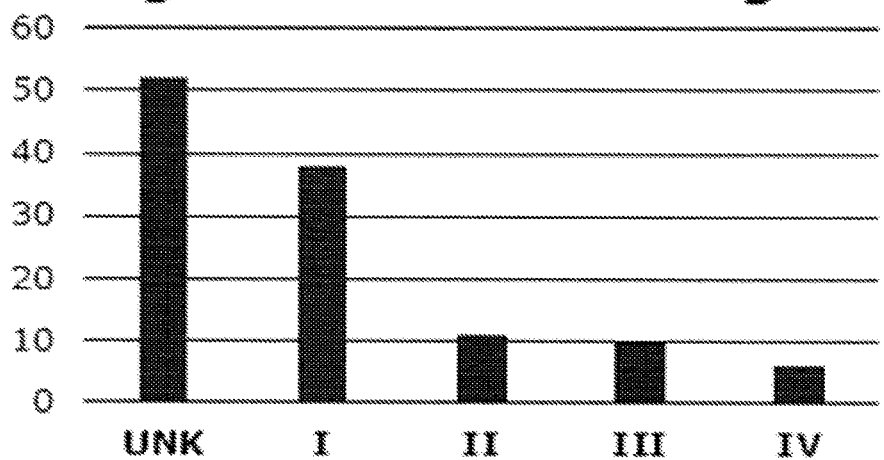

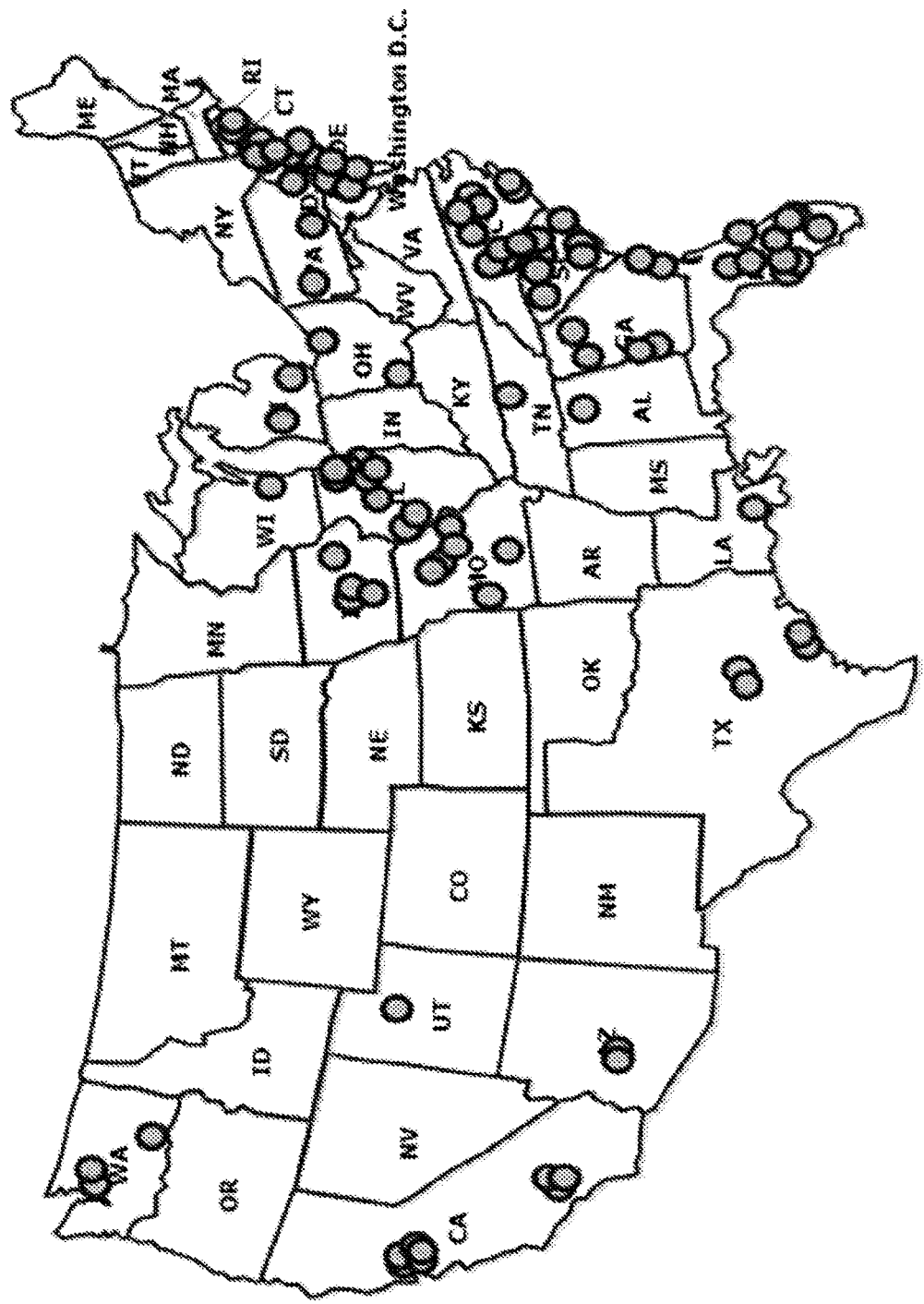
Fig. 68  1000s of prospectively collected samples

Fig. 70
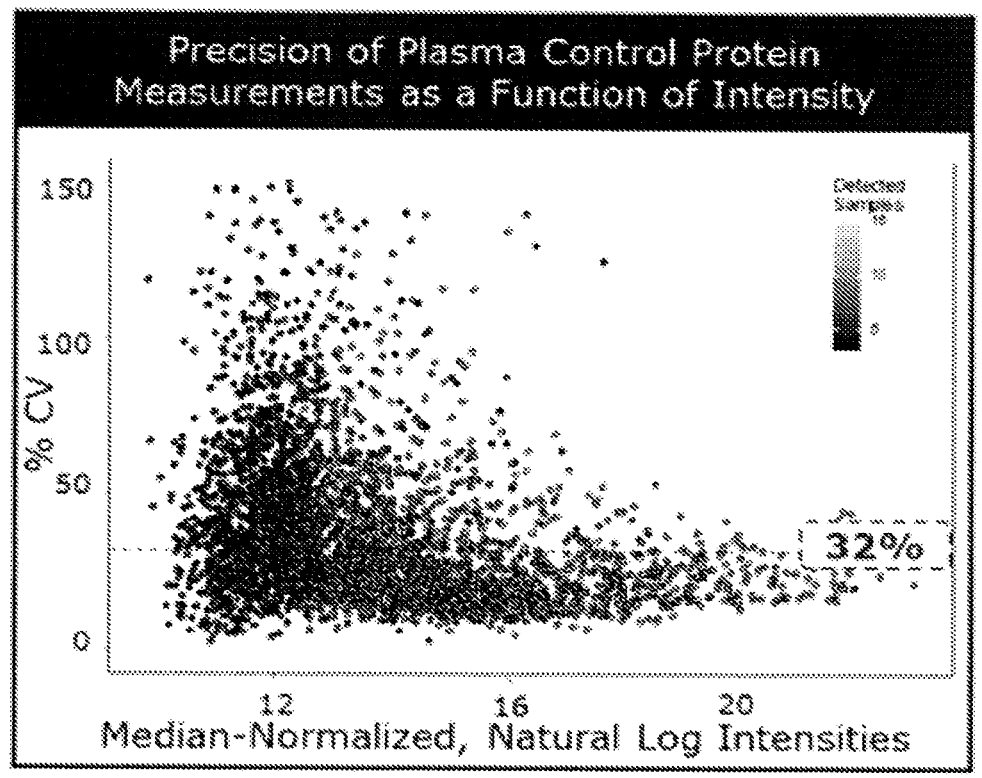
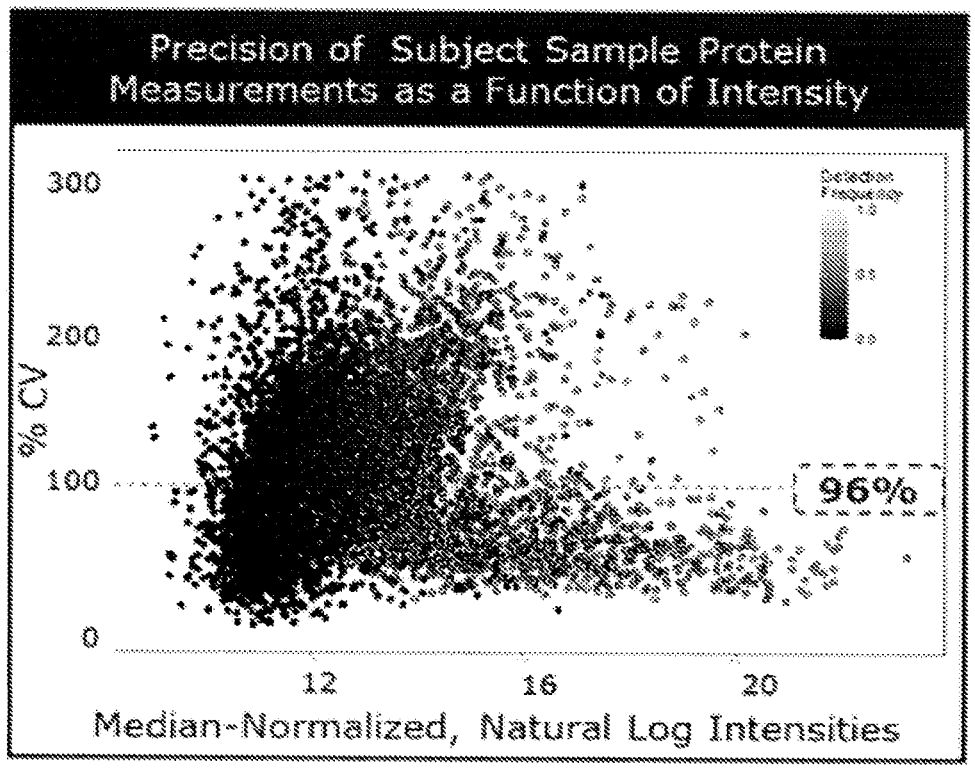

Fig. 72
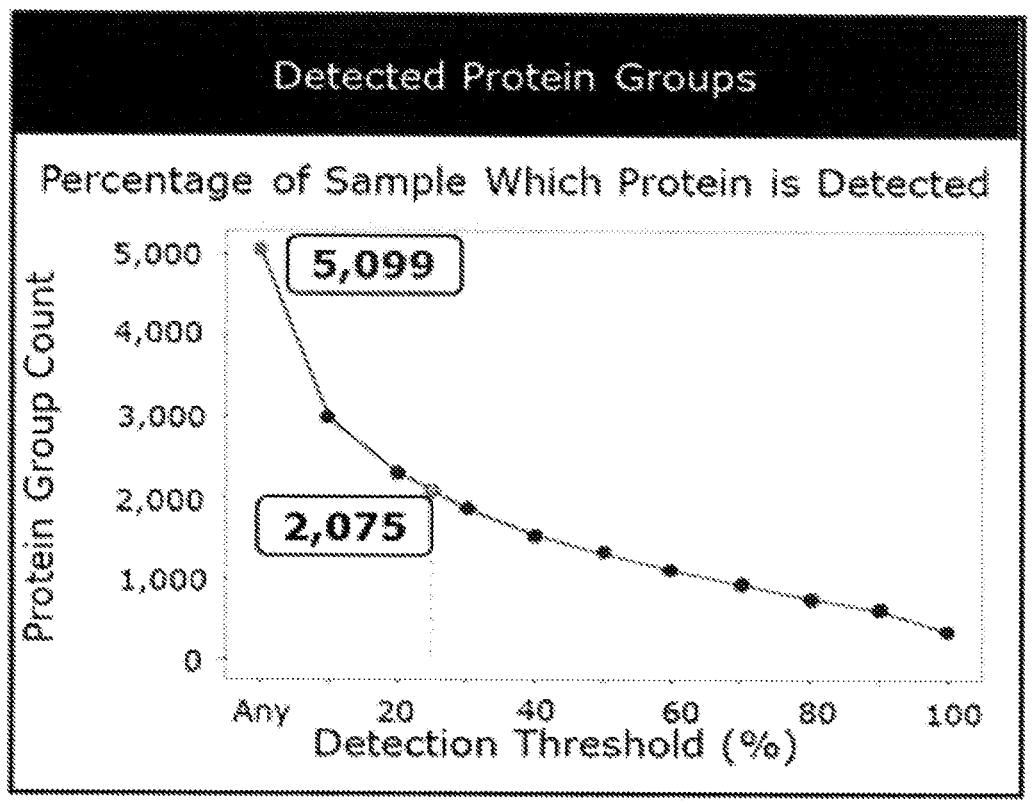
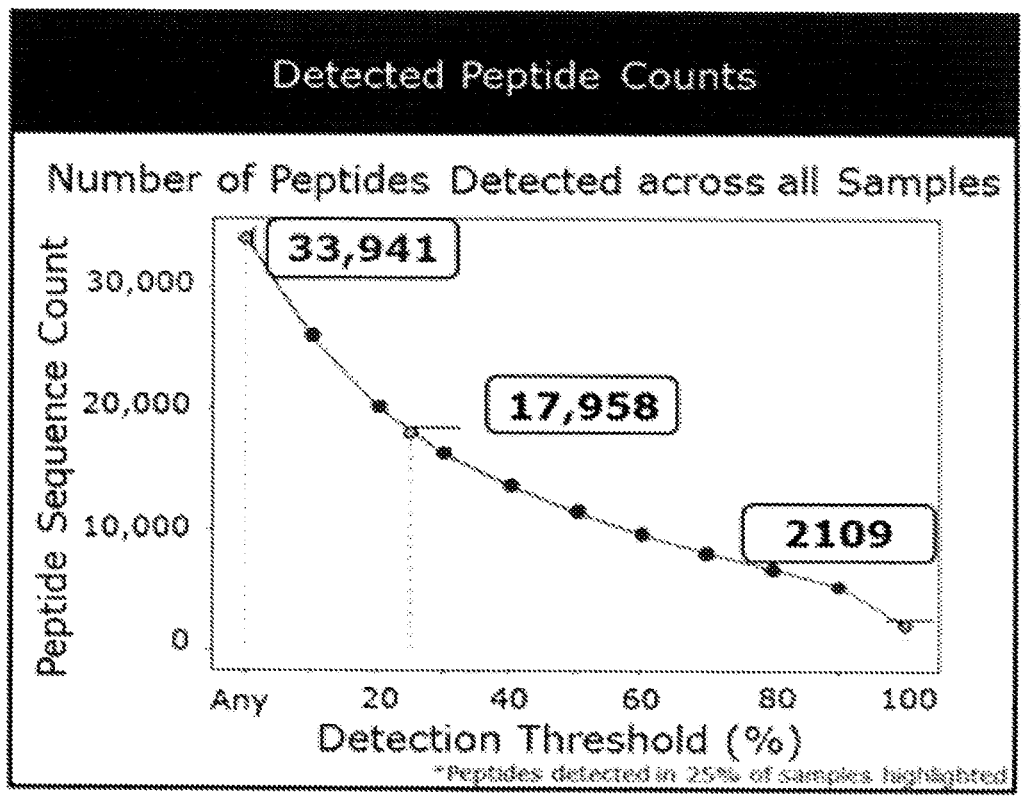

Fig. 88A
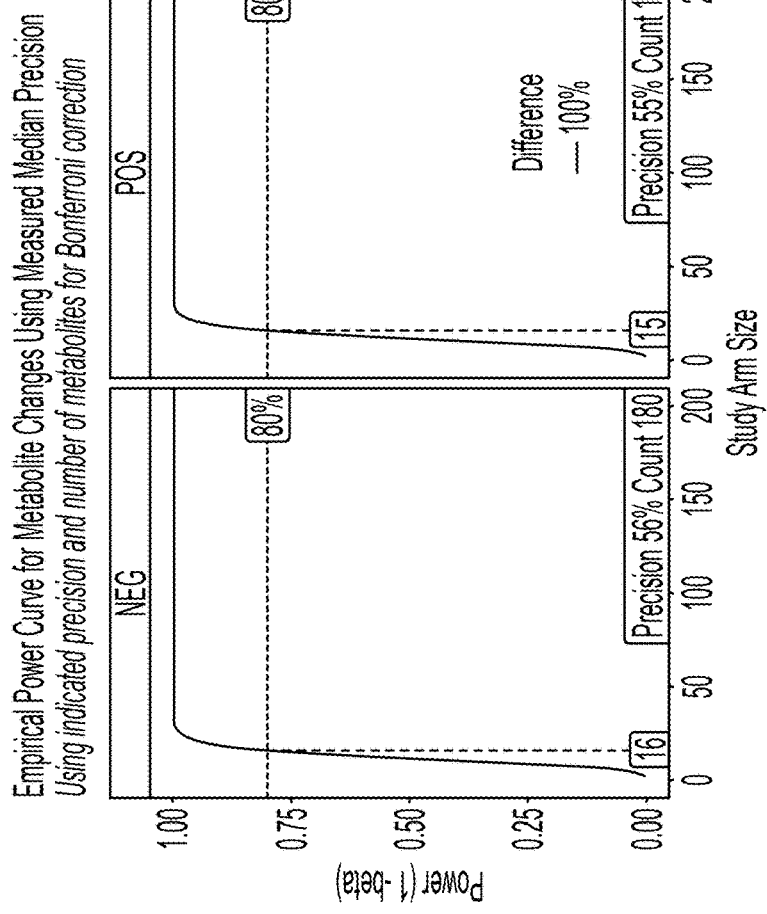
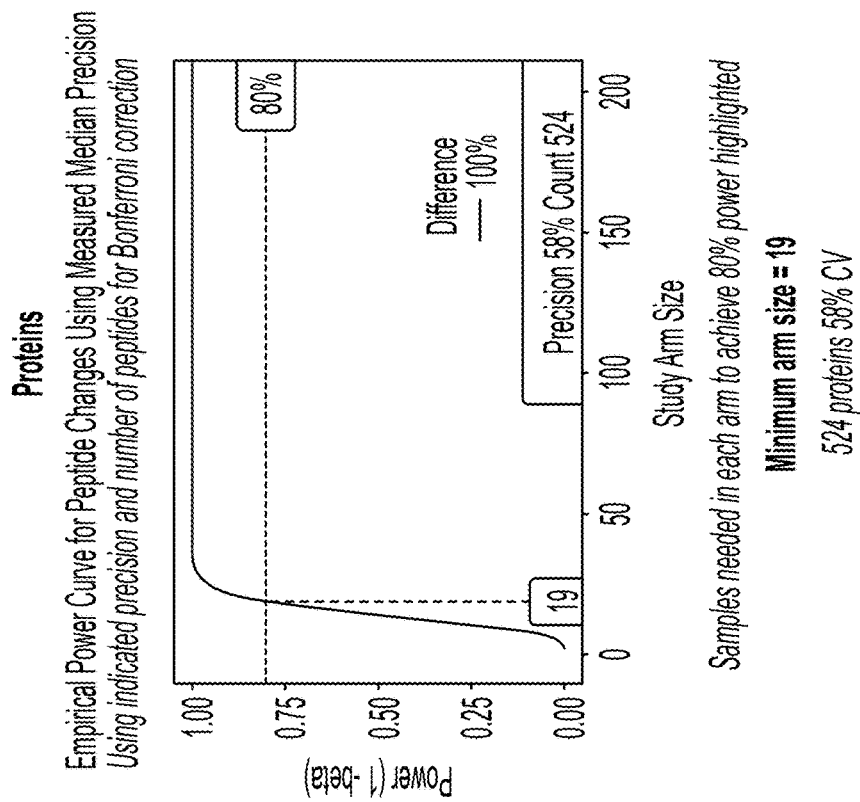

MULTI-OMIC ASSESSMENT USING PROTEINS AND NUCLEIC ACIDS

CROSS-REFERENCE

This application claims the benefit of U.S. Provisional Application No. 63/168,594, filed Mar. 31, 2021, U.S. Provisional Application No. 63/168,634, filed Mar. 31, 2021, U.S. Provisional Application No. 63/183,816, filed May 4, 2021, U.S. Provisional Application No. 63/183,829, filed May 4, 2021, U.S. Provisional Application No. 63/183,844, filed May 4, 2021, U.S. Provisional Application No. 63/183,852, filed May 4, 2021, U.S. Provisional Application No. 63/184,498, filed May 5, 2021, U.S. Provisional Application No. 63/228,533, filed Aug. 2, 2021, U.S. Provisional Application No. 63/228,543, filed Aug. 2, 2021, U.S. Provisional Application No. 63/229,232, filed Aug. 4, 2021, U.S. Provisional Application No. 63/229,242, filed Aug. 4, 2021, U.S. Provisional Application No. 63/256,482, filed Oct. 15, 2021, U.S. Provisional Application No. 63/278,637, filed Nov. 12, 2021, U.S. Provisional Application No. 63/288,825, filed Dec. 13, 2021, U.S. Provisional Application No. 63/288,827, filed Dec. 13, 2021, U.S. Provisional Application No. 63/312,455, filed Feb. 22, 2022, and U.S. Provisional Application No. 63/322,149, filed Mar. 21, 2022, each of which is incorporated by reference herein in its entirety.

BACKGROUND

There is a need for methods of accurately detecting a disease state such as cancer at an early stage. Accurate and early disease detection can improve treatment and prognosis for subjects with the disease.

SUMMARY

Disclosed herein, in some aspects, are multi-omic methods. The method may include obtaining multi-omic data generated from one or more biofluid samples collected from a subject suspected of having a disease state, the multi-omic data comprising proteomic measurements and nucleic acid sequencing measurements; applying a classifier to the multi-omic data to evaluate the disease state; and any one of (i)-(iv): (i) wherein the proteomic measurements are generated after a sample of the one or more biofluid samples has undergone an enrichment protocol that enriches a protein or peptide without enriching another protein or peptide, (ii) wherein the proteomic measurements are generated based on amounts of proteins or peptides added into a sample of the one or more biofluid samples, or (iii) wherein the classifier comprises a performance characteristic comprising an average or median area under the curve (AUC) of a receiver operating characteristic (ROC) curve of at least 0.9, as determined in a data set derived from a randomized, controlled trial of at least 20 subjects having the disease state and over 20 control subjects not having the disease state, or (iv) wherein the evaluation comprises selecting a cancer therapy based on the multi-omic data, the proteomic measurements are generated using mass spectrometry. In some aspects, the proteomic measurements are generated after a sample of the one or more biofluid samples has undergone the enrichment protocol that enriches some proteins without enriching other proteins. In some aspects, the proteomic measurements are generated from proteins adsorbed to nanoparticles. In some aspects, the proteomic measurements are generated based on amounts of proteins added into a sample of the one or more biofluid samples. In some aspects, the proteins added into the sample are labeled. In some aspects, the nucleic acid sequencing measurements comprise mRNA sequencing measurements. In some aspects, the nucleic acid sequencing measurements comprise mRNA sequencing measurements and miRNA sequencing measurements. In some aspects, the multi-omic data comprises measurements of over 45 peptides or protein groups. In some aspects, the evaluation is with at least 4% greater performance than if the classifier was applied to only one type of omic data, wherein the performance comprises sensitivity, at a given specificity, as determined in a data set derived from a randomized, controlled trial of over 25 subjects having the disease state and over 25 control subjects not having the disease state. In some aspects, the classifier is characterized by an average area under the curve (AUC) of a receiver operating characteristic (ROC) curve of at least 0.9, as determined in a data set derived from a randomized, controlled trial of at least 20 subjects having the disease state and over 20 control subjects not having the disease state. In some aspects, applying the classifier to the multi-omic data to evaluate the disease state comprises: applying a first classifier to the proteomic measurements to generate a first label corresponding to a presence, absence, or likelihood of the disease state, applying a second classifier to the nucleic acid sequencing measurements to generate a second label corresponding to a presence, absence, or likelihood of the disease state, and evaluating the disease state based on (a), (b) or (c): (a) a non-weighted average of the first and second labels, (b) a weighted average of the first and second labels, or (c) a majority voting score based on the first and second labels. Some aspects include evaluating the disease state based on the weighted average of the first and second labels, wherein the weighted average is generated by assigning weights to the results of the first and second classifiers based on area under a ROC curve, area under a precision-recall curve, accuracy, precision, recall, sensitivity, F1-score, specificity, or a combination thereof. In some aspects, applying the classifier to the multi-omic data to evaluate the disease state comprises: obtaining a subset of features from among the proteomic measurements; obtaining at least a subset of features from among the nucleic acid sequencing measurements; pooling the subset of features from among the first omic data and the at least a subset of features from among the second omic data to obtained pooled features; and evaluating the disease state based on the pooled features. In some aspects, obtaining a subset of features of from among the first or second omic data comprises obtaining top features based on univariate data. In some aspects, the classifier is trained using deep learning, a hierarchical cluster analysis, a principal component analysis, a partial least squares discriminant analysis, a random forest classification analysis, a support vector machine analysis, a k-nearest neighbors analysis, a naive Bayes analysis, a K-means clustering analysis, or a hidden Markov analysis. In some aspects, the multi-omic data further comprises metabolomic data. In some aspects, the disease state comprises cancer. In some aspects, the cancer is selected from the group consisting of: lung cancer, pancreatic cancer, breast cancer, colon cancer, liver cancer, and ovarian cancer. In some aspects, the evaluation comprises selecting a cancer therapy based on the multi-omic data. Some aspects include, based on the evaluation, administering a chemotherapy, pharmaceutical, radiation or surgical cancer treatment to the subject. In some aspects, the one or more biofluid samples comprise a blood, serum, or plasma sample. In some aspects, the subject is human. Disclosed herein, in some aspects, are multi-omic methods, comprising: obtaining multi-omic data generated from one or more blood, serum, or plasma samples collected from a human subject suspected of having cancer, the multi-omic data comprising proteomic measurements and RNA sequencing measurements; applying a classifier to the multi-omic data to evaluate the cancer; selecting or administering a cancer therapy to the subject based on the evaluation; and any one of (i)-(iii): (i) wherein the proteomic measurements are generated after a sample of the one or more one or more blood, serum, or plasma samples has been enriched by an affinity reagent for a protein or peptide, (ii) wherein the proteomic measurements are generated based on amounts of labeled proteins or peptides added into a sample of the one or more blood, serum, or plasma samples, or (iii) wherein the classifier comprises a performance characteristic comprising an average area under the curve (AUC) of a receiver operating characteristic (ROC) curve of at least 0.9, as determined in a held-out data set derived from a randomized, controlled trial of at least 25 subjects having the disease state and over 25 control subjects not having the disease state. In some embodiments, the proteomic measurements are generated after a sample of the one or more one or more blood, serum, or plasma samples has been enriched by an affinity reagent. In some embodiments, the proteomic measurements are generated based on amounts of labeled proteins added into a sample of the one or more blood, serum, or plasma samples. In some embodiments, the classifier is characterized by an average area under the curve (AUC) of a receiver operating characteristic (ROC) curve of at least 0.9, as determined in a data set derived from a randomized, controlled trial of at least 25 subjects having the disease state and over 25 control subjects not having the disease state.

Disclosed herein, in some aspects, are multi-omic disease detection methods, comprising: obtaining multi-omic data generated from one or more biofluid samples collected from a subject, the multi-omic data comprising a first omic data comprising proteomic data, metabolomic data, transcriptomic data, or genomic data, and a second omic data comprising proteomic data, metabolomic data, transcriptomic data, or genomic data different from the first omic data; and using a first classifier to assign a first label comprising a presence, absence, or likelihood of the disease state to the first omic data, using a second classifier to assign a second label comprising a presence, absence, or likelihood of the disease state to the second omic data, based on the first and second labels, identifying the multi-omic data as indicative or as not indicative of the disease state. In some aspects, the first omic data comprises proteomic data, and the second omic data comprises metabolomic data, transcriptomic data, or genomic data. In some aspects, the proteomic data are generated from contacting a biofluid sample of the biofluid samples with particles such that the particles adsorb biomolecules comprising proteins. In some aspects, the particles comprise carboxylate particles, poly acrylic acid particles, dextran particles, polystyrene particles, dimethylamine particles, amino particles, silica particles, or N-(3-trimethoxysilylpropyl) diethylenetriamine particles. In some aspects, the particles comprise physiochemically distinct groups of nanoparticles. In some aspects, the proteomic data are generated using mass spectrometry, chromatography, liquid chromatography, high-performance liquid chromatography, solid-phase chromatography, a lateral flow assay, an immunoassay, an enzyme-linked immunosorbent assay, a western blot, a dot blot, or immunostaining, or a combination thereof. In some aspects, the genomic or transcriptomic data are generated by sequencing, microarray analysis, hybridization, polymerase chain reaction, electrophoresis, or a combination thereof. In some aspects, the second omic data comprises transcriptomic data. In some aspects, the transcriptomic data comprises mRNA or microRNA expression data. In some aspects, the second omic data comprises genomic data. In some aspects, the genomic data comprises DNA sequence data or epigenetic data. In some aspects, identifying the multi-omic data as indicative or as not indicative of the disease state comprises identifying the multi-omic data as indicative or as not indicative of the disease state based on either the first label or the second label. In some aspects, identifying the multi-omic data as indicative or as not indicative of the disease state comprises generating or obtaining a majority voting score based on the first and second labels. In some aspects, identifying the multi-omic data as indicative or as not indicative of the disease state comprises generating or obtaining a weighted average of the first and second labels. Some aspects include assigning weights to the first and second classifiers based on area under a receiver operating characteristic (ROC) curve, area under a precision-recall curve, accuracy, precision, recall, sensitivity, F1-score, specificity, or a combination thereof, thereby obtaining the weighted average. In some aspects, the first omic data is generated from a first biofluid sample of the biofluid samples, and the second omic data is generated from a second biofluid sample of the biofluid samples. In some aspects, the first biofluid sample is collected in a first container comprising a first collection component comprising heparin, ethylenediaminetetraacetic acid (EDTA), citrate, or an anti-lysis agent, wherein the second biofluid sample is collected in a second container comprising a second collection component different from the first collection component, and which comprises heparin, EDTA, citrate, or an anti-lysis agent. In some aspects, the multi-omic data further comprises a third omic data comprising a third omic data type. The third omic data may comprise a different omic data type or subtype than the first and second omic data. Some aspects include using a third classifier to assign a third label corresponding to a presence, absence, or likelihood of the disease state to the third omic data. In some aspects, identifying the multi-omic data as indicative or as not indicative of the disease state comprises identifying the multi-omic data as indicative or as not indicative of the disease state based on a combination of the first, second, and third labels. Some aspects include using a third classifier to assign a third label comprising a presence, absence, or likelihood of the disease state to a third omic data different from the first and second omic data, and wherein identifying the multi-omic data as indicative or as not indicative of the disease state based on the first and second labels comprises identifying the multi-omic data as indicative or as not indicative of the disease state based on the first, second and third labels. In some aspects, the first omic data type comprises proteomic data, the second omic data type comprises mRNA transcriptomic data, and the third omic data type comprises microRNA transcriptomic data. Some aspects include transmitting or outputting information related to the identification. Some aspects include recommending a treatment of the disease state.

Disclosed herein, in some aspects, are methods comprising: obtaining combined data comprising two, three, or four of: proteomic data, metabolomic data, transcriptomic data, or genomic data, generated from one or more biofluid samples from a subject; and using a classifier to identify the combined data as indicative or as not indicative of one or more disease states. In some aspects, the one or more biofluid samples comprise 1, 2, 3, 4, 5, 6, 7, 8, 9, or 10, or more biofluid samples. In some aspects, the combined data are generated simultaneously. In some aspects, the simultaneous data generation comprises assaying the two, three, or four of proteomic data, metabolomic data, transcriptomic data, or genomic data simultaneously. In some aspects, the simultaneous data generation comprises assaying the two, three, or four of proteomic data, metabolomic data, transcriptomic data, or genomic data on separate locations of an assay substrate. In some aspects, the separate locations comprise separate wells, and the assay substrate comprises an assay plate. In some aspects, the one or more biofluid samples comprise two or more of a whole blood sample, a plasma sample, a serum sample, or a urine sample. In some aspects, the proteomic data are generated from a biofluid sample of the one or more biofluid samples. In some aspects, the metabolomic data are generated from the biofluid sample or from an additional biofluid sample of the one or more biofluid samples, wherein the proteomic data and the metabolomic data are combined to obtain combined data. In some aspects, the classifier identifies the combined data as indicative or as not indicative of one or more disease states with a greater sensitivity or specificity than the proteomic data, metabolomic data, transcriptomic data, or genomic data alone. In some aspects, the classifier comprises features selected from proteomic data, metabolomic data, genomic data, or transcriptomic data. In some aspects, the classifier comprises features selected from a combination of proteomic data, metabolomic data, genomic data, or transcriptomic data. In some aspects, the classifier comprises a plurality of classifiers. In some aspects, the plurality of classifiers comprises 2, 3, or 4, or more classifiers. In some aspects, the plurality of classifiers separately comprise features selected from proteomic data, metabolomic data, genomic data, transcriptomic data, or a combination thereof. In some aspects, using the classifier to identify the combined data as indicative or as not indicative of one or more disease states comprises using the plurality of classifiers to identify the combined data as indicative or as not indicative of one or more disease states. In some aspects, using the classifier to identify the combined data as indicative or as not indicative of one or more disease states comprises picking an output of any one of the plurality of classifiers. In some aspects, using the classifier to identify the combined data as indicative or as not indicative of one or more disease states comprises majority voting across the plurality of classifiers. In some aspects, using the classifier to identify the combined data as indicative or as not indicative of one or more disease states comprises majority voting across a subset of the plurality of classifiers. In some aspects, using the classifier to identify the combined data as indicative or as not indicative of one or more disease states comprises a weighted average of the plurality of classifiers. In some aspects, using the classifier to identify the combined data as indicative or as not indicative of one or more disease states comprises a weighted average of a subset of the plurality of classifiers. In some aspects, weights of the weighted average are assigned based on area under a receiver operating characteristic (ROC) curve. In some aspects, weights of the weighted average are assigned based on area under a precision-recall curve. In some aspects, weights of the weighted average are assigned based on accuracy. In some aspects, weights of the weighted average are assigned based on precision. In some aspects, weights of the weighted average are assigned based on recall. In some aspects, weights of the weighted average are assigned based on sensitivity. In some aspects, weights of the weighted average are assigned based on F1-score. In some aspects, weights of the weighted average are assigned based on specificity.

Disclosed herein, in some aspects, are methods comprising: obtaining proteomic data generated from a biofluid sample from a subject; obtaining metabolomic data, transcriptomic data, or genomic data generated from the biofluid sample or from an additional biofluid sample from the subject, wherein the proteomic data and the metabolomic data, transcriptomic data, or genomic data are combined to obtain combined data; and using a classifier to identify the combined data as indicative or as not indicative of one or more disease states. In some aspects, the proteomic data are generated from contacting the biofluid sample from a subject with particles such that the particles adsorb biomolecules comprising proteins. Some aspects include contacting the biofluid sample from the subject with the particles such that the particles adsorb the biomolecules. Some aspects include analyzing the biomolecules adsorbed to the particles to generate the proteomic data. Some aspects include analyzing the biofluid sample or the additional biofluid sample to generate the metabolomic data. Some aspects include using the classifier to identify the combined data as indicative or as not indicative of the one or more disease states. In some aspects, the proteomic data are generated by measuring a readout indicative of the presence, absence, or amount of the biomolecules. In some aspects, the proteomic data are generated using mass spectrometry, chromatography, liquid chromatography, high-performance liquid chromatography, solid-phase chromatography, a lateral flow assay, an immunoassay, an enzyme-linked immunosorbent assay, a western blot, a dot blot, or immunostaining, or a combination thereof. In some aspects, the proteomic data are generated using mass spectrometry. In some aspects, the proteins comprise secreted proteins. In some aspects, the particles comprise nanoparticles. In some aspects, the particles comprise lipid particles, metal particles, silica particles, or polymer particles. In some aspects, the particles comprise carboxylate particles, poly acrylic acid particles, dextran particles, polystyrene particles, dimethylamine particles, amino particles, silica particles, or N-(3-trimethoxysilylpropyl) diethylenetriamine particles. In some aspects, the particles comprise physiochemically distinct groups of nanoparticles. In some aspects, the metabolomic data are generated from a different biofluid sample than the proteomic data. In some aspects, the metabolomic data are generated using mass spectrometry, electrophoresis, a colorimetric assay, a fluorescence assay, chromatography, liquid chromatography, high-performance liquid chromatography, solid-phase chromatography, a lateral flow assay, an immunoassay, or a combination thereof. In some aspects, the metabolomic data are generated using mass spectrometry. In some aspects, the metabolomic data are generated from the same biofluid sample as the proteomic data. In some aspects, the metabolomic data are generated by analyzing analytes adsorbed to the particles. In some aspects, the metabolomic data comprise lipid metabolite data, carbohydrate metabolite data, vitamin metabolite data, or cofactor metabolite data, or a combination thereof. In some aspects, the biofluid sample comprises a blood sample, a plasma sample, or a serum sample. In some aspects, the additional biofluid sample is collected from the subject in a separate container from the biofluid sample. In some aspects, the combined data are generated from 1, 2, 3, 4, 5, 6, 7, 8, 9, 10, or more samples. In some aspects, the 1, 2, 3, 4, 5, 6, 7, 8, 9, 10, or more samples are separately collected in 1, 2, 3, 4, 5, 6, 7, 8, 9, 10, or more containers. In some aspects, the 1, 2, 3, 4, 5, 6, 7, 8, 9, 10, or more containers comprise multiple components in addition to the samples. In some aspects, the biofluid sample and the additional biofluid samples are collected in separate containers that contain different components in the separate containers. In some aspects, a first container of the separate containers comprises a first component that is different from a second component in a second container of the separate containers. In some aspects, the biofluid sample comprises serum; has been collected in a container comprising ethylenediaminetetraacetic acid (EDTA), citrate, or heparin; or comprises a preservative that prevents cells from lysing. In some aspects, the biofluid sample has been collected in a container comprising ethylenediaminetetraacetic acid (EDTA). In some aspects, the additional biofluid sample comprises a blood sample, a plasma sample, or a serum sample. In some aspects, the additional biofluid sample has been processed to obtain cell-free DNA or to obtain RNA. Some aspects include obtaining genomic or transcriptomic data generated from the biofluid sample, from the additional biofluid sample, or from a third biofluid sample from the subject. In some aspects, the combined data further comprises the genomic or transcriptomic data. Some aspects include analyzing the biofluid sample, the additional biofluid sample, or the third biofluid sample, to generate the genomic or transcriptomic data. In some aspects, the third biofluid sample comprises a blood sample, a plasma sample, or a serum sample. In some aspects, the third biofluid sample has been processed to obtain cell-free DNA or to obtain RNA. Some aspects include using the classifier to identify the combined data as indicative or as not indicative of the one or more disease states. In some aspects, the genomic or transcriptomic data are generated by measuring a readout indicative of the presence, absence, or amount of a nucleic acid. In some aspects, the genomic or transcriptomic data are generated by sequencing, microarray analysis, hybridization, polymerase chain reaction, electrophoresis, or a combination thereof. In some aspects, the genomic or transcriptomic data are generated from a different biofluid sample from the metabolomic data. In some aspects, the genomic or transcriptomic data are generated from the same biofluid sample as the metabolomic data. In some aspects, the genomic or transcriptomic data are generated from a different biofluid sample from the p data. In some aspects, the genomic or transcriptomic data are generated from the same biofluid sample as the proteomic data. In some aspects, the genomic or transcriptomic data are generated by analyzing nucleic acids adsorbed to the particles. In some aspects, the genomic or transcriptomic data comprise genomic data. In some aspects, the genomic data comprise DNA sequence data. In some aspects, the genomic data comprise DNA polymorphism data. In some aspects, the genomic data comprise epigenetic data. In some aspects, the genomic data comprise DNA methylation data. In some aspects, the epigenetic data comprise histone modification data. In some aspects, the histone modification data comprise acetylation data, methylation data, ubiquitylation data, phosphorylation data, sumoylation data, ribosylation data, or citrullination data. In some aspects, the genomic or transcriptomic data comprise transcriptomic data. In some aspects, the transcriptomic data comprise RNA sequence data. In some aspects, the transcriptomic data comprise RNA expression data. In some aspects, the transcriptomic data comprise mRNA, tRNA, rRNA, microRNA, snRNA, snoRNA, or lncRNA expression data. In some aspects, the transcriptomic data comprise mRNA expression data. In some aspects, the transcriptomic data comprise microRNA expression data. In some aspects, the classifier comprises features to identify the combined data as indicative of the one or more disease states. In some aspects, the features comprise control protein measurements, control metabolite measurements, control nucleic acid measurements, mass spectra, m/z ratios, chromatography results, immunoassay results, light or fluorescence intensities, or sequence information. In some aspects, the classifier is trained using deep learning, a hierarchical cluster analysis, a principal component analysis, a partial least squares discriminant analysis, a random forest classification analysis, a support vector machine analysis, a k-nearest neighbors analysis, a naive Bayes analysis, a K-means clustering analysis, or a hidden Markov analysis. In some aspects, the one or more disease states comprise one or more cancers. In some aspects, the one or more cancers comprise lung cancer, breast cancer, prostate cancer, colorectal cancer, colon cancer, melanoma, bladder cancer, lymphoma, leukemia, renal cancer, uterine cancer, pancreatic cancer, or a combination thereof. In some aspects, the classifier discriminates between the one or more disease states. In some aspects, the classifier discriminates between lung cancer, colon cancer, and pancreatic cancer. In some aspects, the classifier discriminates between lung cancer, colon cancer, and pancreatic cancer. In some aspects, the lung cancer comprises non-small-cell lung cancer (NSCLC). Some aspects include generating a report based on the use of the classifier to identify the combined data as indicative or as not indicative of the one or more disease states. In some aspects, the report comprises a likelihood or an indication that the biofluid or subject comprises the one or more disease states. Some aspects include outputting or transmitting the report. In some aspects, the report is used by a medical professional in making a diagnosis, giving medical advice, or providing a treatment for at least one of the one or more disease states. Some aspects include identifying the combined data as indicative of the one or more disease states. In some aspects, the one or more disease states comprises a cancer, and further comprising recommending a cancer treatment for the subject when the combined data is identified as indicative of cancer. In some aspects, the one or more disease states comprises a cancer, and further comprising administering a cancer treatment to the subject when the combined data is identified as indicative of cancer. In some aspects, the cancer treatment comprises chemotherapy, radiation therapy, ablation therapy, embolization, or surgery. Some aspects include using the classifier to identify the combined data as indicative of a first disease state of the one or more disease states, and not indicative of a second disease state of the one or more disease states. Some aspects include administering or recommending a treatment for the first disease state and not the second disease state. Some aspects include identifying the combined data as not indicative of the one or more disease states. Some aspects include observing the subject without providing a treatment to the subject when the combined data is identified as not indicative of the one or more disease states. In some aspects, observing the subject without providing a treatment comprises analyzing the biomolecules in a biofluid sample obtained from the subject at a later time. In some aspects, the subject is a mammal. In some aspects, the subject is a human. In some aspects, the classifier comprises features selected from proteomic data, metabolomic data, genomic data, or transcriptomic data. In some aspects, the classifier comprises features selected from a combination of proteomic data, metabolomic data, genomic data, or transcriptomic data. In some aspects, the classifier comprises a plurality of classifiers. In some aspects, the plurality of classifiers comprises 2, 3, or 4, or more classifiers. In some aspects, the plurality of classifiers separately comprise features selected from proteomic data, metabolomic data, genomic data, transcriptomic data, or a combination thereof. In some aspects, using the classifier to identify the combined data as indicative or as not indicative of one or more disease states comprises using the plurality of classifiers to identify the combined data as indicative or as not indicative of one or more disease states. In some aspects, using the classifier to identify the combined data as indicative or as not indicative of one or more disease states comprises picking an output of any one of the plurality of classifiers. In some aspects, using the classifier to identify the combined data as indicative or as not indicative of one or more disease states comprises majority voting across the plurality of classifiers. In some aspects, using the classifier to identify the combined data as indicative or as not indicative of one or more disease states comprises majority voting across a subset of the plurality of classifiers. In some aspects, using the classifier to identify the combined data as indicative or as not indicative of one or more disease states comprises a weighted average of the plurality of classifiers. In some aspects, using the classifier to identify the combined data as indicative or as not indicative of one or more disease states comprises a weighted average of a subset of the plurality of classifiers. In some aspects, weights of the weighted average are assigned based on area under a receiver operating characteristic (ROC) curve. In some aspects, weights of the weighted average are assigned based on area under a precision-recall curve. In some aspects, weights of the weighted average are assigned based on accuracy. In some aspects, weights of the weighted average are assigned based on precision. In some aspects, weights of the weighted average are assigned based on recall. In some aspects, weights of the weighted average are assigned based on sensitivity. In some aspects, weights of the weighted average are assigned based on F1-score. In some aspects, weights of the weighted average are assigned based on specificity.

Disclosed herein, in some aspects, are methods comprising: obtaining multi-omic data generated from one or more biofluid samples collected from a subject, the multi-omic data comprising a first omic data and a second omic data, wherein the first omic data comprises a first omic data type comprising proteomic data, metabolomic data, transcriptomic data, or genomic data, and wherein the second omic data comprises a second omic data type different from the first omic data type and comprises proteomic data, metabolomic data, transcriptomic data, or genomic data; identifying a first subset of features from among the first omic data; identifying a second subset of features from among the second omic data; pooling the first and second subsets of features; identifying the multi-omic data as indicative or as not indicative of the disease state based on the pooled subsets of features. In some aspects, identifying the first or second subset of features from among the first or second omic data comprises obtaining univariate data for features of the first or second omic data, and identifying the first or second subset as based on the univariate data. In some aspects, the first or second subset of features are identified from among features of a classifier for the first or second omic data. In some aspects, identifying the first or second subset of features from among the first or second omic data comprises obtaining a classifier for the first or second omic data, and identifying the first or second subset as top features of the classifier. In some aspects, identifying the first or second subset of features from among the first or second omic data comprises obtaining a classifier for the first or second omic data, removing one or more features at time from the classifier, and identifying which features reduce the classifier's performance when removed from the classifier.

In some embodiments, the disease or disorder includes pancreatic cancer. Disclosed herein, in some aspects, are multi-omic cancer detection methods for detecting pancreatic cancer. Disclosed herein, in some aspects, are a method of detecting pancreatic cancer in a subject, comprising: identifying a subject at risk of having pancreatic cancer; obtaining a biofluid sample from the subject; contacting the biofluid sample with particles such that the particles adsorb biomolecules comprising proteins to the particles; assaying the biomolecules adsorbed to the particles to generate proteomic data; and classifying the proteomic data as indicative of pancreatic cancer or as not indicative of pancreatic cancer. Disclosed herein, in some aspects, are methods comprising: assaying proteins in a biofluid sample obtained from a subject identified as at risk of having pancreatic cancer to obtain protein measurements; and applying a classifier to the protein measurements, thereby identifying the protein measurements as indicative of the subject having pancreatic cancer, wherein the classifier is generated using proteomic data obtained by contacting training samples with particles such that the particles adsorb proteins in the training samples and assaying the proteins adsorbed to the particles. Disclosed herein, in some aspects, are a method of treatment, comprising: identifying a mass in a pancreas of a subject; obtaining a biofluid sample from the subject; contacting the biofluid sample with particles such that the particles adsorb biomolecules comprising proteins to the particles; assaying the biomolecules adsorbed to the particles to generate proteomic data; and classifying the proteomic data as indicative of the mass comprising pancreatic cancer or as not indicative of the mass comprising pancreatic cancer. Disclosed herein, in some aspects, are methods of evaluating a subject suspected of having pancreatic cancer, comprising: measuring biomarkers in a biofluid sample from the subject, wherein the biomarkers comprise A2GL, AKRIB1, ANPEP, ANTXR1, ANTXR2, BTK, CALR, CDH1, CDH11, CDH2, CDHR2, CILP2, CLEC3B, COL18A1, CRP, EXT1, F13A1, FAT1, FGL1, FLT4, ICAM1, IDH2, LCN2, LPP, MAPK1, MAP2K1, MYH9, NOTCH1, NOTCH2, PIGR, PPP2R1A, PRKAR1A, PXDN, RELN, RHOA, S100A8, S100A9, S100A12, SAA1, SAA2, SERPINA3, SLAIN2, SND1, SVEP1, TSP2, TUBB, TUBB1, or VCAN. Disclosed herein, in some aspects, are methods, comprising: assaying biomolecules in a biofluid sample obtained from a subject suspected of having pancreatic cancer to obtain biomolecule measurements; and identifying the protein measurements as indicative of the subject having the pancreatic cancer or as not having the pancreatic cancer by applying a classifier to the biomolecule measurements, wherein the classifier is characterized by a receiver operating characteristic (ROC) curve having an area under the curve (AUC) greater than 0.7, greater than 0.75, greater than 0.8, greater than 0.85, greater than 0.9, greater than 0.91, greater than 0.92, greater than 0.93, or greater than 0.94, based on biomolecule measurement features. In some aspects, the AUC is no greater than 0.75, no greater than 0.8, no greater than 0.85, no greater than 0.9, no greater than 0.91, no greater than 0.92, no greater than 0.93, no greater than 0.94, no greater than 0.95, or no greater than 0.96. In some aspects, the biomolecules comprise proteins, lipids, or metabolites, or a combination thereof.

In some embodiments, the disease or disorder includes liver cancer. Disclosed herein, in some aspects, are multi-omic cancer detection methods for detecting liver cancer. Disclosed herein, in some aspects, are methods of detecting liver cancer in a subject, comprising: identifying a subject as at risk of having liver cancer; obtaining a biofluid sample from the subject; contacting the biofluid sample with particles such that the particles adsorb biomolecules comprising proteins to the particles; assaying the biomolecules adsorbed to the particles to generate proteomic data; and classifying the proteomic data as indicative of liver cancer or as not indicative of liver cancer. Disclosed herein, in some aspects, are methods comprising: assaying proteins in a biofluid sample obtained from a subject identified as at risk of having liver cancer to obtain protein measurements; and applying a classifier to the protein measurements, thereby identifying the protein measurements as indicative of the subject having liver cancer, wherein the classifier is generated using proteomic data obtained by contacting training samples with particles such that the particles adsorb proteins in the training samples and assaying the proteins adsorbed to the particles. Disclosed herein, in some aspects, are methods of treatment, comprising: identifying a mass in a liver of a subject; obtaining a biofluid sample from the subject; contacting the biofluid sample with particles such that the particles adsorb biomolecules comprising proteins to the particles; assaying the biomolecules adsorbed to the particles to generate proteomic data; and classifying the proteomic data as indicative of the mass comprising liver cancer or as not indicative of liver cancer. Disclosed herein, in some aspects, are methods of detecting liver cancer in a subject, comprising: identifying a subject as at risk of having liver cancer; obtaining a biofluid sample from the subject; assaying lipids in the biofluid sample to obtain lipid data; and classifying the lipid data as indicative of liver cancer or as not indicative of liver cancer.

In some embodiments, the disease or disorder includes ovarian cancer. Disclosed herein, in some aspects, are multiomic cancer detection methods for detecting ovarian cancer. Disclosed herein, in some aspects, are a method of detecting ovarian cancer in a subject, comprising: identifying a subject as at risk of having ovarian cancer; obtaining a biofluid sample from the subject; contacting the biofluid sample with particles such that the particles adsorb biomolecules comprising proteins to the particles; assaying the biomolecules adsorbed to the particles to generate proteomic data; and classifying the proteomic data as indicative of ovarian cancer or as not indicative of ovarian cancer. In some aspects, identifying the subject as at risk of having ovarian cancer comprises identifying the subject as having a computed tomography (CT) scan indicative of ovarian cancer, having a magnetic resonance imaging (MRI) scan indicative of ovarian cancer, having a positron emission tomography (PET) scan indicative of ovarian cancer, having a transvaginal ultrasound indicative of ovarian cancer, having an elevated cancer antigen (CA)-125 level relative to a control or baseline measurement, or having an ovarian cyst, or a combination thereof. Disclosed herein, in some aspects, are a method comprising: assaying proteins in a biofluid sample obtained from a subject identified as at risk of having ovarian cancer to obtain protein measurements; and applying a classifier to the protein measurements, thereby identifying the protein measurements as indicative of the subject having ovarian cancer, wherein the classifier is generated using proteomic data obtained by contacting training samples with particles such that the particles adsorb proteins in the training samples and assaying the proteins adsorbed to the particles. In some aspects, the proteins comprise ANTXR2, BMP1, CILP, EIF2AK2, ENO3, F13B, FGL1, or PEBP4. Disclosed herein, in some aspects, are a method of treatment, comprising: identifying a mass in an ovary of a subject; obtaining a biofluid sample from the subject; contacting the biofluid sample with particles such that the particles adsorb biomolecules comprising proteins to the particles; assaying the biomolecules adsorbed to the particles to generate proteomic data; and classifying the proteomic data as indicative of the mass comprising ovarian cancer or as not indicative of ovarian cancer. Disclosed herein, in some aspects, are methods of detecting ovarian cancer in a subject, comprising: identifying a subject as at risk of having ovarian cancer; obtaining a biofluid sample from the subject; assaying lipids in the biofluid sample to obtain lipid data; and classifying the lipid data as indicative of ovarian cancer or as not indicative of ovarian cancer. In some aspects, the lipids comprise one or more phospholipids.

In some embodiments, the disease or disorder includes colon cancer. Disclosed herein, in some aspects, are multiomic cancer detection methods for detecting colon cancer. Disclosed herein, in some aspects, are methods of detecting colon cancer in a subject, comprising: identifying a subject as at risk of having colon cancer; obtaining a biofluid sample from the subject; contacting the biofluid sample with particles such that the particles adsorb biomolecules comprising proteins to the particles; assaying the biomolecules adsorbed to the particles to generate proteomic data; and classifying the proteomic data as indicative of colon cancer or as not indicative of colon cancer. Disclosed herein, in some aspects, are methods, comprising: assaying proteins in a biofluid sample obtained from a subject identified as at risk of having colon cancer to obtain protein measurements; and applying a classifier to the protein measurements, thereby identifying the protein measurements as indicative of the subject having colon cancer, wherein the classifier is generated using proteomic data obtained by contacting training samples with particles such that the particles adsorb proteins in the training samples and assaying the proteins adsorbed to the particles. In some aspects, the subject is identified as at risk of having colon cancer by identifying the subject as having a computed tomography (CT) scan indicative of colon cancer, having a liver function test (LFT) indicative of colon cancer, having an elevated carcinoembryonic antigen (CEA) level relative to a control or baseline measurement, having blood in a stool, having a fecal immunochemical test (FIT) indicative of colon cancer, or having a colon nodule, or a combination thereof. Disclosed herein, in some aspects, are methods of treatment, comprising: identifying a mass in a colon of a subject; obtaining a biofluid sample from the subject; contacting the biofluid sample with particles such that the particles adsorb biomolecules comprising proteins to the particles; assaying the biomolecules adsorbed to the particles to generate proteomic data; and classifying the proteomic data as indicative of the mass comprising colon cancer or as not indicative of colon cancer.

Disclosed herein, in some aspects, are methods comprising: assaying proteins in a biofluid sample obtained from a subject identified as having a lung nodule to obtain protein measurements; and applying a classifier to the protein measurements to evaluate the lung nodule; and (i), (ii), or (iii): (i) wherein the classifier comprises protein features of the assayed proteins, and wherein the classifier comprises a performance characteristic in identifying lung nodules as cancerous or as non-cancerous, the performance characteristic comprising an average or median area under the curve (AUC) of a receiver operating characteristic (ROC) curve of greater than 0.65 (e.g. greater than 0.7), as determined in a data set derived from a randomized, controlled trial of over 20 subjects having cancerous lung nodules and over 20 control subjects having non-cancerous lung nodules, and as determined in a data set without including clinical features in the classifier, (ii) wherein the classifier is generated using proteomic data obtained by contacting training samples with particles such that the particles adsorb proteins in the training samples and assaying the proteins adsorbed to the particles, or (iii) wherein assaying the proteins comprises contacting the biofluid sample with particles to adsorb the proteins to the particles, and obtaining the protein measurements from the adsorbed proteins. In some aspects, the classifier comprises protein features of the assayed proteins, and is characterized by an average ROC curve having a median AUC greater than 0.7 in identifying lung nodules as cancerous or as non-cancerous, wherein the AUC greater than 0.7 is determined without including non-protein features in a data set derived from a randomized, controlled trial of over 20 subjects having cancerous lung nodules and over 20 control subjects having non-cancerous lung nodules. In some aspects, the classifier is generated using proteomic data obtained by contacting training samples with particles such that the particles adsorb proteins in the training samples and assaying the proteins adsorbed to the particles. In some aspects, assaying the proteins comprises contacting the biofluid sample with particles to adsorb the proteins to the particles, and obtaining the protein measurements from the adsorbed proteins. In some aspects, the classifier is trained using deep learning, a hierarchical cluster analysis, a principal component analysis, a partial least squares discriminant analysis, a random forest classification analysis, a support vector machine analysis, a k-nearest neighbors analysis, a naive Bayes analysis, a K-means clustering analysis, or a hidden Markov analysis. In some aspects, evaluating the lung nodule comprises identifying the protein measurements as indicative that the lung nodule is cancerous. Some aspects include administering a lung cancer treatment to the subject based on the evaluation. In some aspects, the lung cancer treatment comprising chemotherapy, radiation therapy, percutaneous ablation, radiofrequency ablation, cryoablation, microwave ablation, chemoembolization, or surgery. In some aspects, the subject is identified as having the lung nodule through use of a medical imaging device. In some aspects, the classifier identifies lung cancer with a sensitivity and specificity above 60%. In some aspects, the particles comprise nanoparticles. In some aspects, the particles comprise lipid particles, metal particles, silica particles, or polymer particles. In some aspects, the particles comprise physiochemically distinct groups of nanoparticles. In some aspects, the biofluid samples comprises a blood, serum, or plasma sample. In some aspects, the subject is human. In some aspects, the protein measurements comprise a measurement of a protein selected from the group consisting of: APP, IGHG2, SERPING1, SAA2, SERPINF2, GC, IGHA1, HPR, SERPINA3, IGHA1, LTF, SERPINA1, PCSK6, PROS1, BPIF1, C6, CP, A2M, and IGFBP2. Disclosed herein, in some aspects, are methods comprising: assaying proteins in a blood, serum, or plasma sample by mass spectrometry to obtain protein measurements, the sample having been obtained from a human subject identified, using a medical imaging device, as having a lung nodule; applying a classifier to the protein measurements to evaluate the lung nodule; and selecting or administering a lung cancer therapy to the subject based on the evaluation; and (i), (ii), or (iii): (i) wherein the classifier comprises protein features of the assayed proteins, and wherein the classifier comprises a performance characteristic in identifying lung nodules as cancerous or as non-cancerous, the performance characteristic comprising a median area under the curve (AUC) of a receiver operating characteristic (ROC) curve of greater than 0.7, as determined in a held-out data set derived from a randomized, controlled trial of over 25 subjects having cancerous lung nodules and over 25 control subjects having non-cancerous lung nodules, and as determined using only protein features in the classifier, (ii) wherein the classifier is generated using proteomic data obtained by contacting training samples with nanoparticles such that the nanoparticles adsorb proteins in the training samples and assaying the proteins adsorbed to the nanoparticles, or (iii) wherein assaying the proteins comprises contacting the blood, serum, or plasma sample with nanoparticles to adsorb the proteins to the nanoparticles, and obtaining the protein measurements from the adsorbed proteins.

In some embodiments, the classifier comprises protein features of the assayed proteins, and is characterized by an average ROC curve having a median AUC greater than 0.7 in identifying lung nodules as cancerous or as non-cancerous, wherein the AUC greater than 0.7 is determined without including non-protein features in a held-out data set derived from a randomized, controlled trial of over 25 subjects having cancerous lung nodules and over 25 control subjects having non-cancerous lung nodules. In some embodiments, the classifier is generated using proteomic data obtained by contacting training samples with nanoparticles such that the nanoparticles adsorb proteins in the training samples and assaying the proteins adsorbed to the nanoparticles. In some embodiments, assaying the proteins comprises contacting the blood, serum, or plasma sample with nanoparticles to adsorb the proteins to the nanoparticles, and obtaining the protein measurements from the adsorbed proteins.

Disclosed herein, in some aspects, are methods comprising: assaying proteins in a biofluid sample obtained from a subject identified as having a lung nodule to obtain protein measurements; and identifying the protein measurements as indicative of the lung nodule being cancerous or as non-cancerous by applying a classifier to the protein measurements, wherein the classifier is characterized by a receiver operating characteristic (ROC) curve having an area under the curve (AUC) greater than 0.7 based on protein measurement features. In some aspects, the AUC greater than 0.7 is generated without including non-protein clinical features. In some aspects, the non-protein clinical features comprise clinical indicators of lung cancer. In some aspects, the proteins comprise APP, IGHG2, SERPING1, SAA2, SERPINF2, GC, IGHA1, HPR, SERPINA3, IGHA1, LTF, SERPINA1, PCSK6, PROS1, BPIF1, C6, CP, A2M, or IGFBP2.

Disclosed herein, in some aspects, are methods comprising: assaying proteins in a biofluid sample obtained from a subject having or suspected of having a lung nodule to obtain protein measurements; and applying a classifier to the protein measurements to evaluate the lung nodule, wherein the classifier is generated using proteomic data obtained by enriching proteins with an affinity reagent. Disclosed herein, in some aspects, are methods comprising: assaying proteins in a biofluid sample obtained from a subject having or suspected of having a lung nodule to obtain protein measurements; and applying a classifier to the protein measurements, thereby identifying the protein measurements as indicative of the lung nodule being cancerous or non-cancerous, wherein the classifier is generated using proteomic data obtained by contacting training samples with particles such that the particles adsorb proteins in the training samples, and assaying the proteins adsorbed to the particles. Some aspects include obtaining of receiving the biofluid sample of the subject. In some aspects, the subject is identified as having the lung nodule by medical imaging. In some aspects, the medical imaging comprises a computed tomography (CT) scan. Some aspects include performing the medical imaging. Some aspects include identifying the lung nodule in the medical imaging. Some aspects include generating a report based on the identification of the protein measurements as indicative of the lung nodule being cancerous or non-cancerous. In some aspects, the report comprises a likelihood or an indication that the lung nodule is cancerous or non-cancerous. Some aspects include outputting or transmitting the report. In some aspects, the report is used by a medical professional in making a diagnosis, giving medical advice, or providing a treatment for the lung nodule. Some aspects include performing a biopsy on the lung nodule when the protein measurements are classified as indicative of the lung nodule being cancerous. In some aspects, the biopsy confirms a likelihood of the lung nodule being cancerous or non-cancerous. In some aspects, the lung nodule is cancerous. In some aspects, the lung nodule comprises non-small-cell lung carcinoma (NSCLC). In some aspects, the classifier comprises features to indicate the protein measurements as indicative of the lung nodule being cancerous or non-cancerous. In some aspects, the features comprise control protein measurements, mass spectra, m/z ratios, chromatography results, immunoassay results, or light or fluorescence intensities. In some aspects, the classifier is trained using deep learning, a hierarchical cluster analysis, a principal component analysis, a partial least squares discriminant analysis, a random forest classification analysis, a support vector machine analysis, a k-nearest neighbors analysis, a naive Bayes analysis, a K-means clustering analysis, or a hidden Markov analysis. In some aspects, the classifier is capable of identifying lung cancer with a sensitivity of 50% or greater, 60% or greater, 70% or greater, 80% or greater, or 90% or greater. In some aspects, the classifier is capable of identifying lung cancer with a specificity of 50% or greater, 60% or greater, 70% or greater, 80% or greater, or 90% or greater. Some aspects include recommending a lung cancer treatment for the subject when the protein measurements are classified as indicative of the lung nodule being cancerous. Some aspects include administering a lung cancer treatment to the subject when the protein measurements are classified as indicative of the lung nodule being cancerous. In some aspects, the lung cancer treatment comprises chemotherapy, radiation therapy, percutaneous ablation, radiofrequency ablation, cryoablation, microwave ablation, chemoembolization, or surgery. In some aspects, the lung nodule is non-cancerous. Some aspects include observing the subject without performing a biopsy when the protein measurements are classified as indicative of the lung nodule being non-cancerous. In some aspects, observing the subject without performing a biopsy comprises assaying proteins in a second biofluid sample obtained from a subject at a later time. Some aspects include assaying proteins in a second biofluid sample obtained from a subject at a later time. In some aspects, the particles comprise nanoparticles. In some aspects, the particles comprise lipid particles, metal particles, silica particles, or polymer particles. In some aspects, the particles comprise carboxylate particles, poly acrylic acid particles, dextran particles, polystyrene particles, dimethylamine particles, amino particles, silica particles, or N-(3-trimethoxysilylpropyl) diethylenetriamine particles. In some aspects, the particles comprise physiochemically distinct groups of nanoparticles. In some aspects, assaying the proteins comprises contacting the biofluid sample with particles such that the particles adsorb the proteins to the particles. In some aspects, assaying the proteins comprises measuring a readout indicative of the presence, absence, or amount of the biomolecules. In some aspects, assaying the proteins comprises performing mass spectrometry, chromatography, liquid chromatography, high-performance liquid chromatography, solid-phase chromatography, a lateral flow assay, an immunoassay, an enzyme-linked immunosorbent assay, a western blot, a dot blot, or immunostaining, or a combination thereof. In some aspects, assaying the proteins comprises performing mass spectrometry. In some aspects, the proteins comprise secreted proteins. In some aspects, the biofluid comprises blood, plasma, or serum. In some aspects, the lung nodule is less than 3 cm in diameter. In some aspects, the subject has multiple lung nodules. In some aspects, the subject is a mammal. In some aspects, the subject is a human.

Disclosed herein, in some aspects, is a method, comprising: obtaining a biofluid sample of a subject having a lung nodule; contacting the biofluid sample with particles such that the particles adsorb biomolecules comprising proteins to the particles; assaying the biomolecules adsorbed to the particles to generate proteomic data; and classifying the proteomic data as indicative of the lung nodule being cancerous or non-cancerous. In some aspects, the subject is identified as having the lung nodule by medical imaging. In some aspects, the medical imaging comprises a computed tomography (CT) scan. Some aspects include performing the medical imaging. Some aspects include identifying the lung nodule in the medical imaging. Some aspects include performing a biopsy on the lung nodule when the proteomic data is classified as indicative of the lung nodule being cancerous. In some aspects, the biopsy confirms a likelihood of the lung nodule being cancerous or non-cancerous. In some aspects, the lung nodule is cancerous and comprises a tumor. In some aspects, the lung nodule comprises a non-small-cell lung carcinoma (NSCLC). In some aspects, classifying the proteomic data as indicative of the lung nodule being cancerous or non-cancerous comprises applying a classifier to the proteomic data. In some aspects, the classifier comprises features to indicate a likelihood that the lung cancer is cancerous or non-cancerous. In some aspects, the classifier is trained using deep learning, a hierarchical cluster analysis, a principal component analysis, a partial least squares discriminant analysis, a random forest classification analysis, a support vector machine analysis, a k-nearest neighbors analysis, a naive Bayes analysis, a K-means clustering analysis, or a hidden Markov analysis. In some aspects, the proteomic data is indicative of the lung nodule being cancerous or non-cancerous with a sensitivity or specificity of about 80% or greater. Some aspects include recommending a lung cancer treatment for the subject when the proteomic data is classified as indicative of the lung nodule being cancerous. Some aspects include administering a lung cancer treatment to the subject when the proteomic data is classified as indicative of the lung nodule being cancerous. In some aspects, the lung cancer treatment comprises chemotherapy, radiation therapy, percutaneous ablation, radiofrequency ablation, cryoablation, microwave ablation, chemoembolization, or surgery. In some aspects, the lung nodule is non-cancerous and is benign. Some aspects include observing the subject without performing a biopsy when the proteomic data is classified as indicative of the lung nodule being non-cancerous. Some aspects include monitoring the subject and assaying biomolecules in a second biofluid sample obtained from the subject at a later time. In some aspects, the particles comprise nanoparticles. In some aspects, the particles comprise lipid particles, metal particles, silica particles, or polymer particles. In some aspects, the particles comprise carboxylate particles, poly acrylic acid particles, dextran particles, polystyrene particles, dimethylamine particles, amino particles, silica particles, or N-(3-trimethoxysilylpropyl) diethylenetriamine particles. In some aspects, the particles comprise physiochemically distinct groups of nanoparticles. In some aspects, assaying the biomolecules comprises measuring a readout indicative of the presence, absence, or amount of the biomolecules. In some aspects, assaying the biomolecules comprises performing mass spectrometry, chromatography, liquid chromatography, high-performance liquid chromatography, solid-phase chromatography, a lateral flow assay, an immunoassay, an enzyme-linked immunosorbent assay, a western blot, a dot blot, or immunostaining, or a combination thereof. In some aspects, assaying the biomolecules comprises performing mass spectrometry. In some aspects, the proteins comprise secreted proteins. In some aspects, the biofluid comprises blood, plasma, or serum. In some aspects, the lung nodule is less than 3 cm in diameter. In some aspects, the subject has multiple lung nodules. In some aspects, the subject is a mammal. In some aspects, the subject is a human.

Disclosed herein, in some aspects, is a method, comprising: assaying proteins in a biofluid sample obtained from a subject suspected of having a lung nodule to obtain protein measurements; and applying a classifier to the protein measurements, thereby identifying the protein measurements as indicative of the subject having the lung nodule, wherein the classifier is generated using proteomic data obtained by contacting training samples with particles such that the particles adsorb proteins in the training samples and assaying the proteins adsorbed to the particles. Some aspects include recommending that the subject receive a medical imaging such as a CT scan when the protein measurements are indicative of the subject having the lung nodule, and not recommending that the subject receive the medical imaging when the protein measurements are not indicative of the subject having the lung nodule. Some aspects include performing a medical imaging such as a CT scan on the subject when the protein measurements are indicative of the subject having the lung nodule, and not performing the medical imaging on the subject when the protein measurements are not indicative of the subject having the lung nodule. Some aspects include transmitting or receiving a report on a medical imaging such as a CT scan when the protein measurements are indicative of the subject having the lung nodule, and not transmitting or receiving the report when the protein measurements are not indicative of the subject having the lung nodule. In some aspects, the protein measurements indicate the subject as having or as likely to have the lung nodule. In some aspects, the protein measurements indicate the subject as not having or as unlikely to have the lung nodule.

Disclosed herein, in some aspects, is a method, comprising: assaying proteins in a biofluid sample obtained from a subject suspected of having a lung cancer to obtain protein measurements; and applying a classifier to the protein measurements, thereby identifying the protein measurements as indicative of the subject having the lung cancer, wherein the classifier is generated using proteomic data obtained by contacting training samples with particles such that the particles adsorb proteins in the training samples and assaying the proteins adsorbed to the particles. Some aspects include recommending that the subject receive a medical imaging such as a CT scan when the protein measurements are indicative of the subject having the lung cancer, and not recommending that the subject receive the medical imaging when the protein measurements are not indicative of the subject having the lung cancer. Some aspects include performing a medical imaging such as a CT scan on the subject when the protein measurements are indicative of the subject having the lung cancer, and not performing the medical imaging on the subject when the protein measurements are not indicative of the subject having the lung cancer. Some aspects include transmitting or receiving a report on a medical imaging such as a CT scan when the protein measurements are indicative of the subject having the lung cancer, and not transmitting or receiving the report when the protein measurements are not indicative of the subject having the lung cancer. In some aspects, the protein measurements indicate the subject as having or as likely to have the lung cancer. In some aspects, the protein measurements indicate the subject as not having or as unlikely to have the lung cancer. In some aspects, the lung cancer comprises NSCLC.

Disclosed herein, in some aspects, is a method, comprising: obtaining a biofluid sample of a subject suspected of having a lung nodule; contacting the biofluid sample with particles such that the particles adsorb biomolecules comprising proteins to the particles; assaying the biomolecules adsorbed to the particles to generate proteomic data; and based on the proteomic data, classifying the proteomic data as indicative of the subject having the lung nodule or as not indicative of the subject having the lung nodule. Some aspects include recommending that the subject receive a medical imaging such as a CT scan when the proteomic data are indicative of the subject having the lung nodule, and not recommending that the subject receive the medical imaging when the proteomic data are not indicative of the subject having the lung nodule. Some aspects include performing a medical imaging such as a CT scan on the subject when the proteomic data are indicative of the subject having the lung nodule, and not performing the medical imaging on the subject when the proteomic data are not indicative of the subject having the lung nodule. Some aspects include transmitting or receiving a report on a medical imaging such as a CT scan when the proteomic data are indicative of the subject having the lung nodule, and not transmitting or receiving the report when the proteomic data are not indicative of the subject having the lung nodule. In some aspects, the proteomic data indicate the subject as having or as likely to have the lung nodule. In some aspects, the proteomic data indicate the subject as not having or as unlikely to have the lung nodule.

Disclosed herein, in some aspects, is a method, comprising: obtaining a biofluid sample of a subject suspected of having a lung cancer; contacting the biofluid sample with particles such that the particles adsorb biomolecules comprising proteins to the particles; assaying the biomolecules adsorbed to the particles to generate proteomic data; and based on the proteomic data, classifying the proteomic data as indicative of the subject having the lung cancer or as not indicative of the subject having the lung cancer. Some aspects include recommending that the subject receive a medical imaging such as a CT scan when the proteomic data are indicative of the subject having the lung cancer, and not recommending that the subject receive the medical imaging when the proteomic data are not indicative of the subject having the lung cancer. Some aspects include performing a medical imaging such as a CT scan on the subject when the proteomic data are indicative of the subject having the lung cancer, and not performing the medical imaging on the subject when the proteomic data are not indicative of the subject having the lung cancer. Some aspects include transmitting or receiving a report on a medical imaging such as a CT scan when the proteomic data are indicative of the subject having the lung cancer, and not transmitting or receiving the report when the proteomic data are not indicative of the subject having the lung cancer. In some aspects, the proteomic data indicate the subject as having or as likely to have the lung cancer. In some aspects, the proteomic data indicate the subject as not having or as unlikely to have the lung cancer.

Disclosed herein, in some aspects, is a monitoring method, comprising: obtaining a biofluid sample of a subject at risk of a lung cancer recurrence; contacting the biofluid sample with particles such that the particles adsorb biomolecules comprising proteins to the particles; assaying the biomolecules adsorbed to the particles to generate proteomic data; and based on the proteomic data, classifying the proteomic data as indicative of the subject having the lung cancer recurrence or as not indicative of the subject having the lung cancer recurrence. Some aspects include recommending that the subject receive a medical imaging such as a CT scan when the protein measurements are indicative of the subject having the lung cancer recurrence, and not recommending that the subject receive the medical imaging when the protein measurements are not indicative of the subject having the lung cancer recurrence. Some aspects include performing a medical imaging such as a CT scan on the subject when the protein measurements are indicative of the subject having the lung cancer recurrence, and not performing the medical imaging on the subject when the protein measurements are not indicative of the subject having the lung cancer recurrence. Some aspects include transmitting or receiving a report on a medical imaging such as a CT scan when the protein measurements are indicative of the subject having the lung cancer recurrence, and not transmitting or receiving the report when the protein measurements are not indicative of the subject having the lung cancer recurrence. In some aspects, the protein measurements indicate the subject as having or as likely to have the lung cancer recurrence. In some aspects, the protein measurements indicate the subject as not having or as unlikely to have the lung cancer recurrence. In some aspects, the subject has received a lung cancer treatment. In some aspects, the lung cancer treatment comprises chemotherapy, radiotherapy, or surgery. In some aspects, the cancer is potentially resectable. In some aspects, the lung cancer comprises NSCLC.

BRIEF DESCRIPTION OF THE DRAWINGS

FIG. 16 shows graphical results of an integrated models classification analysis and transformation-based classification.

FIG. 23 shows aspects of some genetic or transcript data, such as indications or types of measurements, types of samples, quality control aspects, or sequencing depths that may be used.

FIG. 25 includes some aspects such as subjects or test outcomes that may be included in a method described herein.

FIG. 26A includes a table showing some proteins, OT scores, and a description of some features in a protein classifier.

FIG. 26B includes a table showing some proteins, OT scores, and a description of some features in a protein classifier.

FIG. 29A shows numbers of proteins detected across subject samples in an analysis of biofluid samples from control and cancer patients.

FIG. 29B shows numbers of proteins detected across subject samples in an analysis of biofluid samples from control and cancer patients.

FIG. 32A includes a volcano plot of intensity differences and P-values for proteins adsorbed to nanoparticles and detected in biofluid samples from cancer patients, relative to biofluid samples from control patients. The volcano plot displays magnitude of difference on the x-axis, and significance on the y-axis, with most significant analytes highlighted.

FIG. 33A includes a volcano plot of intensity differences and P-values for lipids detected in biofluid samples from cancer patients, relative to biofluid samples from control patients. The volcano plot displays magnitude of difference on the x-axis, and significance on the y-axis, with the most significant analyte highlighted.

FIG. 34A includes a volcano plot of intensity differences and P-values for metabolites detected in biofluid samples from cancer patients, relative to biofluid samples from control patients. The volcano plot displays magnitude of difference on the x-axis, and significance on the y-axis, with the most significant analyte highlighted.

FIG. 34B includes data for top metabolite AICAR after a metabolomic measurement.

FIG. 39A shows a graphical summary of 18 samples from liver cancer subjects used in Example 17.

FIG. 39B shows coefficient of variation (CV) values for some peptides and proteins obtained in a study described herein.

FIGS. 39C-1 to 39C-6 show an exemplary protein abundance heatmap of samples from subjects with liver cancer and healthy subjects.

FIGS. 39F-1 to 39F-4 show that samples from subjects with liver cancer exhibited distinct lipid profiles and healthy controls. The top 50 lipids based on p-values in this analysis are shown for each patient sample.

FIG. 54 shows examples of biomarkers.

FIG. 59 illustrates some aspects of samples used in a study described herein.

FIG. 68 is an image showing where some samples were collected for a study.

FIG. 70 includes graphical depictions of coefficient of variation (CV) values obtained in a study described herein.

FIG. 72 includes graphical depictions of detected protein groups and peptide counts obtained in a study described herein.

Figure 76:
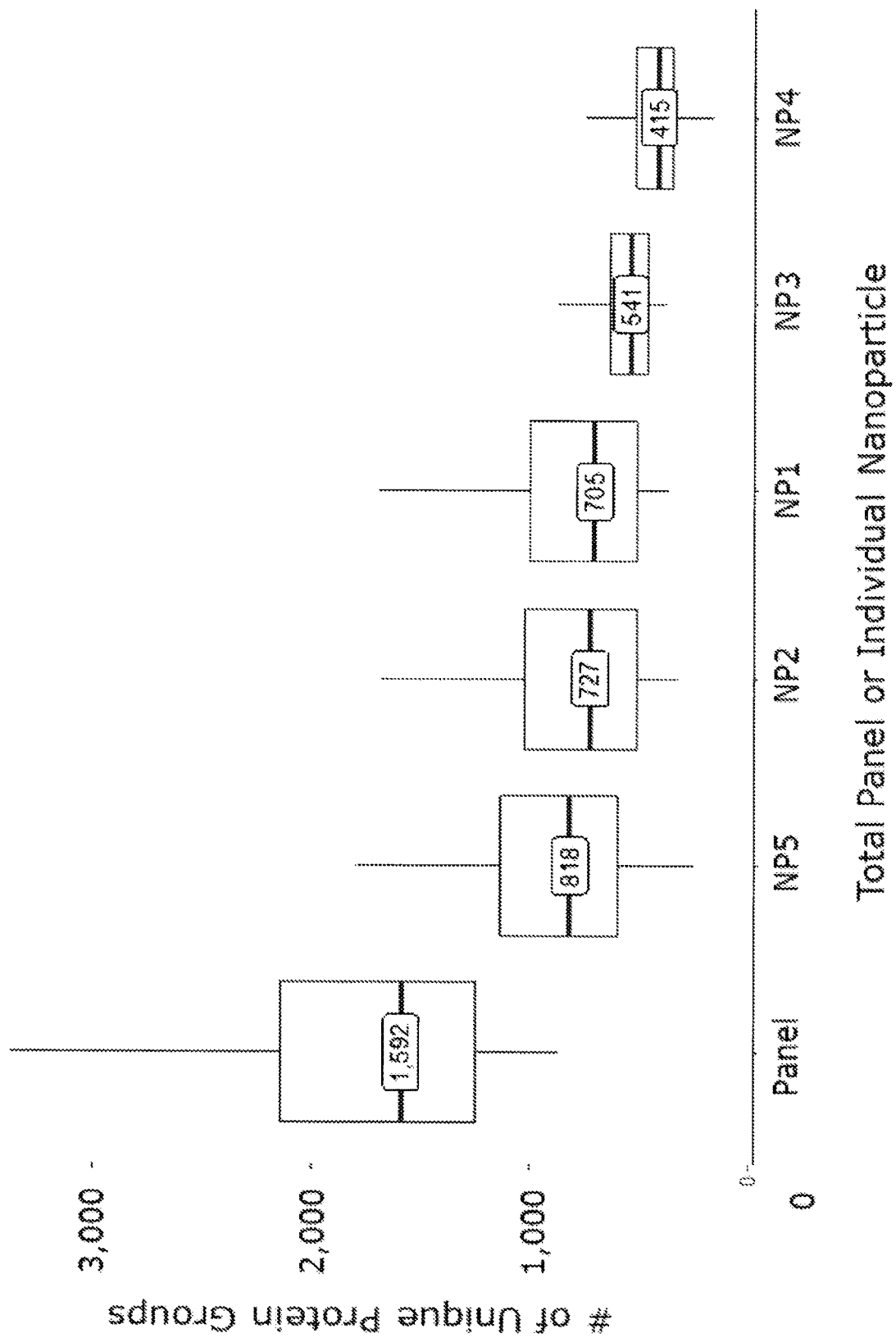

FIG. 76 includes numbers of unique protein groups in some sample data.

Figure 77A:
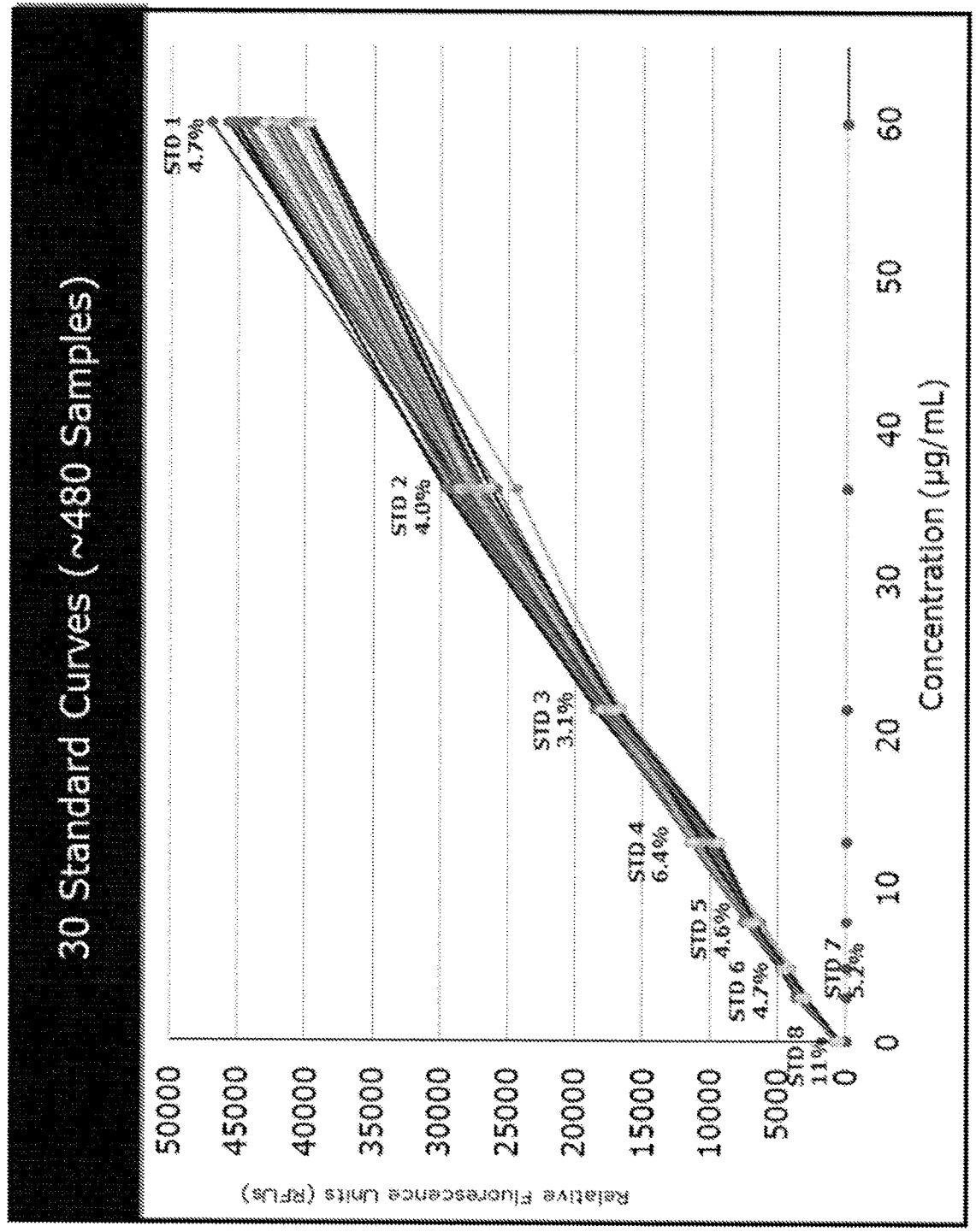

FIG. 77A includes relative fluorescence units relative to concentration for several standard curves.

Figure 77B:
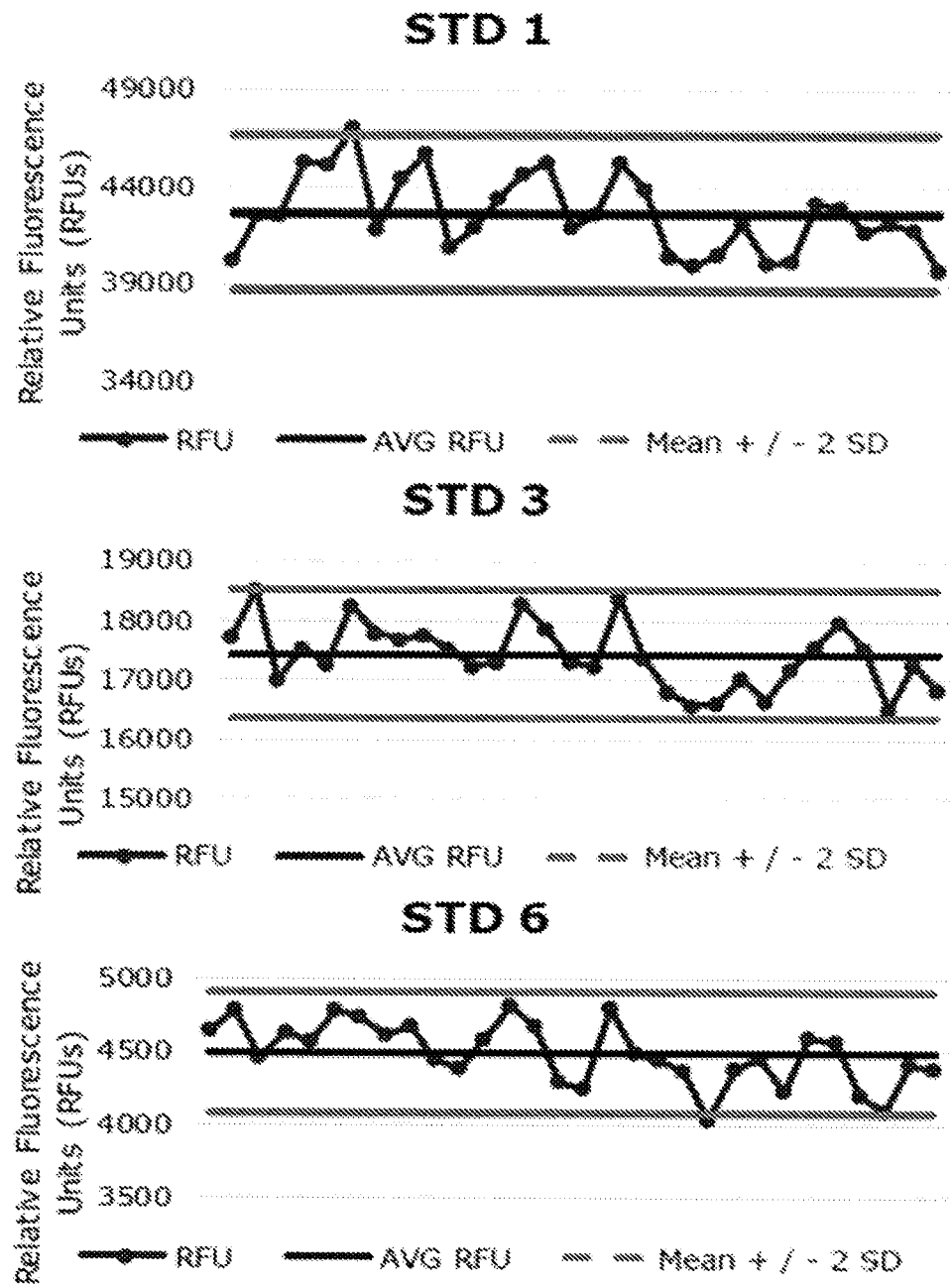

FIG. 77B includes relative fluorescence units of some standard curves.

Figure 78A:
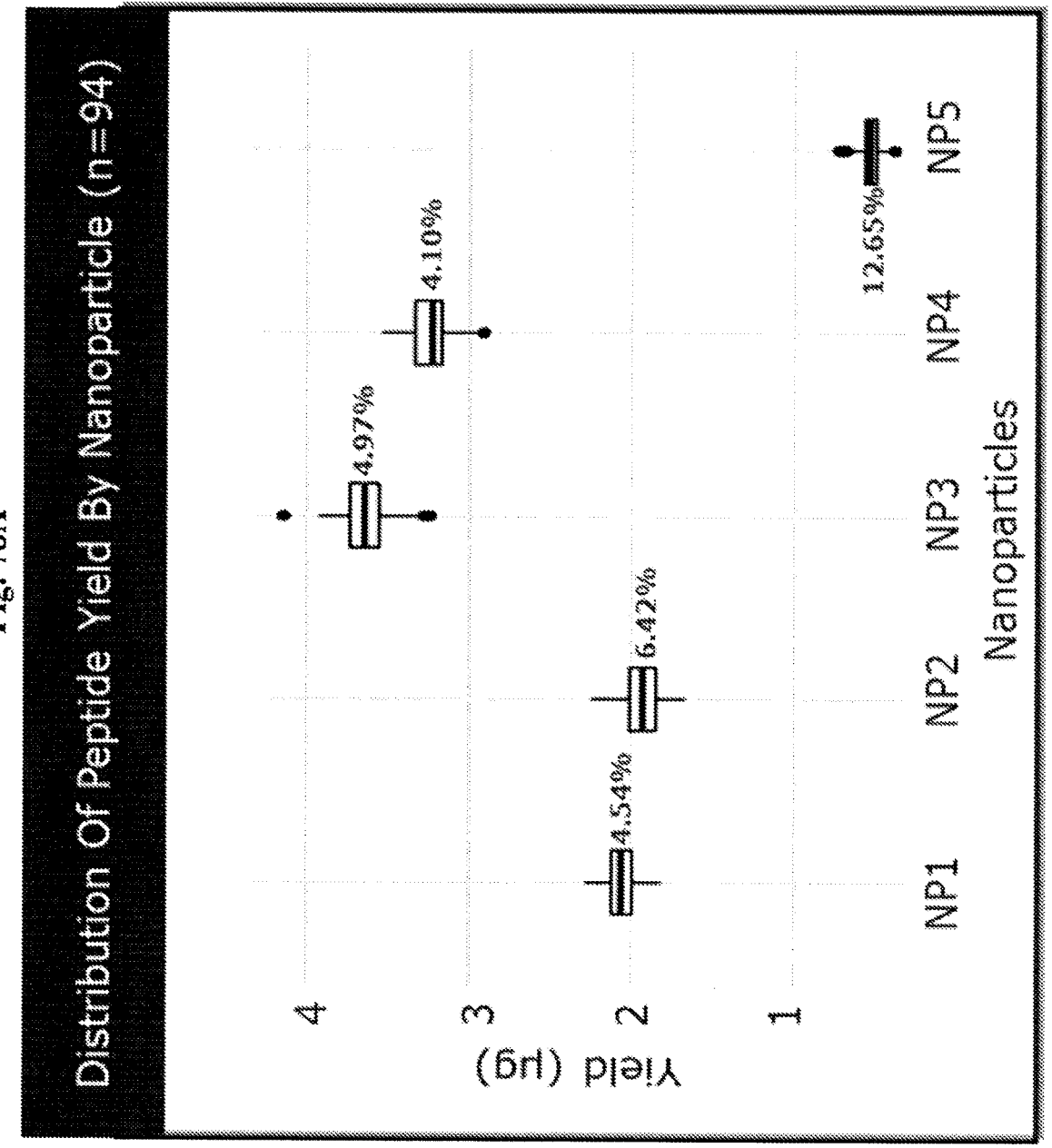

FIG. 78A includes peptide yields for some nanoparticles used in experiments described herein.

Figure 78B:
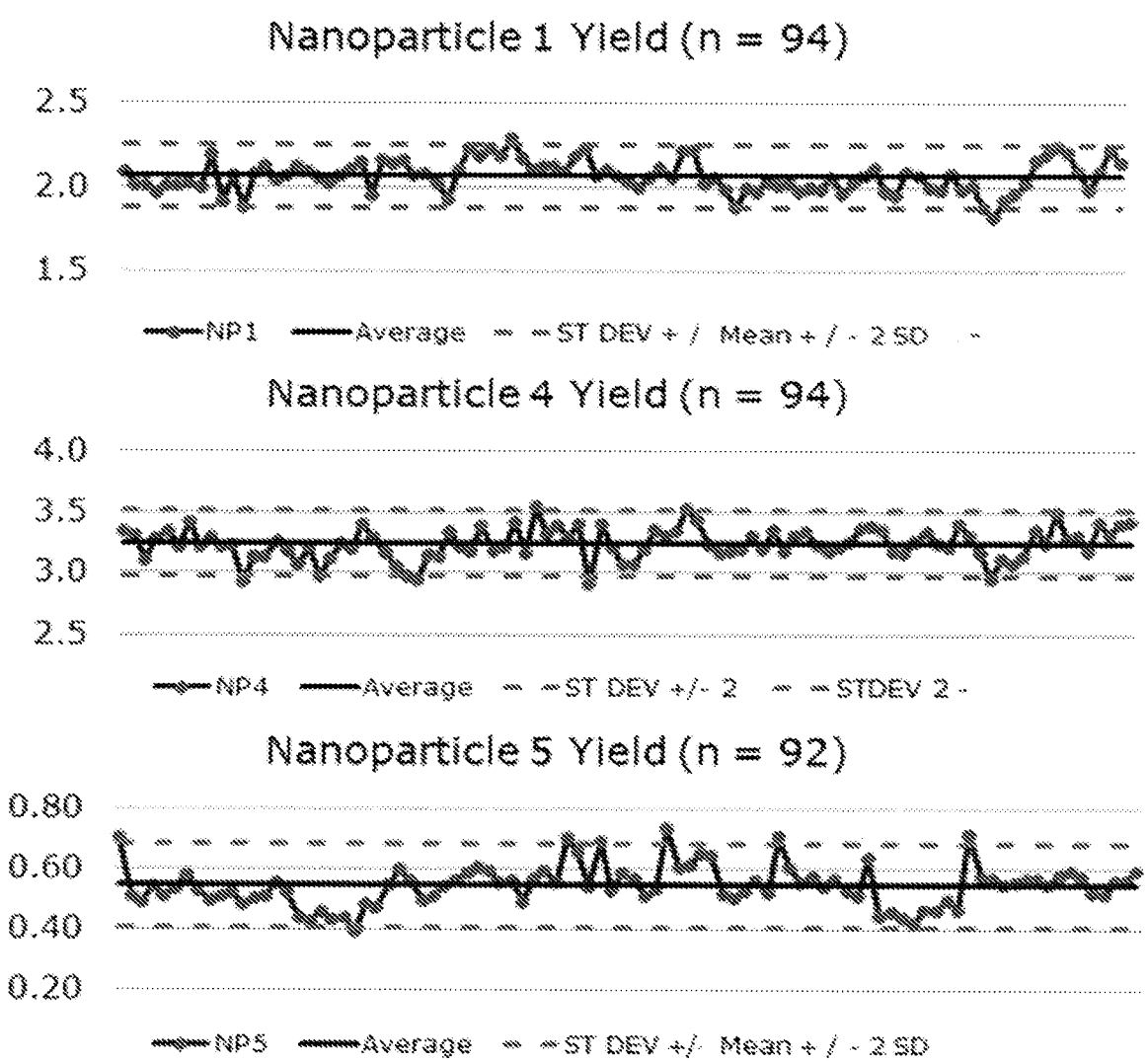

FIG. 78B includes peptide yields for some nanoparticles used in experiments described herein.

Figure 79A:
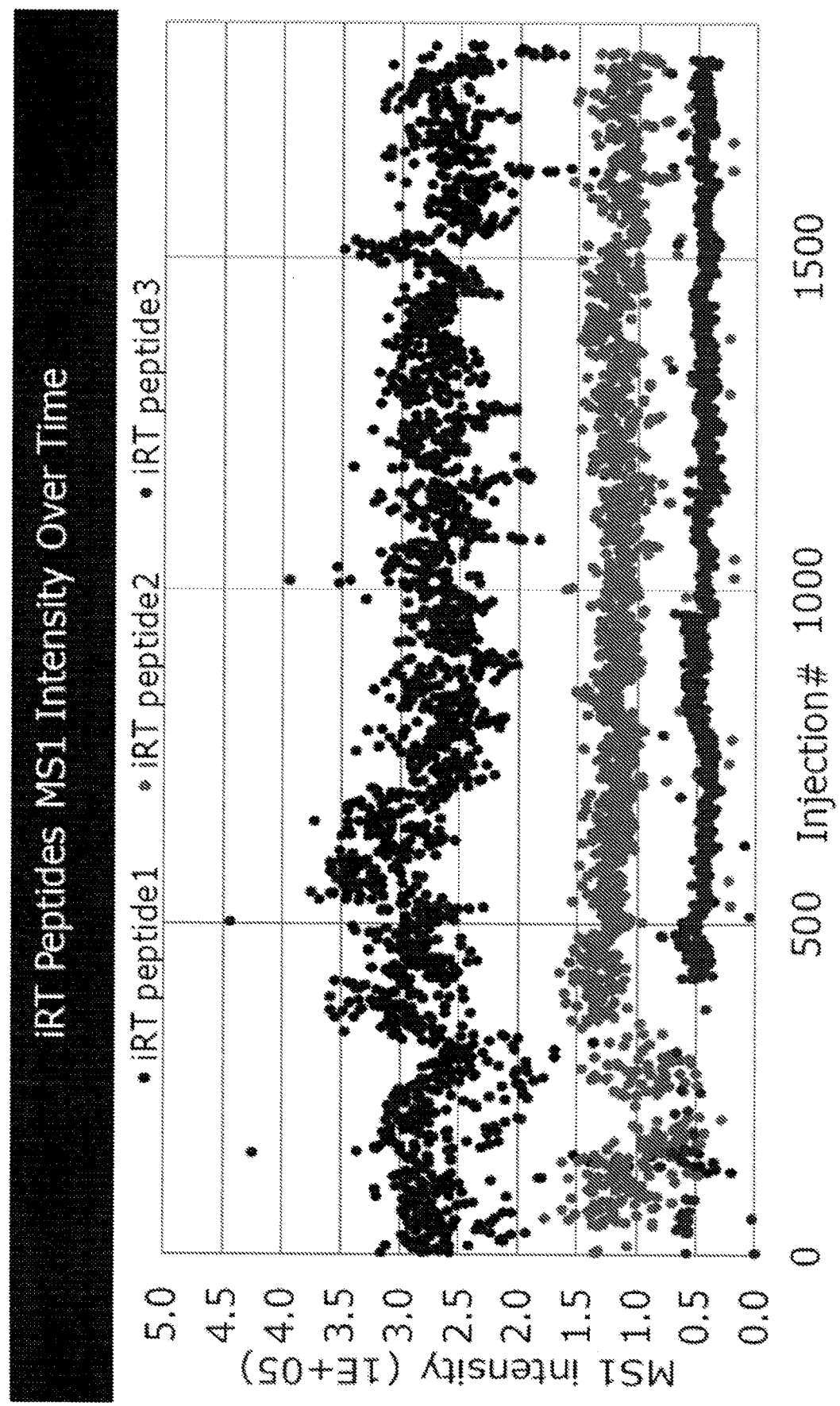

FIG. 79A includes a graph of MS1 intensity over time.

Figure 79B:
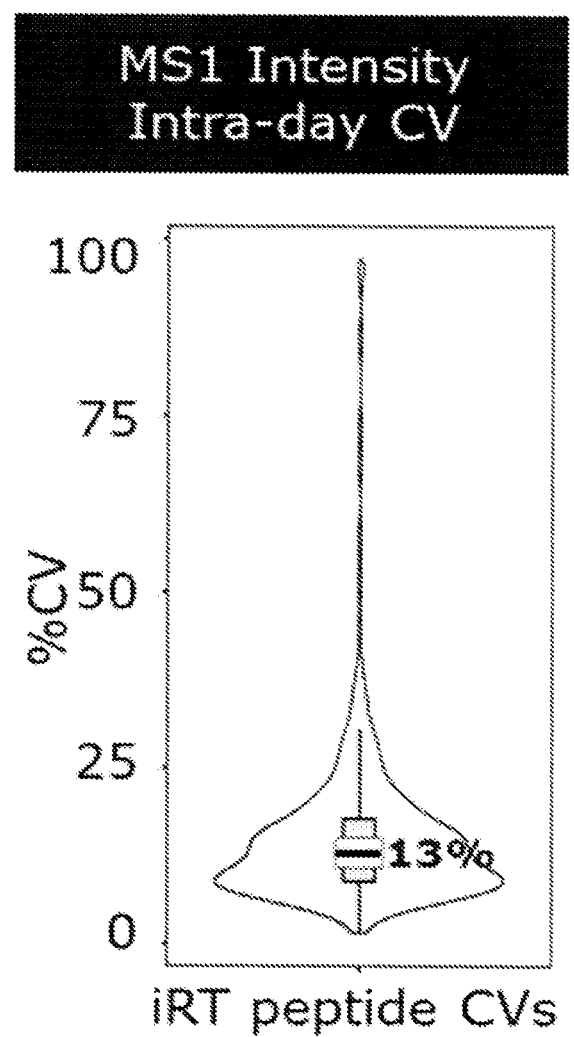

FIG. 79B includes MS1 intensity intra-day CV.

Figure 80A:
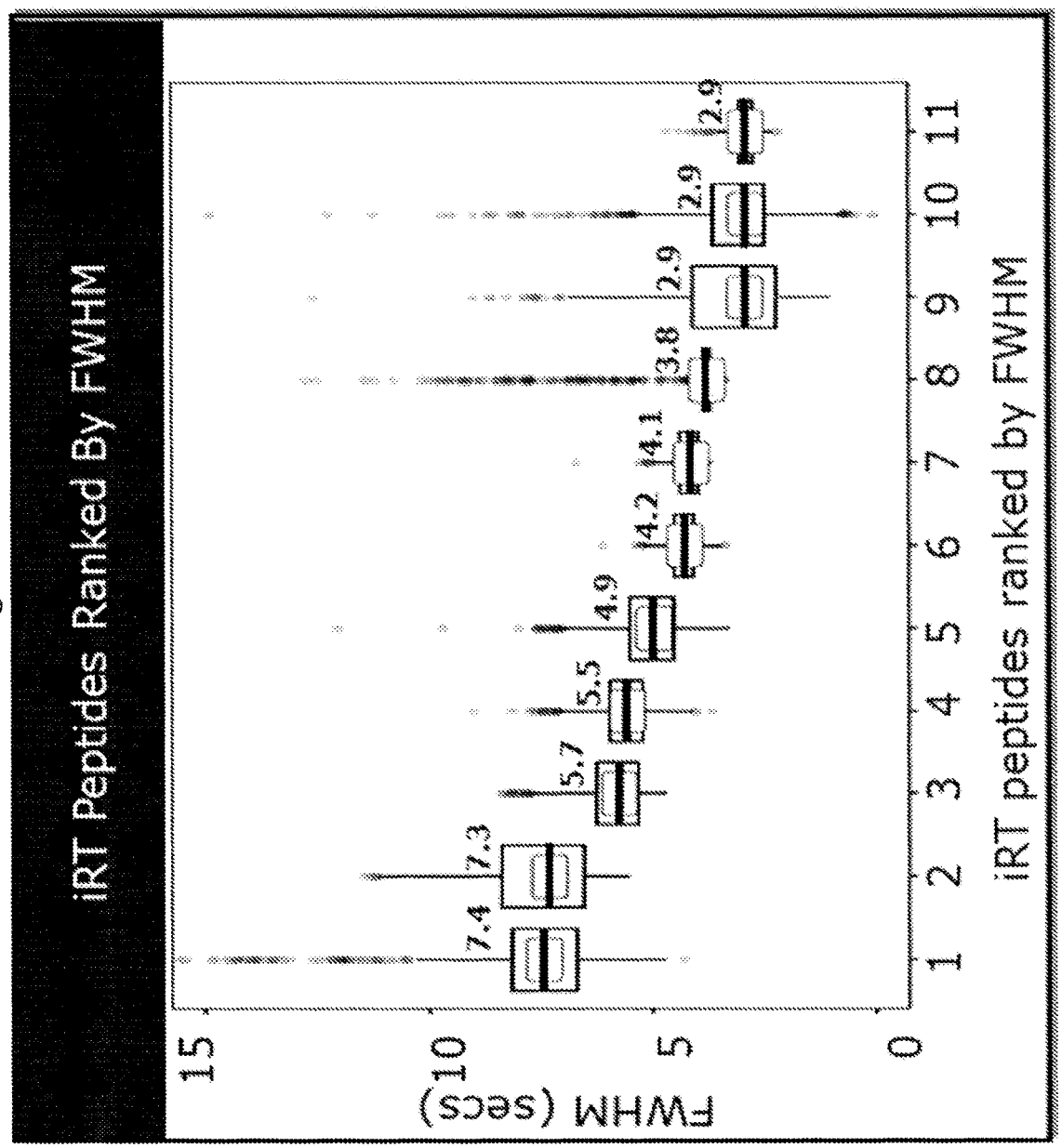

FIG. 80A includes a graph of iRT peptides ranked by FWHM.

Figure 80B:
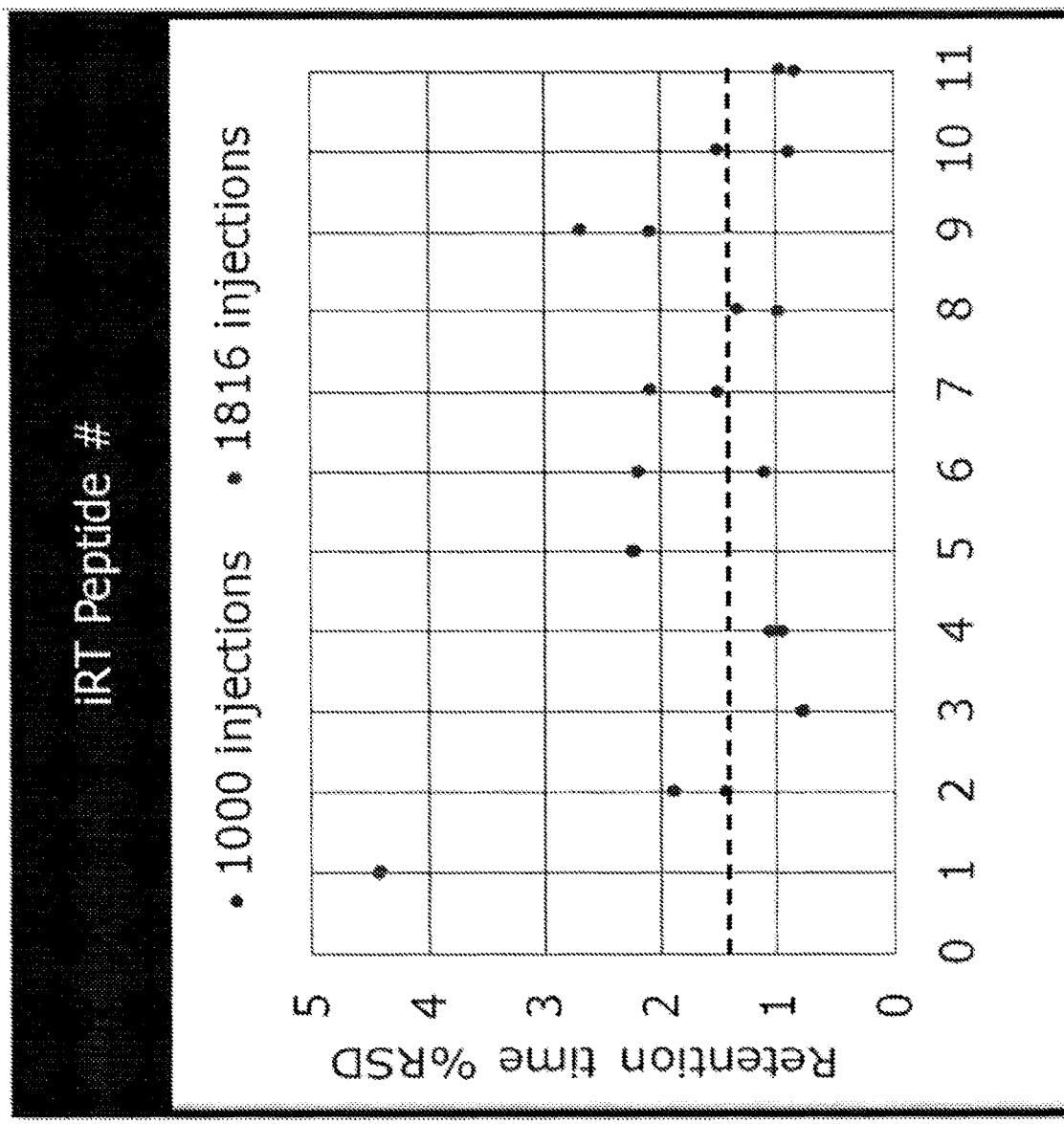

FIG. 80B includes a plot showing retention times.

Figure 81A:
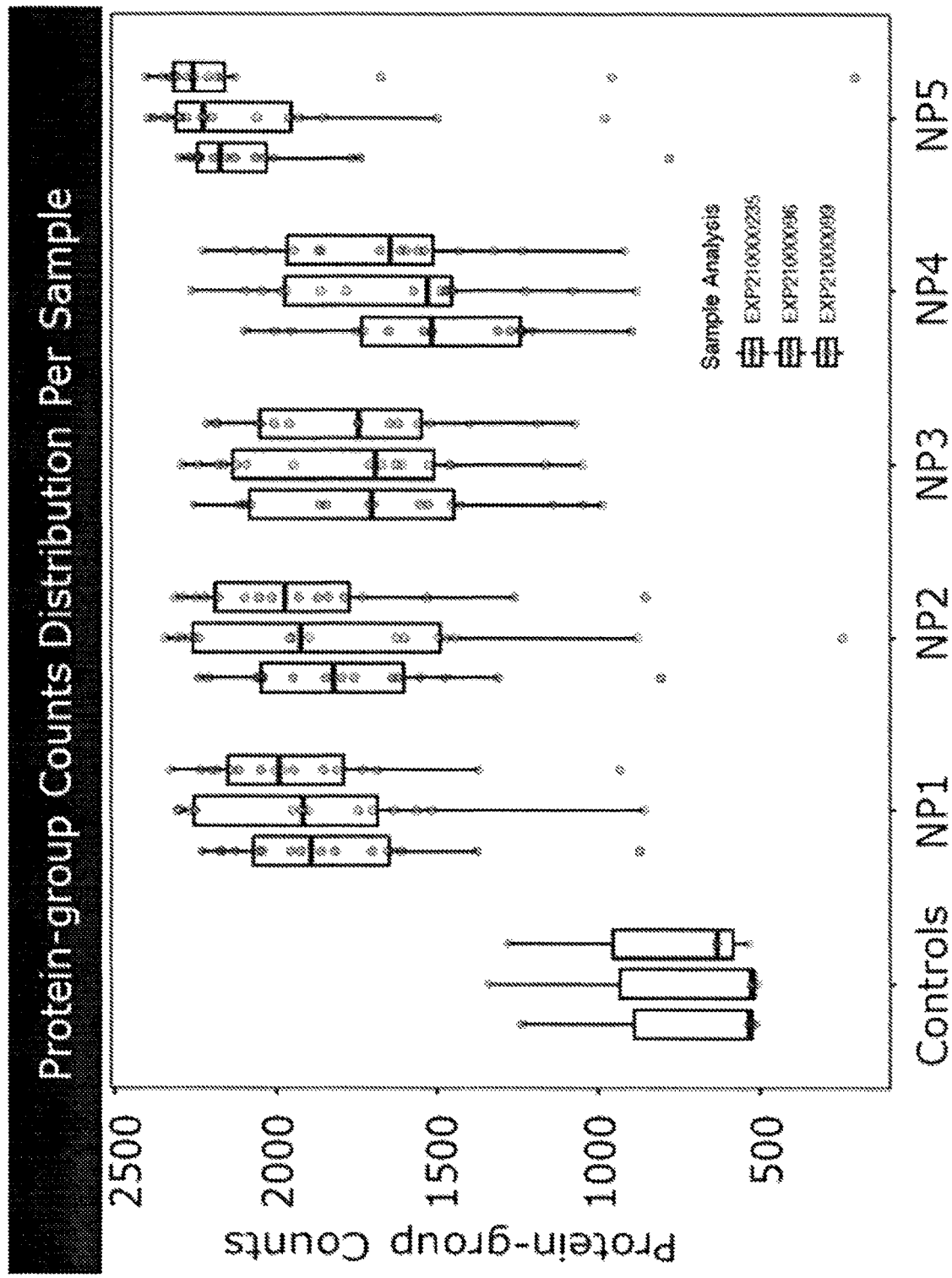

FIG. 81A includes a plot showing protein-group count distributions per sample.

Figure 81B:
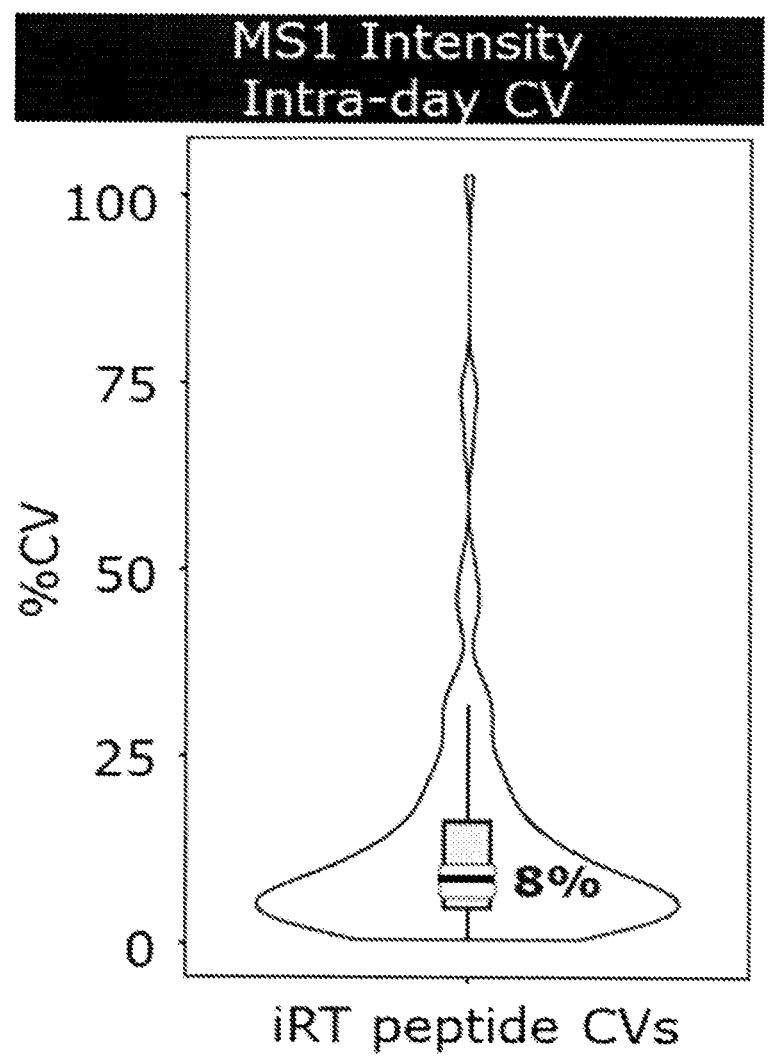

FIG. 81B includes MS1 intensity intra-day CV.

Figure 82:
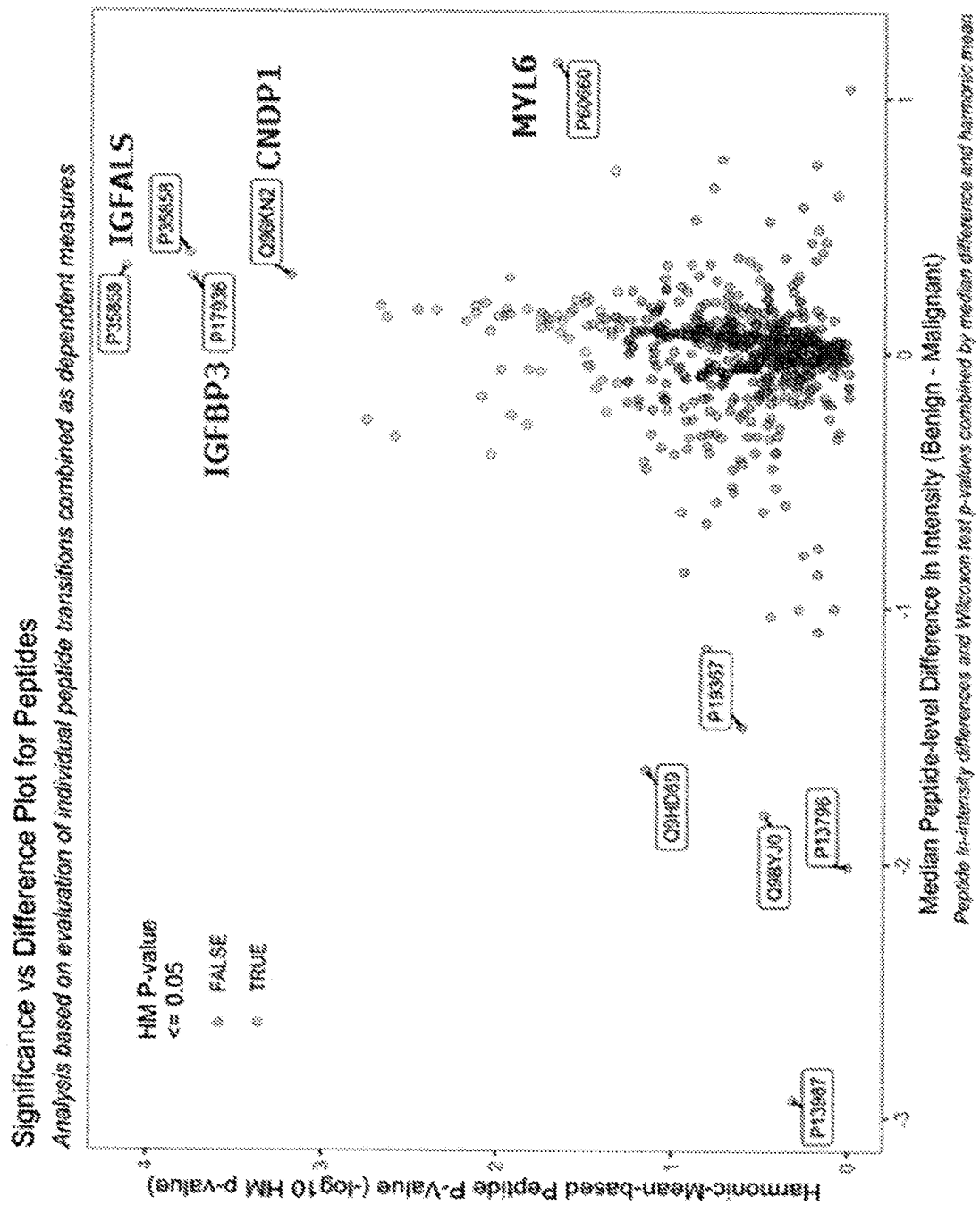

FIG. 82 includes a volcano plot of intensity differences and P-values for peptides detected in biofluid samples. The volcano plot displays median peptide-level differences in intensity on the x-axis and harmonic-mean-based peptide P-values on the y-axis.

Figure 83:
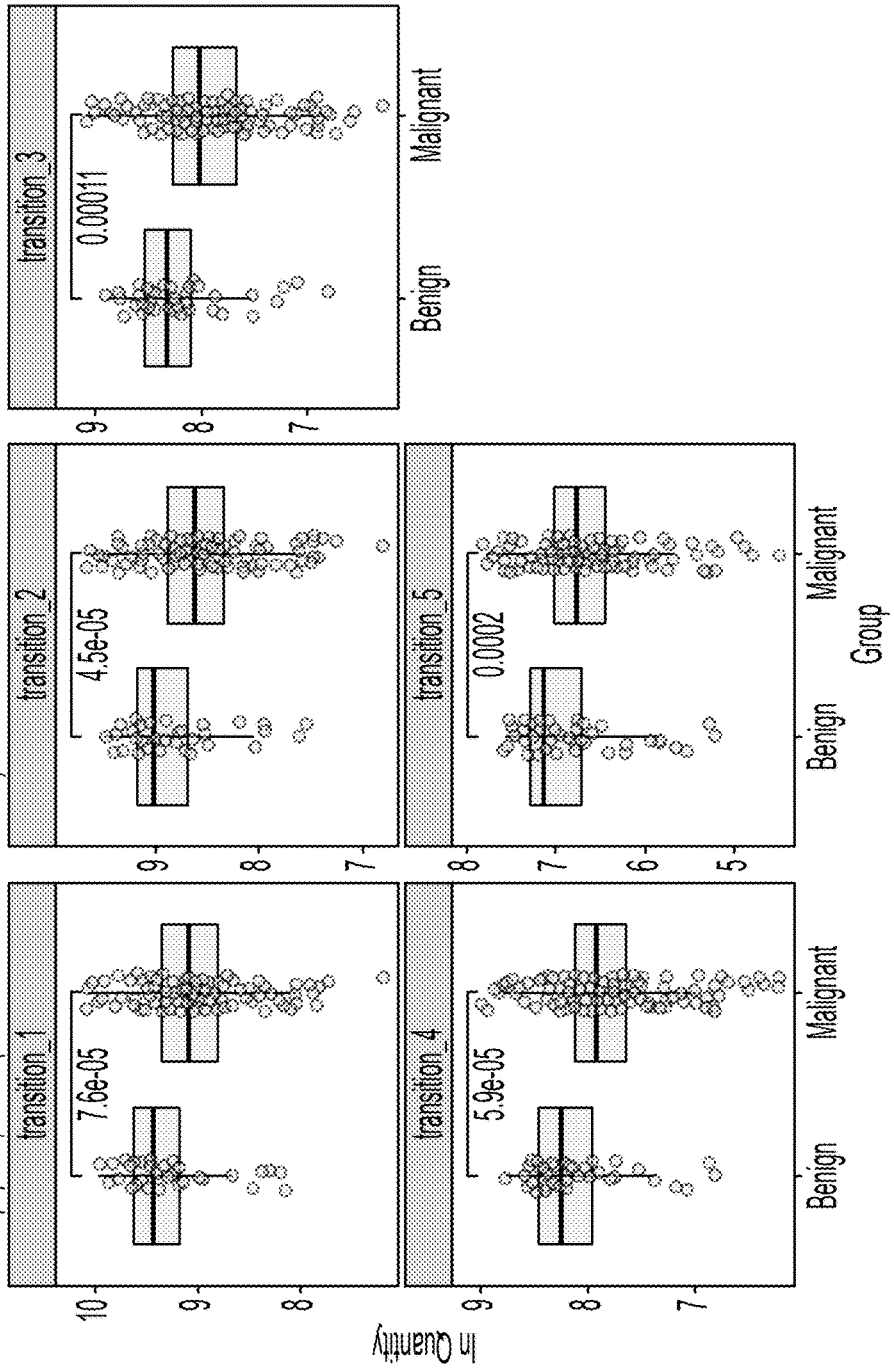

FIG. 83 includes graphs showing some transitions for peptide ANVFVQLPR from protein P35858 in benign and malignant groups.

Figure 84:
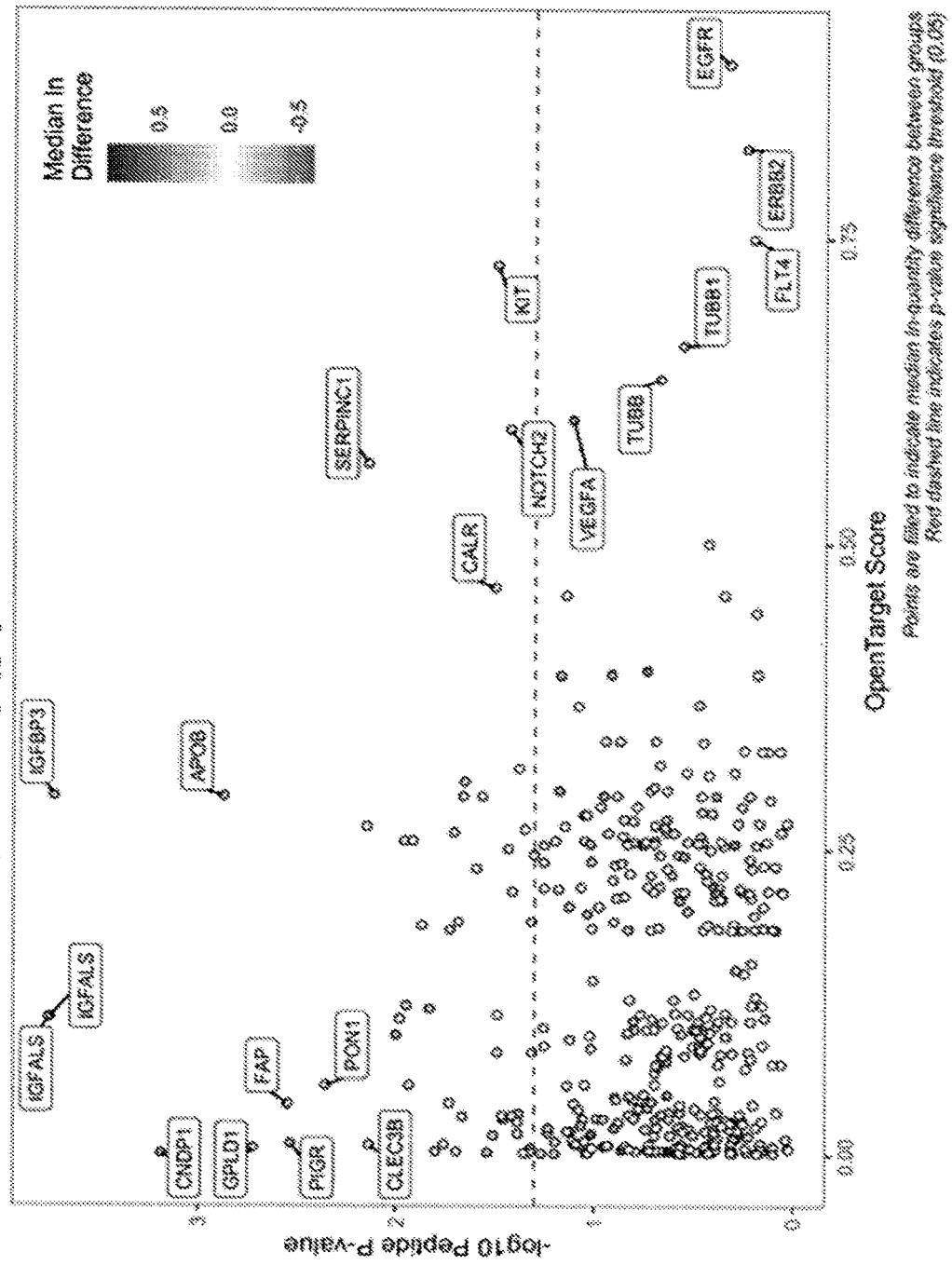

FIG. 84 includes a graph illustrating a comparison of lung cancer OpenTarget (OT) scores to peptide difference significance. The graph displays OpenTarget Scores on the x-axis and P-value on the y-axis.

Figure 85:
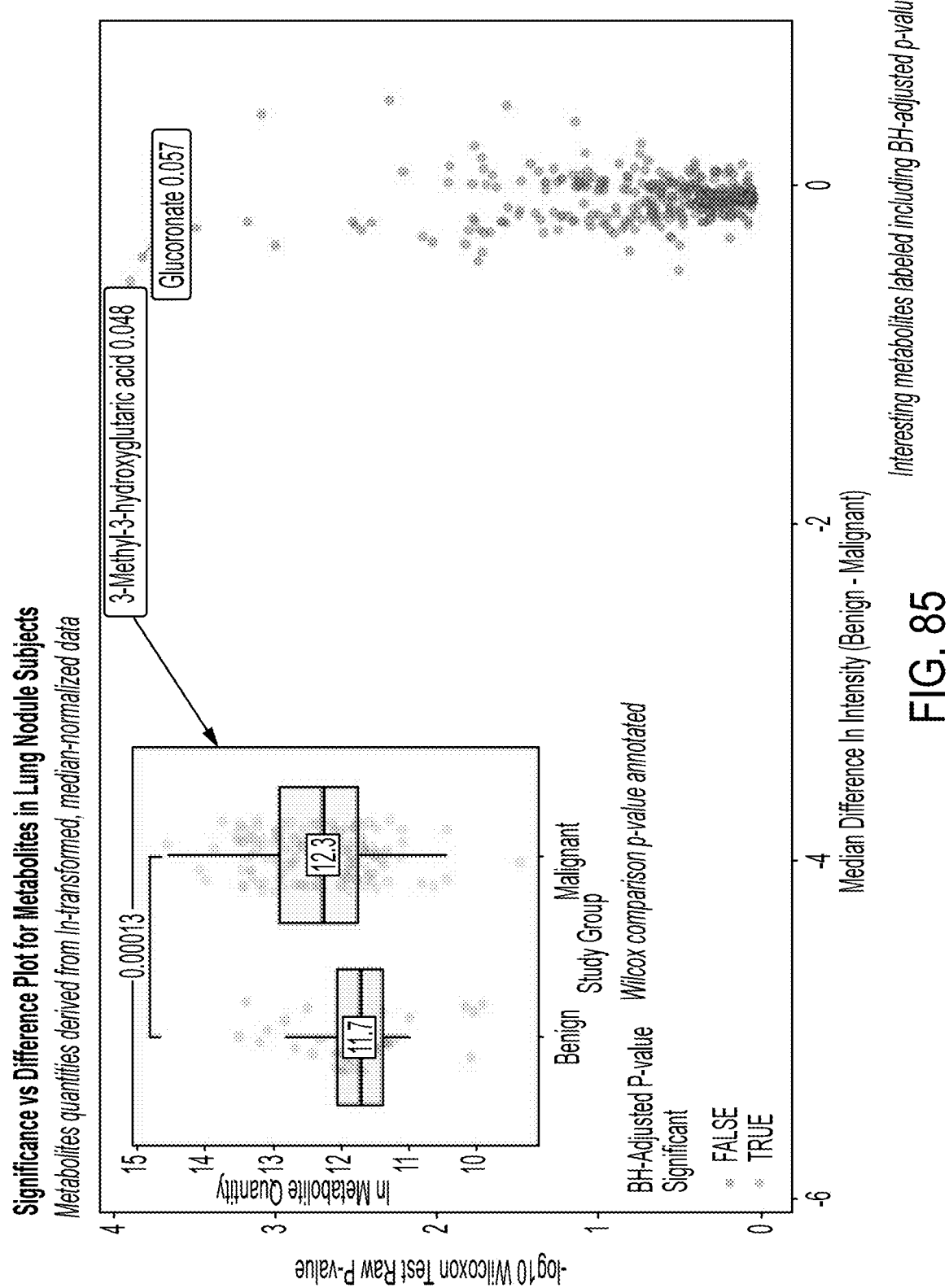

FIG. 85 includes a volcano plot of intensity differences and P-values for metabolites in lung nodule subjects. The volcano plot displays median difference in intensity on the x-axis and P-value on the y-axis.

Figure 86:
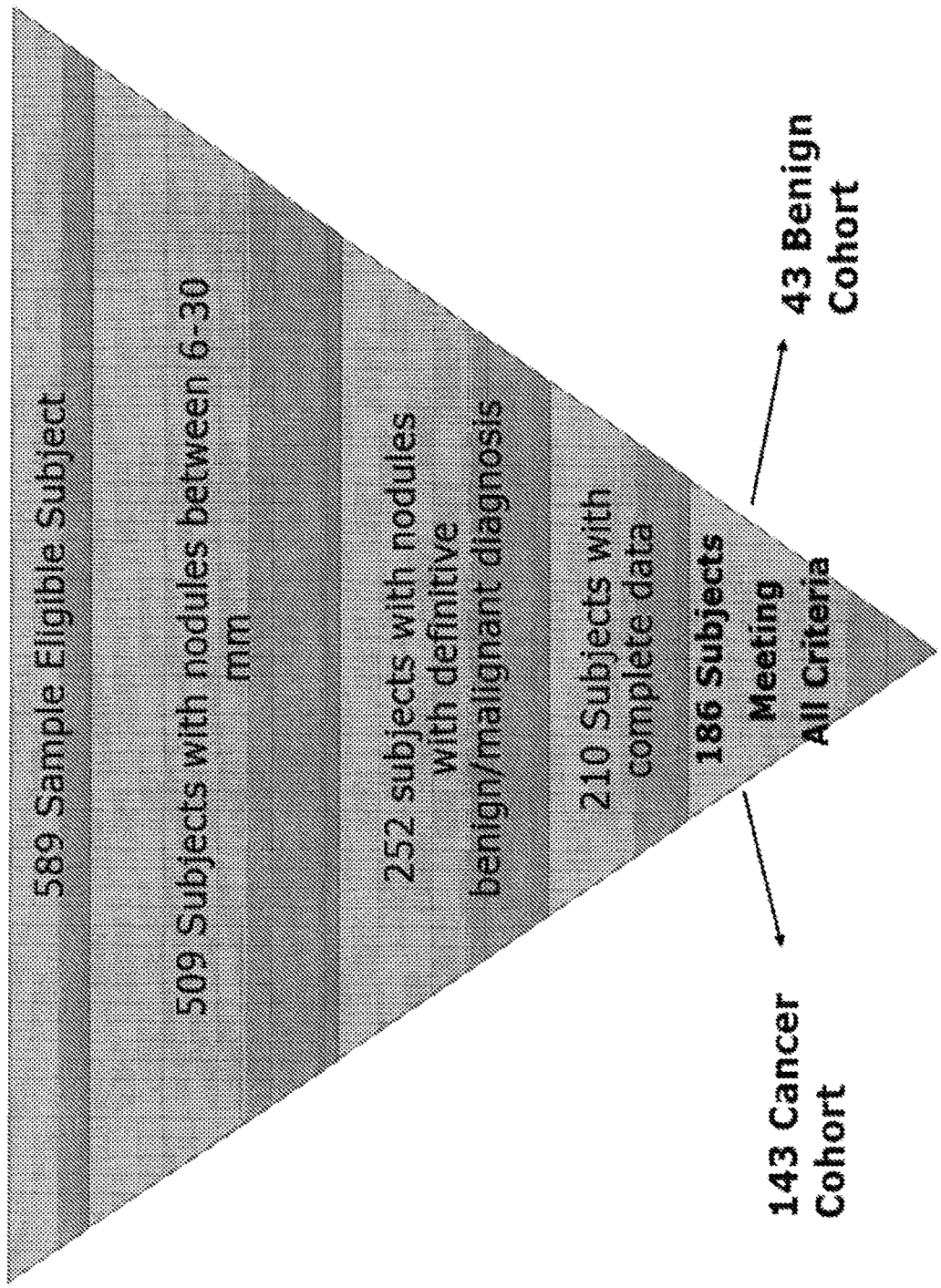

FIG. 86 includes a diagram illustrating the seer-lung discovery sample cohort. The diagram shows that out of 589 eligible subjects, 186 subjects met all criteria.

Figure 87:
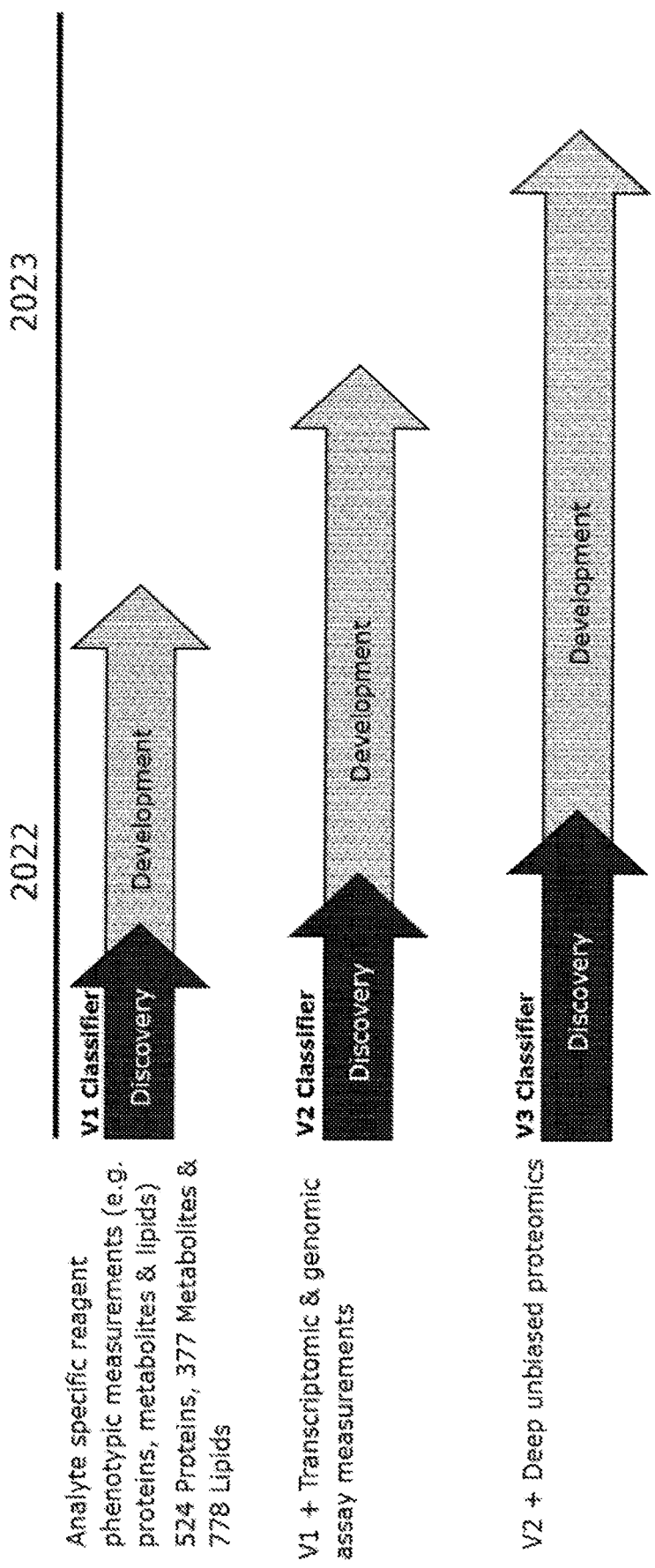

FIG. 87 shows a diagram illustrating the staged approach of version one classifier, version two classifier, and version three classifier discovery through test development.

Figure 88B:
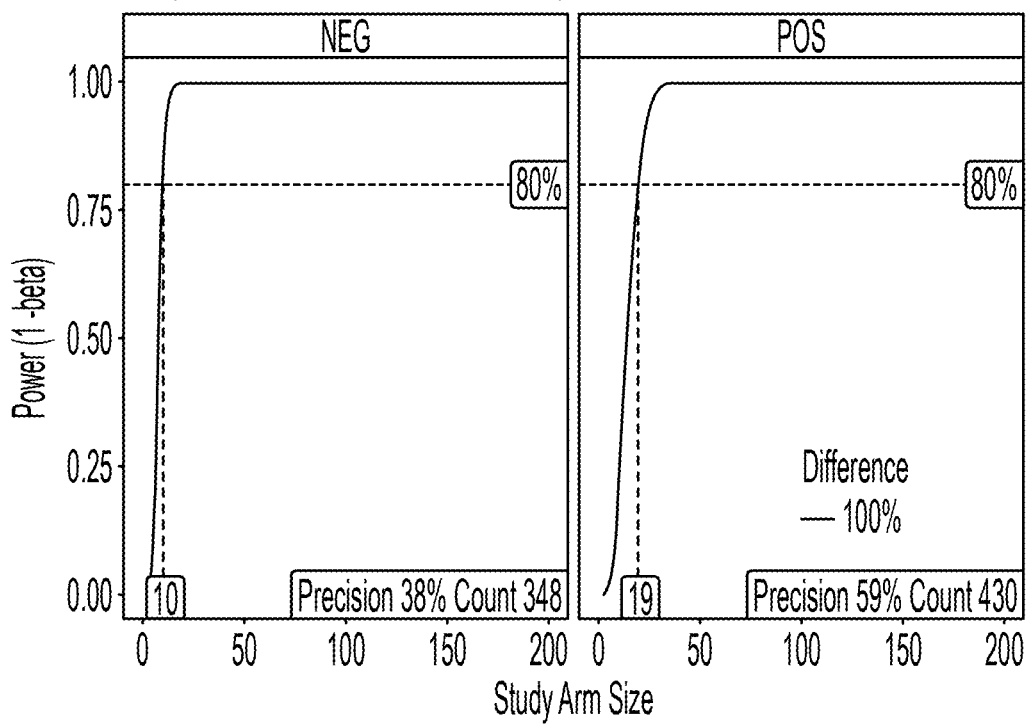

FIGS. 88A and 88B includes graphs showing the power curves for analyte classes. The graphs include curves for proteins, metabolites, and lipids.

Figure 89:
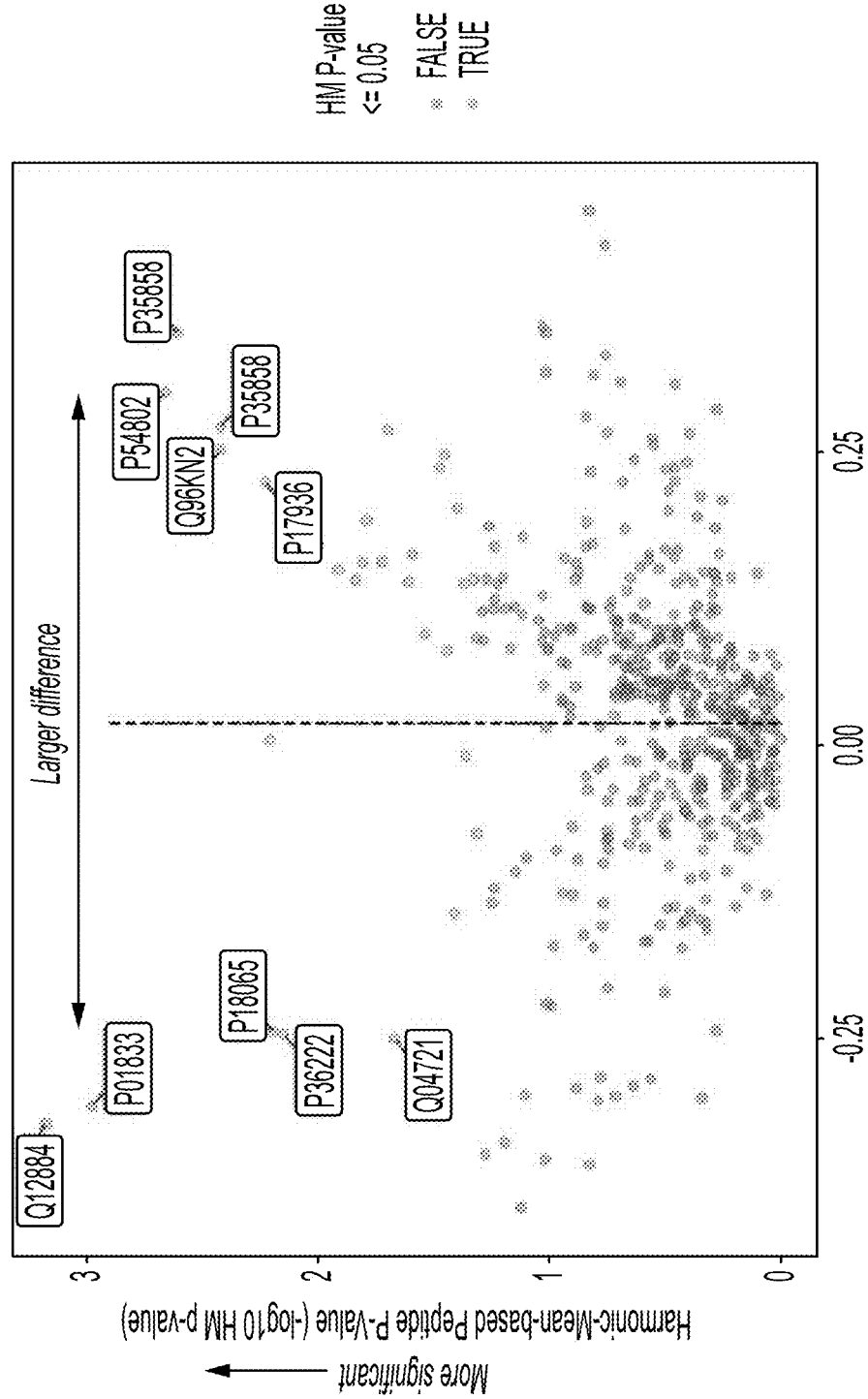

FIG. 89 includes a volcano plot of intensity differences and P-values for peptides in lung nodule subjects. The volcano plot displays median peptide-level difference in intensity on the x-axis and harmonic-mean-based peptide p-value on the y-axis.

Figure 90:
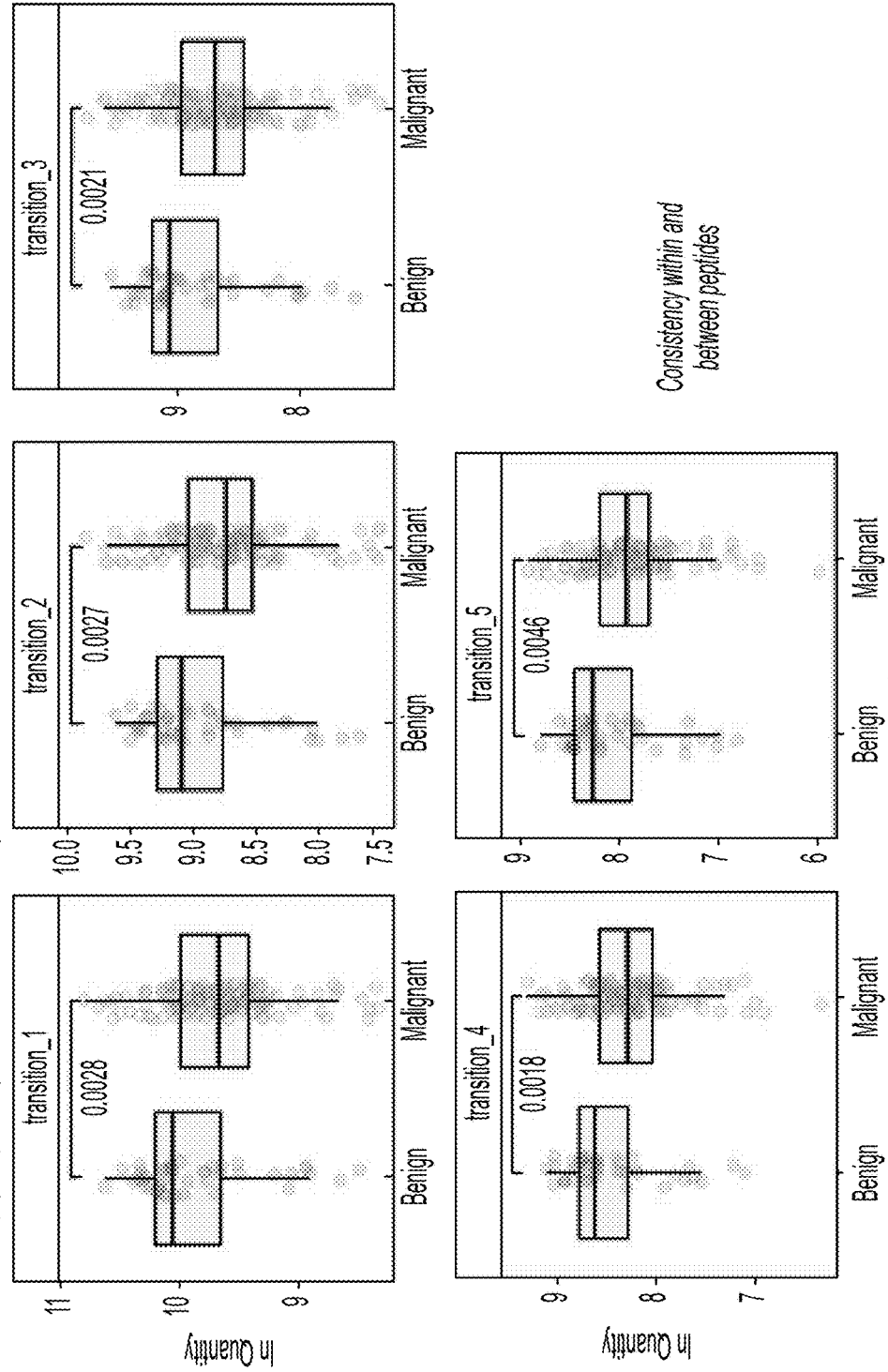

FIG. 90 includes graphs showing some transitions for peptide LEYLLLSR from protein P35858 in benign and malignant groups.

Figure 91:
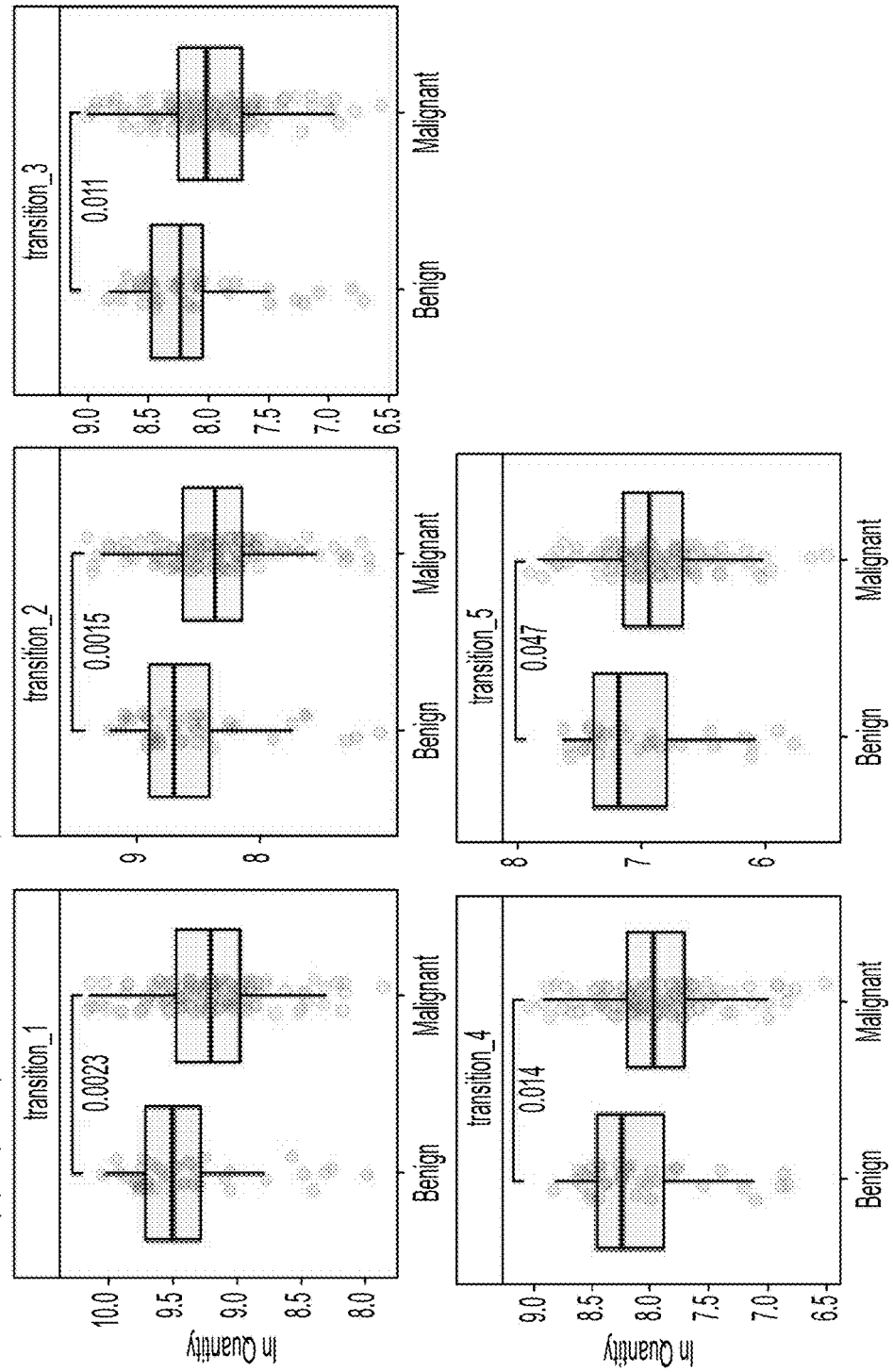

FIG. 91 includes graphs showing some transitions for peptide ANVFVQLPR from protein P35858 in benign and malignant groups.

Figure 92:
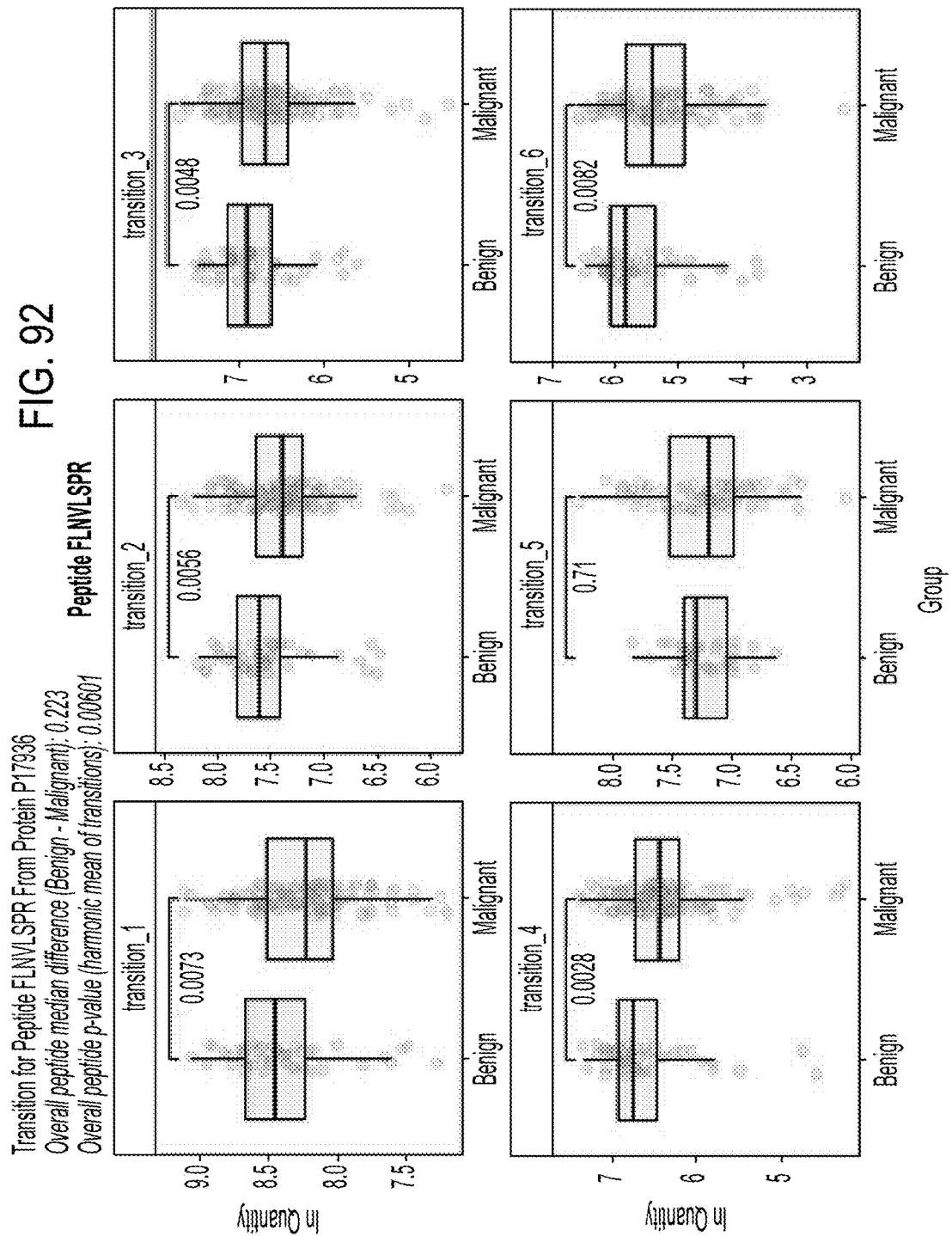

FIG. 92 includes graphs showing some transitions for peptide FLNVLSPR from protein P17936 in benign and malignant groups.

Figure 93:
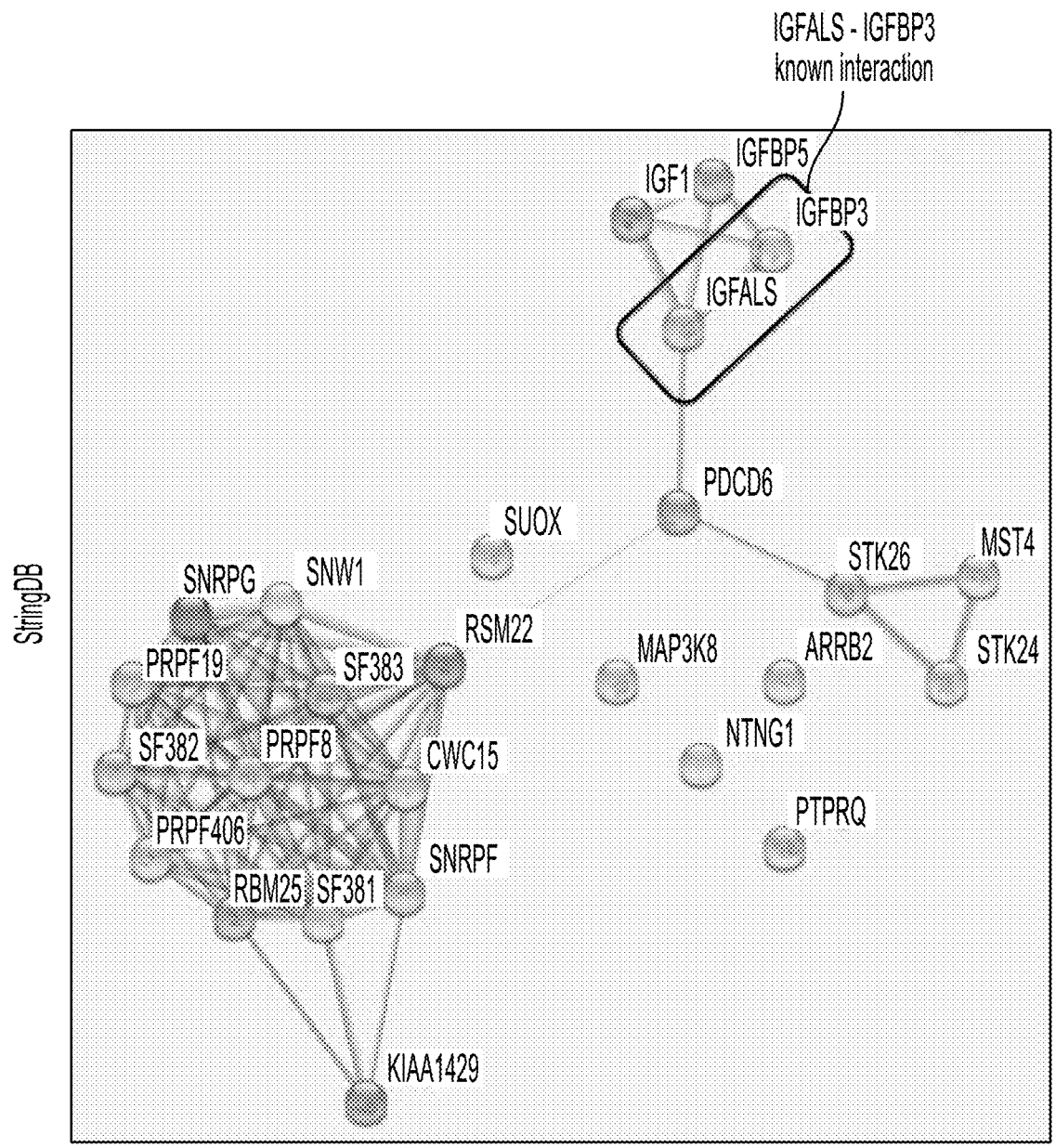

FIG. 93 shows an image depicting StringDB. The image highlights the known interaction of IGFALS and IGFBP3.

Figure 94:
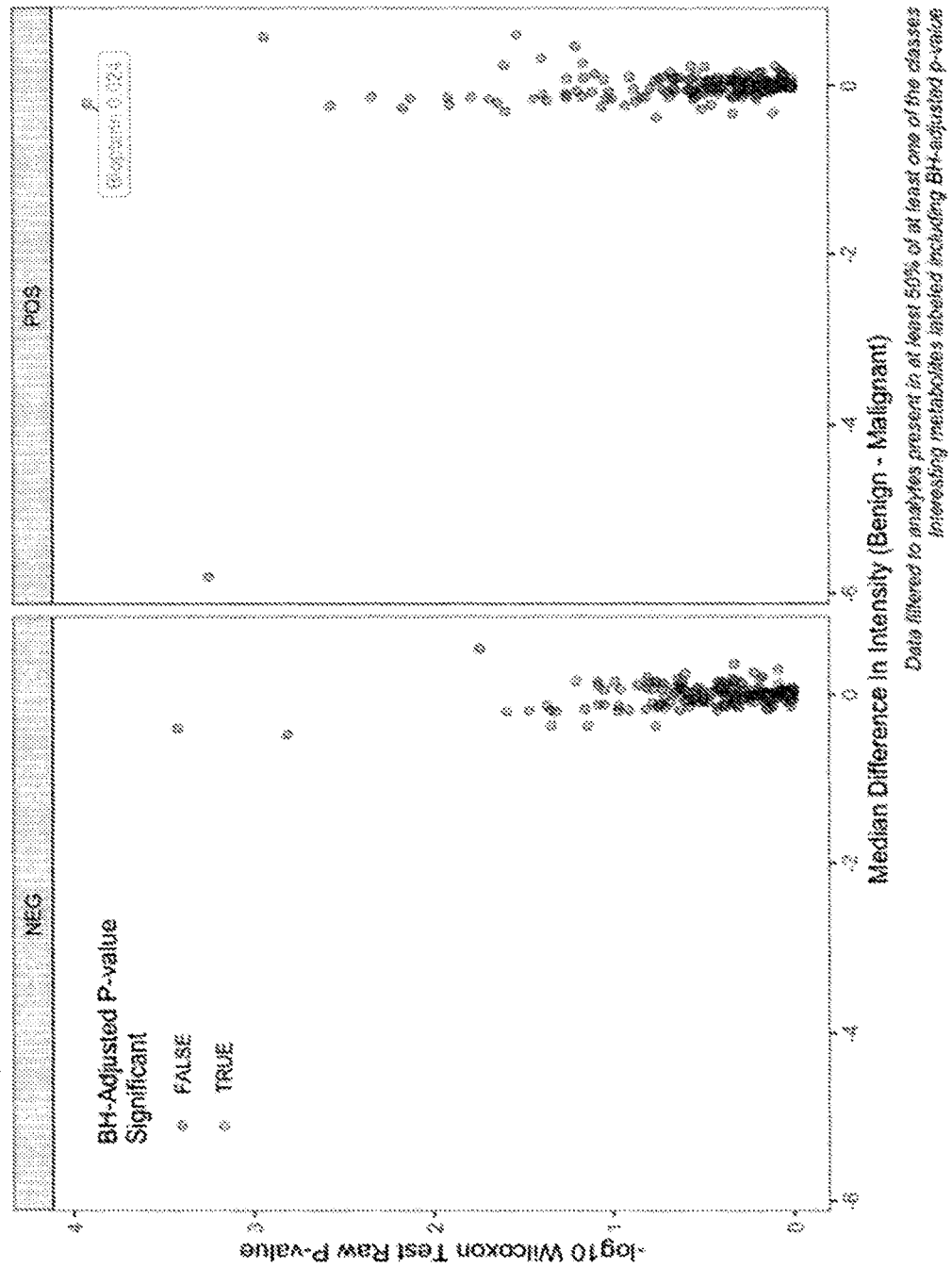

FIG. 94 includes volcano plots of intensity differences and P-values for metabolites in lung nodule subjects. The volcano plots display median difference in intensity on the x-axis and P-value on the y-axis.

Figure 95:
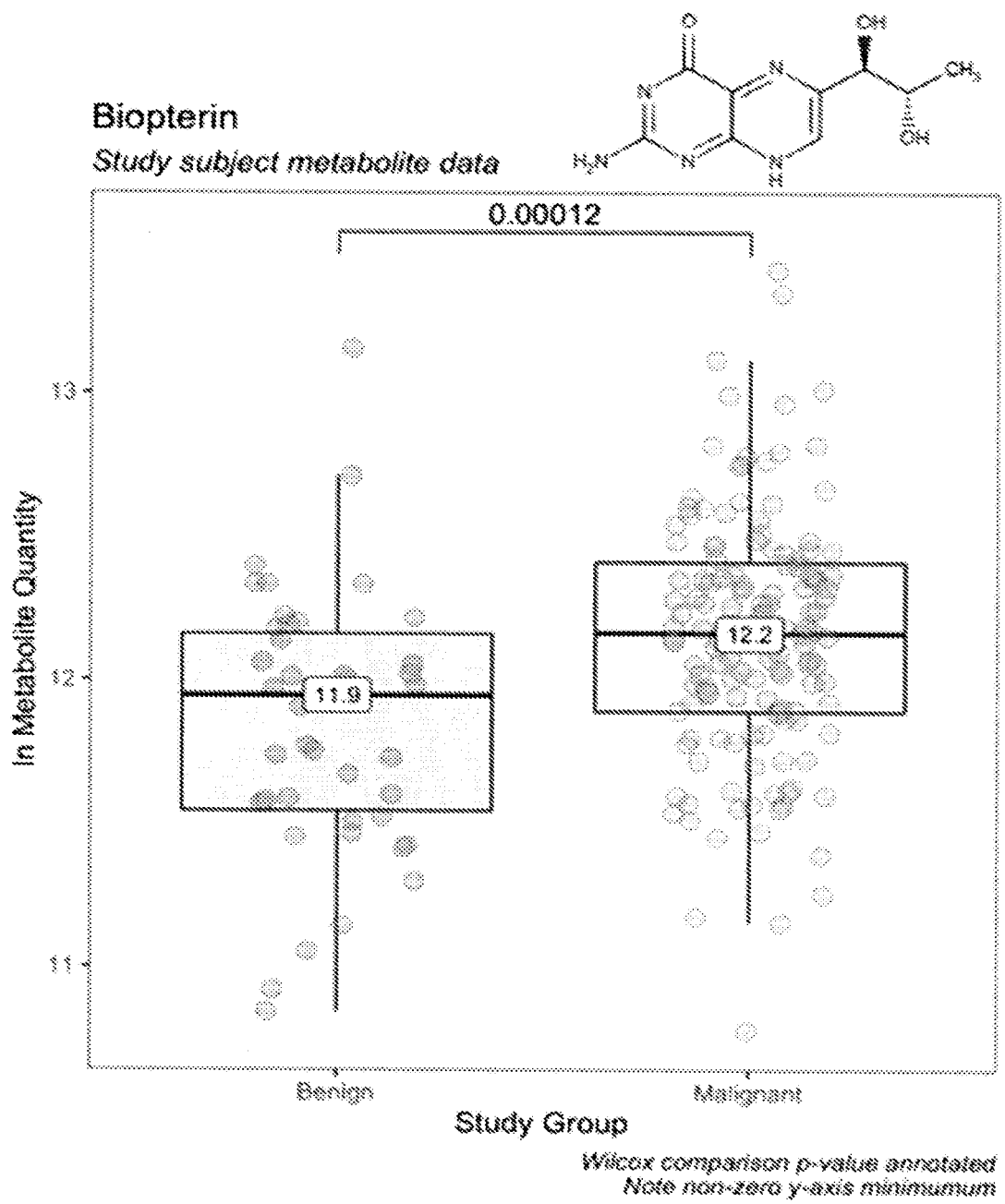

FIG. 95 includes a graph showing biopterin metabolite quantities in benign and malignant groups. The graph displays study group type on the x-axis and metabolite quantity on the y-axis.

Figure 96:
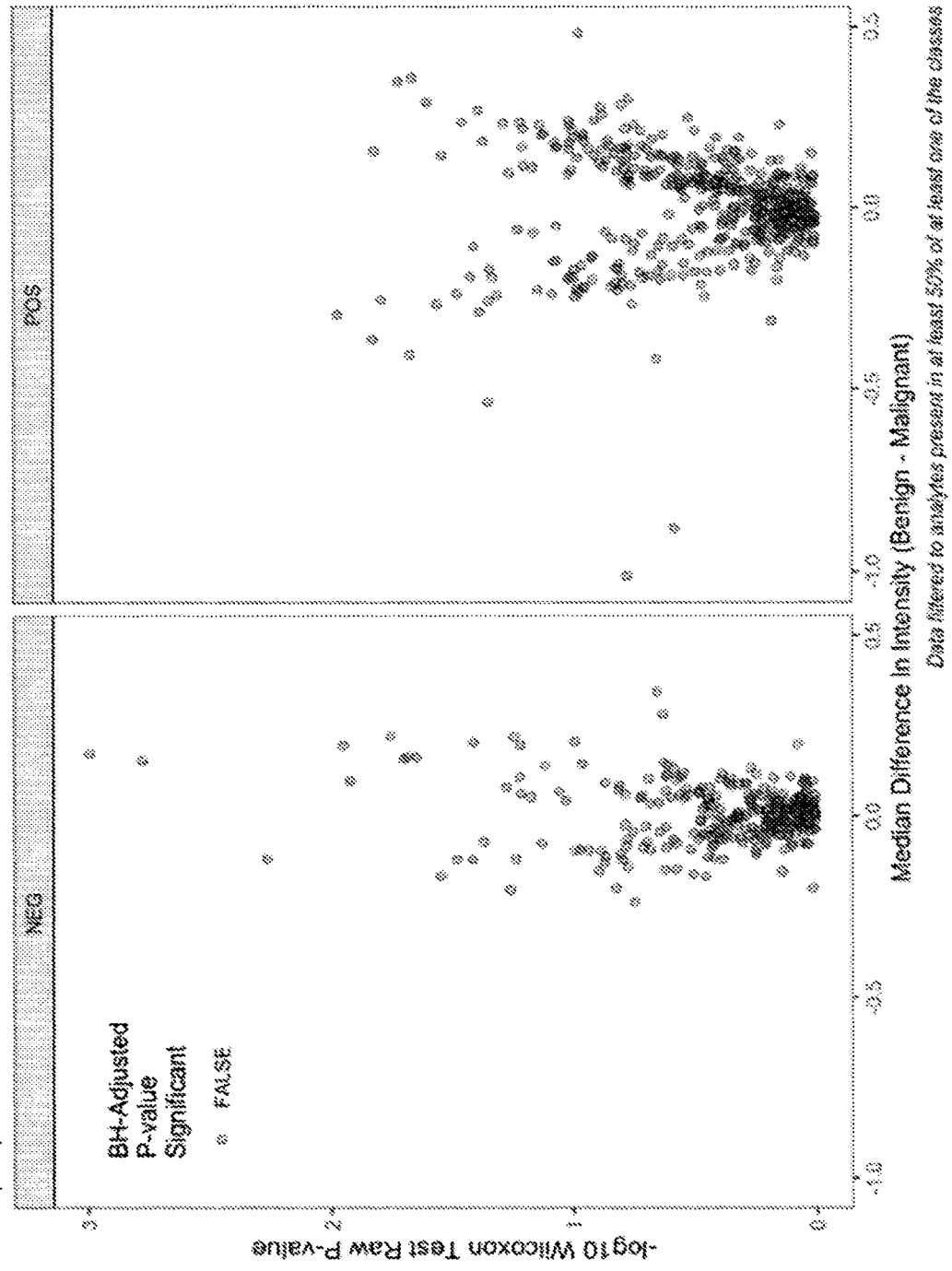

FIG. 96 includes a volcano plot of intensity differences and P-values for lipids in lung nodule subjects. The volcano plots displays median difference in intensity on the x-axis and P-value on the y-axis.

Figure 97:
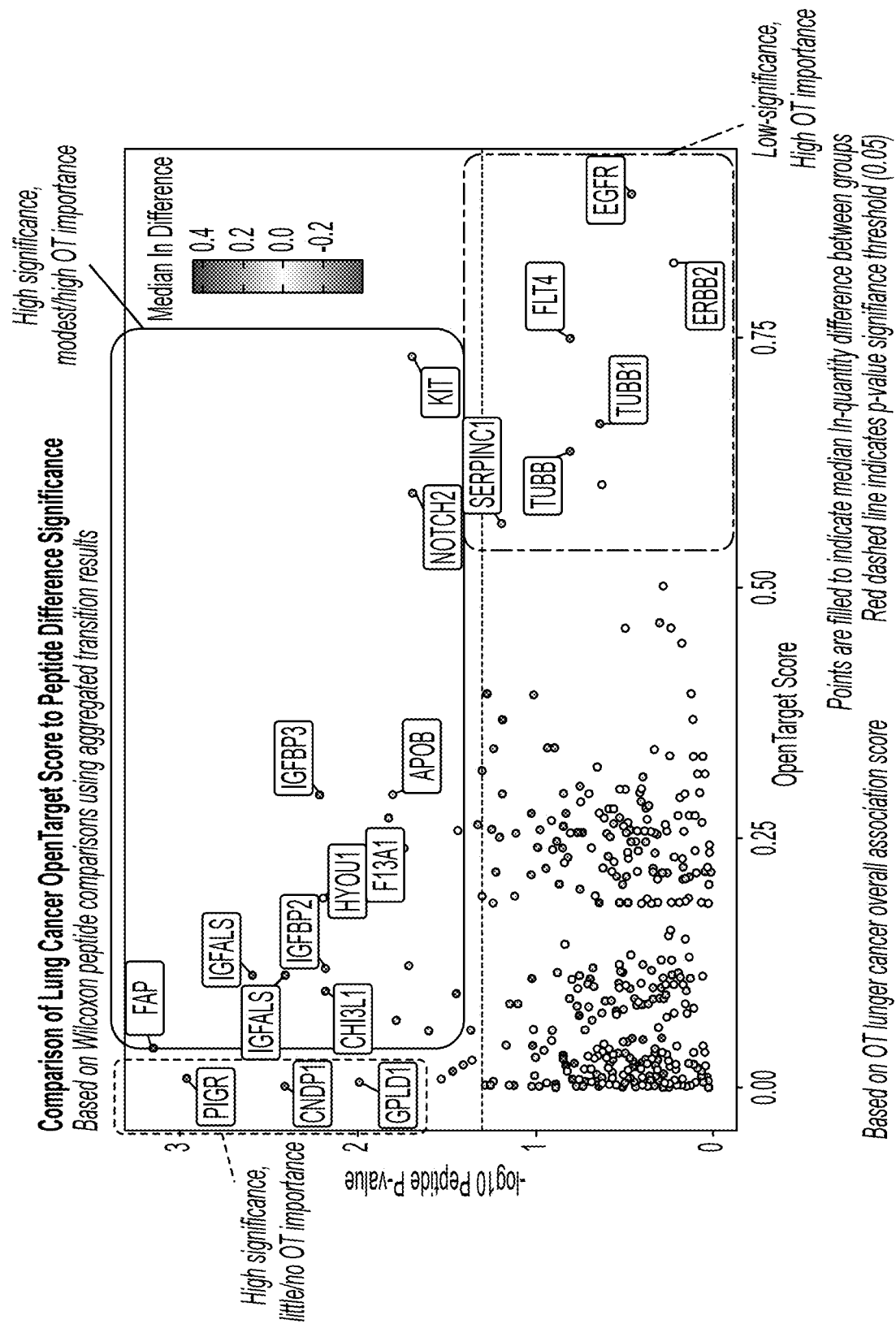

FIG. 97 includes a graph illustrating a comparison of lung cancer OpenTarget (OT) scores to peptide difference significance. The graph displays OpenTarget Score on the x-axis and P-value on the y-axis.

Figure 98:
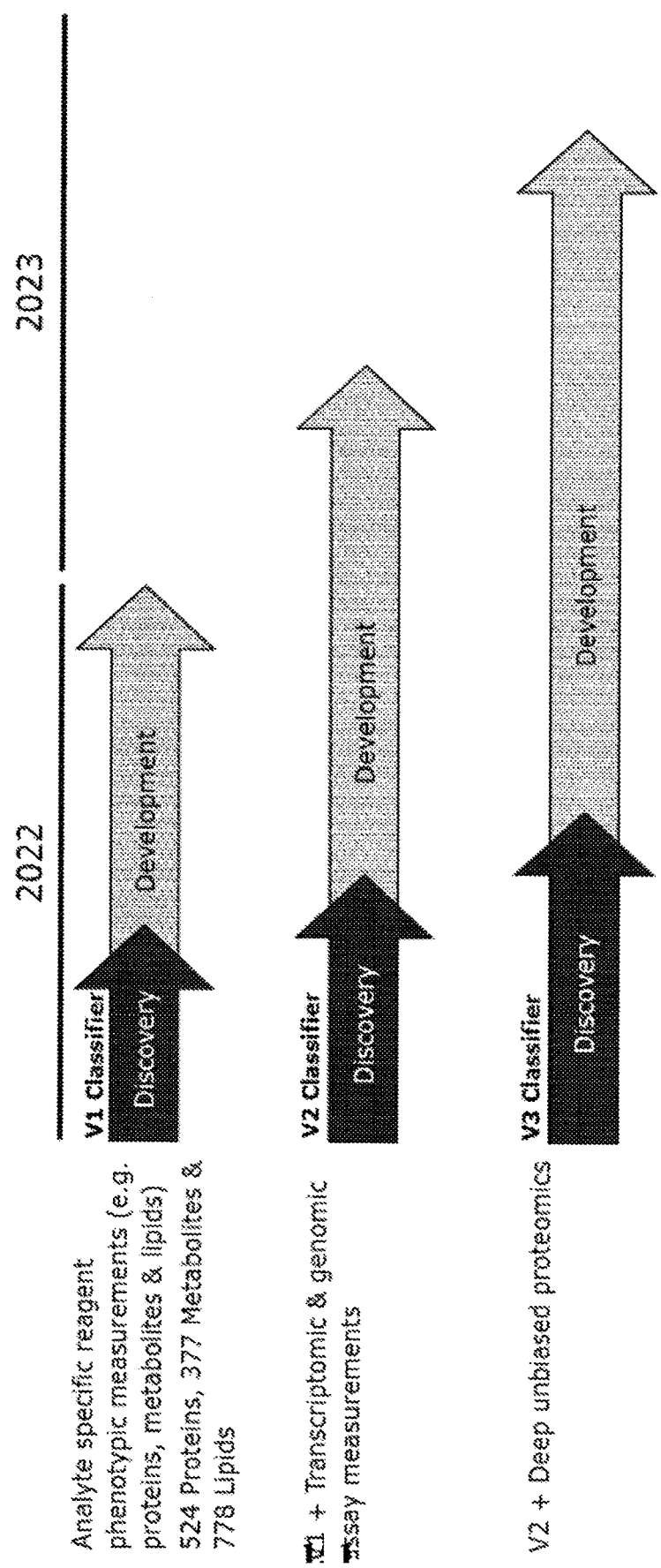

FIG. 98 shows a diagram illustrating the staged approach of version one classifier, version two classifier, and version three classifier discovery through test development.

Figure 99:
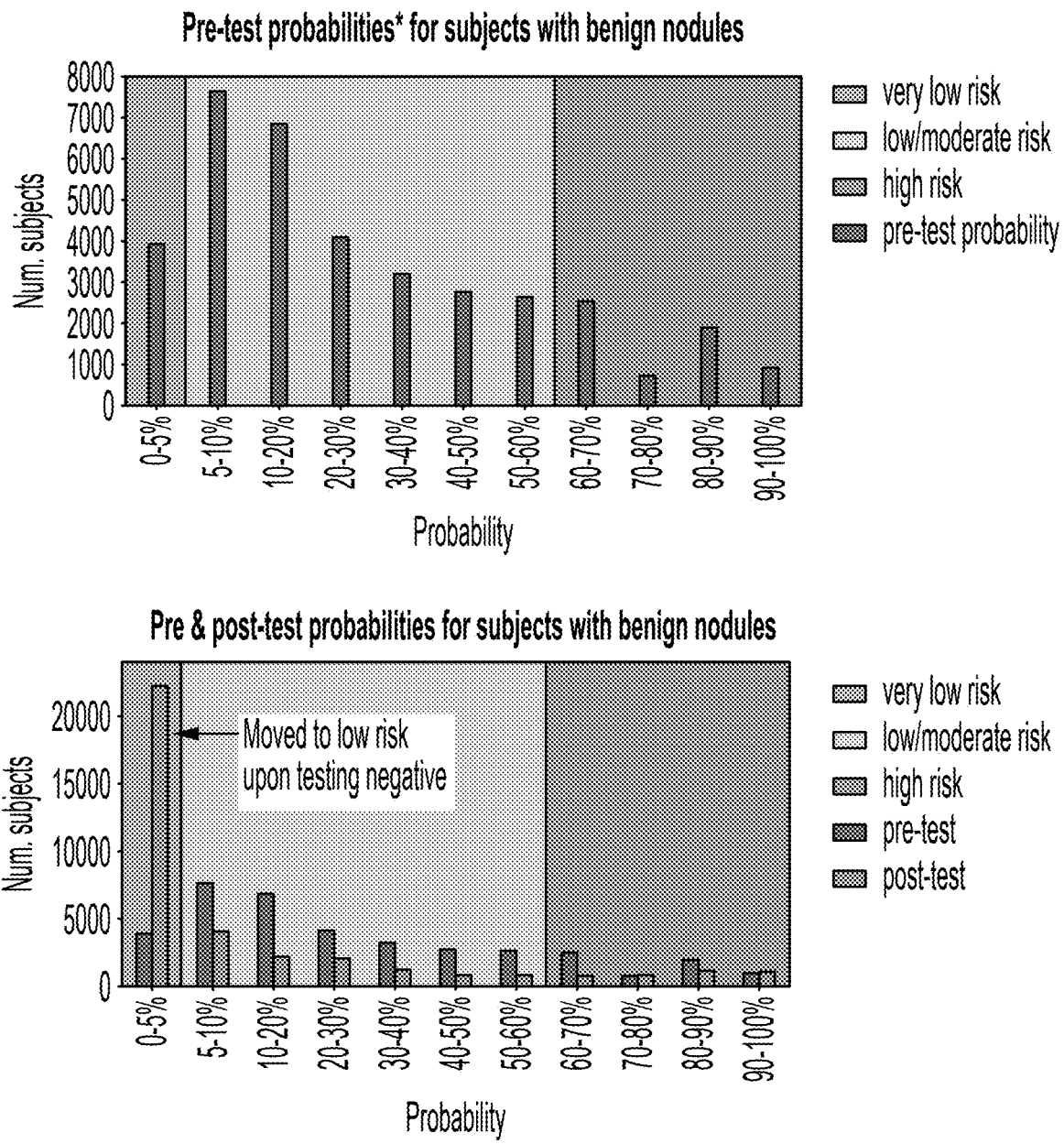

FIG. 99 includes graphs for pre-test probabilities for subjects with benign nodules and pre and post-test probabilities for subjects with benign nodules. The graphs display probability on the x-axis and number of subjects on the y-axis.

Figure 100:
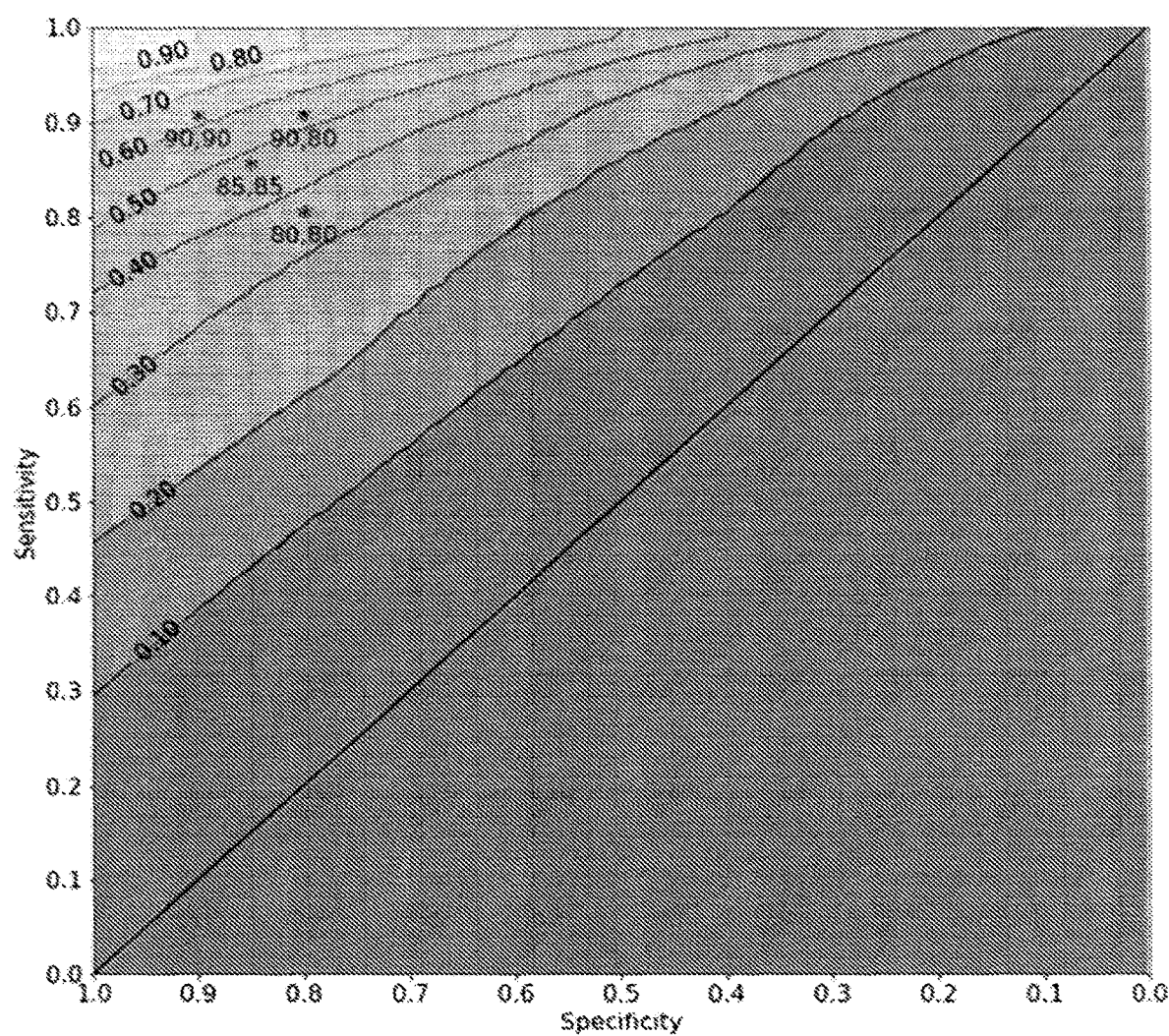

FIG. 100 includes a graph comparing sensitivity to specificity. The graph displays specificity on the x-axis and sensitivity on the y-axis.

Figure 101:
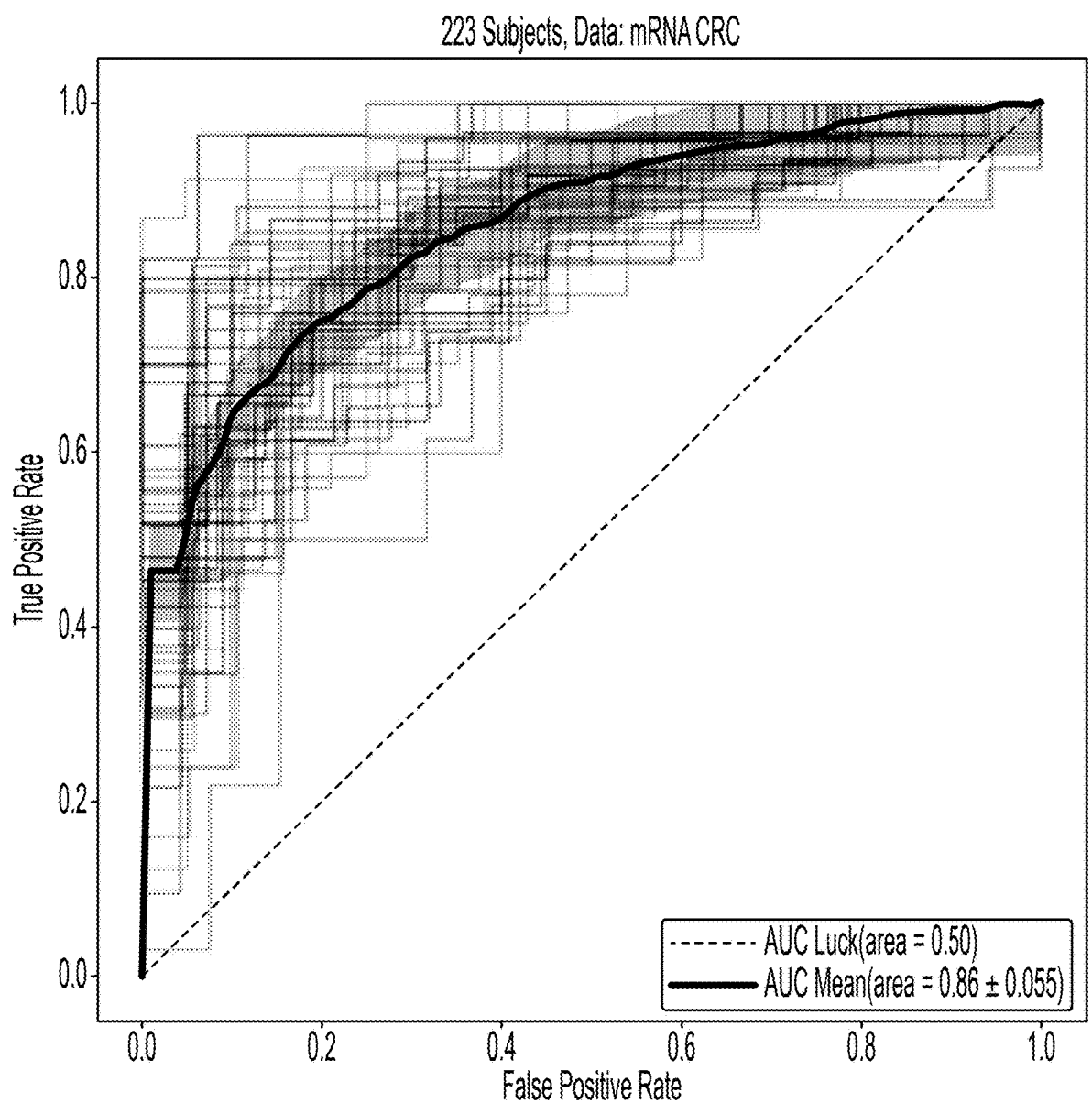

FIG. 101 shows the ROC curve for 223 subjects with mRNA data in the colorectal cancer (CRC) study. The false positive rate is displayed on the x-axis and the true positive rate is displayed on the y-axis. The AUC values are provided.

Figure 102:
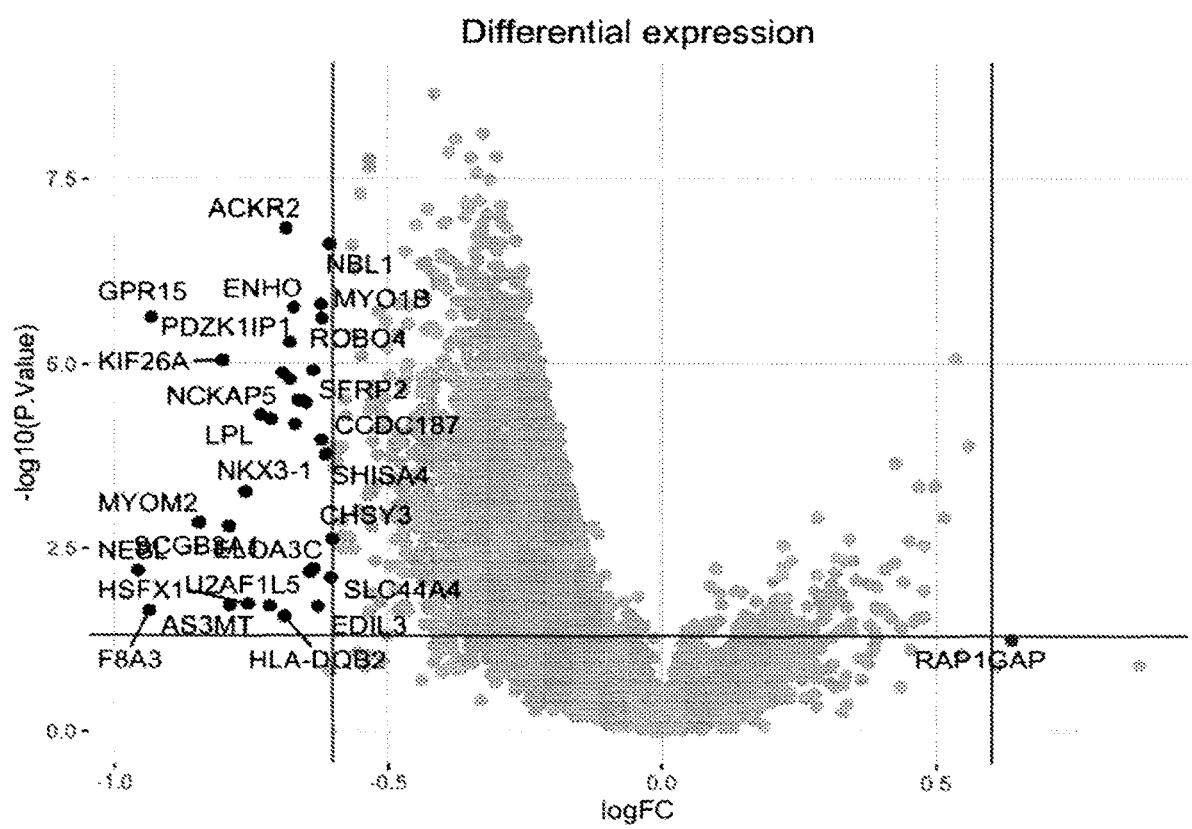

FIG. 102 includes a volcano plot illustrating the differential expression of various genes in the colorectal cancer study.

Figure 103:
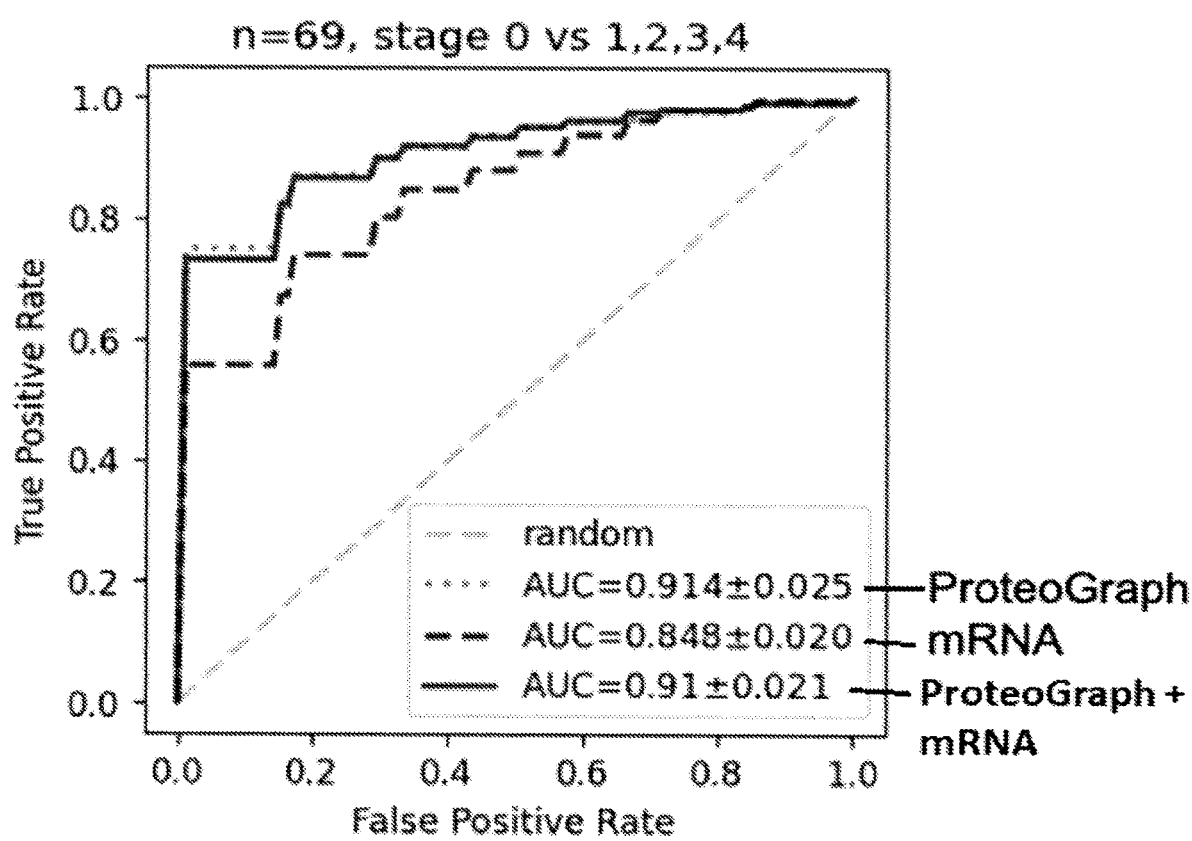

FIG. 103 shows ROC curves for ProteoGraph, mRNA, and ProteoGraph+mRNA. The respective AUC values are provided.

Figure 104:
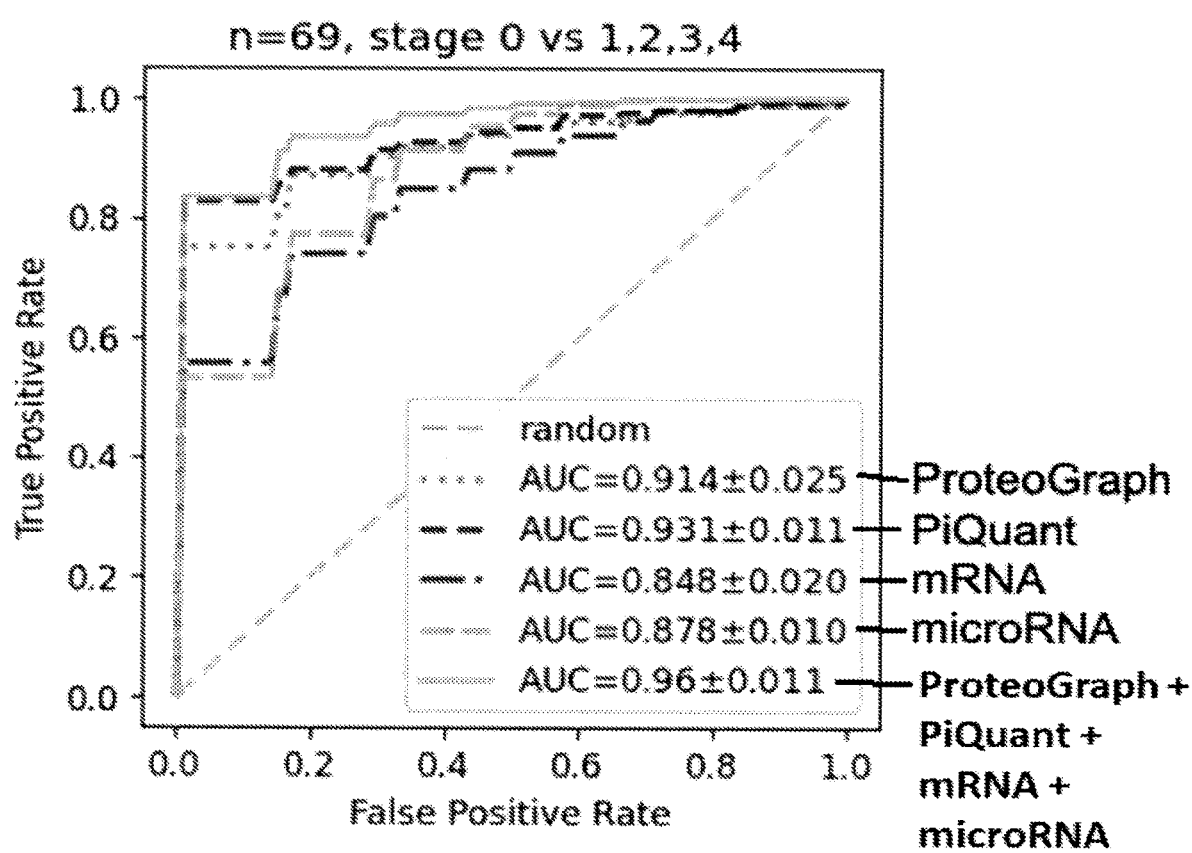

FIG. 104 shows ROC curves for ProteoGraph, PiQuant, mRNA, microRNA, and ProteoGraph+PiQuant+mRNA+microRNA. The respective AUC values are provided.

Figure 105:
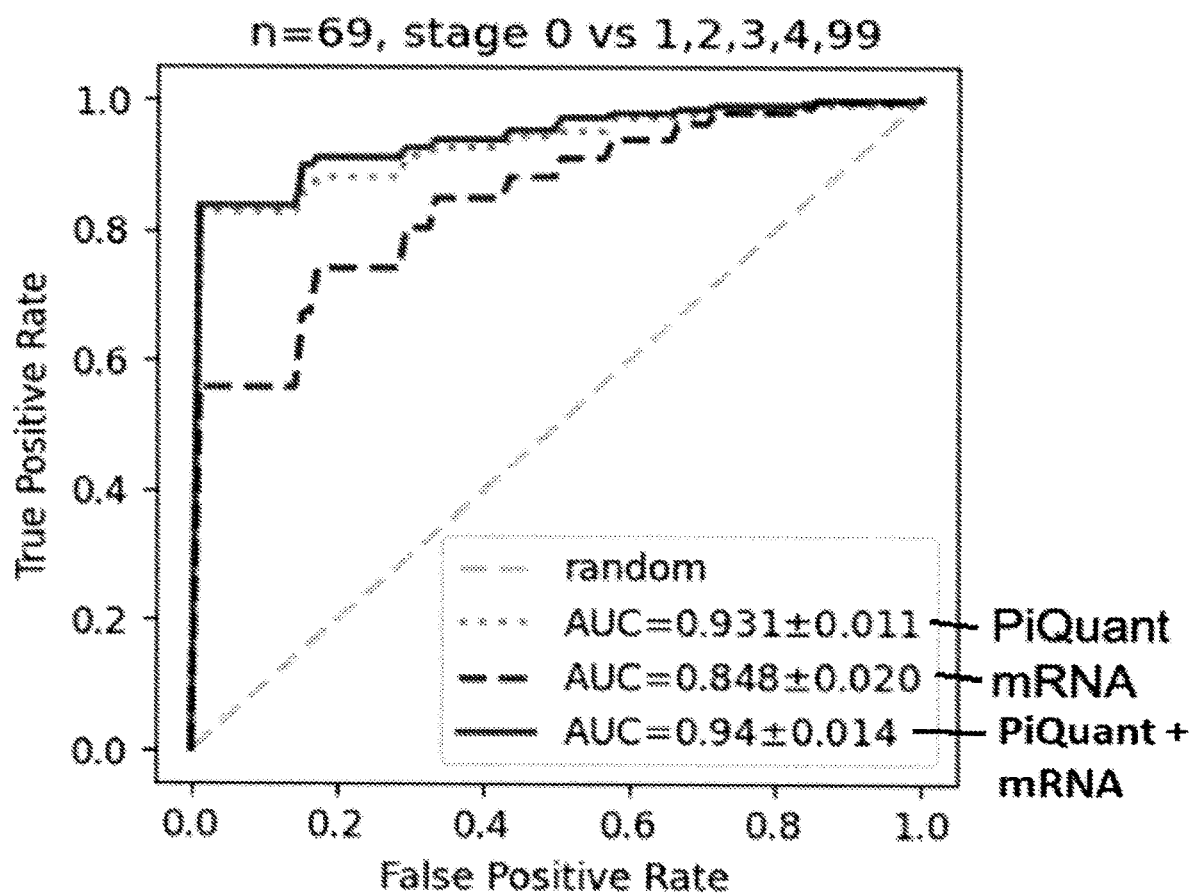

FIG. 105 shows ROC curves for PiQuant, mRNA, and PiQuant+mRNA. The respective AUC values are provided.

Figure 106:
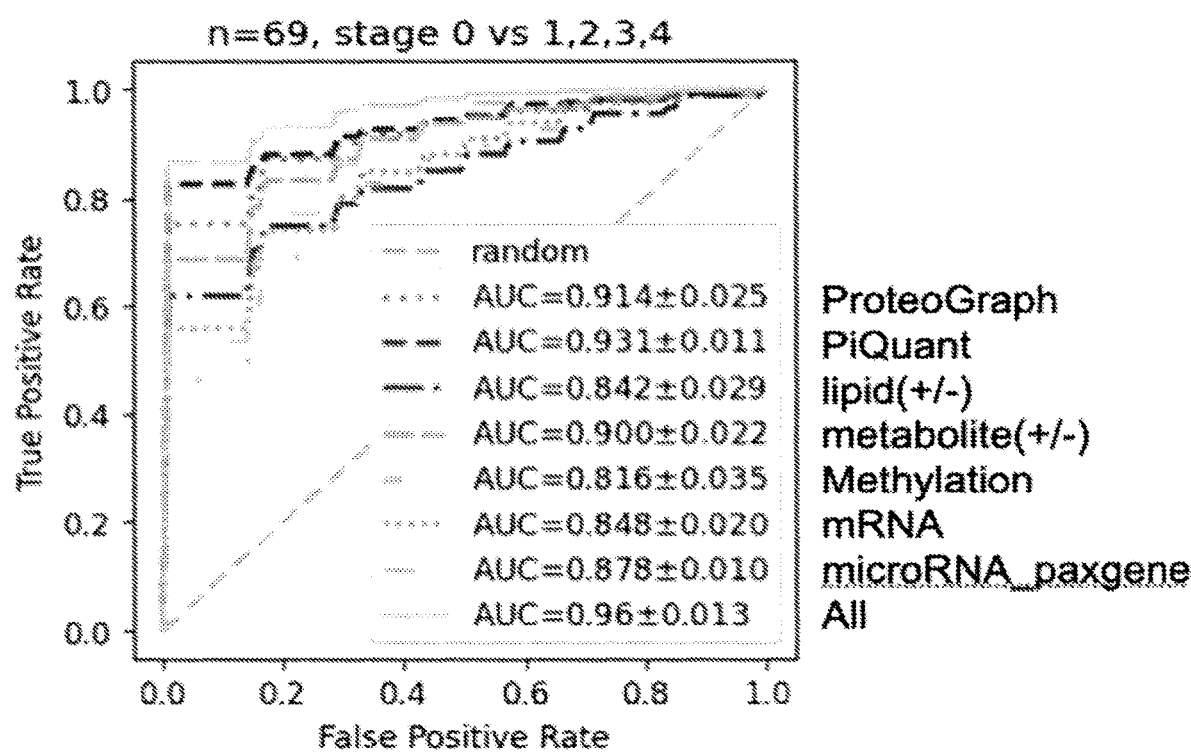

FIG. 106 shows ROC curves for classification based on separate or combined types of biomolecules.

INCORPORATION BY REFERENCE

All publications, patents, and patent applications mentioned in this specification are herein incorporated by reference to the same extent as if each individual publication, patent, or patent application was specifically and individually indicated to be incorporated by reference. To the extent publications and patents or patent applications incorporated by reference contradict the disclosure contained in the specification, the specification is intended to supersede and/or take precedence over any such contradictory material.

DETAILED DESCRIPTION

This disclosure provides non-invasive methods for diagnosing or ruling out the presence of a disease in a subject, or the risk of developing the disease in a subject. The disease may include a cancer such as pancreatic cancer, breast cancer, liver cancer, ovarian cancer, or colon cancer. Identifying an early-stage disease in a subject can save the subject from further development of the disease if treatment is provided early on. Non-invasive tests can also be used to rule out the presence of a disease, thereby saving subjects from having to undergo invasive testing such as a biopsy, which can be painful and stressful, or may risk damaging the subject.

Figure 1A:
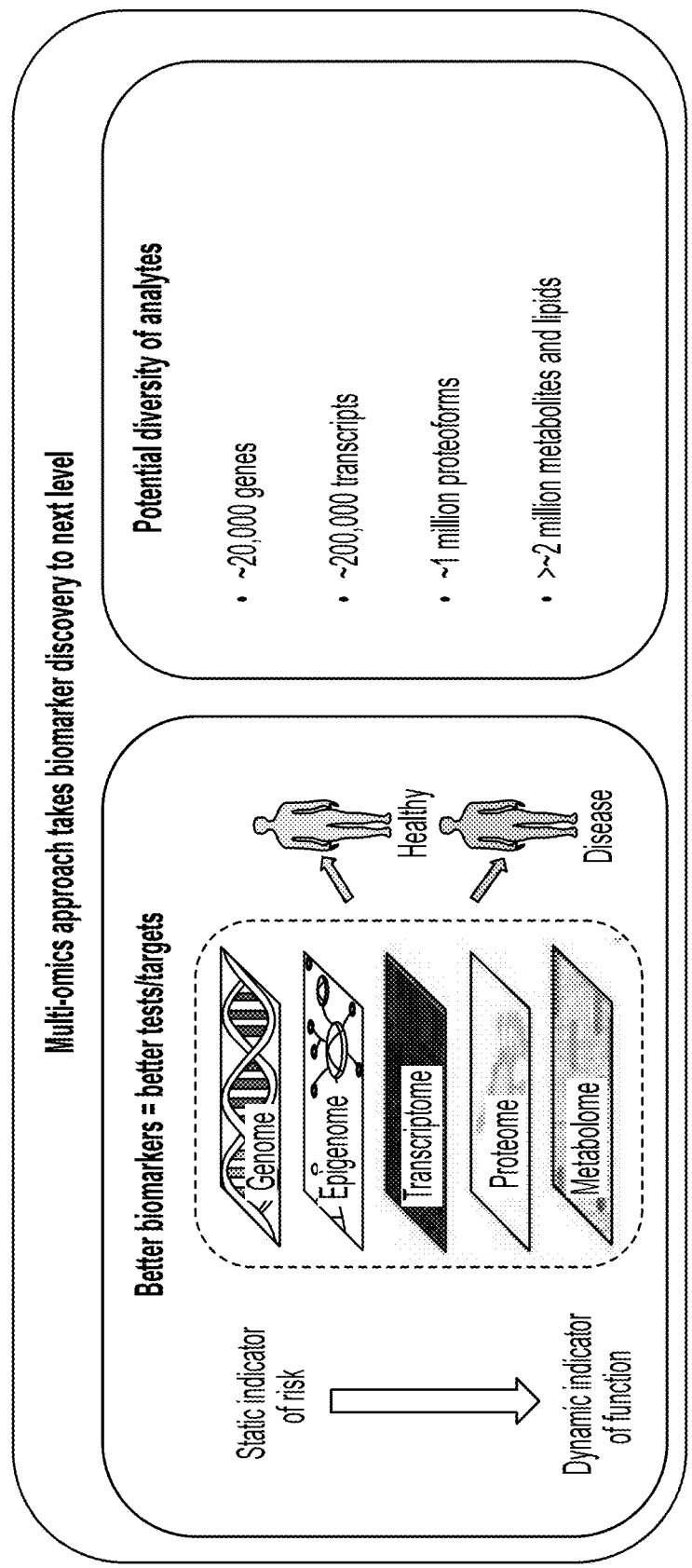
FIG. 1A illustrates a multi-omics approach.
Figure 1B:
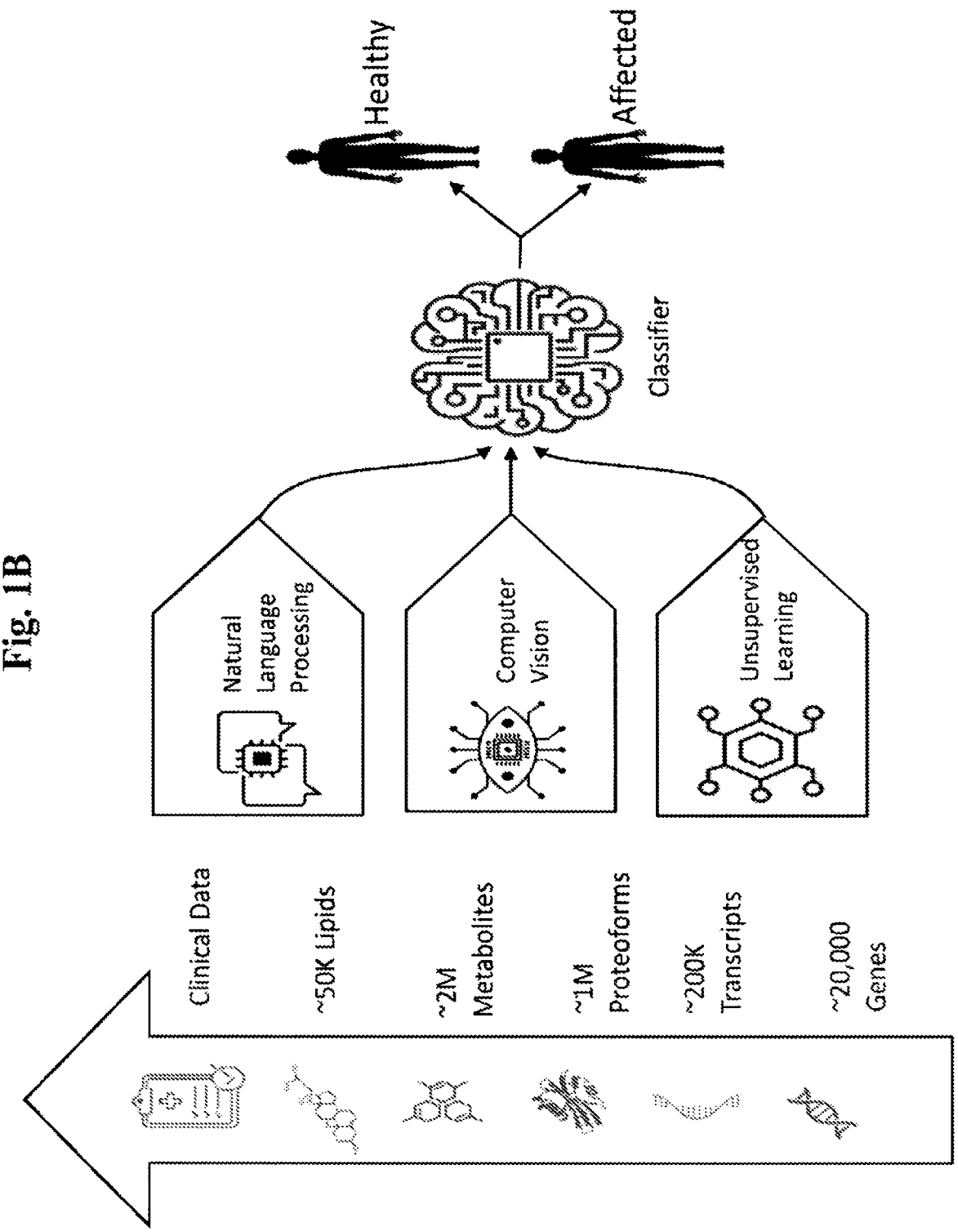
FIG. 1B illustrates combining data sets in a multi-omics approach.
Figure 24:
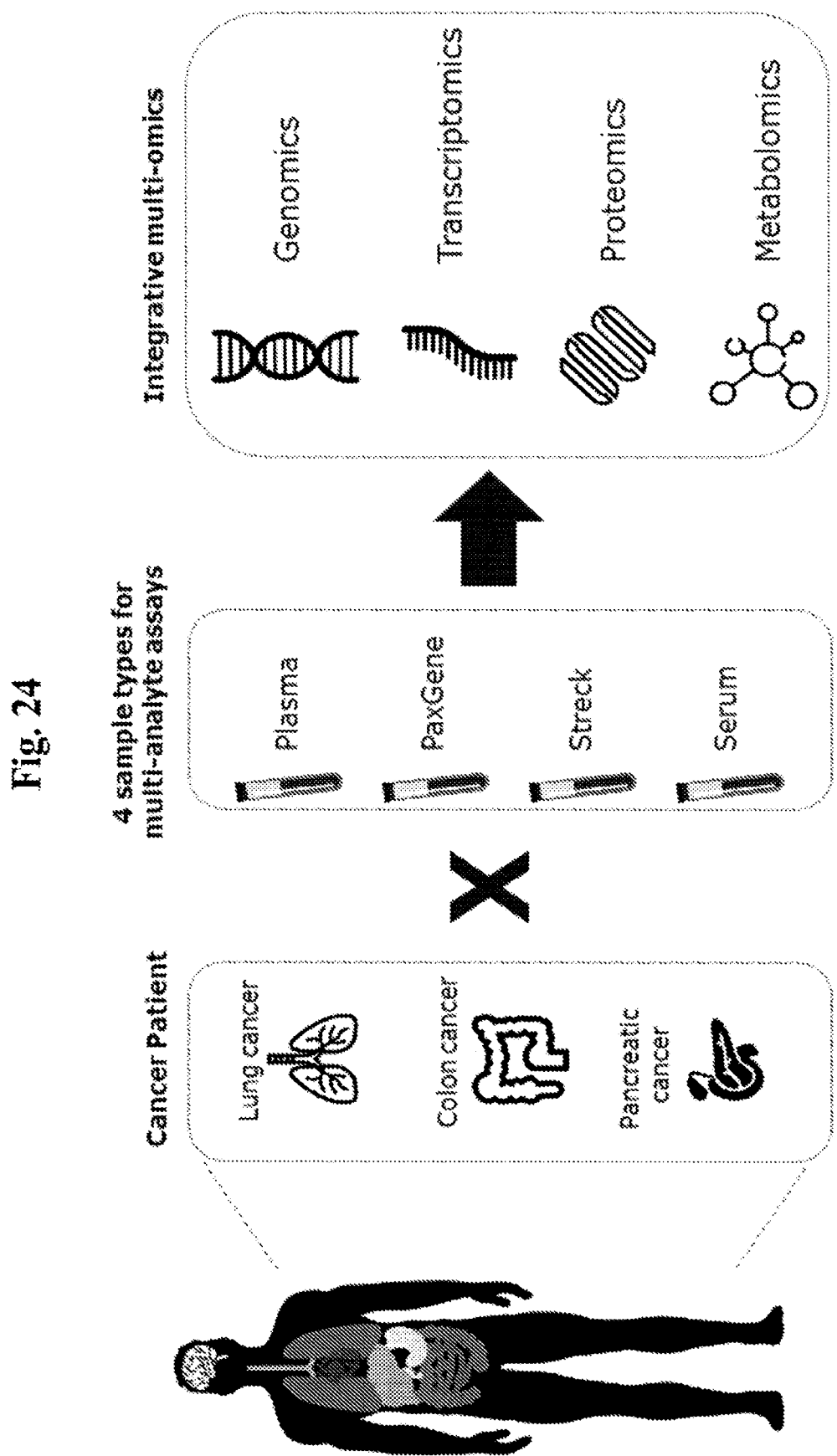
FIG. 24 shows various aspects that may be used in some methods described herein.

A multi-omics approach may unlock the ability to detect a disease at an early stage of development of the disease, and may improve accuracy of detection of the disease. FIG. 1A shows some aspects of a multi-omics approach to early disease detection that may combine genomic DNA or DNA methylation information (an example of what may be a generally static indicator of risk) with molecular phenotype information coming from proteomics or metabolomics, which may be more dynamic indicators of function. FIG. 24 also shows some aspects that may be included in a multiomic method, and includes some examples of disease states that may be detected or assessed. FIG. 1B shows an example of integration of multiple omic data types. Any aspect of these figures may be used in a method described herein.

Figure 2A:
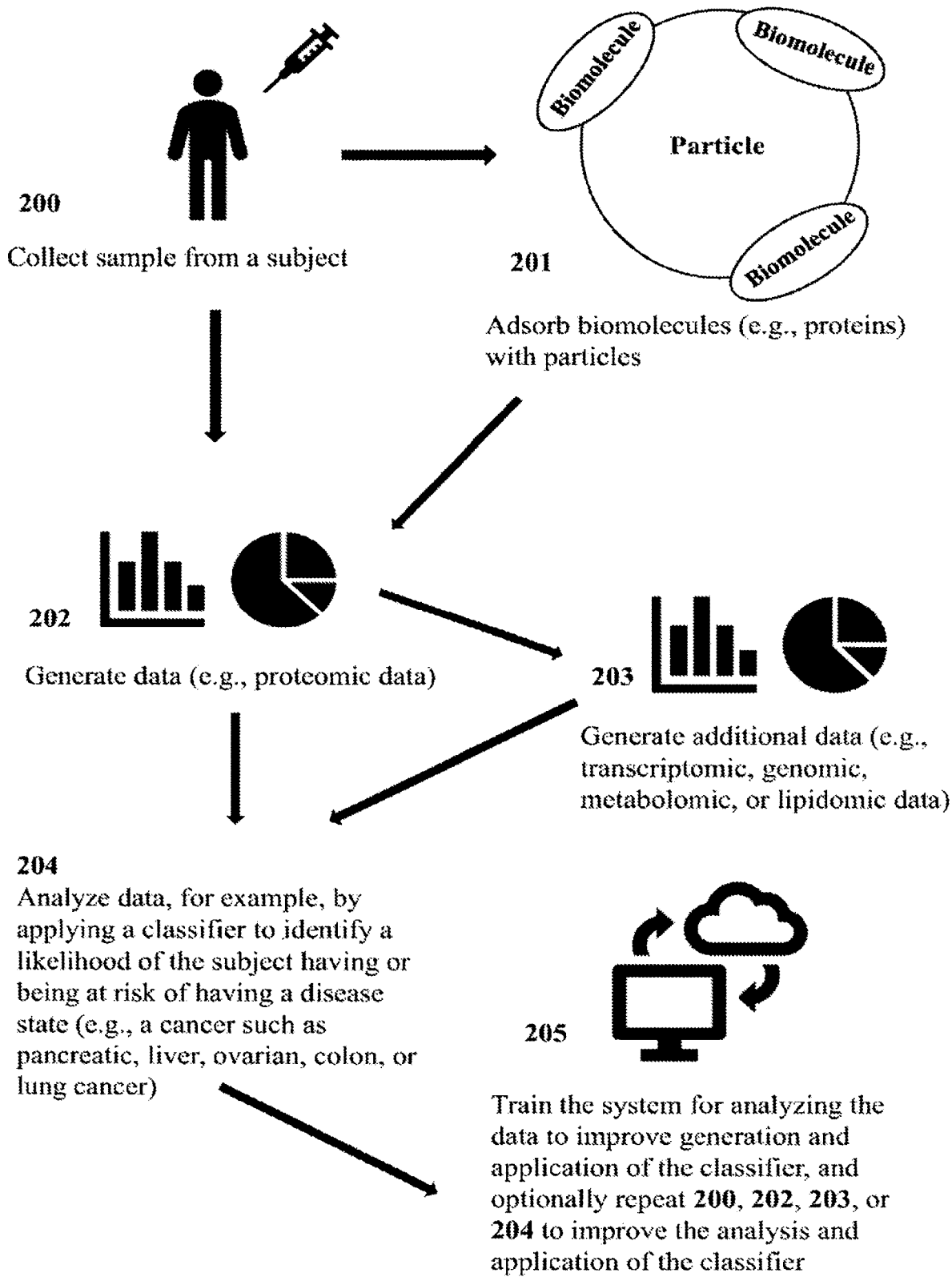
FIG. 2A shows examples of methods for generating and applying the classifiers described herein.
Figure 2B:
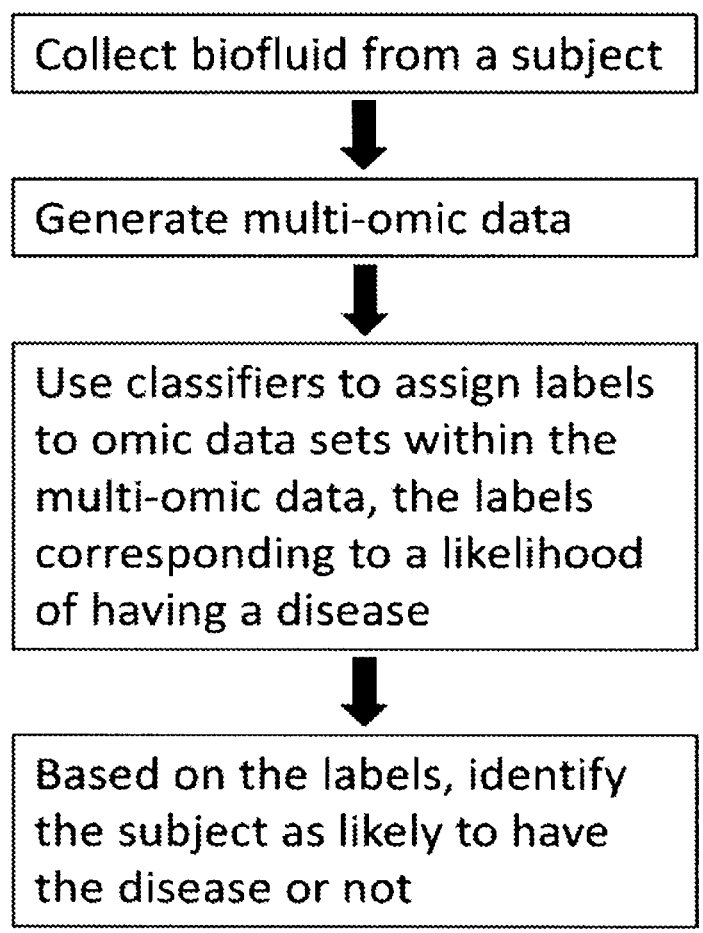
FIG. 2B is a flowchart showing some aspects that may be used in methods herein.

FIG. 2A illustrates a non-limiting example of a method for predicting whether a subject has a disease such as cancer, or is at risk of developing the disease. Analysis may include obtaining a biofluid sample from a subject (200). The sample may be assayed or analyzed. The biofluid sample can be any one of or any combination of the biofluids described herein. The sample can be either: directly analyzed to generate data (202) such as proteomic data; or contacted with particle described herein to obtain adsorbed biomolecules (203) prior to the analysis of 202. After obtaining the data from the analysis of 202, additional analysis (203) can be performed from the sample obtained from 200 or 201 to obtain additional data sets such as transcriptomic data, genomic data, metabolomic data, or a combination thereof. The data or data sets obtained from the analysis of 202 or 203 can be used to generate a classifier (205). The classifier can be applied to identify a likelihood of the subject having or at risk of having the disease. The generation or application of the classifier can be further repeated or refined to improve the analysis. FIG. 2B further illustrates some details that may be used in the methods described herein. Any of the aspects of FIG. 2A or FIG. 2B may be used in a method described herein such as a classification method.

Figure 3A:
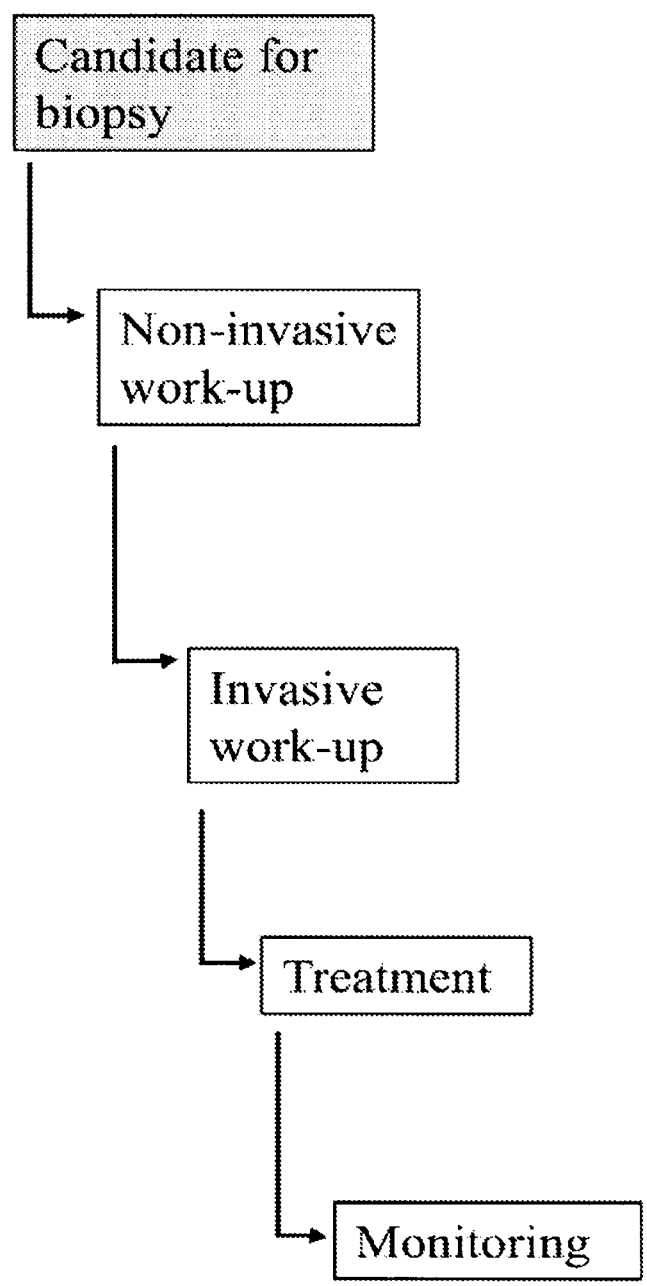
FIG. 3A shows examples of stages in screening and treatment of a patient having or suspected of having a disease state.
Figure 3B:
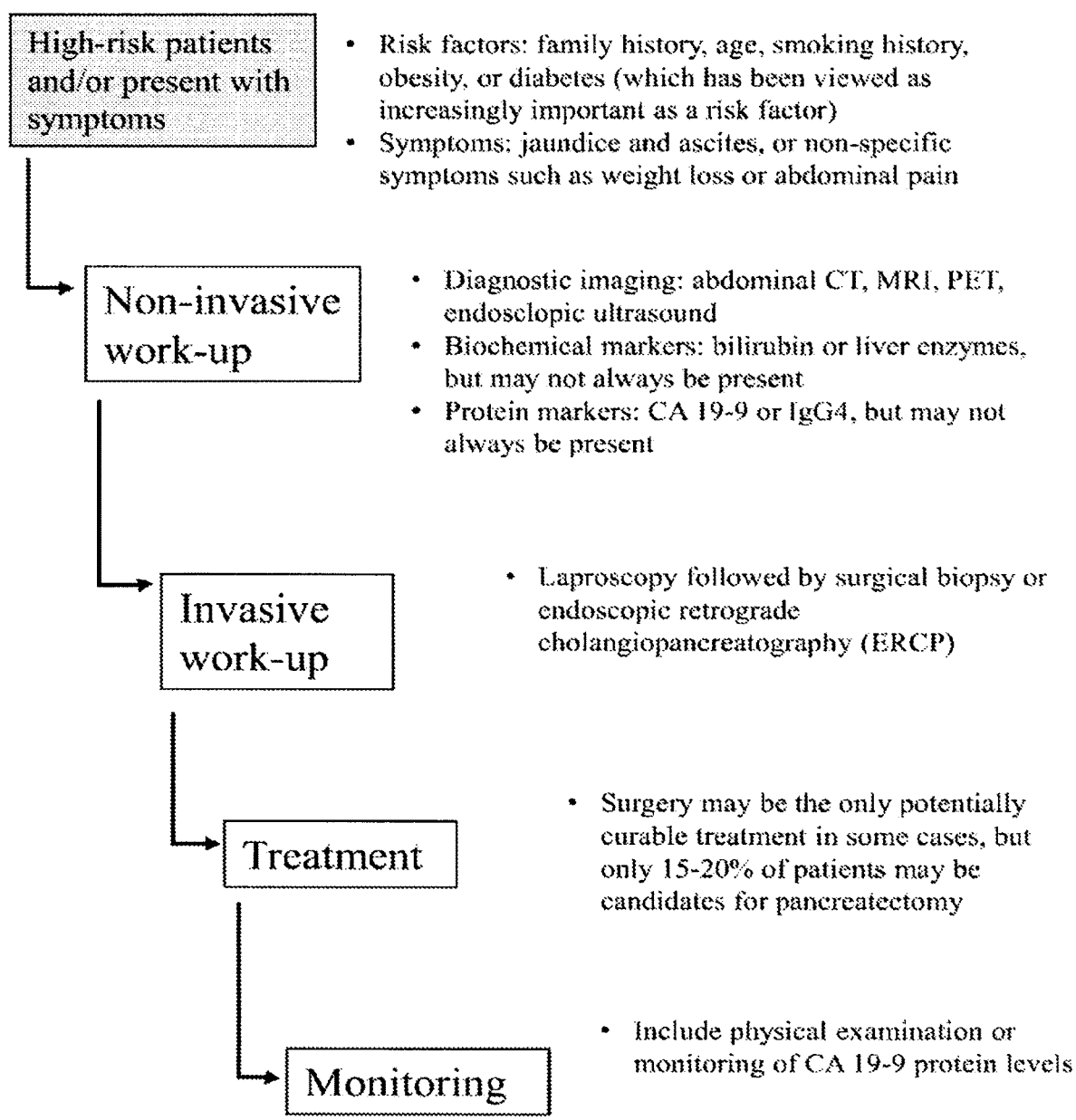
FIG. 3B shows examples of stages in pancreatic cancer patient screening and treatment.
Figure 3C:
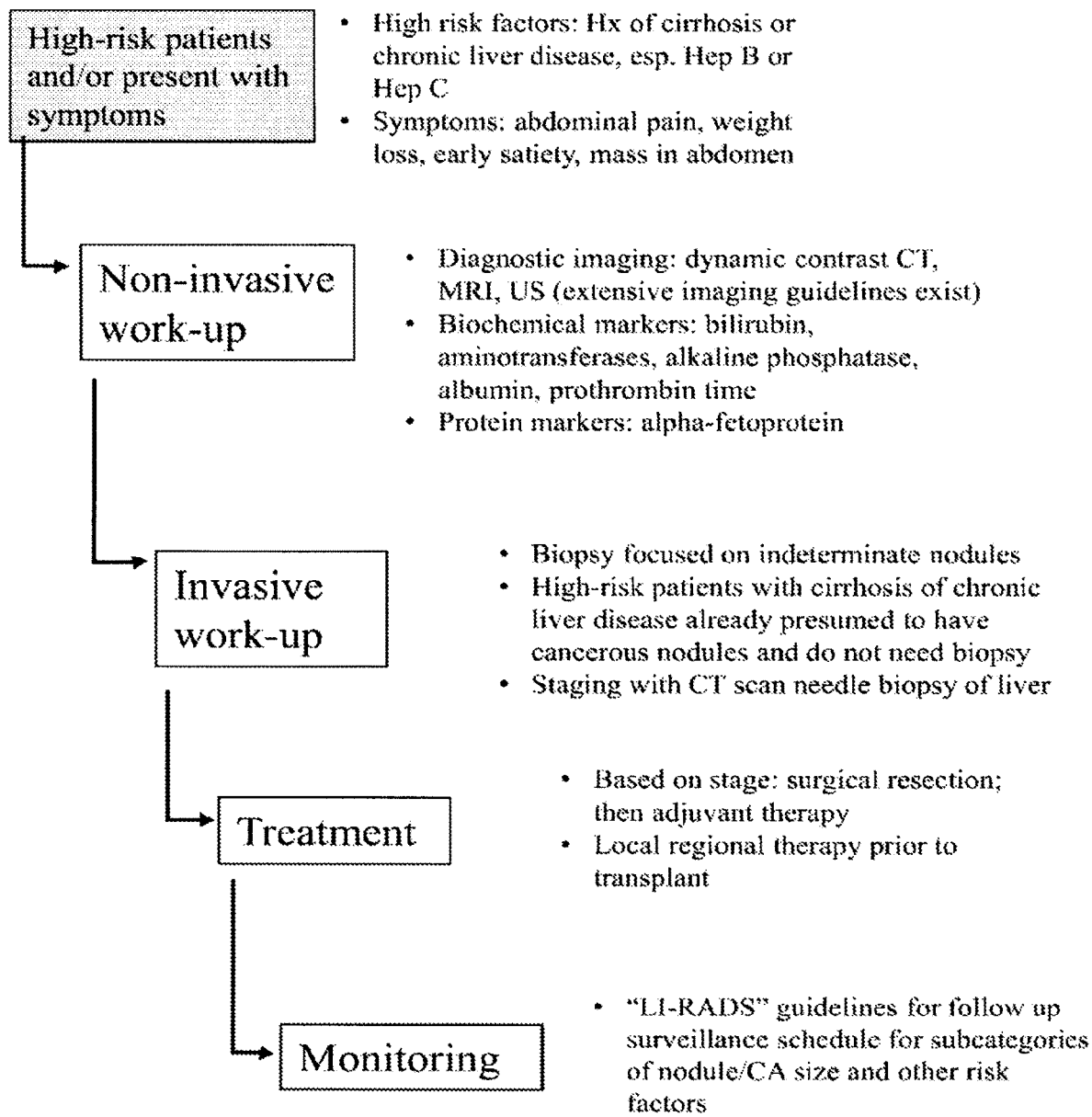
FIG. 3C shows examples of stages in liver cancer patient screening and treatment.
Figure 41:
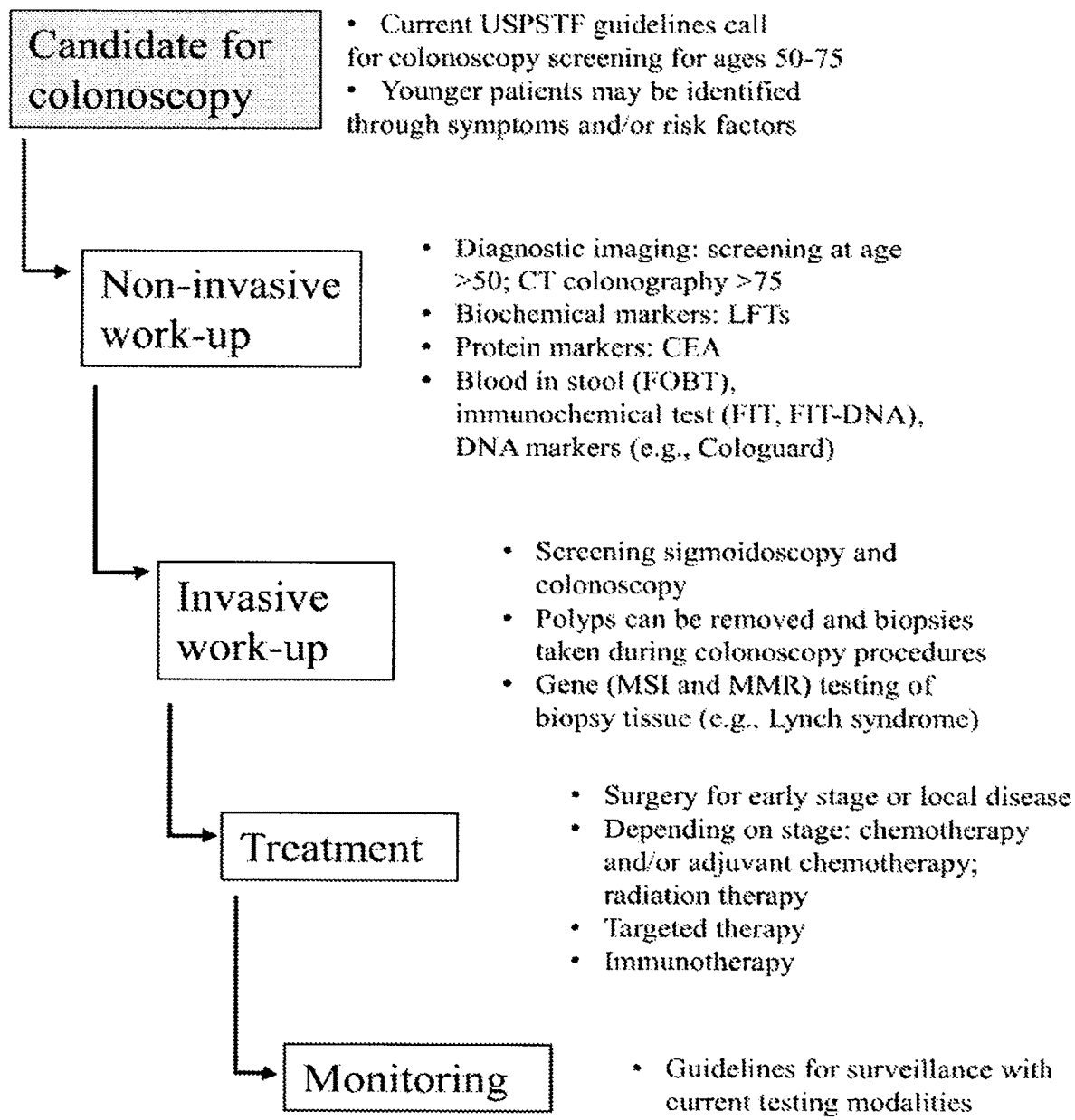
FIG. 41 shows examples of stages in colon cancer patient screening and treatment.

Furthermore, an analysis as illustrated in FIG. 2A or FIG. 2B can be applied before or during a procedure at any step included in FIG. 3A. For example, an evaluation or analysis may be completed early on in a diseased patient's journey before, shortly after, or as part of an invasive workup. It is useful to screen high-risk patients before performing an invasive procedure such as a biopsy or invasive treatment. Generally, an opportunity where a method described herein may be useful, may be in screening high risk patients for early detection of the disease. The methods described herein may be used for such detection with greater accuracy and convenience than other methods. In FIG. 3A, the non-invasive work-up may include medical imaging, or the invasive work-up may include obtaining a biopsy. The biopsy may be of a suspected tumor. Similar patient journeys are shown for pancreatic cancer, liver cancer, and colon cancer in FIG. 3B, FIG. 3C and FIG. 41. An evaluation or analysis may be completed at or before any point in FIG. 3B, FIG. 3C, or FIG. 41.

In some cases where the disease is pancreatic cancer, an opportunity lies in screening high-risk patients before biopsy or pancreatoscopy. For example, a primary opportunity for using the methods described herein includes screening high risk pancreatic cancer patients for early detection with improved accuracy and convenience. In a liver cancer patient's journey, an opportunity lies in screening high risk liver cancer patients before biopsy. For example, a primary opportunity for using the methods described herein may include improving decision making for indeterminate liver nodules to determine the necessity or not of a biopsy. Another opportunity may include surveillance or diagnosis of small, low risk nodules, or follow-up (e.g., 3-6 months) to track small nodule progression. In a colorectal cancer (CRC) patient's journey, an opportunity may lie in screening high risk patients before colonoscopy. Another opportunity may lie in improved decision making for an imaging or biopsy procedure.

Non-invasively obtained samples can be used for disease diagnosis by generating omic data and identifying patterns in the omic data that associate with a disease. Diagnosis of diseases may be improved by combining multiple types of data (e.g., multiple data sets such as omic data sets) into the analysis. For example, combining multiple data types may improve the accuracy of prediction of whether a subject has or does not have a particular disease. Combined data may be more accurate than individual data sets if the individual data sets err independently or do not overlap completely. The methods described herein include generating or obtaining multi-omic data, and using the multi-omic data to make a prediction about whether a subject has or does not have a disease. Various ways of combining or analyzing multi-omic data are described. Uses of the multi-omic data and disease assessment are further elaborated.

Some methods may be used to classify a lung nodule. Lung nodules can be either benign or malignant. Malignant lung nodules can rapidly progress into lung cancer, a common and deadly cancer. Improved identification of malignant and benign lung nodules is needed. On one hand, early diagnosis of a malignant lung nodule can lead to early treatment regimen and a more favorable prognosis for a subject having the malignant lung nodule. On the other hand, non-invasive diagnosis of a benign or non-malignant lung nodule can help in the avoidance of obtaining a lung biopsy, which can be costly and invasive, and thus also be more favorable for a subject having a lung nodule that is not malignant.

However, there has been little progress in the development of useful clinical tests for diagnosing and deciphering lung nodules as benign or malignant. Imaging methods often lead to high degree of misdiagnose (e.g., false positive) rates. Smaller nodules are usually not detected by these imaging methods. Other non-invasive methods such as screening for biomarkers also have limitations. Proteins in plasma may be a useful biomarker discovery matrix given plasma's contact with many tissues in the body. However, plasma proteins can be problematic due to several factors including a wide range of concentration (e.g., 10-orders of magnitude). Complex biochemical workflows have attempted to circumvent these challenges but may not be practical for discovery studies of sufficient size to ensure validation and replication. Alternatively, biomarker studies have been limited to evaluating or re-evaluating existing markers without substantive improvement in clinical performance. Accordingly, there remains a need for methods for diagnosing or screening for the presence of benign or malignant lung nodule based on the analysis of biomarkers in a biofluid sample. The methods described herein may address this need.

Disclosed herein are methods that include obtaining biomolecule data. The biomolecule data may include multi-omics data. The method may include generating or receiving the data, and then using a classifier to make an evaluation. The evaluation may include applying a classifier, identifying a disease, ruling out a presence of a disease, predicting a likelihood of a disease, or selecting a treatment for the disease.

Diseases

The methods described herein may be used to evaluate a disease state. The methods described herein may be used to predict or identify a disease state. A disease state may include a disease or disorder such as cancer. Examples of cancer include lung cancer, colon cancer, pancreatic cancer, liver cancer, ovarian cancer, breast cancer, prostate cancer, melanoma, bladder cancer, lymphoma, leukemia, renal cancer, or uterine cancer. In some aspects, the cancer is breast cancer. A disease may include a disorder. A disease state may include having a comorbidity related to a disease or disorder.

A reference to whether a subject has a disease state or not may include the subject being healthy. A healthy state may exclude a disease state. For example, a healthy state may exclude having cancer. A disease state may exclude being healthy.

The methods may be useful for cancer diagnosis. The methods may be useful for cancer screening. The method may be useful for cancer treatment. The method may include assaying proteins in a biofluid sample obtained from a subject having or suspected of having a nodule such as a lung nodule to obtain protein measurements. The method may include applying a classifier to the protein measurements, thereby identifying the protein measurements as indicative of the lung nodule being cancerous or non-cancerous. In some cases, the classifier is generated using proteomic data obtained by contacting training samples with particles such that the particles adsorb proteins in the training samples, and assaying the proteins adsorbed to the particles. Some aspects include obtaining of receiving the biofluid sample of the subject.

In some aspects, the cancer to be detected by the methods described herein can be pancreatic cancer, liver cancer, ovarian cancer, or colon cancer. Diagnosis of cancer may be improved by obtaining proteomic data or other omic data (such as lipidomic data). Diagnosis of cancer may be improved by combining multiple types of data (e.g., multiple data sets) into the analysis. For example, combining multiple data types comprising proteomic, transcriptomic, genomic, metabolomic, or a combination thereof may improve the accuracy of prediction of whether a subject has the cancer. In some aspects, the methods described herein include generating or obtaining data and using the data to predict whether a subject has or does not have a cancer. The method may include discriminating between cancer types (e.g., liver cancer vs. ovarian cancer). Various ways of combining or analyzing the data are described, and the uses of the data for cancer assessment are further elaborated.

The cancer may be at an early stage or a late stage. An example of an early stage of cancer may include stage I. An early stage may include stage I or II. An early stage may include stage I, II, or III. An example of late stage cancer may include stage 4.

The cancer may include pancreatic cancer. The pancreatic cancer may be early stage pancreatic cancer. In other aspects, the pancreatic cancer may be late stage pancreatic cancer. Non-invasively obtained samples can be used for cancer diagnosis by generating data and identifying patterns in the data that associate with the cancer such as pancreatic cancer. In certain aspects, the method of detecting a cancer may comprise additional screening or diagnosing methods such as a computed tomography (CT) scan indicative of pancreatic cancer, a magnetic resonance imaging (MRI) scan indicative of pancreatic cancer, a positron emission tomography (PET) scan indicative of pancreatic cancer, an ultrasound indicative of pancreatic cancer, a cholangiopancreatography indicative of pancreatic cancer, an angiography indicative of pancreatic cancer, a liver function test (LFT) indicative of pancreatic cancer, an elevated carcinoembryonic antigen (CEA) level relative to a control or baseline measurement, an elevated carbohydrate antigen (CA) 19-9 level relative to a control or baseline measurement, or a combination thereof. In some aspects, the method of detecting pancreatic cancer may comprise identifying a symptom of a subject such as jaundice, abdominal pain, gallbladder or liver enlargement, a blood clot, digestion problems, or depression, or a combination thereof. Any of these aspects may be used in identifying a subject at risk of having pancreatic cancer.

The cancer may include liver cancer. In some aspects, the cancer to be detected by the methods described herein can be liver cancer. The liver cancer may be early stage liver cancer. In other aspects, the liver cancer may be late stage liver cancer. In some cases, the liver cancer can be stage I, II, III, or IV liver cancer. In some instances, the stage of the liver cancer is unknown. Non-invasively obtained samples can be used for cancer diagnosis by generating data and identifying patterns in the data that associate with the cancer such as liver cancer. In certain aspects, the method of detecting a cancer may comprise additional screening or diagnosing methods such as a dynamic contrast computed tomography (CT) scan indicative of liver cancer, having a magnetic resonance imaging (MRI) scan indicative of liver cancer, having a liver function test (LFT) indicative of liver cancer, having an elevated bilirubin level relative to a control or baseline measurement, having an elevated aminotransferase level relative to a control or baseline measurement, having an elevated alkaline phosphatase level relative to a control or baseline measurement, having hypoalbuminemia, having an elevated prothrombin time relative to a control or baseline measurement, having an elevated alpha-fetoprotein level relative to a control or baseline measurement, or having a liver nodule, or a combination thereof. In some aspects, the method of detecting a cancer may comprise identifying symptoms of a subject such as abdominal discomfort, pain, and tenderness, jaundice, white, chalky stools, nausea, vomiting, bruising, or bleeding easily, weakness, or fatigue, or a combination thereof. Any of these aspects may be used in identifying a subject at risk of having liver cancer.

The cancer may include ovarian cancer. In some aspects, the cancer to be detected by the methods described herein can be ovarian cancer. The ovarian cancer may be early stage ovarian cancer. In other aspects, the ovarian cancer may be late stage ovarian cancer. In some cases, the stage of the ovarian cancer may be unknown. In some aspects, the stage of the ovarian cancer may be stage I, II, III, or IV. Non-invasively obtained samples can be used for cancer diagnosis by generating data and identifying patterns in the data that associate with the cancer such as ovarian cancer. In certain aspects, the method of detecting a cancer may comprise additional screening or diagnosing methods such as a computed tomography (CT) scan indicative of ovarian cancer, having a magnetic resonance imaging (MRI) scan indicative of ovarian cancer, having a positron emission tomography (PET) scan indicative of ovarian cancer, having a transvaginal ultrasound indicative of ovarian cancer, having an elevated cancer antigen (CA)-125 level relative to a control or baseline measurement, or having an ovarian cyst, or a combination thereof. In some aspects, the method of detecting cancer may comprise identifying a symptom in a subject such as a heavy feeling in the pelvis, pain in the lower abdomen, bleeding from the vagina, weight gain, weight loss, abnormal periods, unexplained back pain that worsens over time, an increase in urination, gas, nausea, vomiting, or loss of appetite, or a combination thereof. Any of these aspects may be used in identifying a subject at risk of having ovarian cancer.

The cancer may include colon cancer or colorectal cancer (CRC). In some aspects, the cancer to be detected by the methods described herein can be colon cancer. The colon cancer may be early-stage colon cancer. In other aspects, the colon cancer may be late stage colon cancer. Non-invasively obtained samples can be used for cancer diagnosis by generating data and identifying patterns in the data that associate with the cancer such as colon cancer. Diagnosis of cancer may be improved by obtaining proteomic data. In certain aspects, the method of detecting a cancer may comprise additional screening or diagnosing methods such as computed tomography (CT) scan for indication of colon cancer, a liver function test (LFT) for indication of colon cancer, measuring carcinoembryonic antigen (CEA) level relative to a control or baseline measurement, determining blood in a stool, performing a fecal immunochemical test (FIT), or a combination thereof. Any of these aspects may be used in identifying a subject at risk of having a colon cancer. For example, a subject identified as at risk of having colon cancer may be identified as at risk by one of these methods. The non-invasive methods described herein may save a patient who does not have colon cancer from undergoing further invasive testing or treatment procedures such as having a colonoscopy or cancer biopsy taken, or from undergoing a colon cancer treatment procedure. On the other hand, the non-invasive methods described herein may be used to identify a person who likely has colon cancer, and confirm that the patient should undergo further testing (e.g., invasive testing) or treatment procedures. Colon cancer may be an example of colorectal cancer (CRC). References or teachings herein related to colon cancer may be applied to CRC, or vice versa.

The cancer may include lung cancer. An example of lung cancer is non-small cell lung cancer (NSCLC). An example of lung cancer is small cell lung cancer. Disclosed are lung nodule diagnosis methods. The method may be useful for diagnosing, treating, or screening a patient with an identified lung nodule from a computed tomography (CT) scan who has not had a lung biopsy. The method may be useful for informing a medical practitioner regarding a probability of the lung nodule being benign or malignant. With test results from such a method, a medical practitioner may avoid unnecessarily biopsying the patient. For example, the method may be used as a rule-out test. With test results from such a method, a medical practitioner may identify a subject who should be biopsied. For example, the method may be used as a rule-in test.

Disclosed are diagnosis methods for identifying CT imaging candidates. The method may be useful for diagnosing, treating, or screening a patient who may be a CT imaging candidate. The method may be useful for a higher-risk patient (e.g., as defined by USPSTF or another body) who is a candidate for but has not received a CT scan for lung cancer screening. The method may inform a medical practitioner of a probability of the patient having a lung cancer. The method may therefore inform the medical practitioner of an urgency or need to obtain a CT scan of the patient's lungs. Such a method may be useful for high risk patients such as patients who are non-compliant to other CT screening methods. The method may improve selection or compliance of a patient for CT imaging. The method may improve selection or compliance of a patient for biopsy.

Disclosed are methods for recurrent monitoring. The method may be useful for monitoring a patient with a potentially resectable lung cancer. The method may be useful for monitoring a patient that has a post-surgical therapy intervention. The method may be useful for monitoring a patient that has an adjuvant chemotherapy or radiotherapy intervention. The method may be useful for detecting cancer recurrence before a CT scan or other medical imaging. The method may be useful for surveillance testing for recurrence. The method may be tailored or developed in partnership with a patient treatment method.

Described herein is a method, comprising: assaying proteins in a biofluid sample obtained from a subject having or suspected of having a lung nodule to obtain protein measurements; and applying a classifier to the protein measurements, thereby identifying the protein measurements as indicative of the lung nodule being cancerous or non-cancerous, wherein the classifier is generated using proteomic data obtained by contacting training samples with particles such that the particles adsorb proteins in the training samples, and assaying the proteins adsorbed to the particles. The method may be useful for cancer diagnosis or screening.

Described herein is a method, comprising: obtaining a biofluid sample of a subject having a lung nodule; contacting the biofluid sample with particles such that the particles adsorb biomolecules comprising proteins to the particles; assaying the biomolecules adsorbed to the particles to generate proteomic data; and classifying the proteomic data as indicative of the lung nodule being cancerous or non-cancerous. The method may be useful for cancer diagnosis or screening.

Described herein are methods for determining lung nodule-related state in a sample obtained from a subject. In some embodiments, the lung nodule-related state includes the presence or absence of a lung nodule in the subject. In some embodiments, the lung nodule-related state includes determining whether the lung nodule is benign or malignant. In some embodiments, the method comprises screening for lung nodule-related state by assaying biomarkers in the sample obtained from the subject. In some embodiments, the biomarkers comprise at least one protein in the sample. In some embodiments, the sample is a biofluid sample. In some embodiments, the biofluid sample is contacted with a particle described herein to adsorb proteins in the biofluid sample. In some embodiments, the method comprises obtaining proteins measurements of the proteins in the sample. In some embodiments, the method comprises applying a classifier to the protein measurements, thereby identifying the protein measurements as indicative of the lung nodule being cancerous or non-cancerous. In some embodiments, the classifier is generated using proteomic data obtained by contacting training samples with particles such that the particles adsorb proteins in the training samples. The adsorbed proteins can then be assayed by the methods described herein. In some embodiments, the subject is suspected of having a lung nodule or is identified as having the lung nodule by imaging methods described herein. In some embodiments, a report is generated based on the identification of the protein measurements as indicative of the lung nodule being cancerous or non-cancerous. In some embodiments, the report indicates the likelihood or an indication that the lung nodule is cancerous or non-cancerous. In some embodiments, the report indicates that the lung nodule is cancerous. In some embodiments, the report indicates that the lung nodule comprises non-small-cell lung carcinoma (NSCLC). In some embodiments, the method described herein generates a classifier comprising features to indicate the protein measurements as indicative of the lung nodule being cancerous or non-cancerous. In some embodiments, the features comprise control protein measurements, mass spectra, m/z ratios, chromatography results, immunoassay results, or light or fluorescence intensities. In some embodiments, the classifier is trained using any one of the computation or machine leaning methods described herein.

Described herein, in some embodiments, are methods for recommending a lung cancer treatment for the subject when the subject is determined to have malignant lung nodule based on the analysis of the protein measurements described herein. In some embodiments, the protein measurements are classified as indicative of the lung nodule being cancerous.

Disclosed herein, in some aspects, are methods useful for diagnosing, screening, or treating a subject. Some aspects include assaying proteins in a biofluid sample obtained from a subject suspected of having a lung nodule to obtain protein measurements. Some aspects include applying a classifier to the protein measurements. Some aspects include identifying the protein measurements as indicative of the subject having the lung nodule. In some aspects, the classifier is generated using proteomic data obtained by contacting training samples with particles such that the particles adsorb proteins in the training samples and assaying the proteins adsorbed to the particles.

Disclosed herein, in some aspects, are methods useful for diagnosing, screening, or treating a subject. Some aspects include assaying proteins in a biofluid sample obtained from a subject suspected of having a lung cancer to obtain protein measurements. Some aspects include applying a classifier to the protein measurements. Some aspects include identifying the protein measurements as indicative of the subject having the lung cancer. In some aspects, the classifier is generated using proteomic data obtained by contacting training samples with particles such that the particles adsorb proteins in the training samples and assaying the proteins adsorbed to the particles.

Disclosed herein, in some aspects, are methods useful for diagnosing, screening, or treating a subject. Some aspects include obtaining a biofluid sample of a subject suspected of having a lung nodule. Some aspects include contacting the biofluid sample with particles such that the particles adsorb biomolecules comprising proteins to the particles. Some aspects include assaying the biomolecules adsorbed to the particles to generate proteomic data. Some aspects include, based on the proteomic data, classifying the proteomic data as indicative of the subject having the lung nodule or as not indicative of the subject having the lung nodule.

Disclosed herein, in some aspects, are methods useful for diagnosing, screening, or treating a subject. Some aspects include obtaining a biofluid sample of a subject suspected of having a lung cancer. Some aspects include contacting the biofluid sample with particles such that the particles adsorb biomolecules comprising proteins to the particles. Some aspects include assaying the biomolecules adsorbed to the particles to generate proteomic data. Some aspects include, based on the proteomic data, classifying the proteomic data as indicative of the subject having the lung cancer or as not indicative of the subject having the lung cancer.

Disclosed herein, in some aspects, are methods useful for monitoring a subject. Some aspects include obtaining a biofluid sample of a subject at risk of a lung cancer recurrence. Some aspects include contacting the biofluid sample with particles such that the particles adsorb biomolecules comprising proteins to the particles. Some aspects include assaying the biomolecules adsorbed to the particles to generate proteomic data. Some aspects include, based on the proteomic data, classifying the proteomic data as indicative of the subject having the lung cancer recurrence or as not indicative of the subject having the lung cancer recurrence. In some aspects, the subject has received a lung cancer treatment such as chemotherapy, radiotherapy, or surgery. In some aspects, the cancer may be resectable. In some aspects, the lung cancer comprises NSCLC.

In some cases, a lung nodule is described as malignant or cancerous. The terms, malignant and cancerous may be used interchangeably. A malignant or cancerous lung nodule may be referred to as a lung cancer, or vice versa. In some cases, a lung nodule is described as benign or non-cancerous. The terms, benign and non-cancerous may be used interchangeably.

Samples & Subjects

Some aspects relate to a subject. For example, a subject may be evaluated, or a sample from a subject may be evaluated using methods described herein. Multi-omic data may be generated from a sample of a subject.

The methods described herein may be used to identify a subject as likely or at risk to have a disease such as cancer. The subject may have lung cancer, pancreatic cancer, liver cancer, ovarian cancer, or colon cancer. The cancer may include adenocarcinoma, for example pancreatic adenocarcinoma. The subject may have the cancer. The subject may not have the cancer. The subject may have the pancreatic cancer, liver cancer, ovarian cancer, or colon cancer. The subject may not have the pancreatic cancer, liver cancer, ovarian cancer, or colon cancer. The subject may be at risk of having pancreatic cancer, liver cancer, ovarian cancer, or colon cancer. The subject may have a mass (e.g., nodule or cyst) in the pancreas. The subject may have a mass (e.g., nodule) in the liver. The liver cancer may include a hepatocellular carcinoma (HCC). The liver cancer may include stage I, stage II, stage III, or stage IV liver cancer. The subject may have a mass (e.g., nodule or cyst) in one or both ovaries. The ovarian cancer may include stage I, stage II, stage III, or stage IV ovarian cancer. The ovarian cancer may include stage III ovarian cancer. The ovarian cancer may include stage IV ovarian cancer. The subject may have a mass (e.g., nodule) in the colon. The subject may have a lung nodule. cancer. The subject may be at risk of having breast cancer. The subject may have a mass (e.g., nodule or cyst) in the breast.

A sample may be obtained from the subject for purposes of identifying a cancer in the subject. The subject may be suspected of having the cancer or as not having the cancer. The method may be used to confirm or refute the suspected cancer.

Data described herein may be generated from a sample of a subject. The sample may be a biofluid sample or a mass sample (e.g., an abnormal growth biopsied from the subject). Examples of biofluids include blood, serum, or plasma. The sample may include a blood sample. The sample may include a serum sample. The sample may include a plasma sample. One or more biofluid samples may comprise a blood, serum, or plasma sample. Other examples of biofluids include urine, tears, semen, milk, vaginal fluid, mucus, saliva, sweat, or cell homogenate.

A sample may be obtained from the subject for purposes of identifying a disease state in the subject. The subject may be suspected of having the disease state or as not having the disease state. The method may be used to confirm or refute the suspected disease state. In some aspects, a sample from the subject is used in determining whether a mass, nodule (e.g. a lung nodule), or cyst is cancerous or non-cancerous.

A biofluid sample may be obtained from a subject. For example, a blood, serum, or plasma sample may be obtained from a subject by a blood draw. Other ways of obtaining biofluid samples include aspiration or swabbing.

The biofluid sample may be cell-free or substantially cell-free. To obtain a cell-free or substantially cell-free biofluid sample, a biofluid may undergo a sample preparation method such as centrifugation and pellet removal.

A non-biofluid sample may be obtained from a subject or patient. For example, a sample may include a tissue sample. Some examples of organs or tissues that may be sampled include lung, colon, pancreatic, liver, breast, or ovarian tissue. The sample may include a mass taken from the organ or tissue of the subject. The mass may be suspected of being cancerous. The mass may include a nodule (e.g., a colon nodule or liver nodule). The mass may include a cyst (e.g., an ovarian cyst). The nodule or cyst may be identified by a physician as at a high risk or low risk of being cancerous prior to performing the methods described herein. The mass may be biopsied, for example by a needle biopsy procedure. A needle biopsy procedure may include insertion of a thin needle through the subject's abdomen and into the liver to obtain a tissue sample, which may then be examined under a microscope for signs of cancer. The sample may include a cell sample. The sample may include a homogenate of a cell or tissue. The sample may include a supernatant of a centrifuged homogenate of a cell or tissue.

The sample may include lung tissue. The sample may include colon tissue. The sample may include pancreatic tissue. The sample may include liver tissue. The sample may include breast tissue. The sample may include ovarian tissue. The tissue may be cancerous. The tissue may be non-cancerous. The tissue may be suspected of being cancerous. The tissue may be malignant. The tissue may be non-malignant. The tissue may be suspected of being malignant.

The sample (e.g., biofluid or tissue sample) can be obtained from the subject during any phase of a screening procedure, such as before, during, or after a stage shown in FIG. 3A. The sample can be obtained before or during a stage where the subject is a candidate for a biopsy, pancreatoscopy, or colonoscopy, for early detection of a disease. The sample can be obtained before or during a non-invasive work-up, an invasive work-up, treatment, a monitoring stage.

Data may be generated from a single sample, or from multiple samples. Data from multiple samples may be obtained from the same subject. In some cases, different data types are obtained from samples collected differently or in separate containers. A sample may be collected in a container that includes one or more reagents such as a preservation reagent or a biomolecule isolation reagent. Some examples of reagents include heparin, ethylenediaminetetraacetic acid (EDTA), citrate, an anti-lysis agent, or a combination of reagents. Samples from a subject may be collected in multiple containers that include different reagents, such as for preserving or isolating separate types of biomolecules. A sample may be collected in a container that does not include any reagent in the container. The samples may be collected at the same time (e.g., same hour or day), or at different times. A sample may be frozen, refrigerated, heated, or kept at room temperature.

The methods described herein may be used to identify a subject as likely to have a disease state or not. A disease state may include cancer, including pancreatic cancer, liver cancer, ovarian cancer, or colon cancer. Some aspects of the present disclosure include identifying whether a lung nodule of a subject is cancerous or non-cancerous. The lung nodule may be in the subject's lung. The subject may be identified as having the lung nodule. In some aspects, the subject has multiple lung nodules. The subject may have a lung cancer. The subject may be at risk of a lung cancer. The subject may have a lung complication. The subject may have a comorbidity described herein. The subject may have trouble breathing. The subject may have fluid in the lungs.

In some cases, the subject is monitored. For example, information about a likelihood of the subject having a disease state may be used to determine to monitor a subject without providing a treatment to the subject. In other circumstances, the subject may be monitored while receiving treatment to see if a disease state in the subject improves. In some aspects, a subject having a lung nodule may be monitored to determine progression of the lung nodule. A lung nodule in a subject may be monitored. A subject may be treated as described herein.

The subject may be a vertebrate. The subject may be a mammal. The mammal may include a rat, mouse, gerbil, guinea pig, or hamster. The mammal may include a fox, bear, dog, monkey, cow, pig, or sheep. The subject may be a primate. The primate may include an ape or monkey. The primate may include a chimpanzee, a lemur, a bonobo, an orangutan, or a baboon. The subject may be a human. The subject may be an adult (e.g. at least 18-years-old). The subject may be male. The subject may be female. The subject may have a disease state. For example, the subject may have a disease or disorder, a comorbidity of a disease or disorder, or may be healthy.

The methods described herein may include use of a sample such as a biological sample. For example, a method may include determining one or more biomarker measurements in the sample. The biological sample may be from a subject such as a subject with a lung nodule. The biological sample may include a blood sample that has had red blood cells removed. For example, the biological sample may comprise a plasma sample. The biological sample may comprise a serum sample. The biological sample may comprise blood or a blood constituent. The biological sample may comprise a blood sample. A sample described or used herein may be from a subject described herein, such as a subject with an identified lung nodule.

Samples consistent with the methods disclosed herein of assessing for the presence or absence of one or more biomarkers associated with presence or malignancy state of lung nodule. The subject may be a human or a non-human animal. Biological samples may be a biofluid. For example, the biofluid may be plasma, serum, CSF, urine, tear, cell lysates, tissue lysates, cell homogenates, tissue homogenates, nipple aspirates, fecal samples, synovial fluid and whole blood, or saliva. Samples can also be non-biological samples, such as water, milk, solvents, or anything homogenized into a fluidic state. Said biological samples can contain a plurality of proteins or proteomic data, which may be analyzed after adsorption of proteins to the surface of the various particle types in a panel and subsequent digestion of protein coronas. Proteomic data can comprise nucleic acids, peptides, or proteins. Any of the samples herein can contain a number of different analytes, which can be analyzed using the methods disclosed herein. The analytes can be proteins, peptides, small molecules, nucleic acids, metabolites, lipids, or any molecule that could potentially bind or interact with the surface of a particle type.

The sample may be a biofluid. A biological sample may comprise a biofluid sample such as cerebrospinal fluid (CSF), synovial fluid (SF), urine, plasma, serum, tear, crevicular fluid, semen, whole blood, milk, nipple aspirate, ductal lavage, vaginal fluid, nasal fluid, ear fluid, gastric fluid, pancreatic fluid, trabecular fluid, lung lavage, prostatic fluid, sputum, fecal matter, bronchial lavage, fluid from swabbing, bronchial aspirant, sweat, or saliva. A biofluid may be a fluidized solid, for example a tissue homogenate, or a fluid extracted from a biological sample. A biological sample may be, for example, a tissue sample or a fine needle aspiration (FNA) sample. A biological sample may be a cell culture sample. For example, a sample that may be used in the methods disclosed herein can either include cells grow in cell culture or can include acellular material taken from cell cultures. A biofluid may be a fluidized biological sample. For example, a biofluid may be a fluidized cell culture extract. A sample may be extracted from a fluid sample, or a sample may be extracted from a solid sample. For example, a sample may comprise gaseous molecules extracted from a fluidized solid (e.g., a volatile organic compound). In some aspects, the biofluid comprises blood, plasma, or serum.

A method consistent with the present disclosure may comprise collecting (e.g., isolating, enriching, or purifying) a species from biological sample. The species may be a biomolecule (e.g., a protein), a biomacromolecular structure (e.g., a peptide aggregate or a ribosome), a cell, or tissue. The species may be selectively collected from the biological sample. For example, a method may comprise isolating cancer cells from tissue (e.g., as a tissue biopsy) or from a biofluid (e.g., as a liquid biopsy) such as whole blood, plasma, or a buffy coat. The method may include a sample without cancer cells. The species may be treated prior to analysis. For example, a protein may be reduced and degraded, a nucleic acid may be separated from histones, or a cell may be lysed.

The biological samples may be obtained or derived from a human subject. The biological samples may be stored in a variety of storage conditions before processing, such as different temperatures (e.g., at room temperature, under refrigeration or freezer conditions, at 25° C., at 4° C., at −18° C., −20° C., or at −80° C.) or different suspensions (e.g., EDTA collection tubes, cell-free RNA collection tubes, or cell-free DNA collection tubes).

In some cases, a sample may be depleted prior to biomarker analysis. A sample may be depleted using a commercially available kit. For example, a kit that may be used to deplete a sample may be a spin column-based depletion kit, an albumin depletion kit, an immunodepletion kit, or an abundant protein depletion kit. Non-limiting examples of kits that may be used for sample depletion include a PureProteome™ Human Albumin/Immunoglobulin depletion kit (EMD Millipore Sigma), a ProteoPrep® Immunoaffinity Albumin & IgG Depletion Kit (Millipore Sigma), a Seppro® Protein Depletion kit (Millipore Sigma), Top 12 Abundant Protein Depletion Spin Columns (Pierce), or a Proteome Purify™ Immunodepletion Kit (R&D Systems). Depletion may remove a high concentration biomolecule from a sample. For example, a method may comprise removing albumin from a plasma sample prior to low concentration biomarker analysis. The sample may include depleted plasma.

Data Generation and Use

The methods disclosed herein may include obtaining data such as multi-omic data generated from one or more biofluid samples collected from a subject. The data may include biomolecule measurements such as protein measurements, transcript measurements, genetic material measurements, or metabolite measurements. Omic data may include any of the following: proteomic data, genomic data, transcriptomic data, or metabolomic data. This section includes some ways of generating each of these types of omic data. Methods of generating or analyzing omic data may also be applied to methods of generating or analyzing individual biomolecules or sets of biomolecules. Other types of omic data may also be generated. Descriptions of generating or analyzing omic data may be applied to methods of generating or analyzing individual biomolecules or sets of biomolecules that do not necessarily include omic data. Aspects described in relation to biomolecule data may be relevant to biomolecule measurements, or vice versa. The data may be labeled or identified as indicative of a disease or as not indicative of a disease. The data may be labeled or identified as indicative of pancreatic cancer, liver cancer, ovarian cancer, or colon cancer or as not indicative of pancreatic cancer, liver cancer, ovarian cancer, or colon cancer. The methods described herein may include obtaining the multi-omic measurements such as by performing an assay.

The methods described herein may include generating or using omic data. Omic data may include data on all biomolecules of a certain type such as proteins, transcripts, genetic material, or metabolites. Omic data may include data on a subset of the biomolecules. For example, omic data may include data on 500 or more, 750 or more, 1000 or more, 2500 or more, 5000 or more, 10,000 or more, 25,000 or more, biomolecules of a certain type. The methods described herein may include obtaining measurements of over 10, over 20, over 30, over 40, over 50, over 75, over 100, over 250, over 500, over 750, over 1000, over 1250, over 2500, over 5000, over 7500, over 10,000, over 12,500, over 15,000, over 17,500, over 20,000, over 22,500, or over 25,000 biomolecules of a certain type. The methods described herein may include obtaining measurements of less than 10, less than 20, less than 30, less than 40, less than 50, less than 75, less than 100, less than 250, less than 500, less than 750, less than 1000, less than 1250, less than 2500, less than 5000, less than 7500, less than 10,000, less than 12,500, less than 15,000, less than 17,500, less than 20,000, less than 22,500, or less than 25,000 biomolecules of a certain type. Any of the aforementioned numbers of biomolecules may be measured for each of multiple data types. Multi-omic comprises at least 100 measurements of each of the at least two types of omic data. Multi-omic comprises at least 500 measurements of each of the at least two types of omic data. Multi-omic comprises at least 1000 measurements of each of the at least two types of omic data. The data may relate to a presence, absence, or amount of a given biomolecule. Examples of data types may include lipid, protein, peptide, transcript, mRNA, miRNA, DNA sequence, methylation, or metabolite data.

other document were individually and separately indicated to be incorporated by reference for all purposes.

Deep proteome coverage is advantageous to a multiomics approach. New technologies and sample availability address historical challenges to scale proteomics. Some challenges include: access to large well-collected, annotated sample cohorts for specific clinical questions, technical challenges associated with plasma proteomics such as reproducibility, throughput and depth of coverage that may limit translation to the clinic, and reproducible measurement and integration of multi-omic datasets providing novel insights into cancer biology.

The concepts described herein may help address some of these challenges. For example, the use of particles or the inclusion of additional omic types may address these concerns.

Disclosed herein are methods for multi-omic analysis. "Multi-omic(s)" or "multiomic(s)" may include an analytical approach for analyzing biomolecules at a large scale, wherein the data sets are multiple omes, such as proteome, genome, transcriptome, lipidome, and metabolome. Non-limiting examples of multi-omic data may include proteomic data, genomic data, lipidomic data, glycomic data, transcriptomic data, or metabolomics data. "Biomolecule" in "biomolecule corona" can refer to any molecule or biological component that can be produced by, or is present in, a biological organism. Non-limiting examples of biomolecules include proteins (protein corona), polypeptides, polysaccharides, a sugar, a lipid, a lipoprotein, a metabolite, an oligonucleotide, a nucleic acid (DNA, RNA, micro RNA, plasmid, single stranded nucleic acid, double stranded nucleic acid), metabolome, as well as small molecules such as primary metabolites, secondary metabolites, and other natural products, or any combination thereof. In some embodiments, the biomolecule is selected from the group of proteins, nucleic acids, lipids, and metabolites.

Some aspects that may be included in a multi-omic strategy include a well-defined disease biobank with multiple sample types optimized for the multi-omic measurements, development and optimization of novel proteomics technologies to increase proteome coverage and throughput without compromising reproducibility, or an unbiased multi-omics platform deploying state-of-the-art instrumentation and advanced machine learning analysis to transform complex early disease detection.

Proteomic Data

The data such as multi-omic data described herein may include protein data or proteomic data. Proteomic data may involve data about proteins, peptides, or proteoforms. This data may include just peptides or proteins, or a combination of both. An example of a peptide is an amino acid chain. An example of a protein is a peptide or a combination of peptides. For example, a protein may include one, two or more peptides bound together. A protein may be a secreted protein. Proteomic data may include data about various proteoforms. Proteoforms can include different forms of a protein produced from a genome with any variety of sequence variations, splice isoforms, or post-translational modifications. The proteomic data may be generated using an unbiased, non-targeted approach, or may include a specific set of proteins. Aspects described in relation to proteomic data may be relevant to protein data, or vice versa.

Proteomic data may include information on the presence, absence, or amount of various proteins, peptides. For example, proteomic data may include amounts of proteins. A protein amount may be indicated as a concentration or quantity of proteins, for example a concentration of a protein in a biofluid. A protein amount may be relative to another protein or to another biomolecule. Proteomic data may include information on the presence of proteins or peptides. Proteomic data may include information on the absence of proteins or peptides. Proteomic data may be distinguished by subtype, where each subtype includes a different type of protein, peptide, or proteoform.

Proteomic data generally includes data on a number of proteins or peptides. For example, proteomic data may include information on the presence, absence, or amount of 1000 or more proteins or peptides. In some cases, proteomic data may include information on the presence, absence, or amount of 5000, 10,000, 20,000, or more peptides, proteins, or proteoforms. Proteomic data may even include up to about 1 million proteoforms. Proteomic data may include a range of proteins, peptides, or proteoforms defined by any of the aforementioned numbers of proteins, peptides, or proteoforms. Some examples of proteins or peptides that may be included in proteomic data are shown in FIG. 6, FIG. 7, FIG. 10B, or FIG. 15.

In some aspects, the multi-omic data comprises measurements of over 10 peptides or protein groups, over 15 peptides or protein groups, over 20 peptides or protein groups, over 25 peptides or protein groups, over 30 peptides or protein groups, over 35 peptides or protein groups, over 40 peptides or protein groups, over 45 peptides or protein groups, over 50 peptides or protein groups, over 75 peptides or protein groups, over 100 peptides or protein groups, over 250 peptides or protein groups, over 500 peptides or protein groups, over 1,000 peptides or protein groups, over 2,500 peptides or protein groups, over 5,000 peptides or protein groups, over 10,000 peptides or protein groups, over 15,000 peptides or protein groups, or over 20,000 peptides or protein groups. In some aspects, the multi-omic data comprises measurements of at least about 10 peptides or protein groups, at least about 15 peptides or protein groups, at least about 20 peptides or protein groups, at least about 25 peptides or protein groups, at least about 30 peptides or protein groups, at least about 35 peptides or protein groups, at least about 40 peptides or protein groups, at least about 45 peptides or protein groups, at least about 50 peptides or protein groups, at least about 75 peptides or protein groups, at least about 100 peptides or protein groups, at least about 250 peptides or protein groups, at least about 500 peptides or protein groups, at least about 1,000 peptides or protein groups, at least about 2,500 peptides or protein groups, at least about 5,000 peptides or protein groups, at least about 10,000 peptides or protein groups, at least about 15,000 peptides or protein groups, or at least about 20,000 peptides or protein groups. In some aspects, the protein data comprises measurements of no greater than 10 peptides or protein groups, no greater than 15 peptides or protein groups, no greater than 20 peptides or protein groups, no greater than 25 peptides or protein groups, no greater than 30 peptides or protein groups, no greater than 35 peptides or protein groups, no greater than 40 peptides or protein groups, no greater than 45 peptides or protein groups, no greater than 50 peptides or protein groups, no greater than 75 peptides or protein groups, no greater than 100 peptides or protein groups, no greater than 250 peptides or protein groups, no greater than 500 peptides or protein groups, no greater than 1,000 peptides or protein groups, no greater than 2,500 peptides or protein groups, no greater than 5,000 peptides or protein groups, no greater than 10,000 peptides or protein groups, no greater than 15,000 peptides or protein groups, or no greater than 20,000 peptides or protein groups. The peptides or protein groups may comprise or consist of peptides. The peptides or protein groups may comprise or consist of protein groups.

A protein may also include a post-translational modification (PTM). An example of a PTM may include glycosylation. Proteins or peptides may include glycoproteins or glycopeptides. A protein may include a glycoprotein. A peptide may include a glycopeptide. An example of a PTM may include phosphorylation. Proteins or peptides may include phosphoproteins or phosphopeptides. A protein may include a phosphoprotein. A peptide may include a phosphopeptide.

Proteomic data may be generated by any of a variety of methods. Generating proteomic data may include using a detection reagent that binds to a peptide or protein and yields a detectable signal. After use of a detection reagent that binds to a peptide or protein and yields a detectable signal, a readout may be obtained that is indicative of the presence, absence or amount of the protein or peptide. Generating proteomic data may include concentrating, filtering, or centrifuging a sample.

Proteomic data may be generated using mass spectrometry, chromatography, liquid chromatography, high-performance liquid chromatography, solid-phase chromatography, a lateral flow assay, an immunoassay, an enzyme-linked immunosorbent assay, a western blot, a dot blot, or immunostaining, or a combination thereof. Some examples of methods for generating proteomic data include using mass spectrometry, a protein chip, or a reverse-phased protein microarray. Proteomic data may also be generated using an immunoassay such as an enzyme-linked immunosorbent assay, western blot, dot blot, or immunohistochemistry assay. Generating proteomic data may involve use of an immunoassay panel.

One way of obtaining proteomic data includes use of mass spectrometry. An example of a mass spectrometry method includes use of high resolution, two-dimensional electrophoresis to separate proteins from different samples in parallel, followed by selection or staining of differentially expressed proteins to be identified by mass spectrometry. Another method uses stable isotope tags to differentially label proteins from two different complex mixtures. The proteins within a complex mixture may be labeled isotopically and then digested to yield labeled peptides. Then the labeled mixtures may be combined, and the peptides may be separated by multidimensional liquid chromatography and analyzed by tandem mass spectrometry. A mass spectrometry method may include use of liquid chromatography-mass spectrometry (LC-MS), a technique that may combine physical separation capabilities of liquid chromatography (e.g., HPLC) with mass spectrometry.

Proteins may be enriched prior to assaying or measuring them. The enrichment may enrich one set of proteins and not another set, or may enrich a single protein and not another protein. Enrichment may be obtained through the use of an affinity reagent, for example by incubating the affinity reagent with a sample prior to measuring proteins in the sample. The affinity reagent may include an antibody. The affinity reagent may include a particle such as a nanoparticle. Proteins may be adsorbed to the affinity reagent, separated from the rest of the sample, and then assayed by using a proteomic assay described herein.

Generating proteomic data may include contacting a sample with particles such that the particles adsorb biomolecules comprising proteins. The adsorbed proteins may be part of a biomolecule corona. The adsorbed proteins may be measured or identified in generating the proteomic data.

Generating proteomic data may include the use of known amounts internal reference proteins. The reference proteins may be labeled. The label may include an isotopic label. Generating proteomic data may include the use of known amounts of isotopically labeled, internal reference proteins (referred to as "PiQuant"). The internal reference proteins may be spiked into a sample. The internal reference proteins may be used to identify mass spectra of individual endogenous proteins. The internal reference proteins may be used as standards for determining amounts of the individual endogenous proteins. Proteomic measurements may be generated based on amounts of proteins added into a sample of the one or more biofluid samples. Proteomic measurements may be generated based on amounts of labeled proteins added into a sample of the one or more biofluid samples.

Transcriptomic Data

The data such as multi-omic data described herein may include transcript data or transcriptomic data. Transcriptomic data may involve data about nucleotide transcripts such as RNA. Examples of RNA include messenger RNA (mRNA), ribosomal RNA (rRNA), signal recognition particle (SRP) RNA, transfer RNA (tRNA), small nuclear RNA (snRNA), small nucleoar RNA (snoRNA), long noncoding RNA (lncRNA), microRNA (miRNA), noncoding RNA (ncRNA), or piwi-interacting RNA (piRNA), or a combination thereof. The RNA may include mRNA. The RNA may include miRNA. Transcriptomic data may be distinguished by subtype, where each subtype includes a different type of RNA or transcript. For example, mRNA data may be included in one subtype, and data for one or more types of small non-coding RNAs such as miRNAs or piRNAs may be included in another subtype. A miRNA may include a 5p miRNA or a 3p miRNA.

Transcriptomic data may include information on the presence, absence, or amount of various RNAs. For example, transcriptomic data may include amounts of RNAs. An RNA amount may be indicated as a concentration or number or RNA molecules, for example a concentration of an RNA in a biofluid. An RNA amount may be relative to another RNA or to another biomolecule. Transcriptomic data may include information on the presence of RNAs. Transcriptomic data may include information on the absence of RNA. Aspects described in relation to transcriptomic data may be relevant to transcript or RNA data, or vice versa.

Figure 10B:
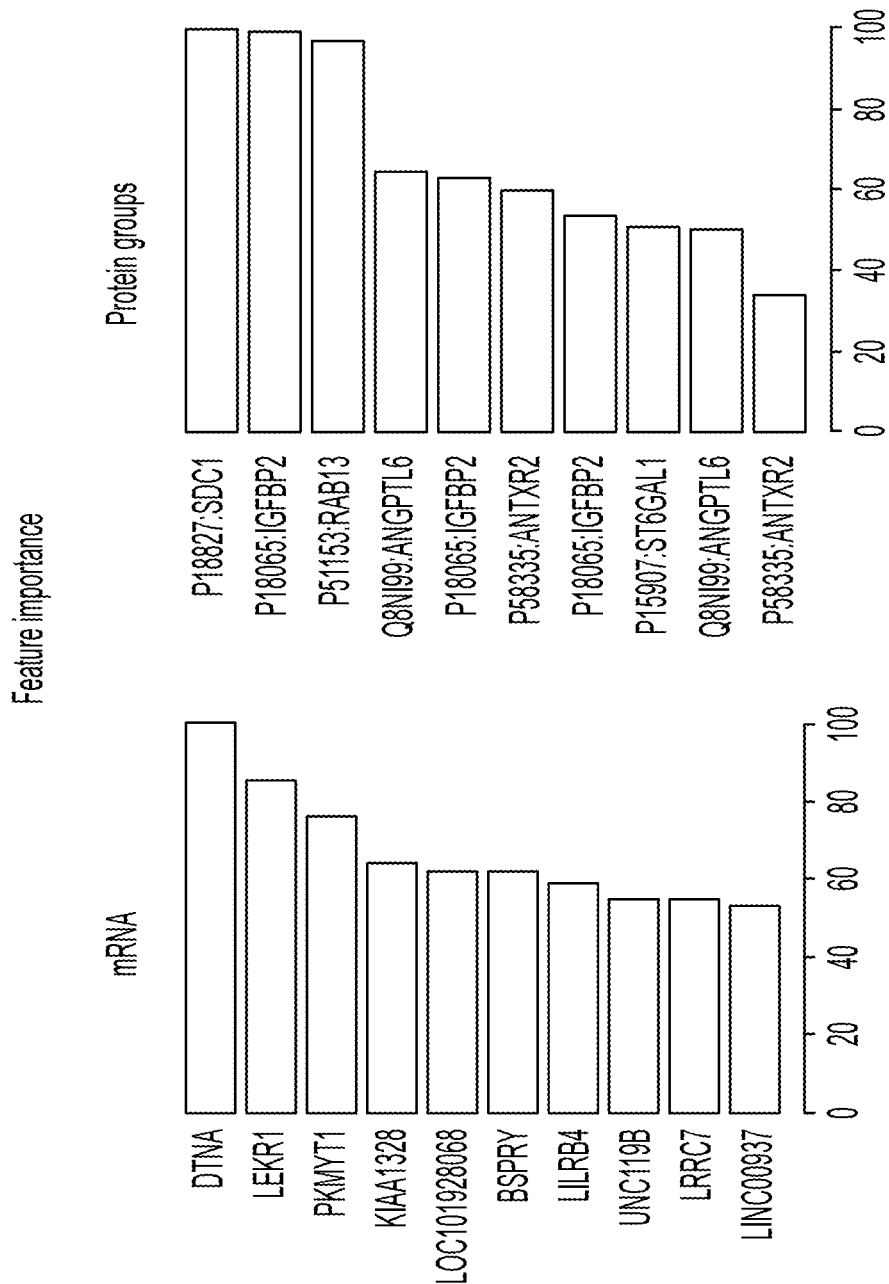
FIG. 10B shows differential mRNAs and proteins where abundances were measured in biofluid samples, and that were used to generate a classifier.
Figure 11A:
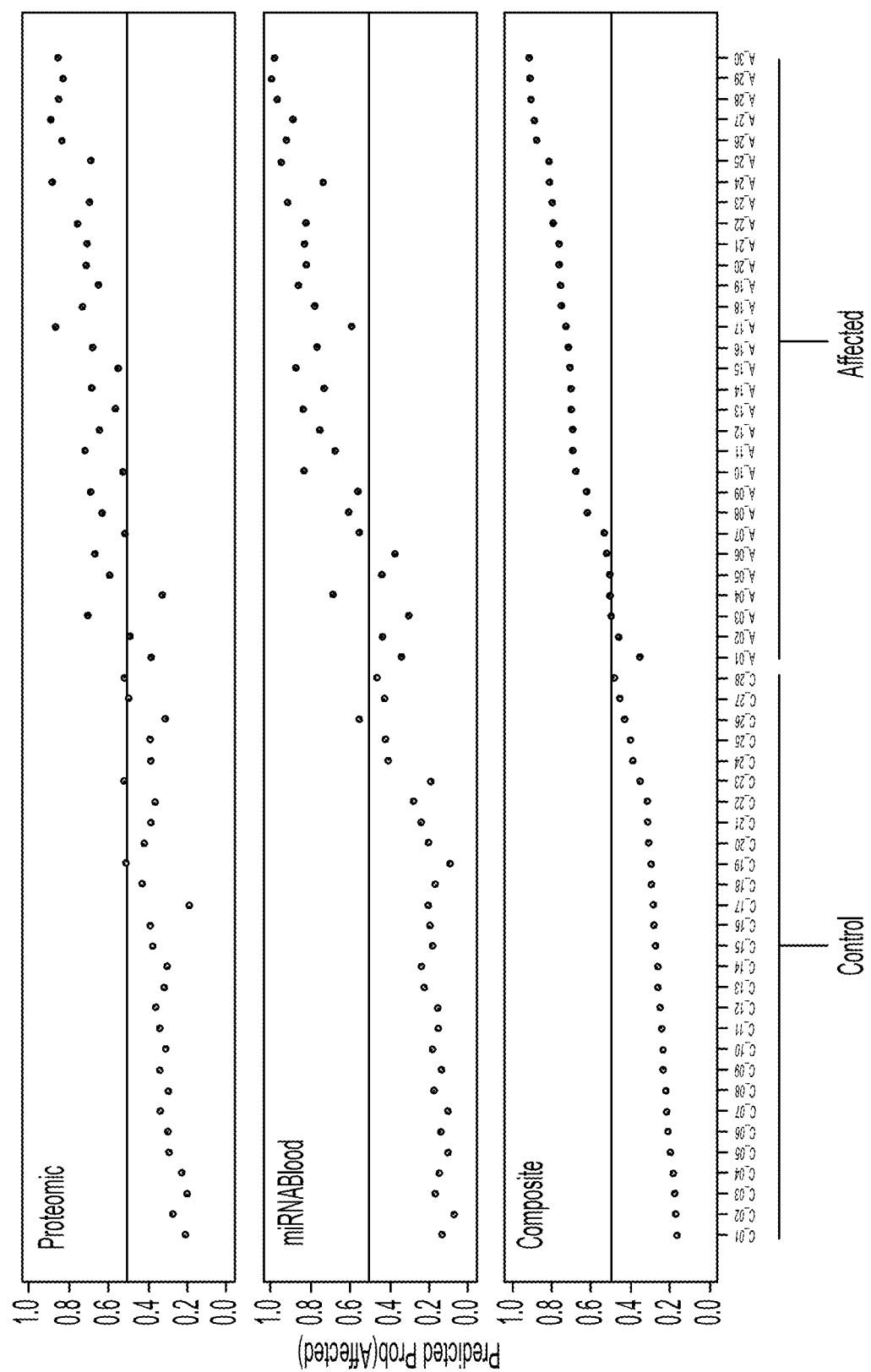
FIG. 11A shows analyses based on proteomic data and microRNA data. The top panel shows results of a classifier trained on proteomic data alone, the middle panel shows results of a classifier trained with microRNA data alone, and the bottom panel shows results of combining the two data types.
Figure 11B:
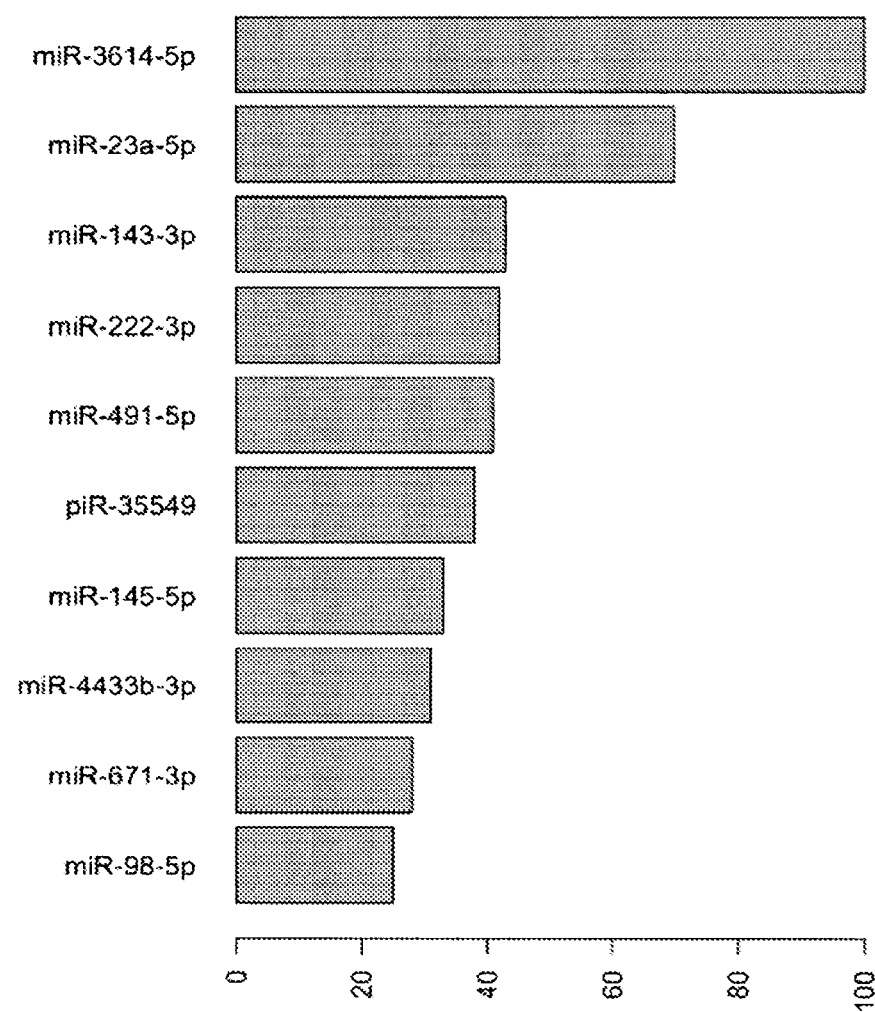
FIG. 11B shows differentially expressed microRNAs that were that used to generate a classifier.
Figure 15:
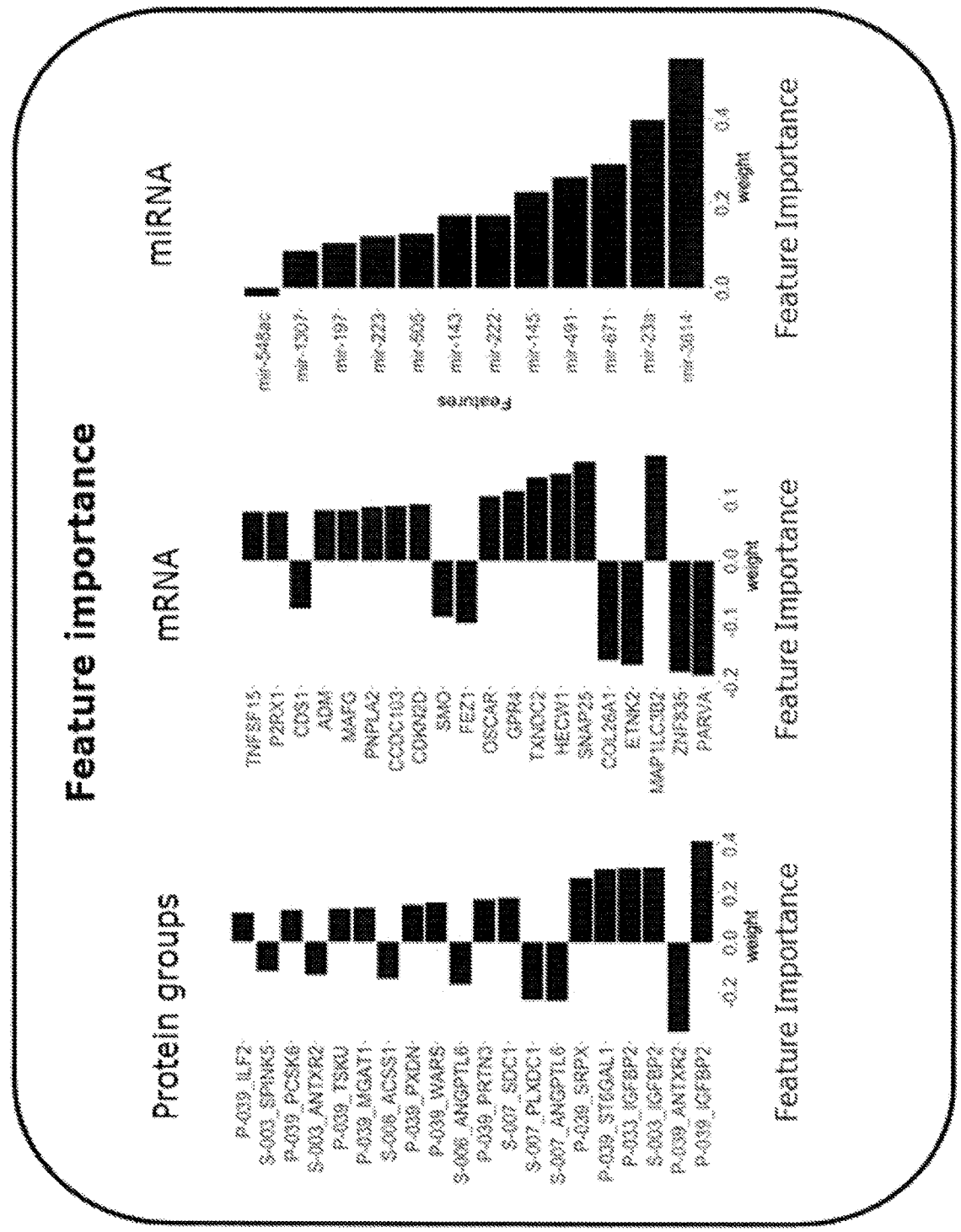
FIG. 15 charts some aspects of a transformation-based classification analysis.

Transcriptomic data generally includes data on a number of RNAs. For example, transcriptomic data may include information on the presence, absence, or amount of 1000 or more RNAs. In some cases, transcriptomic data may include information on the presence, absence, or amount of 5000, 10,000, 20,000, or more RNAs. Transcriptomic data may even include up to about 200,000 transcripts. Transcriptomic data may include a range of transcripts defined by any of the aforementioned numbers of RNAs or transcripts. Some examples of mRNAs that may be included in transcriptomic data are shown in FIG. 10B or FIG. 15. Some examples of microRNAs that may be included in transcriptomic data are shown in FIG. 11B or FIG. 15.

Some examples of mRNAs that may be used as biomarkers are shown in FIG. 10B. 1, 2, 3, 4, 5, 6, 7, 8, 9, or 10 of the mRNAs included in FIG. 10B may be used as biomarkers, for example in determining whether a lung nodule is cancerous or not, or in determining a likelihood of such. Some examples of microRNAs that may be used as biomarkers are shown in FIG. 11B. 1, 2, 3, 4, 5, 6, 7, 8, 9, or 10 of the microRNAs included in FIG. 11B may be used as biomarkers, for example in determining whether a lung nodule is cancerous or not, or in determining a likelihood of such.

Transcriptomic data may be generated by any of a variety of methods. Generating transcriptomic data may include using a detection reagent that binds to an RNA and yields a detectable signal. After use of a detection reagent that binds to an RNA and yields a detectable signal, a readout may be obtained that is indicative of the presence, absence, or amount of the RNA. Generating transcriptomic data may include concentrating, filtering, or centrifuging a sample.

Transcriptomic data may include RNA sequence data. Some examples of methods for generating RNA sequence data include use of sequencing, microarray analysis, hybridization, polymerase chain reaction (PCR), or electrophoresis, or a combination thereof. A microarray may be used for generating transcriptomic data. PCR may be used for generating transcriptomic data. PCR may include quantitative PCR (qPCR). Such methods may include use of a detectable probe (e.g., a fluorescent probe) that intercalates with double-stranded nucleotides, or that binds to a target nucleotide sequence. PCR may include reverse transcriptase quantitative PCR (RT-qPCR). Generating transcriptomic data may involve use of a PCR panel.

RNA sequence data may be generated by sequencing a subject's RNA or by converting the subject's RNA into DNA (e.g., complementary DNA (cDNA)) first and sequencing the DNA. Sequencing may include massive parallel sequencing. Examples of massive parallel sequencing techniques include pyrosequencing, sequencing by reversible terminator chemistry, sequencing-by-ligation mediated by ligase enzymes, or phospholinked fluorescent nucleotides or real-time sequencing. Generating transcriptomic data may include preparing a sample or template for sequencing. A reverse transcriptase may be used to convert RNA into cDNA. Some template preparation methods include use of amplified templates originating from single RNA or cDNA molecules, or single RNA or cDNA molecule templates. Examples of amplification methods include emulsion PCR, rolling circle, or solid-phase amplification.

In addition to any of the above methods, generating transcriptomic data may include contacting a sample with particles such that the particles adsorb biomolecules comprising RNA. The adsorbed RNA may be part of a biomolecule corona. The adsorbed RNA may be measured or identified in generating the transcriptomic data.

Genomic Data

The data such as multi-omic data described herein may include data on genetic material or genomic data. Genomic data may include data about genetic material such as nucleic acids or histones. The nucleic acids may include DNA. Genomic data may include information on the presence, absence, or amount of the genetic material. An amount of genetic material may be indicated as a concentration, absolute number, or may be relative. Aspects described in relation to genomic data may be relevant to nucleic acid or DNA data, or vice versa. Nucleic acid data may include RNA data, or genomic data may include transcriptomic data.

Genomic data may include DNA sequence data. The sequence data may include gene sequences. For example, the genomic data may include sequence data for up to about 20,000 genes. The genomic data may also include sequence data for non-coding DNA regions. DNA sequence data may include information on the presence, absence, or amount of DNA sequences. The DNA sequence data may include information on the presence or absence of a mutation such as a single nucleotide polymorphism. The DNA sequence data may include DNA measurement of an amount of mutated DNA, for example a measurement of mutated DNA from cancer cells.

Genomic data may include epigenetic data. Examples of epigenetic data include DNA methylation data, DNA hydroxymethylation data, or histone modification data. Epigenetic data may include DNA methylation or hydroxymethylation. DNA methylation or hydroxymethylation may be measured in whole or at regions within the DNA. Methylated DNA may include methylated cytosine (e.g., 5-methylcytosine). Cytosine is often methylated at CpG sites and may be indicative of gene activation.

Epigenetic data may include histone modification data. Histone modification data may include the presence, absence, or amount of a histone modification. Examples of histone modifications include serotonylation, methylation, citrullination, acetylation, or phosphorylation. Some specific examples of histone modifications may include lysine methylation, glutamine serotonylation, arginine methylation, arginine citrullination, lysine acetylation, serine phosphorylation, threonine phosphorylation, or tyrosine phosphorylation. Histone modifications may be indicative of gene activation.

Genomic data may be distinguished by subtype, where each subtype includes a different type of genomic data. For example, DNA sequence data may be included in another subtype, and epigenetic data may be included in one subtype, or different types of epigenetic data may be included in different subtypes.

Genomic data may be generated by any of a variety of methods. Generating genomic data may include using a detection reagent that binds to a genetic material such as DNA or histones and yields a detectable signal. After use of a detection reagent that binds to genetic material and yields a detectable signal, a readout may be obtained that is indicative of the presence, absence, or amount of the genetic material. Generating genomic data may include concentrating, filtering, or centrifuging a sample.

Some examples of methods for generating DNA sequence data include use of sequencing, microarray analysis (e.g., a SNP microarray), hybridization, polymerase chain reaction, or electrophoresis, or a combination thereof. DNA sequence data may be generated by sequencing a subject's DNA. Sequencing may include massive parallel sequencing. Examples of massive parallel sequencing techniques include pyrosequencing, sequencing by reversible terminator chemistry, sequencing-by-ligation mediated by ligase enzymes, or phospholinked fluorescent nucleotides or real-time sequencing. Generating genomic data may include preparing a sample or template for sequencing. Some template preparation methods include use of amplified templates originating from single DNA molecules, or single DNA molecule templates. Examples of amplification methods include emulsion PCR, rolling circle, or solid-phase amplification.

DNA methylation can be detected by use of mass spectrometry, methylation-specific PCR, bisulfite sequencing, a HpaII tiny fragment enrichment by ligation-mediated PCR assay, a GlaI hydrolysis and ligation adapter dependent PCR assay, a chromatin immunoprecipitation (ChIP) assay combined with a DNA microarray (a ChIP-on-chip assay), restriction landmark genomic scanning, methylated DNA immunoprecipitation, pyrosequencing of bisulfite treated DNA, a molecular break light assay for DNA adenine methyltransferase activity, methyl sensitive Southern blotting, methylCpG binding proteins, high resolution melt analysis, a methylation sensitive single nucleotide primer extension assay, another methylation assay, or a combination thereof.

Histone modifications may be detected by using mass spectrometry or an immunoassay, an enzyme-linked immunosorbent assay, a western blot, a dot blot, or immunostaining, or a combination thereof.

In addition to any of the above methods, generating genomic data may include contacting a sample with particles such that the particles adsorb biomolecules comprising genetic material. The adsorbed genetic material may be part of a biomolecule corona. The adsorbed genetic material may be measured or identified in generating the genomic data.

FIG. 23 provides aspects that may relate to transcriptomic or genomic data. Data may include circulating free DNA (cfDNA) methylation, mRNA, miRNA, circulating free miRNA (cf-miRNA), or whole exome sequencing data. Any sample type, isolation method, quality control (QC) aspect, or sequencing depth provided in the figure may be included. Any aspect shown in the figure may be included in, or used to generate, data such as multi-omic data.

Lipidomic Data

The data such as multi-omic data described herein may include lipid data or lipidomic data. Lipidomic data may include information on the presence, absence, or amount of various lipids. For example, lipidomic data may include amounts of lipids. A lipid amount may be indicated as a concentration or quantity of lipids, for example a concentration of a lipid in a biofluid. A lipid amount may be relative to another lipid or to another biomolecule. Lipidomic data may include information on the presence of lipids. Lipidomic data may include information on the absence of lipids. Lipid or lipidomic data may be included in metabolite or metabolomic data. Aspects described in relation to lipidomic data may be relevant to lipid data, or vice versa.

Many organisms contain complex arrays of lipids (for example, humans express over 600 types of lipids), whose relative expression can serve as a powerful marker for biological state and health determinations. Lipids are a diverse class of biomolecules which include fatty acids (e.g., long carbohydrates with carboxylate tail groups), di-, tri-, and poly-glycerides, phospholipids, prenols, sterols (e.g., cholesterol), and ladderanes, among many other types. While lipids are primarily found in membranes, free, protein-complexed, and nucleic acid-complexed lipids are typically present in a range of biofluids, and in some cases may be differentially fractionated from membrane bound lipids. For example, lipid-binding proteins (e.g., albumin) may be collected from a sample by immunohistochemical precipitation, and then chemically induced to release bound lipids for subsequent collection and detection.

Lipids may be an integral component in the development of diseases such as cancer. For example, lipids may be key players in cancer biology, as they may affect or be involved in feeding membrane and cell proliferation, lipotoxicity (where lipid content balance may aid in protection from lipotoxicity), empowering cellular processes, membrane biophysics, oncogenic signaling and metastasis, protection from oxidative stress, signaling in the microenvironment, or immune-modulation. Some lipid classes may be relevant to cancers, such as glycerophospholipids in hepatocellular carcinomas, glycerophospholipids and acylcarnitines in prostate cancer, choline containing lipids and phospholipids increase during metastasis, or sphingolipid regulation of cancer cell survival and death.

Lipid data may be generated from a sample after the sample has been treated to isolate or enrich lipids in the sample. Generating lipid data may include concentrating, filtering, or centrifuging a sample. Lipid analysis can comprise lipid fractionation. In many cases, lipids may be readily separated from other biomolecule types for lipid-specific analysis. As many lipids are strongly hydrophobic, organic solvent extractions and gradient chromatography methods can cleanly separate lipids from other biomolecule-types present within a sample. Lipid data may be generated using mass spectrometry. Lipid analysis may then distinguish lipids by class (e.g., distinguish sphingolipids from chlorolipids) or by individual type.

Lipidomic data may be generated by any of a variety of methods. Generating lipidomic data may include using a detection reagent that binds to a lipid and yields a detectable signal. After use of a detection reagent that binds to a lipid and yields a detectable signal, a readout may be obtained that is indicative of the presence, absence or amount of the lipid. Generating lipidomic data may include concentrating, filtering, or centrifuging a sample.

Lipidomic data may be generated using mass spectrometry, chromatography, liquid chromatography, high-performance liquid chromatography, solid-phase chromatography, a lateral flow assay, an immunoassay, an enzyme-linked immunosorbent assay, a western blot, a dot blot, or immunostaining, or a combination thereof. An example of a method for generating lipidomic data includes using mass spectrometry. Mass spectrometry may include a separation method step such as liquid chromatography (e.g., HPLC). Mass spectrometry may include an ionization method such as electron ionization, atmospheric-pressure chemical ionization, electrospray ionization, or secondary electrospray ionization. Mass spectrometry may include surface-based mass spectrometry or secondary ion mass spectrometry. Another example of a method for generating lipidomic data includes nuclear magnetic resonance (NMR). Other examples of methods for generating lipidomic data include Fourier-transform ion cyclotron resonance, ion-mobility spectrometry, electrochemical detection (e.g., coupled to HPLC), or Raman spectroscopy and radiolabel (e.g., when combined with thin-layer chromatography). Some mass spectrometry methods described for generating lipidomic data may be used for generating proteomic data, or vice versa. Lipidomic data may also be generated using an immunoassay such as an enzyme-linked immunosorbent assay, western blot, dot blot, or immunohistochemistry. Generating lipidomic data may involve use of a lipid panel.

In addition to any of the above methods, generating lipidomic data may include contacting a sample with particles such that the particles adsorb biomolecules comprising lipids. The adsorbed lipids may be part of a biomolecule corona. The adsorbed lipids may be measured or identified in generating the lipidomic data.

Generating lipidomic data may include the use of known amounts internal reference lipids. The reference lipids may be labeled. The label may include an isotopic label. Generating lipidomic data may include the use of known amounts of isotopically labeled, internal reference lipids. The internal reference lipids may be spiked into a sample. The internal reference lipids may be used to identify mass spectra of individual endogenous lipids. The internal reference lipids may be used as standards for determining amounts of the individual endogenous lipids. Lipidomic measurements may be generated based on amounts of lipids added into a sample of the one or more biofluid samples. Lipidomic measurements may be generated based on amounts of labeled lipids added into a sample of the one or more biofluid samples.

Lipids may have associations with biology of a disease such as cancer. Lipids may include phospholipids. Examples of phospholipids include phosphatidylethanolamine (PE), phosphatidylcholine (PC), phosphatidylinositol (PI), or phosphatidylglycerol (PG). Some phospholipids are components of cellular membrane and may play roles in cells such as chemical-energy storage, cellular signaling, cell membrane, or cellular interactions within tissue. A lipid may include a ceramide (CER). Ceramides may act as tumor suppressors, and may be a therapeutic pathway to target. For example, the efficacy of some chemotherapeutics and targeted therapies may be dictated by ceramide levels. A lipid may include a diacylglyceride (DAG). A lipid may include a triacylglyceride (TAG). A lipid may include a fatty acid (FA).

Examples of lipids may include PC(20:3_20:3)+AcO, Cer(d18:1/24:0)+H, GlcCer(d18:1/18:0+H, PI(18:0_18:3)–H, Aca(4:0)+H, GlcCer(d18:1/22:0+H, PC(18:2_20:5)+AcO, PC(14:0_18:2)+AcO, LPE(18:3)–H, Cer(d18:0/18:0)+H, DAG(18:1_22:6)+NH4, TAG(54:3_16:0)+NH4, Cer(d18:1/18:0)+H, PC(16:1_20:3)+AcO, LPC(17:0)+AcO, GlcCer(d18:1/24:1+H, DAG(18:1_20:2)+NH4, PE(P-18:0_18:2)+H, Cer(d18:0/24.0)+H, or PE(18:1_20:1)–H. Lipid data may include a measurement of 1, 2, 3, 4, 5, 6, 7, 8, 9, 10, 11, 12, 13, 14, 15, 16, 17, 18, 19 or 20 of these lipids.

Figure 27:
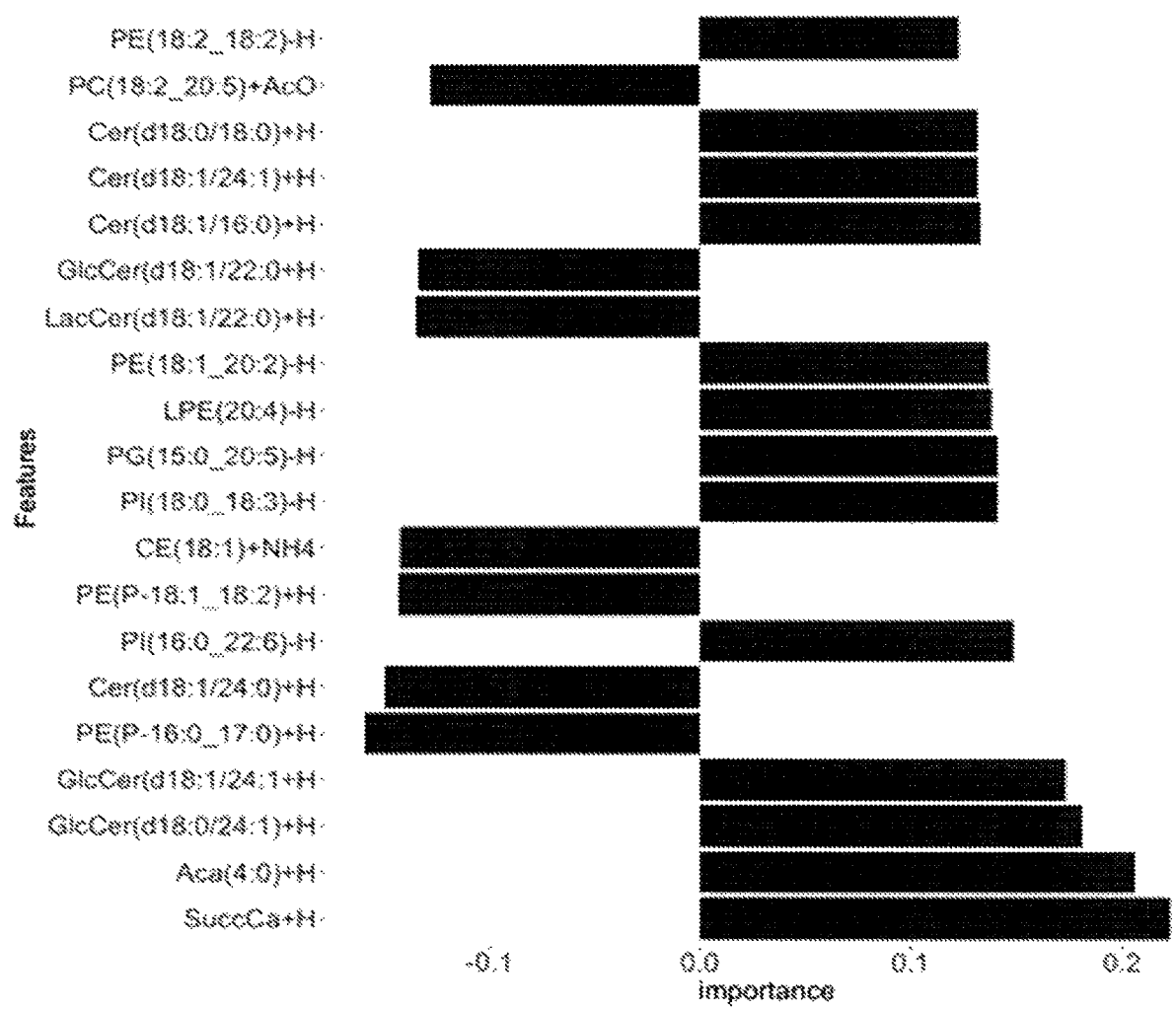
FIG. 27 includes a chart showing feature importance scores for a lipid classifier.

Examples of lipids may include any lipids in FIG. 27. Lipid data may include a measurement of 1, 2, 3, 4, 5, 6, 7, 8, 9, 10, 11, 12, 13, 14, 15, 16, 17, 18, 19, or 20 of these lipids, or a range of any of the aforementioned numbers of lipids from these figures.

Figure 33B:
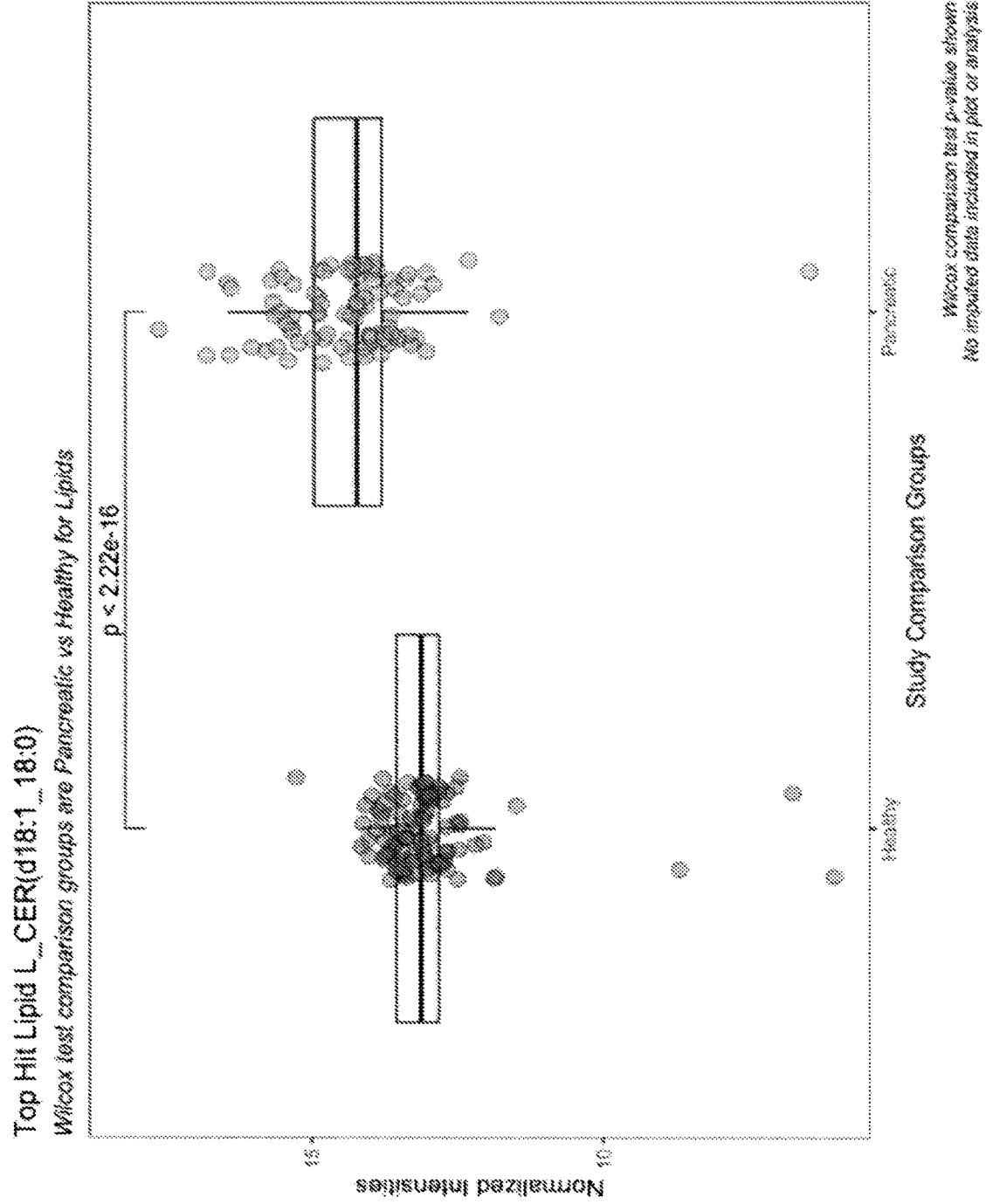
FIG. 33B includes data for top lipid CER(d18:1_18:0) after a lipidomic measurement.
Figure 36:
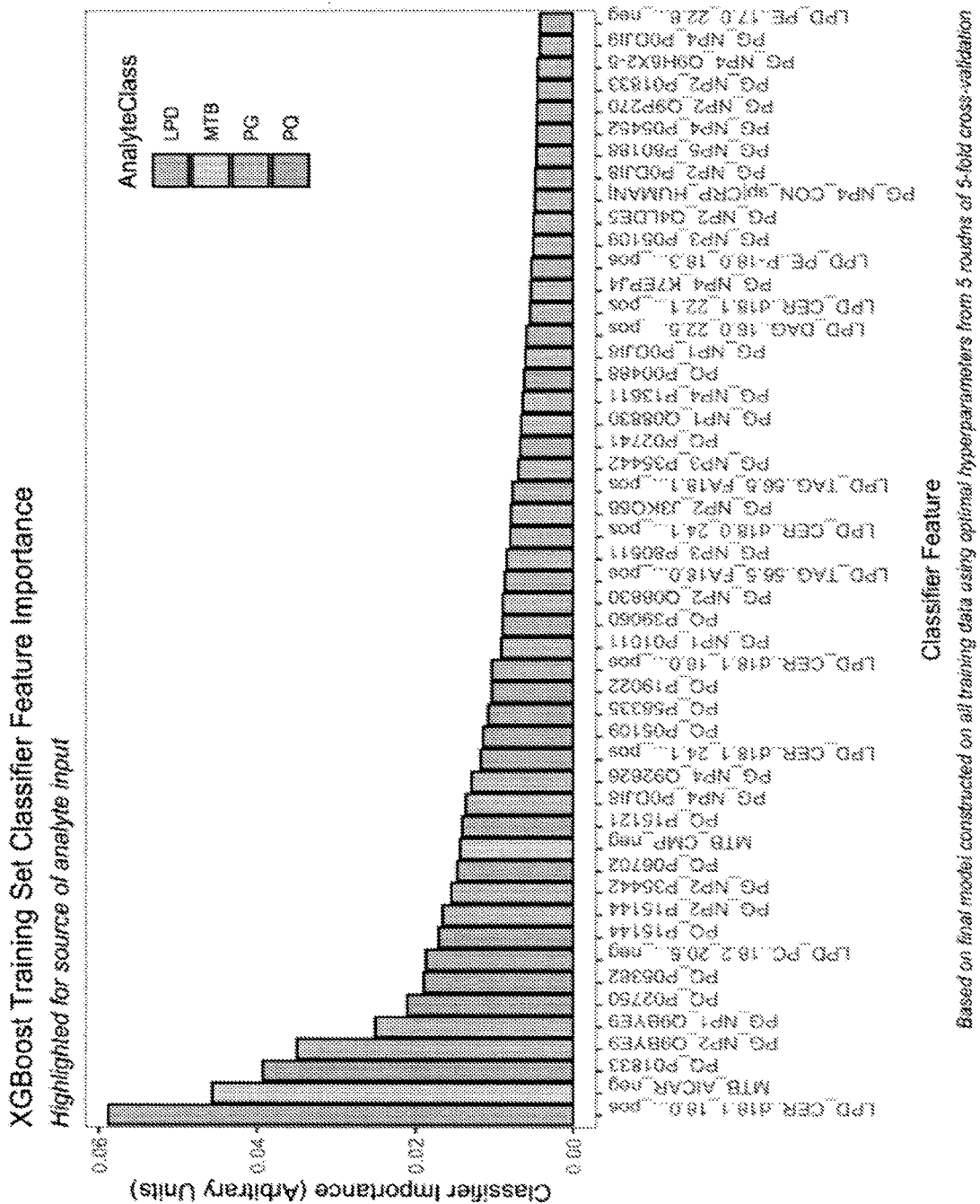
FIG. 36 protein, lipid, and metabolite features included in a classifier.

An example of a lipid is shown in FIG. 33A-33B. A lipid to be detected in a method described herein may include CER(d18:1_10:0). Some examples of lipids are shown in FIG. 36. A lipid to be detected in a method described herein may include CER(d18.1_18.0), PC(18.2_20.5), CER (d18.1_24.1), CER(d18.1_16.0), TAG(56.5_FA18.0), CER (d18.0_24.1), TAG(56.5_FA18.1), DAG(16.0_22.5), CER (d18.1_22.1), PE(P-18.0_18.3), or PE(17.0_22.6). Any number of the aforementioned lipids may be used. Any of the lipids may be used in a classifier.

A lipid measurement may be affected (e.g., decreased) in a sample from a subject having liver cancer relative to a lipid measurement from a control sample, or relative to a baseline measurement. The lipid measurement may include a phospholipid measurement. The lipid measurement may be useful for evaluating liver cancer. The lipid measurement may include a measurement of a lipid or phospholipid, or a combination of lipids or phospholipids, from FIG. 39F or FIG. 39G. The lipid measurement may be useful for evaluating ovarian cancer. The lipid measurement may include a measurement of a lipid or phospholipid, or a combination of lipids or phospholipids, from FIG. 39F or FIG. 40f. The lipid measurement may include a measurement of one or more of the following lipids: LPC.14.0 . . . AcO, LPC.15.0 . . . AcO, LPC.16.0 . . . AcO, LPC.16.1 . . . AcO, LPC.17.0 . . . AcO, LPC.18.0 . . . AcO, LPC.18.1 . . . AcO, LPC.18.2 . . . AcO, LPC.18.3 . . . AcO, LPC.20.2 . . . AcO, LPC.20.3 . . . AcO, LPC.20.4 . . . AcO, LPE.18.0 . . . . H, LPE.18.2 . . . . H, LPE.20.4 . . . . H, PA.18.0_18.2 . . . H, PC.14.0_18.2 . . . AcO, PC.14.0_18.3 . . . AcO, PC.14.0_20.2 . . . AcO, PC.14.0_20.3 . . . AcO, PC.14.0_20.4 . . . AcO, PC.14.0_22.5 . . . AcO, PC.14.0_22.6 . . . AcO, PC.15.0_18.2 . . . AcO, PC.15.0_20.3 . . . AcO, PC.15.0_20.4 . . . AcO, PC.16.0_20.3 . . . AcO, PC.16.1_20.3 . . . AcO, PC.16.1_20.4 . . . AcO, PC.18.0_18.2 . . . AcO, PC.18.0_20.3 . . . AcO, PC.18.1_20.3 . . . AcO, PC.18.1_20.4 . . . AcO, PC.18.1_22.4 . . . AcO, PC.18.1_22.5 . . . AcO, PC.18.2_18.2 . . . AcO, PC.18.2_18.3 . . . AcO, PC.18.2_20.3 . . . AcO, PC.18.2_20.4 . . . AcO, PC.18.2_20.5 . . . AcO, PC.20.2_20.3 . . . . ACO, PC.20.2_20.4 . . . AcO, PC.20.3_20.3 . . . AcO, PC.20.3_20.4 . . . AcO, PC.20.4_20.4 . . . AcO, PC.20.4_22.5 . . . AcO, PE.O.16.0_20.3 . . . H, PE.O.16.0_20.4 . . . H, PE.O.16.0_22.5 . . . H, or PI.18.1_20.4 . . . H, where "LPC" denotes lysophosphatidylcholine, "LPE" denotes lysophosphatidylethanolamine, "PA" denotes phosphatidic acid, "PC" denotes phosphatidylcholine, and "PE" denotes phosphatidylethanolamine. The combination of lipids or phospholipids may include 2, 3, 4, 5, 6, 7, 8, 9, 10, 15, 20, 25, 30, 35, 40, 45, or 50 of the lipids in FIG. 39F, or a range of lipids defined by any two of the aforementioned integers. The combination of lipids or phospholipids may include at least 1, at least 2, at least 3, at least 4, at least 5, at least 6, at least 7, at least 8, at least 9, at least 10, at least 15, at least 20, at least 25, at least 30, at least 35, at least 40, or at least 45, of the lipids in FIG. 39F. The combination of lipids or phospholipids may include less than 3, less than 4, less than 5, less than 6, less than 7, less than 8, less than 9, less than 10, less than 15, less than 20, less than 25, less than 30, less than 35, less than 40, less than 45, or less than 50, of the lipids in FIG. 39F. In some aspects, the combination of lipids does not include any one or more lipids in FIG. 39F or FIG. 39G. In some aspects, the combination of lipids does not include any one or more lipids in FIG. 39F or FIG. 40f.

Any of the following lipids may be useful for evaluating ovarian cancer: LPC.14.0 . . . AcO, LPC.15.0 . . . AcO, LPC.16.0 . . . AcO, LPC.16.1 . . . AcO, LPC.17.0 . . . AcO, LPC.18.0 . . . AcO, LPC.18.1 . . . AcO, LPC.18.2 . . . AcO, LPC.18.3 . . . AcO, LPC.20.2 . . . AcO, LPC.20.3 . . . AcO, or LPC.20.4 . . . AcO.

Any of the following lipids may be useful for evaluating liver cancer: LPC.14.0 . . . AcO, LPC.15.0 . . . AcO, LPC.16.0 . . . AcO, LPC.16.1 . . . AcO, LPC.17.0 . . . AcO, LPC.18.0 . . . AcO, LPC.18.1 . . . AcO, LPC.18.2 . . . AcO, LPC.18.3 . . . AcO, LPC.20.2 . . . AcO, LPC.20.3 . . . AcO, LPC.20.4 . . . AcO, LPE.18.0 . . . . H, LPE.18.2 . . . . H, LPE.20.4 . . . . H, PA.18.0_18.2 . . . . H, PC.14.0_18.2 . . . AcO, PC.14.0_18.3 . . . AcO, PC.14.0_20.2 . . . AcO, PC.14.0_20.3 . . . AcO, PC.14.0_20.4 . . . AcO, PC.14.0_22.5 . . . AcO, PC.14.0_22.6 . . . AcO, PC.15.0_18.2 . . . AcO, PC.15.0_20.3 . . . AcO, PC.15.0_20.4 . . . AcO, PC.16.0_20.3 . . . AcO, PC.16.1_20.3 . . . AcO, PC.16.1_20.4 . . . AcO, PC.18.0_18.2 . . . AcO, PC.18.0_20.3 . . . AcO, PC.18.1_20.3 . . . AcO, PC.18.1_20.4 . . . AcO, PC.18.1_22.4 . . . AcO, PC.18.1_22.5 . . . AcO, PC.18.2_18.2 . . . AcO, PC.18.2_18.3 . . . AcO, PC.18.2_20.3 . . . AcO, PC.18.2_20.4 . . . AcO, PC.18.2_20.5 . . . AcO, PC.20.2_20.3 . . . AcO, PC.20.2_20.4 . . . AcO, PC.20.3_20.3 . . . AcO, PC.20.3_20.4 . . . AcO, PC.20.4_20.4 . . . AcO, PC.20.4_22.5 . . . AcO, PE.O.16.0_20.3 . . . H, PE.O.16.0_20.4 . . . H, PE.O.16.0_22.5 . . . H, or PI.18.1_20.4 . . . H Metabolomic Data The data such as multi-omic data described herein may include metabolite data or metabolomic data. Metabolomic data may include information on small-molecule (e.g., less than 1.5 kDa) metabolites (such as metabolic intermediates, hormones or other signaling molecules, or secondary metabolites). Metabolomic data may involve data about metabolites. Metabolites may include are substrates, intermediates or products of metabolism. A metabolite may include a small molecule. A metabolite may be any molecule less than 1.5 kDa in size. Examples of metabolites may include sugars, lipids, amino acids, fatty acids, phenolic compounds, or alkaloids. Metabolomic data may be distinguished by subtype, where each subtype includes a different type of metabolite. Metabolomic data may include some lipid data. Metabolomic data may comprise lipidomic data. Aspects described in relation to metabolomic data may be relevant to metabolite data, or vice versa. Metabolomic data may include metabolite measurements. Metabolite measurements may include measurements of lipids such as phospholipids.

Metabolomic data may include information on the presence, absence, or amount of various metabolites. For example, metabolomic data may include amounts of metabolites. A metabolite amount may be indicated as a concentration or quantity of metabolites, for example a concentration of a metabolite in a biofluid. A metabolite amount may be relative to another metabolite or to another biomolecule. Metabolomic data may include information on the presence of metabolites. Metabolomic data may include information on the absence of metabolites.

Metabolomic data generally includes data on a number of metabolites. For example, metabolomic data may include information on the presence, absence, or amount of 1000 or more metabolites. In some cases, metabolomic data may include information on the presence, absence, or amount of 5000, 10,000, 20,000, 50,000, 100,000, 500,000, 1 million, 1.5 million, 2 million, or more metabolites, or a range of metabolites defined by any two of the aforementioned numbers of metabolites.

Metabolomic data may be generated by any of a variety of methods. Generating metabolomic data may include using a detection reagent that binds to a metabolite and yields a detectable signal. After use of a detection reagent that binds to a metabolite and yields a detectable signal, a readout may be obtained that is indicative of the presence, absence, or amount of the metabolite. Generating metabolomic data may include concentrating, filtering, or centrifuging a sample.

Metabolomic data may be generated using mass spectrometry, chromatography, liquid chromatography, high-performance liquid chromatography, solid-phase chromatography, a lateral flow assay, an immunoassay, an enzyme-linked immunosorbent assay, a western blot, a dot blot, or immunostaining, or a combination thereof. An example of a method for generating metabolomic data includes using mass spectrometry. Mass spectrometry may include a separation method step such as liquid chromatography (e.g., HPLC). Mass spectrometry may include an ionization method such as electron ionization, atmospheric-pressure chemical ionization, electrospray ionization, or secondary electrospray ionization. Mass spectrometry may include surface-based mass spectrometry or secondary ion mass spectrometry. Another example of a method for generating metabolomic data includes nuclear magnetic resonance (NMR). Other examples of methods for generating metabolomic data include Fourier-transform ion cyclotron resonance, ion-mobility spectrometry, electrochemical detection (e.g., coupled to HPLC), or Raman spectroscopy and radiolabel (e.g., when combined with thin-layer chromatography). Some mass spectrometry methods described for generating metabolomic data may be used for generating proteomic data, or vice versa. Metabolomic data may also be generated using an immunoassay such as an enzyme-linked immunosorbent assay, western blot, dot blot, or immunohistochemistry. Generating metabolomic data may involve use of a lipid panel.

In addition to any of the above methods, generating metabolomic data may include contacting a sample with particles such that the particles adsorb biomolecules comprising metabolites. The adsorbed metabolites may be part of a biomolecule corona. The adsorbed metabolites may be measured or identified in generating the metabolomic data.

Generating metabolomic data may include the use of known amounts internal reference metabolites. The reference metabolites may be labeled. The label may include an isotopic label. Generating metabolomic data may include the use of known amounts of isotopically labeled, internal reference metabolites. The internal reference metabolites may be spiked into a sample. The internal reference metabolites may be used to identify mass spectra of individual endogenous metabolites. The internal reference metabolites may be used as standards for determining amounts of the individual endogenous metabolites. Metabolomic measurements may be generated based on amounts of metabolites added into a sample of the one or more biofluid samples. Metabolomic measurements may be generated based on amounts of labeled metabolites added into a sample of the one or more biofluid samples.

An example of a metabolite is shown in FIG. 34A-34B. A metabolite to be detected in a method described herein may include 5-Aminoimidazole-4-carboxamide ribonucleotide (AICAR). The metabolite may include a nucleotide such as a monophosphate nucleotide. Some examples of metabolites are shown in FIG. 36. A metabolite to be detected in a method described herein may include cytidine monophosphate (CMP). The metabolite may include AICAR or CMP. Metabolites to be detected may include AICAR and CMP. Any number of the aforementioned metabolites may be used. Any of the metabolites may be used in a Use of Particles Samples may be contacted with particles, for example prior to generating data. The data described herein may generated using particles. For example, a method may include contacting a sample with particles such that the particles adsorb biomolecules. The particles may attract different sets of biomolecules than would normally be measured accurately by performing an omics measurement directly on a sample. For example, a dominant biomolecule may make up a large percentage of certain type of biomolecules (e.g., proteins, transcripts, genetic material, or metabolites) in a sample. For example, one protein may make up a large portion of proteins in circulation that is collected by blood sampling. By adhering biomolecules to particles prior to analyzing the biomolecules, a subset of biomolecules may be obtained that does not include the dominant biomolecule. Removing dominant biomolecules in this way may increase the accuracy of biomolecule measurements and sensitivity of an analysis using those measurements.

Examples of biomolecules that may be adsorbed to particles include proteins, transcripts, genetic material, or metabolites. The adsorbed biomolecules may make up a biomolecule corona around the particle. The adsorbed biomolecules may be measured or identified in generating data such as omic data (e.g., proteomic data). In some aspects, the proteomic measurements are generated from proteins adsorbed to nanoparticles. The nanoparticles may enrich the proteins, or may enrich other biomolecule types.

Particles can be made from various materials. Such materials may include metals, magnetic particles, polymers, or lipids. A particle may be made from a combination of materials. A particle may comprise layers of different materials. The different materials may have different properties. A particle may include a core comprising one material, and be coated with another material. The core and the coating may have different properties.

A particle may include a metal. For example, a particle may include gold, silver, copper, nickel, cobalt, palladium, platinum, iridium, osmium, rhodium, ruthenium, rhenium, vanadium, chromium, manganese, niobium, molybdenum, tungsten, tantalum, iron, or cadmium, or a combination thereof.

A particle may be magnetic (e.g., ferromagnetic or ferrimagnetic). A particle comprising iron oxide may be magnetic. A particle may include a superparamagnetic iron oxide nanoparticle (SPION).

A particle may include a polymer. Examples of polymers include polyethylenes, polycarbonates, polyanhydrides, polyhydroxyacids, polypropylfumerates, polycaprolactones, polyamides, polyacetals, polyethers, polyesters, poly(orthoesters), polycyanoacrylates, polyvinyl alcohols, polyurethanes, polyphosphazenes, polyacrylates, polymethacrylates, polycyanoacrylates, polyureas, polystyrenes, or polyamines, a polyalkylene glycol (e.g., polyethylene glycol (PEG)), a polyester (e.g., poly(lactide-co-glycolide) (PLGA), polylactic acid, or polycaprolactone), or a copolymer of two or more polymers, such as a copolymer of a polyalkylene glycol (e.g., PEG) and a polyester (e.g., PLGA). A particle may be made from a combination of polymers.

A particle may include a lipid. Examples of lipids include dioleoylphosphatidylglycerol (DOPG), diacylphosphatidylcholine, diacylphosphatidylethanolamine, ceramide, sphingomyelin, cephalin, cholesterol, cerebrosides and diacylglycerols, dioleoylphosphatidylcholine (DOPC), dimyristoylphosphatidylcholine (DMPC), and dioleoylphosphatidylserine (DOPS), phosphatidylglycerol, cardiolipin, diacylphosphatidylserine, diacylphosphatidic acid, N-dodecanoyl phosphatidylethanolamines, N-succinyl phosphatidylethanolamines, N-glutarylphosphatidylethanolamines, lysylphosphatidylglycerols, palmitoyloleoylphosphatidylglycerol (POPG), lecithin, lysolecithin, phosphatidylethanolamine, lysophosphatidylethanolamine, dioleoylphosphatidylethanolamine (DOPE), dipalmitoyl phosphatidyl ethanolamine (DPPE), dimyristoylphosphoethanolamine (DMPE), distearoyl-phosphatidyl-ethanolamine (DSPE), palmitoyloleoyl-phosphatidylethanolamine (POPE) palmitoyloleoylphosphatidylcholine (POPC), egg phosphatidylcholine (EPC), distearoylphosphatidylcholine (DSPC), dioleoylphosphatidylcholine (DOPC), dipalmitoylphosphatidylcholine (DPPC), dioleoylphosphatidylglycerol (DOPG), dipalmitoylphosphatidylglycerol (DPPG), palmitoyloleyolphosphatidylglycerol (POPG), 16-O-monomethyl PE, 16-O-dimethyl PE, 18-1-trans PE, palmitoyloleoyl-phosphatidylethanolamine (POPE), 1-stearoyl-2-oleoyl-phosphatidyethanolamine (SOPE), phosphatidylserine, phosphatidylinositol, sphingomyelin, cephalin, cardiolipin, phosphatidic acid, cerebrosides, dicetylphosphate, or cholesterol. A particle may be made from a combination of lipids.

Further examples of materials include silica, carbon, carboxylate, polyacrylic acid, carbohydrates, dextran, polystyrene, dimethylamine, amines, or silanes. Some examples of particles include a carboxylate SPION, a phenol-formaldehyde coated SPION, a silica-coated SPION, a polystyrene coated SPION, a carboxylated Poly(styrene-co-methacrylic acid), P (St-co-MAA) coated SPION, a N-(3-Trimethoxysilylpropyl) diethylenetriamine coated SPION, a poly(N-(3-(dimethylamino) propyl) methacrylamide) (PDMAPMA)-coated SPION, a 1,2,4,5-Benzenetetracarboxylic acid coated SPION, a poly(vinylbenzyltrimethylammonium chloride) (PVBTMAC) coated SPION, caboxylate coated with peracetic acid, a poly(oligo (ethylene glycol) methyl ether methacrylate) (POEGMA)-coated SPION, a polystyrene carboxyl functionalized particle, a carboxylic acid particle, a particle with an amino surface, a silica amino functionalized particle, a particle with a Jeffamine surface, or a silica silanol coated particle.

Particles of various sizes may be used. The particles may include nanoparticles. Nanoparticles may be from about 10 nm to about 1000 nm in diameter. For example, the nanoparticles can be at least 10 nm, at least 100 nm, at least 200 nm, at least 300 nm, at least 400 nm, at least 500 nm, at least 600 nm, at least 700 nm, at least 800 nm, at least 900 nm, from 10 nm to 50 nm, from 50 nm to 100 nm, from 100 nm to 150 nm, from 150 nm to 200 nm, from 200 nm to 250 nm, from 250 nm to 300 nm, from 300 nm to 350 nm, from 350 nm to 400 nm, from 400 nm to 450 nm, from 450 nm to 500 nm, from 500 nm to 550 nm, from 550 nm to 600 nm, from 600 nm to 650 nm, from 650 nm to 700 nm, from 700 nm to 750 nm, from 750 nm to 800 nm, from 800 nm to 850 nm, from 850 nm to 900 nm, from 100 nm to 300 nm, from 150 nm to 350 nm, from 200 nm to 400 nm, from 250 nm to 450 nm, from 300 nm to 500 nm, from 350 nm to 550 nm, from 400 nm to 600 nm, from 450 nm to 650 nm, from 500 nm to 700 nm, from 550 nm to 750 nm, from 600 nm to 800 nm, from 650 nm to 850 nm, from 700 nm to 900 nm, or from 10 nm to 900 nm in diameter. A nanoparticle may be less than 1000 nm in diameter. Some examples include diameters of about 50 nm, about 130 nm, about 150 nm, 400-600 nm, or 100-390 nm.

The particles may include microparticles. A microparticle may be a particle that is from about 1 μm to about 1000 μm in diameter. For example, the microparticles can be at least 1 μm, at least 10 μm, at least 100 μm, at least 200 μm, at least 300 μm, at least 400 μm, at least 500 μm, at least 600 μm, at least 700 μm, at least 800 μm, at least 900 μm, from 10 μm to 50 μm, from 50 μm to 100 μm, from 100 μm to 150 μm, from 150 μm to 200 μm, from 200 μm to 250 μm, from 250 μm to 300 μm, from 300 μm to 350 μm, from 350 μm to 400 μm, from 400 μm to 450 μm, from 450 μm to 500 μm, from 500 μm to 550 μm, from 550 μm to 600 μm, from 600 μm to 650 μm, from 650 μm to 700 μm, from 700 μm to 750 μm, from 750 μm to 800 μm, from 800 μm to 850 μm, from 850 μm to 900 μm, from 100 μm to 300 μm, from 150 μm to 350 μm, from 200 μm to 400 μm, from 250 μm to 450 μm, from 300 μm to 500 μm, from 350 μm to 550 μm, from 400 μm to 600 μm, from 450 μm to 650 μm, from 500 μm to 700 μm, from 550 μm to 750 μm, from 600 μm to 800 μm, from 650 μm to 850 μm, from 700 μm to 900 μm, or from 10 μm to 900 μm in diameter. A microparticle may be less than 1000 μm in diameter. Some examples include diameters of 2.0-2.9 μm.

The particles may include physiochemically distinct sets of particles (for example, 2 or more sets of physiochemically particles where 1 set of particles is physiochemically distinct from another set of particles. Examples of physiochemical properties include charge (e.g., positive, negative, or neutral) or hydrophobicity (e.g., hydrophobic or hydrophilic). The particles may include 2, 3, 4, 5, 6, 7, 8, 9, 10, 11, 12, 13, 14, 15, 16, 17, 18, 19, 20, or more sets of particles, or a range of sets of particles including any of said numbers of sets of particles Particles and Types A disease detection method may include use of particles. The methods described herein may include contacting the biological sample with the physiochemically distinct particles to form the biomolecule coronas. The biological sample may be from a subject identified as having a lung nodule. A particle may adsorb biomolecules from a biological sample, thereby forming a biomolecule corona on the surface of the particle. Upon contact with the biological sample, a particle may adsorb a plurality of peptides, proteins, nucleic acids, lipids, saccharides, small molecules (such as metabolites (native and foreign), terpenes, polyketides, and cyclic peptides), or any combination thereof. Accordingly, a method may comprise collecting a subset of biomolecules from a biological sample (e.g., a complex biological sample such as human plasma) on a particle, and analyzing the biomolecules collected on the particle, analyzing the biomolecules remaining in the biological sample, or analyzing the biomolecules collected on the particle and the biomolecules remaining in the biological sample. A biomolecule, a biomolecule corona, or a portion thereof may be eluted from a particle and into a solution prior to analysis. In some aspects, assaying the proteins comprises contacting the biofluid sample with particles such that the particles adsorb the proteins to the particles.

The relationship between particle properties and biomolecule corona composition can be leveraged to manipulate biomolecule collection from a sample. In some cases, a set of particle properties may favor binding of a particular biomolecule type, family, or superfamily. For example, humans express over 100 proteins from the Ras superfamily, which share a conserved GTP-binding motif within a 20 kilodalton (kDa) N-terminal domain. A particle or collection of particles (e.g., a mixture containing 5 types of particles) may be functionalized so as to favor Ras protein adsorption, and thus may be tuned to preferentially adsorb Ras proteins from complex biological samples, enabling their enrichment for further analysis.

A particle or a mixture of different particles may be tailored to broadly profile a sample. In many biological samples, a small number of biomolecules constitute the majority of biological material. For example, over 99% of the protein mass in human plasma is accounted for by just 20 of the roughly 3500 human plasma proteins. Analysis of such samples can be exceedingly challenging, as the small number of abundant biomolecules can saturate a detection or enrichment scheme. A particle or a collection of multiple particle types may be tuned to broadly profile complex biological, such that low abundance biomolecules are preferentially enriched over or along with high abundance biomolecules from complex biological samples. A particle or collection of multiple particle types may comprise similar binding affinities for a large number of biomolecules, thus favoring adsorption of a large number of biomolecules from a sample. A particle may comprise a low affinity for a high abundance or set of high abundance proteins in a sample, and may therefore preferentially adsorb and enrich low abundance biomolecules. A collection of particles may comprise particle types with affinities for different types or classes of biomolecules, such that the collection of particles adsorbs a broad range of biomolecules from the sample. Accordingly, the present disclosure provides a wide range of particle types with distinct physicochemical properties.

Particle types consistent with the methods disclosed herein can be made from various materials. For example, particle materials consistent with the present disclosure include metals, polymers, magnetic materials, and lipids. Magnetic particles may be iron oxide particles. Examples of metal materials include any one of or any combination of gold, silver, copper, nickel, cobalt, palladium, platinum, iridium, osmium, rhodium, ruthenium, rhenium, vanadium, chromium, manganese, niobium, molybdenum, tungsten, tantalum, iron and cadmium, or any other material described in U.S. Pat. No. 7,749,299, the contents of which are herein incorporated by reference in their entirety. A particle may be magnetic (e.g., ferromagnetic or ferrimagnetic). For example, a particle may comprise a superparamagnetic iron oxide nanoparticle (SPION).

The particles may include multiple physiochemically distinct particles (for example, 2 or more sets of physiochemically particles where 1 set of particles is physiochemically distinct from another set of particles. In some aspects, the particles comprise nanoparticles. In some aspects, the particles comprise physiochemically distinct groups of nanoparticles. The physiochemically distinct particles may comprise lipid particles, metal particles, silica particles, or polymer particles. The physiochemically distinct particles may comprise carboxylate particles, poly acrylic acid particles, dextran particles, polystyrene particles, dimethylamine particles, amino particles, silica particles, or N-(3-Trimethoxysilylpropyl) diethylenetriamine particles.

A particle may comprise a polymer. Examples of polymers include any one of or any combination of polyethylenes, polycarbonates, polyanhydrides, polyhydroxyacids, polypropylfumerates, polycaprolactones, polyamides, polyacetals, polyethers, polyesters, poly(orthoesters), polycyanoacrylates, polyvinyl alcohols, polyurethanes, polyphosphazenes, polyacrylates, polymethacrylates, polycyanoacrylates, polyureas, polystyrenes, or polyamines, a polyalkylene glycol (e.g., polyethylene glycol (PEG)), a polyester (e.g., poly(lactide-co-glycolide) (PLGA), polylactic acid, or polycaprolactone), or a copolymer of two or more polymers, such as a copolymer of a polyalkylene glycol (e.g., PEG) and a polyester (e.g., PLGA). The polymer may be a lipid-terminated polyalkylene glycol and a polyester, or any other material disclosed in U.S. Pat. No. 9,549,901, the contents of which are herein incorporated by reference in their entirety.

A particle may comprise a lipid. Examples of lipids that can be used to form the particles of the present disclosure include cationic, anionic, and neutrally charged lipids. For example, particles can be made of any one of or any combination of dioleoylphosphatidylglycerol (DOPG), diacylphosphatidylcholine, diacylphosphatidylethanolamine, ceramide, sphingomyelin, cephalin, cholesterol, cerebrosides and diacylglycerols, dioleoylphosphatidylcholine (DOPC), dimyristoylphosphatidylcholine (DMPC), and dioleoylphosphatidylserine (DOPS), phosphatidylglycerol, cardiolipin, diacylphosphatidylserine, diacylphosphatidic acid, N-dodecanoyl phosphatidylethanolamines, N-succinyl phosphatidylethanolamines, N-glutarylphosphatidylethanolamines, lysylphosphatidylglycerols, palmitoyloleoylphosphatidylglycerol (POPG), lecithin, lysolecithin, phosphatidylethanolamine, lysophosphatidylethanolamine, dioleoylphosphatidylethanolamine (DOPE), dipalmitoyl phosphatidyl ethanolamine (DPPE), dimyristoylphosphoethanolamine (DMPE), distearoyl-phosphatidyl-ethanolamine (DSPE), palmitoyloleoyl-phosphatidylethanolamine (POPE) palmitoyloleoylphosphatidylcholine (POPC), egg phosphatidylcholine (EPC), distearoylphosphatidylcholine (DSPC), dioleoylphosphatidylcholine (DOPC), dipalmitoylphosphatidylcholine (DPPC), dioleoylphosphatidylglycerol (DOPG), dipalmitoylphosphatidylglycerol (DPPG), palmitoyloleoylphosphatidylglycerol (POPG), 16-O-monomethyl PE, 16-O-dimethyl PE, 18-1-trans PE, palmitoyloleoyl-phosphatidylethanolamine (POPE), 1-stearoyl-2-oleoyl-phosphatidyethanolamine (SOPE), phosphatidylserine, phosphatidylinositol, sphingomyelin, cephalin, cardiolipin, phosphatidic acid, cerebrosides, dicetylphosphate, and cholesterol, or any other material listed in U.S. Pat. No. 9,445,994, which is incorporated herein by reference in its entirety. Examples of particles of the present disclosure are provided in Table 1.

TABLE 1

Example particles of the present disclosure

| Batch No. | Type | Particle ID | Description |
|---|---|---|---|
| S-001-001 | HX-13 | SP-001 | Carboxylate (Citrate) superparamagnetic iron oxide NPs (SPION) |
| S-002-001 | HX-19 | SP-002 | Phenol-formaldehyde coated SPION |
| S-003-001 | HX-20 | SP-003 | Silica-coated superparamagnetic iron oxide NPs (SPION) |
| S-004-001 | HX-31 | SP-004 | Polystyrene coated SPION |
| S-005-001 | HX-38 | SP-005 | Carboxylated Poly(styrene-co-methacrylic acid), P(St-co-MAA) coated SPION |
| S-006-001 | HX-42 | SP-006 | N-(3-Trimethoxysilylpropy) diethylenetriamine coated SPION |
| S-007-001 | HX-56 | SP-007 | poly(N-(3-(dimethylamino)propyl) methacrylamide) (PDMAPMA)-coated SPION |
| S-008-001 | HX-57 | SP-008 | 1,2,4,5-Benzenetetracarboxylic acid coated SPION |
| S-009-001 | HX-58 | SP-009 | poly(vinylbenzyltrimethylammonium chloride) (PVBTMAC) coated SPION |

TABLE 1-continued

Example particles of the present disclosure

| Batch No. | Type | Particle ID | Description |
|---|---|---|---|
| S-010-001 | HX-59 | SP-010 | Carboxylate, PAA coated SPION |
| S-011-001 | HX-86 | SP-011 | poly(oligo(ethylene glycol) methyl ether methacrylate) (POEGMA)-coated SPION |
| P-033-001 | P33 | SP-333 | Carboxylate microparticle, surfactant free |
| P-039-003 | P39 | SP-339 | Polystyrene carboxyl functionalized |
| P-041-001 | P41 | SP-341 | Carboxylic acid |
| P-047-001 | P47 | SP-365 | Silica |
| P-048-001 | P48 | SP-348 | Carboxylic acid, 150 nm |
| P-053-001 | P53 | SP-353 | Amino surface microparticle, 0.4-0.6 µm |
| P-056-001 | P56 | SP-356 | Silica amino functionalized microparticle, 0.1-0.39 µm |
| P-063-001 | P63 | SP-363 | Jeffamine surface, 0.1-0.39 µm |
| P-064-001 | P64 | SP-364 | Polystyrene microparticle, 2.0-2.9 µm |
| P-065-001 | P65 | SP-365 | Silica |
| P-069-001 | P69 | SP-369 | Carboxylated Original coating, 50 nm |
| P-073-001 | P73 | SP-373 | Dextran based coating, 0.13 µm |
| P-074-001 | P74 | SP-374 | Silica Silanol coated with lower acidity |

An example of a particle type of the present disclosure may be a carboxylate (Citrate) superparamagnetic iron oxide nanoparticle (SPION), a phenol-formaldehyde coated SPION, a silica-coated SPION, a polystyrene coated SPION, a carboxylated poly(styrene-co-methacrylic acid) coated SPION, a N-(3-Trimethoxysilylpropyl) diethylenetriamine coated SPION, a poly(N-(3-(dimethylamino) propyl) methacrylamide) (PDMAPMA)-coated SPION, a 1,2,4,5-Benzenetetracarboxylic acid coated SPION, a poly(Vinylbenzyltrimethylammonium chloride) (PVBTMAC) coated SPION, a carboxylate, PAA coated SPION, a poly(oligo (ethylene glycol) methyl ether methacrylate) (POEGMA)-coated SPION, a carboxylate microparticle, a polystyrene carboxyl functionalized particle, a carboxylic acid coated particle, a silica particle, a carboxylic acid particle of about 150 nm in diameter, an amino surface microparticle of about 0.4-0.6 µm in diameter, a silica amino functionalized microparticle of about 0.1-0.39 µm in diameter, a Jeffamine surface particle of about 0.1-0.39 µm in diameter, a polystyrene microparticle of about 2.0-2.9 µm in diameter, a silica particle, a carboxylated particle with an original coating of about 50 nm in diameter, a particle coated with a dextran based coating of about 0.13 µm in diameter, or a silica silanol coated particle with low acidity.

Particles that are consistent with the present disclosure can be made and used in methods of forming protein coronas after incubation in a biofluid at a wide range of sizes. A particle of the present disclosure may be a nanoparticle. A nanoparticle of the present disclosure may be from about 10 nm to about 1000 nm in diameter. For example, the nanoparticles disclosed herein can be at least 10 nm, at least 100 nm, at least 200 nm, at least 300 nm, at least 400 nm, at least 500 nm, at least 600 nm, at least 700 nm, at least 800 nm, at least 900 nm, from 10 nm to 50 nm, from 50 nm to 100 nm, from 100 nm to 150 nm, from 150 nm to 200 nm, from 200 nm to 250 nm, from 250 nm to 300 nm, from 300 nm to 350 nm, from 350 nm to 400 nm, from 400 nm to 450 nm, from 450 nm to 500 nm, from 500 nm to 550 nm, from 550 nm to 600 nm, from 600 nm to 650 nm, from 650 nm to 700 nm, from 700 nm to 750 nm, from 750 nm to 800 nm, from 800 nm to 850 nm, from 850 nm to 900 nm, from 100 nm to 300 nm, from 150 nm to 350 nm, from 200 nm to 400 nm, from 250 nm to 450 nm, from 300 nm to 500 nm, from 350 nm to 550 nm, from 400 nm to 600 nm, from 450 nm to 650 nm, from 500 nm to 700 nm, from 550 nm to 750 nm, from 600 nm to 800 nm, from 650 nm to 850 nm, from 700 nm to 900 nm, or from 10 nm to 900 nm in diameter. A nanoparticle may be less than 1000 nm in diameter.

A particle of the present disclosure may be a microparticle. A microparticle may be a particle that is from about 1 µm to about 1000 µm in diameter. For example, the microparticles disclosed here can be at least 1 µm, at least 10 µm, at least 100 µm, at least 200 µm, at least 300 µm, at least 400 µm, at least 500 µm, at least 600 µm, at least 700 µm, at least 800 µm, at least 900 µm, from 10 µm to 50 µm, from 50 µm to 100 µm, from 100 µm to 150 µm, from 150 µm to 200 µm, from 200 µm to 250 µm, from 250 µm to 300 µm, from 300 µm to 350 µm, from 350 µm to 400 µm, from 400 µm to 450 µm, from 450 µm to 500 µm, from 500 µm to 550 µm, from 550 µm to 600 µm, from 600 µm to 650 µm, from 650 µm to 700 µm, from 700 µm to 750 µm, from 750 µm to 800 µm, from 800 µm to 850 µm, from 850 µm to 900 µm, from 100 µm to 300 µm, from 150 µm to 350 µm, from 200 µm to 400 µm, from 250 µm to 450 µm, from 300 µm to 500 µm, from 350 µm to 550 µm, from 400 µm to 600 µm, from 450 µm to 650 µm, from 500 µm to 700 µm, from 550 µm to 750 µm, from 600 µm to 800 µm, from 650 µm to 850 µm, from 700 µm to 900 µm, or from 10 µm to 900 µm in diameter. A microparticle may be less than 1000 µm in diameter.

The ratio between surface area and mass can be a determinant of a particle's properties. For example, the number and types of biomolecules that a particle adsorbs from a solution may vary with the particle's surface area to mass ratio. The particles disclosed herein can have surface area to mass ratios of 3 to 30 $cm^2/mg$, 5 to 50 $cm^2/mg$, 10 to 60 $cm^2/mg$, 15 to 70 $cm^2/mg$, 20 to 80 $cm^2/mg$, 30 to 100 $cm^2/mg$, 35 to 120 $cm^2/mg$, 40 to 130 $cm^2/mg$, 45 to 150 $cm^2/mg$, 50 to 160 $cm^2/mg$, 60 to 180 $cm^2/mg$, 70 to 200 $cm^2/mg$, 80 to 220 $cm^2/mg$, 90 to 240 $cm^2/mg$, 100 to 270 $cm^2/mg$, 120 to 300 $cm^2/mg$, 200 to 500 $cm^2/mg$, 10 to 300 $cm^2/mg$, 1 to 3000 $cm^2/mg$, 20 to 150 $cm^2/mg$, 25 to 120 $cm^2/mg$, or from 40 to 85 $cm^2/mg$. Small particles (e.g., with diameters of 50 nm or less) can have significantly higher surface area to mass ratios, stemming in part from the higher order dependence on diameter by mass than by surface area. In some cases (e.g., for small particles), the particles can have surface area to mass ratios of 200 to 1000 $cm^2/mg$, 500 to 2000 $cm^2/mg$, 1000 to 4000 $cm^2/mg$, 2000 to 8000 $cm^2/mg$, or 4000 to 10000 $cm^2/mg$. In some cases (e.g., for large particles), the particles can have surface area to mass ratios of 1 to 3 $cm^2/mg$, 0.5 to 2 $cm^2/mg$, 0.25 to 1.5 $cm^2/mg$, or 0.1 to 1 $cm^2/mg$.

In some cases, a plurality of particles (e.g., of a particle panel) used with the methods described herein may have a range of surface area to mass ratios. In some cases, the range of surface area to mass ratios for a plurality of particles is less than 100 $cm^2/mg$, 80 $cm^2/mg$, 60 $cm^2/mg$, 40 $cm^2/mg$, 20 $cm^2/mg$, 10 $cm^2/mg$, 5 $cm^2/mg$, or 2 $cm^2/mg$. In some cases, the surface area to mass ratios for a plurality of particles varies by no more than 40%, 30%, 20%, 10%, 5%, 3%, 2%, or 1% between the particles in the plurality. In some cases, the plurality of particles may comprise at least 2, 3, 4, 5, 6, 7, 8, 9, 10, 12, 15, 20, or more different types of particles.

In some cases, a plurality of particles (e.g., in a particle panel) may have a wider range of surface area to mass ratios. In some cases, the range of surface area to mass ratios for a plurality of particles is greater than 100 $cm^2/mg$, 150 $cm^2/mg$, 200 $cm^2/mg$, 250 $cm^2/mg$, 300 $cm^2/mg$, 400 $cm^2/mg$, 500 $cm^2/mg$, 800 $cm^2/mg$, 1000 $cm^2/mg$, 1200 $cm^2/mg$, 1500 $cm^2/mg$, 2000 $cm^2/mg$, 3000 $cm^2/mg$, 5000 $cm^2/mg$, 7500 $cm^2/mg$, 10000 $cm^2/mg$, or more. In some cases, the surface area to mass ratios for a plurality of particles (e.g., within a panel) can vary by more than 100%, 200%, 300%, 400%, 500%, 1000%, 10000% or more. In some cases, the plurality of particles with a wide range of surface area to mass ratios comprises at least 2, 3, 4, 5, 6, 7, 8, 9, 10, 12, 15, 20, or more different types of particles.

A surface functionality may comprise a polymerizable functional group, a positively or negatively charged functional group, a zwitterionic functional group, an acidic or basic functional group, a polar functional group, or any combination thereof. A surface functionality may comprise carboxyl groups, hydroxyl groups, thiol groups, cyano groups, nitro groups, ammonium groups, alkyl groups, imidazolium groups, sulfonium groups, pyridinium groups, pyrrolidinium groups, phosphonium groups, aminopropyl groups, amine groups, boronic acid groups, N-succinimidyl ester groups, PEG groups, streptavidin, methyl ether groups, triethoxylpropylaminosilane groups, PCP groups, citrate groups, lipoic acid groups, BPEI groups, or any combination thereof. A particle from among the plurality of particles may be selected from the group consisting of: micelles, liposomes, iron oxide particles, silver particles, gold particles, palladium particles, quantum dots, platinum particles, titanium particles, silica particles, metal or inorganic oxide particles, synthetic polymer particles, copolymer particles, terpolymer particles, polymeric particles with metal cores, polymeric particles with metal oxide cores, polystyrene sulfonate particles, polyethylene oxide particles, polyoxyethylene glycol particles, polyethylene imine particles, polylactic acid particles, polycaprolactone particles, polyglycolic acid particles, poly(lactide-co-glycolide polymer particles, cellulose ether polymer particles, polyvinylpyrrolidone particles, polyvinyl acetate particles, polyvinylpyrrolidone-vinyl acetate copolymer particles, polyvinyl alcohol particles, acrylate particles, polyacrylic acid particles, crotonic acid copolymer particles, polyethlene phosphonate particles, polyalkylene particles, carboxy vinyl polymer particles, sodium alginate particles, carrageenan particles, xanthan gum particles, gum acacia particles, Arabic gum particles, guar gum particles, pullulan particles, agar particles, chitin particles, chitosan particles, pectin particles, karaya tum particles, locust bean gum particles, maltodextrin particles, amylose particles, corn starch particles, potato starch particles, rice starch particles, tapioca starch particles, pea starch particles, sweet potato starch particles, barley starch particles, wheat starch particles, hydroxypropylated high amylose starch particles, dextrin particles, levan particles, elsinan particles, gluten particles, collagen particles, whey protein isolate particles, casein particles, milk protein particles, soy protein particles, keratin particles, polyethylene particles, polycarbonate particles, polyanhydride particles, polyhydroxyacid particles, polypropylfumerate particles, polycaprolactone particles, polyamine particles, polyacetal particles, polyether particles, polyester particles, poly(orthoester) particles, polycyanoacrylate particles, polyurethane particles, polyphosphazene particles, polyacrylate particles, polymethacrylate particles, polycyanoacrylate particles, polyurea particles, polyamine particles, polystyrene particles, poly(lysine) particles, chitosan particles, dextran particles, poly(acrylamide) particles, derivatized poly (acrylamide) particles, gelatin particles, starch particles, chitosan particles, dextran particles, gelatin particles, starch particles, poly-β-amino-ester particles, poly(amido amine) particles, poly lactic-co-glycolic acid particles, polyanhydride particles, bioreducible polymer particles, and 2-(3-aminopropylamino) ethanol particles, and any combination thereof.

A plurality of particles (e.g. physicochemically distinct particles) may include one or more particle types selected from the group consisting of carboxylate (Citrate) superparamagnetic iron oxide nanoparticle (SPION), a phenol-formaldehyde coated SPION, a silica-coated SPION, a polystyrene coated SPION, a carboxylated poly(styrene-co-methacrylic acid) coated SPION, a N-(3-Trimethoxysilylpropyl) diethylenetriamine coated SPION, a poly(N-(3-(dimethylamino) propyl) methacrylamide) (PD-MAPMA)-coated SPION, a 1,2,4,5-Benzenetetracarboxylic acid coated SPION, a poly(Vinylbenzyltrimethylammonium chloride) (PVBTMAC) coated SPION, a carboxylate, PAA coated SPION, a poly(oligo (ethylene glycol) methyl ether methacrylate) (POEGMA)-coated SPION, a carboxylate microparticle, a polystyrene carboxyl functionalized particle, a carboxylic acid coated particle, a silica particle, a carboxylic acid particle, an amino surface particle, a silica amino functionalized particle, a Jeffamine surface particle, a polystyrene particle, a particle coated with a dextran based coating of about 0.13 μm in diameter, or a silica silanol coated particle.

A plurality of particles (e.g. physicochemically distinct particles) may include one or more particle types selected from the group consisting of carboxylate (Citrate) superparamagnetic iron oxide nanoparticle (SPION), a phenol-formaldehyde coated SPION, a silica-coated SPION, a polystyrene coated SPION, a carboxylated poly(styrene-co-methacrylic acid) coated SPION, a N-(3-Trimethoxysilylpropyl) diethylenetriamine coated SPION, a poly(N-(3-(dimethylamino) propyl) methacrylamide) (PD-MAPMA)-coated SPION, a 1,2,4,5-Benzenetetracarboxylic acid coated SPION, a poly(Vinylbenzyltrimethylammonium chloride) (PVBTMAC) coated SPION, a carboxylate, PAA coated SPION, a poly(oligo (ethylene glycol) methyl ether methacrylate) (POEGMA)-coated SPION, a carboxylate microparticle, a polystyrene carboxyl functionalized particle, a carboxylic acid coated particle, a silica particle, a carboxylic acid particle, an amino surface particle, a silica amino functionalized particle, a Jeffamine surface particle, a polystyrene particle, a particle coated with a dextran based coating of about 0.13 μm in diameter, or a silica silanol coated particle.

A plurality of particles (e.g. physicochemically distinct particles) may include one or more particle types selected from the group consisting of silica particles, poly(acrylamide) particles, polyethylene glycol particles, or a combination thereof. One or more of the particles may include a paramagnetic or superparamagnetic core material. Particles may include silica particles. Particles may include poly (acrylamide) particles. Particles may include polyethylene glycol particles.

A plurality of particles may comprise multiple particle types. In some cases, a plurality of particles comprises at least 2 types of particles. In some cases, a plurality of particles comprises at least 3 types of particles. In some cases, a plurality of particles comprises at least 5 types of particles. In some cases, a plurality of particles comprises at least 6 types of particles. In some cases, a plurality of particles comprises at least 8 types of particles. In some cases, a plurality of particles comprises at least 10 types of particles. In some cases, a plurality of particles comprises at least 12 types of particles. In some cases, a plurality of particles comprises at least 15 types of particles. In some cases, a plurality of particles comprises at least 18 types of particles. In some cases, a plurality of particles comprises at least 20 types of particles.

A Particle may comprise layers with distinct properties. A particle may comprise a core with a first set of properties and a shell with a second set of properties. A particle may comprise multiple shells with distinct properties (e.g., a core comprising a first material, an inner shell comprising a second material, and an outer shell comprising a third material). A layer of a particle may comprise a plurality of materials. For example, a layer of a particle may comprise a plurality of polymers. The polymers may be homogeneously interspersed within the layer, may be phase separated, or may be unevenly applied.

In some cases, the one or more physicochemical properties are selected from the group consisting of: composition, size, surface charge, hydrophobicity, hydrophilicity, surface functionality, surface topography, surface curvature, shape, and any combination thereof. In some embodiments, the surface functionality comprises a chemical functionalization. In some embodiments, the small molecule functionalization comprises an amine functionalization, a carboxylate functionalization, a monosaccharide functionalization, an oligosaccharide functionalization, a phosphate sugar functionalization, a sulfate sugar functionalization, an alcohol functionalization, a ether functionalization, an ester functionalization, an amide functionalization, a carbonate functionalization, a carbamate functionalization, a urea functionalization, a benzyl functionalization, a phenyl functionalization, a phenol functionalization, an aniline functionalization, an imidazole functionalization, an indole functionalization, a fluoride functionalization, a chloride functionalization, a bromide functionalization, a sulfide functionalization, a nitro functionalization, a thiol functionalization, a nitrogenous base functionalization, an aminopropyl functionalization, a boronic acid functionalization, an N-succinimidyl ester functionalization, a PEG functionalization, a methyl ether functionalization, a triethoxylpropylaminosilane functionalization, a silicon alkoxide functionalization, a phenol-formaldehyde functionalization, an organosilane functionalization, an ethylene glycol functionalization, a PCP functionalization, a citrate functionalization, a lipoic acid functionalization, or any combination thereof. In some embodiments, the small molecule functionalization comprises a silica functionalized particle, an amine functionalized particle, a silicon alkoxide functionalized particle, a polystyrene functionalized particle, and a saccharide functionalized particle. In some embodiments, the small molecule functionalization comprises an amine functionalization, a phosphate sugar functionalization, a carboxylate functionalization, a silica functionalization, an organosilane functionalization, or any combination thereof. In some embodiments, the small molecule functionalization comprises a silica functionalization, an ethylene glycol functionalization, and an amine functionalization, or any combination thereof.

A particle of the present disclosure may be synthesized, or a particle of the present disclosure may be purchased from a commercial vendor. For example, particles consistent with the present disclosure may be purchased from commercial vendors including Sigma-Aldrich, Life Technologies, Fisher Biosciences, nanoComposix, Nanopartz, Spherotech, and other commercial vendors. A suitable particle of the present disclosure may be purchased from a commercial vendor and further modified, coated, or functionalized.

The present disclosure includes compositions and methods that comprise two or more particles from among differing in at least one physicochemical property. Such compositions and methods may comprise at least 2 to at least 20 particles from among the plurality of particles differ in at least one physicochemical property. Such compositions and methods may comprise at least 3 to at least 6 particles from among the plurality of particles differ in at least one physicochemical property. Such compositions and methods may comprise at least 4 to at least 8 particles from among the plurality of particles differ in at least one physicochemical property. Such compositions and methods may comprise at least 4 to at least 10 particles from among the plurality of particles differ in at least one physicochemical property. Such compositions and methods may comprise at least 5 to at least 12 particles from among the plurality of particles differ in at least one physicochemical property. Such compositions and methods may comprise at least 6 to at least 14 particles from among the plurality of particles differ in at least one physicochemical property. Such compositions and methods may comprise at least 8 to at least 15 particles from among the plurality of particles differ in at least one physicochemical property. Such compositions and methods may comprise at least 10 to at least 20 particles from among the plurality of particles differ in at least one physicochemical property. Such compositions and methods may comprise at least 2 distinct particle types, at least 3 distinct particle types, at least 4 distinct particle types, at least 5 distinct particle types, at least 6 distinct particle types, at least 7 distinct particle types, at least 8 distinct particle types, at least 9 distinct particle types, at least 10 distinct particle types, at least 11 distinct particle types, at least 12 distinct particle types, at least 13 distinct particle types, at least 14 distinct particle types, at least 15 distinct particle types, at least 20 distinct particle types, at least 25 particle types, or at least 30 distinct particle types.

A particle of the present disclosure may be contacted with a biological sample (e.g., a biofluid) to form a biomolecule corona. Upon contacting the complex biological sample, one or more types of particles of a plurality of particles may adsorb 100 or more types of proteins (e.g., in a 100 µl aliquot of a biological sample comprising 100 pM of a type of particle, the about $10^{10}$ particles of the given type collectively may adsorb 100 or more types of proteins). The particle and biomolecule corona may be separated from the biological sample, for example by centrifugation, magnetic separation, filtration, or gravitational separation. The particle types and biomolecule corona may be separated from the biological sample using a number of separation techniques. Non-limiting examples of separation techniques include comprises magnetic separation, column-based separation, filtration, spin column-based separation, centrifugation, ultracentrifugation, density or gradient-based centrifugation, gravitational separation, or any combination thereof. A protein corona analysis may be performed on the separated particle and biomolecule corona. A protein corona analysis may comprise identifying one or more proteins in the biomolecule corona, for example by mass spectrometry. A method may comprise contacting a single particle type (e.g., a particle of a type listed in Table 1) to a biological sample. A method may also comprise contacting a plurality of particle types (e.g., a plurality of the particle types provided in Table 1) to a biological sample. The plurality of particle types may be combined and contacted to the biological sample in a single sample volume. The plurality of particle types may be sequentially contacted to a biological sample and separated from the biological sample prior to contacting a subsequent particle type to the biological sample. Protein corona analysis of the biomolecule corona may compress the dynamic range of the analysis compared to a total protein analysis method.

Contacting a biological sample with a particle or plurality of particles may comprise adding a defined concentration of particles to the biological sample. Contacting a biological sample with a particle or plurality of particles may comprise adding from 1 pM to 100 nM of particles to the biological sample. Contacting a biological sample with a particle or plurality of particles may comprise adding from 1 pM to 500 pM of particles to the biological sample. Contacting a biological sample with a particle or plurality of particles may comprise adding from 10 pM to 1 nM of particles to the biological sample. Contacting a biological sample with a particle or plurality of particles may comprise adding from 100 pM to 10 nM of particles to the biological sample. Contacting a biological sample with a particle or plurality of particles may comprise adding from 500 pM to 100 nM of particles to the biological sample. Contacting a biological sample with a particle or plurality of particles may comprise adding from 50 µg/ml to 300 µg/ml (particle mass to biological sample volume) of particles to the biological sample. Contacting a biological sample with a particle or plurality of particles may comprise adding from 100 µg/ml to 500 µg/ml of particles to a biological sample. Contacting a biological sample with a particle or plurality of particles may comprise adding from 250 µg/ml to 750 µg/ml of particles to the biological sample. Contacting a biological sample with a particle or plurality of particles may comprise adding from 400 µg/ml to 1 mg/ml of particles to the biological sample. Contacting a biological sample with a particle or plurality of particles may comprise adding from 600 µg/ml to 1.5 mg/ml of particles to the biological sample. Contacting a biological sample with a particle or plurality of particles may comprise adding from 800 µg/ml to 2 mg/ml of particles to the biological sample. Contacting a biological sample with a particle or plurality of particles may comprise adding from 1 mg/ml to 3 mg/ml of particles to the biological sample. Contacting a biological sample with a particle or plurality of particles may comprise adding from 2 mg/ml to 5 mg/ml of particles to the biological sample. Contacting a biological sample with a particle or plurality of particles may comprise adding than 5 mg/ml of particles to the biological sample.

Particles in a plurality of particles may have varying degrees of size and shape uniformity. The standard deviation in diameter for a collection of particles of a particular type may be less than 20%, 10%, 5%, or 2% of the average diameter for the particle type (e.g., less than 2 nm for a particle with an average diameter of 100 nm). This may correspond to a low polydispersity index for a sample comprising a plurality of particles, less than 2, less than 1, less than 0.8, less than 0.6, less than 0.5, less than 0.4, less than 0.3, less than 0.2, less than 0.1, or less than 0.05. Conversely, a plurality of particles may have a high degree of variance in average size and shape. The polydispersity index for a sample comprising a plurality of particles may be greater than 3, greater than 4, greater than 5, greater than 8, greater than 10, greater than 12, greater than 15, or greater than 20. Size and shape uniformity among a plurality of particles can affect the number and types of biomolecules that adsorb to the particles. For some methods, size uniformity (e.g., a low polydispersity index) among particles enables greater enrichment of particular biomolecules, and a stronger correspondence between enriched biomolecule abundance and particle type. For some methods, low size uniformity enables collection of a greater number of types of biomolecules.

Disclosed herein methods that include obtaining a data set comprising proteins detected in biomolecule coronas corresponding to physiochemically distinct particles incubated with a biological sample. The biological sample may include a blood sample that has had red blood cells removed (e.g. a cell-free sample). The physiochemically distinct types of particles yield different biomolecule coronas. The physiochemically distinct types of particles yield different biomarkers. The physiochemically distinct types of particles yield different mass spectral patterns.

Particle Panels

The present disclosure provides compositions and methods of use thereof for assaying a sample for proteins. Compositions described herein include particle panels comprising one or more than one distinct particle types. Particle panels described herein can vary in the number of particle types and the diversity of particle types in a single panel. For example, particles in a panel may vary based on size, polydispersity, shape and morphology, surface charge, surface chemistry and functionalization, and base material. Panels may be incubated with a sample to be analyzed for proteins and protein concentrations. Proteins in the sample adsorb to the surface of the different particle types in the particle panel to form a protein corona. The exact protein and the concentration of protein that adsorbs to a certain particle type in the particle panel may depend on the composition, size, and surface charge of said particle type. Thus, each particle type in a panel may have different protein coronas due to adsorbing a different set of proteins, different concentrations of a particular protein, or a combination thereof. Each particle type in a panel may have mutually exclusive protein coronas or may have overlapping protein coronas. Overlapping protein coronas can overlap in protein identity, in protein concentration, or both.

The present disclosure also provides methods for selecting a particle types for inclusion in a panel depending on the sample type. Particle types included in a panel may be a combination of particles that are optimized for removal of highly abundant proteins. Particle types also consistent for inclusion in a panel are those selected for adsorbing particular proteins of interest. The particles can be nanoparticles. The particles can be microparticles. The particles can be a combination of nanoparticles and microparticles.

The particle panels disclosed herein can be used to identify the number of distinct proteins disclosed herein, and/or any of the specific proteins disclosed herein, over a wide dynamic range. For example, the particle panels disclosed herein comprising distinct particle types, can enrich for proteins in a sample over the entire dynamic range at which proteins are present in a sample (e.g., a plasma sample). In some cases, a particle panel including any number of distinct particle types disclosed herein, enriches proteins over a dynamic range of at least 2 orders of magnitude. In some cases, a particle panel including any number of distinct particle types disclosed herein, enriches proteins over a dynamic range of at least 3 orders of magnitude. In some cases, a particle panel including any number of distinct particle types disclosed herein, enriches proteins over a dynamic range of at least 4 orders of magnitude. In some cases, a particle panel including any number of distinct particle types disclosed herein, enriches proteins over a dynamic range of at least 5 orders of magnitude. In some cases, a particle panel including any number of distinct particle types disclosed herein, enriches proteins over a dynamic range of at least 6 orders of magnitude. In some cases, a particle panel including any number of distinct particle types disclosed herein, enriches proteins over a dynamic range of at least 7 orders of magnitude. In some cases, a particle panel including any number of distinct particle types disclosed herein, enriches proteins over a dynamic range of at least 8 orders of magnitude. In some cases, a particle panel including any number of distinct particle types disclosed herein, enriches proteins over a dynamic range of at least 9 orders of magnitude. In some cases, a particle panel including any number of distinct particle types disclosed herein, enriches proteins over a dynamic range of at least 10 orders of magnitude. In some cases, a particle panel including any number of distinct particle types disclosed herein, enriches proteins over a dynamic range of at least 11 orders of magnitude. In some cases, a particle panel including any number of distinct particle types disclosed herein, enriches proteins over a dynamic range of at least 12 orders of magnitude. In some cases, a particle panel including any number of distinct particle types disclosed herein, enriches proteins over a dynamic range of from 3 to 5 orders of magnitude. In some cases, a particle panel including any number of distinct particle types disclosed herein, enriches proteins over a dynamic range of from 3 to 6 orders of magnitude. In some cases, a particle panel including any number of distinct particle types disclosed herein, enriches proteins over a dynamic range of from 4 to 8 orders of magnitude. In some cases, a particle panel including any number of distinct particle types disclosed herein, enriches proteins over a dynamic range of from 5 to 8 orders of magnitude. In some cases, a particle panel including any number of distinct particle types disclosed herein, enriches proteins over a dynamic range of from 6 to 10 orders of magnitude. In some cases, a particle panel including any number of distinct particle types disclosed herein, enriches proteins over a dynamic range of from 8 to 12 orders of magnitude. For example, a particle panel may collect proteins at mM and a fM concentrations in a sample, thereby enriching proteins over a 12 order of magnitude range.

A particle panel including any number of distinct particle types disclosed herein, enriches a single protein or protein group. In some cases, the single protein or protein group may comprise proteins having different post-translational modifications. For example, a first particle type in the particle panel may enrich a protein or protein group having a first post-translational modification, a second particle type in the particle panel may enrich the same protein or same protein group having a second post-translational modification, and a third particle type in the particle panel may enrich the same protein or same protein group lacking a post-translational modification. In some cases, the particle panel including any number of distinct particle types disclosed herein, enriches a single protein or protein group by binding different domains, sequences, or epitopes of the single protein or protein group. For example, a first particle type in the particle panel may enrich a protein or protein group by binding to a first domain of the protein or protein group, and a second particle type in the particle panel may enrich the same protein or same protein group by binding to a second domain of the protein or protein group.

A particle panel may comprise a combination of particles with silica and polymer surfaces. For example, a particle panel may comprise a SPION coated with a thin layer of silica, a SPION coated with poly(dimethyl aminopropyl methacrylamide) (PDMAPMA), and a SPION coated with poly(ethylene glycol) (PEG). A particle panel consistent with the present disclosure could also comprise two or more particles selected from the group consisting of silica coated SPION, an N-(3-Trimethoxysilylpropyl) diethylenetriamine coated SPION, a PDMAPMA coated SPION, a carboxyl-functionalized polyacrylic acid coated SPION, an amino surface functionalized SPION, a polystyrene carboxyl functionalized SPION, a silica particle, and a dextran coated SPION. A particle panel consistent with the present disclosure may also comprise two or more particles selected from the group consisting of a surfactant free carboxylate microparticle, a carboxyl functionalized polystyrene particle, a silica coated particle, a silica particle, a dextran coated particle, an oleic acid coated particle, a boronated nanopowder coated particle, a PDMAPMA coated particle, a Poly(glycidyl methacrylate-benzylamine) coated particle, and a Poly(N-[3-(Dimethylamino) propyl]methacrylamide-co-[2-(methacryloyloxy)ethyl]dimethyl-(3-sulfopropyl) ammonium hydroxide, P (DMAPMA-co-SBMA) coated particle. A particle panel consistent with the present disclosure may comprise silica-coated particles, N-(3-Trimethoxysilylpropyl) diethylenetriamine coated particles, poly(N-(3-(dimethylamino) propyl) methacrylamide) (PDMAPMA)-coated particles, phosphate-sugar functionalized polystyrene particles, amine functionalized polystyrene particles, polystyrene carboxyl functionalized particles, ubiquitin functionalized polystyrene particles, dextran coated particles, or any combination thereof.

The particle panels disclosed herein can be used to identifying a number of proteins, peptides, or protein groups using the workflow described herein (MS analysis of distinct biomolecule coronas corresponding to distinct particle types in the particle panel, collectively referred to as the "Proteograph" workflow). Feature intensities, as disclosed herein, are derived from the intensity of a discrete spike ("feature") seen on a plot of mass to charge ratio versus intensity from a mass spectrometry run of a sample. These features can correspond to variably ionized fragments of peptides and/or proteins. Using the data analysis methods described herein, feature intensities can be sorted into protein groups. Protein groups refer to two or more proteins that are identified by a shared peptide sequence. Alternatively, a protein group can refer to one protein that is identified using a unique identifying sequence. For example, if in a sample, a peptide sequence is assayed that is shared between two proteins (Protein 1: XYZZX and Protein 2: XYZYZ), a protein group could be the "XYZ protein group" having two members (protein 1 and protein 2). Alternatively, if the peptide sequence is unique to a single protein (Protein 1), a protein group could be the "ZZX" protein group having one member (Protein 1). Each protein group can be supported by more than one peptide sequence. Protein detected or identified according to the instant disclosure can refer to a distinct protein detected in the sample (e.g., distinct relative other proteins detected using mass spectrometry). Thus, analysis of proteins present in distinct coronas corresponding to the distinct particle types in a particle panel, yields a high number of feature intensities. This number decreases as feature intensities are processed into distinct peptides, further decreases as distinct peptides are processed into distinct proteins, and further decreases as peptides are grouped into protein groups (two or more proteins that share a distinct peptide sequence).

Particle panels disclosed herein for assessing the presence or absence of one or more biomarkers associated with lung cancer (e.g., NSCLC) can have at least 1 distinct particle type, at least 2 distinct particle types, at least 3 distinct particle types, at least 4 distinct particle types, at least 5 distinct particle types, at least 6 distinct particle types, at least 7 distinct particle types, at least 8 distinct particle types, at least 9 distinct particle types, at least 10 distinct particle types, at least 11 distinct particle types, at least 12 distinct particle types, at least 13 distinct particle types, at least 14 distinct particle types, at least 15 distinct particle types, at least 16 distinct particle types, at least 17 distinct particle types, at least 18 distinct particle types, at least 19 distinct particle types, at least 20 distinct particle types, at least 25 distinct particle types, at least 30 distinct particle types, at least 35 distinct particle types, at least 40 distinct particle types, at least 45 distinct particle types, at least 50 distinct particle types, at least 55 distinct particle types, at least 60 distinct particle types, at least 65 distinct particle types, at least 70 distinct particle types, at least 75 distinct particle types, at least 80 distinct particle types, at least 85 distinct particle types, at least 90 distinct particle types, at least 95 distinct particle types, at least 100 distinct particle types, from 1 to 5 distinct particle types, from 5 to 10 distinct particle types, from 10 to 15 distinct particle types, from 15 to 20 distinct particle types, from 20 to 25 distinct particle types, from 25 to 30 distinct particle types, from 30 to 35 distinct particle types, from 35 to 40 distinct particle types, from 40 to 45 distinct particle types, from 45 to 50 distinct particle types, from 50 to 55 distinct particle types, from 55 to 60 distinct particle types, from 60 to 65 distinct particle types, from 65 to 70 distinct particle types, from 70 to 75 distinct particle types, from 75 to 80 distinct particle types, from 80 to 85 distinct particle types, from 85 to 90 distinct particle types, from 90 to 95 distinct particle types, from 95 to 100 distinct particle types, from 1 to 100 distinct particle types, from 20 to 40 distinct particle types, from 5 to 10 distinct particle types, from 3 to 7 distinct particle types, from 2 to 10 distinct particle types, from 6 to 15 distinct particle types, or from 10 to 20 distinct particle types. In particular embodiments, the present disclosure provides a panel size of from 3 to 10 particle types. In particular embodiments, the present disclosure provides a panel size of from 4 to 11 distinct particle types. In particular embodiments, the present disclosure provides a panel size of from 5 to 15 distinct particle types. In particular embodiments, the present disclosure provides a panel size of from 5 to 15 distinct particle types. In particular embodiments, the present disclosure provides a panel size of from 8 to 12 distinct particle types. In particular embodiments, the present disclosure provides a panel size of from 9 to 13 distinct particle types. In particular embodiments, the present disclosure provides a panel size of 10 distinct particle types. The particle types may include nanoparticle types.

A particle panel may be designed to broadly profile a proteome, such as the human plasma proteome. A major challenge in analyzing the human proteome is that more than 99% of mass of the roughly 3500 proteins in human plasma is accounted for by just 20 proteins. Plasma analysis methods are often saturated by these 20 proteins, and provide minimal profiling depth into the remaining proteins. A particle panel of the present disclosure may comprise a combination of particles that facilitates collection of at least 200, at least 300, at least 400, at least 500, at least 600, at least 700, at least 800, at least 900, at least 1000, at least 1100, at least 1200, at least 1300, at least 1400, at least 1500, at least 1600, at least 1700, at least 1800, at least 1900, at least 2000, at least 2100, or at least 2200 distinct proteins from a single biological sample. A particle panel of the present disclosure may comprise a combination of particles that facilitates collection of at least 4%, at least 5%, at least 6%, at least 8%, at least 10%, at least 12%, at least 15%, at least 20%, at least 25%, at least 30%, at least 35%, at least 40%, at least 45%, at least 50%, at least 55%, at least 60%, at least 65%, or at least 70% of the types of proteins from a complex biological sample, such as human plasma. This may be achieved by providing a plurality of particles (e.g., as a particle panel) with distinct protein binding profiles. A particle panel may comprise two particles which, upon contact with a biological sample, form protein coronas with fewer than 80%, fewer than 70%, fewer than 60%, fewer than 50%, fewer than 40%, fewer than 30%, fewer than 25%, fewer than 20%, fewer than 15%, or fewer than 10% of proteins in common. In some cases, the biological sample is human plasma.

Figure 53:
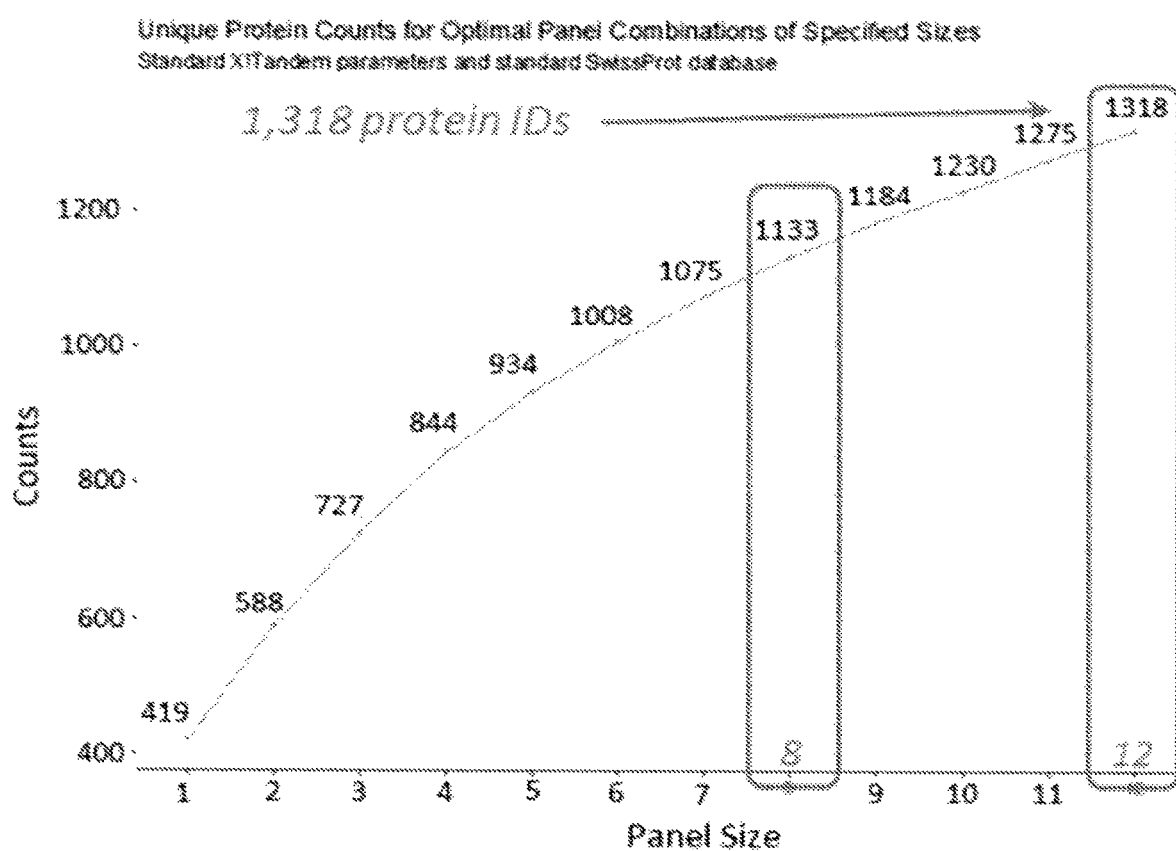
FIG. 53 shows protein counts (e.g. number of proteins identified from corona analysis) for panel sizes ranging from 1 particle type to 12 particle types.

Increasing the number of particle types in a panel can increase the number of proteins that can be identified in a given sample. An example of how increasing panel size may increase the number of identified proteins is shown in FIG. 53, in which a panel size of one particle type identified 419 different proteins, a panel size of two particle types identified 588 different proteins, a panel size of three particle types identified 727 different proteins, a panel size of four particle types identified 844 proteins, a panel size of five particle types identified 934 different proteins, a panel size of six particle types identified 1008 different proteins, a panel size of seven particle types identified 1075 different proteins, a panel size of eight particle types identified 1133 different proteins, a panel size of nine particle types identified 1184 different proteins, a panel size of 10 particle types identified 1230 different proteins, a panel size of 11 particle types identified 1275 different proteins, and a panel size of 12 particle types identified 1318 different proteins.

Dynamic Range

Some methods described herein (e.g. biomolecule corona analysis) may comprise assaying biomolecules in a sample of the present disclosure across a wide dynamic range. The dynamic range of biomolecules assayed in a sample may be a range of biomolecule abundances as measured by an assay method (e.g., mass spectrometry, chromatography, gel electrophoresis, spectroscopy, or immunoassays) for the biomolecules contained within a sample. For example, an assay capable of detecting proteins across a wide dynamic range may be capable of detecting proteins of very low abundance to proteins of very high abundance. The dynamic range of an assay may be directly related to the slope of assay signal intensity as a function of biomolecule abundance. For example, an assay with a low dynamic range may have a low (but positive) slope of the assay signal intensity as a function of biomolecule abundance, e.g., the ratio of the signal detected for a high abundance biomolecule to the ratio of the signal detected for a low abundance biomolecule may be lower for an assay with a low dynamic range than an assay with a high dynamic range. In specific cases, dynamic range may refer to the dynamic range of proteins within a sample or assaying method.

The methods described herein may compress the dynamic range of an assay. The dynamic range of an assay may be compressed relative to another assay if the slope of the assay signal intensity as a function of biomolecule abundance is lower than that of the other assay. For example, a plasma sample assayed using protein corona analysis with mass spectrometry may have a compressed dynamic range compared to a plasma sample assayed using mass spectrometry alone, directly on the sample or compared to provided abundance values for plasma proteins in databases (e.g., the database provided in Keshishian et al., Mol. Cell Proteomics 14, 2375-2393 (2015), also referred to herein as the "Carr database"). The compressed dynamic range may enable the detection of more low abundance biomolecules in a biological sample using biomolecule corona analysis with mass spectrometry than using mass spectrometry alone.

Collecting biomolecules on a particle prior to analysis (e.g., mass spectrometric or ELISA analysis) may compress the dynamic range of the analysis. Two proteins present at a ratio of 106:1 within a biological sample may be differentially adsorbed on a particle and eluted into a solution such that their new ratio is 104:1. Such differential adsorption may enable simultaneous detection of two biomolecules with a concentration difference greater than the dynamic range of an analytical technique. For example, mass spectrometric analysis is often limited to measuring species within a 4-6 order of magnitude concentration range, and thus can be unable to simultaneously detect two biomolecules present at a 108-fold concentration difference. Biomolecule corona-based enrichment of a sample may concentrate a dilute biomolecule (e.g., a first protein) relative to a second biomolecule (e.g., a second protein), thereby enabling simultaneous detection of the two biomolecules with one analytical method. Analogously, particle-based enrichment may enable quantification of a low concentration biomolecule in a sample. The dynamic range over which an analyte may be quantified is often narrower than the dynamic range over which an analyte may be detected. For example, ELISA often covers a dynamic range spanning 2-3 orders of magnitude, while providing accurate concentration quantitation over less than 2 orders of magnitude. Particle-based enrichment may increase the number of biomolecule targets within a desired concentration range, thereby enabling simultaneous quantification of two or more biomolecules present in a biological sample at concentrations outside of the dynamic range for concentration quantitation of an analytical technique.

Accordingly, various methods of the present disclosure comprise detecting two biomolecules present in a biological sample with a concentration difference greater than a dynamic range of a detection method. Many of the biomarker pairs disclosed herein span concentration ranges beyond the limits of detection of biomolecule analysis techniques (e.g., immunostaining or LC-MS/MS), and accordingly can be unidentifiable or unquantifiable without the enrichment-based methods of the present disclosure. In some cases, a method of the present disclosure comprises detecting two biomolecules (e.g., two proteins) at concentrations differing by at least 3-orders of magnitude in a biological sample (e.g., 1 mg/ml and 1 µg/ml, or 50 µM and 50 nM). In some cases, a method of the present disclosure comprises detecting of two biomolecules (e.g., two proteins) at concentrations differing by at least 4-orders of magnitude in a biological sample (e.g., 1 mg/ml and 100 ng/ml, or 50 µM and 5 nM). In some cases, a method of the present disclosure comprises detecting of two biomolecules (e.g., two proteins) at concentrations differing by at least 5-orders of magnitude in a biological sample (e.g., detection of HBA and NOTUM in human plasma). In some cases, a method of the present disclosure comprises detecting of two biomolecules (e.g., two proteins) at concentrations differing by at least 5-orders of magnitude in a biological sample (e.g., detection of ITIH2 and ANGL6 in human plasma). In some cases, a method of the present disclosure comprises detecting of two biomolecules (e.g., two proteins) at concentrations differing by at least 6-orders of magnitude in a biological sample (e.g., detection of HBA and NOTUM in human plasma). In some cases, a method of the present disclosure comprises detecting of two biomolecules (e.g., two proteins) at concentrations differing by at least 7-orders of magnitude in a biological sample (e.g., detection of ceruloplasmin and RLA2 in human plasma). In some cases, a method of the present disclosure comprises detecting of two biomolecules (e.g., two proteins) at concentrations differing by at least 7-orders of magnitude in a biological sample (e.g., detection of human serum albumin and CAN2 in human plasma). In some cases, a method of the present disclosure comprises detecting of two biomolecules (e.g., two proteins) at concentrations differing by at least 7-orders of magnitude in a biological sample (e.g., detection of human serum albumin and Interleukin 6 in human plasma).

The dynamic range of a proteomic analysis assay may be the ratio of the signal produced by highest abundance proteins (e.g., the highest 10% of proteins by abundance) to the signal produced by the lowest abundance proteins (e.g., the lowest 10% of proteins by abundance). Compressing the dynamic range of a proteomic analysis may comprise decreasing the ratio of the signal produced by the highest abundance proteins to the signal produced by the lowest abundance proteins for a first proteomic analysis assay relative to that of a second proteomic analysis assay. The protein corona analysis assays disclosed herein may compress the dynamic range relative to the dynamic range of a total protein analysis method (e.g., mass spectrometry, gel electrophoresis, or liquid chromatography).

Provided herein are several methods for compressing the dynamic range of a biomolecular analysis assay to facilitate the detection of low abundance biomolecules relative to high abundance biomolecules. For example, a particle type of the present disclosure can be used to serially interrogate a sample. Upon incubation of the particle type in the sample, a biomolecule corona comprising forms on the surface of the particle type. If biomolecules are directly detected in the sample without the use of said particle types, for example by direct mass spectrometric analysis of the sample, the dynamic range may span a wider range of concentrations, or more orders of magnitude, than if the biomolecules are directed on the surface of the particle type. Thus, using the particle types disclosed herein may be used to compress the dynamic range of biomolecules in a sample. Without being limited by theory, this effect may be observed due to more capture of higher affinity, lower abundance biomolecules in the biomolecule corona of the particle type and less capture of lower affinity, higher abundance biomolecules in the biomolecule corona of the particle type.

A dynamic range of a proteomic analysis assay may be the slope of a plot of a protein signal measured by the proteomic analysis assay as a function of total abundance of the protein in the sample. Compressing the dynamic range may comprise decreasing the slope of the plot of a protein signal measured by a proteomic analysis assay as a function of total abundance of the protein in the sample relative to the slope of the plot of a protein signal measured by a second proteomic analysis assay as a function of total abundance of the protein in the sample. The protein corona analysis assays disclosed herein may compress the dynamic range relative to the dynamic range of a total protein analysis method (e.g., mass spectrometry, gel electrophoresis, or liquid chromatography).

Biomarker Analysis in Biological Samples

The methods of use thereof disclosed herein can identify a large number of biomarkers in a biological sample (e.g., a biofluid). Non-limiting examples of biological samples that may be analyzed using the methods (e.g. protein corona analysis) described herein include biofluid samples (e.g., cerebral spinal fluid (CSF), synovial fluid (SF), urine, plasma, serum, tears, semen, whole blood, milk, nipple aspirate, ductal lavage, vaginal fluid, nasal fluid, ear fluid, gastric fluid, pancreatic fluid, trabecular fluid, lung lavage, prostatic fluid, sputum, fecal matter, bronchial lavage, fluid from swabbings, bronchial aspirants, sweat or saliva), fluidized solids (e.g., a tissue homogenate), or samples derived from cell culture. For example, a particle disclosed herein can be incubated with any biological sample disclosed herein to form a protein corona comprising at least 100 unique proteins, at least 120 unique proteins, at least 140 unique proteins, at least 160 unique proteins, at least 180 unique proteins, at least 200 unique proteins, at least 220 unique proteins, at least 240 unique proteins, at least 260 unique proteins, at least 280 unique proteins, at least 300 unique proteins, at least 320 unique proteins, at least 340 unique proteins, at least 360 unique proteins, at least 380 unique proteins, at least 400 unique proteins, at least 420 unique proteins, at least 440 unique proteins, at least 460 unique proteins, at least 480 unique proteins, at least 500 unique proteins, at least 520 unique proteins, at least 540 unique proteins, at least 560 unique proteins, at least 580 unique proteins, at least 600 unique proteins, at least 620 unique proteins, at least 640 unique proteins, at least 660 unique proteins, at least 680 unique proteins, at least 700 unique proteins, at least 720 unique proteins, at least 740 unique proteins, at least 760 unique proteins, at least 780 unique proteins, at least 800 unique proteins, at least 820 unique proteins, at least 840 unique proteins, at least 860 unique proteins, at least 880 unique proteins, at least 900 unique proteins, at least 920 unique proteins, at least 940 unique proteins, at least 960 unique proteins, at least 980 unique proteins, at least 1000 unique proteins, from 100 to 1000 unique proteins, from 150 to 950 unique proteins, from 200 to 900 unique proteins, from 250 to 850 unique proteins, from 300 to 800 unique proteins, from 350 to 750 unique proteins, from 400 to 700 unique proteins, from 450 to 650 unique proteins, from 500 to 600 unique proteins, from 200 to 250 unique proteins, from 250 to 300 unique proteins, from 300 to 350 unique proteins, from 350 to 400 unique proteins, from 400 to 450 unique proteins, from 450 to 500 unique proteins, from 500 to 550 unique proteins, from 550 to 600 unique proteins, from 600 to 650 unique proteins, from 650 to 700 unique proteins, from 700 to 750 unique proteins, from 750 to 800 unique proteins, from 800 to 850 unique proteins, from 850 to 900 unique proteins, from 900 to 950 unique proteins, from 950 to 1000 unique proteins. Similar numbers of proteins may be assessed in some cases without the use of particles, or with an assay method described herein. In some embodiments, several different types of particles can be used, separately or in combination, to identify large numbers of proteins in a particular biological sample. In other words, particles can be multiplexed in order to bind and identify large numbers of proteins in a biological sample.

The methods disclosed herein can be used to identify various biological states in a particular biological sample. For example, a biological state can refer to an elevated or low level of a particular protein or a set of proteins, or may be evidenced by a ratio between the abundances of two or more biomolecules. In other examples, a biological state can refer to identification of a disease, such as cancer. The biological state may include a cancerous lung nodule. The biological state may include a non-cancerous lung nodule. One or more particle types can be incubated with a biological sample, such as human plasma, allowing for formation of a protein corona. Said protein corona can then be analyzed in order to identify a pattern of proteins. The analysis may comprise gel electrophoresis, mass spectrometry, chromatography, ELISA, immunohistology, or any combination thereof. Analysis of protein corona (e.g., by mass spectrometry or gel electrophoresis) may be referred to as corona analysis. The pattern of proteins can be compared to the same methods carried out on a control sample. Upon comparison of the patterns of proteins, it may be identified that the first sample comprises an elevated level of markers corresponding to a particular type of lung cancer. The particles and methods of use thereof, can thus be used to diagnose a particular disease state.

An assay may comprise protein collection of particles, protein digestion, and mass spectrometric analysis (e.g., MS, LC-MS, LC-MS/MS). The digestion may comprise chemical digestion, such as by cyanogen bromide or 2-Nitro-5-thiocyanatobenzoic acid (NTCB). The digestion may comprise enzymatic digestion, such as by trypsin or pepsin. The digestion may comprise enzymatic digestion by a plurality of proteases. The digestion may comprise a protease selected from among the group consisting of trypsin, chymotrypsin, Glu C, Lys C, elastase, subtilisin, proteinase K, thrombin, factor X, Arg C, papaine, Asp N, thermolysine, pepsin, aspartyl protease, cathepsin D, zinc mealloprotease, glycoprotein endopeptidase, proline, aminopeptidase, prenyl protease, caspase, kex2 endoprotease, or any combination thereof. A digestion method may randomly cleave peptides or may cleave peptides at a specific position or set of positions. An assay may utilize a plurality of digestion methods (e.g., two or more proteases). An assay may comprise splitting a sample into multiple portions, and subjecting the portions to different digestion methods and separate analyses (e.g., separate mass spectrometric analyses). The digestion may cleave peptides at a specific position (e.g., at methionines) or sequence (e.g., glutamate-histidine-glutamate). The digestion may enable similar proteins to be distinguished. For example, an assay may resolve 8 distinct proteins as a single protein group with a first digestion method, and as 8 separate proteins with distinct signals with a second digestion method. The digestion may generate an average peptide fragment length of 8 to 15 amino acids. The digestion may generate an average peptide fragment length of 12 to 18 amino acids. The digestion may generate an average peptide fragment length of 15 to 25 amino acids. The digestion may generate an average peptide fragment length of 20 to 30 amino acids. The digestion may generate an average peptide fragment length of 30 to 50 amino acids.

Various methods of the present disclosure enable measurement over a broad concentration range. Biomolecule analysis methods are often limited to narrow concentration ranges. For example, mass spectrometric proteomic analyses are often limited to 3, 4, or 5 orders of magnitude in concentration. Thus, the presence of relatively high concentration biomolecules (e.g., present at mg/ml concentrations) may mask detection of lower concentration biomolecules, and furthermore may limit the accuracy of low concentration biomolecule quantitation. Methods of the present disclosure may enable detection of molecules spanning at least 5, at least 6, at least 7, at least 8, at least 9, at least 10, at least 11, or at least 12 orders of magnitude in concentration. Thus, a method of the present disclosure may detect and quantitate a relatively high concentration biomolecule and a relatively low concentration biomolecule from a single sample without first depleting biomolecules from the sample. For example, a plasma assay consistent with the present disclosure may simultaneously quantitate albumin (present at around 40 mg/ml) and interleukin 10 (present at around 6 pg/ml) from a single, non-depleted plasma sample, thereby simultaneously detecting two species who concentrations differ by about 10 orders of magnitude.

Biomarkers for Detection of Cancer

Proteins may be included as biomarkers for disease detection. The disease detection may include detection of cancer through the use of biomarkers such as proteins. The proteins may be generated as part of protein data or proteomic data.

Examples of proteins may include any protein in FIG. 26A-26B. Protein data may include a measurement of 1, 2, 3, 4, 5, 6, 7, 8, 9, 10, 11, 12, 13, 14, or 15 of these proteins, or a range of any of the aforementioned numbers of proteins from these figures.

Figure 30A:
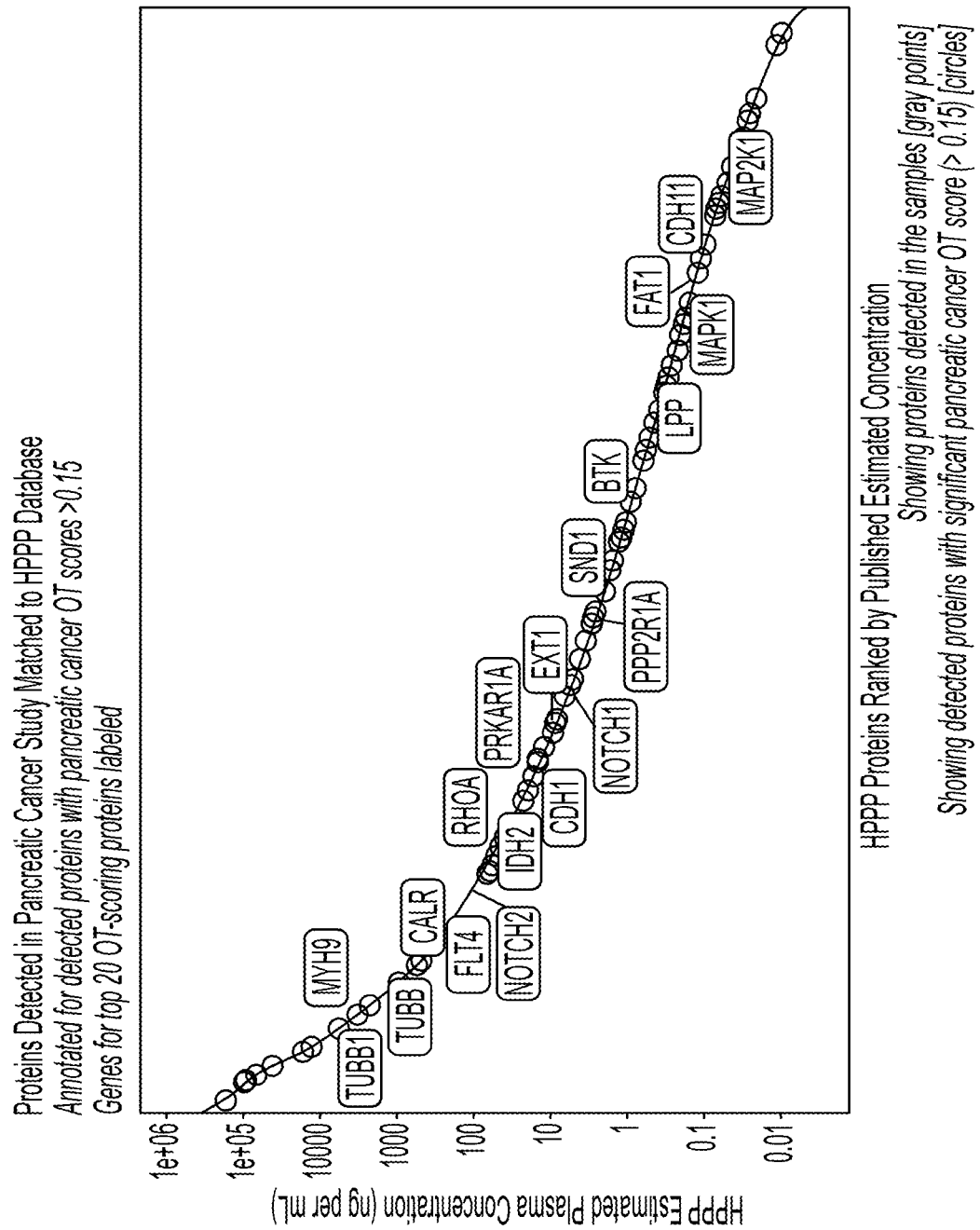
FIG. 30A shows a plot of some top proteins differentially detected in biofluid samples from cancer patients relative to biofluid samples from control patients.
Figure 32B:
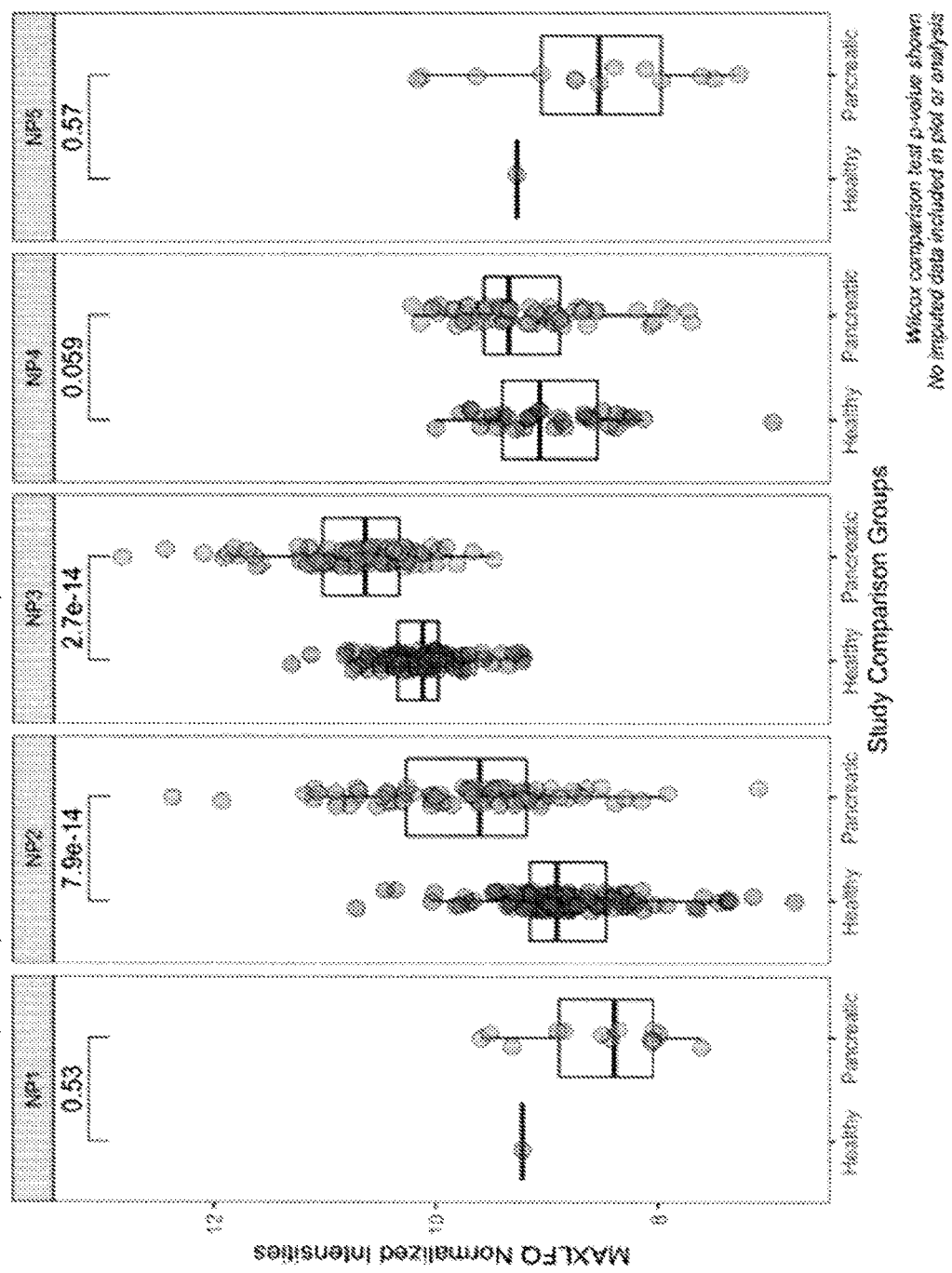
FIG. 32B includes data for top protein P35442 after a particle-based measurement method.
Figure 32C:
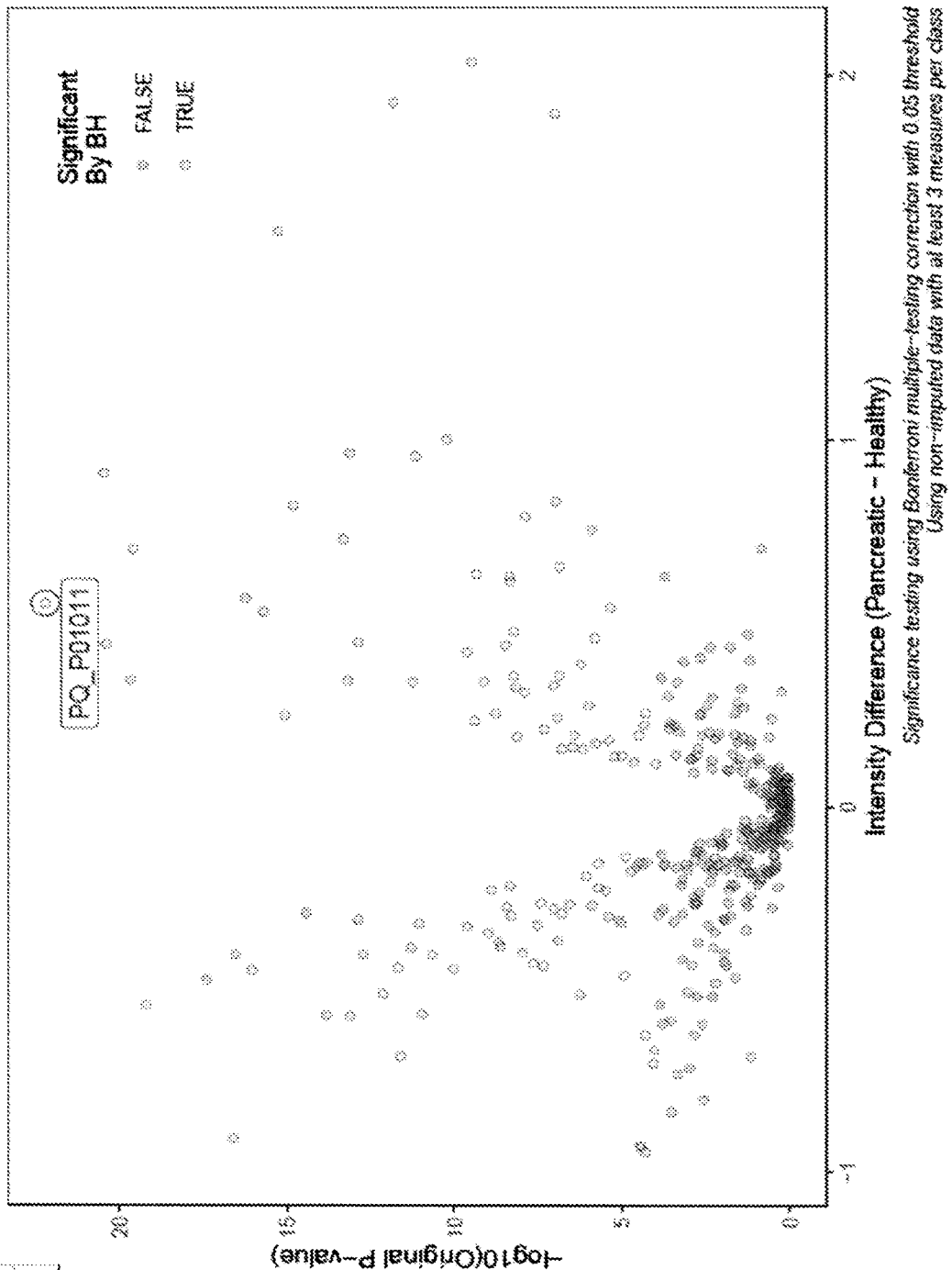
FIG. 32C includes a volcano plot of intensity differences and P-values for proteins detected in biofluid samples from cancer patients, relative to biofluid samples from control patients. The volcano plot displays magnitude of difference on the x-axis, and significance on the y-axis, with the most significant analyte highlighted.
Figure 32D:
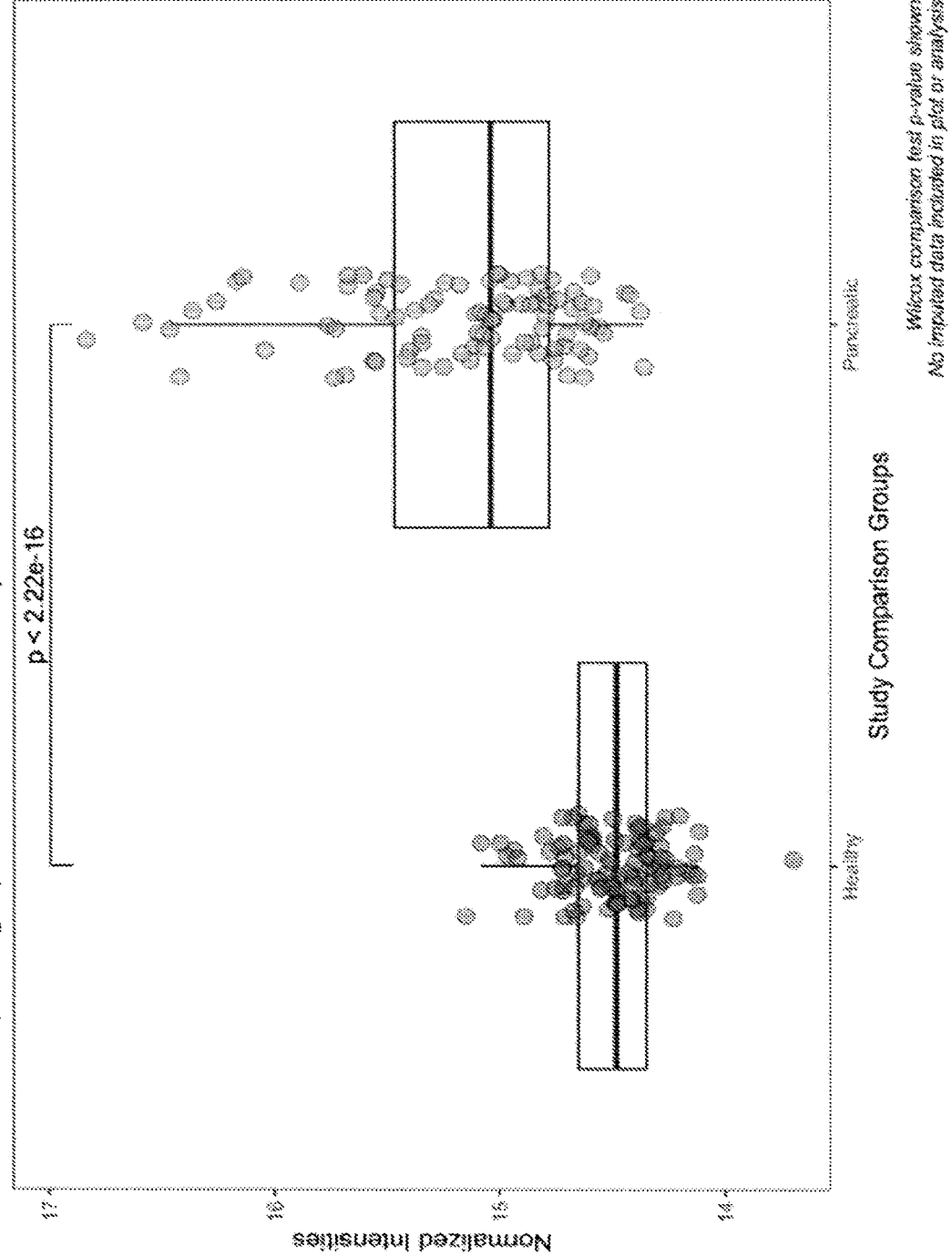
FIG. 32D includes data for top protein P01011 after a proteomic measurement.

Some examples of proteins are shown in FIG. 30A. Proteins that may be detected in a method described herein include Myosin-9 (MYH9), Tubulin beta-1 chain (TUBB1), Tubulin beta chain (TUBB), Calreticulin (CALR), Vascular endothelial growth factor receptor 3 (FLT4), Neurogenic locus notch homolog protein 2 (NOTCH2), Transforming protein RhoA (RHOA), Isocitrate dehydrogenase [NADP], mitochondrial (IDH2), Cadherin-1 (CDH1), cAMP-dependent protein kinase type I-alpha regulatory subunit (PRKAR1A), Neurogenic locus notch homolog protein 1 (NOTCH1), Exostosin-1 (EXT1), Serine/threonine-protein phosphatase 2A 65 kDa regulatory subunit A alpha isoform (PPP2R1A), Staphylococcal nuclease domain-containing protein 1 (SND1), Tyrosine-protein kinase BTK (BTK), Lipoma-preferred partner (LPP), Mitogen-activated protein kinase (MAPK1), Fat1 protein (FAT1), Cadherin-11 (CDH11), or Dual specificity mitogen-activated protein kinase kinase 1 (MAP2K1). Another example of a protein is shown in FIG. 32A-32B. A protein to be detected in a method described herein may include Thrombospondin-2 (TSP2 or P35442). Another example of a protein is shown in FIG. 32C-32D. A protein to be detected in a method described herein may include P01011. Some examples of proteins are shown in FIG. 36. A protein to be detected in a method described herein may include Polymeric immunoglobulin receptor (PIGR, UniProt P01833), Cadherin-related family member 2 (CDHR2, UniProt Q9BYE9), Leucine-rich alpha-2-glycoprotein (LRG1 or A2GL, UniProt P02750), Intercellular adhesion molecule 1 (ICAM1, UniProt P05362), Aminopeptidase N (AMPN or ANPEP, UniProt P15144), Thrombospondin-2 (TSP2, UniProt P35442), Protein S100-A9 (S10A9 or S100A9, UniProt P06702), Aldo-keto reductase family 1 member B1 (ALDR or AKRIB1, UniProt P15121), Serum amyloid A-1 protein (SAA1, UniProt P0DJI8), Peroxidasin homolog (PXDN, UniProt Q92626), Protein S100-A8 (S10A8 or S100A8, UniProt P05109), Anthrax toxin receptor 2 (ANTR2 or ANTXR2, UniProt P58335), Cadherin-2 (CADH2 or CDH2, UniProt P19022), Alpha-1-antichymotrypsin (AACT or SERPINA3, UniProt P01011), Collagen alpha-1 (XVIII) chain (COIA1 or COL18A1, UniProt P39060), Fibrinogen-like protein 1 (FGL1, UniProt Q08830), Protein S100-A12 (S10AC or S100A12, UniProt P80511), Reelin (RELN, UniProt J3KQ66), C-reactive protein (CRP, UniProt P02741), Versican core protein (CSPG2 or VCAN, UniProt P13611), Coagulation factor XIII A chain (F13A or F13A1, UniProt P00488), Cartilage intermediate layer protein 2 (CILP2, UniProt K7EPJ4), Sushi, von Willebrand factor type A, EGF and pentraxin domain-containing protein 1 (SVEP1, UniProt Q4LDE5), Neutrophil gelatinase-associated lipocalin (NGAL or LCN2, UniProt P80188), Tetranectin (TETN or CLEC3B, UniProt P05452), SLAIN motif-containing protein 2 (SLAI2 or SLAIN2, UniProt Q9P270), Anthrax toxin receptor 1 (ANTR1 or ANTXR1, UniProt Q9H6X2, e.g. isoform 5 [UniProt Q9H6X2-5]), or Serum amyloid A-2 protein (SAA2, UniProt P0DJI9). Any number of the aforementioned proteins may be used. Any of the proteins may be used in a classifier.

Examples of proteins may include SERPINA1, HPR, EPS15L1, ORM2, CTSH, CRP, SAA4, COLEC10, HIST1H4I, APOM, ORM1, P0DOX8, IGKV1-8, IGKV1-9, ANGPTL6, SERPINA3, PXDN, IGKC, HP, APCS, or ITIH2. Protein data may include a measurement of 1, 2, 3, 4, 5, 6, 7, 8, 9, 10, 11, 12, 13, 14, 15, 16, 17, 18, 19, 20, or 21 of these proteins, or a range of any of the aforementioned numbers of these proteins.

A method may include measuring biomarkers in a biofluid sample. A method may include using biomarkers in a biofluid sample. The biomarkers may include A2GL, AKRIB1, ANPEP, ANTXR1, ANTXR2, BTK, CALR, CDH1, CDH11, CDH2, CDHR2, CILP2, CLEC3B, COL18A1, CRP, EXT1, F13A1, FAT1, FGL1, FLT4, ICAM1, IDH2, LCN2, LPP, MAPK1, MAP2K1, MYH9, NOTCH1, NOTCH2, PIGR, PPP2R1A, PRKAR1A, PXDN, RELN, RHOA, S100A8, S100A9, S100A12, SAA1, SAA2, SERPINA3, SLAIN2, SND1, SVEP1, TSP2, TUBB, TUBB1, or VCAN. In some aspects, the biomarkers comprise 1, 2, 3, 4, 5, 6, 7, 8, 9, 10, 11, 12, 13, 14, 15, 20, 25, 30, 35, 40, 45, or 48 of the aforementioned biomarkers, or a range of biomarkers defined by any two of the aforementioned integers.

Proteomic data may include protein measurements. A protein measurement may be increased or decreased in a sample from a subject having liver cancer relative to a protein measurement from a control sample, or relative to a baseline measurement. The protein measurement may include a measurement of a protein, or a combination of proteins, from FIG. 39C or FIG. 39D. For example, the protein measurement may include a measurement of one or more of the following proteins: 3-ketoacyl-CoA thiolase, peroxisomal (ACAA1), adenosine deaminase 2 (ADA2), angiotensinogen (AGT), acidic leucine-rich nuclear phosphoprotein 32 family member A (ANP32A), aquaporin-1 (AQP1), actin-related protein 2/3 complex subunit 1B (ARPC1B), asialoglycoprotein receptor 2 (ASGR2), aspartyl/asparaginyl beta-hydroxylase (ASPH), calreticulin (CALR), F-actin-capping protein subunit alpha-1 (CAPZA1), Carbonyl reductase [NADPH] 1 (CBR1), CD5 antigen-like (CD5L), cell migration-inducing and hyaluronan-binding protein (CEMIP), chordin-like protein 1 (CHRDL1), beta-Ala-His dipeptidase (CNDP1), collagen alpha-1 (XIV) chain (COL14A1), collagen alpha-1 (VI) chain (COL6A1), dnaJ homolog subfamily B member 11 (DNAJB11), desmocollin-2 (DSC2), desmoglein-2 (DSG2), bifunctional glutamate/proline—tRNA ligase (EPRS1), endothelial cell-specific molecule 1 (ESM1), electron transfer flavoprotein subunit beta (ETFB), fibroleukin (FGL2), four and a half LIM domains protein 1 (FHL1), fibromodulin (FMOD), fructosamine-3-kinase (FN3K), glypican-1 (GPC1), phosphatidylinositol-glycan-specific phospholipase D (GPLD1), glyoxylate reductase/hydroxypyruvate reductase (GRHPR), trifunctional enzyme subunit alpha, mitochondrial (HADHA), hepatoma-derived growth factor (HDGF), HLA class I histocompatibility antigen, C alpha chain (HLA.C), insulin-like growth factor-binding protein complex acid labile subunit (IGFALS), insulin-like growth factor-binding protein 2 (IGFBP2), insulin-like growth factor-binding protein 5 (IGFBP5), interleukin enhancer-binding factor 2 (ILF2), integrin alpha-M (ITGAM), galectin-3-binding protein (LGALS3BP), amine oxidase [flavin-containing] B (MAOB), methyltransferase-like protein 7A (METTL7A), myeloperoxidase (MPO), nicotinamide phosphoribosyltransferase (NAMPT), NIF3-like protein 1 (NIF3L1), neuropilin-1 (NRP1), nucleobindin-1 (NUCB1), beta-parvin (PARVB), profilin-1 (PFN1), glycerol-3-phosphate phosphatase (PGP), peptidase inhibitor 16 (PI16), polymeric immunoglobulin receptor (PIGR), phosphomevalonate kinase (PMVK), proteoglycan 4 (PRG4), trypsin-2 (PRSS2), 26S proteasome regulatory subunit 6B (PSMC4), pentraxin-related protein PTX3 (PTX3), peroxidasin homolog (PXDN), rab GTPase-activating protein 1 (RABGAP1), 60S ribosomal protein L12 (RPL12), 40S ribosomal protein S7 (RPS7), protein S100-A8 (S100A8), protein S100-A9 (S100A9), serum amyloid A-1 protein (SAA1), sushi, von Willebrand factor type A, EGF and pentraxin domain-containing protein 1 (SVEP1), transgelin-2 (TAGLN2), transferrin receptor protein 1 (TFRC), transforming growth factor-beta-induced protein ig-h3 (TGFBI), Talin-1 (TLN1), tenascin (TNC), tropomyosin alpha-1 chain (TPM1), tubulin alpha-1C chain (TUBA1C), or versican core protein (VCAN). In some aspects, the proteins comprise ACAA1, ADA2, AGT, ANP32A, AQP1, ARPC1B, ASGR2, ASPH, CALR, CAPZA1, CBR1, CD5L, CEMIP, CHRDL1, CNDP1, COL14A1, COL6A1, DNAJB11, DSC2, DSG2, EPRS1, ESM1, ETFB, FGL2, FHL1, FMOD, FN3K, GPC1, GPLD1, GRHPR, HADHA, HDGF, HLA.C, IGFALS, IGFBP2, IGFBP5, ILF2, ITGAM, LGALS3BP, MAOB, METTL7A, MPO, NAMPT, NIF3L1, NRP1, NUCB1, PARVB, PFN1, PGP, PI16, PIGR, PMVK, PRG4, PRSS2, PSMC4, PTX3, PXDN, RABGAP1, RPL12, RPS7, S100A8, S100A9, SAA1, SVEP1, TAGLN2, TFRC, TGFB1, TLN1, TNC, TPM1, TUBA1C, or VCAN, or a combination thereof. The combination of proteins may include 2, 3, 4, 5, 6, 7, 8, 9, 10, 15, 20, 25, 30, 35, 40, 45, 50, 55, 60, 65, 70, or 72 of the proteins in FIG. 39C, or a range of proteins defined by any two of the aforementioned integers. The combination of proteins may include at least 1, at least 2, at least 3, at least 4, at least 5, at least 6, at least 7, at least 8, at least 9, at least 10, at least 15, at least 20, at least 25, at least 30, at least 35, at least 40, at least 45, at least 50, at least 55, at least 60, at least 65, or at least 70, of the proteins in FIG. 39C. The combination of proteins may include less than 3, less than 4, less than 5, less than 6, less than 7, less than 8, less than 9, less than 10, less than 15, less than 20, less than 25, less than 30, less than 35, less than 40, less than 45, less than 50, less than 55, less than 60, less than 65, less than 70, or less than 72, of the proteins in FIG. 39C. In some aspects, the combination of proteins does not include one or more of the proteins in FIG. 39C or FIG. 39D. In some aspects, the proteins comprise a protein useful for lung nodule assessment such as APP, IGHG2, SERPING1, SAA2, SERPINF2, GC, IGHA1, HPR, SERPINA3, IGHA1, LTF, SERPINA1, PCSK6, PROS1, BPIF1, C6, CP, A2M, or IGFBP2.

Proteomic data may include protein measurements. A protein measurement may be increased or decreased in a sample from a subject having ovarian cancer relative to a protein measurement from a control sample, or relative to a baseline measurement. The protein measurement may include a measurement of a protein, or a combination of proteins, from FIG. 40c. For example, the protein measurement may include a measurement of one or more of the following proteins: anthrax toxin receptor 2 (ANTXR2), bone morphogenetic protein 1 (BMP1), cartilage intermediate layer protein 1 (CILP), Interferon-induced double-stranded RNA-activated protein kinase (EIF2AK2), beta-enolase (ENO3), coagulation factor XIII B chain (F13B), fibrinogen-like protein 1 (FGL1), or phosphatidylethanolamine-binding protein 4 (PEBP4). The protein may include ANTXR2. The protein may include BMP1. The protein may include CILP. The protein may include EIF2AK2. The protein may include ENO3. The protein may include F13B. The protein may include FGL1. The protein may include PEBP4. The combination of proteins may include 2, 3, 4, 5, 6, 7, or 8 of the proteins in FIG. 40C, or a range of proteins defined by any two of the aforementioned integers. The combination of proteins may include at least 1, at least 2, at least 3, at least 4, at least 5, at least 6, or at least 7, of the proteins in FIG. 40C. The combination of proteins may include less than 3, less than 4, less than 5, less than 6, less than 7, or less than 8, of the proteins in FIG. 40C. In some aspects, the combination of proteins does not include one or more of the proteins in FIG. 40C or FIG. 39E Described herein are biomarkers that can be analyzed by the methods described herein for determining whether the subject does not have lung nodule, benign lung nodule, or a malignant lung nodule. In some embodiments, the biomarker is a protein. In some embodiments, the biomarker is nucleic acid encoding any one of the protein or peptide fragment of the protein described herein. In some aspects, the biomarkers comprise proteins such as secreted proteins.

Biomarkers disclosed herein (e.g. related to a disease state such as NSCLC, a comorbidity, or a healthy state) can include at least one of the following: Protein S100-A9 (P06702; S10A9_HUMAN), C-reactive protein (P02741; CRP_HUMAN), Inter-alpha-trypsin inhibitor heavy chain H2 (P19823; ITIH2_HUMAN), Protein S100-A8 (P05109; S10A8_HUMAN), Serine protease HTRA1 (Q92743; HTRA1_HUMAN), Angiopoietin-related protein 6 (Q8NI99; ANGL6_HUMAN), Haptoglobin-related protein (P00739; HPTR_HUMAN), C—C motif chemokine 18 (P55774; CCL18_HUMAN), Actin, cytoplasmic 1 (P60709; ACTB_HUMAN), Actin, cytoplasmic 2 (P63261; ACTG_HUMAN), Serum amyloid A-1 protein (P0DJI8; SAA1_HUMAN), Immunoglobulin kappa constant (P01834; IGKC_HUMAN), Angiopoietin-related protein 6 (Q8NI99; ANGL6_HUMAN), Peroxidasin homolog (Q92743; PXDN_HUMAN), Anthrax toxin receptor 2 (P58335; ANTR2_HUMAN), Tubulin alpha-1A chain (Q71U36; TBA1A_HUMAN), Syndecan-1 (P18827; SDC1_HUMAN), Serum amyloid A-2 protein (P0DJI9; SAA2_HUMAN), Versican core protein (P13611; CSPG2_HUMAN), Anthrax toxin receptor 1 (Q9H6X2; ANTR1_HUMAN), Palmitoleoyl-protein carboxylesterase NOTUM (Q6P988; NOTUM_HUMAN), Cartilage intermediate layer protein 1 (075339; CILP1_HUMAN), Calpain-2 catalytic subunit (P17655; CAN2_HUMAN), 60S acidic ribosomal protein P2 (P05387; RLA2_HUMAN), Beta-galactoside alpha-2,6-sialyltransferase 1 (P15907; SIAT1_HUMAN), and Platelet glycoprotein Ib beta chain (P13224; GP1BB_HUMAN). The biomarkers may include any biomarker or biomarkers in FIG. 52. Any one or more of the above biomarkers in various combinations can be used to train a classifier for distinguishing if a subject has lung cancer (e.g., NSCLC) or is co-morbid or healthy. Any one or more of the above biomarkers in various combinations can be used to train a classifier for distinguishing if a subject has a cancerous lung nodule or a non-cancerous lung nodule. In some embodiments, at least one of said biomarkers, at least two of said biomarkers, at least three of said biomarkers, at least four of said biomarkers, at least five of said biomarkers, at least six of said biomarkers, at least seven of said biomarkers, at least eight of said biomarkers, at least nine of said biomarkers, at least 10 of said biomarkers, at least 15 of said biomarkers, at least 20 of said biomarkers, at least 25 of said biomarkers, or all of said biomarkers together can be used to train a classifier for distinguishing if a subject has a cancerous lung nodule or a non-cancerous lung nodule. In some embodiments, at least one of said biomarkers, at least two of said biomarkers, at least three of said biomarkers, at least four of said biomarkers, at least five of said biomarkers, at least six of said biomarkers, at least seven of said biomarkers, at least eight of said biomarkers, at least nine of said biomarkers, at least 10 of said biomarkers, at least 15 of said biomarkers, at least 20 of said biomarkers, at least 25 of said biomarkers, or all of said biomarkers together can be used in a diagnostic assay to determine if a subject has a cancerous lung nodule or a non-cancerous lung nodule. The diagnostic assay can be carried out with the trained classifiers disclosed herein. In some cases where use of a biomarker is described, a biomolecule may be used. A biomarker may include a classifier feature disclosed herein.

The present disclosure provides methods for detecting low abundance peptides in complex biological samples. Many of the diagnostic peptides of the present disclosure are inaccessible through traditional blood analysis methods due to the high concentrations of albumin, immunoglobulins, and other high abundance blood proteins. A diagnostic peptide may be present at 3-, 4-, 5-, 6-, 7-, 8-, 9-, 10-, 11-, 12- or more orders of magnitude lower concentration than the highest abundance proteins in a blood sample, and accordingly will cannot be detected by many traditional proteomic methods. The present disclosure provides methods for enriching low abundance biomolecules (e.g., proteins) from complex biological samples such as plasma, and also for quantifying the enriched biomolecules.

Examples of lung cancer diagnostic peptides are provided in Table 2. Additional diagnostic peptide examples for various cancers are provided in other figures or tables. A method of the present disclosure may comprise assaying a sample from a subject to detect a presence, absence, or abundance of one or more peptides or fragments of peptides from among the peptides listed in Table 2 or another table or figure provided herein. In some cases, a method comprises identifying a ratio between abundances of two peptides or fragments of peptides from among the peptides listed in Table 2 or another table or figure provided herein. In some cases, a method comprises identifying a ratio between abundances of a peptide or fragment of a peptide from among the peptides listed in Table 2 or another table or figure provided herein and a separate peptide from the same biological sample. For example, a method may comprise identifying a ratio of the relative abundance of APOC1 and ceruloplasmin in a plasma sample from a subject with a lung nodule. In some cases, the method comprises assaying the sample to detect a presence, absence, or abundance of one or more peptides or fragments of peptides from among the group consisting of Angiopoietin-related protein 6 (ANGL6), Palmitoleoyl-protein carboxylesterase NOTUM (NOTUM), Cartilage intermediate layer protein 1 (CILP1), 60S acidic ribosomal protein P2 (RLA2), and Platelet glycoprotein Ib beta chain (GP1BB). In some cases, the method comprises assaying a sample to detect a presence, absence, or abundance of at least 2, at least 3, at least 4, at least 5, at least 6, at least 8, at least 10, at least 12, at least 15, at least 20, at least 25, at least 30, or at least 35 peptides or fragments of peptides from among the peptides listed in Table 2 or another table or figure provided herein.

The methods of the present disclosure enable quantification of disparate biomarkers spanning wide concentration ranges. In some cases, a lung cancer (e.g., NSCLC) is evidenced by the relative concentrations of two or more proteins from a sample from a patient. In some cases, a method of the present disclosure comprises identifying abundance (e.g., concentration) ratios between at least 2 peptides from among the peptides listed in Table 2 or another table or figure provided herein. In some cases, a method of the present disclosure comprises identifying abundance ratios between at least 3 peptides from among the peptides listed in Table 2 or another table or figure provided herein. In some cases, a method of the present disclosure comprises identifying abundance ratios between at least 4 peptides from among the peptides listed in Table 2 or another table or figure provided herein. In some cases, a method of the present disclosure comprises identifying abundance ratios between at least 5 peptides from among the peptides listed in Table 2 or another table or figure provided herein. In some cases, a method of the present disclosure comprises identifying abundance ratios between at least 6 peptides from among the peptides listed in Table 2 or another table or figure provided herein. In some cases, a method of the present disclosure comprises identifying abundance ratios between at least 7 peptides from among the peptides listed in Table 2 or another table or figure provided herein. In some cases, a method of the present disclosure comprises identifying abundance ratios between at least 8 peptides from among the peptides listed in Table 2 or another table or figure provided herein. In some cases, a method of the present disclosure comprises identifying abundance ratios between at least 9 peptides from among the peptides listed in Table 2 or another table or figure provided herein. In some cases, a method of the present disclosure comprises identifying abundance ratios between at least 10 peptides from among the peptides listed in Table 2 or another table or figure provided herein. In some cases, a method of the present disclosure comprises identifying abundance ratios between at least 12 peptides from among the peptides listed in Table 2 or another table or figure provided herein. In some cases, a method of the present disclosure comprises identifying abundance ratios between at least 15 peptides from among the peptides listed in Table 2 or another table or figure provided herein. In some cases, a method of the present disclosure comprises identifying abundance ratios between at least 20 peptides from among the peptides listed in Table 2 or another table or figure provided herein. In some cases, a method of the present disclosure comprises identifying abundance ratios between at least 25 peptides from among the peptides listed in Table 2 or another table or figure provided herein. In some cases, the sample is a blood sample (e.g., plasma).

In some cases, the method comprises assaying a sample to detect a presence, absence, or abundance of at least 2, at least 3, at least 4, or all 5 of ANGL6, NOTUM, CILP1, RLA2 or GP1BB. In some cases, one or more peptides or fragments of peptides from among the peptides listed in Table 2 are selected from the group consisting of actin (e.g., beta actin), anthrax toxin receptor 2, cartilage intermediate layer protein 1, collectin 11, and kallistatin. In some cases, one or more peptides or fragments of peptides from among the peptides listed in Table 2 are selected from the group consisting of Angiopoietin-related protein 6 (ANGL6), Serine protease HTRA1 (HTRA1), Peroxidasin homolog (PXDN), C—C motif chemokine 18 (CCL18), Anthrax toxin receptor 2 (ANTR2), Tubulin alpha-1A chain (TBA1A), Syndecan-1 (SDC1), Serum amyloid A-2 protein (SAA2), Versican core protein (CSPG2), Anthrax toxin receptor 1 (ANTR1), Palmitoleoyl-protein carboxylesterase NOTUM (NOTUM), Cartilage intermediate layer protein 1 (CILP1), Calpain-2 catalytic subunit (CAN2), 60S acidic ribosomal protein P2 (RLA2), Beta-galactoside alpha-2,6-sialyltransferase 1 (SIAT1), and Platelet glycoprotein Ib beta chain (GP1BB). In some cases, one or more peptides or fragments of peptides from among the peptides listed in Table 2 are selected from the group consisting of wherein the one or more biomarkers further comprise Leucine-rich alpha-2-glycoprotein (A2GL), Actin, cytoplasmic 1 (ACTB), Actin, cytoplasmic 2 (ACTG), Apolipoprotein C-I (APOC1), Apolipoprotein M (APOM), Voltage-dependent calcium channel subunit alpha-2/delta-1 (CA2D1), Cadherin-13 (CAD13), Beta-Ala-His dipeptidase (CNDP1), Ciliary neurotrophic factor receptor subunit alpha (CNTFR), Collectin-11 (COL11), C-reactive protein (CRP), Hemoglobin subunit alpha (HBA), Haptoglobin-related protein (HPT), Haptoglobin-related protein (HPTR), Inter-alpha-trypsin inhibitor heavy chain H2 (ITIH2), Kallistatin (KAIN), Plasma kallikrein (KLKB1), Neural cell adhesion molecule 1 (NCAM1), Protein S100-A8 (S10A8), Protein S100-A9 (S10A9), and Structural maintenance of chromosomes protein 4 (SMC4). In some cases, one or more peptides or fragments of peptides from among the peptides listed in Table 2 are selected from the group consisting of A2GL, ACTB, ACTG, APOC1, APOM, CA2D1, CAD13, CNDP1, CNTFR, COL11, CRP, HBA, HPT, HPTR, ITIH2, KAIN, KLKB1, NCAM1, S10A8, S10A9 or SMC4. In some cases, one or more peptides or fragments of peptides from among the peptides listed in Table 2 comprise at least 2, at least 3, at least 4, at least 5, at least 6, at least 7, at least 8, at least 9, at least 10, at least 11, at least 12, at least 13, at least 14, at least 15, at least 16, at least 17, at least 18, at least 19, or at least 20 of A2GL, ACTB, ACTG, APOC1, APOM, CA2D1, CAD13, CNDP1, CNTFR, COL11, CRP, HBA, HPT, HPTR, ITIH2, KAIN, KLKB1, NCAM1, S10A8, S10A9 or SMC4.

TABLE 2

Diagnostic Peptides

| Peptide | Approximate Blood Plasma Concentration (mg/ml) in some average patient populations |
| --- | --- |
| 6 sialyltransferase 1 (SIAT1/ST6GAL1) | $1.5 \times 10^{-5}$ |
| 60S acidic ribosomal protein P2 (RLA2) | $7.3 \times 10^{-7}$ |
| Actin | — |
| Angiopoietin related protein 6 (ANGL6) | $4.5 \times 10^{-7}$ |
| Anthrax toxin receptor 1 (ANTR1) | $4.1 \times 10^{-6}$ |
| Anthrax toxin receptor 2 (ANTR2) | $6.6 \times 10^{-6}$ |
| Apolipoprotein C I (APOC1) | $4.0 \times 10^{-4}$ |
| Apolipoprotein M (APOM); | $8.6 \times 10^{-6}$ |
| Beta Ala His dipeptidase (CNDP1) | $1.9 \times 10^{-3}$ |
| Beta-galactoside alpha-2,6-sialyltransferase 1 (SIAT1/ST6Gal I) | $1.5 \times 10^{-5}$ |
| C motif chemokine 18 (CCL18) | $5.3 \times 10^{-5}$ |
| C reactive protein (CRP) | $1.7 \times 10^{-3}$ |
| Cadherin 13 (CAD13) | $2.3 \times 10^{-4}$ |
| Calpain 2 Catalytic Subunit (CAN2) | $1.5 \times 10^{-6}$ |
| Cartilage intermediate layer protein 1 (CILP1) | $1.1 \times 10^{-5}$ |
| Ciliary neurotrophic factor receptor subunit alpha (CNTFR) | $3.6 \times 10^{-5}$ |
| Collectin 11 (COL11) | $3.0 \times 10^{-5}$ |
| Cytoplasmic 1 (ACTB) | — |
| Cytoplasmic 2 (ACTG) | — |
| Haptoglobin related protein (HPT/HPR) | $4.9 \times 10^{-2}$ |
| Hemoglobin subunit alpha (HBA) | $1.7 \times 10^{-2}$ |
| Inter alpha trypsin inhibitor heavy chain H2 (ITIH2) | $2.2 \times 10^{-2}$ |
| Kallistatin (KAIN) | $2.2 \times 10^{-3}$ |
| Leucine rich alpha glycoprotein (A2GL) | — |
| Neural cell adhesion molecule 1 (NCAM1) | $2.8 \times 10^{-3}$ |
| Palmitoleoyl protein carboxylesterase (NOTUM) | $5.9 \times 10^{-8}$ |
| Peroxidasin homolog (PXDN) | $4.0 \times 10^{-6}$ |
| Plasma kallikrein (KLKB1) | $2.9 \times 10^{-2}$ |
| Platelet glycoprotein Ib beta chain (GP1BB) | $1.1 \times 10^{-4}$ |
| Protein S100 A8 (S10A8) | $3.0 \times 10^{-6}$ |
| Protein S100 A9 (S10A9) | $8.4 \times 10^{-6}$ |
| Serine protease HTRA1 (HTRA1) | $1.2 \times 10^{-6}$ |
| Serum amyloid A2 protein (SAA2) | $1.1 \times 10^{-2}$ |
| Syndecan 1 (SDC1) | $6.3 \times 10^{-5}$ |
| Structural maintenance of chromosomes protein 4 (SMC4) | — |
| Tubulin alpha 1A chain (TBA1A) | — |
| Versican core protein (CSPG2) | $5.2 \times 10^{-6}$ |
| Voltage dependent calcium channel subunit alpha 2/delta 1 (CA2D1) | — |

In some cases, a method comprises detecting a presence, absence, or abundance of one or more peptides selected from the group consisting of Angiopoietin-related protein 6 (ANGL6), Serine protease HTRA1 (HTRA1), Peroxidasin homolog (PXDN), C—C motif chemokine 18 (CCL18), Anthrax toxin receptor 2 (ANTR2), Tubulin alpha-1A chain (TBA1A), Syndecan-1 (SDC1), Serum amyloid A-2 protein (SAA2), Versican core protein (CSPG2), Anthrax toxin receptor 1 (ANTR1), Palmitoleoyl-protein carboxylesterase NOTUM (NOTUM), Cartilage intermediate layer protein 1 (CILP1), Calpain-2 catalytic subunit (CAN2), 60S acidic ribosomal protein P2 (RLA2), Beta-galactoside alpha-2,6-sialyltransferase 1 (SIAT1), and Platelet glycoprotein Ib beta chain (GP1BB). In some cases, a method comprises identifying a ratio between abundances of two peptides selected from the group consisting of Angiopoietin-related protein 6 (ANGL6), Serine protease HTRA1 (HTRA1), Peroxidasin homolog (PXDN), C—C motif chemokine 18 (CCL18), Anthrax toxin receptor 2 (ANTR2), Tubulin alpha-1A chain (TBA1A), Syndecan-1 (SDC1), Serum amyloid A-2 protein (SAA2), Versican core protein (CSPG2), Anthrax toxin receptor 1 (ANTR1), Palmitoleoyl-protein carboxylesterase NOTUM (NOTUM), Cartilage intermediate layer protein 1 (CILP1), Calpain-2 catalytic subunit (CAN2), 60S acidic ribosomal protein P2 (RLA2), Beta-galactoside alpha-2,6-sialyltransferase 1 (SIAT1), and Platelet glycoprotein Ib beta chain (GP1BB). In some cases, a method comprises detecting a presence, absence, or abundance of at least 2, at least 3, at least 4, at least 5, at least 6, at least 8, at least 10, at least 12, or at least 15 peptides selected from the group consisting of Angiopoietin-related protein 6 (ANGL6), Serine protease HTRA1 (HTRA1), Peroxidasin homolog (PXDN), C—C motif chemokine 18 (CCL18), Anthrax toxin receptor 2 (ANTR2), Tubulin alpha-1A chain (TBA1A), Syndecan-1 (SDC1), Serum amyloid A-2 protein (SAA2), Versican core protein (CSPG2), Anthrax toxin receptor 1 (ANTR1), Palmitoleoyl-protein carboxylesterase NOTUM (NOTUM), Cartilage intermediate layer protein 1 (CILP1), Calpain-2 catalytic subunit (CAN2), 60S acidic ribosomal protein P2 (RLA2), Beta-galactoside alpha-2,6-sialyltransferase 1 (SIAT1), and Platelet glycoprotein Ib beta chain (GP1BB).

The biomarkers (e.g. proteins) may include an angiopoietin-related protein, a serine protease, a peroxidasin homolog, a C—C motif chemokine, an anthrax toxin receptor, a tubulin protein, a syndecan protein, a serum amyloid A protein, a versican protein, an anthrax toxin receptor protein, a palmitoleoyl-protein carboxylesterase protein, a cartilage intermediate layer protein, a calpain protein or subunit, a 60S acidic ribosomal protein, a beta-galactoside alpha-2,6-sialyltransferase protein, or a platelet glycoprotein, or a subunit or fragment of any of the aforementioned proteins. A biomarker may include an angiopoietin-related protein. A biomarker may include a serine protease. A biomarker may include a peroxidasin homolog. A biomarker may include a C—C motif chemokine. A biomarker may include an anthrax toxin receptor. A biomarker may include a tubulin protein. A biomarker may include a syndecan protein. A biomarker may include a serum amyloid A protein. A biomarker may include a versican protein. A biomarker may include an anthrax toxin receptor protein. A biomarker may include a palmitoleoyl-protein carboxylesterase protein. A biomarker may include a cartilage intermediate layer protein. A biomarker may include a calpain protein or subunit. A biomarker may include a 60S acidic ribosomal protein. A biomarker may include a beta-galactoside alpha-2,6-sialyltransferase protein. A biomarker may include a platelet glycoprotein. A biomarker may be secreted.

The biomarkers (e.g. proteins) may include Angiopoietin-related protein 6 (ANGL6), Serine protease HTRA1 (HTRA1), Peroxidasin homolog (PXDN), C—C motif chemokine 18 (CCL18), Anthrax toxin receptor 2 (ANTR2), Tubulin alpha-1A chain (TBA1A), Syndecan-1 (SDC1), Serum amyloid A-2 protein (SAA2), Versican core protein (CSPG2), Anthrax toxin receptor 1 (ANTR1), Palmitoleoyl-protein carboxylesterase NOTUM (NOTUM), Cartilage intermediate layer protein 1 (CILP1), Calpain-2 catalytic subunit (CAN2), 60S acidic ribosomal protein P2 (RLA2), Beta-galactoside alpha-2,6-sialyltransferase 1 (SIAT1), or Platelet glycoprotein Ib beta chain (GP1BB). The biomarkers (e.g. proteins) may include Angiopoietin-related protein 6 (ANGL6), Serine protease HTRA1 (HTRA1), Peroxidasin homolog (PXDN), C—C motif chemokine 18 (CCL18), Anthrax toxin receptor 2 (ANTR2), Tubulin alpha-1A chain (TBA1A), Syndecan-1 (SDC1), Serum amyloid A-2 protein (SAA2), Versican core protein (CSPG2), Anthrax toxin receptor 1 (ANTR1), Palmitoleoyl-protein carboxylesterase NOTUM (NOTUM), Cartilage intermediate layer protein 1 (CILP1), Calpain-2 catalytic subunit (CAN2), 60S acidic ribosomal protein P2 (RLA2), Beta-galactoside alpha-2,6-sialyltransferase 1 (SIAT1), and Platelet glycoprotein Ib beta chain (GP1BB).

In some cases, the biomarker is a secreted protein. In some aspects, the biomarker includes a protein involved in a metabolic pathway. In some aspects, the biomarker includes a protein involved in oxidative phosphorylation.

In some cases, the biomarker includes a cell-free RNA. In some cases, the biomarker is an RNA encoding a secreted protein. In some aspects, the biomarker includes an mRNA encoding a protein involved in a metabolic pathway. In some aspects, the biomarker includes an mRNA encoding a protein involved in oxidative phosphorylation.

The biomarkers may include ANGL6, HTRA1, PXDN, ANTR2, CSPG2, ANTR1, NOTUM, CILP1, CAN2, or GP1BB. The biomarkers may include ANGL6, HTRA1, PXDN, ANTR2, CSPG2, ANTR1, NOTUM, CILP1, CAN2, and GP1BB.

In some cases, a method comprises assaying a plasma sample to detect a presence, absence, or abundance of one or more peptides or fragments of peptides from among the peptides listed in Table 2 or another table or figure provided herein. In some cases, a method comprises assaying a buffy coat sample to detect a presence, absence, or abundance of one or more peptides or fragments of peptides from among the peptides listed in Table 2 or another table or figure provided herein. In some cases, a method comprises assaying a granulocyte sample to detect a presence, absence, or abundance of one or more peptides or fragments of peptides from among the peptides listed in Table 2 or another table or figure provided herein. In some cases, a method comprises assaying homogenized tissue (e.g. a homogenized lung biopsy tissue sample) to detect a presence, absence, or abundance of one or more peptides or fragments of peptides from among the peptides listed in Table 2 or another table or figure provided herein.

The present methods enable rapid and deep biomolecule profiling from complex biological samples. In many cases, a method detects and identifies hundreds or thousands of distinct biomolecules. Such broad analysis enables deeper profiling of complex samples, and increases the diagnostic utility of individual peptides. A method of the present disclosure may comprise assaying a sample from a subject to detect a presence, absence, or abundance of at least 50 peptides from a biological sample along with one or more additional peptides or fragments of peptides from among the peptides listed in Table 2 or another table or figure provided herein. A method of the present disclosure may comprise assaying a sample from a subject to detect a presence, absence, or abundance of at least 100 peptides from a biological sample along with one or more additional peptides or fragments of peptides from among the peptides listed in Table 2 or another table or figure provided herein. A method of the present disclosure may comprise assaying a sample from a subject to detect a presence, absence, or abundance of at least 200 peptides from a biological sample along with one or more additional peptides or fragments of peptides from among the peptides listed in Table 2 or another table or figure provided herein. A method of the present disclosure may comprise assaying a sample from a subject to detect a presence, absence, or abundance of at least 400 peptides from a biological sample along with one or more additional peptides or fragments of peptides from among the peptides listed in Table 2 or another table or figure provided herein. A method of the present disclosure may comprise assaying a sample from a subject to detect a presence, absence, or abundance of at least 600 peptides from a biological sample along with one or more additional peptides or fragments of peptides from among the peptides listed in Table 2 or another table or figure provided herein. A method of the present disclosure may comprise assaying a sample from a subject to detect a presence, absence, or abundance of at least 800 peptides from a biological sample along with one or more additional peptides or fragments of peptides from among the peptides listed in Table 2 or another table or figure provided herein. A method of the present disclosure may comprise assaying a sample from a subject to detect a presence, absence, or abundance of at least 1000 peptides from a biological sample along with one or more additional peptides or fragments of peptides from among the peptides listed in Table 2 or another table or figure provided herein. A method of the present disclosure may comprise assaying a sample from a subject to detect a presence, absence, or abundance of at least 1200 peptides from a biological sample along with one or more additional peptides or fragments of peptides from among the peptides listed in Table 2 or another table or figure provided herein. A method of the present disclosure may comprise assaying a sample from a subject to detect a presence, absence, or abundance of at least 1400 peptides from a biological sample along with one or more additional peptides or fragments of peptides from among the peptides listed in Table 2 or another table or figure provided herein. A method of the present disclosure may comprise assaying a sample from a subject to detect a presence, absence, or abundance of at least 1600 peptides from a biological sample along with one or more additional peptides or fragments of peptides from among the peptides listed in Table 2 or another table or figure provided herein. A method of the present disclosure may comprise assaying a sample from a subject to detect a presence, absence, or abundance of at least 1800 peptides from a biological sample along with one or more additional peptides or fragments of peptides from among the peptides listed in Table 2 or another table or figure provided herein. A method of the present disclosure may comprise identifying abundance or signal intensity (e.g., mass spectrometric signal intensity) ratios between at least a subset of the at least 50, at least 100, at least 200, at least 400, at least 600, at least 800, at least 1000, at least 1200, at least 1400, at least 1600, or at least 1800 peptides and one or more additional peptides or fragments of peptides from among the peptides listed in Table 2 or another table or figure provided herein.

A method of the present disclosure may comprise monitoring a lung cancer progression over time. A method of the present disclosure may comprise monitoring a lung nodule over time. A method may comprise collecting two samples from a patient at two different points in time, and detecting at least two peptides from among the peptides listed in Table 2 or another table or figure provided herein in each of the samples. A method may comprise collecting two samples from a patient at two different points in time, and detecting at least three peptides from among the peptides listed in Table 2 or another table or figure provided herein in each of the samples. A method may comprise collecting two samples from a patient at two different points in time, and detecting at least four peptides from among the peptides listed in Table 2 or another table or figure provided herein in each of the samples. A method may comprise collecting two samples from a patient at two different points in time, and detecting at least five peptides from among the peptides listed in Table 2 or another table or figure provided herein in each of the samples. A method may comprise collecting two samples from a patient at two different points in time, and detecting at least six peptides from among the peptides listed in Table 2 or another table or figure provided herein in each of the samples. A method may comprise collecting two samples from a patient at two different points in time, and detecting at least seven peptides from among the peptides listed in Table 2 or another table or figure provided herein in each of the samples. A method may comprise collecting two samples from a patient at two different points in time, and detecting at least eight peptides from among the peptides listed in Table 2 or another table or figure provided herein in each of the samples. A method may comprise collecting two samples from a patient at two different points in time, and detecting at least nine peptides from among the peptides listed in Table 2 or another table or figure provided herein in each of the samples. A method may comprise collecting two samples from a patient at two different points in time, and detecting at least ten peptides from among the peptides listed in Table 2 or another table or figure provided herein in each of the samples. A method may comprise collecting two samples from a patient at two different points in time, and detecting at least twelve peptides from among the peptides listed in Table 2 or another table or figure provided herein in each of the samples. A method may comprise collecting two samples from a patient at two different points in time, and detecting at least fifteen peptides from among the peptides listed in Table 2 or another table or figure provided herein in each of the samples. A method may comprise collecting two samples from a patient at two different points in time, and detecting at least twenty peptides from among the peptides listed in Table 2 or another table or figure provided herein in each of the samples. The second of the two samples may be collected at least 1 week, at least 2 weeks, at least 3 weeks, at least 4 weeks, at least 5 weeks, at least 6 weeks, at least 8 weeks, at least 12 weeks, at least 15 weeks, at least 18 weeks, at least 24 weeks, at least 36 weeks, at least 52 weeks, at least 78 weeks, at least 104 weeks, at least 130 weeks, at least 156 weeks, at least 208 weeks, or at least 260 weeks apart. A sample or both samples may be collected during the course of a cancer treatment, such as chemotherapy, to determine the efficacy of the treatment. A sample may be collected during a cancer remission stage in order to detect the reemergence, dormancy, or progression to complete remission.

Disclosed herein are methods that include biomarkers. The biomarkers may include Angiopoietin-related protein 6 (ANGL6), Palmitoleoyl-protein carboxylesterase NOTUM (NOTUM), Cartilage intermediate layer protein 1 (CILP1), 60S acidic ribosomal protein P2 (RLA2), and Platelet glycoprotein Ib beta chain (GP1BB), or a peptide fragment thereof. The biomarkers may include at least 1, at least 2, at least 3, or at least 4, of: ANGL6, NOTUM, CILP1, RLA2 or GP1BB. The biomarkers may include ANGL6, NOTUM, CILP1, RLA2 and GP1BB. In some cases, any of these biomarkers are useful for identifying a lung nodule as being cancerous or not. The biomarkers may be included in a classifier for distinguishing the lung nodule as being cancerous or not.

Disclosed herein are methods that include biomarkers. The biomarkers may include Angiopoietin-related protein 6 (ANGL6), Serine protease HTRA1 (HTRA1), Peroxidasin homolog (PXDN), C—C motif chemokine 18 (CCL18), Anthrax toxin receptor 2 (ANTR2), Tubulin alpha-1A chain (TBA1A), Syndecan-1 (SDC1), Serum amyloid A-2 protein (SAA2), Versican core protein (CSPG2), Anthrax toxin receptor 1 (ANTR1), Palmitoleoyl-protein carboxylesterase NOTUM (NOTUM), Cartilage intermediate layer protein 1 (CILP1), Calpain-2 catalytic subunit (CAN2), 60S acidic ribosomal protein P2 (RLA2), Beta-galactoside alpha-2,6-sialyltransferase 1 (SIAT1), or Platelet glycoprotein Ib beta chain (GP1BB), or a peptide fragment thereof. The biomarkers may include at least 1, at least 2, at least 3, at least 4, at least 5, at least 6, at least 7, at least 8, at least 9, at least 10, at least 11, at least 12, at least 13, at least 14, or at least 15, of: ANGL6, HTRA1, PXDN, CCL18, ANTR2, TBA1A, SDC1, SAA2, CSPG2, ANTR1, NOTUM, CILP1, CAN2, RLA2, SIAT1 or GP1BB. The biomarkers may include ANGL6, HTRA1, PXDN, CCL18, ANTR2, TBA1A, SDC1, SAA2, CSPG2, ANTR1, NOTUM, CILP1, CAN2, RLA2, SIAT1 and GP1BB. The biomarkers may be included in a classifier.

Disclosed herein are methods that include biomarkers. The biomarkers may include Leucine-rich alpha-2-glycoprotein (A2GL), Actin, cytoplasmic 1 (ACTB), Actin, cytoplasmic 2 (ACTG), Apolipoprotein C-I (APOC1), Apolipoprotein M (APOM), Voltage-dependent calcium channel subunit alpha-2/delta-1 (CA2D1), Cadherin-13 (CAD13), Beta-Ala-His dipeptidase (CNDP1), Ciliary neurotrophic factor receptor subunit alpha (CNTFR), Collectin-11 (COL11), C-reactive protein (CRP), Hemoglobin subunit alpha (HBA), Haptoglobin-related protein (HPT), Haptoglobin-related protein (HPTR), Inter-alpha-trypsin inhibitor heavy chain H2 (ITIH2), Kallistatin (KAIN), Plasma kallikrein (KLKB1), Neural cell adhesion molecule 1 (NCAM1), Protein S100-A8 (S10A8), Protein S100-A9 (S10A9), or Structural maintenance of chromosomes protein 4 (SMC4). The biomarkers may include at least 1, at least 2, at least 3, at least 4, at least 5, at least 6, at least 7, at least 8, at least 9, at least 10, at least 11, at least 12, at least 13, at least 14, at least 15, at least 16, at least 17, at least 18, at least 19, or at least 20, of: A2GL, ACTB, ACTG, APOC1, APOM, CA2D1, CAD13, CNDP1, CNTFR, COL11, CRP, HBA, HPT, HPTR, ITIH2, KAIN, KLKB1, NCAM1, S10A8, S10A9 or SMC4. The biomarkers may include A2GL, ACTB, ACTG, APOC1, APOM, CA2D1, CAD13, CNDP1, CNTFR, COL11, CRP, HBA, HPT, HPTR, ITIH2, KAIN, KLKB1, NCAM1, S10A8, S10A9 and SMC4. The biomarkers may be included in a classifier.

Disclosed herein are methods or classifiers that include a biomarker (or multiple biomarkers). The biomarker may include ANGL6. The biomarker may include HTRA1. The biomarker may include PXDN. The biomarker may include CCL18. The biomarker may include ANTR2. The biomarker may include TBA1A. The biomarker may include SDC1. The biomarker may include SAA2. The biomarker may include CSPG2. The biomarker may include ANTR1. The biomarker may include NOTUM. The biomarker may include CILP1. The biomarker may include CAN2. The biomarker may include RLA2. The biomarker may include SIAT1. The biomarker may include GP1BB. The biomarker may include A2GL. The biomarker may include ACTB. The biomarker may include ACTG. The biomarker may include APOC1. The biomarker may include APOM. The biomarker may include CA2D1. The biomarker may include CAD13. The biomarker may include CNDP1. The biomarker may include CNTFR. The biomarker may include COL11. The biomarker may include CRP. The biomarker may include HBA. The biomarker may include HPT. The biomarker may include HPTR. The biomarker may include ITIH2. The biomarker may include KAIN. The biomarker may include KLKB1. The biomarker may include NCAM1. The biomarker may include S10A8. The biomarker may include S10A9. The biomarker may include SMC4.

Disclosed herein are methods or classifiers that include biomarkers. The biomarkers may exclude ANGL6. The biomarkers may exclude HTRA1. The biomarkers may exclude PXDN. The biomarkers may exclude CCL18. The biomarkers may exclude ANTR2. The biomarkers may exclude TBA1A. The biomarkers may exclude SDC1. The biomarkers may exclude SAA2. The biomarkers may exclude CSPG2. The biomarkers may exclude ANTR1. The biomarkers may exclude NOTUM. The biomarkers may exclude CILP1. The biomarkers may exclude CAN2. The biomarkers may exclude RLA2. The biomarkers may exclude SIAT1. The biomarkers may exclude GP1BB. The biomarkers may exclude A2GL. The biomarkers may exclude ACTB. The biomarkers may exclude ACTG. The biomarkers may exclude APOC1. The biomarkers may exclude APOM. The biomarkers may exclude CA2D1. The biomarkers may exclude CAD13. The biomarkers may exclude CNDP1. The biomarkers may exclude CNTFR. The biomarkers may exclude COL11. The biomarkers may exclude CRP. The biomarkers may exclude HBA. The biomarkers may exclude HPT. The biomarkers may exclude HPTR. The biomarkers may exclude ITIH2. The biomarkers may exclude KAIN. The biomarkers may exclude KLKB1. The biomarkers may exclude NCAM1. The biomarkers may exclude S10A8. The biomarkers may exclude S10A9. The biomarkers may exclude SMC4.

Figure 7:
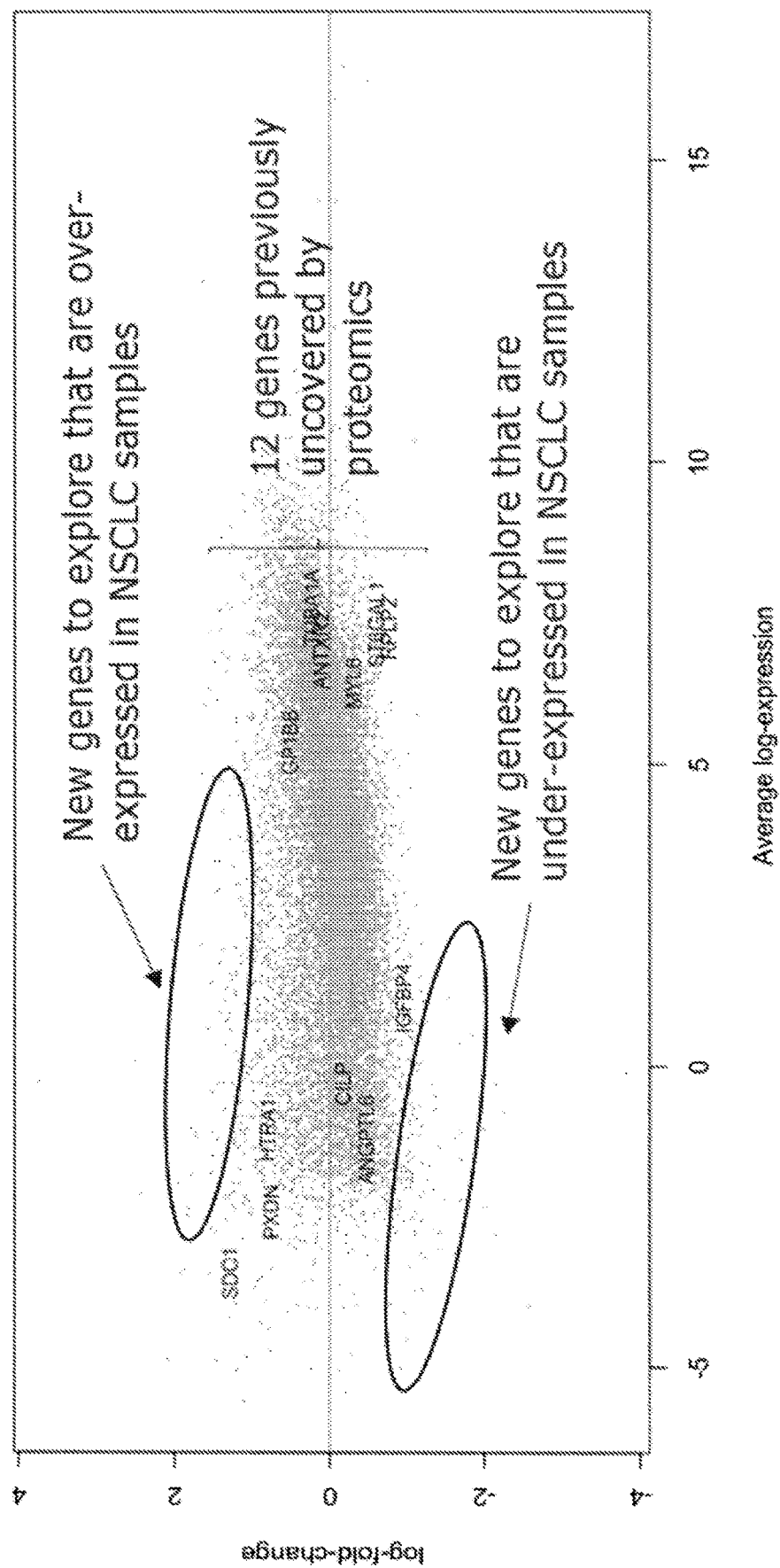
FIG. 7 shows a diagram illustrating expression of some proteins in samples of diseased subjects relative to control subjects. Several genes were differentially expressed (under expressed or over expressed) between groups (NSCLC and healthy samples).

In some embodiments, the biomarker includes one or more biomarkers included in FIG. 7. In some embodiments, the biomarker includes Syndecan-1 (SDC1), Peroxidasin homolog (PXDN), Serine protease HTRA1 (HTRA1), Cartilage intermediate layer protein 1 (CILP), Angiopoietin-related protein 6 (ANGPTL6), Insulin-like growth factor-binding protein 4 (IGFBP4), Platelet glycoprotein Ib beta chain (GP1BB), Myosin light polypeptide 6 (MYL6), Anthrax toxin receptor 2 (ANTXR2), Tubulin alpha-1A chain (TUBA1A), Beta-galactoside alpha-2,6-sialyltransferase 1 (ST6GAL1), or 60S acidic ribosomal protein P2 (RPLP2). In some embodiments, the biomarker includes SDC1. In some embodiments, the biomarker includes PXDN. In some embodiments, the biomarker includes HTRA1. In some embodiments, the biomarker includes CILP. In some embodiments, the biomarker includes ANGPTL6. In some embodiments, the biomarker includes IGFBP4. In some embodiments, the biomarker includes GP1BB. In some embodiments, the biomarker includes MYL6. In some embodiments, the biomarker includes ANTXR2. In some embodiments, the biomarker includes TUBA1A. In some embodiments, the biomarker includes ST6GAL1. In some embodiments, the biomarker includes RPLP2. The biomarkers may include all of the proteins in FIG. 7. The biomarkers may include 1, 2, 3, 4, 5, 6, 7, 8, 9, 10, 11, or 12 of the proteins in FIG. 7, or a range of proteins defined by any two of the aforementioned integers. The biomarkers may include at least 1, at least 2, at least 3, at least 4, at least 5, at least 6, at least 7, at least 8, at least 9, at least 10, or at least 11, of the proteins in FIG. 7. In some aspects, the biomarkers include less than 3, less than 4, less than 5, less than 6, less than 7, less than 8, less than 9, less than 10, less than 11, or less than 12, of the proteins in FIG. 7. In some aspects, the biomarkers excludes a protein in FIG. 7.

In some embodiments, the biomarker includes one or more mRNA biomarkers included in FIG. 10B. In some embodiments, the mRNA biomarker includes a Dystrobrevin alpha (DTNA), Leucine-, glutamate- and lysine-rich protein 1 (LEKR), Membrane-associated tyrosine- and threonine-specific cdc2-inhibitory kinase (PKMYT1), Protein hinderin (KIAA1328), LOC101928068, B box and SPRY domain-containing protein (BSPRY), Leukocyte immunoglobulin-like receptor subfamily B member 4 (LILRB4), Protein unc-119 homolog B (UNC119B), Leucine-rich repeat-containing protein 7 (LRRC7), or LINC00937 mRNA. In some embodiments, the mRNA biomarker includes a DTNA mRNA. In some embodiments, the mRNA biomarker includes a LEKR mRNA. In some embodiments, the mRNA biomarker includes a PKMYT1 mRNA. In some embodiments, the mRNA biomarker includes a KIAA1328 mRNA. In some embodiments, the mRNA biomarker includes a LOC101928068 mRNA. In some embodiments, the mRNA biomarker includes a BSPRY mRNA. In some embodiments, the mRNA biomarker includes a LILRB4 mRNA. In some embodiments, the mRNA biomarker includes a UNC119B mRNA. In some embodiments, the mRNA biomarker includes a LRRC7 mRNA. In some embodiments, the mRNA biomarker includes a LINC00937 mRNA. The biomarkers may include all of the mRNAs in FIG. 10B. The biomarkers may include 1, 2, 3, 4, 5, 6, 7, 8, 9, or 10 of the mRNAs in FIG. 10B, or a range of mRNAs defined by any two of the aforementioned integers. The biomarkers may include at least 1, at least 2, at least 3, at least 4, at least 5, at least 6, at least 7, at least 8, or at least 9, of the mRNAs in FIG. 10B. In some aspects, the biomarkers include less than 3, less than 4, less than 5, less than 6, less than 7, less than 8, less than 9, or less than 10, of the mRNAs in FIG. 10B. In some aspects, the biomarkers excludes a mRNAs in FIG. 10B.

In some embodiments, the biomarker includes one or more protein biomarkers included in FIG. 10B. In some embodiments, the biomarker includes Syndecan-1 (SDC1), Insulin-like growth factor-binding protein 2 (IGFBP2), Ras-related protein Rab-13 (RAB13), Angiopoietin-related protein 6 (ANGPTL6), Anthrax toxin receptor 2 (ANTXR2), or Beta-galactoside alpha-2,6-sialyltransferase 1 (ST6GAL1). In some embodiments, the biomarker includes SDC1. In some embodiments, the biomarker includes IGFBP2. In some embodiments, the biomarker includes RAB13. In some embodiments, the biomarker includes ANGPTL6. In some embodiments, the biomarker includes ANTXR2. In some embodiments, the biomarker includes ST6GAL1. The biomarkers may include all of the proteins in FIG. 10B. The biomarkers may include 1, 2, 3, 4, 5, 6, 7, 8, 9, or 10 of the proteins in FIG. 10B, or a range of proteins defined by any two of the aforementioned integers. The biomarkers may include at least 1, at least 2, at least 3, at least 4, at least 5, at least 6, at least 7, at least 8, or at least 9, of the proteins in FIG. 10B. In some aspects, the biomarkers include less than 3, less than 4, less than 5, less than 6, less than 7, less than 8, less than 9, or less than 10, of the proteins in FIG. 10B. In some aspects, the biomarkers excludes a protein in FIG. 10B.

Figure 58:
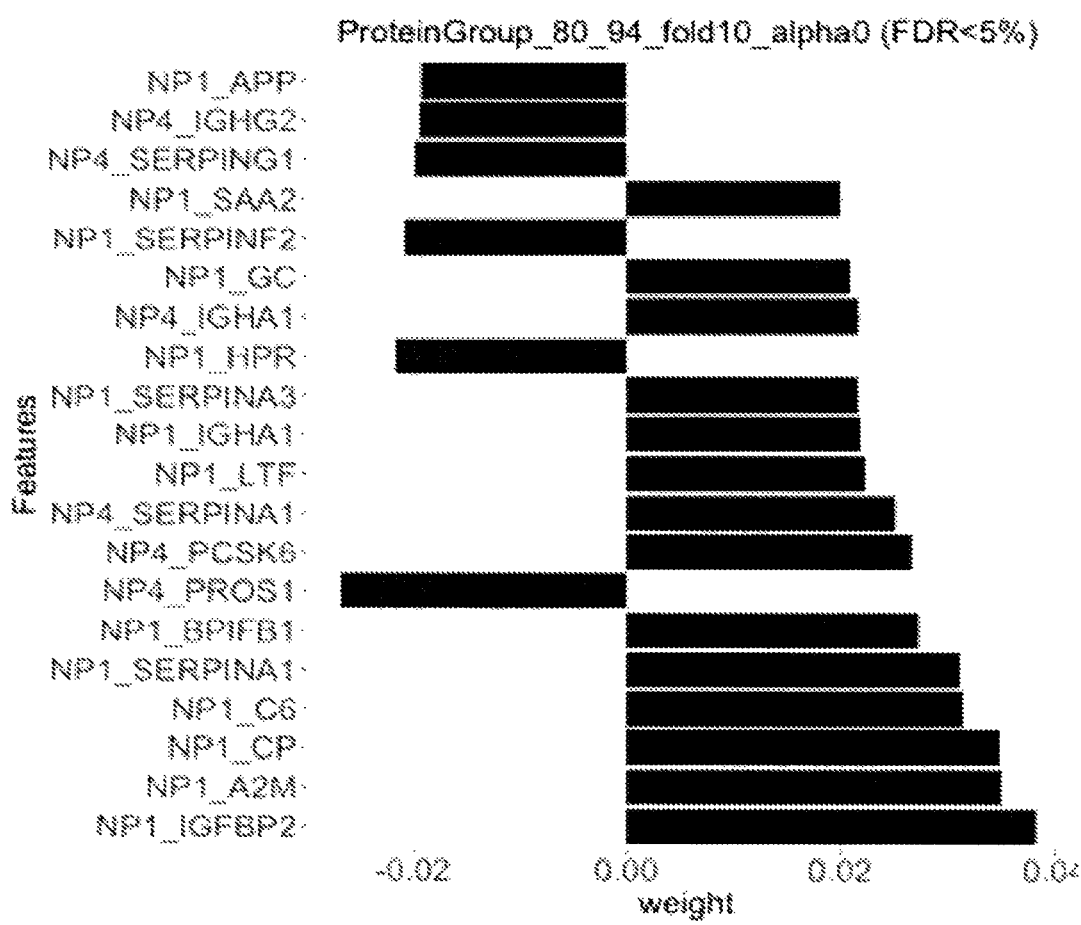
FIG. 58 shows the feature information and importance of the lung nodule classifier shown in FIG. 57.

In some embodiments, the biomarker is a biomarker included in FIG. 58. In some embodiments, the biomarker includes Amyloid-beta A4 protein (APP), Immunoglobulin heavy constant gamma 2 (IGHG2), Plasma protease C1 inhibitor (SERPING1), Serum amyloid A-2 protein (SAA2), Alpha-2-antiplasmin (SERPINF2), Vitamin D-binding protein (GC), Immunoglobulin heavy constant alpha 1 (IGHA1), Haptoglobin-related protein (HPR), Alpha-1-antichymotrypsin (SERPINA3), Lactotransferrin (LTF), Alpha-1-antiproteinase (SERPINA1), Proprotein convertase subtilisin/kexin type 6 (PCSK6), Vitamin K-dependent protein S (PROS1), BPIF1, Complement component C6 (C6), Ceruloplasmin (CP), Alpha-2-macroglobulin (A2M), or Insulin-like growth factor-binding protein 2 (IGFBP2). In some embodiments, the biomarker includes APP. In some embodiments, the biomarker includes IGHG2. In some embodiments, the biomarker includes SERPING1. In some embodiments, the biomarker includes SAA2. In some embodiments, the biomarker includes SERPINF2. In some embodiments, the biomarker includes CG. In some embodiments, the biomarker includes IGHA1. In some embodiments, the biomarker includes HPR. In some embodiments, the biomarker includes SERPINA3. In some embodiments, the biomarker includes LTF. In some embodiments, the biomarker includes SERPINA1. In some embodiments, the biomarker includes PCSK6. In some embodiments, the biomarker includes PROS1. In some embodiments, the biomarker includes BPIF1. In some embodiments, the biomarker includes C6. In some embodiments, the biomarker includes CP. In some embodiments, the biomarker includes A2M. In some embodiments, the biomarker includes IGFBP2. In some embodiments, the biomarker includes a plurality of biomarkers.

In some embodiments, the biomarkers include 1, 2, 3, 4, 5, 6, 7, 8, 9, 10, 11, 12, 13, 14, 15, 16, 17, 18, 19, or 20 of the biomarkers included in FIG. 58. In some embodiments, the biomarkers include 1, 2, 3, 4, 5, 6, 7, 8, 9, 10, 11, 12, 13, 14, 15, 16, 17, 18, or 19, or a range defined by any two of the aforementioned integers, of the biomarkers included in FIG. 58. In some embodiments, the biomarkers include at least 1, at least 2, at least 3, at least 4, at least 5, at least 6, at least 7, at least 8, at least 9, at least 10, at least 11, at least 12, at least 13, at least 14, at least 15, at least 16, at least 17, or at least 18, of the biomarkers included in FIG. 58. In some embodiments, the biomarkers include no more than 1, no more than 2, no more than 3, no more than 4, no more than 5, no more than 6, no more than 7, no more than 8, no more than 9, no more than 10, no more than 11, no more than 12, no more than 13, no more than 14, no more than 15, no more than 16, no more than 17, no more than 18, or no more than 19, of the biomarkers included in FIG. 58. In some embodiments, the biomarkers include all of the biomarkers included in FIG. 58. The biomarkers may include APP. The biomarkers may include IGHG2. The biomarkers may include SERPING1. The biomarkers may include SAA2. The biomarkers may include SERPINF2. The biomarkers may include GC. The biomarkers may include IGHA1. The biomarkers may include HPR. The biomarkers may include SERPINA3. The biomarkers may include LTF. The biomarkers may include SERPINA1. The biomarkers may include PCSK6. The biomarkers may include PROS1. The biomarkers may include BPIFB1. The biomarkers may include C6. The biomarkers may include CP. The biomarkers may include A2M. The biomarkers may include IGFBP2.

Figure 62A:
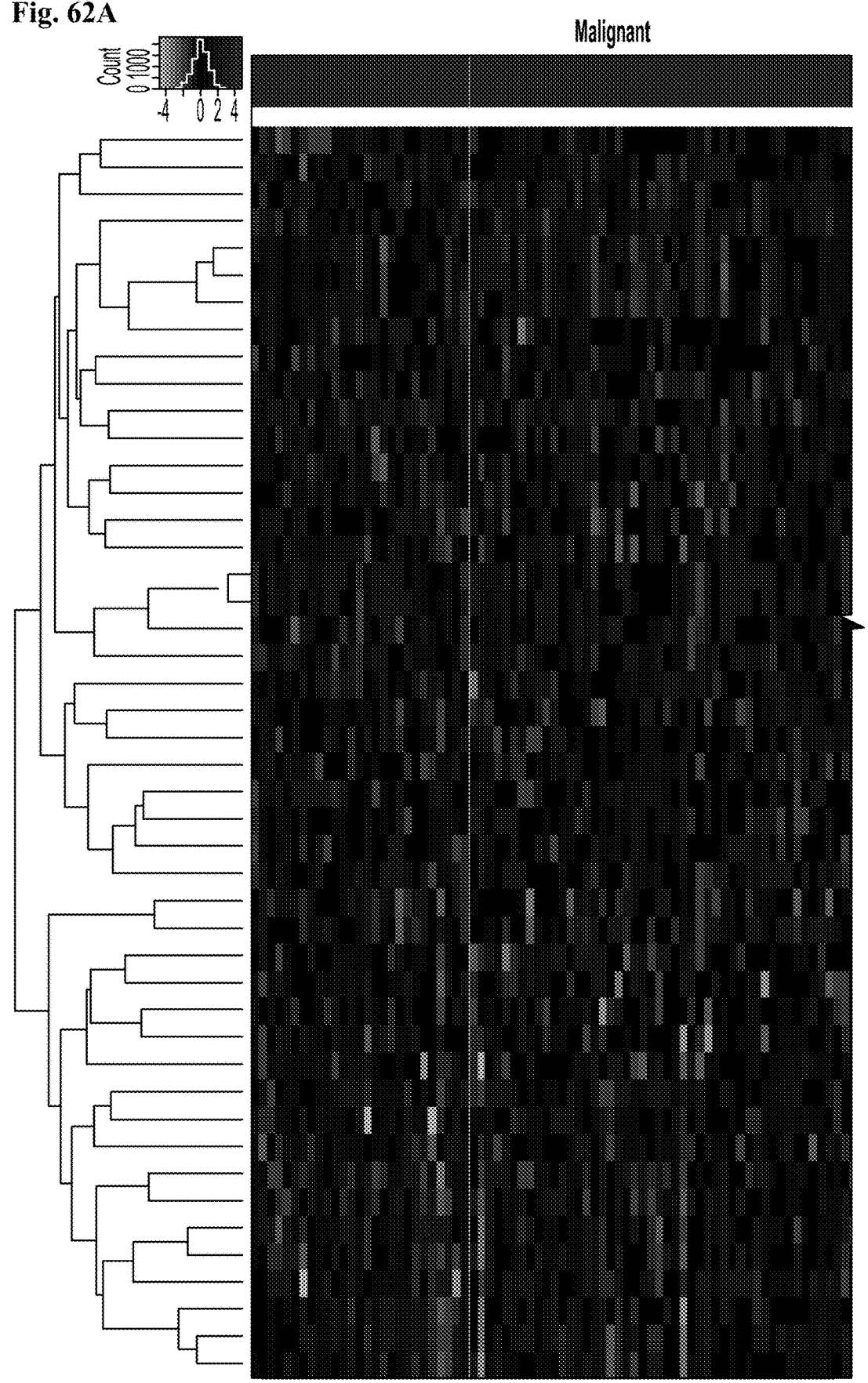
FIGS. 62A and 62B include a protein abundance heatmap of samples from subjects having malignant and benign lung nodules.
Figure 62B:
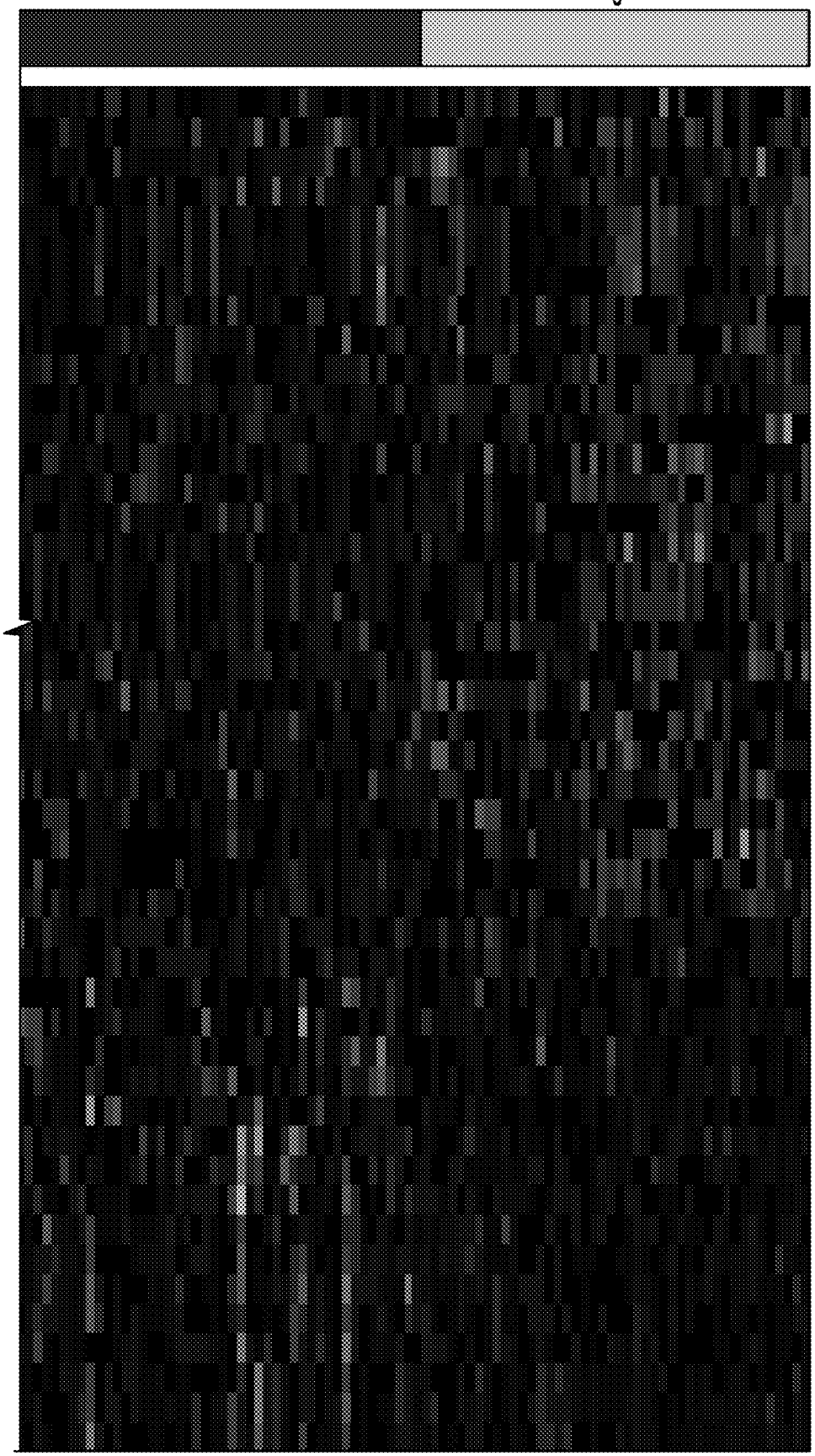

In some embodiments, the biomarkers include any protein in FIG. 62. For example, the biomarkers may include any of the following proteins: ADAM DEC1 (ADAMDEC1), Angiopoietin-related protein 6 (ANGPTL6), BPI fold-containing family B member 1 (BPIFB1), Complement C1q subcomponent subunit A (C1QA), Complement C1q subcomponent subunit B (C1QB), Complement component C6 (C6), Complement component C8 gamma chain (C8G), Cholesteryl ester transfer protein (CETP), Chromogranin-A (CHGA), Secretogranin-1 (CHGB), Cartilage intermediate layer protein 1 (CILP), Beta-Ala-His dipeptidase (CNDP1), Collagen alpha-1 (XVIII) chain (COL18A1), Collectin-10 (COLEC10), Src substrate cortactin (CTTN), Dematin (DMTN), Desmocollin-3 (DSC3), Coagulation factor XI (F11), Prothrombin (F2), Gelsolin (GSN), Granzyme H (GZMH), Hyaluronan-binding protein 2 (HABP2), Insulin-like growth factor II (IGF2), Insulin-like growth factor-binding protein complex acid labile subunit (IGFALS), Insulin-like growth factor-binding protein 2 (IGFBP2), Insulin-like growth factor-binding protein 3 (IGFBP3), Immunoglobulin kappa constant (IGKC), Alpha-lactalbumin (LALBA), Latent-transforming growth factor beta-binding protein 2 (LTBP2), Matrix metalloproteinase-19 (MMP19), Inactive serine protease PAMR1 (PAMR1), Phosphoglycerate kinase 1 (PGK1), Polymeric immunoglobulin receptor (PIGR), Retinol-binding protein 4 (RBP4), Alpha-1-antiproteinase (SERPINA1), Alpha-1-antichymotrypsin (SERPINA3), Sushi, von Willebrand factor type A, EGF and pentraxin domain-containing protein 1 (SVEP1), or Tsukushi (TSKU). The biomarkers may include 1, 2, 3, 4, 5, 6, 7, 8, 9, 10, 15, 20, 25, 30, 35, or 38 of the proteins in FIG. 62, or a range of proteins defined by any two of the aforementioned integers. The biomarkers may include at least 1, at least 2, at least 3, at least 4, at least 5, at least 6, at least 7, at least 8, at least 9, at least 10, at least 15, at least 20, at least 25, at least 30, or at least 35, of the proteins in FIG. 62. In some aspects, the biomarkers include less than 3, less than 4, less than 5, less than 6, less than 7, less than 8, less than 9, less than 10, less than 15, less than 20, less than 25, less than 30, less than 35, or less than 38, of the proteins in FIG. 62. In some aspects, the biomarkers excludes a protein in FIG. 62.

Figure 63:
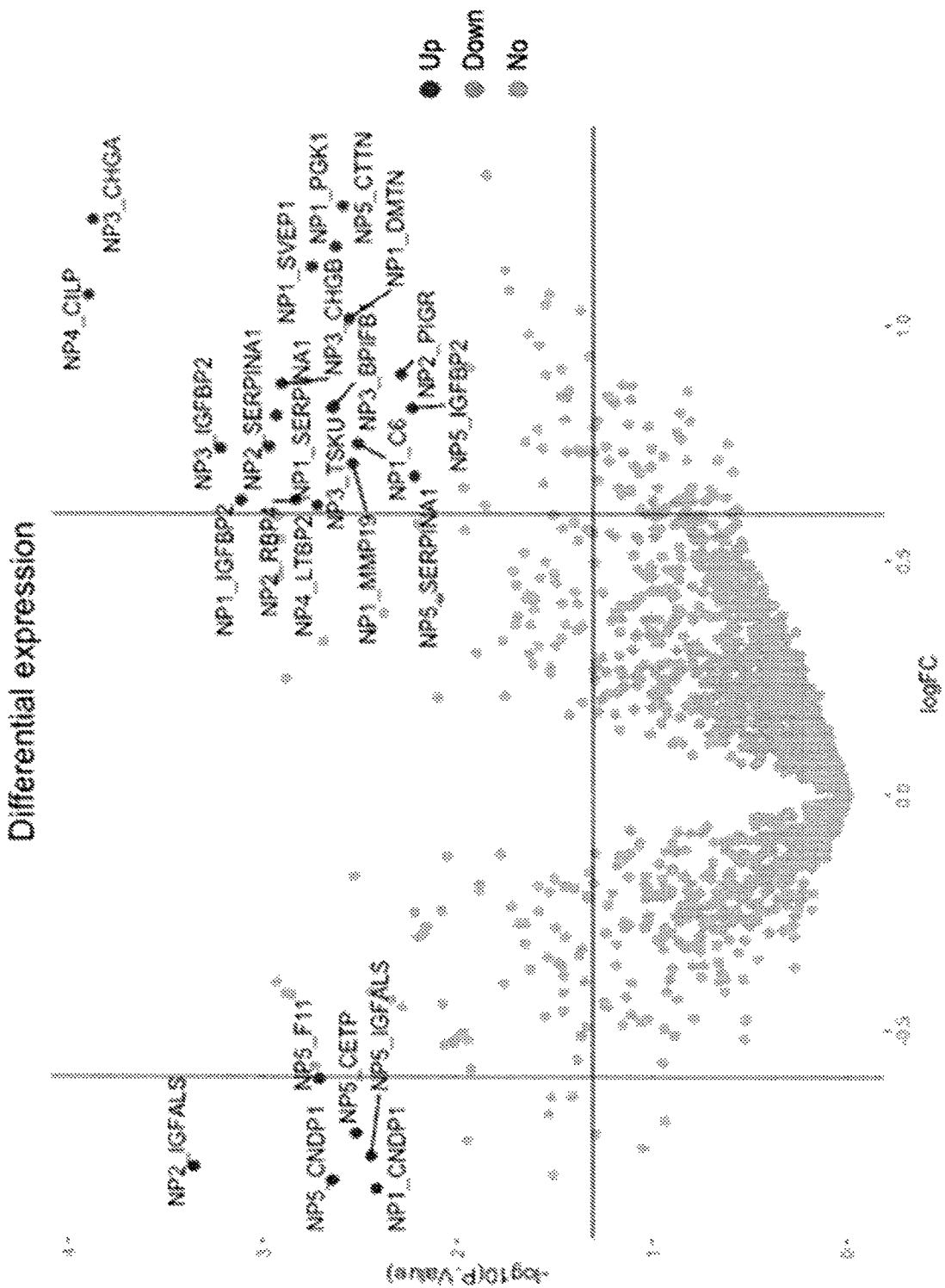
FIG. 63 includes a volcano diagram plotting log-fold changes in protein abundances against negative log of p-value.

In some embodiments, the biomarkers include any protein in FIG. 63. The biomarkers may include all of the proteins in FIG. 63. The biomarkers may include 1, 2, 3, 4, 5, 6, 7, 8, 9, 10, 15, 20, or 25 of the proteins in FIG. 63, or a range of proteins defined by any two of the aforementioned integers. The biomarkers may include at least 1, at least 2, at least 3, at least 4, at least 5, at least 6, at least 7, at least 8, at least 9, at least 10, at least 15, or at least 20, of the proteins in FIG. 63. In some aspects, the biomarkers include less than 3, less than 4, less than 5, less than 6, less than 7, less than 8, less than 9, less than 10, less than 15, less than 20, or less than 25 of the proteins in FIG. 63. In some aspects, the biomarkers excludes a protein in FIG. 63.

Figure 64:
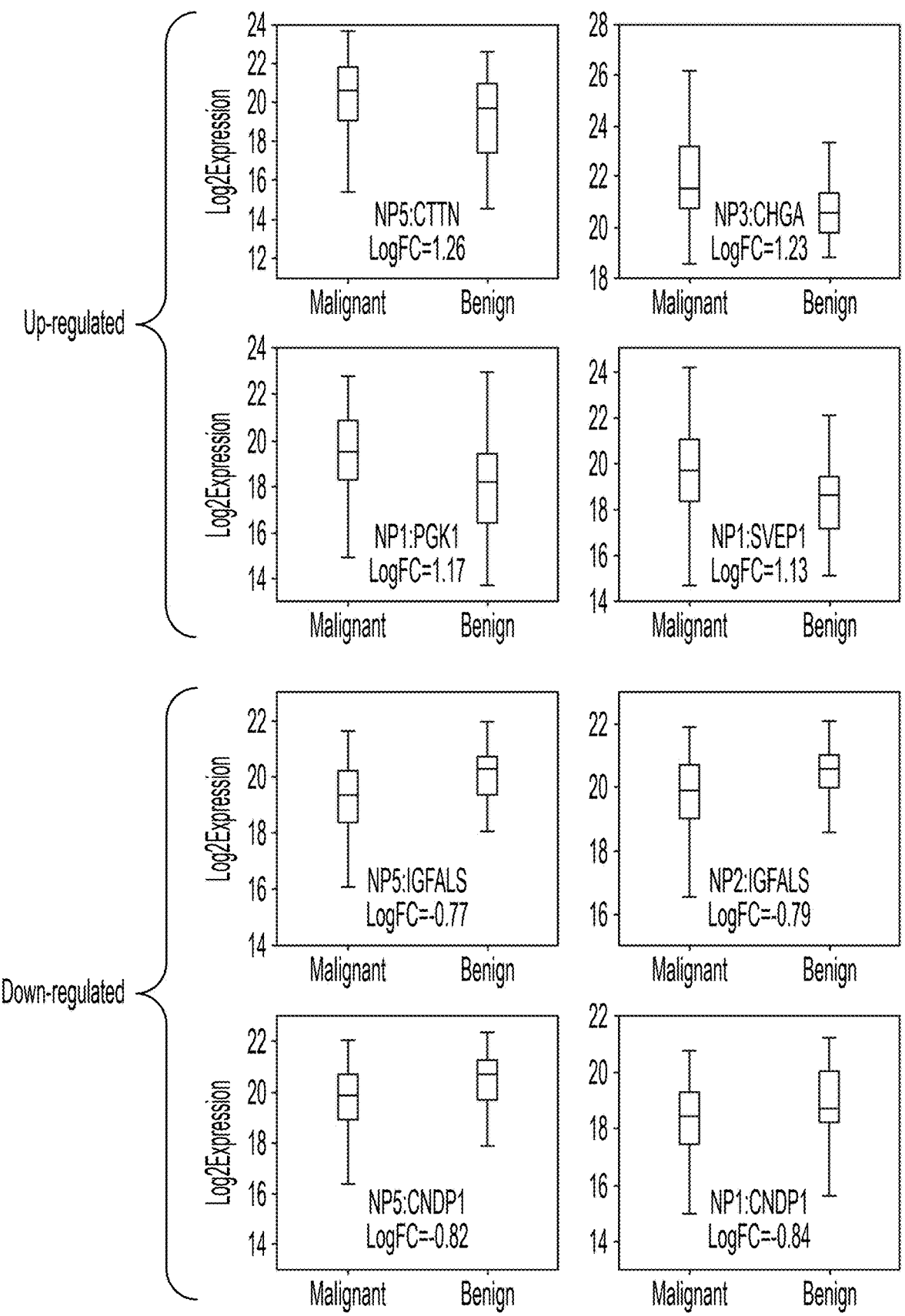
FIG. 64 illustrates some example proteins from an initial univariate analysis.

In some embodiments, the biomarkers include any protein in FIG. 64. In some aspects, the biomarkers excludes a protein in FIG. 64. The biomarkers may include CTTN. The biomarkers may include PGK1. The biomarkers may include IGFALS. The biomarkers may include CNDP1. The biomarkers may include CHGA. The biomarkers may include SVEP1.

Figure 74:
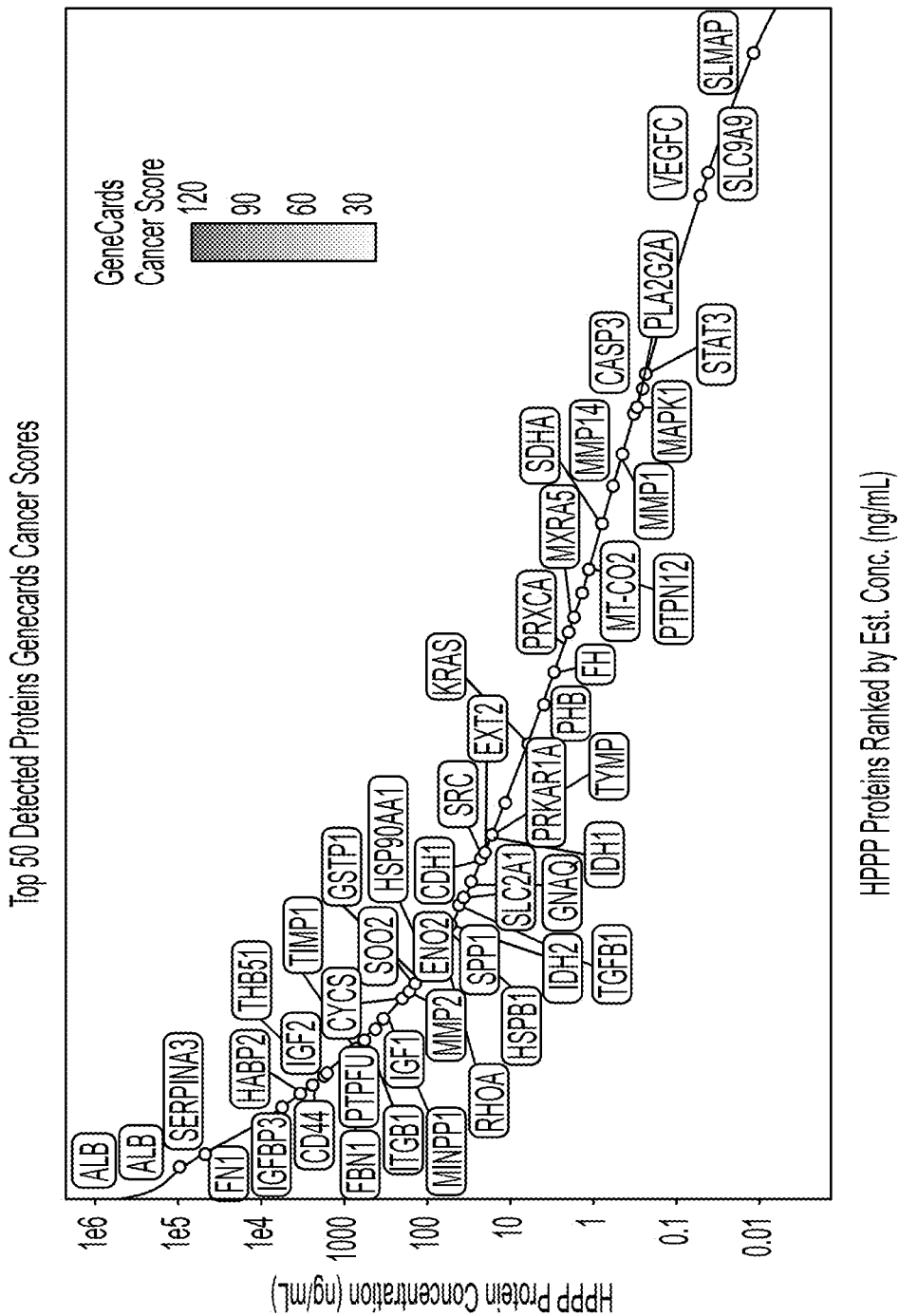
FIG. 74 includes a graphical depiction of protein concentrations for data obtained in a study described herein.

In some embodiments, the biomarkers include any protein in FIG. 74. For example, the biomarkers may include any of ALB, CASP3, CD44, CDH1, CYCS, ENO2, EXT2, FBN1, FH, FN1, GNAQ, GSTP1, HABP2, HSP90AA1, IDH1, IDH2, IGF1, IGF2, IGFBP3, ITGB1, KRAS, MAPK1, MINPP1, MMP1, MMP14, MMP2, MT-CO2, MXRA5, PHB, PLA2G2A, PRKAR1A, PRKCA, PTPN12, PTPRJ, RHOA1, SDHA, SERPINA3, SLC2A1, SLC9A9, SLMAP, SOD2, SPP1, SRC, STAT3, TGFB1, THBS1, TIMP1, TYMP, or VEGFC. The biomarkers may include all of the proteins in FIG. 74. The biomarkers may include 1, 2, 3, 4, 5, 6, 7, 8, 9, 10, 15, 20, 25, 30, 35, 40, 45, or 49 of the proteins in FIG. 74, or a range of proteins defined by any two of the aforementioned integers. The biomarkers may include at least 1, at least 2, at least 3, at least 4, at least 5, at least 6, at least 7, at least 8, at least 9, at least 10, at least 15, at least 20, at least 25, at least 30, or at least 35, of the proteins in FIG. 74. In some aspects, the biomarkers include less than 3, less than 4, less than 5, less than 6, less than 7, less than 8, less than 9, less than 10, less than 15, less than 20, less than 25, less than 30, less than 35, less than 40, less than 45, or less than 49, of the proteins in FIG. 74. In some aspects, the biomarkers excludes a protein in FIG. 74.

Examples of biomarkers may include any of: insulin-like growth factor-binding protein complex acid labile subunit (IGFALS; e.g. as described at UniProt accession no. P35858), insulin-like growth factor-binding protein 3 (IG-FBP3, e.g. as described at UniProt accession no. P17936), beta-Ala-His dipeptidase (CNDP1, e.g. as described at Uni-Prot accession no. Q96KN2), myosin light polypeptide 6 (MYL6, e.g. as described at UniProt accession no. P60660), resistin (RETN, e.g. as described at UniProt accession no. Q9HD89), hexokinase-1 (HK1, e.g. as described at UniProt accession no. P19367), fibroblast growth factor-binding protein 2 (FGFBP2, e.g. as described at UniProt accession no. Q9BYJ0), CD59 glycoprotein (CD59, e.g. as described at UniProt accession no. P13987), or plastin-2 (LCP1, e.g. as described at UniProt accession no. P13796). A protein may be referred to by name, symbol, or UniProt accession no. In some embodiments, the biomarkers include any biomarker in FIG. 82. In some embodiments, the biomarker is P35858. In some embodiments, the biomarker is P17936. In some embodiments, the biomarker is Q96KN2. In some embodiments, the biomarker is P60660. In some embodiments, the biomarker is Q9HD89. In some embodiments, the biomarker is P19367. In some embodiments, the biomarker is Q9BYJ0. In some embodiments, the biomarker is P13987. In some embodiments, the biomarker is P13796. In some embodiments, the biomarker is IGFALS. In some embodiments, the biomarker is IGFBP3. In some embodiments, the biomarker is CNDP1. In some embodiments, the biomarker is MYL6.

In some embodiments, the biomarkers include any biomarker in FIG. 84. In some embodiments, the biomarker is IGFALS. In some embodiments, the biomarker is CNDP1. In some embodiments, the biomarker is GPLD1. In some embodiments, the biomarker is FAP. In some embodiments, the biomarker is PIGR. In some embodiments, the biomarker is PON1. In some embodiments, the biomarker is CLEC3B. In some embodiments, the biomarker is IGFBP3. In some embodiments, the biomarker is APOB. In some embodiments, the biomarker is SERPINC1. In some embodiments, the biomarker is CALR. In some embodiments, the biomarker is NOTCH2. In some embodiments, the biomarker is KIT. In some embodiments, the biomarker is VEGFA. In some embodiments, the biomarker is TUBB. In some embodiments, the biomarker is TUBB1. In some embodiments, the biomarker is FLT4. In some embodiments, the biomarker is ERBB2. In some embodiments, the biomarker is EGFR.

In some embodiments, the biomarkers include any biomarker in FIG. 85. In some embodiments, the biomarker is 3-Methyl-3-hydroxyglutaric acid. In some embodiments, the biomarker is Glucoronate.

In some embodiments, the biomarkers include any biomarker in FIG. 89. In some embodiments, the biomarker is Q12884. In some embodiments, the biomarker is P01833. In some embodiments, the biomarker is P18065. In some embodiments, the biomarker is P36222. In some embodiments, the biomarker is Q04721. In some embodiments, the biomarker is P54802. In some embodiments, the biomarker is P35858. In some embodiments, the biomarker is Q96KN2. In some embodiments, the biomarker is P17936.

In some embodiments, the biomarker is a biomarker included in FIG. 94. In some embodiments, the biomarker is biopterin.

In some embodiments, the biomarker is a biomarker included in FIG. 97. In some embodiments, the biomarker is FAP. In some embodiments, the biomarker is PIGR. In some embodiments, the biomarker is IGFALS. In some embodiments, the biomarker is CNDP1. In some embodiments, the biomarker is IGFBP2. In some embodiments, the biomarker is CHI3L1. In some embodiments, the biomarker is GPLD1. In some embodiments, the biomarker is HYOU1. In some embodiments, the biomarker is F13A1. In some embodiments, the biomarker is IGFBP3. In some embodiments, the biomarker is APOB. In some embodiments, the biomarker is NOTCH2. In some embodiments, the biomarker is KIT. In some embodiments, the biomarker is SERPINC1. In some embodiments, the biomarker is TUBB. In some embodiments, the biomarker is FLT4. In some embodiments, the biomarker is TUBB1. In some embodiments, the biomarker is EGFR. In some embodiments, the biomarker is ERBB2.

In some embodiments, the biomarker is a biomarker included in FIG. 102. In some embodiments, the biomarker is ACKR2. In some embodiments, the biomarker is NBL1. In some embodiments, the biomarker is ENHO. In some embodiments, the biomarker is GPR15. In some embodiments, the biomarker is PDZKIIP1. In some embodiments, the biomarker is MYO1B. In some embodiments, the biomarker is ROBO4. In some embodiments, the biomarker is KIF26A. In some embodiments, the biomarker is NCKAP5. In some embodiments, the biomarker is SFRP2. In some embodiments, the biomarker is LPL. In some embodiments, the biomarker is CCDC187. In some embodiments, the biomarker is NKX3-1. In some embodiments, the biomarker is SHISA4. In some embodiments, the biomarker is CHSY3. In some embodiments, the biomarker is MYOM2. In some embodiments, the biomarker is NEBL. In some embodiments, the biomarker is SCGB3A1. In some embodiments, the biomarker is ELOA3C. In some embodiments, the biomarker is U2AF1L5. In some embodiments, the biomarker is HSFX1. In some embodiments, the biomarker is AS3MT. In some embodiments, the biomarker is F8A3. In some embodiments, the biomarker is HLA-DQB2. In some embodiments, the biomarker is EDIL3. In some embodiments, the biomarker is SLC44A4. In some embodiments, the biomarker is RAP1GAP.

The biomarker may include an mRNA encoding any of the protein biomarkers disclosed herein. The biomarker may include a protein encoded by any of the mRNA biomarkers disclosed herein.

Although several examples of protein biomarkers have been included, other types of biomolecules may be useful for biomarkers. For example, biomolecules such as genetic material, transcripts, or metabolites may be used as biomarkers in the methods described herein.

Disclosed herein, in some aspects, are methods, comprising: assaying biomarkers in a biofluid sample obtained from a subject identified as having a lung nodule to obtain biomarker measurements, wherein the biomarkers comprises at least 1 (e.g. at least 1, 2, 3, 4, 5, 6, 7, 8, 9, or 10, or more) biomarker disclosed herein; and identifying the biomarker measurements as indicative of the lung nodule being cancerous or as non-cancerous. The biomarkers may include biomarkers disclosed in FIG. 52, FIG. 6, FIG. 54, FIG. 6, FIG. 7, FIG. 10B, FIG. 11B, FIG. 58, FIG. 62, FIG. 63, FIG. 64, FIG. 65A, FIG. 5B, FIG. 67 or FIG. 74.

Further Detection Methods

The present disclosure provides a variety of methods for detecting biomolecules (e.g. biomarkers such as protein biomarkers) from a biological sample. Some embodiments include obtaining a biomarker measurement. The biomarker measurement may include a protein measurement such as a protein concentration or amount. Some embodiments include measuring a biomarker. The biological sample may be from a subject with a lung nodule. Biomolecular (e.g., proteomic) data of the biological sample can be identified, measured, and quantified using a number of different analytical techniques. For example, proteomic data can be analyzed using SDS-PAGE or any gel-based separation technique. Alternatively, proteomic data can be identified, measured, and quantified using mass spectrometry, high performance liquid chromatography, LC-MS/MS, Edman Degradation, an immunoaffinity technique, binding reagent analysis (e.g., immunostaining or an aptamer binding assay), an enzyme linked immunosorbent assay (ELISA), chromatography, western blot analysis, mass spectrometric analysis, or any combination thereof. The biomolecules may be enriched on a particle or particle panel prior to analysis. A subset of biomolecules from a biological sample may be collected on a particle, optionally eluted into a solution, optionally treated (e.g., digested or chemically reduced), and analyzed. Particle-based biomolecule collection may enrich a biomolecule from a biological sample, thereby enabling rapid detection and quantification of a low abundance biomolecule.

Various methods of the present disclosure for detecting a biomolecule comprise binding reagent analysis. A biological sample or collection of biomolecules from a biological sample may be contacted with a target-specific binding reagent, such as an antibody, an affibody, an affimer, an alphabody, an avimer, a DARPin, a chimeric antigen receptor, a T-cell receptor, an aptamer, or a fragment thereof. A binding reagent may be detectable. A binding reagent may comprise a barcode sequence that enables detection and quantification of the binding reagent by nucleic acid sequencing analysis. A binding reagent may comprise an optically detectable label or moiety (e.g., a fluorescent protein such as GFP or YFP or a fluorescent dye). Binding reagent analysis may comprise a plurality of binding reagents targeting a plurality of biomolecules and comprising different detectable signals (e.g., nucleic acid barcode sequences or optically detectable moieties), thereby enabling multiplexed detection and quantification of selected biomarkers from the sample. For example, a sample may be contacted with a plurality of antibodies comprising distinct detectable labels and targeting different proteins from among the proteins listed in Table 2, another table or figure, or a classifier feature disclosed herein. In some cases, a binding reagent may contact a biomolecule covalently or non-covalently immobilized to a substrate (e.g., a membrane, a surface, a resin, or a slide). In some cases, a binding reagent may contact a biomolecule adsorbed to a particle (e.g., disposed in a biomolecule corona of a particle).

In some aspects, assaying the proteins comprises measuring a readout indicative of the presence, absence or amount of the biomolecules. In some aspects, assaying the proteins comprises performing mass spectrometry, chromatography, liquid chromatography, high-performance liquid chromatography, solid-phase chromatography, a lateral flow assay, an immunoassay, an enzyme-linked immunosorbent assay, a western blot, a dot blot, or immunostaining, or a combination thereof. In some aspects, assaying the proteins comprises performing mass spectrometry.

Various methods of the present disclosure for detecting a biomolecule comprise ELISA. A method may comprise sandwich ELISA analysis, in which a biomolecule (e.g., a peptide from among the peptides listed in Table 2, another table or figure, or a classifier feature disclosed herein) is contacted to a first antibody immobilized to a solid phase and a second antibody coupled to a detectable moiety (e.g., an optically detectable dye molecule), wherein the first antibody comprises a first paratope for a first epitope on the biomolecule and the second antibody comprises a second paratope for a second epitope on the biomolecule. An ELISA assay may comprise immobilizing a biomolecule of interest to a substrate (e.g., a glass slide or the bottom of a well of a multiwell plate), and contacting the biomolecule with a first antibody comprising a binding affinity for the biomolecule. The first antibody may be coupled to a detectable moiety, or may be contacted to a second antibody that is coupled to a detectable moiety and which binds to the first antibody. ELISA assays can comprise low detection limits (e.g., >1 µg/ml) for target detection and quantitation, and may thus be suitable for analyzing a cancer biomarker disclosed herein.

A method of the present disclosure may comprise mass spectrometric analysis of a biomolecule such as a protein, a peptide, or a portion thereof. The mass spectrometric analysis can be performed in tandem with a chromatographic separation technique, such as liquid chromatography, such that biomolecules or biomolecule fragments are subjected to mass spectrometric analysis at different points in time. Mass spectrometric analysis may comprise two or more mass analysis steps (e.g., tandem mass spectrometry), such that an ion is fragmented and then subjected to further analysis.

The methods described herein may include measuring a biomarker (e.g. one or more biomarkers) in a sample from a subject. Measuring a biomarker may include performing an assay method. Measuring a biomarker may include performing mass spectrometry, chromatography, liquid chromatography, high-performance liquid chromatography, solid-phase chromatography, a lateral flow assay, an immunoassay, an enzyme-linked immunosorbent assay, a western blot, a dot blot, or immunostaining, or a combination thereof. Measuring a biomarker may include performing mass spectrometry. Measuring a biomarker may include performing chromatography. Measuring a biomarker may include performing liquid chromatography. Measuring a biomarker may include performing high-performance liquid chromatography. Measuring a biomarker may include performing solid-phase chromatography. Measuring a biomarker may include performing a lateral flow assay. Measuring a biomarker may include performing an immunoassay. Measuring a biomarker may include performing an enzyme-linked immunosorbent assay. Measuring a biomarker may include performing a blot such as a western blot. Measuring a biomarker may include performing dot blot. Measuring a biomarker may include performing immunostaining. Measuring a biomarker may include contacting a biological sample with a plurality of physiochemically distinct nanoparticles. Measuring a biomarker may include performing a combination of assay methods. For example, a method described herein may include use of particles followed by an immunoassay such as an ELISA to assess proteins or biomolecules of biomolecule or protein coronas. The methods described herein may include detecting the proteins of the biomolecule coronas by mass spectrometry, chromatography, liquid chromatography, high-performance liquid chromatography, solid-phase chromatography, a lateral flow assay, an immunoassay, an enzyme-linked immunosorbent assay, a western blot, a dot blot, or immunostaining, or a combination thereof. The methods described herein may include detecting the proteins of the biomolecule coronas by mass spectrometry.

Measuring a biomarker may include using a detection reagent that binds to a protein and yields a detectable signal. The methods described herein may include detecting the proteins comprises measuring a readout indicative of the presence, absence or amounts of the proteins. Measuring a biomarker may include measuring a readout indicative of the presence, absence or amounts of the one or more biomarkers.

A method may include concentrating biomarkers in a sample prior to measuring the biomarkers. Measuring a biomarker may include concentrating a sample. Measuring a biomarker may include filtering a sample. Measuring a biomarker may include centrifuging a sample.

Measuring a biomarker may include contacting the sample with an assay reagent. The assay reagent may include a particle. The assay reagent may include an antibody. The assay reagent may include a biomolecule binding molecule.

The biological sample may contain one or more analytes capable of being assayed, such as cell-free ribonucleic acid (cfRNA) molecules suitable for assaying to generate transcriptomic data, cell-free deoxyribonucleic acid (cfDNA) molecules suitable for assaying to generate genomic data, proteins suitable for assaying to generate proteomic data, metabolites suitable for assaying to generate metabolomic data, or a mixture or combination thereof. One or more such analytes (e.g., cfRNA molecules, cfDNA molecules, proteins, or metabolites) may be isolated or extracted from one or more biological samples of a subject for downstream assaying using one or more suitable assays.

After obtaining a biological sample from the subject, the biological sample may be processed to generate datasets indicative of a lung nodule-related state of the subject. For example, a presence, absence, or quantitative assessment of nucleic acid molecules of the biological sample at a panel of lung nodule-related state-associated genomic loci (e.g., quantitative measures of RNA transcripts or DNA at the lung nodule-related state-associated genomic loci), proteomic data comprising quantitative measures of proteins of the dataset at a panel of lung nodule-related state-associated proteins, and/or metabolome data comprising quantitative measures of a panel of lung nodule-related state-associated metabolites may be indicative of a lung nodule-related state. Processing the biological sample obtained from the subject may comprise (i) subjecting the biological sample to conditions that are sufficient to isolate, enrich, or extract a plurality of nucleic acid molecules, proteins, and/or metabolites, and (ii) assaying the plurality of nucleic acid molecules, proteins, and/or metabolites to generate the dataset.

In some embodiments, a plurality of nucleic acid molecules is extracted from the biological sample and subjected to sequencing to generate a plurality of sequencing reads. The nucleic acid molecules may comprise ribonucleic acid (RNA) or deoxyribonucleic acid (DNA). The nucleic acid molecules (e.g., RNA or DNA) may be extracted from the biological sample by a variety of methods, such as a FastDNA Kit protocol from MP Biomedicals, a QIAamp DNA cell-free biological mini kit from Qiagen, or a cell-free biological DNA isolation kit protocol from Norgen Biotek. The extraction method may extract all RNA or DNA molecules from a sample. Alternatively, the extract method may selectively extract a portion of RNA or DNA molecules from a sample. Extracted RNA molecules from a sample may be converted to DNA molecules by reverse transcription (RT).

The sequencing may be performed by any suitable sequencing methods, such as massively parallel sequencing (MPS), paired-end sequencing, high-throughput sequencing, next-generation sequencing (NGS), shotgun sequencing, single-molecule sequencing, nanopore sequencing, semiconductor sequencing, pyrosequencing, sequencing-by-synthesis (SBS), sequencing-by-ligation, sequencing-by-hybridization, and RNA-Seq (Illumina).

The sequencing may comprise nucleic acid amplification (e.g., of RNA or DNA molecules). In some embodiments, the nucleic acid amplification is polymerase chain reaction (PCR). A suitable number of rounds of PCR (e.g., PCR, qPCR, reverse-transcriptase PCR, digital PCR, etc.) may be performed to sufficiently amplify an initial amount of nucleic acid (e.g., RNA or DNA) to a desired input quantity for subsequent sequencing. In some cases, the PCR may be used for global amplification of target nucleic acids. This may comprise using adapter sequences that may be first ligated to different molecules followed by PCR amplification using universal primers. PCR may be performed using any of a number of commercial kits, e.g., provided by Life Technologies, Affymetrix, Promega, Qiagen, etc. In other cases, only certain target nucleic acids within a population of nucleic acids may be amplified. Specific primers, possibly in conjunction with adapter ligation, may be used to selectively amplify certain targets for downstream sequencing. The PCR may comprise targeted amplification of one or more genomic loci, such as genomic loci associated with lung nodule-related states. The sequencing may comprise use of simultaneous reverse transcription (RT) and polymerase chain reaction (PCR), such as a OneStep RT-PCR kit protocol by Qiagen, NEB, Thermo Fisher Scientific, or Bio-Rad.

RNA or DNA molecules isolated or extracted from a biological sample may be tagged, e.g., with identifiable tags, to allow for multiplexing of a plurality of samples. Any number of RNA or DNA samples may be multiplexed. For example a multiplexed reaction may contain RNA or DNA from at least about 2, 3, 4, 5, 6, 7, 8, 9, 10, 11, 12, 13, 14, 15, 16, 17, 18, 19, 20, 25, 30, 35, 40, 45, 50, 55, 60, 65, 70, 75, 80, 85, 90, 95, 100, or more than 100 initial biological samples. For example, a plurality of biological samples may be tagged with sample barcodes such that each DNA molecule may be traced back to the sample (and the subject) from which the DNA molecule originated. Such tags may be attached to RNA or DNA molecules by ligation or by PCR amplification with primers.

After subjecting the nucleic acid molecules to sequencing, suitable bioinformatics processes may be performed on the sequence reads to generate the data indicative of the presence, absence, or relative assessment of the lung nodule-related state. For example, the sequence reads may be aligned to one or more reference genomes (e.g., a genome of one or more species such as a human genome). The aligned sequence reads may be quantified at one or more genomic loci to generate the datasets indicative of the lung nodule-related state. For example, quantification of sequences corresponding to a plurality of genomic loci associated with lung nodule-related states may generate the datasets indicative of the lung nodule-related state.

The biological sample may be processed without any nucleic acid extraction. For example, the lung nodule-related state may be identified or monitored in the subject by using probes configured to selectively enrich nucleic acid (e.g., RNA or DNA) molecules corresponding to the plurality of lung nodule-related state-associated genomic loci. The genomic loci may correspond to nucleic acids encoding the biomarkers described herein. The probes may be nucleic acid primers. The probes may have sequence complementarity with nucleic acid sequences from one or more of the plurality of lung nodule-related state-associated genomic loci or genomic regions. The plurality of lung nodule-related state-associated genomic loci or genomic regions may comprise at least 2, at least 3, at least 4, at least 5, at least 6, at least 7, at least 8, at least 9, at least 10, at least 11, at least 12, at least 13, at least 14, at least 15, at least 16, at least 17, at least 18, at least 19, at least 20, at least about 25, at least about 30, at least about 35, at least about 40, at least about 45, at least about 50, at least about 55, at least about 60, at least about 65, at least about 70, at least about 75, at least about 80, at least about 85, at least about 90, at least about 95, at least about 100, or more distinct lung nodule-related state-associated genomic loci or genomic regions. Aspects disclosed in this section related to a lung nodule or to lung cancer may be relevant to detecting another disease state or cancer. The plurality of lung nodule-related state-associated genomic loci or genomic regions may comprise one or more members (e.g., 1, 2, 3, 4, 5, 6, 7, 8, 9, 10, 11, 12, 13, 14, 15, 16, 17, 18, 19, 20, about 25, about 30, about 35, about 40, about 45, about 50, about 55, about 60, about 65, about 70, about 75, about 80, or more) encoding any one of the biomarkers in Table 2, or another table or figure.

The probes may be nucleic acid molecules (e.g., RNA or DNA) having sequence complementarity with nucleic acid sequences (e.g., RNA or DNA) of the one or more genomic loci (e.g., lung nodule-related state-associated genomic loci). These nucleic acid molecules may be primers or enrichment sequences. The assaying of the biological sample using probes that are selective for the one or more genomic loci (e.g., lung nodule-related state-associated genomic loci) may comprise use of array hybridization (e.g., microarray-based), polymerase chain reaction (PCR), or nucleic acid sequencing (e.g., RNA sequencing or DNA sequencing). In some embodiments, DNA or RNA may be assayed by one or more of: isothermal DNA/RNA amplification methods (e.g., loop-mediated isothermal amplification (LAMP), helicase dependent amplification (HDA), rolling circle amplification (RCA), recombinase polymerase amplification (RPA)), immunoassays, electrochemical assays, surface-enhanced Raman spectroscopy (SERS), quantum dot (QD)-based assays, molecular inversion probes, droplet digital PCR (ddPCR), CRISPR/Cas-based detection (e.g., CRISPR-typing PCR (ctPCR), specific high-sensitivity enzymatic reporter un-locking (SHERLOCK), DNA endonuclease targeted CRISPR trans reporter (DETECTR), and CRISPR-mediated analog multi-event recording apparatus (CAMERA)), and laser transmission spectroscopy (LTS).

The assay readouts may be quantified at one or more genomic loci (e.g., lung nodule-related state-associated genomic loci) to generate the data indicative of the lung nodule-related state. For example, quantification of array hybridization or polymerase chain reaction (PCR) corresponding to a plurality of genomic loci (e.g., lung nodule-related state-associated genomic loci) may generate data indicative of the lung nodule-related state. Assay readouts may comprise quantitative PCR (qPCR) values, digital PCR (dPCR) values, digital droplet PCR (ddPCR) values, fluorescence values, etc., or normalized values thereof. The assay may be a home use test configured to be performed in a home setting.

In some embodiments, multiple assays are used to process biological samples of a subject. For example, a first assay may be used to process a first biological sample obtained or derived from the subject to generate a first dataset; and based at least in part on the first dataset, a second assay different from said first assay may be used to process a second biological sample obtained or derived from the subject to generate a second dataset indicative of said lung nodule-related state. The first assay may be used to screen or process biological samples of a set of subjects, while the second or subsequent assays may be used to screen or process biological samples of a smaller subset of the set of subjects. The first assay may have a low cost and/or a high sensitivity of detecting one or more lung nodule-related states (e.g., lung nodule-related complication), that is amenable to screening or processing biological samples of a relatively large set of subjects. The second assay may have a higher cost and/or a higher specificity of detecting one or more lung nodule-related states (e.g., lung nodule-related complication), that is amenable to screening or processing biological samples of a relatively small set of subjects (e.g., a subset of the subjects screened using the first assay). The second assay may generate a second dataset having a specificity (e.g., for one or more lung nodule-related states such as lung nodule-related complications) greater than the first dataset generated using the first assay. As an example, one or more biological samples may be processed using a cfRNA assay on a large set of subjects and subsequently a metabolomics assay on a smaller subset of subjects, or vice versa. The smaller subset of subjects may be selected based at least in part on the results of the first assay.

Alternatively, multiple assays may be used to simultaneously process biological samples of a subject. For example, a first assay may be used to process a first biological sample obtained or derived from the subject to generate a first dataset indicative of the lung nodule-related state; and a second assay different from the first assay may be used to process a second biological sample obtained or derived from the subject to generate a second dataset indicative of the lung nodule-related state. Any or all of the first dataset and the second dataset may then be analyzed to assess the lung nodule-related state of the subject. For example, a single diagnostic index or diagnosis score can be generated based on a combination of the first dataset and the second dataset. As another example, separate diagnostic indexes or diagnosis scores can be generated based on the first dataset and the second dataset.

The biological samples may be processed using a metabolomics assay. For example, a metabolomics assay can be used to identify a quantitative measure (e.g., indicative of a presence, absence, or relative amount) of each of a plurality of lung nodule-related state-associated metabolites in a biological sample of the subject. The metabolomics assay may be configured to process biological samples such as a blood sample or a urine sample (or derivatives thereof) of the subject. A quantitative measure (e.g., indicative of a presence, absence, or relative amount) of lung nodule-related state-associated metabolites in the biological sample may be indicative of one or more lung nodule-related states. The metabolites in the biological sample may be produced (e.g., as an end product or a byproduct) as a result of one or more metabolic pathways corresponding to lung nodule-related state-associated genes. Assaying one or more metabolites of the biological sample may comprise isolating or extracting the metabolites from the biological sample. The metabolomics assay may be used to generate datasets indicative of the quantitative measure (e.g., indicative of a presence, absence, or relative amount) of each of a plurality of lung nodule-related state-associated metabolites in the biological sample of the subject.

The metabolomics assay may analyze a variety of metabolites in the biological sample, such as small molecules, lipids, amino acids, peptides, nucleotides, hormones and other signaling molecules, cytokines, minerals and elements, polyphenols, fatty acids, dicarboxylic acids, alcohols and polyols, alkanes and alkenes, keto acids, glycolipids, carbohydrates, hydroxy acids, purines, prostanoids, catecholamines, acyl phosphates, phospholipids, cyclic amines, amino ketones, nucleosides, glycerolipids, aromatic acids, retinoids, amino alcohols, pterins, steroids, carnitines, leukotrienes, indoles, porphyrins, sugar phosphates, coenzyme A derivatives, glucuronides, ketones, sugar phosphates, inorganic ions and gases, sphingolipids, bile acids, alcohol phosphates, amino acid phosphates, aldehydes, quinones, pyrimidines, pyridoxals, tricarboxylic acids, acyl glycines, cobalamin derivatives, lipoamides, biotin, and polyamines.

The metabolomics assay may comprise, for example, one or more of: mass spectroscopy (MS), targeted MS, gas chromatography (GC), high performance liquid chromatography (HPLC), capillary electrophoresis (CE), nuclear magnetic resonance (NMR) spectroscopy, ion-mobility spectrometry, Raman spectroscopy, electrochemical assay, or immune assay.

The biological samples may be processed using a methylation-specific assay. For example, a methylation-specific assay can be used to identify a quantitative measure (e.g., indicative of a presence, absence, or relative amount) of methylation each of a plurality of lung nodule-related state-associated genomic loci in a biological sample of the subject. The methylation-specific assay may be configured to process biological samples such as a blood sample or a urine sample (or derivatives thereof) of the subject. A quantitative measure (e.g., indicative of a presence, absence, or relative amount) of methylation of lung nodule-related state-associated genomic loci in the biological sample may be indicative of one or more lung nodule-related states. The methylation-specific assay may be used to generate datasets indicative of the quantitative measure (e.g., indicative of a presence, absence, or relative amount) of methylation of each of a plurality of lung nodule-related state-associated genomic loci in the biological sample of the subject.

The methylation-specific assay may comprise, for example, one or more of: a methylation-aware sequencing (e.g., using bisulfite treatment), pyrosequencing, methylation-sensitive single-strand conformation analysis (MS-SSCA), high-resolution melting analysis (HRM), methylation-sensitive single-nucleotide primer extension (MS-SnuPE), base-specific cleavage/MALDI-TOF, microarray-based methylation assay, methylation-specific PCR, targeted bisulfite sequencing, oxidative bisulfite sequencing, mass spectroscopy-based bisulfite sequencing, or reduced representation bisulfite sequence (RRBS).

The biological samples may be processed using a proteomics assay. For example, a proteomics assay can be used to identify a quantitative measure (e.g., indicative of a presence, absence, or relative amount) of each of a plurality of lung nodule-related state-associated proteins or polypeptides in a biological sample of the subject. The proteomics assay may be configured to process biological samples such as a blood sample or a urine sample (or derivatives thereof) of the subject. A quantitative measure (e.g., indicative of a presence, absence, or relative amount) of lung nodule-related state-associated proteins or polypeptides in the biological sample may be indicative of one or more lung nodule-related states. The proteins or polypeptides in the biological sample may be produced (e.g., as an end product or a byproduct) as a result of one or more biochemical pathways corresponding to lung nodule-related state-associated genes. Assaying one or more proteins or polypeptides of the biological sample may comprise isolating or extracting the proteins or polypeptides from the biological sample. The proteomics assay may be used to generate datasets indicative of the quantitative measure (e.g., indicative of a presence, absence, or relative amount) of each of a plurality of lung nodule-related state-associated proteins or polypeptides in the biological sample of the subject.

The proteomics assay may analyze a variety of proteins or polypeptides in the biological sample, such as proteins made under different cellular conditions (e.g., development, cellular differentiation, or cell cycle). The proteomics assay may comprise, for example, one or more of: an antibody-based immunoassay, an Edman degradation assay, a mass spectrometry-based assay (e.g., matrix-assisted laser desorption/ionization (MALDI) and electrospray ionization (ESI)), a top-down proteomics assay, a bottom-up proteomics assay, a mass spectrometric immunoassay (MSIA), a stable isotope standard capture with anti-peptide antibodies (SISCAPA) assay, a fluorescence two-dimensional differential gel electrophoresis (2-D DIGE) assay, a quantitative proteomics assay, a protein microarray assay, or a reverse-phased protein microarray assay. The proteomics assay may detect post-translational modifications of proteins or polypeptides (e.g., phosphorylation, ubiquitination, methylation, acetylation, glycosylation, oxidation, and nitrosylation). The proteomics assay may identify or quantify one or more proteins or polypeptides from a database (e.g., Human Protein Atlas, PeptideAtlas, and UniProt).

Such descriptive labels may provide an identification of secondary clinical tests that may be appropriate to perform on the subject, and may comprise, for example, an imaging test, a blood test, a computed tomography (CT) scan, a magnetic resonance imaging (MRI) scan, an ultrasound scan, a chest X-ray, a positron emission tomography (PET) scan, a PET-CT scan, a cell-free biological cytology, an amniocentesis, or any combination thereof. For example, such descriptive labels may provide a prognosis of the lung nodule-related state of the subject.

A method may comprise collecting tissue or a cell from a biological sample. The tissue or cell may be collected from a tissue or liquid biological sample. The tissue or cell may be collected directly from a patient. The tissue or cell may be collected from tissue suspected to be cancerous or premalignant. In some cases, the tissue or cell is selected from a biological sample isolated from a patient. The method may comprise identifying a cell or tissue subsection of interest from the biological sample. For example, a method may comprise isolating lung tissue in a transthoracic lung biopsy, identifying potentially cancerous cells through immunohistological staining, and isolating a potentially cancerous cell for further analysis.

A method may comprise parallel analysis of two or more species. The species may be compared to determine a disease state (e.g., the type and stage of a disease) of a sample. The species may originate from a single subject (e.g., a single patient suspected of having early stage non-small cell lung cancer), or from different subjects (e.g., a health patient and a lung cancer patient). The species may comprise a healthy species and a diseased or potentially diseased species. The species may be collected from the same biological sample, for example from a single tissue section, or from different biological samples, for example from separate blood and tissue samples.

Parallel analysis of two or more species may increase the accuracy of a diagnosis. In some cases, multi-species analysis comprises a known healthy species and a suspected or known diseased species (e.g., a cell from healthy tissue and a cell from cancerous tissue). Analysis of the healthy and diseased species may identify the stage of disease of the diseased species. In some cases, the first species may be suspected of comprising a disease and the second species (e.g., a portion of a plasma sample) may comprise potential biomarkers for that disease. In particular cases, the first species may be suspected of comprising a disease and the second species may comprise blood or a portion of a blood sample (e.g., plasma or a buffy coat). For example, a squamous cell may be identified as cancerous through DNA sequencing, and then identified as an early stage cancer cell based on a plasma proteomic profile of the patient.

Computer Systems

Certain aspects of the methods described herein may be carried out using a computer system. For example, omic data analysis may be carried out using a computer system. Likewise, multi-omic or multiple data may be obtained through the use of a computer system. A readout indicative of the presence, absence or amount of a biomolecule (e.g., protein, transcript, genetic material, or metabolite) may be obtained at least in part using a computer system. The computer system may be used to carry out a method of using a classifier to assign a label corresponding to a presence, absence, or likelihood of a disease state to omic data, or to identify multi-omic or multiple data sets as indicative or as not indicative of the disease state. In certain aspects, the disease is cancer. The cancer may include pancreatic cancer, liver cancer, ovarian cancer, or colon cancer. The cancer can be early-stage or late stage. A computer system may be used to identify whether a lung nodule of a subject is cancerous or non-cancerous. The computer system may generate a report identifying a likelihood of the subject having a disease state. The computer system may transmit the report. For example, a diagnostic laboratory may transmit a report regarding the disease state identification to a medical practitioner. A computer system may receive a report.

Figure 4:
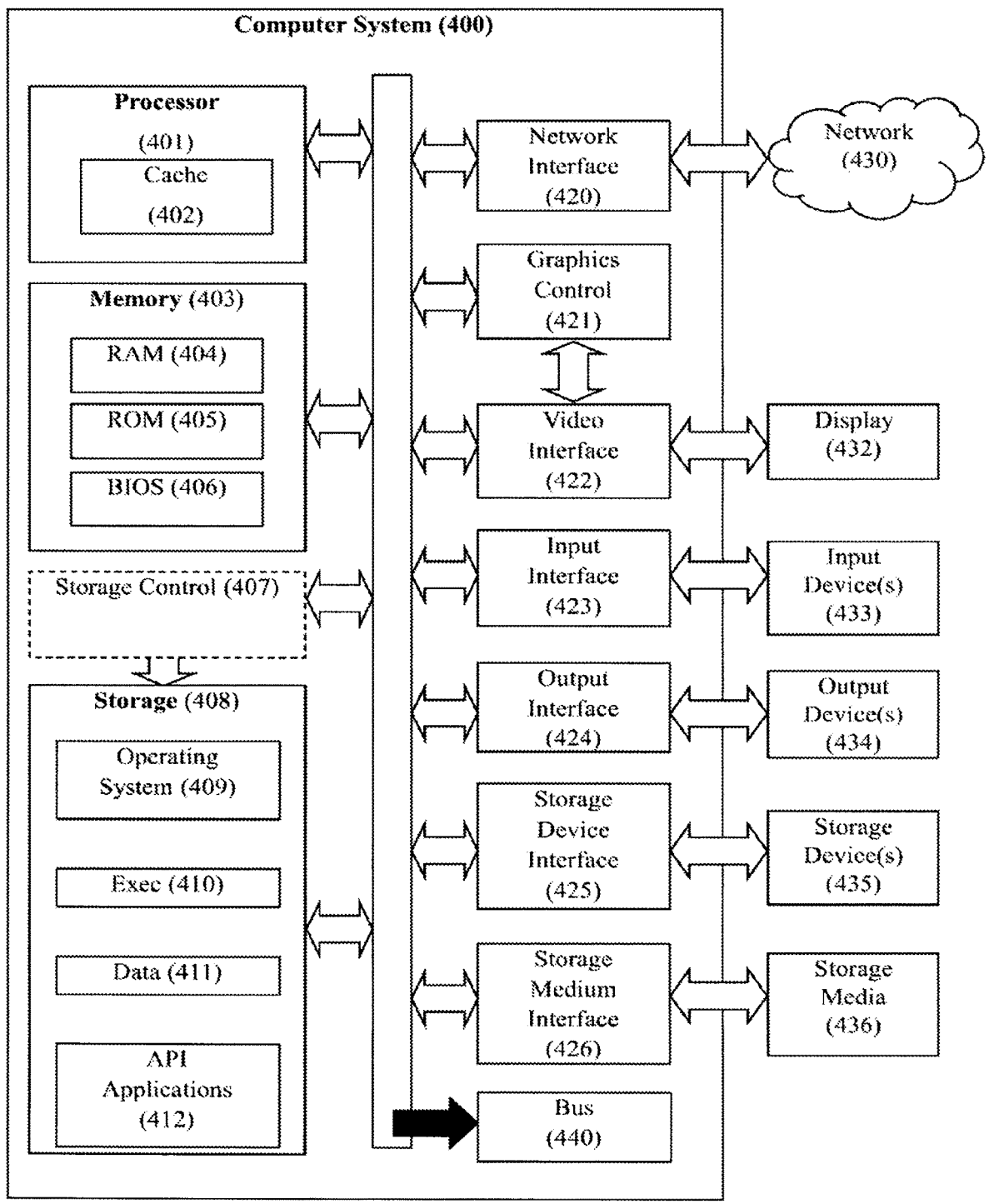
FIG. 4 shows a non-limiting example of a computing device; in this case, a device with one or more processors, memory, storage, and a network interface.

A computer system that carries out a method described herein may include some or all of the components shown in FIG. 4. Referring to FIG. 4, a block diagram is shown depicting an example of a machine that includes a computer system 400 (e.g., a processing or computing system) within which a set of instructions can execute for causing a device to perform or execute any one or more of the aspects and/or methodologies for static code scheduling of the present disclosure. The components in FIG. 4 are examples, and do not limit the scope of use or functionality of any hardware, software, embedded logic component, or a combination of two or more such components implementing particular aspects.

Computer system 400 may include one or more processors 401, a memory 403, and a storage 408 that communicate with each other, and with other components, via a bus 440. The bus 440 may also link a display 432, one or more input devices 433 (which may, for example, include a keypad, a keyboard, a mouse, a stylus, etc.), one or more output devices 434, one or more storage devices 435, and various tangible storage media 436. All of these elements may interface directly or via one or more interfaces or adaptors to the bus 440. For instance, the various tangible storage media 436 can interface with the bus 440 via storage medium interface 426. Computer system 400 may have any suitable physical form, including but not limited to one or more integrated circuits (ICs), printed circuit boards (PCBs), mobile handheld devices (such as mobile telephones or PDAs), laptop or notebook computers, distributed computer systems, computing grids, or servers.

Computer system 400 includes one or more processor(s) 401 (e.g., central processing units (CPUs) or general purpose graphics processing units (GPGPUs)) that carry out functions. Processor(s) 401 optionally contains a cache memory unit 402 for temporary local storage of instructions, data, or computer addresses. Processor(s) 401 are configured to assist in execution of computer readable instructions. Computer system 400 may provide functionality for the components depicted in FIG. 4 as a result of the processor(s) 401 executing non-transitory, processor-executable instructions embodied in one or more tangible computer-readable storage media, such as memory 403, storage 408, storage devices 435, and/or storage medium 436. The computer-readable media may store software that implements particular aspects, and processor(s) 401 may execute the software. Memory 403 may read the software from one or more other computer-readable media (such as mass storage device(s) 435, 436) or from one or more other sources through a suitable interface, such as network interface 420. The software may cause processor(s) 401 to carry out one or more processes or one or more steps of one or more processes described or illustrated herein. Carrying out such processes or steps may include defining data structures stored in memory 403 and modifying the data structures as directed by the software.

The memory 403 may include various components (e.g., machine readable media) including, but not limited to, a random access memory component (e.g., RAM 404) (e.g., static RAM (SRAM), dynamic RAM (DRAM), ferroelectric random access memory (FRAM), phase-change random access memory (PRAM), etc.), a read-only memory component (e.g., ROM 405), and any combinations thereof. ROM 405 may act to communicate data and instructions unidirectionally to processor(s) 401, and RAM 404 may act to communicate data and instructions bidirectionally with processor(s) 401. ROM 405 and RAM 404 may include any suitable tangible computer-readable media described below.

In one example, a basic input/output system 406 (BIOS), including basic routines that help to transfer information between elements within computer system 400, such as during start-up, may be stored in the memory 403.

Fixed storage 408 is connected bidirectionally to processor(s) 401, optionally through storage control unit 407. Fixed storage 408 provides additional data storage capacity and may also include any suitable tangible computer-readable media described herein. Storage 408 may be used to store operating system 409, executable(s) 410, data 411, applications 412 (application programs), and the like. Storage 408 can also include an optical disk drive, a solid-state memory device (e.g., flash-based systems), or a combination of any of the above. Information in storage 408 may, in appropriate cases, be incorporated as virtual memory in memory 403.

In one example, storage device(s) 435 may be removably interfaced with computer system 400 (e.g., via an external port connector (not shown)) via a storage device interface 425. Particularly, storage device(s) 435 and an associated machine-readable medium may provide non-volatile and/or volatile storage of machine-readable instructions, data structures, program modules, and/or other data for the computer system 400. In one example, software may reside, completely or partially, within a machine-readable medium on storage device(s) 435. In another example, software may reside, completely or partially, within processor(s) 401.

Bus 440 connects a wide variety of subsystems. Herein, reference to a bus may encompass one or more digital signal lines serving a common function, where appropriate. Bus 440 may be any of several types of bus structures including, but not limited to, a memory bus, a memory controller, a peripheral bus, a local bus, and any combinations thereof, using any of a variety of bus architectures. As an example, and not by way of limitation, such architectures may include an Industry Standard Architecture (ISA) bus, an Enhanced ISA (EISA) bus, a Micro Channel Architecture (MCA) bus, a Video Electronics Standards Association local bus (VLB), a Peripheral Component Interconnect (PCI) bus, a PCI-Express (PCI-X) bus, an Accelerated Graphics Port (AGP) bus, HyperTransport (HTX) bus, serial advanced technology attachment (SATA) bus, or any combination thereof.

Computer system 400 may also include an input device 433. In one example, a user of computer system 400 may enter commands and/or other information into computer system 400 via input device(s) 433. Examples of an input device(s) 433 include, but are not limited to, an alpha-numeric input device (e.g., a keyboard), a pointing device (e.g., a mouse or touchpad), a touchpad, a touch screen, a multi-touch screen, a joystick, a stylus, a gamepad, an audio input device (e.g., a microphone, a voice response system, etc.), an optical scanner, a video or still image capture device (e.g., a camera), or any combinations thereof. The input device may include a Kinect, Leap Motion, or the like. Input device(s) 433 may be interfaced to bus 440 via any of a variety of input interfaces 423 (e.g., input interface 423) including, but not limited to, serial, parallel, game port, USB, FIREWIRE, THUNDERBOLT, or any combination of the above.

When computer system 400 is connected to network 430, computer system 400 may communicate with other devices, specifically mobile devices and enterprise systems, distributed computing systems, cloud storage systems, cloud computing systems, and the like, connected to network 430. Communications to and from computer system 400 may be sent through network interface 420. For example, network interface 420 may receive incoming communications (such as requests or responses from other devices) in the form of one or more packets (such as Internet Protocol (IP) packets) from network 430, and computer system 400 may store the incoming communications in memory 403 for processing. Computer system 400 may similarly store outgoing communications (such as requests or responses to other devices) in the form of one or more packets in memory 403 and communicated to network 430 from network interface 420. Processor(s) 401 may access these communication packets stored in memory 403 for processing.

Examples of the network interface 420 include, but are not limited to, a network interface card, a modem, or any combination thereof. Examples of a network 430 or network segment 430 include, but are not limited to, a distributed computing system, a cloud computing system, a wide area network (WAN) (e.g., the Internet, an enterprise network), a local area network (LAN) (e.g., a network associated with an office, a building, a campus or other relatively small geographic space), a telephone network, a direct connection between two computing devices, a peer-to-peer network, or any combinations thereof. A network, such as network 430, may employ a wired and/or a wireless mode of communication. In general, any network topology may be used.

Information and data can be displayed through a display 432. Examples of a display 432 include, but are not limited to, a cathode ray tube (CRT), a liquid crystal display (LCD), a thin film transistor liquid crystal display (TFT-LCD), an organic liquid crystal display (OLED) such as a passive-matrix OLED (PMOLED) or active-matrix OLED (AMOLED) display, a plasma display, or any combinations thereof. The display 432 can interface to the processor(s) 401, memory 403, and fixed storage 408, as well as other devices, such as input device(s) 433, via the bus 440. The display 432 is linked to the bus 440 via a video interface 422, and transport of data between the display 432 and the bus 440 can be controlled via the graphics control 421. The display may be a video projector. The display may be a head-mounted display (HMD) such as a VR headset. Suitable VR headsets may include, by way of non-limiting examples, HTC Vive, Oculus Rift, Samsung Gear VR, Microsoft HoloLens, Razer OSVR, FOVE VR, Zeiss VR One, Avegant Glyph, Freefly VR headset, or the like. The display may include a combination of devices such as those disclosed herein.

In addition to a display 432, computer system 400 may include one or more other peripheral output devices 434 including, but not limited to, an audio speaker, a printer, a storage device, or any combinations thereof. Such peripheral output devices may be connected to the bus 440 via an output interface 424. Examples of an output interface 424 include, but are not limited to, a serial port, a parallel connection, a USB port, a FIREWIRE port, a THUNDERBOLT port, or any combinations thereof.

In addition, or as an alternative, computer system 400 may provide functionality as a result of logic hardwired or otherwise embodied in a circuit, which may operate in place of or together with software to execute one or more processes or one or more steps of one or more processes described or illustrated herein. Reference to software in this disclosure may encompass logic, and reference to logic may encompass software. Moreover, reference to a computer-readable medium may encompass a circuit (such as an IC) storing software for execution, a circuit embodying logic for execution, or both, where appropriate. The present disclosure encompasses any suitable combination of hardware, software, or both.

Those of skill in the art will appreciate that the various illustrative logical blocks, modules, circuits, and algorithm steps described in connection with aspects disclosed herein may be implemented as electronic hardware, computer software, or combinations of both. To clearly illustrate this interchangeability of hardware and software, various illustrative components, blocks, modules, circuits, and steps have been described above generally in terms of their functionality.

The various illustrative logical blocks, modules, and circuits described in connection with aspects disclosed herein may be implemented or performed with a general purpose processor, a digital signal processor (DSP), an application specific integrated circuit (ASIC), a field programmable gate array (FPGA) or other programmable logic device, discrete gate or transistor logic, discrete hardware components, or any combination thereof designed to perform the functions described herein. A general purpose processor may be a microprocessor, but in the alternative, the processor may be any conventional processor, controller, microcontroller, or state machine. A processor may also be implemented as a combination of computing devices, e.g., a combination of a DSP and a microprocessor, a plurality of microprocessors, one or more microprocessors in conjunction with a DSP core, or any other such configuration.

The steps of a method or algorithm described in connection with aspects disclosed herein may be embodied directly in hardware, in a software module executed by one or more processor(s), or in a combination of the two. A software module may reside in RAM memory, flash memory, ROM memory, EPROM memory, EEPROM memory, registers, hard disk, a removable disk, a CD-ROM, or any other form of storage medium known in the art. An example storage medium is coupled to the processor such the processor can read information from, and write information to, the storage medium. In the alternative, the storage medium may be integral to the processor. The processor and the storage medium may reside in an ASIC. The ASIC may reside in a user terminal. In the alternative, the processor and the storage medium may reside as discrete components in a user terminal.

In accordance with the description herein, suitable computing devices may include, by way of non-limiting examples, server computers, desktop computers, laptop computers, notebook computers, sub-notebook computers, netbook computers, netpad computers, set-top computers, media streaming devices, handheld computers, Internet appliances, mobile smartphones, tablet computers, personal digital assistants, video game consoles, and vehicles. Those of skill in the art will also recognize that select televisions, video players, and digital music players with optional computer network connectivity are suitable for use in the system described herein. Suitable tablet computers may include those with booklet, slate, or convertible configurations, known to those of skill in the art.

The computing device may include an operating system configured to perform executable instructions. The operating system is, for example, software, including programs and data, which manages the device's hardware and provides services for execution of applications. Those of skill in the art will recognize that suitable server operating systems include, by way of non-limiting examples, FreeBSD, OpenBSD, NetBSD®, Linux, Apple® Mac OS X Server®, Oracle® Solaris®, Windows Server®, and Novell® NetWare®. Those of skill in the art will recognize that suitable personal computer operating systems include, by way of non-limiting examples, Microsoft® Windows®, Apple® Mac OS X®, UNIX®, and UNIX-like operating systems such as GNU/Linux®. The operating system may be provided by cloud computing. Those of skill in the art will also recognize that suitable mobile smartphone operating systems include, by way of non-limiting examples, Nokia® Symbian® OS, Apple® iOS®, Research In Motion® BlackBerry OS®, Google® Android®, Microsoft® Windows Phone® OS, Microsoft® Windows Mobile® OS, Linux®, and Palm® WebOS®.

In some cases, the platforms, systems, media, or methods disclosed herein include one or more non-transitory computer readable storage media encoded with a program including instructions executable by an operating system of a computer system. The computer system may be networked. A computer readable storage medium may be a tangible component of a computing device. A computer readable storage medium may be removable from a computing device. A computer readable storage medium may include any of, by way of non-limiting examples, CD-ROMs, DVDs, flash memory devices, solid state memory, magnetic disk drives, magnetic tape drives, optical disk drives, distributed computing systems including cloud computing systems and services, or the like. In some cases, the program and instructions are permanently, substantially permanently, semi-permanently, or non-transitorily encoded on the media.

Non-Transitory Computer Readable Storage Medium

In some embodiments, the platforms, systems, media, and methods disclosed herein include one or more non-transitory computer readable storage media encoded with a program including instructions executable by the operating system of an optionally networked computing device. In further embodiments, a computer readable storage medium is a tangible component of a computing device. In still further embodiments, a computer readable storage medium is optionally removable from a computing device. In some embodiments, a computer readable storage medium includes, by way of non-limiting examples, CD-ROMs, DVDs, flash memory devices, solid state memory, magnetic disk drives, magnetic tape drives, optical disk drives, distributed computing systems including cloud computing systems and services, and the like. In some cases, the program and instructions are permanently, substantially permanently, semi-permanently, or non-transitorily encoded on the media.

Computer Program

In some embodiments, the platforms, systems, media, and methods disclosed herein include at least one computer program, or use of the same. A computer program includes a sequence of instructions, executable by one or more processor(s) of the computing device's CPU, written to perform a specified task. Computer readable instructions may be implemented as program modules, such as functions, objects, Application Programming Interfaces (APIs), computing data structures, and the like, that perform particular tasks or implement particular abstract data types. In light of the disclosure provided herein, those of skill in the art will recognize that a computer program may be written in various versions of various languages.

The functionality of the computer readable instructions may be combined or distributed as desired in various environments. In some embodiments, a computer program comprises one sequence of instructions. In some embodiments, a computer program comprises a plurality of sequences of instructions. In some embodiments, a computer program is provided from one location. In other embodiments, a computer program is provided from a plurality of locations. In various embodiments, a computer program includes one or more software modules. In various embodiments, a computer program includes, in part or in whole, one or more web applications, one or more mobile applications, one or more standalone applications, one or more web browser plug-ins, extensions, add-ins, or add-ons, or combinations thereof.

Web Application

In some embodiments, a computer program includes a web application. In light of the disclosure provided herein, those of skill in the art will recognize that a web application, in various embodiments, utilizes one or more software frameworks and one or more database systems. In some embodiments, a web application is created upon a software framework such as Microsoft®.NET or Ruby on Rails (RoR). In some embodiments, a web application utilizes one or more database systems including, by way of non-limiting examples, relational, non-relational, object oriented, associative, and XML database systems. In further embodiments, suitable relational database systems include, by way of non-limiting examples, Microsoft® SQL Server, mySQL™, and Oracle®. Those of skill in the art will also recognize that a web application, in various embodiments, is written in one or more versions of one or more languages. A web application may be written in one or more markup languages, presentation definition languages, client-side scripting languages, server-side coding languages, database query languages, or combinations thereof. In some embodiments, a web application is written to some extent in a markup language such as Hypertext Markup Language (HTML), Extensible Hypertext Markup Language (XHTML), or extensible Markup Language (XML). In some embodiments, a web application is written to some extent in a presentation definition language such as Cascading Style Sheets (CSS). In some embodiments, a web application is written to some extent in a client-side scripting language such as Asynchronous Javascript and XML (AJAX), Flash® Actionscript, Javascript, or Silverlight®. In some embodiments, a web application is written to some extent in a server-side coding language such as Active Server Pages (ASP), ColdFusion®, Perl, Java™, JavaServer Pages (JSP), Hypertext Preprocessor (PHP), Python™, Ruby, Tcl, Smalltalk, WebDNA®, or Groovy. In some embodiments, a web application is written to some extent in a database query language such as Structured Query Language (SQL). In some embodiments, a web application integrates enterprise server products such as IBM® Lotus Domino®. In some embodiments, a web application includes a media player element. In various further embodiments, a media player element utilizes one or more of many suitable multimedia technologies including, by way of non-limiting examples, Adobe® Flash®, HTML 5, Apple® QuickTime®, Microsoft® Silverlight®, Java™, and Unity®.

Figure 55:
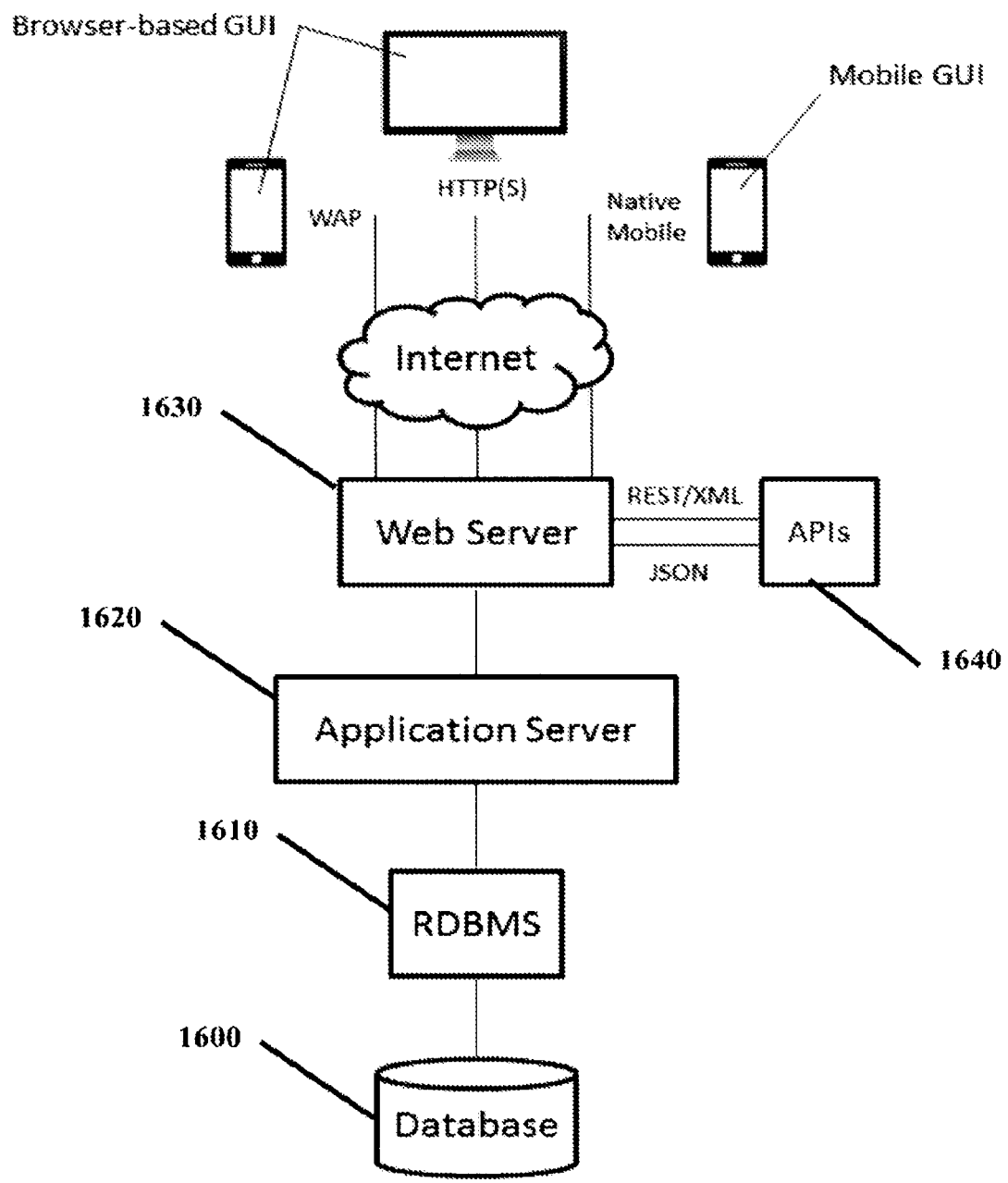
FIG. 55 shows a non-limiting example of a web/mobile application provision system; in this case, a system providing browser-based and/or native mobile user interfaces.

Referring to FIG. 55, in a particular embodiment, an application provision system comprises one or more databases 1600 accessed by a relational database management system (RDBMS) 1610. Suitable RDBMSs include Firebird, MySQL, PostgreSQL, SQLite, Oracle Database, Microsoft SQL Server, IBM DB2, IBM Informix, SAP Sybase, SAP Sybase, Teradata, and the like. In this embodiment, the application provision system further comprises one or more application severs 1620 (such as Java servers, .NET servers, PHP servers, and the like) and one or more web servers 1630 (such as Apache, IIS, GWS and the like). The web server(s) optionally expose one or more web services via app application programming interfaces (APIs) 1640. Via a network, such as the Internet, the system provides browser-based and/or mobile native user interfaces.

Figure 56:
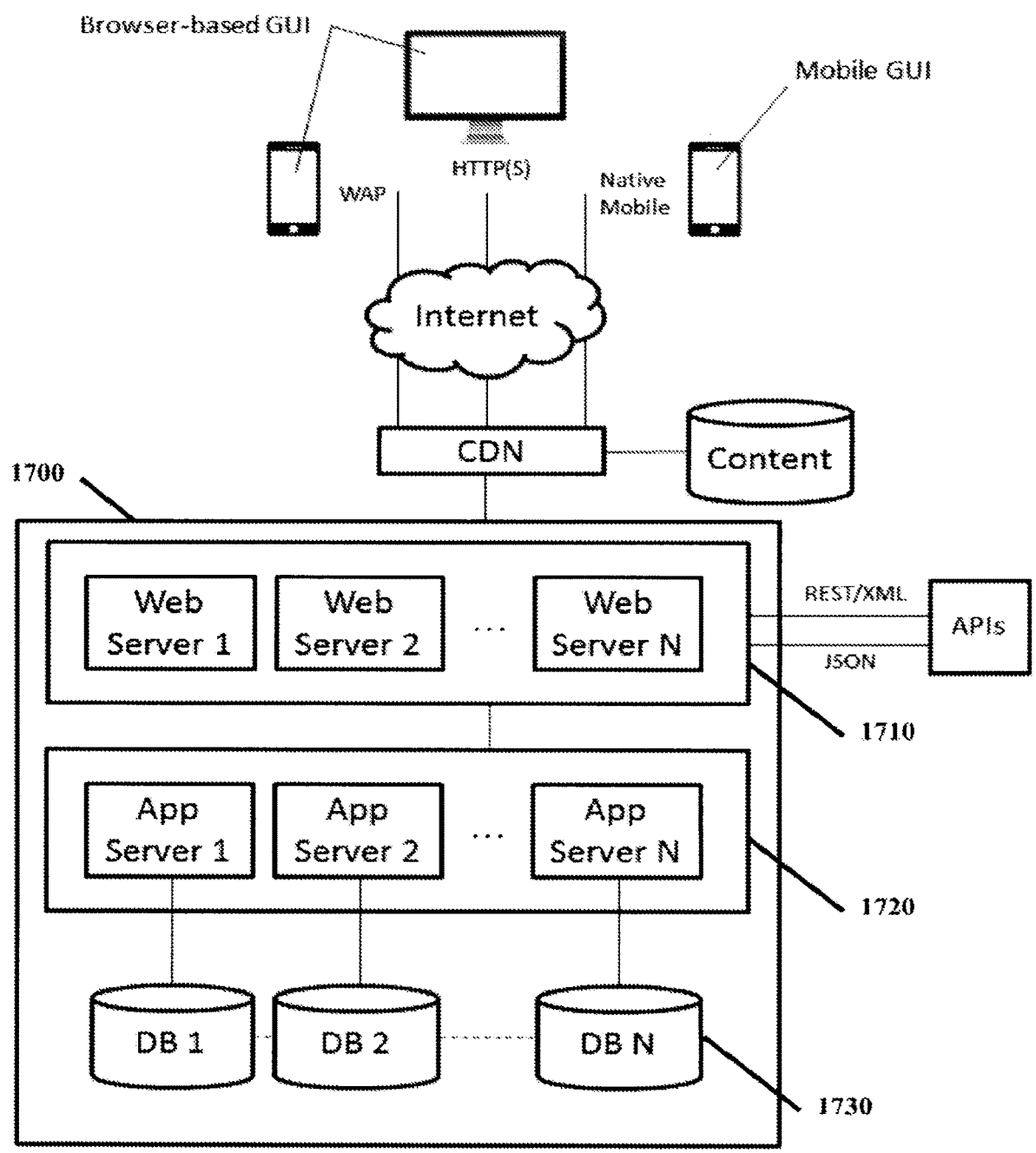
FIG. 56 shows a non-limiting example of a cloud-based web/mobile application provision system; in this case, a system comprising an elastically load balanced, auto-scaling web server and application server resources as well as synchronously replicated databases.

Referring to FIG. 56, in a particular embodiment, an application provision system alternatively has a distributed, cloud-based architecture 1700 and comprises elastically load balanced, auto-scaling web server resources 1710 and application server resources 1720 as well synchronously replicated databases 1730.

Mobile Application

In some embodiments, a computer program includes a mobile application provided to a mobile computing device. In some embodiments, the mobile application is provided to a mobile computing device at the time it is manufactured. In other embodiments, the mobile application is provided to a mobile computing device via the computer network described herein.

In view of the disclosure provided herein, a mobile application is created by techniques using hardware, languages, and development environments Suitable programming languages include, by way of non-limiting examples, C, C++, C #, Objective-C, Java™, Javascript, Pascal, Object Pascal, Python™, Ruby, VB.NET, WML, and XHTML/HTML with or without CSS, or combinations thereof.

Suitable mobile application development environments are available from several sources. Commercially available development environments include, by way of non-limiting examples, AirplaySDK, alcheMo, Appcelerator®, Celsius, Bedrock, Flash Lite, .NET Compact Framework, Rhomobile, and WorkLight Mobile Platform. Other development environments are available without cost including, by way of non-limiting examples, Lazarus, MobiFlex, MoSync, and Phonegap. Also, mobile device manufacturers distribute software developer kits including, by way of non-limiting examples, iPhone and iPad (iOS) SDK, Android™ SDK, BlackBerry® SDK, BREW SDK, Palm® OS SDK, Symbian SDK, webOS SDK, and Windows® Mobile SDK.

Those of skill in the art will recognize that several commercial forums are available for distribution of mobile applications including, by way of non-limiting examples, Apple® App Store, Google® Play, Chrome WebStore, BlackBerry® App World, App Store for Palm devices, App Catalog for webOS, Windows® Marketplace for Mobile, Ovi Store for Nokia® devices, Samsung® Apps, and Nintendo® DSi Shop.

Standalone Application

In some embodiments, a computer program includes a standalone application, which is a program that is run as an independent computer process, not an add-on to an existing process, e.g., not a plug-in. Those of skill in the art will recognize that standalone applications are often compiled. A compiler is a computer program(s) that transforms source code written in a programming language into binary object code such as assembly language or machine code. Suitable compiled programming languages include, by way of non-limiting examples, C, C++, Objective-C, COBOL, Delphi, Eiffel, Java™, Lisp, Python™, Visual Basic, and VB.NET, or combinations thereof. Compilation is often performed, at least in part, to create an executable program. In some embodiments, a computer program includes one or more executable complied applications.

Web Browser Plug-In

In some embodiments, the computer program includes a web browser plug-in (e.g., extension, etc.). In computing, a plug-in is one or more software components that add specific functionality to a larger software application. Makers of software applications support plug-ins to enable third-party developers to create abilities which extend an application, to support easily adding new features, and to reduce the size of an application. When supported, plug-ins enable customizing the functionality of a software application. For example, plug-ins are commonly used in web browsers to play video, generate interactivity, scan for viruses, and display particular file types. Those of skill in the art will be familiar with several web browser plug-ins including, Adobe® Flash® Player, Microsoft® Silverlight®, and Apple® QuickTime®. In some embodiments, the toolbar comprises one or more web browser extensions, add-ins, or add-ons. In some embodiments, the toolbar comprises one or more explorer bars, tool bands, or desk bands.

In view of the disclosure provided herein, those of skill in the art will recognize that several plug-in frameworks are available that enable development of plug-ins in various programming languages, including, by way of non-limiting examples, C++, Delphi, Java™, PHP, Python™, and VB.NET, or combinations thereof.

Web browsers (also called Internet browsers) are software applications, designed for use with network-connected computing devices, for retrieving, presenting, and traversing information resources on the World Wide Web. Suitable web browsers include, by way of non-limiting examples, Microsoft® Internet Explorer®, Mozilla® Firefox®, Google® Chrome, Apple® Safari®, Opera Software® Opera®, and KDE Konqueror. In some embodiments, the web browser is a mobile web browser. Mobile web browsers (also called microbrowsers, mini-browsers, and wireless browsers) are designed for use on mobile computing devices including, by way of non-limiting examples, handheld computers, tablet computers, netbook computers, subnotebook computers, smartphones, music players, personal digital assistants (PDAs), and handheld video game systems. Suitable mobile web browsers include, by way of non-limiting examples, Google® Android® browser, RIM Blackberry® Browser, Apple® Safari®, Palm® Blazer, Palm® WebOS® Browser, Mozilla Firefox® for mobile, Microsoft® Internet Explorer® Mobile, Amazon® Kindle® Basic Web, Nokia® Browser, Opera Software® Opera® Mobile, and Sony® PSP™ browser.

Software Modules

In some embodiments, the platforms, systems, media, and methods disclosed herein include software, server, and/or database modules, or use of the same. The software modules disclosed herein are implemented in a multitude of ways. In various embodiments, a software module comprises a file, a section of code, a programming object, a programming structure, or combinations thereof. In further various embodiments, a software module comprises a plurality of files, a plurality of sections of code, a plurality of programming objects, a plurality of programming structures, or combinations thereof. In various embodiments, the one or more software modules comprise, by way of non-limiting examples, a web application, a mobile application, and a standalone application. In some embodiments, software modules are in one computer program or application. In other embodiments, software modules are in more than one computer program or application. In some embodiments, software modules are hosted on one machine. In other embodiments, software modules are hosted on more than one machine. In further embodiments, software modules are hosted on a distributed computing platform such as a cloud computing platform. In some embodiments, software modules are hosted on one or more machines in one location. In other embodiments, software modules are hosted on one or more machines in more than one location.

Databases

In some embodiments, the platforms, systems, media, and methods disclosed herein include one or more databases, or use of the same. In view of the disclosure provided herein, those of skill in the art will recognize that many databases are suitable for storage and retrieval of lung nodule-related analysis and information described herein. In various embodiments, suitable databases include, by way of non-limiting examples, relational databases, non-relational databases, object oriented databases, object databases, entity-relationship model databases, associative databases, and XML databases. Further non-limiting examples include SQL, PostgreSQL, MySQL, Oracle, DB2, and Sybase. In some embodiments, a database is internet-based. In further embodiments, a database is web-based. In still further embodiments, a database is cloud computing-based. In a particular embodiment, a database is a distributed database. In other embodiments, a database is based on one or more local computer storage devices.

Methods Using Computer Systems

The methods described herein can utilize one or more computers. The method may be used to identify whether a lung nodule of a subject is cancerous or non-cancerous. The method may include use of a biomarker measurement. The method may include use of a classifier described herein. The method may include performing an aspect of an assay such as data analysis.

The computer can be used for managing customer and sample information such as sample or customer tracking, database management, analyzing molecular profiling data, analyzing cytological data, storing data, billing, marketing, reporting results, storing results, or a combination thereof. The computer can include a monitor or other graphical interface for displaying data, results, billing information, marketing information (e.g. demographics), customer information, or sample information. The computer can also include means for data or information input. The computer can include a processing unit and fixed or removable media or a combination thereof. The computer can be accessed by a user in physical proximity to the computer, for example via a keyboard and/or mouse, or by a user that does not necessarily have access to the physical computer through a communication medium such as a modem, an internet connection, a telephone connection, or a wired or wireless communication signal carrier wave. In some cases, the computer can be connected to a server or other communication device for relaying information from a user to the computer or from the computer to a user. In some cases, the user can store data or information obtained from the computer through a communication medium on media, such as removable media. It is envisioned that data relating to the methods can be transmitted over such networks or connections for reception and/or review by a party. The receiving party can be but is not limited to an individual, a health care provider or a health care manager. In one instance, a computer-readable medium includes a medium suitable for transmission of a result of an analysis of a biological sample. The medium can include a result of a subject, wherein such a result is derived using the methods described herein.

The entity obtaining the sample information can enter it into a database for the purpose of one or more of the following: inventory tracking, assay result tracking, order tracking, customer management, customer service, billing, and sales. Sample information can include, but is not limited to: customer name, unique customer identification, customer associated medical professional, indicated assay or assays, assay results, adequacy status, indicated adequacy tests, medical history of the individual, preliminary diagnosis, suspected diagnosis, sample history, insurance provider, medical provider, third party testing center or any information suitable for storage in a database. Sample history can include but is not limited to: age of the sample, type of sample, method of acquisition, method of storage, or method of transport.

The database can be accessible by a customer, medical professional, insurance provider, or other third party. Database access can take the form of digital processing communication such as a computer or telephone. The database can be accessed through an intermediary such as a customer service representative, business representative, consultant, independent testing center, or medical professional. The availability or degree of database access or sample information, such as assay results, can change upon payment of a fee for products and services rendered or to be rendered. The degree of database access or sample information can be restricted to comply with generally accepted or legal requirements for patient or customer confidentiality.

Machine Learning

The methods described herein can comprise computer-implemented methods of supervised or unsupervised learning methods, including SVM, random forests, clustering algorithm (or software module), gradient boosting, logistic regression, and/or decision trees. The machine learning methods as described herein can improve generation of suggestions based on recording and analyzing any of the identifiers, lab results, patient outcomes, or any other relevant medical information as described herein. In some cases, the machine learning methods can intentionally group or separate treatment options. In some embodiments, some treatment options can be intentionally clustered or removed from any one phase of the plurality of phases of the medical care encounter. Machine learning may be used to train a classifier described herein, for example in training a classifier to distinguish samples from subjects with benign or cancerous lung nodules.

Supervised learning algorithms can be algorithms that rely on the use of a set of labeled, paired training data examples to infer the relationship between an input data and output data. Unsupervised learning algorithms can be algorithms used to draw inferences from training data sets to output data. Unsupervised learning algorithms can comprise cluster analysis, which can be used for exploratory data analysis to find hidden patterns or groupings in process data. One example of an unsupervised learning method can comprise principal component analysis. Principal component analysis can comprise reducing the dimensionality of one or more variables. The dimensionality of a given variables can be at least 1, 5, 10, 50, 100, 200, 300, 400, 500, 600, 700, 800, 900, 1000, 1100, 1200 1300, 1400, 1500, 1600, 1700, 1800, or greater. The dimensionality of a given variables can be 1800 or less, 1600 or less, 1500 or less, 1400 or less, 1300 or less, 1200 or less, 1100 or less, 1000 or less, 900 or less, 800 or less, 700 or less, 600 or less, 500 or less, 400 or less, 300 or less, 200 or less, 100 or less, 50 or less, or 10 or less.

The computer-implemented methods can comprise statistical techniques. In some embodiments, statistical techniques can comprise linear regression, classification, resampling methods, subset selection, shrinkage, dimension reduction, nonlinear models, tree-based methods, support vector machines, unsupervised learning, or any combination thereof.

A linear regression can be a method to predict a target variable by fitting a best linear relationship between a dependent and independent variable. The best fit can mean that the sum of all distances between a shape and actual observations at each point is the least. Linear regression can comprise simple linear regression and multiple linear regression. A simple linear regression can use a single independent variable to predict a dependent variable. A multiple linear regression can use more than one independent variable to predict a dependent variable by fitting a best linear relationship.

A classification can be a data mining technique that assigns categories to a collection of data in order to achieve accurate predictions and analysis. Classification techniques can comprise logistic regression and discriminant analysis. Logistic regression can be used when a dependent variable is dichotomous (binary). Logistic regression can be used to discover and describe a relationship between one dependent binary variable and one or more nominal, ordinal, interval or ratio-level independent variables. A resampling can be a method comprising drawing repeated samples from original data samples. A resampling can not involve a utilization of a generic distribution tables in order to compute approximate probability values. A resampling can generate a unique sampling distribution on a basis of an actual data. In some embodiments, a resampling can use experimental methods, rather than analytical methods, to generate a unique sampling distribution. Resampling techniques can comprise bootstrapping and cross-validation. Bootstrapping can be performed by sampling with replacement from original data and take "not chosen" data points as test cases. Cross validation can be performed by split training data into a plurality of parts.

A subset selection can identify a subset of predictors related to a response. A subset selection can comprise a best-subset selection, forward stepwise selection, backward stepwise selection, hybrid method, or any combination thereof. In some instances, shrinkage fits a model involving all predictors, but estimated coefficients are shrunken towards zero relative to the least squares estimates. This shrinkage can reduce variance. A shrinkage can comprise ridge regression and a lasso. A dimension reduction can reduce a problem of estimating n+1 coefficients to a simpler problem of m+1 coefficients, where m<n. It can be attained by computing n different linear combinations, or projections, of variables. Then these n projections are used as predictors to fit a linear regression model by least squares. Dimension reduction can comprise principal component regression and partial least squares. A principal component regression can be used to derive a low dimensional set of features from a large set of variables. A principal component used in a principal component regression can capture a large amount of variance in data using linear combinations of data in subsequently orthogonal directions. The partial least squares can be a supervised alternative to principal component regression because partial least squares can make use of a response variable in order to identify new features.

A nonlinear regression can be a form of regression analysis in which observational data are modeled by a function which is a nonlinear combination of model parameters and depends on one or more independent variables. A nonlinear regression can comprise a step function, piecewise function, spline, generalized additive model, or any combination thereof.

Tree-based methods can be used for both regression and classification problems. Regression and classification problems can involve stratifying or segmenting the predictor space into a number of simple regions. Tree-based methods can comprise bagging, boosting, random forest, or any combination thereof. Bagging can decrease a variance of prediction by generating additional data for training from the original dataset using combinations with repetitions to produce multistep of the same carnality/size as original data.

Boosting can calculate an output using several different models and then average a result using a weighted average approach. A random forest algorithm can draw random bootstrap samples of a training set. Support vector machines can be classification techniques. Support vector machines can comprise finding a hyperplane that best separates two classes of points with the maximum margin. Support vector machines can constrain an optimization problem such that a margin is maximized subject to a constraint that it perfectly classifies data.

Unsupervised methods can be methods to draw inferences from datasets comprising input data without labeled responses. Unsupervised methods can comprise clustering, principal component analysis, k-Mean clustering, hierarchical clustering, or any combination thereof.

Algorithms

After using one or more assays to process one or more biological samples derived from the subject to generate one or more datasets indicative of the lung nodule-related state or lung nodule-related complication, an algorithm such as a trained algorithm may be used to process one or more of the datasets (e.g., at each of a plurality of lung nodule-related state-associated genomic loci) to determine the lung nodule-related state. For example, the trained algorithm may be used to determine quantitative measures of sequences at each of the plurality of lung nodule-related state-associated genomic loci in the biological samples. The trained algorithm may be configured to identify the lung nodule-related state with an accuracy of at least about 50%, at least about 55%, at least about 60%, at least about 65%, at least about 70%, at least about 75%, at least about 80%, at least about 85%, at least about 90%, at least about 95%, at least about 96%, at least about 97%, at least about 98%, at least about 99%, or more than 99% for at least about 25, at least about 50, at least about 100, at least about 150, at least about 200, at least about 250, at least about 300, at least about 350, at least about 400, at least about 450, at least about 500, or more than about 500 independent samples. A classifier described herein may include a trained algorithm.

The trained algorithm may comprise a supervised machine learning algorithm. The trained algorithm may comprise a classification and regression tree (CART) algorithm. The supervised machine learning algorithm may comprise, for example, a Random Forest, a support vector machine (SVM), a neural network, or a deep learning algorithm. The trained algorithm may comprise an unsupervised machine learning algorithm.

The trained algorithm may be configured to accept a plurality of input variables and to produce one or more output values based on the plurality of input variables. The plurality of input variables may comprise one or more datasets indicative of a lung nodule-related state. For example, an input variable may comprise a number of sequences corresponding to or aligning to each of the plurality of lung nodule-related state-associated genomic loci. The plurality of input variables may also include clinical health data of a subject.

The trained algorithm may comprise a classifier, such that each of the one or more output values comprises one of a fixed number of possible values (e.g., a linear classifier, a logistic regression classifier, etc.) indicating a classification of the biological sample by the classifier. The trained algorithm may comprise a binary classifier, such that each of the one or more output values comprises one of two values (e.g., {0, 1}, {positive, negative}, or {high-risk, low-risk}) indicating a classification of the biological sample by the classifier. The trained algorithm may be another type of classifier, such that each of the one or more output values comprises one of more than two values (e.g., {0, 1, 2}, {positive, negative, or indeterminate}, or {high-risk, intermediate-risk, or low-risk}) indicating a classification of the biological sample by the classifier. The output values may comprise descriptive labels, numerical values, or a combination thereof. Some of the output values may comprise descriptive labels. Such descriptive labels may provide an identification or indication of the disease or disorder state of the subject, and may comprise, for example, positive, negative, high-risk, intermediate-risk, low-risk, or indeterminate. Such descriptive labels may provide an identification of a treatment for the subject's lung nodule-related state, and may comprise, for example, a therapeutic intervention, a duration of the therapeutic intervention, and/or a dosage of the therapeutic intervention suitable to treat a lung nodule-related condition. Such descriptive labels may provide an identification of secondary clinical tests that may be appropriate to perform on the subject, and may comprise, for example, an imaging test, a blood test, a computed tomography (CT) scan, a magnetic resonance imaging (MRI) scan, an ultrasound scan, a chest X-ray, a positron emission tomography (PET) scan, a PET-CT scan, a cell-free biological cytology, an amniocentesis, a non-invasive prenatal test (NIPT), or any combination thereof. For example, such descriptive labels may provide a prognosis of the lung nodule-related state of the subject. As another example, such descriptive labels may provide a relative assessment of the lung nodule-related state (e.g., an estimated gestational age in number of days, weeks, or months) of the subject. Some descriptive labels may be mapped to numerical values, for example, by mapping "positive" to 1 and "negative" to 0.

Some of the output values may comprise numerical values, such as binary, integer, or continuous values. Such binary output values may comprise, for example, {0, 1}, {positive, negative}, or {high-risk, low-risk}. Such integer output values may comprise, for example, {0, 1, 2}. Such continuous output values may comprise, for example, a probability value of at least 0 and no more than 1. Such continuous output values may comprise, for example, an un-normalized probability value of at least 0. Such continuous output values may indicate a prognosis of the lung nodule-related state of the subject. Some numerical values may be mapped to descriptive labels, for example, by mapping 1 to "positive" and 0 to "negative."

Some of the output values may be assigned based on one or more cutoff values. For example, a binary classification of samples may assign an output value of "positive" or 1 if the sample indicates that the subject has at least a 50% probability of having a lung nodule-related state (e.g., lung nodule-related complication). For example, a binary classification of samples may assign an output value of "negative" or 0 if the sample indicates that the subject has less than a 50% probability of having a lung nodule-related state (e.g., lung nodule-related complication). In this case, a single cutoff value of 50% is used to classify samples into one of the two possible binary output values. Examples of single cutoff values may include about 1%, about 2%, about 5%, about 10%, about 15%, about 20%, about 25%, about 30%, about 35%, about 40%, about 45%, about 50%, about 55%, about 60%, about 65%, about 70%, about 75%, about 80%, about 85%, about 90%, about 91%, about 92%, about 93%, about 94%, about 95%, about 96%, about 97%, about 98%, and about 99%.

As another example, a classification of samples may assign an output value of "positive" or 1 if the sample indicates that the subject has a probability of having a lung nodule-related state (e.g., lung nodule-related complication) of at least about 50%, at least about 55%, at least about 60%, at least about 65%, at least about 70%, at least about 75%, at least about 80%, at least about 85%, at least about 90%, at least about 91%, at least about 92%, at least about 93%, at least about 94%, at least about 95%, at least about 96%, at least about 97%, at least about 98%, at least about 99%, or more. The classification of samples may assign an output value of "positive" or 1 if the sample indicates that the subject has a probability of having a lung nodule-related state (e.g., lung nodule-related complication) of more than about 50%, more than about 55%, more than about 60%, more than about 65%, more than about 70%, more than about 75%, more than about 80%, more than about 85%, more than about 90%, more than about 91%, more than about 92%, more than about 93%, more than about 94%, more than about 95%, more than about 96%, more than about 97%, more than about 98%, or more than about 99%.

The classification of samples may assign an output value of "negative" or 0 if the sample indicates that the subject has a probability of having a lung nodule-related state (e.g., lung nodule-related complication) of less than about 50%, less than about 45%, less than about 40%, less than about 35%, less than about 30%, less than about 25%, less than about 20%, less than about 15%, less than about 10%, less than about 9%, less than about 8%, less than about 7%, less than about 6%, less than about 5%, less than about 4%, less than about 3%, less than about 2%, or less than about 1%. The classification of samples may assign an output value of "negative" or 0 if the sample indicates that the subject has a probability of having a lung nodule-related state (e.g., lung nodule-related complication) of no more than about 50%, no more than about 45%, no more than about 40%, no more than about 35%, no more than about 30%, no more than about 25%, no more than about 20%, no more than about 15%, no more than about 10%, no more than about 9%, no more than about 8%, no more than about 7%, no more than about 6%, no more than about 5%, no more than about 4%, no more than about 3%, no more than about 2%, or no more than about 1%.

The classification of samples may assign an output value of "indeterminate" or 2 if the sample is not classified as "positive", "negative", 1, or 0. In this case, a set of two cutoff values is used to classify samples into one of the three possible output values. Examples of sets of cutoff values may include {1%, 99%}, {2%, 98%}, {5%, 95%}, {10%, 90%}, {15%, 85%}, {20%, 80%}, {25%, 75%}, {30%, 70%}, {35%, 65%}, {40%, 60%}, and {45%, 55%}. Similarly, sets of n cutoff values may be used to classify samples into one of n+1 possible output values, where n is any positive integer.

The trained algorithm may be trained with a plurality of independent training samples. Each of the independent training samples may comprise a biological sample from a subject, associated datasets obtained by assaying the biological sample (as described elsewhere herein), and one or more known output values corresponding to the biological sample (e.g., a clinical diagnosis, prognosis, absence, or treatment efficacy of a lung nodule-related state of the subject). Independent training samples may comprise biological samples and associated datasets and outputs obtained or derived from a plurality of different subjects. Independent training samples may comprise biological samples and associated datasets and outputs obtained at a plurality of different time points from the same subject (e.g., on a regular basis such as weekly, biweekly, or monthly). Independent training samples may be associated with presence of the lung nodule-related state (e.g., training samples comprising biological samples and associated datasets and outputs obtained or derived from a plurality of subjects known to have the lung nodule-related state). Independent training samples may be associated with absence of the lung nodule-related state (e.g., training samples comprising biological samples and associated datasets and outputs obtained or derived from a plurality of subjects who are known to not have a previous diagnosis of the lung nodule-related state or who have received a negative test result for the lung nodule-related state).

The trained algorithm may be trained with at least about 5, at least about 10, at least about 15, at least about 20, at least about 25, at least about 30, at least about 35, at least about 40, at least about 45, at least about 50, at least about 100, at least about 150, at least about 200, at least about 250, at least about 300, at least about 350, at least about 400, at least about 450, or at least about 500 independent training samples. The independent training samples may comprise biological samples associated with presence of the lung nodule-related state and/or biological samples associated with absence of the lung nodule-related state. The trained algorithm may be trained with no more than about 500, no more than about 450, no more than about 400, no more than about 350, no more than about 300, no more than about 250, no more than about 200, no more than about 150, no more than about 100, or no more than about 50 independent training samples associated with presence of the lung nodule-related state. In some embodiments, the biological sample is independent of samples used to train the trained algorithm.

The trained algorithm may be trained with a first number of independent training samples associated with presence of the lung nodule-related state and a second number of independent training samples associated with absence of the lung nodule-related state. The first number of independent training samples associated with presence of the lung nodule-related state may be no more than the second number of independent training samples associated with absence of the lung nodule-related state. The first number of independent training samples associated with presence of the lung nodule-related state may be equal to the second number of independent training samples associated with absence of the lung nodule-related state. The first number of independent training samples associated with presence of the lung nodule-related state may be greater than the second number of independent training samples associated with absence of the lung nodule-related state.

The trained algorithm may be configured to identify the lung nodule-related state at an accuracy of at least about 50%, at least about 55%, at least about 60%, at least about 65%, at least about 70%, at least about 75%, at least about 80%, at least about 81%, at least about 82%, at least about 83%, at least about 84%, at least about 85%, at least about 86%, at least about 87%, at least about 88%, at least about 89%, at least about 90%, at least about 91%, at least about 92%, at least about 93%, at least about 94%, at least about 95%, at least about 96%, at least about 97%, at least about 98%, at least about 99%, or more; for at least about 5, at least about 10, at least about 15, at least about 20, at least about 25, at least about 30, at least about 35, at least about 40, at least about 45, at least about 50, at least about 100, at least about 150, at least about 200, at least about 250, at least about 300, at least about 350, at least about 400, at least about 450, or at least about 500 independent training samples. The accuracy of identifying the lung nodule-related state by the trained algorithm may be calculated as the percentage of independent test samples (e.g., subjects known to have the lung nodule-related state or subjects with negative clinical test results for the lung nodule-related state) that are correctly identified or classified as having or not having the lung nodule-related state.

The trained algorithm may be configured to identify the lung nodule-related state with a positive predictive value (PPV) of at least about 5%, at least about 10%, at least about 15%, at least about 20%, at least about 25%, at least about 30%, at least about 35%, at least about 40%, at least about 50%, at least about 55%, at least about 60%, at least about 65%, at least about 70%, at least about 75%, at least about 80%, at least about 81%, at least about 82%, at least about 83%, at least about 84%, at least about 85%, at least about 86%, at least about 87%, at least about 88%, at least about 89%, at least about 90%, at least about 91%, at least about 92%, at least about 93%, at least about 94%, at least about 95%, at least about 96%, at least about 97%, at least about 98%, at least about 99%, or more. The PPV of identifying the lung nodule-related state using the trained algorithm may be calculated as the percentage of biological samples identified or classified as having the lung nodule-related state that correspond to subjects that truly have the lung nodule-related state.

The trained algorithm may be configured to identify the lung nodule-related state with a negative predictive value (NPV) of at least about 5%, at least about 10%, at least about 15%, at least about 20%, at least about 25%, at least about 30%, at least about 35%, at least about 40%, at least about 50%, at least about 55%, at least about 60%, at least about 65%, at least about 70%, at least about 75%, at least about 80%, at least about 81%, at least about 82%, at least about 83%, at least about 84%, at least about 85%, at least about 86%, at least about 87%, at least about 88%, at least about 89%, at least about 90%, at least about 91%, at least about 92%, at least about 93%, at least about 94%, at least about 95%, at least about 96%, at least about 97%, at least about 98%, at least about 99%, or more. The NPV of identifying the lung nodule-related state using the trained algorithm may be calculated as the percentage of biological samples identified or classified as not having the lung nodule-related state that correspond to subjects that truly do not have the lung nodule-related state.

The trained algorithm may be configured to identify the lung nodule-related state with a clinical sensitivity at least about 5%, at least about 10%, at least about 15%, at least about 20%, at least about 25%, at least about 30%, at least about 35%, at least about 40%, at least about 50%, at least about 55%, at least about 60%, at least about 65%, at least about 70%, at least about 75%, at least about 80%, at least about 81%, at least about 82%, at least about 83%, at least about 84%, at least about 85%, at least about 86%, at least about 87%, at least about 88%, at least about 89%, at least about 90%, at least about 91%, at least about 92%, at least about 93%, at least about 94%, at least about 95%, at least about 96%, at least about 97%, at least about 98%, at least about 99%, at least about 99.1%, at least about 99.2%, at least about 99.3%, at least about 99.4%, at least about 99.5%, at least about 99.6%, at least about 99.7%, at least about 99.8%, at least about 99.9%, at least about 99.99%, at least about 99.999%, or more. The clinical sensitivity of identifying the lung nodule-related state using the trained algorithm may be calculated as the percentage of independent test samples associated with presence of the lung nodule-related state (e.g., subjects known to have the lung nodule-related state) that are correctly identified or classified as having the lung nodule-related state.

The trained algorithm may be configured to identify the lung nodule-related state with a clinical specificity of at least about 5%, at least about 10%, at least about 15%, at least about 20%, at least about 25%, at least about 30%, at least about 35%, at least about 40%, at least about 50%, at least about 55%, at least about 60%, at least about 65%, at least about 70%, at least about 75%, at least about 80%, at least about 81%, at least about 82%, at least about 83%, at least about 84%, at least about 85%, at least about 86%, at least about 87%, at least about 88%, at least about 89%, at least about 90%, at least about 91%, at least about 92%, at least about 93%, at least about 94%, at least about 95%, at least about 96%, at least about 97%, at least about 98%, at least about 99%, at least about 99.1%, at least about 99.2%, at least about 99.3%, at least about 99.4%, at least about 99.5%, at least about 99.6%, at least about 99.7%, at least about 99.8%, at least about 99.9%, at least about 99.99%, at least about 99.999%, or more. The clinical specificity of identifying the lung nodule-related state using the trained algorithm may be calculated as the percentage of independent test samples associated with absence of the lung nodule-related state (e.g., subjects with negative clinical test results for the lung nodule-related state) that are correctly identified or classified as not having the lung nodule-related state.

The trained algorithm may be configured to identify the cancer or the lung nodule-related state with an Area-Under-Curve (AUC) of at least about 0.50, at least about 0.55, at least about 0.60, at least about 0.65, at least about 0.70, at least about 0.75, at least about 0.80, at least about 0.81, at least about 0.82, at least about 0.83, at least about 0.84, at least about 0.85, at least about 0.86, at least about 0.87, at least about 0.88, at least about 0.89, at least about 0.90, at least about 0.91, at least about 0.92, at least about 0.93, at least about 0.94, at least about 0.95, at least about 0.96, at least about 0.97, at least about 0.98, at least about 0.99, or more. The AUC may be calculated as an integral of the Receiver Operator Characteristic (ROC) curve (e.g., the area under the ROC curve) associated with the trained algorithm in classifying biological samples as having or not having the lung nodule-related state. The AUC may comprise an average AUC. The AUC may comprise a mean AUC.

Disclosed herein, in some aspects, is a method, comprising: assaying proteins in a biofluid sample obtained from a subject identified as having a lung nodule to obtain protein measurements; and identifying the protein measurements as indicative of the lung nodule being cancerous or as non-cancerous by applying a classifier to the protein measurements, wherein the classifier is characterized by a receiver operating characteristic (ROC) curve having an area under the curve (AUC) greater than 0.5, greater than 0.6, greater than 0.7, greater than 0.75, or greater than 0.8, based on protein measurement features. In some aspects, the AUC is greater than about 0.5, greater than about 0.6, greater than about 0.7, greater than about 0.75, or greater than about 0.8, based on protein measurement features. The AUC may comprise an average AUC. The AUC may comprise a mean AUC.

In some aspects, the classifier does not include clinical features. In some aspects, the classifier includes clinical features. The clinical features may include non-protein clinical features. In some aspects, the AUC is generated without the classifier including non-protein clinical features. In some aspects, the non-protein clinical features comprise clinical indicators of lung cancer.

The trained algorithm may be adjusted or tuned to improve one or more of the performance, accuracy, PPV, NPV, clinical sensitivity, clinical specificity, or AUC of identifying the lung nodule-related state. The trained algorithm may be adjusted or tuned by adjusting parameters of the trained algorithm (e.g., a set of cutoff values used to classify a biological sample as described elsewhere herein, or weights of a neural network). The trained algorithm may be adjusted or tuned continuously during the training process or after the training process has completed.

After the trained algorithm is initially trained, a subset of the inputs may be identified as most influential or most important to be included for making high-quality classifications. For example, a subset of the plurality of lung nodule-related state-associated genomic loci may be identified as most influential or most important to be included for making high-quality classifications or identifications of lung nodule-related states (or sub-types of lung nodule-related states). The plurality of lung nodule-related state-associated genomic loci or a subset thereof may be ranked based on classification metrics indicative of each genomic locus's influence or importance toward making high-quality classifications or identifications of lung nodule-related states (or sub-types of lung nodule-related states). Such metrics may be used to reduce, in some cases significantly, the number of input variables (e.g., predictor variables) that may be used to train the trained algorithm to a desired performance level (e.g., based on a desired minimum accuracy, PPV, NPV, clinical sensitivity, clinical specificity, AUC, or a combination thereof). For example, if training the trained algorithm with a plurality comprising several dozen or hundreds of input variables in the trained algorithm results in an accuracy of classification of more than 99%, then training the trained algorithm instead with only a selected subset of no more than about 5, no more than about 10, no more than about 15, no more than about 20, no more than about 25, no more than about 30, no more than about 35, no more than about 40, no more than about 45, no more than about 50, or no more than about 100 such most influential or most important input variables among the plurality can yield decreased but still acceptable accuracy of classification (e.g., at least about 50%, at least about 55%, at least about 60%, at least about 65%, at least about 70%, at least about 75%, at least about 80%, at least about 81%, at least about 82%, at least about 83%, at least about 84%, at least about 85%, at least about 86%, at least about 87%, at least about 88%, at least about 89%, at least about 90%, at least about 91%, at least about 92%, at least about 93%, at least about 94%, at least about 95%, at least about 96%, at least about 97%, at least about 98%, or at least about 99%). The subset may be selected by rank-ordering the entire plurality of input variables and selecting a predetermined number (e.g., no more than about 5, no more than about 10, no more than about 15, no more than about 20, no more than about 25, no more than about 30, no more than about 35, no more than about 40, no more than about 45, no more than about 50, or no more than about 100) of input variables with top classification metrics.

Figure 57:
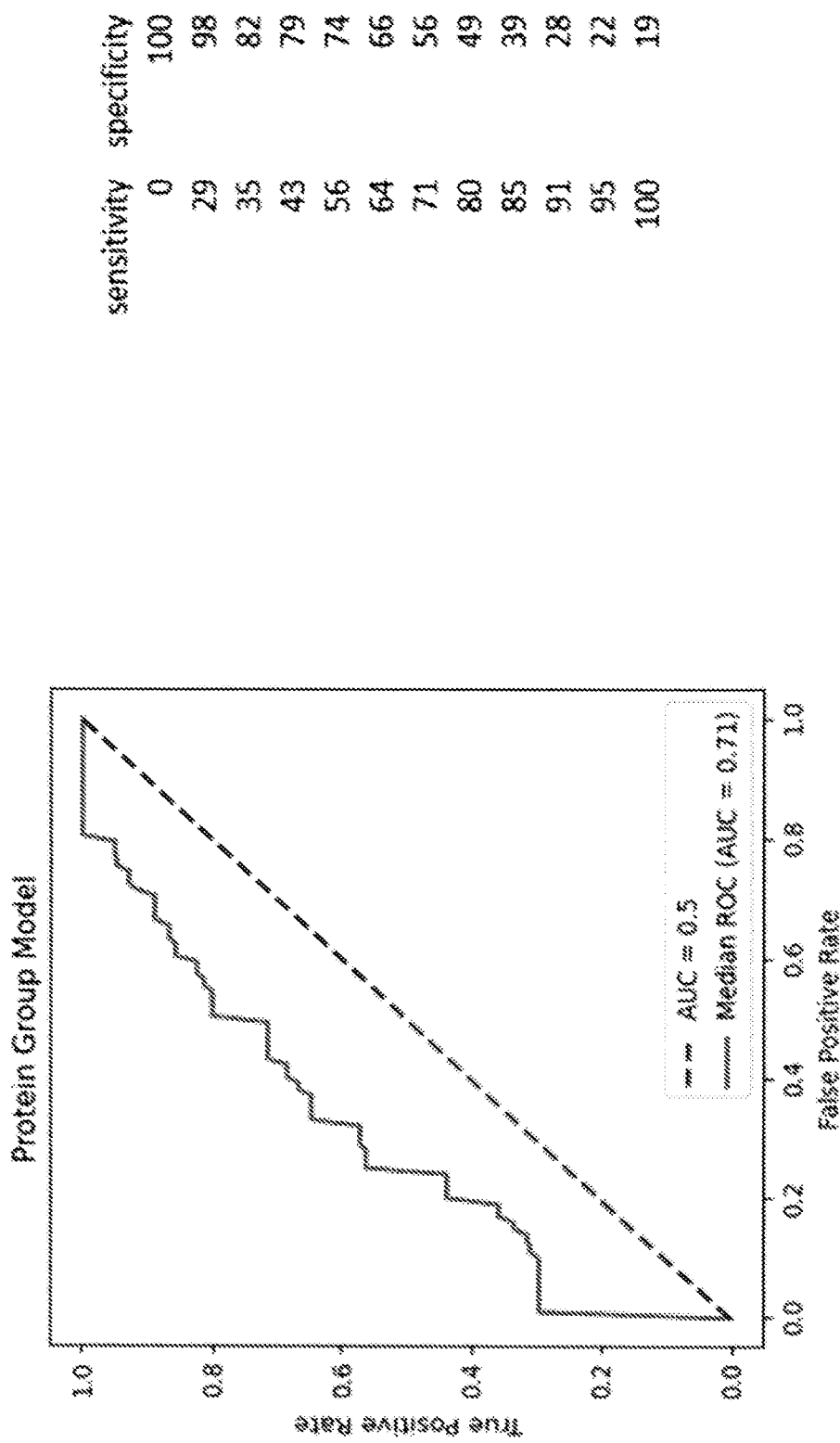
FIG. 57 shows an ROC curve for lung nodule classifier, where the sensitivities and the corresponding specificities are listed.

FIG. 57 illustrates data from an example lung nodule classifier generated from the methods described herein to determine whether a lung nodule is malignant or benign. In some embodiments, a classifier described herein has a sensitivity or specificity at least as great as depicted in FIG. 57. In some embodiments, a classifier described herein has a sensitivity and specificity at least as great as depicted in FIG. 57. FIG. 58 illustrates feature information and importance for the lung nodule classifier shown in FIG. 57. In some embodiments, the classifier uses one or more features included in FIG. 58. The median AUC of 0.71 shown in FIG. 57 was obtained using a classifier that included protein features, without including clinical risk factors (such as age, smoking status, nodule diameter, nodule spiculation status, or nodule location) as features.

Data Integration and Analysis

Separate omic data sets may be integrated into an analysis for more accurate prediction or identification of a disease (e.g. cancer) than individual omic data sets would provide for. For example, a method may include using more than one classifier to identify a disease state (e.g. pancreatic cancer, liver cancer, ovarian cancer, or colon cancer) in a subject, where each classifier is used to analyze a separate omic data set and each classifier is independent of the other. When the classifiers err independently from each other, the combined analysis may be more accurate than an analysis using one classifier corresponding to only one omic data set. Alternatively, separate omic data sets may be combined into one multi-omic data set or analyzed by a single classifier.

A classifier may used in a variety of methods. Some examples of such methods may include the following:

A multi-omic method comprising: obtaining multi-omic data generated from one or more biofluid samples collected from a subject suspected of having a disease state, the multi-omic data comprising mass spectrometry measurements and nucleic acid sequencing measurements; and applying a classifier to the multi-omic data to evaluate the disease state.

A multi-omic method comprising: obtaining multi-omic data generated from one or more biofluid samples collected from a subject suspected of having a disease state, the multi-omic data comprising proteomic measurements and nucleic acid sequencing measurements; and applying a classifier to the multi-omic data to evaluate the disease state.

A multi-omic method comprising: obtaining multi-omic data generated from one or more biofluid samples collected from a subject suspected of having a disease state, the multi-omic data comprising at least two types of omic data selected from the group consisting of: proteomic measurements, metabolomic measurements, lipidomic measurements, mRNA sequencing measurements, microRNA sequencing measurements, and genome methylation measurements; and applying one or more classifiers to the multi-omic data to evaluate the disease state.

A multi-omic method comprising: obtaining multi-omic data generated from one or more blood, serum, or plasma samples collected from a human subject suspected of having cancer, the multi-omic data comprising proteomic measurements and RNA sequencing measurements; and applying a classifier to the multi-omic data to evaluate the cancer. Disclosed herein, in some aspects, are multi-omic methods, comprising: obtaining multi-omic data generated from one or more blood, serum, or plasma samples collected from a human subject suspected of having cancer, the multi-omic data comprising proteomic measurements and a second type of omic data selected from the group consisting of: metabolomic measurements, lipidomic measurements, mRNA sequencing measurements, microRNA sequencing measurements, and genome methylation measurements; and applying a classifier to the multi-omic data to evaluate the cancer.

A multi-omic method comprising: obtaining multi-omic data generated from one or more blood, serum, or plasma samples collected from a human subject suspected of having cancer, the multi-omic data comprising proteomic measurements, mRNA sequencing measurements, and microRNA sequencing measurements; and applying a classifier to the multi-omic data to evaluate the cancer.

A multi-omic method comprising: obtaining multi-omic data generated from one or more biofluid samples collected from a subject suspected of having a disease state, the multi-omic data comprising proteomic measurements and metabolomic measurements or lipidomic measurements; and applying a classifier to the multi-omic data to evaluate the disease state.

A multi-omic method comprising: obtaining multi-omic data generated from one or more biofluid samples collected from a subject suspected of having a disease state, the multi-omic data comprising proteomic measurements, nucleic acid sequencing measurements, and metabolomic measurements; and applying a classifier to the multi-omic data to evaluate the disease state.

A multi-omic method, comprising: obtaining multi-omic data generated from one or more biofluid samples collected from a subject suspected of having a disease state, the multi-omic data comprising proteomic measurements and mRNA sequencing measurements; and applying a classifier to the multi-omic data to evaluate the disease state A multi-omic method, comprising: obtaining multi-omic data generated from one or more biofluid samples collected from a subject suspected of having a disease state, the multi-omic data comprising proteomic measurements and nucleic acid sequencing measurements, wherein the proteomic measurements comprise measurements of over 45 peptides or protein groups; and applying a classifier to the multi-omic data to evaluate the disease state.

A multi-omic method, comprising: obtaining multi-omic data generated from one or more biofluid samples collected from a subject suspected of having a disease state, the multi-omic data comprising mass spectrometry proteomic measurements and nucleic acid sequencing measurements; and applying a classifier to the multi-omic data to evaluate the disease state.

A multi-omic method, comprising: obtaining multi-omic data generated from one or more biofluid samples collected from a subject suspected of having a disease state, the multi-omic data comprising proteomic measurements and nucleic acid sequencing measurements; and applying a classifier to the multi-omic data to evaluate the disease state, wherein the classifier is characterized by an average area under the curve (AUC) of a receiver operating characteristic (ROC) curve of at least 0.9, as determined in a data set derived from a randomized, controlled trial of at least 20 subjects having the disease state and over 20 control subjects not having the disease state.

Some methods may use only one classifier, or may analyze or evaluate only one type of data such as only one type of omic data. For example, a method may include applying a classifier to proteomic measurements or only proteomic measurements to perform an evaluation.

Clinical parameters may be included in an analysis or classifier. For example, a classifier may include classification features based on clinical parameters. Examples of clinical parameters may include medical or social history aspects such as including smoking use, alcohol use, height, weight, vital signs, disease co-morbidity, family history of disease (e.g., cancer), or medication use, or a combination thereof. Clinical parameters may include age, gender, race, or smoking status, or a combination thereof. Clinical parameters may include any or all of the following clinical risk factors: age, smoking status, nodule diameter, nodule spiculation status, or nodule location. Any number of these clinical parameters may be used.

Clinical parameters may be excluded from a classifier or method described herein. For example, a classifier may evaluate a disease state using protein measurements or other biomolecule measurements without the use of clinical parameters. Likewise, a classifier may evaluate a lung nodule using protein measurements or other biomolecule measurements without the use of clinical parameters or clinical risk factors.

Separate data sets may be integrated into an analysis for more accurate prediction or identification of a cancer than individual data sets would provide for. For example, a method may include using more than one classifier to identify a lung cancer in a subject, where each classifier is used to analyze a separate data set and each classifier is independent of the other. When the classifiers err independently from each other, the combined analysis may be more accurate than an analysis using one classifier corresponding to only one data set. Alternatively, separate data sets may be combined into one data set or analyzed by a single classifier.

A method involving multiple classifiers may include using a first classifier to generate or assign a first label corresponding to a presence, absence, or likelihood of a disease state (e.g. cancer) to a first omic data set. The method may further include using a second classifier to generate or assign a second label corresponding to a presence, absence, or likelihood of a disease state to a second omic data set. The method may further include using a third classifier to generate or assign a third label corresponding to a presence, absence, or likelihood of a disease state to a third omic data set. The method may further include using a fourth classifier to generate or assign a fourth label corresponding to a presence, absence, or likelihood of a disease state to a fourth omic data set. Additional classifiers may be used to generate or assign labels to further omic data sets. Each classifier may be trained using omic data or combined omic data from samples of diseased and control subjects. Further, each classifier may include a stand-alone machine learning model or an ensemble of machine-learning models trained on the same input features. Classifiers may be trained using computer vision, natural language processing, or unsupervised learning, or a combination thereof. Classifiers may be trained using data sets from multiple samples, for example thousands of samples.

Figure 5:
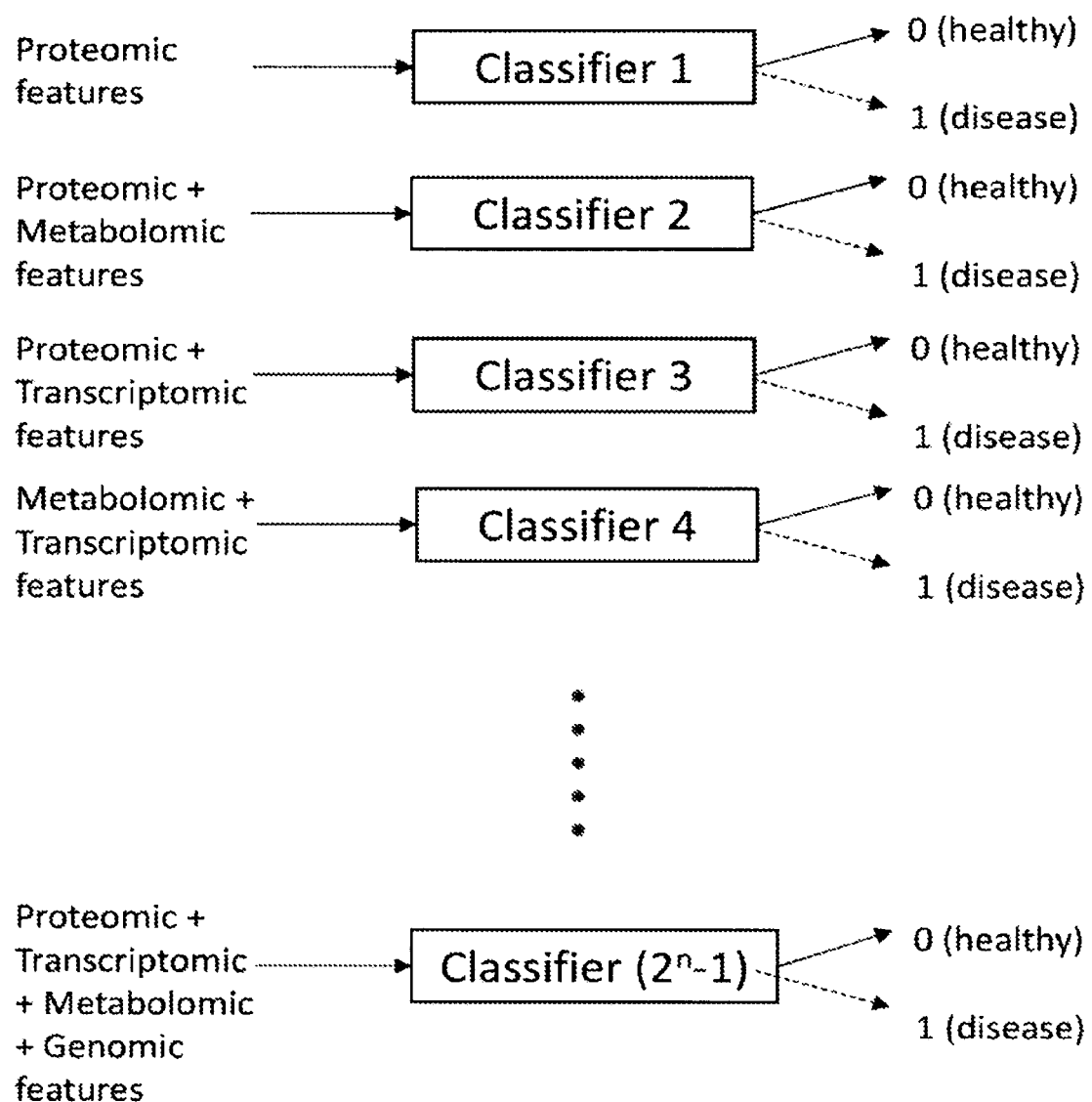
FIG. 5 shows a diagram of classifier and feature information, in accordance with some aspects described herein.

Some classifiers may analyze a combined data set such as a combined omic data set, whereas other classifiers may analyze only one omic data set. For example, an additional classifier may generate or assign a label corresponding to a presence, absence, or likelihood of a disease state (e.g. cancer) to a combined omic data set. The combined omic data set may include any combination of two or more types or subtypes of omic data. For example, omic data types may include proteomic data, transcriptomic data, genomic data, or metabolomic data. Each classifier may make a determination of the disease state as shown in FIG. 5.

The labels generated or assigned by each classifier may be used to identify the data (e.g. multi-omic data) as indicative or as not indicative of the disease state (e.g. cancer). This may entail picking a label assigned by any one or more of the classifiers, or may entail generating or obtaining a majority voting score based on the first and second labels.

Identifying multiple data sets or multi-omic data as indicative or as not indicative of the disease state may include majority voting across of some or all of the classifier-generated labels. For example, the final determination of whether the subject is likely to have the disease state such as cancer or not may be identified based on whether more classifiers assigned labels corresponding to the presence of the disease state or whether more classifiers assigned labels corresponding to the absence of the disease state. Identifying the multi-omic data as indicative or as not indicative of the disease state may include generating or using a weighted average of some or all of the classifier-generated labels.

Identifying the data (e.g. multi-omic data) as indicative or as not indicative of a disease state such as cancer may include obtaining or generating a weighted average of the labels generated or assigned by some or all of the classifiers. Weights of the weighted average may be based on one or more of: area under a ROC curve, area under a precision-recall curve, accuracy, precision, recall, sensitivity, F1-score, or specificity.

A method involving multiple classifiers may include identifying data as indicative or as not indicative of a disease state such as cancer. This may be done based on choosing a label assigned by an individual classifier, or by combining the labels assigned by multiple classifiers. The method may include identifying data as indicative or as not indicative of the disease state based on a combination of a first label and a second label, each assigned by separate classifiers. The data may be identified as indicative of the disease state based further on a third label, a fourth label, or one or more additional labels. The data may be identified as indicative of the disease state based on a first and third label, or based on a first and fourth label, where, for example, one or more of the labels are not included in the final determination.

Identifying the multi-omic data as indicative or as not indicative of the disease state may include obtaining or generating a weighted average of the labels generated or assigned by some or all of the classifiers. Weights of the weighted average may be based on one or more of: area under a receiver operating characteristic (ROC) curve, area under a precision-recall curve, accuracy, precision, recall, sensitivity, F1-score, or specificity. In some aspects, applying the classifier to the multi-omic data to evaluate the disease state comprises: applying a first classifier to the proteomic measurements to generate a first label corresponding to a presence, absence, or likelihood of the disease state, applying a second classifier to the nucleic acid sequencing measurements to generate a second label corresponding to a presence, absence, or likelihood of the disease state, and evaluating the disease state based on (a), (b) or (c): (a) a non-weighted average of the first and second labels, (b) a weighted average of the first and second labels, or (c) a majority voting score based on the first and second labels. Some aspects include evaluating the disease state based on the weighted average of the first and second labels, wherein the weighted average is generated by assigning weights to the results of the first and second classifiers based on area under a ROC curve, area under a precision-recall curve, accuracy, precision, recall, sensitivity, F1-score, specificity, or a combination thereof.

A method involving multiple classifiers may include identifying multi-omic data as indicative or as not indicative of a disease state. This may be done based on choosing a label assigned by an individual classifier, or by combining the labels assigned by multiple classifiers. The method may include identifying multi-omic data as indicative or as not indicative of the disease state based on a combination of a first label and a second label, each assigned by separate classifiers. The multi-omic data may be identified as indicative of the disease state based further on a third label, a fourth label, or one or more additional labels. The multi-omic data may be identified as indicative of the disease state based on a first and third label, or based on a first and fourth label, where, for example, one or more of the labels are not included in the final determination. An example of a method involving multiple classifiers is shown in FIG. 2. A method may include some or all of the steps in FIG. 2.

Disclosed herein, in some aspects, are multi-omic lung cancer detection methods, comprising: obtaining multi-omic data generated from one or more biofluid samples collected from a subject, the multi-omic data comprising a first omic data and a second omic data, wherein the first omic data comprises a first omic data type comprises proteomic data, metabolomic data, transcriptomic data, or genomic data, and wherein the second omic data comprises a second omic data type different from the first omic data type and comprises proteomic data, metabolomic data, transcriptomic data, or genomic data; using a first classifier to assign a first label corresponding to a presence, absence, or likelihood of lung cancer to the first omic data; using a second classifier to assign a second label corresponding to a presence, absence, or likelihood of lung cancer to the second omic data; and based on a combination of the first and second labels, identifying the multi-omic data as indicative or as not indicative of lung cancer, wherein the first and second classifiers are independent, and wherein the combination of the first and second labels identifies the multi-omic data as indicative or as not indicative of lung cancer with greater accuracy than the first or second label alone.

Figure 13A:
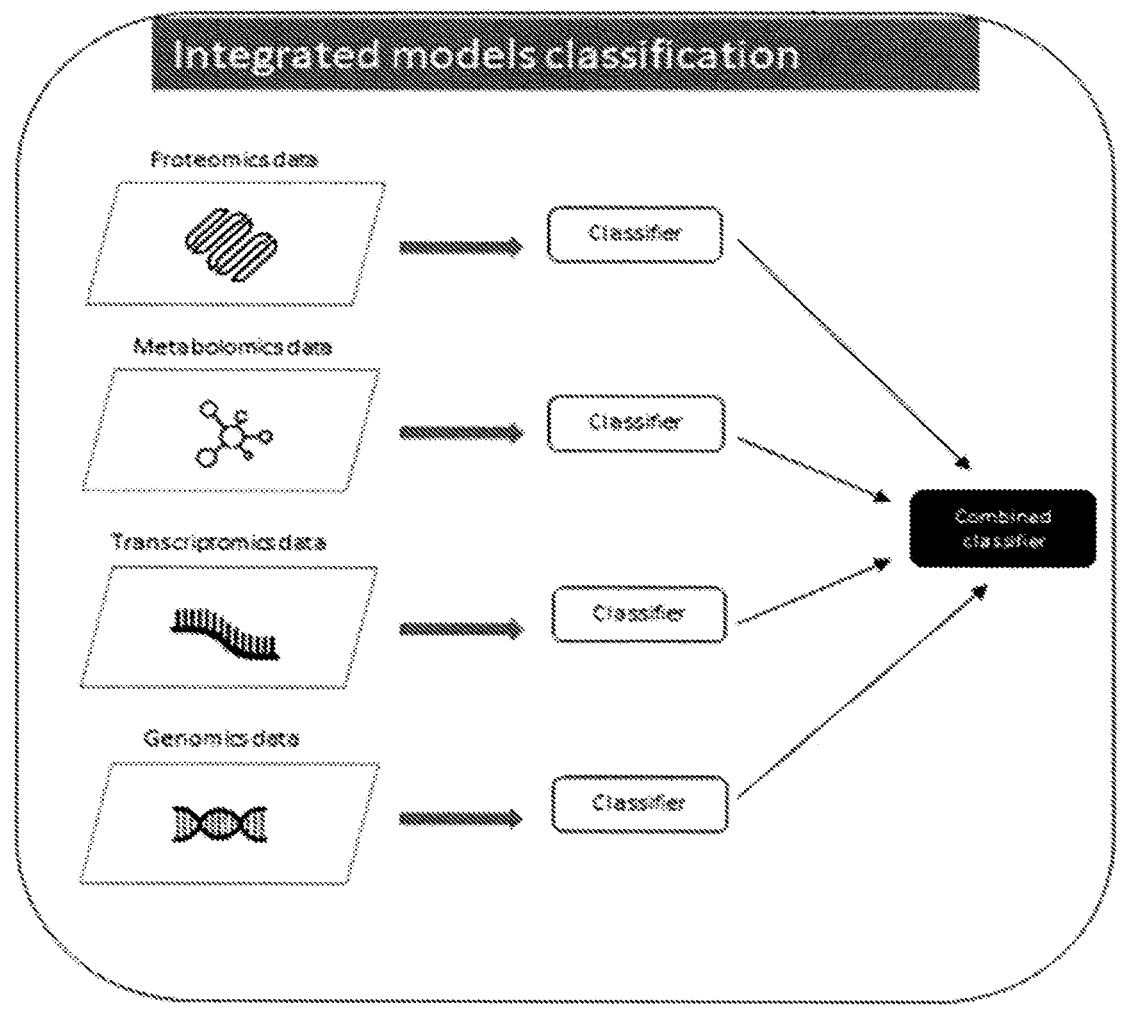
FIG. 13A shows some aspects that may be used in integrated models classification.

A method may include integrated models classification. Some aspects that may be included in integrated models classification are shown in FIG. 13A. A method using integrated models classification may include combining predicted probabilities or classifier calls of classifiers trained on each analyte or data type separately. Combination of probabilities can be via taking a weighted mean with weights assigned according to AUC. In some cases, a first classifier generates a prediction or label for a first omic data, a second classifier generates a prediction or label for a second omic data, optionally one or more additional classifiers each generate a prediction or label for one or more additional omic data, and the predictions or label are combined. The combined predictions or labels may be used in identifying multi-omic data as indicative or as not indicative of a disease state. The identification may be performed by the combined classifier of FIG. 13A. Some aspects relate to a combined classifier for use in a method described herein, such as a method that includes use of integrated models classification. Some aspects relate to a set of classifiers for use in a method described herein, such as a method that includes use of integrated models classification.

Figure 13B:
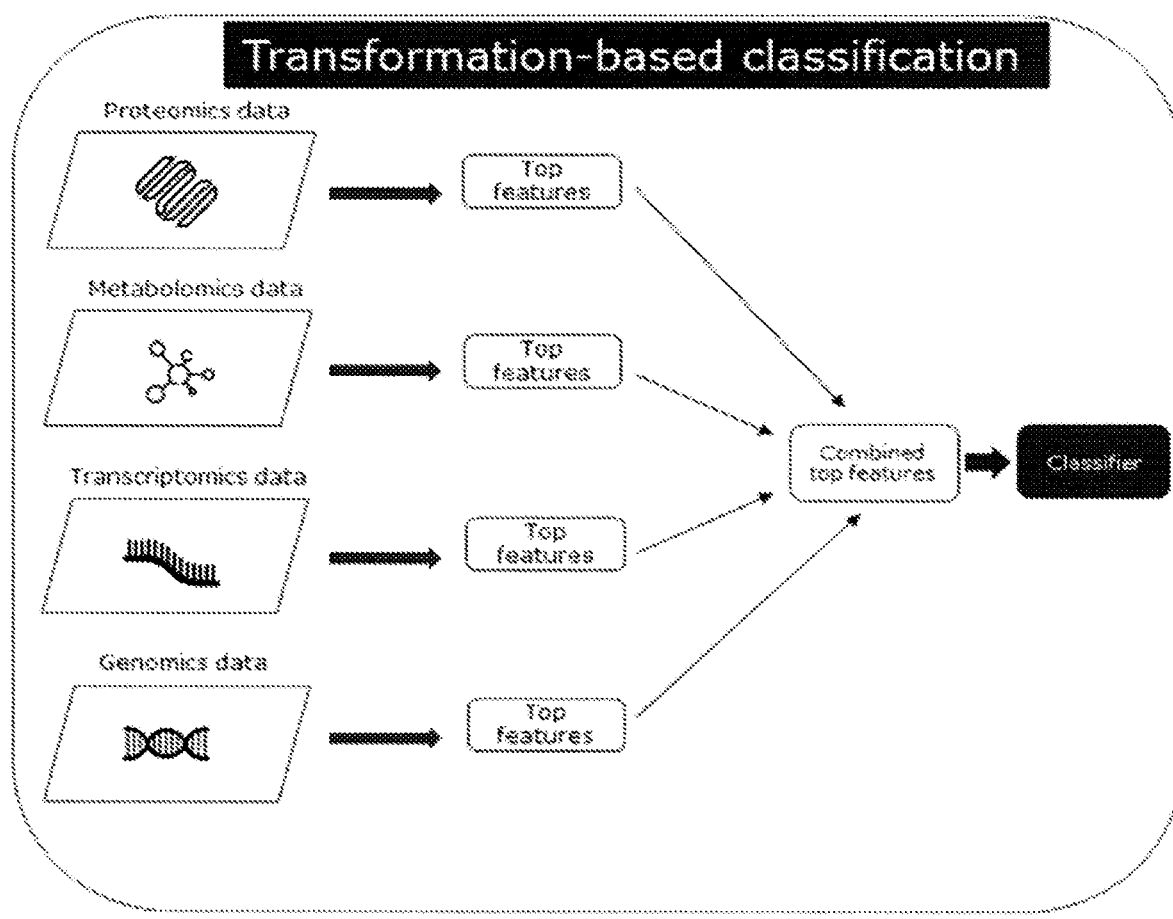
FIG. 13B shows some aspects that may be used in transformation-based classification.

A method may include transformation-based classification. Some aspects that may be included in transformation-based classification are shown in FIG. 13B. Transformation-based classification may include picking top features from each analyte or data type, pool the features, and train one classifier on the pooled features. Transformation-based classification may include any of the following 3 methods:

First method: top features can be picked by training a "pre" classifier first and looking at the top features.

Second Method: another way is to perform a univariate analysis and pick the differentially abundant features for each analyte or data type.

Third method: remove one feature at a time and look at drop in the "pre" classifier performance (AUC). Those which cause the highest drop in performance may be the top features for that particular analyte or data type.

Some aspects relate to a classifier generated using one of these methods, for use in a method described herein. For example, some aspects include a classifier trained by: identifying a subset of features from among a first omic data type; identifying a subset of features from among the second omic data type; pooling the subsets of features from among the first and second omic data types to generate pooled features; and training the classifier with the pooled features to identify multi-omic data comprising the first and second omic data types as indicative or as not indicative of a disease state.

The classifier may include a subset of features identified and pooled from separate omic data sets. The features may be identified by obtaining univariate data for features of an omic data set, and identifying top features from among the univariate data. The subset of features may be identified from among features of classifiers for the separate omic data sets. The features may be identified by obtaining a classifier for an omic data set, and identifying top features of the classifier. The features may be identified by obtaining a classifier for an omic data set, removing one or more features at time from the classifier, and identifying which features reduce the classifier's performance the most when removed from the classifier. Artificial intelligence or machine learning methods may be useful to develop classifiers in the multi-omics system, particularly when using larger data sets or when using a combination of several different types of omic data.

In some aspects, applying the classifier to the multi-omic data to evaluate the disease state comprises: obtaining a subset of features from among the proteomic measurements; obtaining at least a subset of features from among the nucleic acid sequencing measurements; pooling the subset of features from among the first omic data and the at least a subset of features from among the second omic data to obtained pooled features; evaluating the disease state based on the pooled features. In some aspects, obtaining a subset of features of from among the first or second omic data comprises obtaining top features based on univariate data.

Transformation-based classification may be useful in that it may reduce the number of features to be used in an analysis. For example, transformation-based classification may reduce the number of features to be used in an analysis from 1000's to less than 100 (e.g. 10 to 30, 10 to 50, or 10 to 75) or perhaps a few dozen. This may speed up computer processing in, for example, identifying multi-omic data as indicative or as not indicative of a disease state, because it may reduce the amount of computations to be processed relative to a method using a non-reduced number of features.

Figure 19:
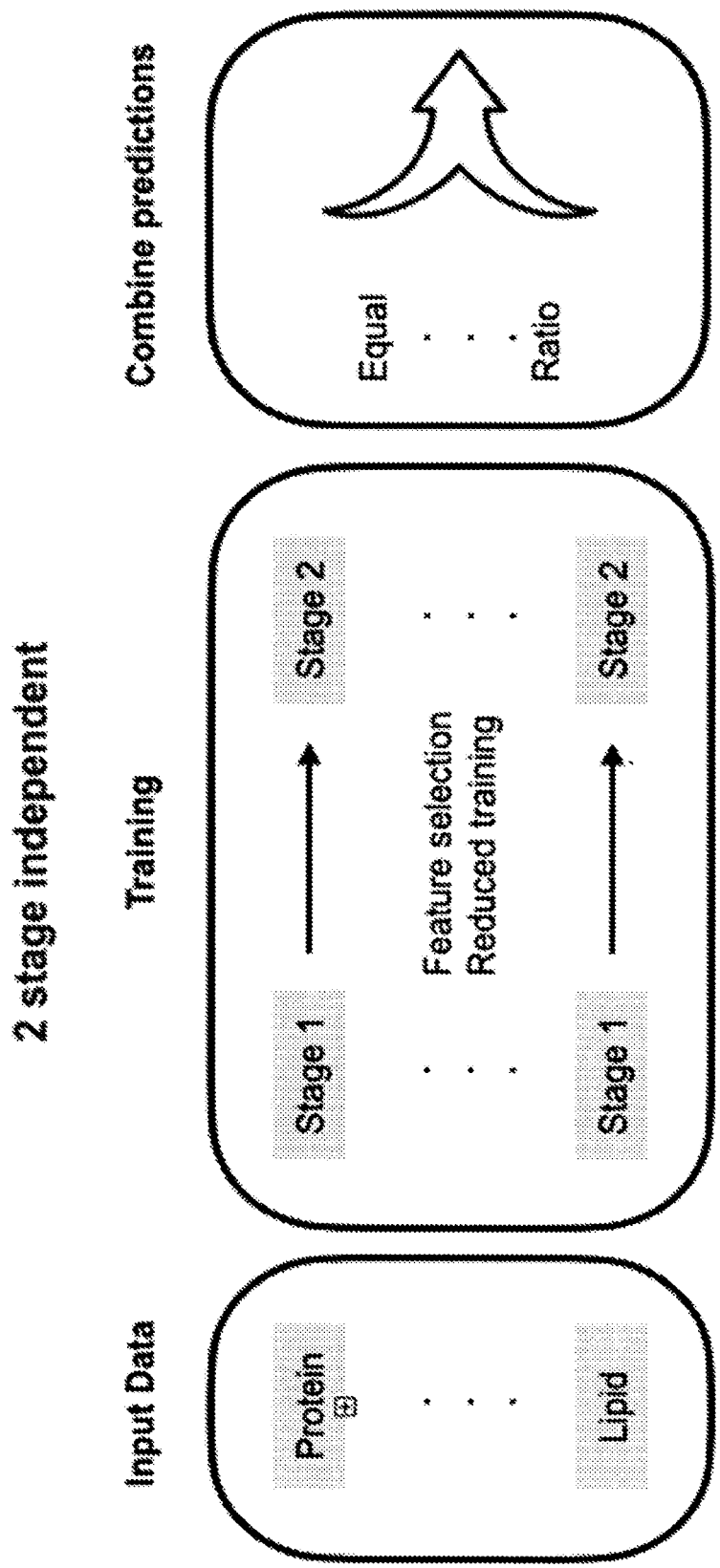
FIG. 19 shows aspects of a 2-stage machine learning framework for analyzing and training multiple data types.

FIG. 19 shows aspects of a 2-stage machine learning framework that may be used in the methods described herein. The 2-stage framework may include training an individual model for each feature type (e.g. proteins, lipids, or metabolites). The framework may include combining predictions for assessment on the test set. Various models may be used at stage 1. For example, stage 1, may include use of a random forest model for a first data type (e.g. proteins) or a logistic regression model the first data type or for a second data type (e.g. lipids). For stage 2, a subset of top features (e.g. top 20 predictive proteins) may be selected from stage 1. Step 2 may include retraining the model using the subset of features. The retraining may be on the same training data. Step 2 may include model results without retraining.

Figure 17:
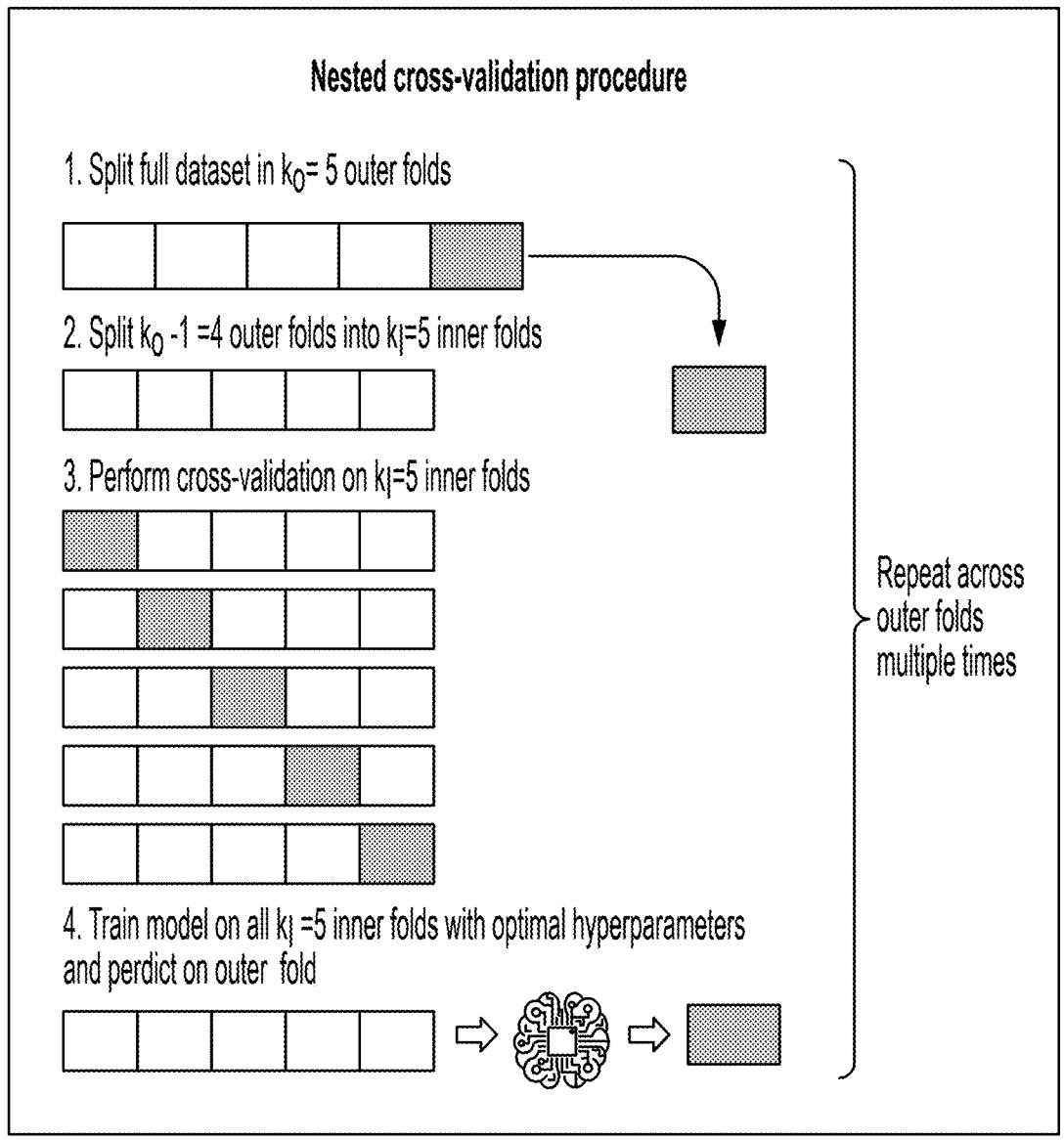
FIG. 17 shows a non-limiting example of a flowchart of machine training algorithm for improving the sensitivity and specificity of the classifier for predicating a disease described herein.

A machine learning algorithm may be used for training or improving sensitivity or specificity of a classifier. FIG. 17 illustrates some aspects that may be used for improving the sensitivity and specificity of a classifier or machine training algorithm for predicating a disease. The aspects in this figure may be involved in developing receiver operating characteristic (ROC) curves. Each fold in the outer loop may act like a hold-out set in that may be unseen during training. The process can be repeated across multiple shuffles of a dataset. Additional practices can be utilized to prevent overfitting, reducing model complexity, feature reduction, or regularization.

Machine learning methods may include elastic net, support vector machines, sparse neural networks, random forests, or XGBoost. A classifier may be trained using deep learning, a hierarchical cluster analysis, a principal component analysis, a partial least squares discriminant analysis, a random forest classification analysis, a support vector machine analysis, a k-nearest neighbors analysis, a naive Bayes analysis, a K-means clustering analysis, or a hidden Markov analysis. A classifier may be trained using deep learning. A classifier may be trained using a hierarchical cluster analysis. A classifier may be trained using a principal component analysis. A classifier may be trained using a partial least squares discriminant analysis. A classifier may be trained using a random forest classification analysis. A classifier may be trained using a support vector machine analysis. A classifier may be trained using a k-nearest neighbors analysis. A classifier may be trained using a naive Bayes analysis. A classifier may be trained using a K-means clustering analysis. A classifier may be trained using a hidden Markov analysis.

The methods described herein, when analyzing data described herein such as proteomic data, transcriptomic data, genomic data, or metabolomic data, can include generating or using a classifier for indicating the subject of having or at risk of having a disease state with a certain sensitivity or specificity. A method described herein may generate or use a classifier from the data for indicating the subject of having or at risk of having a disease state with a sensitivity of at least about 25%, at least about 30%, at least about 35%, at least about 40%, at least about 45%, at least about 50%, at least about 55%, at least about 60%, at least about 65%, at least about 70%, at least about 75%, at least about 80%, at least about 85%, or at least about 90%. The sensitivity may be at least about 91%, at least about 92%, at least about 93%, or at least about 94%.

A method described herein may generate or use a classifier from the data for indicating the subject of having or at risk of having a disease state with a specificity of at least about 50%, at least about 60%, at least about 70%, at least about 80%, or at least about 90%. The specificity may in some instances be at least about 91%, at least about 92%, at least about 93%, at least about 94%, at least about 95%, at least about 96%, at least about 97%, at least about 98%, at least about 99%, or at least about 99.5%.

A method described herein may generate or use a classifier from the data for indicating the subject of having or at risk of having a disease state with a sensitivity or specificity no greater than about 25%, no greater than about 30%, no greater than about 35%, no greater than about 40%, no greater than about 45%, no greater than about 50%, no greater than about 55%, no greater than about 60%, no greater than about 65%, no greater than about 70%, no greater than about 75%, no greater than about 80%, no greater than about 85%, or no greater than about 90%. The sensitivity or specificity may in some instances be no greater than about 91%, no greater than about 92%, no greater than about 93%, no greater than about 94%, no greater than about 95%, no greater than about 96%, no greater than about 97%, no greater than about 98%, no greater than about 99%, or no greater than about 99.5%.

The sensitivity may be greater than 40%, for example, when the specificity is 99.5%. The sensitivity may be greater than 40%. The sensitivity may be about 44% and the specificity may be about 99.5%. The sensitivity may be about 57% and the specificity may be about 90%.

Multiple types of data may be used together in an evaluation. The evaluation may be at least 1% greater performance, at least 2% greater performance, at least 3% greater performance, at least 4% greater performance, at least 5% greater performance, at least 6% greater performance, at least 7% greater performance, at least 8% greater performance, at least 9% greater performance, at least 10% greater performance, at least 15% greater performance, at least 20% greater performance, at least 25% greater performance, at least 30% greater performance, at least 35% greater performance, at least 40% greater performance, at least 45% greater performance, at least 50% greater performance, at least 55% greater performance, at least 60% greater performance, at least 65% greater performance, at least 70% greater performance, at least 75% greater performance, at least 80% greater performance, at least 85% greater performance, or at least 90% greater performance than if the classifier was applied to only one type of omic data. In some aspects, the evaluation is less than 1% greater performance, less than 2% greater performance, less than 3% greater performance, less than 4% greater performance, less than 5% greater performance, less than 6% greater performance, less than 7% greater performance, less than 8% greater performance, less than 9% greater performance, less than 10% greater performance, less than 15% greater performance, less than 20% greater performance, less than 25% greater performance, less than 30% greater performance, less than 35% greater performance, less than 40% greater performance, less than 45% greater performance, less than 50% greater performance, less than 55% greater performance, less than 60% greater performance, less than 65% greater performance, less than 70% greater performance, less than 75% greater performance, less than 80% greater performance, less than 85% greater performance, or less than 90% greater performance than if the classifier was applied to only one type of omic data. The performance may comprise a sensitivity. The performance may comprise a specificity. The performance may comprise a sensitivity, at a given specificity. The performance may comprise an average area under a curve, such as of an ROC plot. The performance may comprise a determination of false-positives. The performance may comprise a determination of false-negatives. The performance may be determined in a hold-out data set. The performance may be determined in held-out samples.

The performance may include a minimum accuracy, positive predictive value (PPV), negative predictive value (NPV), clinical sensitivity, clinical specificity, area under the curve (AUC), or a combination thereof. The performance may include a minimum accuracy. The performance may include a positive predictive value (PPV). The performance may include a negative predictive value (NPV). The performance may include clinical sensitivity. The performance may include clinical specificity. The performance may include area under the curve (AUC). The performance may include a combination of positive predictive value (PPV), negative predictive value (NPV), clinical sensitivity, clinical specificity, and area under the curve (AUC). A minimum accuracy, PPV, NPV, clinical sensitivity, clinical specificity, or combination thereof may be at least about 50%, at least about 55%, at least about 60%, at least about 65%, at least about 70%, at least about 75%, at least about 80%, at least about 81%, at least about 82%, at least about 83%, at least about 84%, at least about 85%, at least about 86%, at least about 87%, at least about 88%, at least about 89%, at least about 90%, at least about 91%, at least about 92%, at least about 93%, at least about 94%, at least about 95%, at least about 96%, at least about 97%, at least about 98%, or at least about 99%. Any of the aforementioned percentages may be included as a maximum performance. As another example, a minimum AUC may be at least about 0.50, at least about 0.55, at least about 0.60, at least about 0.65, at least about 0.70, at least about 0.75, at least about 0.80, at least about 0.81, at least about 0.82, at least about 0.83, at least about 0.84, at least about 0.85, at least about 0.86, at least about 0.87, at least about 0.88, at least about 0.89, at least about 0.90, at least about 0.91, at least about 0.92, at least about 0.93, at least about 0.94, at least about 0.95, at least about 0.96, or at least about 0.97. Any of the aforementioned values may be included as a maximum AUC. The AUC may comprise an average AUC. The AUC may comprise a mean AUC.

Prediction of a disease state risk or identification of the disease may include predicting a risk of the disease in the subject, identifying the disease in the subject, predicting a lack of risk or a low risk of the disease in the subject, or identifying the subject as having a healthy or disease free state. The disease state may include having the disease. The disease state may include a healthy state or not having the disease.

The methods described herein, when analyzing data described herein such as proteomic data, transcriptomic data, genomic data, or metabolomic data, can include generating or using a classifier for indicating the subject of having or at risk of having cancer with a certain sensitivity or specificity. The cancer can include pancreatic cancer, liver cancer, ovarian cancer, or colon cancer. In some aspects, a method described herein generates or uses a classifier from the data for indicating the subject of having or at risk of having a cancer such as pancreatic cancer, liver cancer, ovarian cancer, or colon cancer with a sensitivity of at least about 50%, at least about 60%, at least about 70%, at least about 80%, or at least about 90%. The sensitivity may be at a given specificity. In some aspects, a method described herein generates or uses a classifier from the data for indicating the subject of having or at risk of having a cancer such as pancreatic cancer, liver cancer, ovarian cancer, or colon cancer with a specificity of at least about 50%, at least about 60%, at least about 70%, at least about 80%, or at least about 90%. In some aspects, the proteomic data is indicative of cancer (e.g. colon cancer, breast cancer, liver cancer, lung cancer, pancreatic cancer, or pancreatic cancer) with a sensitivity or specificity of at least about 50%, at least 51%, at least 52%, at least 53%, at least 54%, at least 55%, at least 56%, at least 57%, at least 58%, or at least 59%. In some aspects, the proteomic data is indicative of cancer with a sensitivity or specificity of at least about 60%, at least 61%, at least 62%, at least 63%, at least 64%, at least 65%, at least 66%, at least 67%, at least 68%, or at least 69%. In some aspects, the proteomic data is indicative of cancer with a sensitivity or specificity of at least about 70%, at least 71%, at least 72%, at least 73%, at least 74%, at least 75%, at least 76%, at least 77%, at least 78%, or at least 79%. In some aspects, the proteomic data is indicative of cancer with a sensitivity or specificity of at least about 80%, at least 81% at least 82% at least 83%, at least 84%, at least 85%, at least 86%, at least 87%, at least 88%, or at least 89%. In some aspects, the proteomic data is indicative of cancer with a sensitivity or specificity of at least about 90%, at least 91%, at least 92%, at least 93%, at least 94%, at least 95%, at least 96%, at least 97%, at least 98%, or at least 99%. In some aspects, the proteomic data is indicative of cancer (e.g. colon cancer, breast cancer, liver cancer, lung cancer, pancreatic cancer, or pancreatic cancer) with a sensitivity or specificity of less than about 50%, less than 51%, less than 52%, less than 53%, less than 54%, less than 55%, less than 56%, less than 57%, less than 58%, or less than 59%. In some aspects, the proteomic data is indicative of cancer with a sensitivity or specificity of less than about 60%, less than 61%, less than 62%, less than 63%, less than 64%, less than 65%, less than 66%, less than 67%, less than 68%, or less than 69%. In some aspects, the proteomic data is indicative of cancer with a sensitivity or specificity of less than about 70%, less than 71%, less than 72%, less than 73%, less than 74%, less than 75%, less than 76%, less than 77%, less than 78%, or less than 79%. In some aspects, the proteomic data is indicative of cancer with a sensitivity or specificity of less than about 80%, less than 81% less than 82% less than 83%, less than 84%, less than 85%, less than 86%, less than 87%, less than 88%, or less than 89%. In some aspects, the proteomic data is indicative of colon cancer with a sensitivity or specificity of less than about 90%, less than 91%, less than 92%, less than 93%, less than 94%, less than 95%, less than 96%, less than 97%, less than 98%, or less than 99%. In some aspects, a method described herein generates or uses a classifier from the data for indicating the subject of having or at risk of having pancreatic cancer, liver cancer, ovarian cancer, or colon cancer with a sensitivity or specificity no greater than about 50%, no greater than about 60%, no greater than about 70%, no greater than about 80%, no greater than about 90%, or no greater than about 95%.

Some aspects include evaluating a disease state such as cancer (e.g. lung cancer, liver cancer, pancreatic cancer, ovarian cancer, or colon cancer). The evaluation may include identifying a likelihood of a cancer or other disease state using a classifier. A classifier may include a performance characteristic such as a receiver operating characteristic (ROC) curve. The ROC curve may be generated by plotting the true positive rate (TPR) against the false positive rate (FPR) at various threshold settings. TPR may be calculated as true positives (TP)/condition positives (P). P may include a number of real positive cases in a data set. TP may include a test result that correctly indicates a presence of a condition such as a disease state (e.g. cancer). TPR may be calculated as TP/(TP+false negative (FN)). FN may include a test result which wrongly indicates that a particular condition or attribute is absent. TPR may be calculated as 1−false negative rate (FNR). FPR may be calculated as false positives (FP)/condition negatives (N). FP may include a test result which wrongly indicates that a particular condition or attribute is present. N may include the number of real negative cases (e.g. cases without the cancer or other disease state) in the data. FPR may be calculated as FP/(FP+true negative (TN)). TN may include a test result that correctly indicates the absence of a condition or characteristic. FPR may be calculated as 1−true negative rate (TNR).

The ROC curve may comprise an area under the curve (AUC). The AUC may be a value or ratio between 0 and 1, or may be a percentage. For a predictor, f, an unbiased estimator of its AUC can be expressed by the following Wilcoxon-Mann-Whitney statistic:

$$AUC(f) = \frac{\sum_{t_0 \in \mathcal{D}^0} \sum_{t_1 \in \mathcal{D}^1} 1[f(t_0) < f(t_1)]}{|\mathcal{D}^0| \cdot |\mathcal{D}^1|},$$

where $1[f(t_0)<f(t_1)]$ denotes an indicator function which returns 1 iff $f(t_0)<f(t_1)$ otherwise return 0; $D^0$ is the set of negative examples, and $D^1$ is the set of positive examples. The AUC may be 0.60, 0.65, 0.70, 0.75, 0.80, 0.85, 0.86, 0.87, 0.88, 0.89, 0.90, 0.91, 0.92, 0.93, 0.94, 0.95, 0.96, 0.97, or 0.98, or a range defined by any two of the aforementioned values. The AUC may be about 0.60, about 0.65, about 0.70, about 0.75, about 0.80, about 0.85, about 0.86, about 0.87, about 0.88, about 0.89, about 0.90, about 0.91, about 0.92, about 0.93, about 0.94, about 0.95, about 0.96, about 0.97, or about 0.98, or a range defined by any two of the aforementioned values.

The classifier may be characterized by a ROC curve having an AUC greater than 0.65, greater than 0.7, greater than 0.75, greater than 0.8, greater than 0.85, or greater than 0.9, based on biomolecule measurement features. The AUC may be greater than 0.7. The AUC may be greater than 0.91. The AUC may be greater than 0.92. The AUC may be greater than 0.93. The AUC may be greater than 0.94. The AUC may be greater than 0.95. The AUC may be greater than 0.96. The AUC may be about 0.91. The AUC may be about 0.955. The AUC may be about 0.965. In some aspects, the AUC is no greater than 0.75, no greater than 0.8, no greater than 0.85, no greater than 0.9, no greater than 0.91, no greater than 0.92, no greater than 0.93, no greater than 0.94, no greater than 0.95, no greater than 0.96, no greater than 0.97, or no greater than 0.98. The AUC may be generated without including non-protein clinical features such as clinical indicators of a cancer such as lung cancer, pancreatic cancer, or another cancer. The AUC may comprise an average AUC. The AUC may comprise a mean AUC.

The AUC, accuracy, sensitivity, or specificity may be determined in a data set derived from a randomized, controlled trial of over 25 subjects having the disease state and over 25 control subjects not having the disease state. In some aspects, the number of subjects having the disease state may be at least 1, at least 2, at least 3, at least 4, at least 5, at least 10, at least 20, at least 50, at least 75, at least 100, at least 150, at least 200, at least 300, at least 400, at least 500, at least 600, at least 700, at least 800, at least 900, or at least 1,000 subjects. In some aspects, the number of subjects having the disease state may be no more than 1, no more than 2, no more than 3, no more than 4, no more than 5, no more than 10, no more than 20, no more than 50, no more than 75, no more than 100, no more than 150, no more than 200, no more than 300, no more than 400, no more than 500, no more than 600, no more than 700, no more than 800, no more than 900, or no more than 1,000 subjects. In some aspects, the number of control subjects not having the disease state may be at least 1, at least 2, at least 3, at least 4, at least 5, at least 10, at least 20, at least 50, at least 75, at least 100, at least 150, at least 200, at least 300, at least 400, at least 500, at least 600, at least 700, at least 800, at least 900, or at least 1,000 subjects. In some aspects, the number of control subjects not having the disease state may be no more than 1, no more than 2, no more than 3, no more than 4, no more than 5, no more than 10, no more than 20, no more than 50, no more than 75, no more than 100, no more than 150, no more than 200, no more than 300, no more than 400, no more than 500, no more than 600, no more than 700, no more than 800, no more than 900, or no more than 1,000 subjects. The subjects in the randomized, controlled trial may be included in a held-out group such as a group separate from a group a classifier is generated or trained from.

A method described herein may include use of a classifier. A method described herein may include generating a classifier. A method described herein may include using a classifier to identify a disease state based on the data set. A method described herein may include applying a classifier to biomarker measurements. The biomarker measurements may be taken from a sample of a subject having a lung nodule. The classifier may be useful for differentiating a cancerous lung nodule from a benign or non-cancerous lung nodule.

In some aspects, the classifier comprises features to indicate the protein measurements as indicative of the lung nodule being cancerous or non-cancerous. In some aspects, the features comprise control protein measurements, mass spectra, m/z ratios, chromatography results, immunoassay results, or light or fluorescence intensities. In some aspects, the classifier is trained using deep learning, a hierarchical cluster analysis, a principal component analysis, a partial least squares discriminant analysis, a random forest classification analysis, a support vector machine analysis, a k-nearest neighbors analysis, a naive Bayes analysis, a K-means clustering analysis, or a hidden Markov analysis. In some aspects, the classifier is capable of identifying lung cancer with a sensitivity of 50% or greater, 60% or greater, 70% or greater, 80% or greater, or 90% or greater. In some aspects, the classifier is capable of identifying lung cancer with a specificity of 50% or greater, 60% or greater, 70% or greater, 80% or greater, or 90% or greater.

The method of determining a set of proteins associated with the disease or disorder and/or disease state include the analysis of the biomarkers (e.g., a corona or proteins) of the at least one or two samples. This determination, analysis or statistical classification is done by methods including, but not limited to, for example, a wide variety of supervised and unsupervised data analysis, machine learning, deep learning, and clustering approaches including hierarchical cluster analysis (HCA), principal component analysis (PCA), Partial least squares Discriminant Analysis (PLS-DA), random forest, logistic regression, decision trees, support vector machine (SVM), k-nearest neighbors, naive bayes, linear regression, polynomial regression, SVM for regression, K-means clustering, and hidden Markov models, among others. In other words, the proteins (e.g., in the corona) of each sample are compared/analyzed with each other to determine with statistical significance what patterns are common between the proteins of the subject to determine a set of proteins that is associated with the disease or disorder or disease state. Any of such methods may be used to generate a classifier for use herein.

A model may be trained with the one or more biomarkers using deep learning, a hierarchical cluster analysis, a principal component analysis, a partial least squares discriminant analysis, a random forest classification analysis, a support vector machine analysis, a k-nearest neighbors analysis, a naive bayes analysis, a K-means clustering analysis, or a hidden Markov analysis. A model may be trained with the one or more biomarkers using deep learning. A model may be trained with the one or more biomarkers using a hierarchical cluster analysis. A model may be trained with the one or more biomarkers using a principal component analysis. A model may be trained with the one or more biomarkers using a partial least squares discriminant analysis. A model may be trained with the one or more biomarkers using a random forest classification analysis. A model may be trained with the one or more biomarkers using a support vector machine analysis. A model may be trained with the one or more biomarkers using a k-nearest neighbors analysis. A model may be trained with the one or more biomarkers using a naive bayes analysis. A model may be trained with the one or more biomarkers using a K-means clustering analysis. A model may be trained with the one or more biomarkers using a hidden Markov analysis. A method described herein may include use of the model. A method may include generating the model.

The model may be trained with measurements of biomarkers (such as any of those described herein) in a control sample from a control subject. In some cases, the one or more biomarkers the model is trained with do not include depleted plasma proteins. The control subject may have a specific stage of NSCLC.

Generally, machine learning algorithms are used to construct models that accurately assign class labels to examples based on the input features that describe the example (e.g., healthy, co-morbid, or NSCLC Stage 1, 2, or 3). In some case it may be advantageous to employ machine learning and/or deep learning approaches for the methods described herein. For example, machine learning can be used to associate a ser of biomarkers with various disease states (e.g. no disease, precursor to a disease, having early or late stage of the disease, etc.). For example, in some cases, one or more machine learning algorithms are employed in connection with a method of the invention to analyze data detected and obtained by the protein coronas and sets of proteins derived therefrom. For example, in one embodiment, machine learning can be coupled with the particle panels described herein to determine not only if a subject has a pre-stage of cancer, cancer, or does not have or develop cancer, but also to distinguish the type of cancer, for example, distinguish a lung cancer such as NSCLC. The classifier may have an increased protein detection consistency relative to a second classifier generated using proteomic data from depleted plasma samples. For example, the classifier may be generated by contacting samples with particles, and may have an increased protein detection consistency relative to a second classifier generated using proteomic data from depleted plasma samples not contacted with the particles.

Determination, analysis or statistical classification is done by methods including, but not limited to, for example, a wide variety of supervised and unsupervised data analysis and clustering approaches such as hierarchical cluster analysis (HCA), principal component analysis (PCA), Partial least squares Discriminant Analysis (PLSDA), machine learning (also referred to as random forest), logistic regression, decision trees, support vector machine (SVM), k-nearest neighbors, naive bayes, linear regression, polynomial regression, SVM for regression, K-means clustering, and hidden Markov models, among others. A system or method may analyze biomarkers such as a protein set or protein corona of the present disclosure. The analysis may include comparing/analyzing the biomarkers of one or more (e.g., several) samples to determine with statistical significance what patterns are common between the biomarkers to determine biomarkers (e.g. a protein set) that is associated with the biological state. The system or method can develop classifiers to detect and discriminate different protein sets or protein corona (e.g., characteristic of the composition of a protein corona). Data collected from a method or system described herein (e.g., a system including a sensor array) can be used to train a machine learning algorithm, for example an algorithm that receives array measurements from a patient and outputs specific biomolecule corona compositions from each patient.

Machine learning can be generalized as the ability of a learning machine to perform accurately on new, unseen examples/tasks after having experienced a learning data set. Machine learning may include the following concepts and methods. Supervised learning concepts may include AODE; Artificial neural network, such as Backpropagation, Autoencoders, Hopfield networks, Boltzmann machines, Restricted Boltzmann Machines, and Spiking neural networks; Bayesian statistics, such as Bayesian network and Bayesian knowledge base; Case-based reasoning; Gaussian process regression; Gene expression programming; Group method of data handling (GMDH); Inductive logic programming; Instance-based learning; Lazy learning; Learning Automata; Learning Vector Quantization; Logistic Model Tree; Minimum message length (decision trees, decision graphs, etc.), such as Nearest Neighbor Algorithm and Analogical modeling; Probably approximately correct learning (PAC) learning; Ripple down rules, a knowledge acquisition methodology; Symbolic machine learning algorithms; Support vector machines; Random Forests; Ensembles of classifiers, such as Bootstrap aggregating (bagging) and Boosting (meta-algorithm); Ordinal classification; Information fuzzy networks (IFN); Conditional Random Field; ANOVA; Linear classifiers, such as Fisher's linear discriminant, Linear regression, Logistic regression, Multinomial logistic regression, Naive Bayes classifier, Perceptron, Support vector machines; Quadratic classifiers; k-nearest neighbor; Boosting; Decision trees, such as C4.5, Random forests, ID3, CART, SLIQ SPRINT; Bayesian networks, such as Naive Bayes; and Hidden Markov models. Unsupervised learning concepts may include; Expectation-maximization algorithm; Vector Quantization; Generative topographic map; Information bottleneck method; Artificial neural network, such as Self-organizing map; Association rule learning, such as, Apriori algorithm, Eclat algorithm, and FPgrowth algorithm; Hierarchical clustering, such as Singlelinkage clustering and Conceptual clustering; Cluster analysis, such as, K-means algorithm, Fuzzy clustering, DBSCAN, and OPTICS algorithm; and Outlier Detection, such as Local Outlier Factor. Semi-supervised learning concepts may include; Generative models; Low-density separation; Graph-based methods; and Co-training. Reinforcement learning concepts may include; Temporal difference learning; Q-learning; Learning Automata; and SARSA. Deep learning concepts may include; Deep belief networks; Deep Boltzmann machines; Deep Convolutional neural networks; Deep Recurrent neural networks; and Hierarchical temporal memory.

The methods described herein may include use of a classifier to identify or distinguish a disease state of a lung nodule such as lung cancer (e.g. NSCLC). The classifier may distinguish the disease state from a comorbidity such as a chronic lung disorder, chronic obstructive pulmonary disease, emphysema, cardiovascular disease, hypertension, pulmonary fibrosis, or asthma.

The classifier may be generated by removing or filtering out biomolecules associated with acute phase response. In some aspects, said classifier is configured to remove acute-phase-response bias or stress protein bias. In some aspects, said classifier comprises features that relate to proteins. Said features may be selected to exclude acute-phase response and/or stress protein bias in said biological sample.

Figure 52A:
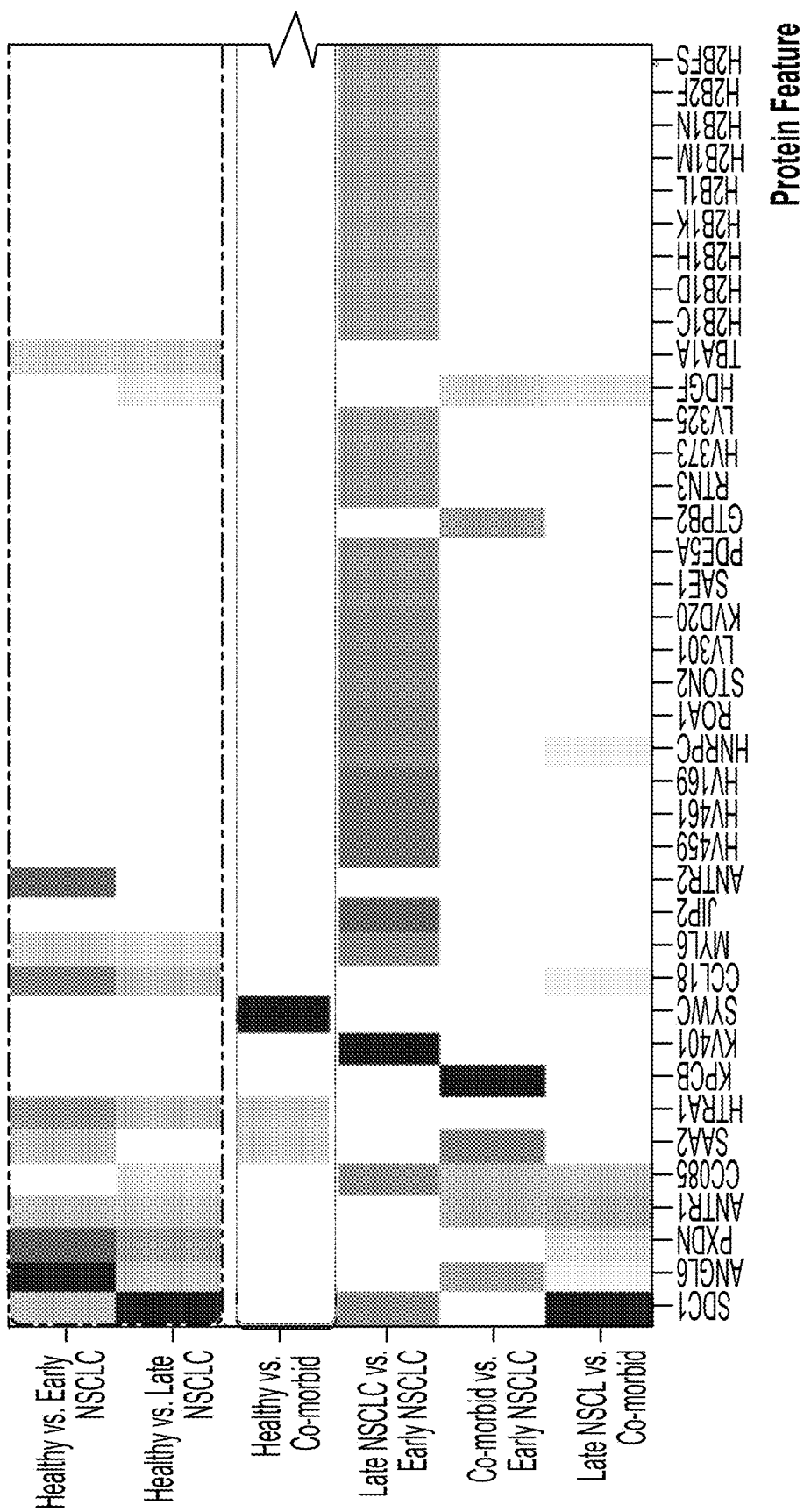
FIG. 52 shows some differentiating features in study group comparisons.
Figure 52B:
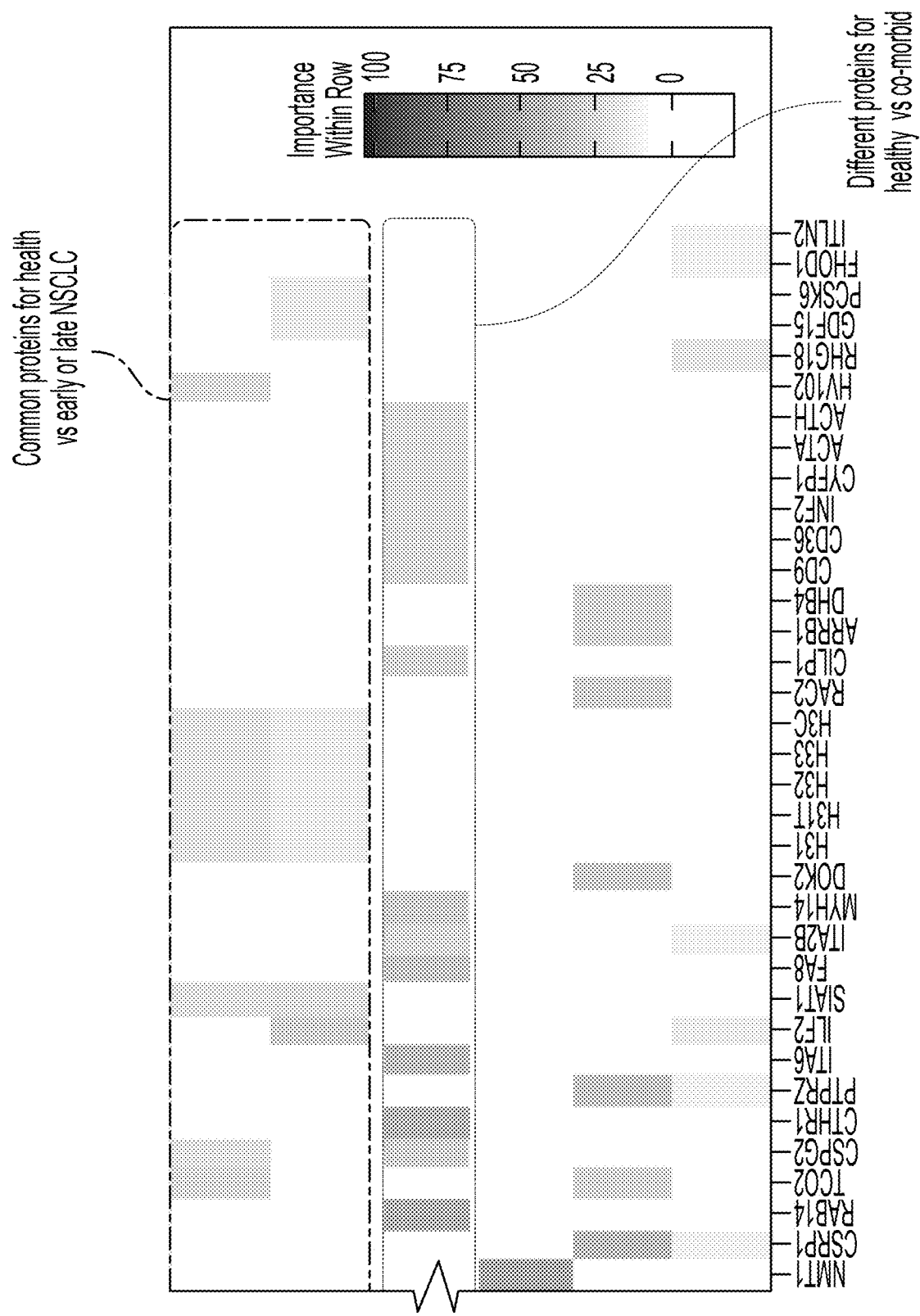

The classifier may comprise features (e.g., biomarker information) to distinguish between a disease state or other state (e.g., a healthy or comorbid state) in FIG. 52. Any of the features or biomarkers in FIG. 52 may be used in a method that distinguishes between the disease state or other state. The biomarker information may include information comprising an expression level or an amount of a biomarker.

The classifier may comprise features to distinguish between the presence or absence of NSCLC. For example, the features may include information on one of more biomarkers including: SDC1, ANGL6, PXDN, ANTR1, CC085, SAA2, HTRA1, KPCB, KV401, CCL18, MYL6, ANTR2, GTPB2, HDGF, TBA1A, CSRP1, TCO2, CSPG2, PTPRZ, ILF2, SIAT1, ITA2B, DOK2, H31, H31T, H32, H33, H3C, RAC2, ARRB1, DHB4, HV102, RHG18, GDF15, PCSK6, FHOD1, or ITLN2, or any combination thereof. Any of these features or biomarkers may be included in a method that distinguishes between the presence or absence of NSCLC.

The classifier may comprise features to distinguish between a healthy state and early stage NSCLC (e.g. NSCLC stage 1, 2, and/or 3). Such features may include information on one of more biomarkers including: SDC1, ANGL6, PXDN, ANTR1, SAA2, HTRA1, CCL18, MYL6, ANTR2, TBA1A, TCO2, CSPG2, SIAT1, H31, H31T, H32, H33, H3C, or HV102, or any combination thereof. Any of these features or biomarkers may be included in a method that distinguishes between a healthy state and early stage NSCLC.

The classifier may comprise features to distinguish between a healthy state and late stage NSCLC (e.g. NSCLC stage 4). Such features may include information on one of more biomarkers including: SDC1, ANGL6, PXDN, ANTR1, CC085, HTRA1, CCL18, MYL6, HDGF, TBA1A, ILF2, SIAT1, H31, H31T, H32, H33, H3C, GDF15, or PCSK6, or any combination thereof. Any of these features or biomarkers may be included in a method that distinguishes between a healthy state and late stage NSCLC.

The classifier may comprise features to distinguish between a healthy state and a comorbidity. Such features may include information on one of more biomarkers including: SAA2, HTRA1, SYWC, RAB14, CSPG2, CTHR1, ITA6, FA8, ITA2B, DOK2, CILP1, CD9, CD36, INF2, CYFP1, ACTA, or ACTH, or any combination thereof. Any of these features or biomarkers may be included in a method that distinguishes between a healthy state and a comorbidity.

The classifier may comprise features to distinguish between early stage NSCLC and late stage NSCLC. For example, the features may include information on one of more biomarkers including: SDC1, CC085, KV401, MYL6, JIP2, HV459, HV461, HV169, HNRPC, ROA1, STON2, LV301, KVD20, SAEI, PDE5A, RTN3, HV373, LV325, H2B1C, H2B1D, H2B1H, H2B1K, H2B1L, H2B1M, H2BIN, H2B2F, H2BFS, or NMT1, or any combination thereof. Any of these features or biomarkers may be included in a method that distinguishes between early stage NSCLC and late stage NSCLC.

The classifier may comprise features to distinguish between early stage NSCLC and a comorbidity. For example, the features may include information on one of more biomarkers including: ANGL6, ANTR1, CC085, SAA2, KPCB, GTPB2, HDGF, CSRP1, TCO2, PTPRZ, DOK2, RAC2, ARRB1, or DHB4, or any combination thereof. Any of these features or biomarkers may be included in a method that distinguishes between early stage NSCLC and a comorbidity.

The classifier may comprise features to distinguish between late stage NSCLC and a comorbidity. For example, the features may include information on one of more biomarkers including: SDC1, ANGL6, PXDN, ANTR1, CC085, CCL18, HNRPC, HDGF, CSRP1, PTPRZ, ILF2, ITA2B, RHG18, FHOD1, or ITLN2, or any combination thereof. Any of these features or biomarkers may be included in a method that distinguishes between late stage NSCLC and a comorbidity In some aspects, a first or second omic data type comprises proteomic data. In some aspects, the first or second omic data type comprises transcriptomic data. In some aspects, the transcriptomic data comprise mRNA or microRNA expression data. In some aspects, the first or second omic data type comprises genomic data. In some aspects, the genomic data comprise DNA sequence data or epigenetic data. In some aspects, the epigenetic data comprise DNA methylation data, DNA hydroxymethylation data, or histone modification data. In some aspects, the first or second omic data type comprises metabolomic data.

Some aspects include identifying the multi-omic data as indicative or as not indicative of lung cancer comprises generating or obtaining a majority voting score based on the first and second labels. In some aspects, identifying the multi-omic data as indicative or as not indicative of lung cancer comprises generating or obtaining a weighted average of the first and second labels. Some aspects include assigning weights to the first and second classifiers, thereby obtaining the weighted average. In some aspects, the weights are assigned based on area under a ROC curve, area under a precision-recall curve, accuracy, precision, recall, sensitivity, F1-score, specificity, or a combination thereof. In some aspects, the first and second classifiers err independently with regard to lung cancer identification. Some aspects include transmitting or outputting a report comprising information on the identification. Some aspects include transmitting or outputting a recommendation of a treatment of the subject based on the lung cancer identification.

In some embodiments, the multi-omic data further comprises a third omic data comprising a third omic data type. The third omic data may comprise a different omic data type or subtype than the first and second omic data. Some aspects include using a third classifier to assign a third label corresponding to a presence, absence, or likelihood of the lung cancer to the third omic data. In some aspects, identifying the multi-omic data as indicative or as not indicative of the lung cancer comprises identifying the multi-omic data as indicative or as not indicative of the lung cancer based on a combination of the first, second, and third labels. Some aspects include using a third classifier to assign a third label comprising a presence, absence, or likelihood of the lung cancer to a third omic data different from the first and second omic data, and wherein identifying the multi-omic data as indicative or as not indicative of the lung cancer based on the first and second labels comprises identifying the multi-omic data as indicative or as not indicative of the lung cancer based on the first, second and third labels. In some aspects, the first omic data type comprises proteomic data, the second omic data type comprises mRNA transcriptomic data, and the third omic data type comprises microRNA transcriptomic data. Some aspects include transmitting or outputting information related to the identification. Some aspects include recommending a treatment of the lung cancer.

Treatment

Disclosed herein are methods comprising administering a treatment or therapy to a subject in need thereof. The methods described herein may include selecting or administering a cancer therapy to the subject based on an evaluation. Some aspects include making a clinical decision based on an evaluation. Some aspects include selecting a therapy for the subject based on an evaluation. Some aspects include administering a therapy to the subject based on an evaluation. Some aspects include administering a pharmaceutical, radiation or surgical cancer treatment to the subject based on an evaluation.

In some aspects, the cancer described herein is pancreatic cancer. The methods described herein may include recommending or administering a pancreatic cancer treatment for the subject when the proteomic data is classified as indicative of pancreatic cancer. In certain aspects, the method recommends administering a pancreatic cancer treatment to the subject when the proteomic data is classified as indicative of pancreatic cancer. In certain aspects, the method recommends performing a biopsy or pancreatoscopy when the proteomic data is classified as indicative of pancreatic cancer. In certain aspects, the method recommends observation of the subject without administering a pancreatic cancer treatment to the subject. In certain aspects, the method recommends observation of the subject without obtaining a biopsy or pancreatoscopy of the subject, when the proteomic data is not classified as indicative of pancreatic cancer. In certain aspects, the method recommends observing the subject without administering a pancreatic cancer treatment to the subject. In certain aspects, the method recommends observing the subject without obtaining a biopsy or pancreatoscopy of the subject, when the proteomic data is not classified as indicative of pancreatic cancer. The decision to treat the subject, or to obtain a biopsy or not, may be based on whether the proteomic data is indicative of a mass in the subject's pancreas (e.g., a pancreatic cyst) being cancerous or not. For example, a physician may find a pancreatic cyst by CT scanning, and then order a blood test that involves a method described herein.

In some aspects, the cancer described herein is liver cancer. The methods described herein may include recommending or administering a liver cancer treatment for the subject when the proteomic data is classified as indicative of liver cancer. In certain aspects, the method recommends administering a liver cancer treatment to the subject when the proteomic data is classified as indicative of liver cancer. In certain aspects, the method recommends performing a biopsy or diagnostic imaging of liver when the proteomic data is classified as indicative of liver cancer. In certain aspects, the method recommends observation of the subject without administering a liver cancer treatment to the subject. In certain aspects, the method recommends observation of the subject without obtaining a biopsy or diagnostic imaging of liver of the subject, when the proteomic data is not classified as indicative of liver cancer. In certain aspects, the method recommends observing the subject without administering a liver cancer treatment to the subject. In certain aspects, the method recommends observing the subject without obtaining a biopsy or diagnostic imaging of liver of the subject, when the proteomic data is not classified as indicative of liver cancer. The decision to treat the subject, or to obtain a biopsy or not, may be based on whether the proteomic data is indicative of a mass in the subject's liver (e.g., a liver nodule) being cancerous or not. For example, a physician may find a liver nodule by CT scanning, and then order a blood test that involves a method described herein.

In some aspects, the cancer described herein is ovarian cancer. The methods described herein may include recommending or administering an ovarian cancer treatment for the subject when the proteomic data is classified as indicative of ovarian cancer. In certain aspects, the method recommends administering an ovarian cancer treatment to the subject when the proteomic data is classified as indicative of ovarian cancer. In certain aspects, the method recommends performing a biopsy or diagnostic imaging of one or both ovaries of a subject when the proteomic data is classified as indicative of ovarian cancer. In certain aspects, the method recommends observation of the subject without administering an ovarian cancer treatment to the subject. In certain aspects, the method recommends observation of the subject without obtaining a biopsy or diagnostic imaging of ovarian of the subject, when the proteomic data is not classified as indicative of ovarian cancer. In certain aspects, the method recommends observing the subject without administering an ovarian cancer treatment to the subject. In certain aspects, the method recommends observing the subject without obtaining a biopsy or diagnostic imaging of ovarian of the subject, when the proteomic data is not classified as indicative of ovarian cancer. The decision to treat the subject, or to obtain a biopsy or not, may be based on whether the proteomic data is indicative of a mass in one or both of the subject's ovaries (e.g., an ovarian cyst) being cancerous or not. For example, a physician may find an ovarian cyst by CT scanning, and then order a blood test that involves a method described herein.

In some aspects, the cancer described herein is colon cancer. The methods described herein may include recommending or administering a colon cancer treatment for the subject when the proteomic data is classified as indicative of colon cancer. In certain aspects, the method recommends administering a colon cancer treatment to the subject when the proteomic data is classified as indicative of colon cancer. In certain aspects, the method recommends performing a biopsy or colonoscopy when the proteomic data is classified as indicative of colon cancer. In certain aspects, the method recommends observation of the subject without administering a colon cancer treatment to the subject. In certain aspects, the method recommends observation of the subject without obtaining a biopsy or colonoscopy of the subject, when the proteomic data is not classified as indicative of colon cancer. In certain aspects, the method recommends observing the subject without administering a colon cancer treatment to the subject. In certain aspects, the method recommends observing the subject without obtaining a biopsy or colonoscopy of the subject, when the proteomic data is not classified as indicative of colon cancer. The decision to treat the subject, or to obtain a biopsy or not, may be based on whether the proteomic data is indicative of a mass in the subject's colon (e.g., a colon nodule) being cancerous or not. For example, a physician may find a colon nodule by CT scanning, and then order a blood test that involves a method described herein. When the subject is identified as not having the disease state, the subject may avoid an otherwise unfavorable disease treatment (and associated side effects of the disease treatment), or is able to avoid having to be biopsied or tested invasively for the disease state. When the subject is identified as not having the disease state, the subject may be monitored without receiving a treatment. When the subject is identified as not having the disease state, the subject may be monitored without receiving a biopsy. In some cases, the subject identified as not having the disease state may be treated with palliative care such as a pharmaceutical composition for pain. In some cases, the subject is identified as having another disease different from the initially suspected disease state, and is provided treatment for the other disease.

When the subject is identified as having the disease state, the subject may be provided a treatment for the disease state. For example, if the disease state is cancer, the subject may be provided a cancer treatment. For example, if the cancer is pancreatic cancer, the subject may be provided a pancreatic cancer treatment; if the cancer is liver cancer, the subject may be provided a liver cancer treatment; if the cancer is ovarian cancer, the subject may be provided an ovarian cancer treatment; and if the cancer is colon cancer, the subject may be provided a colon cancer treatment. Examples of treatments include surgery, organ transplantation, administration of a pharmaceutical composition, radiation therapy, chemotherapy, immunotherapy, hormone therapy, monoclonal antibody treatment, stem cell transplantation, gene therapy, or chimeric antigen receptor (CAR)-T cell or transgenic T cell administration.

In certain aspects, the cancer is pancreatic cancer, and the pancreatic cancer treatment comprises chemotherapy, radiation therapy, immunotherapy, targeted therapy, surgery, or surgical resection, or a combination thereof. In certain aspects, the method recommends pancreatic cancer treatment comprising administration of a pharmaceutical composition comprising capecitabine, erlotinib, fluorouracil, gemcitabine, irinotecan, leucovorin, nab-paclitaxel, nanoliposomal irinotecan, oxaliplatin, olaparib, or larotrectinib, or a combination thereof.

In certain aspects, the cancer is liver cancer, and the liver cancer treatment comprises chemotherapy, radiation therapy, immunotherapy, targeted therapy, surgery, surgical resection, liver transplantation, radiofrequency ablation, percutaneous ethanol injection, chemoembolization, or radioembolization, or a combination thereof. In certain aspects, the method recommends liver cancer treatment comprising administration of a pharmaceutical composition comprising bevacizumab, atezolizumab, sorafenib, lenvatinib, cabozantinib, regorafenib, ramucirumab, pembrolizumab, nivolumab, or ipilimumab or a combination thereof.

In certain aspects, the cancer is ovarian cancer, and the ovarian cancer treatment comprises chemotherapy, radiation therapy, immunotherapy, targeted therapy, hormone therapy, surgery, surgical resection, an oophorectomy, or cytoreductive surgery, or a combination thereof. In certain aspects, the method recommends ovarian cancer treatment comprising administration of a pharmaceutical composition comprising a platinum-based agent, doxorubicin, paclitaxel, docetaxel, gemcitabine, etoposide, pemetrexed, cyclophosphamide, topotecan, vinorelbine, irinotecan, a poly(ADP-ribose) polymerase (PARP) inhibitor, niraparib, olaparib, rucaparib, an anti-angiogenesis inhibitor, bevacizumab, or a combination thereof.

In certain aspects, the cancer is colon cancer, and the colon cancer treatment comprises chemotherapy, radiation therapy, immunotherapy, targeted therapy, surgery, surgical resection, endoscopy, laparoscopic surgery, cytoreductive surgery, or hyperthermic intraperitoneal chemotherapy, or a combination thereof. In certain aspects, the method recommends colon cancer treatment comprising administration of a pharmaceutical composition comprising capecitabine, fluorouracil (5-FU), irinotecan, oxaliplatin, trifluridine, tipiracil, bevacizumab, regorafenib, ziv-aflibercept, cetuximab, panitumumab, pembrolizumab, nivolumab, or ipilimumab, or a combination thereof.

When the subject is identified as having the disease state, the subject may be further evaluated for the disease state. For example, a subject suspected of having the disease state may be subjected to a biopsy after a method disclosed herein indicates that he or she may have the disease state.

Some cases include recommending a treatment or monitoring of the subject. For example, a medical practitioner may receive a report generated by a method described herein. The report may indicate a likelihood of the subject having a disease state. The medical practitioner may then provide or recommend the treatment or monitoring to the subject or to another medical practitioner. Some cases include recommending a treatment for the subject. Some cases include recommending monitoring of the subject.

An example of a disease that may be tested includes cancer. The cancer may be a lung cancer such as non-small cell-lung cancer. The cancer may be stage 1. The cancer may be stage 2. The cancer may be stage 1 or 2 (e.g., early stage). The cancer may be stage 3. The cancer may be stage 4. The cancer may be any of stages 1-4. The cancer may be an unidentified stage. Where lung cancer (or another cancer is the disease of interest), any aspect of FIG. 25 may be included or integrated into a method described herein. For example, a subject may undergo a blood test when the subject is suspected of having a cancer such as lung cancer. The subject may have not yet received a computed tomography (CT) scan to check for lung nodules, may be under consideration for treatment with an immune checkpoint inhibitor (ICI), or may have potentially resectable cancer.

Some aspects include recommending a lung cancer treatment for the subject when the protein measurements are classified as indicative of the lung nodule being cancerous. Some aspects include administering a lung cancer treatment to the subject when the protein measurements are classified as indicative of the lung nodule being cancerous. In some aspects, the lung cancer treatment comprises chemotherapy, radiation therapy, percutaneous ablation, radiofrequency ablation, cryoablation, microwave ablation, chemoembolization, or surgery.

Some aspects include observing the subject without performing a biopsy when the protein measurements are classified as indicative of the lung nodule being non-cancerous. In some aspects, observing the subject without performing a biopsy comprises assaying proteins in a second biofluid sample obtained from a subject at a later time. Some aspects include assaying proteins in a second biofluid sample obtained from a subject at a later time.

The treatment may include watchful waiting, for example, when the subject is identified as not likely to have the cancer, or when a mass is identified as non-malignant. Some methods include watchful waiting when a cancer is identified in a patient.

Various methods of the present disclosure comprise treating disease states such as cancer in a patient in need thereof, wherein a biomarker such as a peptide from among the peptides listed in Table 2, or another table or figure, is identified in a sample in the patient. The treatment or therapy may be administered in response to, or based on, the biomarker measurements described herein. The biomarkers may be measured using a method described herein.

A method described herein may include administering a cancer treatment to the subject. A method described herein may include administering a lung disease treatment to the subject. A method described herein may include administering a lung cancer treatment to the subject. A method described herein may include administering a lung disease treatment other than a cancer treatment to the subject. A method described herein may include administering a NSCLC treatment to the subject. A method described herein may include administering a cancer treatment to the subject based on the disease state of the subject. A method described herein may include administering a lung treatment to the subject based on the disease state of the subject. A method described herein may include administering a NSCLC treatment to the subject based on the disease state of the subject.

Disclosed herein are methods of treatment. The method may include obtaining or receiving a measurement of one or more biomarkers described herein. The measurements may be in a sample from a subject suspected of having a lung cancer. The method may include administering a lung cancer treatment to the subject based on a presence of the one or more biomarkers. The method may include monitoring the subject without providing the lung cancer treatment to the subject based on an absence of the one or more biomarkers. Some embodiments include identifying the subject as having the lung cancer and administering the treatment.

The biomarkers may include peptides. In some cases, at least two peptides, at least three peptides, four peptides, five peptides, eight peptides, ten peptides, fifteen peptides, or twenty peptides from among the peptides listed in Table 2, or another table or figure, are identified in a sample in the patient. In some cases, the treatment type, duration, dosage, or frequency is determined by the combination or relative abundances of peptides from among the peptides listed in Table 2, or another table or figure, which are identified in the sample from the patient. In some cases, the treatment efficacy is determined by the combination or relative abundances of peptides from among the peptides listed in Table 2, or another table or figure, which are identified in the sample from the patient. In some cases, the combination or relative abundances of peptides from among the peptides listed in Table 2, or another table or figure, diagnoses the patient as having or not having cancer. In some cases, the combination or relative abundances of peptides from among the peptides listed in Table 2, or another table or figure, diagnoses the type of cancer. In some cases, the combination or relative abundances of peptides from among the peptides listed in Table 2, or another table or figure, indicates whether a cancer treatment should or should not be administered to the patient. In some cases, the sample is a plasma sample. In some cases, the cancer is a lung cancer such as NSCLC.

Various methods of the present disclosure comprise tracking the progress of a cancer treatment. A method may comprise biomarker detection in a plurality of samples collected from a patient over a period of time. In some cases, a method comprises measuring changes in the level of at least one peptide from among the peptides listed in Table 2, or another table or figure, in samples from the patient over a period of time to determine whether to discontinue or modify (e.g., adjust administration frequency or dose) a treatment. For example, a method may comprise measuring the concentrations of at least two proteins selected from the group consisting of ANGL6, NOTUM, CILP1, RLA2, and GP1BB in plasma samples collected in biweekly intervals from the patient, and determining when to discontinue a treatment or to start a secondary treatment based on the change in concentrations of the at least two proteins.

In some cases, the treatment comprises chemotherapy. Some examples of chemotherapy may include adriamycin, amsacrine, azathioprine, bleomycin, busulfan, capecitabine, carboplatin, chlorambucil, cisplatin, cyclophosphamide, cytarabine, daunorubicin, docetaxel, doxorubicin, epirubicin, etoposide, floxuridine, fludarabine, gemcitabine, ifosfamide, iproplatin, irinotecan, leucovorin, mechlorethamine, melphalan, mercaptopurine, methotrexate, mitomycin, mitoxantrone, nitrosoureas, oxaliplatin, paclitaxel, plicamycin, podophyllotoxin, satraplatin, spiroplatin, teniposide, thiotepa, topotecan, uramustine, vinblastine, vincristine, vindesine, vinorelbine, oxaliplatin, cisplatin, carboplatin, spiroplatin, iproplatin, satraplatin, cyclophosphamide, ifosfamide, chlorambucil, busulfan, melphalan, mechlorethamine, uramustine, thiotepa, nitrosoureas, 5-fluorouracil, azathioprine, 6-mercaptopurine, methotrexate, leucovorin, capecitabine, cytarabine, floxuridine, fludarabine, gemcitabine, vincristine, vinblastine, vinorelbine, vindesine, podophyllotoxin, paclita docetaxel, irinotecan, topotecan, amsacrine, etoposide, teniposide, doxorubicin, adriamycin, daunorubicin, epirubicin, actinomycin, bleomycin, mitomycin, mitoxantrone, plicamycin or any combination thereof. In some cases, the treatment comprises an immunotherapy. In some cases, the treatment comprises hormone therapy. In some cases, the treatment comprises monoclonal antibody treatment. In some cases, the treatment comprises an mTOR inhibitor. In some cases, the treatment comprises a stem cell transplant. In some cases, the treatment comprises radiation therapy. In some cases, the treatment comprises gene therapy. In some cases, the treatment comprises chimeric antigen receptor (CAR)-T cell or transgenic T cell administration. In some cases, the treatment comprises resection surgery. For example, a CT scan may identify adenocarcinoma tumors in a patient, and analysis of a protein selected from the group consisting of ANGL6, NOTUM, CILP1, RLA2, and GP1BB from a blood sample from the patient may determine that the tumors are malignant, and therefore that removing the tumors is likely to lead to a favorable outcome.

In some cases, the treatment includes a cancer treatment. In some cases, the treatment includes multiple cancer treatments. The cancer treatment may include an anti-cancer treatment such as any of the following: Abemaciclib, Abiraterone Acetate, ABRAXANE (Paclitaxel Albumin-stabilized Nanoparticle Formulation), ABVD, ABVE, ABVE-PC, AC, Acalabrutinib, AC-T, ACTEMRA (Tocilizumab), ADCETRIS (Brentuximab Vedotin), ADE, Ado-Trastuzumab Emtansine, Adriamycin (Doxorubicin Hydrochloride), Afatinib Dimaleate, AFINITOR (Everolimus), AKYNZEO (Netupitant and Palonosetron Hydrochloride), ALDARA (Imiquimod), Aldesleukin, ALECENSA (Alectinib), Alectinib, Alemtuzumab, ALTAMTA (Pemetrexed Disodium), ALIQOPA (Copanlisib Hydrochloride), Alkeran for Injection (Melphalan Hydrochloride), Alkeran Tablets (Melphalan), ALOXI (Palonosetron Hydrochloride), Alpelisib, ALUNBRIG (Brigatinib), AMELUZ (Aminolevulinic Acid Hydrochloride), Amifostine, Aminolevulinic Acid Hydrochloride, Anastrozole, Apalutamide, Aprepitant, Aranesp (Darbepoetin Alfa), AREDIA (Pamidronate Disodium), ARIMIDEX (Anastrozole), AROMASIN (Exemestane), ARRANON (Nelarabine), Arsenic Trioxide, ARZERRA (Ofatumumab), Asparaginase Erwinia chrysanthemi, ASPARLAS (Calaspargase Pegol-mknl), Atezolizumab, Avapritinib, AVASTIN (Bevacizumab), Avelumab, Axicabtagene Ciloleucel, Axitinib, AYVAKIT (Avapritinib), Azacitidine, AZEDRA (Iobenguane I 131), BALVERSA (Erdafitinib), BAVENCIO (Avelumab), BEACOPP, Belantamab Mafodotin-blmf, BELEODAQ (Belinostat), Belinostat, Bendamustine Hydrochloride, BENDEKA (Bendamustine Hydrochloride), BEP, BESPONSA (Inotuzumab Ozogamicin), Bevacizumab, Bexarotene, Bicalutamide, BiCNU (Carmustine), Binimetinib, BLENREP (Belantamab Mafodotin-blmf), Bleomycin Sulfate, Blinatumomab, BLINCYTO (Blinatumomab), Bortezomib, BOSULIF (Bosutinib), Bosutinib, BRAFTOVI (Encorafenib), Brentuximab Vedotin, Brexucabtagene Autoleucel, Brigatinib, BRUKINSA (Zanubrutinib), BuMel, Busulfan, BUSULFEX (Busulfan), Cabazitaxel, CABLIVI (Caplacizumab-yhdp), CABOMETYX (Cabozantinib-S-Malate), Cabozantinib-S-Malate, CAF, Calaspargase Pegol-mknl, CALQUENCE (Acalabrutinib), CAMPATH (Alemtuzumab), CAMPTOSAR (Irinotecan Hydrochloride), Capecitabine, Caplacizumab-yhdp, Capmatinib Hydrochloride, CAPOX, CARAC (Fluorouracil—Topical), Carboplatin, CARBOPLATIN-TAXOL, Carfilzomib, Carmustine, Carmustine Implant, CASODEX (Bicalutamide), CEM, Cemiplimab-rwlc, Ceritinib, CERUBIDINE (Daunorubicin Hydrochloride), CERVARIX (Recombinant HPV Bivalent Vaccine), Cetuximab, CEV, Chlorambucil, CHLORAMBUCIL-PREDNISONE, CHOP, Cisplatin, Cladribine, Clofarabine, Clolar (Clofarabine), CMF, Cobimetinib Fumarate, COMETRIQ (Cabozantinib-S-Malate), Copanlisib Hydrochloride, COPDAC, COPIKTRA (Duvelisib), COPP, COPP-ABV, COSMEGEN (Dactinomycin), COTELLIC (Cobimetinib Fumarate), Crizotinib, CVP, Cyclophosphamide, CYRAMZA (Ramucirumab), Cytarabine, Dabrafenib Mesylate, Dacarbazine, DACOGEN (Decitabine), Dacomitinib, Dactinomycin, Daratumumab, Daratumumab and Hyaluronidase-fihj, Darbepoetin Alfa, Darolutamide, DARZALEX (Daratumumab), DARZALEX Faspro (Daratumumab and Hyaluronidase-fihj), Dasatinib, Daunorubicin Hydrochloride, Daunorubicin Hydrochloride and Cytarabine Liposome, DAURISMO (Glasdegib Maleate), Decitabine, Decitabine and Cedazuridine, Defibrotide Sodium, DEFITELIO (Defibrotide Sodium), Degarelix, Denileukin Diftitox, Denosumab, Dexamethasone, Dexrazoxane Hydrochloride, Dinutuximab, Docetaxel, DOXIL (Doxorubicin Hydrochloride Liposome), Doxorubicin Hydrochloride, Doxorubicin Hydrochloride Liposome, Durvalumab, Duvelisib, Efudex (Fluorouracil—Topical), ELIGARD (Leuprolide Acetate), ELITEK (Rasburicase), ELLENCE (Epirubicin Hydrochloride), Elotuzumab, ELOXATIN (Oxaliplatin), Eltrombopag Olamine, ELZONRIS (Tagraxofusp-erzs), Emapalumab-lzsg, EMEND (Aprepitant), EMPLICITI (Elotuzumab), Enasidenib Mesylate, Encorafenib, Enfortumab Vedotin-ejfv, ENHERTU (Fam-Trastuzumab Deruxtecan-nxki), Entrectinib, Enzalutamide, Epirubicin Hydrochloride, EPOCH, Epoetin Alfa, EPOGEN (Epoetin Alfa), ERBITUX (Cetuximab), Erdafitinib, Eribulin Mesylate, ERIVEDGE (Vismodegib), ERLEADA (Apalutamide), Erlotinib Hydrochloride, ERWINAZE (Asparaginase Erwinia chrysanthemi), ETHYOL (Amifostine), ETOPOPHOS (Etoposide Phosphate), Etoposide, Etoposide Phosphate, Everolimus, EVISTA (Raloxifene Hydrochloride), EVOMELA (Melphalan Hydrochloride), Exemestane, 5-FU (Fluorouracil Injection), 5-FU (Fluorouracil—Topical), Fam-Trastuzumab Deruxtecan-nxki, FARESTON (Toremifene), FARYDAK (Panobinostat), FASLODEX (Fulvestrant), FEC, Fedratinib Hydrochloride, FEMARA (Letrozole), Filgrastim, FIRMAGON (Degarelix), Fludarabine Phosphate, FLUOROPLEX (Fluorouracil—Topical), Fluorouracil Injection, Fluorouracil—Topical, Flutamide, FOLFIRI, FOLFIRI-BEVACIZUMAB, FOLFIRI-CETUXIMAB, FOLFIRINOX, FOLFOX, FOLOTYN (Pralatrexate), Fostamatinib Disodium, FULPHILA (Pegfilgrastim), FU-LV, Fulvestrant, FAMIFANT (Emapalumab-lzsg), GARDASIL (Recombinant HPV Quadrivalent Vaccine), GARDASIL 9 (Recombinant HPV Nonavalent Vaccine), GAVRETP (Pralsetinib), GAZYVA (Obinutuzumab), Gefitinib, Gemcitabine Hydrochloride, GEMCITABINE-CISPLATIN, GEMCITABINE-OXALIPLATIN, Gemtuzumab Ozogamicin, GEMZAR (Gemcitabine Hydrochloride), GILOTRIF (Afatinib Dimaleate), Gilteritinib Fumarate, Glasdegib Maleate, GLEEVEC (Imatinib Mesylate), GLIADEL WAFER (Carmustine Implant), Glucarpidase, Goserelin Acetate, Granisetron, Granisetron Hydrochloride, GRANIX (Filgrastim), HALAVEN (Eribulin Mesylate), HEMANGEOL (Propranolol Hydrochloride), HERCEPTIN HYLECTA (Trastuzumab and Hyaluronidase-oysk), HERCEPTIN (Trastuzumab), HPV Bivalent Vaccine, Recombinant, HPV Nonavalent Vaccine, Recombinant, HPV Quadrivalent Vaccine, Recombinant, HYEAMTIN (Topotecan Hydrochloride), HYDREA (Hydroxyurea), Hydroxyurea, Hyper-CVAD, IBRANCE (Palbociclib), Ibritumomab Tiuxetan, Ibrutinib, ICE, ICLUSIG (Ponatinib Hydrochloride), IDAMYCIN PFS (Idarubicin Hydrochloride), Idarubicin Hydrochloride, Idelalisib, IDHIFA (Enasidenib Mesylate), Ifex (Ifosfamide), Ifosfamide, IL-2 (Aldesleukin), Imatinib Mesylate, Imbruvica (Ibrutinib), IMFINZI (Durvalumab), Imiquimod, IMLYGIC (Talimogene Laherparepvec), INFUGEM (Gemcitabine Hydrochloride), INLYTA (Axitinib), Inotuzumab Ozogamicin, INQOVI (Decitabine and Cedazuridine), Inrebic (Fedratinib Hydrochloride), Interferon Alfa-2b, Recombinant, Interleukin-2 (Aldesleukin), Intron A (Recombinant Interferon Alfa-2b), Iobenguane I 131, Ipilimumab, IRESSA (Gefitinib), Irinotecan Hydrochloride, Irinotecan Hydrochloride Liposome, Isatuximab-irfc, ISTODAX (Romidepsin), Ivosidenib, Ixabepilone, Ixazomib Citrate, IXEMPRA (Ixabepilone), JAKAFI (Ruxolitinib Phosphate), JEB, JELMYTO (Mitomycin), JEVTANA (Cabazitaxel), KADCYLA (Ado-Trastuzumab Emtansine), KEPIVANCE (Palifermin), KEYTRUDA (Pembrolizumab), KISQALI (Ribociclib), KOSELUGO (Selumetinib Sulfate), KYMRIAH (Tisagenlecleucel), KYPROLIS (Carfilzomib), Lanreotide Acetate, Lapatinib Ditosylate, Larotrectinib Sulfate, Lenvatinib Mesylate, LENVIMA (Lenvatinib Mesylate), Letrozole, Leucovorin Calcium, LEUKERAN (Chlorambucil), Leuprolide Acetate, LEVULAN KERASTIK (Aminolevulinic Acid Hydrochloride), LIBTAYO (Cemiplimab-rwlc), Lomustine, LONSURF (Trifluridine and Tipiracil Hydrochloride), LORBRENA (Lorlatinib), Lorlatinib, LUMOXITI (Moxetumomab Pasudotox-tdfk), Lupron Depot (Leuprolide Acetate), Lurbinectedin, Luspatercept-aamt, LUTATHERA (Lutetium Lu 177-Dotatate), Lutetium (Lu 177-Dotatate), LYNPARZA (Olaparib), MARQIBO (Vincristine Sulfate Liposome), MATULANE (Procarbazine Hydrochloride), Mechlorethamine Hydrochloride, Megestrol Acetate, MEKINIST (Trametinib), MEKTOVI (Binimetinib), Melphalan, Melphalan Hydrochloride, Mercaptopurine, Mesna, MESNEX (Mesna), Methotrexate Sodium, Methylnaltrexone Bromide, Midostaurin, Mitomycin, Mitoxantrone Hydrochloride, Mogamulizumab-kpkc, MONJUVI (Tafasitamab-cxix), Moxetumomab Pasudotox-tdfk, MOZOBIL (Plerixafor), MVAC, MVASI (Bevacizumab), MYLERAN (Busulfan), MYLOTARG (Gemtuzumab Ozogamicin), Nanoparticle Paclitaxel (Paclitaxel Albumin-stabilized Nanoparticle Formulation), Necitumumab, Nelarabine, Neratinib Maleate, NERLYNX (Neratinib Maleate), Netupitant and Palonosetron Hydrochloride, NEULASTA (Pegfilgrastim), NEUPOGEN (Filgrastim), NEXAVAR (Sorafenib Tosylate), NILANDRON (Nilutamide), Nilotinib, Nilutamide, NINLARO (Ixazomib Citrate), Niraparib Tosylate Monohydrate, Nivolumab, NPLATE (Romiplostim), NUBEQA (Darolutamide), NYVEPRIA (Pegfilgrastim), Obinutuzumab, ODOMZO (Sonidegib), OEPA, Ofatumumab, OFF, Olaparib, Omacetaxine Mepesuccinate, ONCASPAR (Pegaspargase), Ondansetron Hydrochloride, ONIVYDE (Irinotecan Hydrochloride Liposome), ONTAK (Denileukin Diftitox), ONUREG (Azacitidine), OPDIVO (Nivolumab), OPPA, Osimertinib Mesylate, Oxaliplatin, Paclitaxel, Paclitaxel Albumin-stabilized Nanoparticle Formulation, PAD, PADCEV (Enfortumab Vedotin-ejfv), Palbociclib, Palifermin, Palonosetron Hydrochloride, Palonosetron Hydrochloride and Netupitant, Pamidronate Disodium, Panitumumab, Panobinostat, Pazopanib Hydrochloride, PCV, PEB, Pegaspargase, Pegfilgrastim, Peginterferon Alfa-2b, PEG-INTRON (Peginterferon Alfa-2b), PEMAZYRE (Pemigatinib), Pembrolizumab, Pemetrexed Disodium, Pemigatinib, PERJETA (Pertuzumab), Pertuzumab, Pertuzumab, Trastuzumab, and Hyaluronidase-zzxf, Pexidartinib Hydrochloride, PHESGO (Pertuzumab, Trastuzumab, and Hyaluronidase-zzxf), PIQRAY (Alpelisib), Plerixafor, Polatuzumab Vedotin-piiq, POLIVY (Polatuzumab Vedotin-piiq), Ponatinib Hydrochloride, PORTRAZZA (Necitumumab), POTELIGEO (Mogamulizumab-kpkc), Pralatrexate, Pralsetinib, Prednisone, Procarbazine Hydrochloride, PROCRIT (Epoetin Alfa), PROLEUKIN (Aldesleukin), PROLIA (Denosumab), PROMACTA (Eltrombopag Olamine), Propranolol Hydrochloride, Provenge (Sipuleucel-T), PURINETHOL (Mercaptopurine), PURIXAN (Mercaptopurine), QINLOCK (Ripretinib), Radium 223 Dichloride, Raloxifene Hydrochloride, Ramucirumab, Rasburicase, Ravulizumab-cwvz, REBLOZYL (Luspatercept-aamt), R-CHOP, R-CVP, Recombinant Human Papillomavirus (HPV) Bivalent Vaccine, Recombinant Human Papillomavirus (HPV) Nonavalent Vaccine, Recombinant Human Papillomavirus (HPV) Quadrivalent Vaccine, Recombinant Interferon Alfa-2b, Regorafenib, RELISTOR (Methylnaltrexone Bromide), R-EPOCH, RETACRIT (Epoetin Alfa), RETEVMO (Selpercatinib), Ribociclib, R-ICE, Ripretinib, RITUXAN (Rituximab), RETUXAN HYCELA (Rituximab and Hyaluronidase Human), Rituximab, Rituximab and Hyaluronidase Human, Rolapitant Hydrochloride, Romidepsin, Romiplostim, ROZLYTREK (Entrectinib), Rubidomycin (Daunorubicin Hydrochloride), RUBRACA (Rucaparib Camsylate), Rucaparib Camsylate, Ruxolitinib Phosphate, RYDAPT (Midostaurin), Sacituzumab Govitecan-hziy, SANCUSO (Granisetron), SARCLISA (Isatuximab-irfc), Sclerosol Intrapleural Aerosol (Talc), Selinexor, Selpercatinib, Selumetinib Sulfate, Siltuximab, Sipuleucel-T, Somatuline Depot (Lanreotide Acetate), Sonidegib, Sorafenib Tosylate, SPRYCEL (Dasatinib), STANFORD V, Sterile Talc Powder (Talc), STERITALC (Talc), STIVARGA (Regorafenib), Sunitinib Malate, SUSTOL (Granisetron), SUTENT (Sunitinib Malate), SYLATRON (Peginterferon Alfa-2b), SYLVANT (Siltuximab), SYNRIBO (Omacetaxine Mepesuccinate), TABLOID (Thioguanine), TABRECTA (Capmatinib Hydrochloride), TAC, Tafasitamab-cxix, TAFINLAR (Dabrafenib Mesylate), Tagraxofusp-erzs, TAGRISSO (Osimertinib Mesylate), Talazoparib Tosylate, Talc, Talimogene Laherparepvec, TALZENNA (Talazoparib Tosylate), Tamoxifen Citrate, TARCEVA (Erlotinib Hydrochloride), TARGRETIN (Bexarotene), TASIGNA (Nilotinib), TAVALISSA (Fostamatinib Disodium), TAXOTERE (Docetaxel), Tazemetostat Hydrobromide, TAZVERIK (Tazemetostat Hydrobromide), TECARTUS (Brexucabtagene Autoleucel), TECENTRIQ (Atezolizumab), TEMODAR (Temozolomide), Temozolomide, Temsirolimus, Thioguanine, Thiotepa, TIBOSOVO (Ivosidenib), Tisagenlecleucel, Tocilizumab, TOLAK (Fluorouracil—Topical), Topotecan Hydrochloride, Toremifene, TORISEL (Temsirolimus), TOTECT (Dexrazoxane Hydrochloride), TPF, Trabectedin, Trametinib, Trastuzumab, Trastuzumab and Hyaluronidase-oysk, TREANDA (Bendamustine Hydrochloride), TREXALL (Methotrexate Sodium), Trifluridine and Tipiracil Hydrochloride, TRISENOX (Arsenic Trioxide), TRODELVY (Sacituzumab Govitecan-hziy), TRUXIMA (Rituximab), Tucatinib, TUKYSA (Tucatinib), TURALIO (Pexidartinib Hydrochloride), TYKERB (Lapatinib Ditosylate), ULTOMIRIS (Ravulizumab-cwvz), UDENYCA (Pegfilgrastim), UNITUXIN (Dinutuximab), Uridine Triacetate, VAC, Valrubicin, VALSTAR (Valrubicin), Vandetanib, VAMP, VARUBI (Rolapitant Hydrochloride), VECTIBIX (Panitumumab), VeIP, VELCADE (Bortezomib), Vemurafenib, VENELEXTA (Venetoclax), Venetoclax, VERZENIO (Abemaciclib), VIDAZA (Azacitidine), Vinblastine Sulfate, Vincristine Sulfate, Vincristine Sulfate Liposome, Vinorelbine Tartrate, VIP, Vismodegib, VISTOGARD (Uridine Triacetate), VITRAKVI (Larotrectinib Sulfate), VIZIMPRO (Dacomitinib), VORAXAZE (Glucarpidase), Vorinostat, VOTRIENT (Pazopanib Hydrochloride), VYXEOS (Daunorubicin Hydrochloride and Cytarabine Liposome), XALKORI (Crizotinib), XATMEP (Methotrexate Sodium), XELODA (Capecitabine), XELIRI, XELOX, XGEVA (Denosumab), XOFIGO (Radium 223 Dichloride), XOSPATA (Gilteritinib Fumarate), XPOVIO (Selinexor), XTANDI (Enzalutamide), YERVOY (Ipilimumab), YESCARTA (Axicabtagene Ciloleucel), YONDELIS (Trabectedin), YONDSA (Abiraterone Acetate), ZALTRAP (Ziv-Aflibercept), Zanubrutinib, ZARXIO (Filgrastim), ZEJULA (Niraparib Tosylate Monohydrate), ZELBORAF (Vemurafenib), ZEPZELCA (Lurbinectedin), ZEVANLIN (Ibritumomab Tiuxetan), ZIEXTENZO (Pegfilgrastim), ZINECARD (Dexrazoxane Hydrochloride), ZIRABEV (Bevcizumab), Ziv-Aflibercept, ZOFRAN (Ondansetron Hydrochloride), ZOLADEX (Goserelin Acetate), Zoledronic Acid, ZOLINZA (Vorinostat), Zometa (Zoledronic Acid), Zyclara (Imiquimod), ZYDELIG (Idelalisib), Zykadia (Ceritinib), or ZYTIGA (Abiraterone Acetate).

Disease Detection and Monitoring

Described herein are methods that may be useful for disease detection such as cancer detection, or for disease monitoring such as cancer monitoring, or for monitoring a mass, cyst, or nodule to see whether it becomes cancerous. This section includes several details relevant to lung nodules and lung cancer, as well as other aspects. The details described in relation to a lung nodule may be relevant to a mass, nodule, or cyst of another tissue. The details described in relation to a lung nodule may be relevant to another disease state or cancer.

A method may include obtaining or analyzing biomolecule measurements such as multi-omic biomolecule measurements to evaluate a mass, nodule, or cyst. The mass, nodule, or cyst may be identified by medical imaging. The evaluation may involve an indication or likelihood of the mass, nodule, or cyst being cancerous or not. The evaluation may avoid a need to biopsy the mass, nodule, or cyst. The evaluation may indicate that the mass, nodule, or cyst is cancerous or likely to be cancerous. Some aspects include performing a biopsy on a mass, nodule, or cyst when the biomolecule measurements are classified as indicative of the mass, nodule, or cyst being cancerous. In some aspects, the biopsy confirms a likelihood of the mass, nodule, or cyst being cancerous or non-cancerous. In some aspects, the mass, nodule, or cyst is cancerous. In some aspects, the mass, nodule, or cyst is non-cancerous. Some examples of cancers may include lung cancer, pancreatic cancer, liver cancer, ovarian cancer, or colon cancer.

The method may include obtaining a biofluid sample of a subject having a lung nodule. The method may include contacting the biofluid sample with particles such that the particles adsorb biomolecules comprising proteins to the particles. The method may include assaying the biomolecules adsorbed to the particles to generate proteomic data. The method may include classifying the proteomic data as indicative of the lung nodule being cancerous or non-cancerous.

Some embodiments include identifying the subject as having the lung nodule. The identification may include performing medical imaging on the subject, or receiving medical imaging information regarding the subject. The medical imaging may include a CT scan.

In some aspects, the subject is identified as having the lung nodule by medical imaging. In some aspects, the medical imaging comprises a computed tomography (CT) scan. Some aspects include performing the medical imaging. Some aspects include identifying the lung nodule in the medical imaging. Some aspects include generating a report based on the identification of the protein measurements as indicative of the lung nodule being cancerous or non-cancerous. In some aspects, the report comprises a likelihood or an indication that the lung nodule is cancerous or non-cancerous. Some aspects include outputting or transmitting the report. In some aspects, the report is used by a medical professional in making a diagnosis, giving medical advice, or providing a treatment for the lung nodule.

Some aspects include recommending that the subject receive a medical imaging such as a CT scan when proteomic data are indicative of the subject having the lung cancer, and not recommending that the subject receive the medical imaging when proteomic data are not indicative of the subject having the lung cancer. Some aspects include performing a medical imaging such as a CT scan on the subject when proteomic data are indicative of the subject having the lung cancer, and not performing the medical imaging on the subject when proteomic data are not indicative of the subject having the lung cancer. Some aspects include transmitting or receiving a report on a medical imaging such as a CT scan when proteomic data are indicative of the subject having the lung cancer, and not transmitting or receiving the report when proteomic data are not indicative of the subject having the lung cancer. In some aspects, proteomic data indicate the subject as having or as likely to have the lung cancer. In some aspects, proteomic data indicate the subject as not having or as unlikely to have the lung cancer.

Some aspects include recommending that the subject receive a medical imaging such as a CT scan when protein measurements are indicative of the subject having the lung cancer, and not recommending that the subject receive the medical imaging when protein measurements are not indicative of the subject having the lung cancer. Some aspects include performing a medical imaging such as a CT scan on the subject when protein measurements are indicative of the subject having the lung cancer, and not performing the medical imaging on the subject when protein measurements are not indicative of the subject having the lung cancer. Some aspects include transmitting or receiving a report on a medical imaging such as a CT scan when protein measurements are indicative of the subject having the lung cancer, and not transmitting or receiving the report when protein measurements are not indicative of the subject having the lung cancer. In some aspects, protein measurements indicate the subject as having or as likely to have the lung cancer. In some aspects, protein measurements indicate the subject as not having or as unlikely to have the lung cancer.

In some aspects, the lung nodule is less than 3 cm in diameter. In some aspects, the lung nodule is less than 2.5 cm in diameter. In some aspects, the lung nodule is less than 2 cm in diameter. In some aspects, the lung nodule is less than 1.5 cm in diameter. In some aspects, the lung nodule is less than 1 cm in diameter. In some aspects, the lung nodule is less than 0.5 cm in diameter. In some aspects, the lung nodule is at least 3 cm in diameter. In some aspects, the lung nodule is at least 2.5 cm in diameter. In some aspects, the lung nodule is at least 2 cm in diameter. In some aspects, the lung nodule is at least 1.5 cm in diameter. In some aspects, the lung nodule is at least 1 cm in diameter. In some aspects, the lung nodule is at least 0.5 cm in diameter.

Some aspects include performing a biopsy on the lung nodule when the protein measurements are classified as indicative of the lung nodule being cancerous. In some aspects, the biopsy confirms a likelihood of the lung nodule being cancerous or non-cancerous. In some aspects, the lung nodule is cancerous. In some aspects, the lung nodule comprises non-small-cell lung carcinoma (NSCLC). In some aspects, the lung nodule is non-cancerous.

A classifier may be used in determining whether the subject has a malignant or benign lung nodule. One or more of the biomarkers disclosed herein can be used in an assay for determining whether the subject has a lung nodule that is benign or malignant. In some cases, one or more biomarkers disclosed herein can be used for detection or identification of a malignant lung nodule in a sample from the subject. In some cases, one or more biomarkers disclosed herein can be used for detection or identification of a benign lung nodule in a sample from the subject.

The malignant lung nodule may be described herein as a lung cancer. The lung cancer can be non-small cell lung cancer (NSCLC). The lung cancer can be adenosquamous carcinoma of the lung. The lung cancer can comprise a lung nodule. The lung cancer can be or include metastatic lung cancer. The lung cancer can be large cell neuroendocrine carcinoma. The lung cancer can be salivary gland-type lung carcinoma. The lung cancer can be mesothelioma. In some cases, the present disclosure provides methods of identifying a lung cancer biomarker disclosed herein from a sample from a patient (e.g., by mass spectrometry or ELISA). In some cases, the present disclosure provides methods of obtaining a sample from a subject, incubating said sample with the particle panels disclosed herein, and performing targeted mass spectrometry on the biomolecule corona formed on various particle types of the particle panel to assess for the presence or absence of one or more of the biomarkers disclosed herein associated with NSCLC. A classifier disclosed herein can be used to further process the protein data obtained using the methods described above to classify the sample as healthy, co-morbid, or NSCLC.

The biomarkers of the present disclosure may not only be used to detect or identify the presence of lung cancer, but may also identify the type and stage of lung cancer in a patient. Determining lung cancer stage, type, and malignancy is often beyond the scope of present methods, as little is established about the genetic and molecular factors which mediate lung cancer progression. While treatment success is highly dependent on accurate lung cancer characterization, current methods for ascertaining information on the state of lung cancer in a patient are often slow, invasive, expensive, and time intensive. There is a long outstanding need for rapid, non-invasive methods which can accurately diagnose lung cancer stage and type. The methods bridge this shortcoming by enabling lung cancer identification and characterization from small volumes of patient samples.

In many cases, the method of the present disclosure can detect or identify lung cancer from less than 100 mL, less than 50 mL, less than 30 mL, less than 25 mL, less than 20 mL, less than 15 mL, less than 10 mL, less than 8 mL, less than 6 mL, less than 5 mL, less than 3 mL, less than 2 mL, or less than 1 mL of blood (e.g., plasma) from a patient. Furthermore, a number of methods of the present disclosure may determine a type of lung cancer from a patient from less than 100 mL, less than 50 mL, less than 30 mL, less than 25 mL, less than 20 mL, less than 15 mL, less than 10 mL, less than 8 mL, less than 6 mL, less than 5 mL, less than 3 mL, less than 2 mL, or less than 1 mL of blood (e.g., plasma) from the patient. The methods of the present disclosure may also determine a stage of a lung cancer from a patient from less than 100 mL, less than 50 mL, less than 30 mL, less than 25 mL, less than 20 mL, less than 15 mL, less than 10 mL, less than 8 mL, less than 6 mL, less than 5 mL, less than 3 mL, less than 2 mL, or less than 1 mL of blood (e.g., plasma) from the patient.

A method of the present disclosure may comprise monitoring cancer progression in a patient, for example, non-invasively monitoring a lung nodule in the subject. Various methods of the present disclosure are able to distinguish between healthy, early stage, and late stage cancers. A method of the present disclosure may also be capable of determining whether a patient is in complete or partial remission. A method may thus comprise analyzing samples from a patient collected at separate points in time. Such methods may identify and then track health or cancer progression in a patient without the need for invasive or expensive procedures. Tracking early phase cancers can be particularly challenging and time intensive for a patient, as small, localized cancers often require biopsies or lengthy imaging sessions for detection. Conversely, the present disclosure provides a variety of methods for tracking small and localized cancers through blood analysis alone. For example, a patient with a stage 0 or stage 1 lung cancer may undergo bimonthly plasma analyses consistent with methods of the present disclosure to monitor for cancer metastasis or progression. A patient may undergo diagnostic analyses of the present disclosure in daily, twice weekly, weekly, biweekly, monthly, bimonthly, quarterly (once every 3 months), twice yearly, yearly, or biyearly intervals. A patient may be regularly monitored to track remission, early phase cancer status, late phase cancer status, or maintenance of a healthy or pre-cancerous status. In some cases, the particles and methods of the present disclosure can be used to diagnose lung cancer up to one year prior, up to two years prior, up to three years prior, up to four years prior, up to five years prior, up to six years prior, up to seven years prior, up to eight years prior, up to nine years prior, up to 10 years prior, up to 15 years prior, up to 20 years prior, or up to 25 years prior to development of symptoms of the lung cancer.

In some cases, the entire assay time from obtaining a sample, sample preparation, incubation of a particle panel with the sample, and LC-MS (e.g., targeted mass spectrometry) to identify proteins or protein groups, can be about 8 hours. In some embodiments, the entire assay time from a single pooled sample, including sample preparation and LC-MS, can be about at least 1 hour, at least 2 hours, at least 3 hours, at least 4 hours, at least 5 hours, at least 6 hours, at least 7 hours, at least 8 hours, at least 9 hours, at least 10 hours, under 20 hours, under 19 hours, under 18 hours, under 17 hours, under 16 hours, under 15 hours, under 14 hours, under 13 hours, under 12 hours, under 11 hours, under 10 hours, under 9 hours, under 8 hours, under 7 hours, under 6 hours, under 5 hours, under 4 hours, under 3 hours, under 2 hours, under 1 hour, at least 5 min to 10 min, at least 10 min to 20 min, at least 20 min to 30 min, at least 30 min to 40 min, at least 40 min to 50 min, at least 50 min to 60 min, at least 1 hour to 1.5 hours, at least 1.5 hour to 2 hours, at least 2 hour to 2.5 hours, at least 2.5 hour to 3 hours, at least 3 hour to 3.5 hours, at least 3.5 hour to 4 hours, at least 4 hour to 4.5 hours, at least 4.5 hour to 5 hours, at least 5 hour to 5.5 hours, at least 5.5 hour to 6 hours, at least 6 hour to 6.5 hours, at least 6.5 hour to 7 hours, at least 7 hour to 7.5 hours, at least 7.5 hour to 8 hours, at least 8 hour to 8.5 hours, at least 8.5 hour to 9 hours, at least 9 hour to 9.5 hours, or at least 9.5 hour to 10 hours.

A disease state may be identified with a sensitivity or specificity of about 80% or greater. The disease state may be identified with a sensitivity or specificity of about 85% or greater. The disease state may be identified with a sensitivity or specificity of about 90% or greater. The disease state may be identified with a sensitivity or specificity of about 95% or greater.

In some embodiments, any of the classifiers disclosed herein can be build using any of the biomarkers disclosed herein to determine whether a sample from a subject has a disease state selected from: healthy, co-morbid, NSCLC Stage 1, NSCLC Stage 2, NSCLC Stage 3, NSCLC Stage 4, or NSCLC Stages 1, 2, or 3. In some embodiments, the classifier is capable of distinguishing samples as healthy versus NSCLC Stages 1, 2, or 3 with a high sensitivity and high specificity. In some embodiments, the classifier is capable of distinguishing samples as co-morbid versus NSCLC Stages 1, 2, or 3 with a high sensitivity and high specificity.

The present disclosure provides a number of peptides which can be diagnostic of a cancerous or non-cancerous lung nodule. In some cases, the absence, presence, or abundance of a single peptide may be indicative of a particular cancer. However, in many cases, collective analysis of a plurality of peptides disclosed herein may yield considerably higher accuracy diagnoses. A method of the present disclosure may not only identify a cancer in a patient, but also the stage (e.g., stage I versus stage II, stage I versus stage III, early stage versus late stage), the degree of metastasis, and the tissue or site of origin. Furthermore, a method of the present disclosure may complement another form of analysis. For example, an immunohistological analysis of a tissue biopsy may be paired with a plasma proteomic analysis to increase the accuracy of a cancer diagnosis. Alternatively, a single method of the present disclosure may be sufficient for accurate cancer diagnosis.

An advantage of many of the methods of the present disclosure may be low invasiveness and minimal patient participation. In many cases, diagnostic peptides of the present disclosure may be identified in blood (e.g., whole blood, granulocyte, buffy coat, or plasma) samples, and may provide equal or greater diagnostic insight than intensive tissue biopsies or lengthy and expensive imaging procedures.

The methods described herein may include detection or discernment of a disease state. The disease state may comprise a lung cancer. The disease state may comprise lung cancer (e.g., a cancerous lung nodule). The disease state may comprise non-small cell lung cancer (NSCLC). The lung cancer may include NSCLC. The NSCLC may comprise early stage NSCLC (e.g., stage 1 NSCLC, stage 2 NSCLC, or stage 3 NSCLC). The NSCLC may comprise late stage NSCLC (e.g., stage 4 NSCLC).

A method described herein may include identifying a subject as having a disease state such as a cancer based on the biomarker measurements. Disclosed herein are methods of evaluating a status of a cancer. The method may include measuring biomarkers in a biological sample. The sample may be from a subject suspected of having the cancer. For example, the subject may be identified as having a lung nodule. The measurements may be to obtain biomarker measurements. The method may include obtaining the biomarker measurements. The biomarkers may include biomarkers described herein.

A method described herein may include identifying a biological sample from a subject as being indicative of a healthy state (e.g., a benign lung nodule), a cancer state (a cancerous lung nodule), or a comorbidity thereof (e.g., when subject has a benign lung nodule and a comorbidity) in the subject, based on biomarker measurements obtained in the subject. The cancer may be a lung cancer such as NSCLC. The method may include use of a classifier such as a classifier described herein. The method may distinguish the comorbidity from the cancer state. The method may distinguish the healthy state from the cancer state. The method may distinguish the comorbidity from the healthy state. The pulmonary comorbidity may include a disease other than the cancer.

A method described herein may identify or distinguish a comorbidity. The comorbidity may be a pulmonary comorbidity. The pulmonary comorbidity may include a lung disease other than the cancer. The pulmonary comorbidity may be selected from the group consisting of: chronic obstructive pulmonary disease (COPD), emphysema, cardiovascular disease, hypertension, pulmonary fibrosis, asthma, a chronic lung disease, and any combination thereof. The pulmonary comorbidity may include COPD. The pulmonary comorbidity may include emphysema. The pulmonary comorbidity may include a cardiovascular disease. The pulmonary comorbidity may include hypertension. The pulmonary comorbidity may include pulmonary fibrosis. The pulmonary comorbidity may include asthma. The pulmonary comorbidity may include a chronic lung disease.

Disclosed herein is a method for assaying one or more biomarkers in a sample from a subject suspected of having a cancerous lung nodule. The method may include measuring the one or more biomarkers in the sample. The measurement may include detecting a presence of the one or more biomarkers. The measurement may include detecting an absence of the one or more biomarkers. The measurement may include detecting an amount of the one or more biomarkers. The biomarkers may include any biomarkers described herein, for example a biomarker selected from the group consisting of: Angiopoietin-related protein 6 (ANGL6), Palmitoleoyl-protein carboxylesterase NOTUM (NOTUM), Cartilage intermediate layer protein 1 (CILP1), 60S acidic ribosomal protein P2 (RLA2), and Platelet glycoprotein Ib beta chain (GP1BB), or a peptide fragment thereof.

Disclosed herein is a method for assaying one or more biomarkers in a sample from a subject suspected of having a cancerous lung nodule comprising a non-small cell lung carcinoma (NSCLC). The measurement may include detecting a presence of the one or more biomarkers. The measurement may include detecting an absence of the one or more biomarkers. The measurement may include detecting an amount of the one or more biomarkers. The biomarkers may include any biomarkers described herein, for example a biomarker selected from the group consisting of: Angiopoietin-related protein 6 (ANGL6), Serine protease HTRA1 (HTRA1), Peroxidasin homolog (PXDN), C—C motif chemokine 18 (CCL18), Anthrax toxin receptor 2 (ANTR2), Tubulin alpha-1A chain (TBA1A), Syndecan-1 (SDC1), Serum amyloid A-2 protein (SAA2), Versican core protein (CSPG2), Anthrax toxin receptor 1 (ANTR1), Palmitoleoyl-protein carboxylesterase NOTUM (NOTUM), Cartilage intermediate layer protein 1 (CILP1), Calpain-2 catalytic subunit (CAN2), 60S acidic ribosomal protein P2 (RLA2), Beta-galactoside alpha-2,6-sialyltransferase 1 (SIAT1), or Platelet glycoprotein Ib beta chain (GP1BB), or a peptide fragment thereof.

A method may include comparing an amount of a biomarker to a control. The control may include an index. The control may include a threshold. The control may include a control sample from a control subject. In some cases, the control sample comprises a blood sample, a plasma sample, or a serum sample. In some cases, the control subject does not have the lung cancer. The control subject may have a lung nodule. The control subject may have a non-cancerous lung nodule.

In some cases, the lung cancer comprises a stage 1-4 NSCLC. In some cases, the subject has the lung cancer. In some cases, the control subject has a stage 1-4 NSCLC. In some cases, the NSCLC of the subject comprises a different stage than the NSCLC of the control subject.

The control subject may have a chronic lung disorder, chronic obstructive pulmonary disease, emphysema, cardiovascular disease, hypertension, pulmonary fibrosis, or asthma. The control subject may have a lung disorder. The control subject may have a chronic lung disorder. The control subject may have chronic obstructive pulmonary disease. The control subject may have emphysema. The control subject may have a cardiovascular disease. The control subject may have hypertension. The control subject may have fibrosis. The control subject may have pulmonary fibrosis. The control subject may have asthma.

A method may include identifying the subject as having the lung cancer, or as not having the lung cancer, based on the measurement of the one or more biomarkers. A method may include identifying a presence or absence of lung cancer cells or components thereof in the sample based on the measurement of the one or more biomarkers. A presence of the one or more biomarkers may be indicative of a presence of NSCLC cells or components thereof in the sample. A method may include identifying a likelihood of the subject having the lung cancer based on the measurement of the one or more biomarkers. A method may include identifying the subject as having the lung cancer based on the measurement of the one or more biomarkers. A method may include identifying the stage of the cancer based on the measurement.

A method may include assaying a biological sample from a subject to identify biomolecules. A method may include using a classifier to identify that the sample is positive for non-small cell lung cancer (NSCLC) based on the biomolecules identified. A method may include using a classifier to identify that the sample is negative for non-small cell lung cancer (NSCLC) based on the biomolecules identified. The classifier may be generated with data from samples assayed using a plurality of particles having physicochemically distinct properties to yield the data. The classifier may be trained using data from the sample, wherein the samples comprise known healthy samples and known NSCLC samples. The biomolecules may include proteins or biomarkers described herein. The data may include proteomic data identifying a presence or an absence of proteins in the samples. A lung nodule in a subject may be identified or monitored. For example, a cancerous lung nodule may be monitored for disease progression. A non-cancerous lung nodule may be monitored for disease progression. A non-cancerous lung nodule may be monitored to determine whether it becomes cancerous or not. The monitoring may be over time. For example, an assay described herein may be performed more than once on a subject, at two given times, in monitoring the subject. A subject may be monitored or identified.

Some aspects include obtaining a baseline measurement from the subject. Some aspects include obtaining a baseline biomarker measurement from the subject. Some embodiments include obtaining a measurement from the subject. Some embodiments include obtaining a biomarker measurement from the subject. Some embodiments include comparing the measurement to the baseline measurement. Some embodiments include comparing the biomarker measurement to the baseline biomarker measurement.

After using a classifier or trained algorithm to process the dataset, a lung nodule-related state (e.g., cancerous or non-cancerous) or lung nodule-related complication may be identified or monitored in the subject. A subject who has not been assessed using a classifier or trained algorithm may be identified or monitored. A lung nodule in a subject who has not been assessed using a classifier or trained algorithm may be identified or monitored. The identification may be based at least in part on quantitative measures of sequence reads of the dataset at a panel of lung nodule-related state-associated genomic loci (e.g., quantitative measures of RNA transcripts or DNA at the lung nodule-related state-associated genomic loci), proteomic data comprising quantitative measures of proteins of the dataset at a panel of lung nodule-related state-associated proteins, and/or metabolome data comprising quantitative measures of a panel of lung nodule-related state-associated metabolites.

The lung nodule-related state may be identified in the subject at an accuracy of at least about 50%, at least about 55%, at least about 60%, at least about 65%, at least about 70%, at least about 75%, at least about 80%, at least about 81%, at least about 82%, at least about 83%, at least about 84%, at least about 85%, at least about 86%, at least about 87%, at least about 88%, at least about 89%, at least about 90%, at least about 91%, at least about 92%, at least about 93%, at least about 94%, at least about 95%, at least about 96%, at least about 97%, at least about 98%, at least about 99%, or more. The accuracy of identifying the lung nodule-related state by the trained algorithm may be calculated as the percentage of independent test samples (e.g., subjects known to have the lung nodule-related state or subjects with negative clinical test results for the lung nodule-related state) that are correctly identified or classified as having or not having the lung nodule-related state.

The lung nodule-related state may be identified in the subject with a positive predictive value (PPV) of at least about 5%, at least about 10%, at least about 15%, at least about 20%, at least about 25%, at least about 30%, at least about 35%, at least about 40%, at least about 50%, at least about 55%, at least about 60%, at least about 65%, at least about 70%, at least about 75%, at least about 80%, at least about 81%, at least about 82%, at least about 83%, at least about 84%, at least about 85%, at least about 86%, at least about 87%, at least about 88%, at least about 89%, at least about 90%, at least about 91%, at least about 92%, at least about 93%, at least about 94%, at least about 95%, at least about 96%, at least about 97%, at least about 98%, at least about 99%, or more. The PPV of identifying the lung nodule-related state using the trained algorithm may be calculated as the percentage of biological samples identified or classified as having the lung nodule-related state that correspond to subjects that truly have the lung nodule-related state.

The lung nodule-related state may be identified in the subject with a negative predictive value (NPV) of at least about 5%, at least about 10%, at least about 15%, at least about 20%, at least about 25%, at least about 30%, at least about 35%, at least about 40%, at least about 50%, at least about 55%, at least about 60%, at least about 65%, at least about 70%, at least about 75%, at least about 80%, at least about 81%, at least about 82%, at least about 83%, at least about 84%, at least about 85%, at least about 86%, at least about 87%, at least about 88%, at least about 89%, at least about 90%, at least about 91%, at least about 92%, at least about 93%, at least about 94%, at least about 95%, at least about 96%, at least about 97%, at least about 98%, at least about 99%, or more. The NPV of identifying the lung nodule-related state using the trained algorithm may be calculated as the percentage of biological samples identified or classified as not having the lung nodule-related state that correspond to subjects that truly do not have the lung nodule-related state.

The lung nodule-related state may be identified in the subject with a clinical sensitivity of at least about 5%, at least about 10%, at least about 15%, at least about 20%, at least about 25%, at least about 30%, at least about 35%, at least about 40%, at least about 50%, at least about 55%, at least about 60%, at least about 65%, at least about 70%, at least about 75%, at least about 80%, at least about 81%, at least about 82%, at least about 83%, at least about 84%, at least about 85%, at least about 86%, at least about 87%, at least about 88%, at least about 89%, at least about 90%, at least about 91%, at least about 92%, at least about 93%, at least about 94%, at least about 95%, at least about 96%, at least about 97%, at least about 98%, at least about 99%, at least about 99.1%, at least about 99.2%, at least about 99.3%, at least about 99.4%, at least about 99.5%, at least about 99.6%, at least about 99.7%, at least about 99.8%, at least about 99.9%, at least about 99.99%, at least about 99.999%, or more. The clinical sensitivity of identifying the lung nodule-related state using the trained algorithm may be calculated as the percentage of independent test samples associated with presence of the lung nodule-related state (e.g., subjects known to have the lung nodule-related state) that are correctly identified or classified as having the lung nodule-related state.

The lung nodule-related state may be identified in the subject with a clinical specificity of at least about 5%, at least about 10%, at least about 15%, at least about 20%, at least about 25%, at least about 30%, at least about 35%, at least about 40%, at least about 50%, at least about 55%, at least about 60%, at least about 65%, at least about 70%, at least about 75%, at least about 80%, at least about 81%, at least about 82%, at least about 83%, at least about 84%, at least about 85%, at least about 86%, at least about 87%, at least about 88%, at least about 89%, at least about 90%, at least about 91%, at least about 92%, at least about 93%, at least about 94%, at least about 95%, at least about 96%, at least about 97%, at least about 98%, at least about 99%, at least about 99.1%, at least about 99.2%, at least about 99.3%, at least about 99.4%, at least about 99.5%, at least about 99.6%, at least about 99.7%, at least about 99.8%, at least about 99.9%, at least about 99.99%, or more. The clinical specificity of identifying the lung nodule-related state using the trained algorithm may be calculated as the percentage of independent test samples associated with absence of the lung nodule-related state (e.g., subjects with negative clinical test results for the lung nodule-related state) that are correctly identified or classified as not having the lung nodule-related state.

Some aspects of the present disclosure provide a method for determining that a subject is at risk of having malignant lung nodule, comprising assaying a biological sample derived from the subject to generate a dataset that is indicative of said risk of having malignant lung nodule at a specificity of at least 80%, and using a trained algorithm that is trained on samples independent of the biological sample to determine that the subject is at risk of having malignant lung nodule at an accuracy of at least about 50%, at least about 55%, at least about 60%, at least about 65%, at least about 70%, at least about 75%, at least about 80%, at least about 81%, at least about 82%, at least about 83%, at least about 84%, at least about 85%, at least about 86%, at least about 87%, at least about 88%, at least about 89%, at least about 90%, at least about 91%, at least about 92%, at least about 93%, at least about 94%, at least about 95%, at least about 96%, at least about 97%, at least about 98%, at least about 99%, or more.

After the lung nodule-related state is identified in a subject, a sub-type of the lung nodule-related state (e.g., selected from among a plurality of sub-types of the lung nodule-related state) may further be identified. The sub-type of the lung nodule-related state may be determined based at least in part on the quantitative measures of sequence reads of the dataset at a panel of lung nodule-related state-associated genomic loci (e.g., quantitative measures of RNA transcripts or DNA at the lung nodule-related state-associated genomic loci), proteomic data comprising quantitative measures of proteins of the dataset at a panel of lung nodule-related state-associated proteins, and/or metabolome data comprising quantitative measures of a panel of lung nodule-related state-associated metabolites.

In some embodiments, a classifier or trained algorithm may determine that the subject is at risk of having malignant lung nodule of at least about 5%, at least about 10%, at least about 15%, at least about 20%, at least about 25%, at least about 30%, at least about 35%, at least about 40%, at least about 50%, at least about 55%, at least about 60%, at least about 65%, at least about 70%, at least about 75%, at least about 80%, at least about 81%, at least about 82%, at least about 83%, at least about 84%, at least about 85%, at least about 86%, at least about 87%, at least about 88%, at least about 89%, at least about 90%, at least about 91%, at least about 92%, at least about 93%, at least about 94%, at least about 95%, at least about 96%, at least about 97%, at least about 98%, at least about 99%, or more.

The trained algorithm may determine that the subject is at risk of having malignant lung nodule at an accuracy of at least about 50%, at least about 55%, at least about 60%, at least about 65%, at least about 70%, at least about 75%, at least about 80%, at least about 81%, at least about 82%, at least about 83%, at least about 84%, at least about 85%, at least about 86%, at least about 87%, at least about 88%, at least about 89%, at least about 90%, at least about 91%, at least about 92%, at least about 93%, at least about 94%, at least about 95%, at least about 96%, at least about 97%, at least about 98%, at least about 99%, at least about 99.1%, at least about 99.2%, at least about 99.3%, at least about 99.4%, at least about 99.5%, at least about 99.6%, at least about 99.7%, at least about 99.8%, at least about 99.9%, at least about 99.99%, at least about 99.999%, or more.

Upon identifying the subject as having the lung nodule-related state, the subject may be optionally provided with a therapeutic intervention (e.g., prescribing an appropriate course of treatment to treat the lung nodule-related state of the subject). The therapeutic intervention may comprise a prescription of an effective dose of a drug, a further testing or evaluation of the lung nodule-related state, a further monitoring of the lung nodule-related state, an induction or inhibition of labor, or a combination thereof. If the subject is currently being treated for the lung nodule-related state with a course of treatment, the therapeutic intervention may comprise a subsequent different course of treatment (e.g., to increase treatment efficacy due to non-efficacy of the current course of treatment).

The therapeutic intervention may comprise recommending the subject for a secondary clinical test to confirm a diagnosis of the lung nodule-related state. This secondary clinical test may comprise an imaging test, a blood test, a computed tomography (CT) scan, a magnetic resonance imaging (MRI) scan, an ultrasound scan, a chest X-ray, a positron emission tomography (PET) scan, a PET-CT scan, a cell-free biological cytology, an amniocentesis, a non-invasive prenatal test (NIPT), or any combination thereof. The secondary clinical test may comprise a CT scan.

The quantitative measures of sequence reads of the dataset at the panel of lung nodule-related state-associated genomic loci (e.g., quantitative measures of RNA transcripts or DNA at the lung nodule-related state-associated genomic loci), proteomic data comprising quantitative measures of proteins of the dataset at a panel of lung nodule-related state-associated proteins, and/or metabolome data comprising quantitative measures of a panel of lung nodule-related state-associated metabolites may be assessed over a duration of time to monitor a patient (e.g., subject who has a lung nodule-related state or who is being treated for lung nodule-related state). In such cases, the quantitative measures of the dataset of the patient may change during the course of treatment. For example, the quantitative measures of the dataset of a patient with decreasing risk of the lung nodule-related state due to an effective treatment may shift toward the profile or distribution of a healthy subject (e.g., a subject without a lung nodule-related complication). Conversely, for example, the quantitative measures of the dataset of a patient with increasing risk of the lung nodule-related state due to an ineffective treatment may shift toward the profile or distribution of a subject with higher risk of the lung nodule-related state or a more advanced lung nodule-related state.

The lung nodule-related state of the subject may be monitored by monitoring a course of treatment for treating the lung nodule-related state of the subject. The monitoring may comprise assessing the lung nodule-related state of the subject at two or more time points. The assessing may be based at least on the quantitative measures of sequence reads of the dataset at a panel of lung nodule-related state-associated genomic loci (e.g., quantitative measures of RNA transcripts or DNA at the lung nodule-related state-associated genomic loci), proteomic data comprising quantitative measures of proteins of the dataset at a panel of lung nodule-related state-associated proteins, and/or metabolome data comprising quantitative measures of a panel of lung nodule-related state-associated metabolites determined at each of the two or more time points.

In some embodiments, a difference in the quantitative measures of sequence reads of the dataset at a panel of lung nodule-related state-associated genomic loci (e.g., quantitative measures of RNA transcripts or DNA at the lung nodule-related state-associated genomic loci), proteomic data comprising quantitative measures of proteins of the dataset at a panel of lung nodule-related state-associated proteins, and/or metabolome data comprising quantitative measures of a panel of lung nodule-related state-associated metabolites determined between the two or more time points may be indicative of one or more clinical indications, such as (i) a diagnosis of the lung nodule-related state of the subject, (ii) a prognosis of the lung nodule-related state of the subject, (iii) an increased risk of the lung nodule-related state of the subject, (iv) a decreased risk of the lung nodule-related state of the subject, (v) an efficacy of the course of treatment for treating the lung nodule-related state of the subject, and (vi) a non-efficacy of the course of treatment for treating the lung nodule-related state of the subject.

In some embodiments, a difference in the quantitative measures of sequence reads of the dataset at a panel of lung nodule-related state-associated genomic loci (e.g., quantitative measures of RNA transcripts or DNA at the lung nodule-related state-associated genomic loci), proteomic data comprising quantitative measures of proteins of the dataset at a panel of lung nodule-related state-associated proteins, and/or metabolome data comprising quantitative measures of a panel of lung nodule-related state-associated metabolites determined between the two or more time points may be indicative of a diagnosis of the lung nodule-related state of the subject. For example, if the lung nodule-related state was not detected in the subject at an earlier time point but was detected in the subject at a later time point, then the difference is indicative of a diagnosis of the lung nodule-related state of the subject. A clinical action or decision may be made based on this indication of diagnosis of the lung nodule-related state of the subject, such as, for example, prescribing a new therapeutic intervention for the subject. The clinical action or decision may comprise recommending the subject for a secondary clinical test to confirm the diagnosis of the lung nodule-related state. This secondary clinical test may comprise an imaging test, a blood test, a computed tomography (CT) scan, a magnetic resonance imaging (MRI) scan, an ultrasound scan, a chest X-ray, a positron emission tomography (PET) scan, a PET-CT scan, a cell-free biological cytology, an amniocentesis, a non-invasive prenatal test (NIPT), or any combination thereof.

In some embodiments, a difference in the quantitative measures of sequence reads of the dataset at a panel of lung nodule-related state-associated genomic loci (e.g., quantitative measures of RNA transcripts or DNA at the lung nodule-related state-associated genomic loci), proteomic data comprising quantitative measures of proteins of the dataset at a panel of lung nodule-related state-associated proteins, and/or metabolome data comprising quantitative measures of a panel of lung nodule-related state-associated metabolites determined between the two or more time points may be indicative of a prognosis of the lung nodule-related state of the subject.

In some embodiments, a difference in the quantitative measures of sequence reads of the dataset at a panel of lung nodule-related state-associated genomic loci (e.g., quantitative measures of RNA transcripts or DNA at the lung nodule-related state-associated genomic loci), proteomic data comprising quantitative measures of proteins of the dataset at a panel of lung nodule-related state-associated proteins, and/or metabolome data comprising quantitative measures of a panel of lung nodule-related state-associated metabolites determined between the two or more time points may be indicative of the subject having an increased risk of the lung nodule-related state. For example, if the lung nodule-related state was detected in the subject both at an earlier time point and at a later time point, and if the difference is a negative difference (e.g., the quantitative measures of sequence reads of the dataset at a panel of lung nodule-related state-associated genomic loci (e.g., quantitative measures of RNA transcripts or DNA at the lung nodule-related state-associated genomic loci), proteomic data comprising quantitative measures of proteins of the dataset at a panel of lung nodule-related state-associated proteins, and/or metabolome data comprising quantitative measures of a panel of lung nodule-related state-associated metabolites increased from the earlier time point to the later time point), then the difference may be indicative of the subject having an increased risk of the lung nodule-related state. A clinical action or decision may be made based on this indication of the increased risk of the lung nodule-related state, e.g., prescribing a new therapeutic intervention or switching therapeutic interventions (e.g., ending a current treatment and prescribing a new treatment) for the subject. The clinical action or decision may comprise recommending the subject for a secondary clinical test to confirm the increased risk of the lung nodule-related state. This secondary clinical test may comprise an imaging test, a blood test, a computed tomography (CT) scan, a magnetic resonance imaging (MRI) scan, an ultrasound scan, a chest X-ray, a positron emission tomography (PET) scan, a PET-CT scan, a cell-free biological cytology, an amniocentesis, a non-invasive prenatal test (NIPT), or any combination thereof.

In some embodiments, a difference in the quantitative measures of sequence reads of the dataset at a panel of lung nodule-related state-associated genomic loci (e.g., quantitative measures of RNA transcripts or DNA at the lung nodule-related state-associated genomic loci), proteomic data comprising quantitative measures of proteins of the dataset at a panel of lung nodule-related state-associated proteins, and/or metabolome data comprising quantitative measures of a panel of lung nodule-related state-associated metabolites determined between the two or more time points may be indicative of the subject having a decreased risk of the lung nodule-related state. For example, if the lung nodule-related state was detected in the subject both at an earlier time point and at a later time point, and if the difference is a positive difference (e.g., the quantitative measures of sequence reads of the dataset at a panel of lung nodule-related state-associated genomic loci (e.g., quantitative measures of RNA transcripts or DNA at the lung nodule-related state-associated genomic loci), proteomic data comprising quantitative measures of proteins of the dataset at a panel of lung nodule-related state-associated proteins, and/or metabolome data comprising quantitative measures of a panel of lung nodule-related state-associated metabolites decreased from the earlier time point to the later time point), then the difference may be indicative of the subject having a decreased risk of the lung nodule-related state. A clinical action or decision may be made based on this indication of the decreased risk of the lung nodule-related state (e.g., continuing or ending a current therapeutic intervention) for the subject. The clinical action or decision may comprise recommending the subject for a secondary clinical test to confirm the decreased risk of the lung nodule-related state. This secondary clinical test may comprise an imaging test, a blood test, a computed tomography (CT) scan, a magnetic resonance imaging (MRI) scan, an ultrasound scan, a chest X-ray, a positron emission tomography (PET) scan, a PET-CT scan, a cell-free biological cytology, an amniocentesis, a non-invasive prenatal test (NIPT), or any combination thereof.

In some embodiments, a difference in the quantitative measures of sequence reads of the dataset at a panel of lung nodule-related state-associated genomic loci (e.g., quantitative measures of RNA transcripts or DNA at the lung nodule-related state-associated genomic loci), proteomic data comprising quantitative measures of proteins of the dataset at a panel of lung nodule-related state-associated proteins, and/or metabolome data comprising quantitative measures of a panel of lung nodule-related state-associated metabolites determined between the two or more time points may be indicative of an efficacy of the course of treatment for treating the lung nodule-related state of the subject. For example, if the lung nodule-related state was detected in the subject at an earlier time point but was not detected in the subject at a later time point, then the difference may be indicative of an efficacy of the course of treatment for treating the lung nodule-related state of the subject. A clinical action or decision may be made based on this indication of the efficacy of the course of treatment for treating the lung nodule-related state of the subject, e.g., continuing or ending a current therapeutic intervention for the subject. The clinical action or decision may comprise recommending the subject for a secondary clinical test to confirm the efficacy of the course of treatment for treating the lung nodule-related state. This secondary clinical test may comprise an imaging test, a blood test, a computed tomography (CT) scan, a magnetic resonance imaging (MRI) scan, an ultrasound scan, a chest X-ray, a positron emission tomography (PET) scan, a PET-CT scan, a cell-free biological cytology, an amniocentesis, a non-invasive prenatal test (NIPT), or any combination thereof.

In some embodiments, a difference in the quantitative measures of sequence reads of the dataset at a panel of lung nodule-related state-associated genomic loci (e.g., quantitative measures of RNA transcripts or DNA at the lung nodule-related state-associated genomic loci), proteomic data comprising quantitative measures of proteins of the dataset at a panel of lung nodule-related state-associated proteins, and/or metabolome data comprising quantitative measures of a panel of lung nodule-related state-associated metabolites determined between the two or more time points may be indicative of a non-efficacy of the course of treatment for treating the lung nodule-related state of the subject. For example, if the lung nodule-related state was detected in the subject both at an earlier time point and at a later time point, and if the difference is a negative or zero difference (e.g., the quantitative measures of sequence reads of the dataset at a panel of lung nodule-related state-associated genomic loci (e.g., quantitative measures of RNA transcripts or DNA at the lung nodule-related state-associated genomic loci), proteomic data comprising quantitative measures of proteins of the dataset at a panel of lung nodule-related state-associated proteins, and/or metabolome data comprising quantitative measures of a panel of lung nodule-related state-associated metabolites increased or remained at a constant level from the earlier time point to the later time point), and if an efficacious treatment was indicated at an earlier time point, then the difference may be indicative of a non-efficacy of the course of treatment for treating the lung nodule-related state of the subject. A clinical action or decision may be made based on this indication of the non-efficacy of the course of treatment for treating the lung nodule-related state of the subject, e.g., ending a current therapeutic intervention and/or switching to (e.g., prescribing) a different new therapeutic intervention for the subject. The clinical action or decision may comprise recommending the subject for a secondary clinical test to confirm the non-efficacy of the course of treatment for treating the lung nodule-related state. This secondary clinical test may comprise an imaging test, a blood test, a computed tomography (CT) scan, a magnetic resonance imaging (MRI) scan, an ultrasound scan, a chest X-ray, a positron emission tomography (PET) scan, a PET-CT scan, a cell-free biological cytology, an amniocentesis, a non-invasive prenatal test (NIPT), or any combination thereof.

In another aspect, the present disclosure provides a computer-implemented method for predicting a risk of having malignant lung nodule of a subject, comprising: (a) receiving clinical health data of the subject, wherein the clinical health data comprises a plurality of quantitative or categorical measures of said subject; (b) using a trained algorithm to process the clinical health data of the subject to determine a risk score indicative of the risk of having malignant lung nodule of the subject; and (c) electronically outputting a report indicative of the risk score indicative of the risk of having malignant lung nodule of the subject.

In some embodiments, for example, the clinical health data comprises one or more quantitative measures of the subject, such as age, weight, height, body mass index (BMI), blood pressure, heart rate, glucose levels, or a combination thereof. As another example, the clinical health data can comprise one or more categorical measures, such as race, ethnicity, history of medication or other clinical treatment, history of tobacco use, history of alcohol consumption, daily activity or fitness level, genetic test results, blood test results, or imaging results.

In some embodiments, the computer-implemented method for predicting a risk of having malignant lung nodule of a subject is performed using a computer or mobile device application. For example, a subject can use a computer or mobile device application to input her own clinical health data, including quantitative and/or categorical measures. The computer or mobile device application can then use a trained algorithm to process the clinical health data to determine a risk score indicative of the risk of having malignant lung nodule of the subject. The computer or mobile device application can then display a report indicative of the risk score indicative of the risk of having malignant lung nodule of the subject.

Kits

Various aspects of the present disclosure provide kits for detecting (e.g., quantifying) biomarkers disclosed herein. A kit may comprise a reagent for detecting a protein, peptide, or other biomolecule from Table 2, or another table or figure. An example of such a reagent may include an anti-SAA2 antibody. A kit may comprise multiple reagents for detecting multiple proteins, peptides, or other biomolecules. A kit may comprise reagents for an immunoassay (e.g. ELISA). A kit may also comprise a reagent for detecting a biomolecule not useful as a biomarker for a lung cancer. For example, a kit may comprise reagents for quantifying ANTR1 and ANTR2 in a biological sample, as well as a reagent for quantifying ceruloplasmin, such that the ANTR1- and ANTR2-specific reagents generate lung cancer-specific information from the sample, and the ceruloplasmin-specific agent is configured to serve as a calibration standard or control. A kit may comprise reagents for detecting at least one biomarker, at least two biomarkers, at least three biomarkers, at least four biomarkers, at least five biomarkers, at least six biomarkers, at least eight biomarkers, at least ten biomarkers, at least twelve biomarkers, at least fifteen biomarkers, at least twenty biomarkers, at least twenty five biomarkers, at least thirty biomarkers, at least forty biomarkers, at least forty five biomarkers, at least fifty biomarkers disclosed herein. Any number of biomarkers may be used. The biomarkers may optionally include biomarkers not disclosed herein. A kit may comprise immunoassay (e.g. ELISA) reagents for detecting at least one, at least two, at least three, at least four, at least five, at least six, at least eight, at least ten, at least twelve, at least fifteen, at least twenty, at least twenty five, at least thirty, or at least forty biomarkers listed or described herein, and optionally for at least one biomarker not listed or described herein.

A kit may comprise a particle or a particle panel. Particles from the particle panel may be provided collectively (e.g., as a mixture) or separately. For example, a kit may comprise a particle panel with 8 particle-types, each particle-type provided in a separate well within a 96-well plate. A kit may comprise a particle panel comprising at least one, at least two, at least three, at least four, at least five, at least six, at least eight, at least ten, at least twelve, or at least fifteen particles from among the particles in Table 1. A kit may comprise multiple compositions comprising the same particle or plurality of particles in different conditions (e.g., mixed with or suspended in different buffers or solutions) or in different amounts. For example, a well plate may comprise a set of wells with 20 µg of a particle, a set of wells with 40 µg of the particle, and a set of wells with 80 µg of the particle. A kit may comprise a buffer for suspending a particle, eluting a biomolecule from a particle, or for washing a particle. A kit may comprise a reagent for chemically modifying (e.g., a reductant) or digesting (e.g., a protease) a protein. A kit may comprise a plurality of reagents for enriching a subset of proteins from a sample (e.g., a particle panel) and preparing the subset of proteins for mass spectrometric analysis (e.g., trypsin, a buffer, an alkylating reagent, and a reductant). A kit may comprise a reagent for lysing a virus or a cell (e.g., a lysis buffer).

A kit may be configured for multiplexed analysis. A kit may comprise a plurality of reagents, and may be configured to interrogate multiple portions of a biological sample under different conditions or with different reagents. A kit may comprise a plurality of partitions, such as a plurality of wells within a well plate or a plurality of Eppendorf tubes. A partition may be pre-packaged with a reagent. For example, a kit may comprise a well plate with a plurality of wells containing different affinity reagents specific for different proteins, peptides, or other biomolecules disclosed herein.

A kit may be compatible for use with a commercial instrument. For example, a kit may comprise a well plate configured for fluorescence measurements in a microplate reader, or may comprise a sample vial compatible with a commercial mass spectrometer.

Certain Terminology

Use of absolute or sequential terms, for example, "will," "will not," "shall," "shall not," "must," "must not," "first," "initially," "next," "subsequently," "before," "after," "lastly," and "finally," are not meant to limit scope of the present embodiments disclosed herein but as an example.

As used herein, the singular forms "a", "an" and "the" are intended to include the plural forms as well, unless the context clearly indicates otherwise. Furthermore, to the extent that the terms "including", "includes", "having", "has", "with", or variants thereof are used in either the detailed description and/or the claims, such terms are intended to be inclusive in a manner similar to the term "comprising."

As used herein, the phrases "at least one", "one or more", and "and/or" are open-ended expressions that are both conjunctive and disjunctive in operation. For example, each of the expressions "at least one of A, B and C", "at least one of A, B, or C", "one or more of A, B, and C", "one or more of A, B, or C" and "A, B, and/or C" means A alone, B alone, C alone, A and B together, A and C together, B and C together, or A, B and C together.

As used herein, "or" may refer to "and", "or," or "and/or" and may be used both exclusively and inclusively. For example, the term "A or B" may refer to "A or B", "A but not B", "B but not A", and "A and B". In some cases, context may dictate a particular meaning.

Any systems, methods, software, and platforms described herein are modular. Accordingly, terms such as "first" and "second" do not necessarily imply priority, order of importance, or order of acts.

The term "about" when referring to a number or a numerical range means that the number or numerical range referred to is an approximation within experimental variability (or within statistical experimental error), and the number or numerical range may vary from, for example, from 1% to 15% of the stated number or numerical range. In examples, the term "about" refers to +10% of a stated number or value.

The terms "increased", "increasing", or "increase" are used herein to generally mean an increase by a statically significant amount. In some aspects, the terms "increased," or "increase," mean an increase of at least 10% as compared to a reference level, for example an increase of at least about 10%, at least about 20%, or at least about 30%, or at least about 40%, or at least about 50%, or at least about 60%, or at least about 70%, or at least about 80%, or at least about 90% or up to and including a 100% increase or any increase between 10-100% as compared to a reference level, standard, or control. Other examples of "increase" include an increase of at least 2-fold, at least 5-fold, at least 10-fold, at least 20-fold, at least 50-fold, at least 100-fold, at least 1000-fold or more as compared to a reference level.

The terms "decreased", "decreasing", or "decrease" are used herein generally to mean a decrease by a statistically significant amount. In some aspects, "decreased" or "decrease" means a reduction by at least 10% as compared to a reference level, for example a decrease by at least about 20%, or at least about 30%, or at least about 40%, or at least about 50%, or at least about 60%, or at least about 70%, or at least about 80%, or at least about 90% or up to and including a 100% decrease (e.g., absent level or non-detectable level as compared to a reference level), or any decrease between 10-100% as compared to a reference level. In the context of a marker or symptom, by these terms is meant a statistically significant decrease in such level. The decrease can be, for example, at least 10%, at least 20%, at least 30%, at least 40% or more, and is preferably down to a level accepted as within the range of normal for an individual without a given disease.

EXAMPLES

The following illustrative examples are representative of aspects of classifiers, systems, or methods described herein and are not meant to be limiting in any way.

Example 1. Generating Classifiers with Multi-Omic and Clinical Datasets

Combining different omics types will lead to unprecedented results in terms of scale, diversity, and richness. Experiments will proceed using samples from numerous subjects. Each sample will be profiled to derive genomic, transcriptomic, proteomic, metabolomic and lipidomic results, and these molecular results will be combined with clinical information. Artificial intelligence may be used to discover patterns and interactions that drive clinical differences. Deep learning algorithms will be developed that may include aspects of computer vision, natural language processing, or unsupervised learning to discover patterns in the results and identify biomarkers which can help drive discrimination of disease states in subjects. The methods may be used widely across the process from processing raw results to developing robust classifiers.

Example 2. Multi-Omics Classifiers

An ensemble of classifiers is trained to make a cancer/healthy call based on features from proteomic, metabolomic, genomic, and transcriptomic results. Each classifier takes a combination of features from the n omics for a total of ($2^n-1$) different classifiers. Further, each classifier can be a stand-alone machine learning model, or an ensemble of machine-learning models trained on the same input features. An example diagram showing some aspects that may be included in some methods and classifiers disclosed herein is shown in FIG. 5.

A final call is made by one of the following methods:
Picking output of any one of the trained classifiers.
Majority voting across all classifiers or a subset of classifiers.
Weighted average of outputs of all classifiers or subset of classifiers with weights assigned based on one (or a combination) of the following:
1. Area Under ROC Curve
2. Area Under Precision-Recall Curve
3. Accuracy
4. Precision
5. Recall/Sensitivity
6. F1-score
7. Specificity Example 3. Multi-Omics Analyses for Improving Diagnosis of a Disease State Using RNAs and Proteins Multi-omics studies utilizing the methods described herein were used to generate classifiers for accurately diagnosing a disease state. To exemplify the methods described herein for identifying a disease state such as a lung cancer, 30 samples from healthy human ("control") subjects and 30 samples from subjects with late-stage NSCLC (8 samples of Stage 3b/c and 22 samples of Stage 4) ("affected") were analyzed. A hypothesis for this study was that combining data types (e.g., mRNA and/or miRNA with protein levels) could improve disease state classification such as cancer or lung cancer classification. Similarly, combining data types could be useful for determining a likelihood of a lung nodule being cancerous.

Biofluid samples were collected in EDTA plasma tubes, serum tubes, PAXgene RNA tubes, and Streck Blood Cell Collection tubes. For obtaining plasma, blood was collected into EDTA plasma tubes and centrifuged within 1 h of collection, and the plasma fraction was aspirated and frozen within one hour of centrifugation prior to initial storage at −70° C. and subsequent shipment on dry ice. Study plasma samples were thawed at 4° C., realiquoted, and refrozen once prior to generation of results. Proteomic results were generated after contacting plasma samples with particles to adsorb proteins from the plasma onto a corona around each particle, thereby obtaining adsorbed proteins for mass spectrometry analysis, as disclosed in Blume et al., "Rapid, deep and precise profiling of the plasma proteome with multi-nanoparticle protein corona," Nat Comms. (2020) 11:3662 (hereinafter "Blume 2020"). The particles used here, selected for a panel in Blume 2020, included 5 physiochemically distinct particle types (designated "NP1," "NP2," "NP3," "NP4," and "NP5"). These particles were purchased commercially from Seer, Inc. where they were identified as S-003, S-006, S-007, P-039, and P-073, respectively. The mass spectrometry analysis included the use of liquid chromatography-mass spectrometry (LC-MS). MicroRNA and mRNA results were obtained from biofluid samples using RNA sequencing. The biofluid samples used for the analysis of microRNA and mRNA were full blood samples collected in PAXgene RNA tubes (although use of other biofluid sample types such as plasma or serum are also envisioned). PAXgene RNA tubes include an RNA stabilization reagent. Separate sequencing libraries were prepared for obtaining microRNA and mRNA results.

Figure 6:
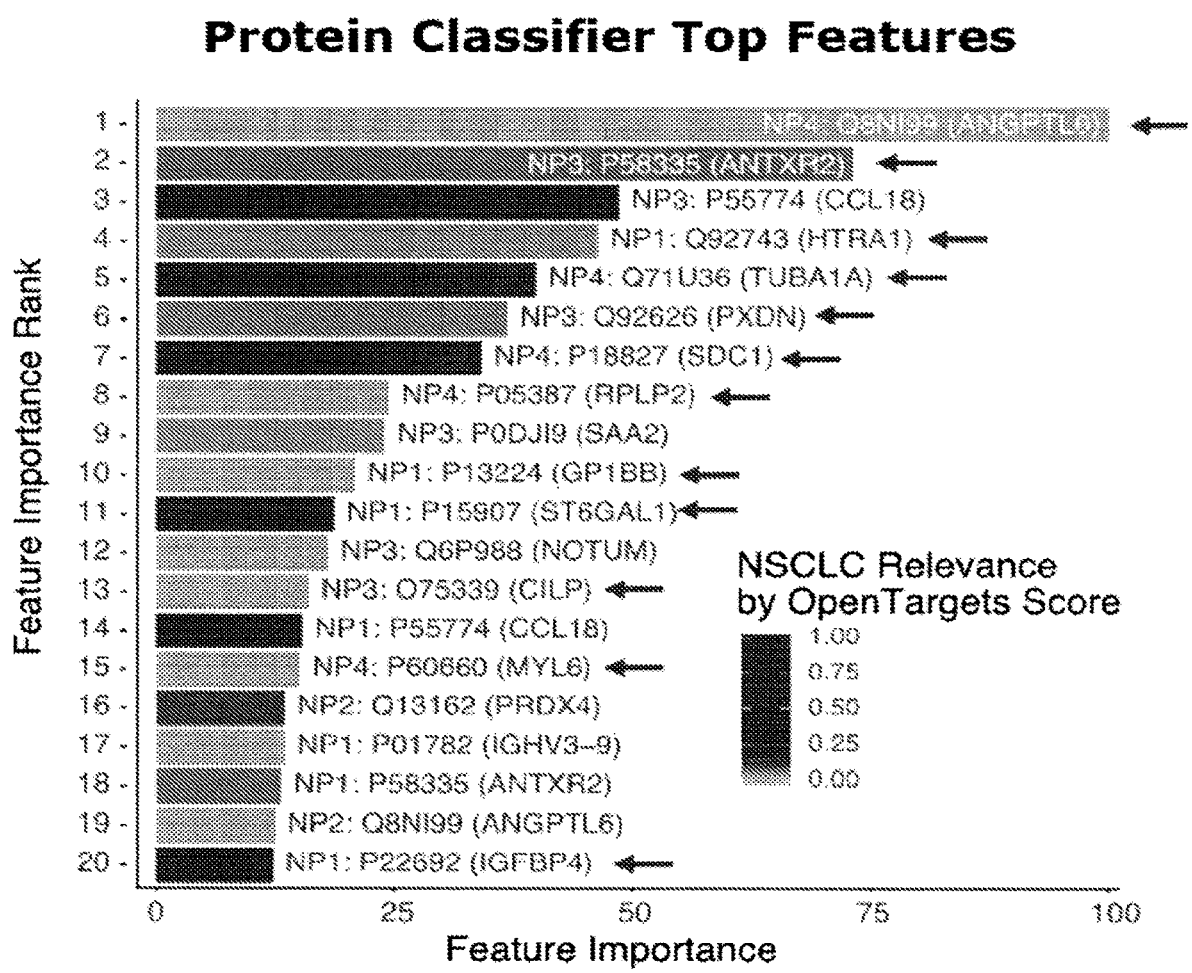
FIG. 6 shows a graph describing differential expression of some proteins that may be used to generate a classifier to diagnosing a disease state.

FIG. 6 and FIG. 7 illustrate differential protein expression of multiple genes between healthy or NSCLC samples used for classifier generation in Blume 2020. Blume 2020 measured protein abundances from 141 samples of early stage NSCLC and healthy samples and trained a classifier to distinguish between cancer and healthy states, and obtained an AUC ROC of approximately 0.91. The top 20 features in that study for classifying healthy versus early NSCLC are included in FIG. 6, with the bar darkness showing the associated Open Targets Scores for lung carcinoma targets. The genes annotated in FIG. 6 and FIG. 7 drove classification in Blume 2020, but additional differentially expressed genes were also discovered here (e.g., circled in FIG. 7) that were under or over expressed in samples of healthy patients versus patients with lung cancer. The additional genes (e.g., expression levels of RNA or protein) may be further analyzed using multi-omics methods described herein. The genes in FIG. 7 include SDC1, PXDN, HTRA1, CILP, ANGPTL6, IGFBP4, GP1BB, MYL6, ANTXR2, TUBA1A, ST6GAL1, and RPLP2.

Figure 8:
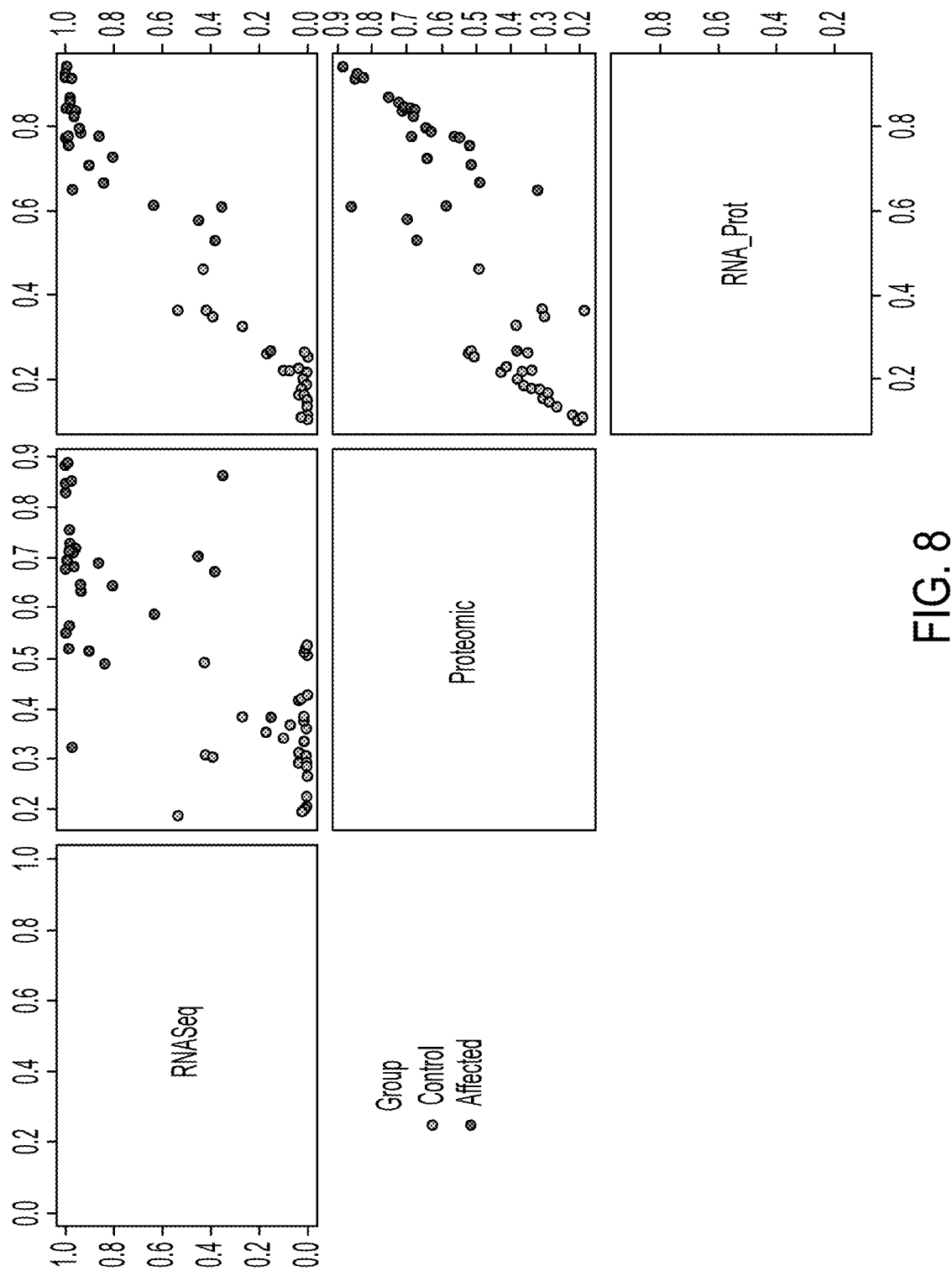
FIG. 8 shows scatterplot pairs plot predictions against one another in pairs. RNASeq: predicted probability (Affected) based on RNA-Seq Data; Proteomic: predicted probability (Affected) based on Proteomic Data; and RNA_Prot: predicted probability (Affected) based on both RNA-Seq and Proteomic Data.
Figure 9:
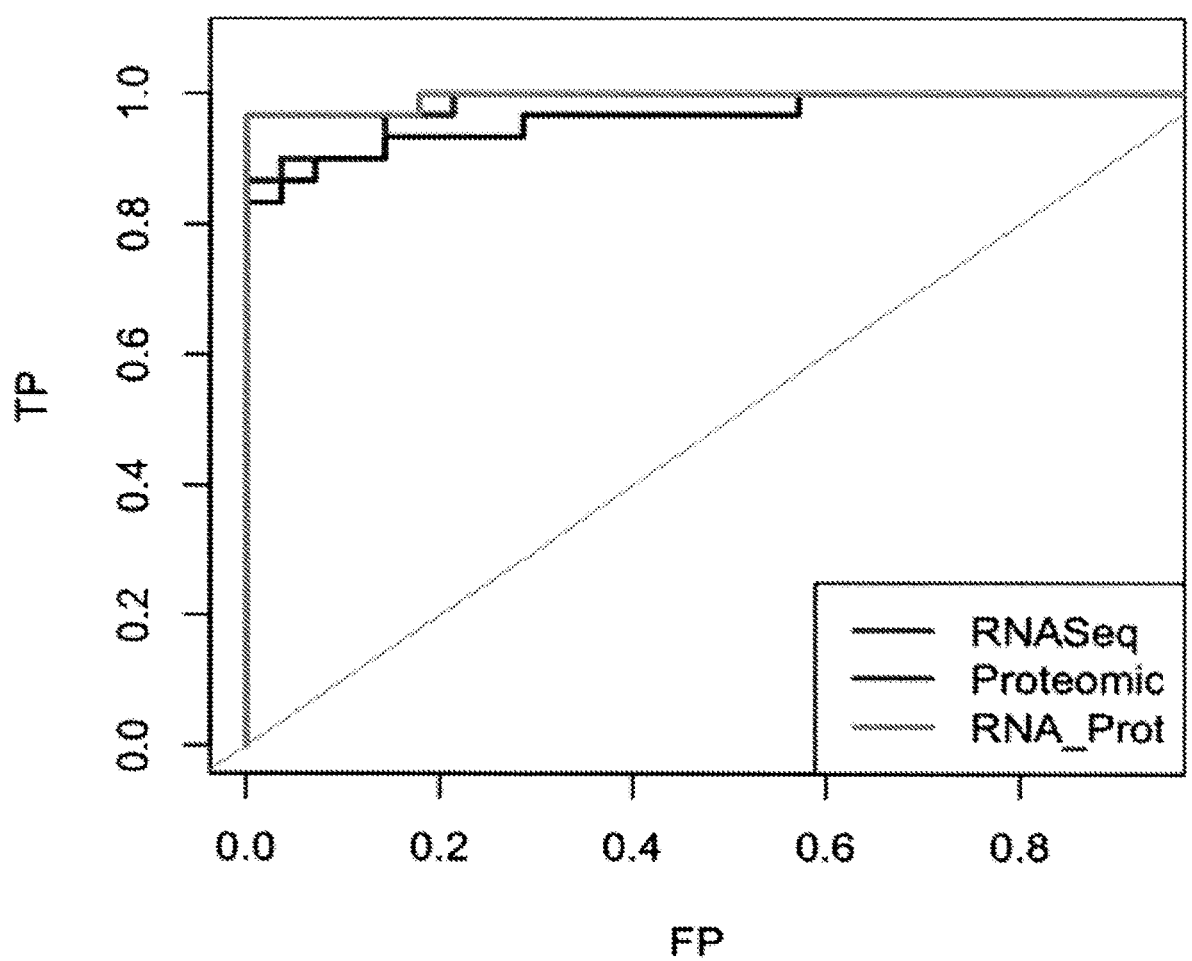
FIG. 9 includes receiver operating characteristic (ROC) curves, and shows an increased area under the curve (AUC) for combined mRNA transcriptomic data and proteomic data compared to either mRNA transcriptomic data or proteomic data alone.
Figure 10A:
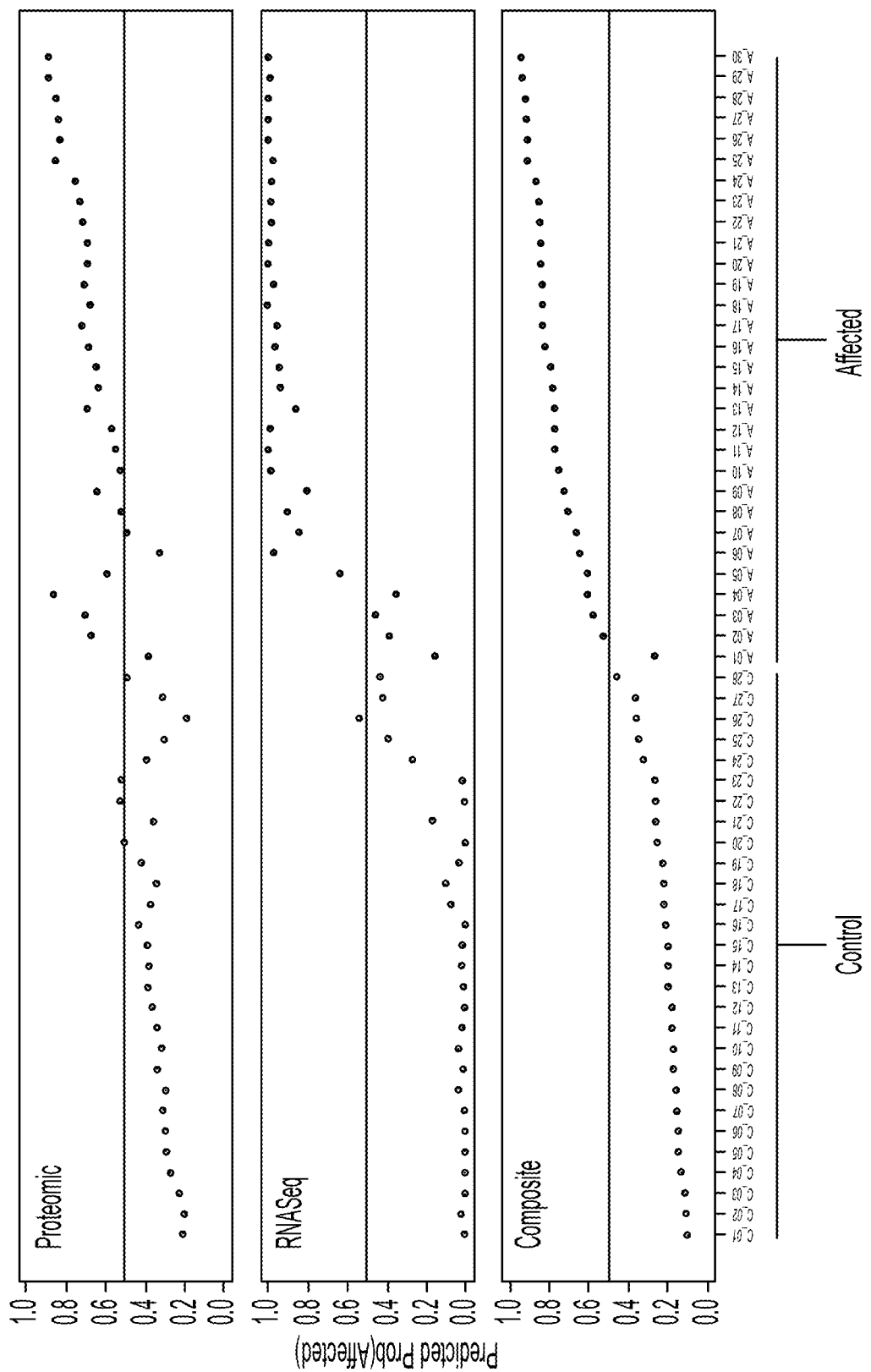
FIG. 10A shows additive multi-omics classification of 30 samples from subjects with a disease state and 30 samples from control subjects, and includes mRNA transcriptomic data, proteomic data, and combined mRNA transcriptomic and proteomic data.

FIG. 8, FIG. 9, and FIG. 10A illustrate increased accuracy for diagnosing a disease state by analyzing biomolecules by a multi-omics approach as opposed to analysis based on only one dataset (e.g., only one dataset selected from proteomic results, metabolomic results, transcriptomic results, or genomic results). In this example, the disease state was NSCLC. FIG. 8 and FIG. 10A illustrate scatter plots of samples obtained from a control group and an affected (subjects with lung cancer) group, where overlapping of the scatters between the samples of these two groups were observed based on analysis of mRNA transcriptomic results ("RNASeq") and proteomic results ("Proteomic"). The overlap was decreased when the analysis was based on a combination of both mRNA transcriptomic results and proteomic results ("RNA_Prot" or "Composite"). The combined RNA_Prot analysis included an average of output probabilities generated by separate classifiers for each result type (here: mRNA and proteomic results). FIG. 9 illustrates increased ROC, AUC, and TP (true positive), and decreased FP (false positive) in identifying biofluid samples as coming from subjects having lung cancer when the combined classification results of both mRNA transcriptomic results and proteomic results were analyzed compared to the mRNA transcriptomic results or proteomic results alone.

FIG. 10A shows some results of classifier training, and composite results generated by averaging the results of each classifier. The figure illustrates that classifiers accurately identified samples as being from healthy subjects or subjects with NSCLC, and that combining mRNA transcriptomic results and proteomic results increased the accuracy. The X axis illustrates the 60 samples, healthy in light gray and NSCLC in dark gray. The horizontal line in the middle of each plot indicates a classification threshold of 0.5. Samples above the line were classified as NSCLC, and those below were classified as healthy. Out in the wings of the plots, the separate proteomic results and mRNA classifiers were accurate, but in the middle there were miss calls. But when combine results from the two omics data types were combined, that classification accuracy improved. The missed calls (e.g., false positives or false negatives) in the proteomics classifier were corrected by the mRNA classifier, and vice versa, indicating that the two datasets were complementary. FIG. 10B shows feature importance for separate classifiers trained on the two datasets, which show again that the features driving discrimination did not have overlap and were therefore complementary.

Combining proteomic results with small non-coding RNA results (mostly microRNA results, and referred to here as microRNA results) resulted in a similar pattern where the combined results were used to more accurately identify a disease state than the individual data types. FIG. 11A illustrates that combining proteomic results ("Proteomic") and microRNA (miRNA) results ("miRNABlood") resulted in more accurate identification of sample as being from the healthy sample group or the NSCLC sample group. The composite analysis for microRNA and proteomic results included an average of output probabilities generated by separate classifiers for each data type (here: miRNA and proteomic results). The combined classification results are shown in the bottom panel of the figure and are labeled with the term, "Composite." Similar to the combination of mRNA and proteomic results, missed calls (e.g., false positives or false negatives) associated with one dataset was corrected by another when combining miRNA results with proteomic results. FIG. 11B illustrates differential expression of some microRNAs that were used in classifier generation. The microRNA results included piwi interacting RNA (piR)-35549.

Figure 12:
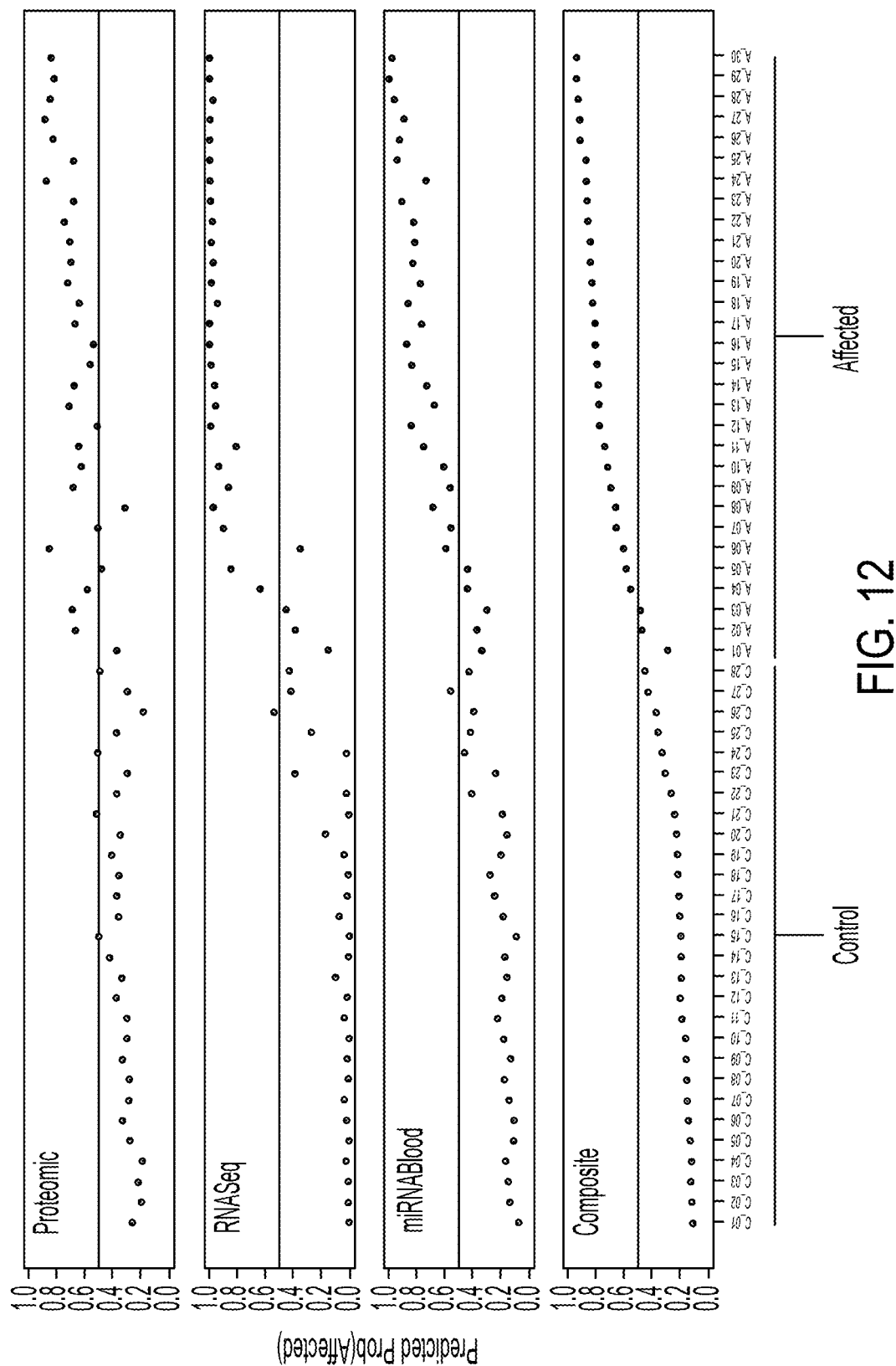
FIG. 12 shows analyses that compare combining three omics data types (proteomic, mRNA, and miRNA) relative to using only one of each of the three data types.

A further composite analysis was performed for mRNA, miRNA and proteomic results, in which an average of output probabilities generated by separate classifiers for each result type (here: mRNA, microRNA and proteomic results). FIG. 12 illustrates that composite results generated from analyzing a combination of the proteomic results, mRNA results, and microRNA results were even more accurate and robust in identifying the samples compared to the classifiers from FIG. 10A or FIG. 11A. Classification results generated using all 3 data sets are shown in the bottom panel of FIG. 12, and are labeled with the term, "Composite." The combined results had 3 missed calls in classifying the 60 samples (5%), where the proteomic results had 6 missed calls (10%), the mRNA results had 5 missed calls (8%), and the miRNA results had 6 missed calls (10%). By combining the analysis of all three result types, including proteomic results, mRNA results, and microRNA results, the classifier yielded complementary signal in this study.

Figure 14:
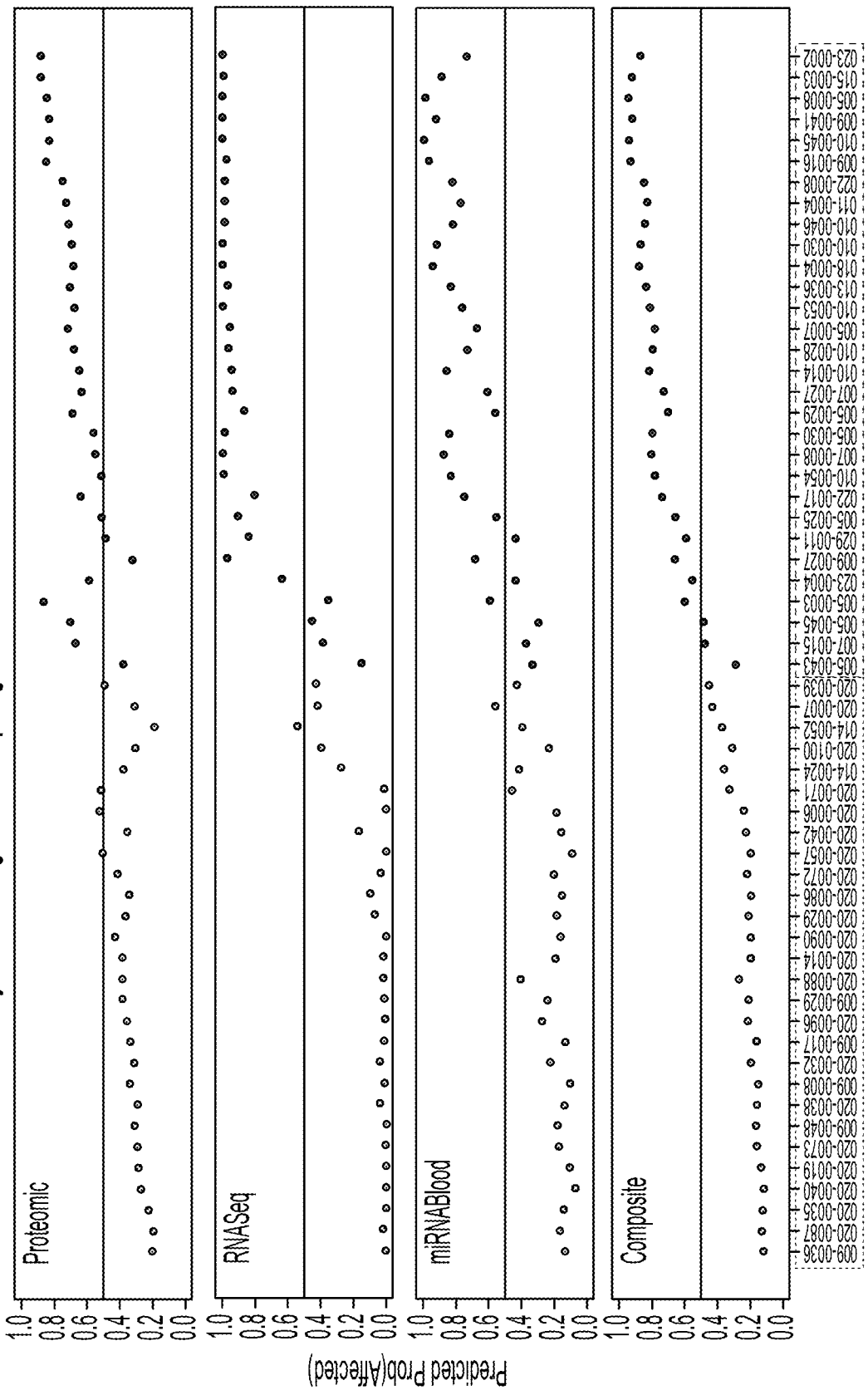
FIG. 14 shows graphical results of an integrated models classification analysis.

Example 4. Further Multi-Omics Analyses for Improving Diagnosis of a Disease State Using RNAs and Proteins Additional analyses were performed using the same samples as in Example 3. FIG. 14 illustrates results of a multi-omics analysis that included integrated models classification. The results on the Y axis include a predicted probability for each subject on whether the subject is affected with a disease state (here, late stage lung cancer), based on the use of separate classifiers or based on the integrated models classification. The X axis shows each subject, and indicates whether the subject was previously established to be affected by the disease state. The combination of proteomic, mRNA and miRNA models resulted in an improved classification model that demonstrated complementary signals. In future experiments, additional 'omics will be tested for signal optimization, including methylated DNA, mutations, and metabolites (e.g., lipids and amino acids). The unbiased approach used here allowed for selection of the combination of analytes for test performance (e.g., scientific, intellectual property, cost, test format, etc.).

FIG. 15 illustrates some aspects of a transformation-based classification strategy that utilized top 'omics features as input. The top features identified from individual 'omics classification models of proteomics, mRNA, and miRNA results are included in the figure. The top features from each classification model were quite different, and may be used as input for a combined classifier. The protein group features include combinations of proteins and particle types, although the proteins may be used as biomarkers in some cases without the use of said particles.

FIG. 16 illustrates a comparison of the composite results of the integrated models classification versus the transformation-based classification. The results on the Y axis include a predicted probability for each subject on whether the subject is affected with a disease state (here, late stage lung cancer), based on each classification analysis. The X axis shows each subject, and indicates whether the subject was previously established to be affected by the disease state. Both the transformation-based classification and the integrated models classification showed improved classification power when compared to individual classification models. The transformation-based classification may have some advantages in terms of reduced processing time and simplicity compared to the integrated models classification. The classifications differed in number of total classifier features. As such, the transformation-based classification contained dozens of total classifier features while the integrated models classification contained thousands of total classifier features.

Example 5. Multi-Omics Analysis Using Lipids and Proteins

Figures 18A, 18B:
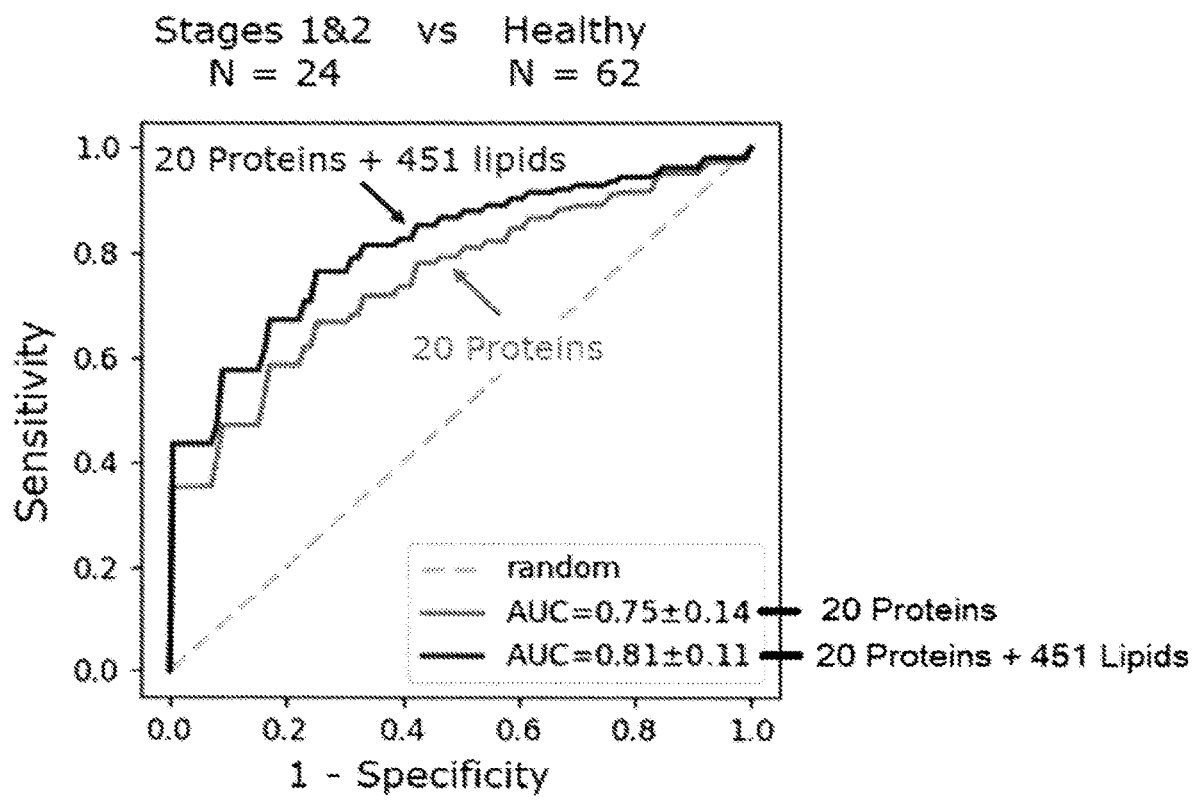
FIG. 18A shows ROC curves of some protein data and combined protein+lipid data for disease state classification.
FIG. 18B includes sensitivity aspects of an analysis of protein data, lipid data, and combined protein+lipid data for disease state classification.

FIG. 18A includes results of an analysis using lipids and proteins. In the analysis, the top 20 predictive proteins from a proteomic dataset were combined with a panel of 451 lipids to improve classifier performance. Further results are shown in FIG. 18B, where including lipid data with the protein data improved sensitivity by about 10%, relative to the protein data alone. The results in this example were obtained from biofluid samples from 86 subjects including 24 subjects with lung cancer (stage 1 or stage 2 non-small-cell lung cancer) and 62 healthy subjects without cancer. The biofluid samples included plasma samples.

Example 6. Further Multi-Omics Analysis Using Lipids and Proteins

To assess disease state prediction (such as determining stage 1 and 2 lung cancer or non-cancer) from a biofluid sample, 86 samples were obtained, including 7 from subjects with stage 2 non-small-cell lung cancer (NSCLC), 17 from subjects with stage 1 NSCLC, and 62 from healthy individuals without cancer. These samples were the same as in Example 5. 12,800 nanoparticle-protein group pairs and 633 lipids were assayed in the samples (positive and negative modes) associated with stage 1 or stage 2 lung cancer or with healthy samples for classifier generation and assessment.

Machine Learning Architecture

FIG. 19 illustrates a multi-omics framework a 2-stage architecture that was used. The framework included training an individual model for each feature type (proteins and lipids) and then combining all predictions for assessment on the test set. The training was done at two different stages. For stage 1, a random forest model was used for the proteins, and a logistic regression model was used for the lipids. For stage 2, a subset of top 20 predictive proteins was selected from stage 1, and the model was retrained using this subset on the same training data. For lipids, the logistic regression result of stage 1 was used without retraining. Predictions at the end of each stage were combined, and performance on the test set was assessed. The data in this example illustrate the usefulness of a combination of lipid and protein data in disease state prediction.

Results

Figures 20A, 20B:
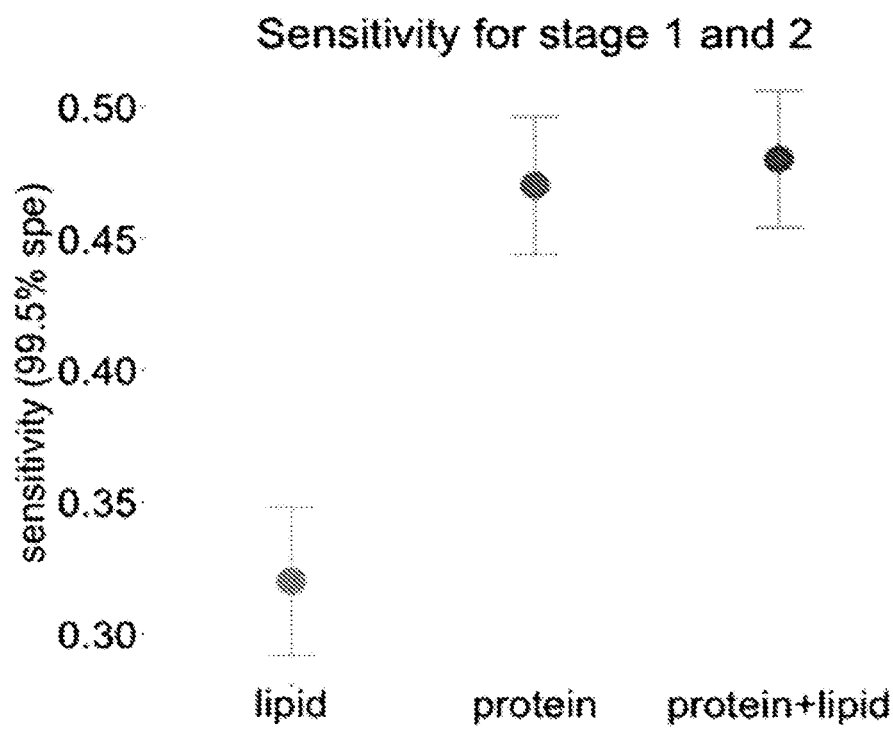
FIG. 20A includes sensitivity aspects of an analysis of protein data, lipid data, and combined protein+lipid data for disease state classification.
FIG. 20B includes sensitivity aspects of an analysis of protein data, lipid data, and combined protein+lipid data for disease state classification.
Figure 20C:
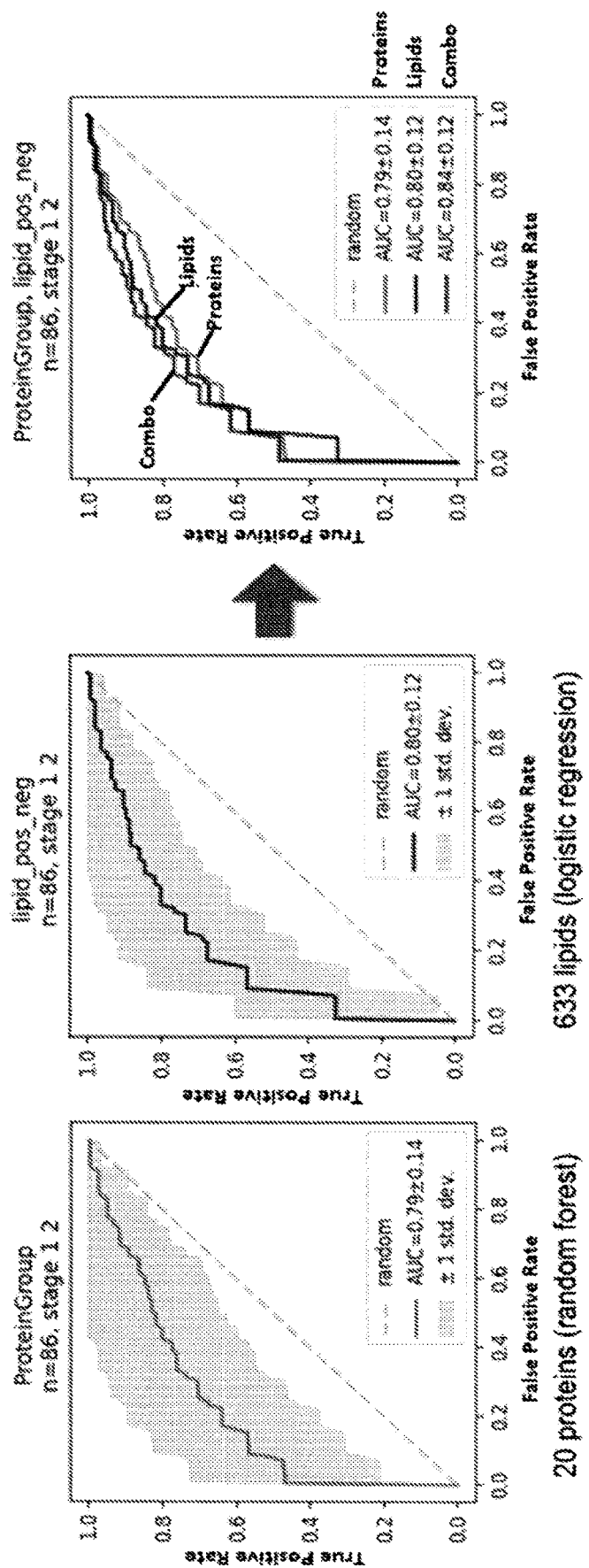
FIG. 20C shows ROC curves of some protein data, lipid data, and combined protein+lipid data for disease state classification.

At each run, performance on the test set was assessed using 20 proteins and all available lipids. 100 ROC curves were obtained (5 fold cross validation, repeated 20 times), and an average AUC of 0.79 for proteins, 0.80 for lipids, and 0.84 for the combination of proteins and lipids was further obtained (FIG. 20A).

Sensitivity data are included in FIG. 20B. The sensitivity at 99.5% specificity was 0.47 for proteins, 0.32 for lipids, and 0.48 for the combination of both. The sensitivity at 90% specificity was 0.57 for proteins, 0.57 for lipids and 0.61 for the combination of both.

Feature Importance

For feature importance assessment, average feature importance (including weights for logistic regression and mean decrease in impurity for random forest) was calculated across 100 iterations (5 fold cross validation, repeated 20 times) and these were used as reference values.

Next, the framework was run 500 times (5 fold cross validation, repeated 100 times) with permuted labels to build an empirical null distribution of "no relation between features and outcome." A p-value for each feature was the number of cases (count) more extreme than the reference value over 500. The count was set at 1 if no extreme value was detected. Top predictive features for proteins were chosen as those that had a p-value lower than 0.05 and FDR<25%.

The following proteins were identified as predictive of lung cancer after correcting for age, gender and race, without site 10: SERPINA1, HPR, EPS15L1, ORM2, CTSH, CRP, SAA4, COLEC10, HIST1H4I, APOM, ORM1, P0DOX8, IGKV1-8; IGKV1-9, ANGPTL6, SERPINA3, PXDN, IGKC, HP, APCS, and ITIH2. The following lipids were also identified in like manner: PC (20:3_20:3)+AcO, Cer(d18:1/24:0)+H, GlcCer(d18:1/18:0+H, PI(18:0_18:3)–H, Aca(4:0)+H, GlcCer(d18:1/22:0+H, PC(18:2_20:5)+AcO, PC(14:0_18:2)+AcO, LPE(18:3)–H, Cer(d18:0/18:0)+H, DAG(18:1_22:6)+NH4, TAG(54:3_16:0)+NH4, Cer (d18:1/18:0)+H, PC(16:1_20:3)+AcO, LPC(17:0)+AcO, GlcCer(d18:1/24:1+H, DAG (18:1_20:2)+NH4, PE(P-18:0_18:2)+H, Cer(d18:0/24.0)+H, and PE(18:1_20:1)–H.

Example 7. Multi-Omics Analysis Using Proteins, Lipids, and Clinical Parameters

Figure 21:
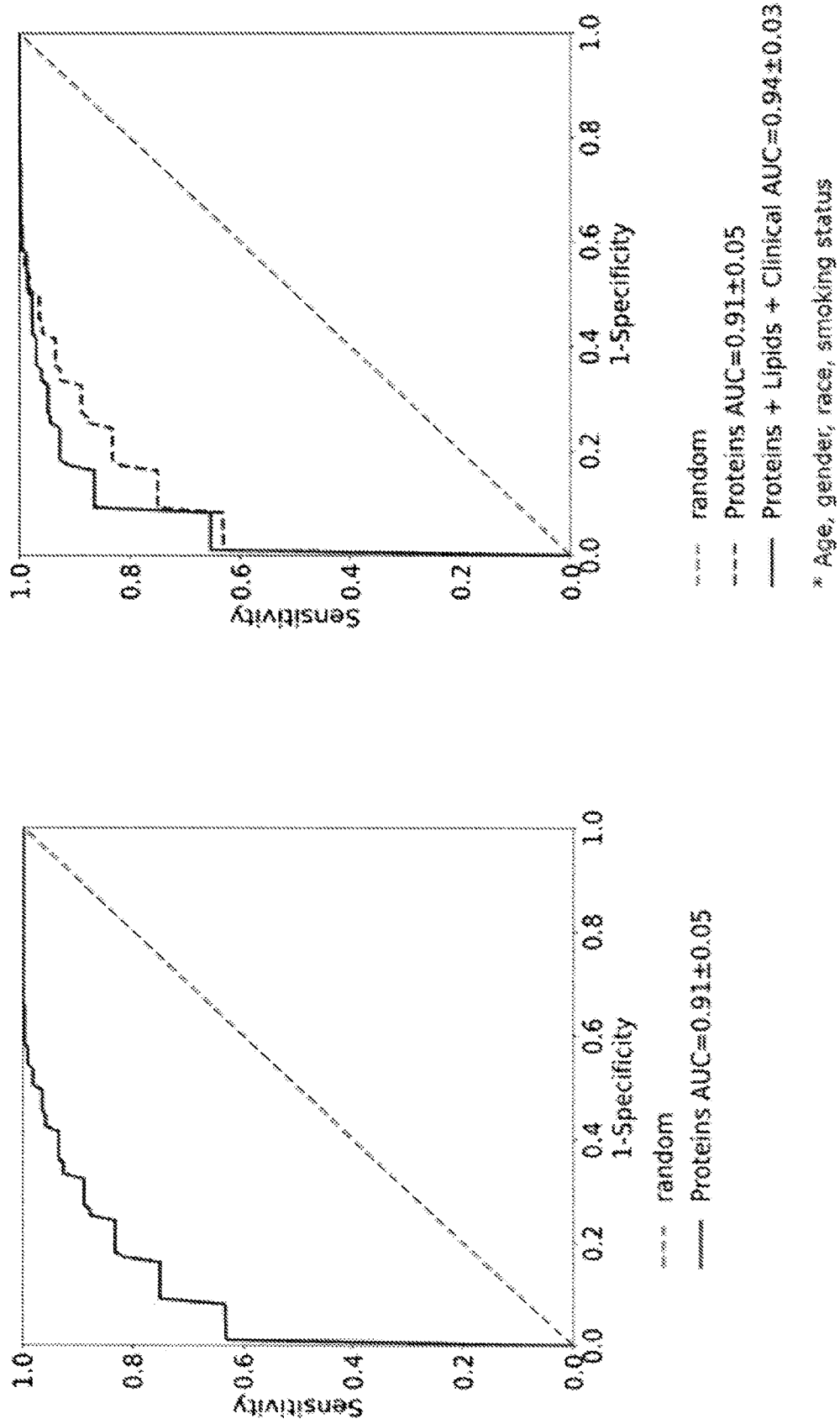
FIG. 21 shows ROC curves of some protein data, and combined protein+lipid+clinical parameter data for disease state classification.

FIG. 21 illustrates results generated from classifiers trained from 83 biofluid samples, including 24 samples from subjects with lung cancer and 59 healthy control samples. The subjects with lung cancer had either stage 1 or 2 non-small-cell lung cancer (NSCLC). The biofluid samples included plasma samples. The combination of analyzing proteins, lipids, and clinical parameters (right panel) improved classification accuracy as determined by area under the curve (AUC) of a receiver operating characteristic (ROC) curve, relative to analysis of only proteins (left panel). The clinical parameters used in this experiments included age, gender, race, and smoking status.

The classifiers included the following total numbers of features for any given data type: 12800 features for Proteograph (split between among separate types of particles) and 633 for lipid.

Example 8. Proteomic and Lipidomic Analyses

A 156-sample cohort of diseased and control samples was assessed. The samples from diseased subjects included samples from subjects with non-small-cell lung cancer (NSCLC). The 156 samples included biofluid samples from 17 stage I cancer, 7 stage II cancer, 22 stage III cancer, 31 stage IV cancer, and 79 healthy control subjects. The subjects' ages ranged between 42 years to 88 years with the median age being 67 years. 43% male. The biofluid samples included plasma samples.

Clinical data was also obtained from subjects, including medical and social history including smoking and alcohol history, height, weight, vital signs, medical history (past and current), co-morbidities, family history of cancer, and concomitant medications.

Proteomic data in this example was generated by liquid chromatography-mass spectrometry (LC-MS) after adsorbing proteins from the samples to a set of 5 nanoparticles commercially available from Seer, Inc. The nanoparticles were a subset of a 10-particle panel in Blume 2020. Lipidomic data were also obtained using LC-MS, but not after contact with the nanoparticles.

Receiver operating characteristic (ROC) curves were generated by training a random forest classifier on proteomic data and/or other data using a nested cross validation procedure shown in FIG. 17. Each fold in the outer loop acted like a hold-out set in that it was not seen during training. The process was repeated across multiple shuffles of the dataset. Additional machine learning best practices were followed to prevent overfitting, for example, reducing model complexity, feature reduction, and regularization.

In the nested cross validation method, a 5-fold nested cross validation was performed with 30 repeats. Thus, 150 runs were generated in total. Across the 150 runs, 15 proteins were found to be consistently present amongst the top features. These 15 proteins are included in FIG. 26A-26B. For the top proteins lung-cancer associated Open Targets (OT) scores (platform.opentargets.org/) were identified. Of the top proteins, some may be used in clinical practice, studied to detect cancer, or play some role in cancer initiation, progression and metastasis.

On a stand-alone basis an interim analysis showed that a classifier built using only lipidomic data had an AUC of 0.81±0.06 for Stage I and II NSCLC. Major representation of phospholipids, ceramides, and glucosylceramides among the top features was observed. Some top lipids from the analysis are included in FIG. 27. These types of lipids may have associations with cancer biology. Phospholipids (e.g., PE, PC, PI, or PG) were included in 9 of 20 top features. Ceramide was included in 8 or 20 top features.

The classifiers described in this example may be combined to improve cancer classification. Features from the classifiers described in this example may be combined for use in a classifier to improve cancer detection or classification. For example, protein and lipid features may be combined to improve lung cancer detection by a combined classifier.

Unique combination(s) of proteins, metabolites, and genomic features that provide improved sensitivity and specificity performance for tests will be sought. It is possible to develop simpler models using fewer features, and this will be tested as part of further classifier development work. A major advantage of using the unbiased multi-omics approach is that large datasets can be used to develop optimal classifiers across multiple dimensions, e.g., sensitivity/specificity performance, simplicity of assay, or cost.

As a machine learning good practice, PCA was performed on datasets as an early step in the analyses in this and other Examples described herein. The PCA distribution here was reviewed to ensure that there were no confounding factors related to age, gender, or sample collection site.

Example 9. Further Proteomic and Lipidomic Analyses

Additional data was obtained from the 156 samples described in Example 8. The proteomic analysis included generation of a classifier with useful features spanning 8 orders of magnitude in concentration within the biofluid samples. The features included novel proteins not otherwise associated with lung cancer, and proteins with known associations with lung cancer, some of which may be novel with regard to NSCLC.

Figure 22A:
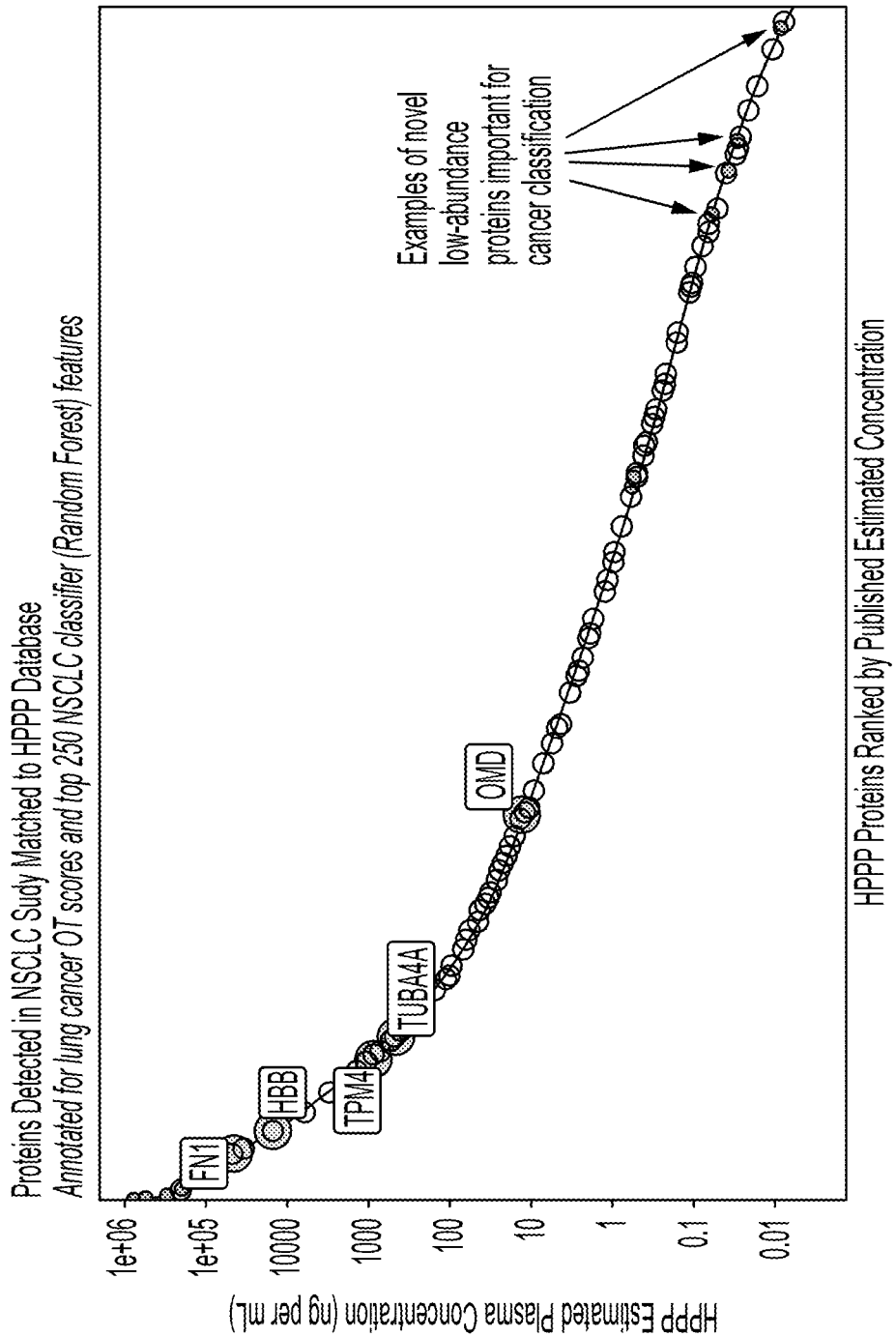
FIG. 22A shows information related to some protein data.

FIG. 22A shows all detected proteins as dots, and their concentrations from the human plasma proteome project (HPPP). Proteins with a lung cancer Open Targets (OT) score>0.3 are shown using a different shade of gray than the rest, while the top 250 most important features for the trained classifier are shown with another different gray shade. Gene symbol callouts are provided in the figure for top classifiers with high OT scores.

Figure 22B:
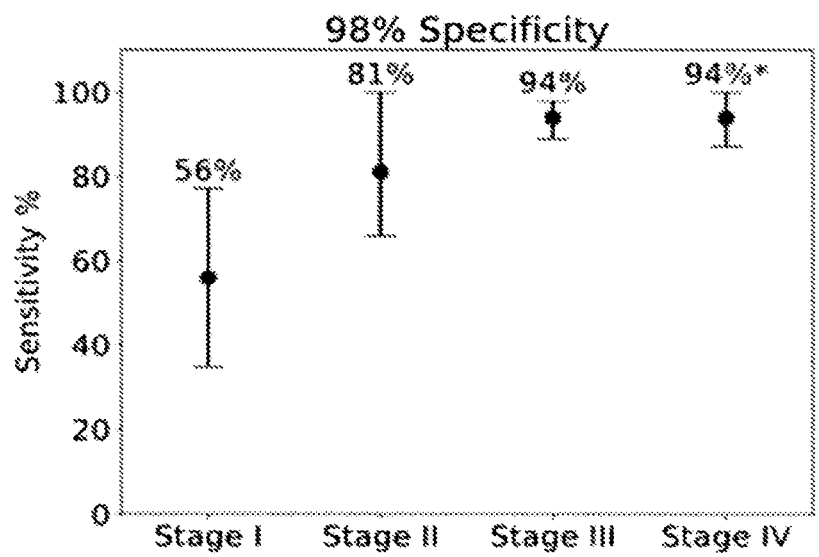
FIG. 22B shows some classifier performance aspects.
Figure 22C:
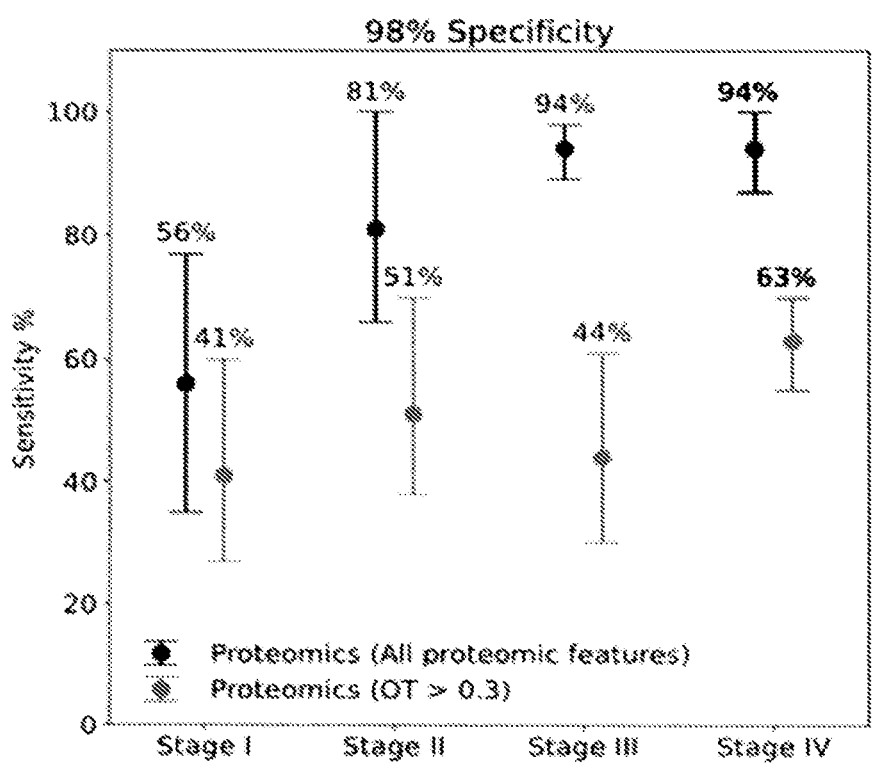
FIG. 22C shows some classifier performance aspects with and without inclusion of some features.

FIG. 22B shows the classifier's sensitivity at a given level of specificity, broken down by cancer stage. The data in this figure demonstrate that a strong biological signal for cancer detection was obtained. FIG. 22C shows the classifier's sensitivity at a given level of specificity as in FIG. 22B when all proteomic features, relative to sensitivity data at the given level of specificity using only the proteomic features that had OT scores above 0.3.

Example 10. Identifying a Likelihood of Pancreatic Cancer in a Subject

A subject comes into a doctor's office having jaundice and abdominal pain. The doctor determines that the subject may be at risk of having cancer, and performs a non-invasive work-up, including a CT scan but nothing of note is detected. A plasma sample is obtained from the patient to be analyzed by the methods described herein. The lab measures the presence and abundance of several proteins. The lab then applies a classifier to generate an output report to the physician for determining whether the subject has pancreatic cancer. The report indicates that the patient likely has pancreatic cancer. It's possible that the pancreatic cancer is small and developing at an early stage, which explains the why scan did not detect the pancreatic cancer. The physician asks the patient to return for regular check-up once every 6 months to continue monitoring the pancreatic cancer. During one of the subsequent check-ups, the analysis of the biofluid sample obtained from the subject indicates that the pancre-

Example 11. Deep, Unbiased Multi-Omics Approach for Identification of Pancreatic Cancer Biomarkers from Blood Pancreatic cancer is the seventh leading cause of cancer related death worldwide and the third leading cause of cancer related death in the USA. The low survival rate of pancreatic cancer is often due to challenges in early detection of disease, highlighting the need for early diagnostic test development. While cancer signatures are less challenging to identify at the localized pancreatic tumor via biopsy, cancer signals found in the blood stream due to cellular leakage, metastasis, signaling, or innate immune response may also be useful due to reduced invasive sampling.

Challenges encountered in liquid biopsy cancer biomarker discovery studies have included analyte degradation and dilution in a complex biological matrix, which limit high specificity and sensitivity measurements. To overcome these challenges, a comprehensive multi-omics platform was developed that facilitates uncovering previously untapped information to gain a more holistic biological perspective at unprecedented depths and integrate molecular signatures across complex levels of biology. Implementation of this approach has led to the discovery of new pancreatic cancer specific biomarkers and a deeper understanding of the integrated pathways of pancreatic cancer.

Figure 28A:
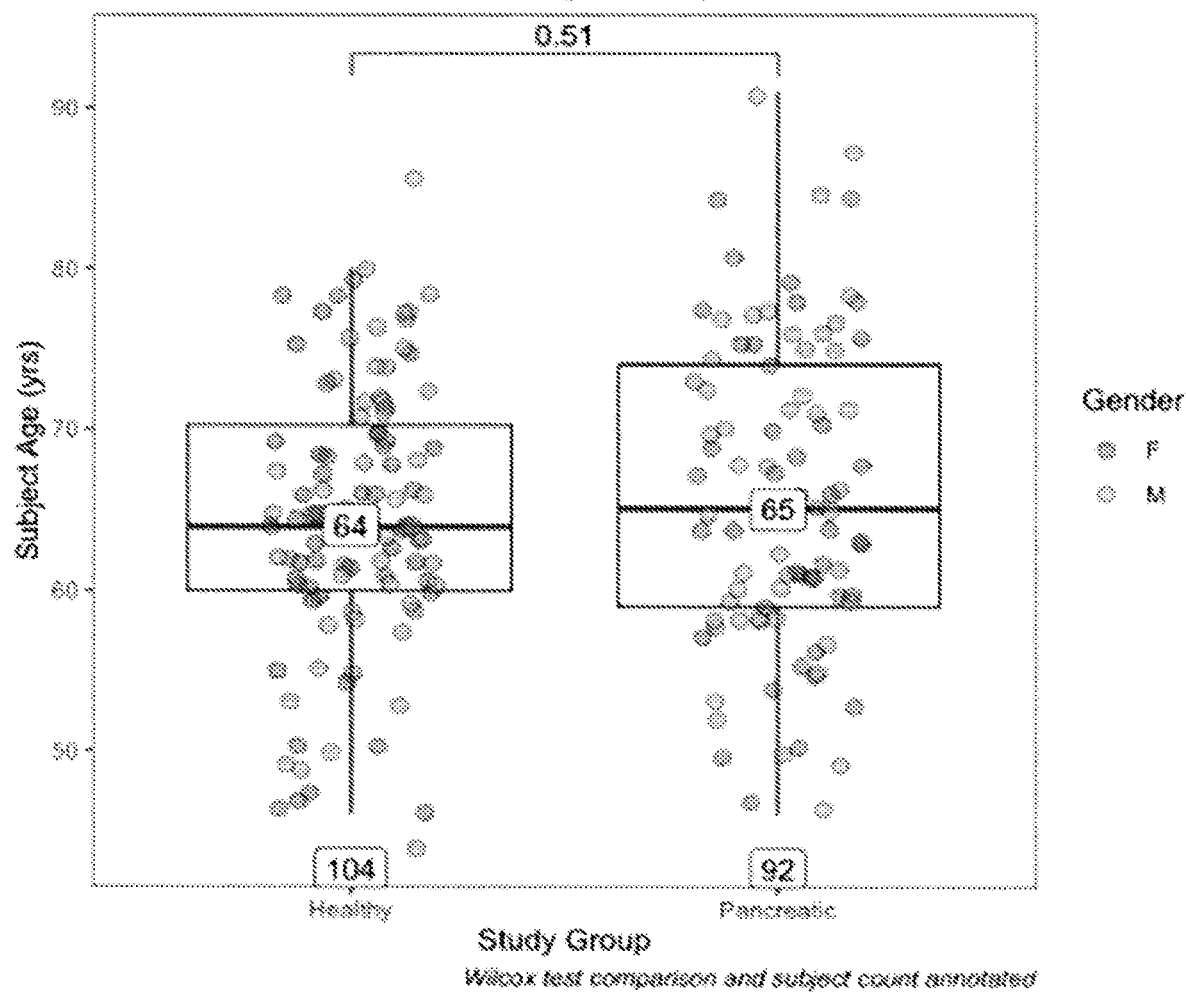
FIG. 28A shows results of a Wilcox test for age comparisons and Fisher's exact test for gender proportionality.
Figure 28B:
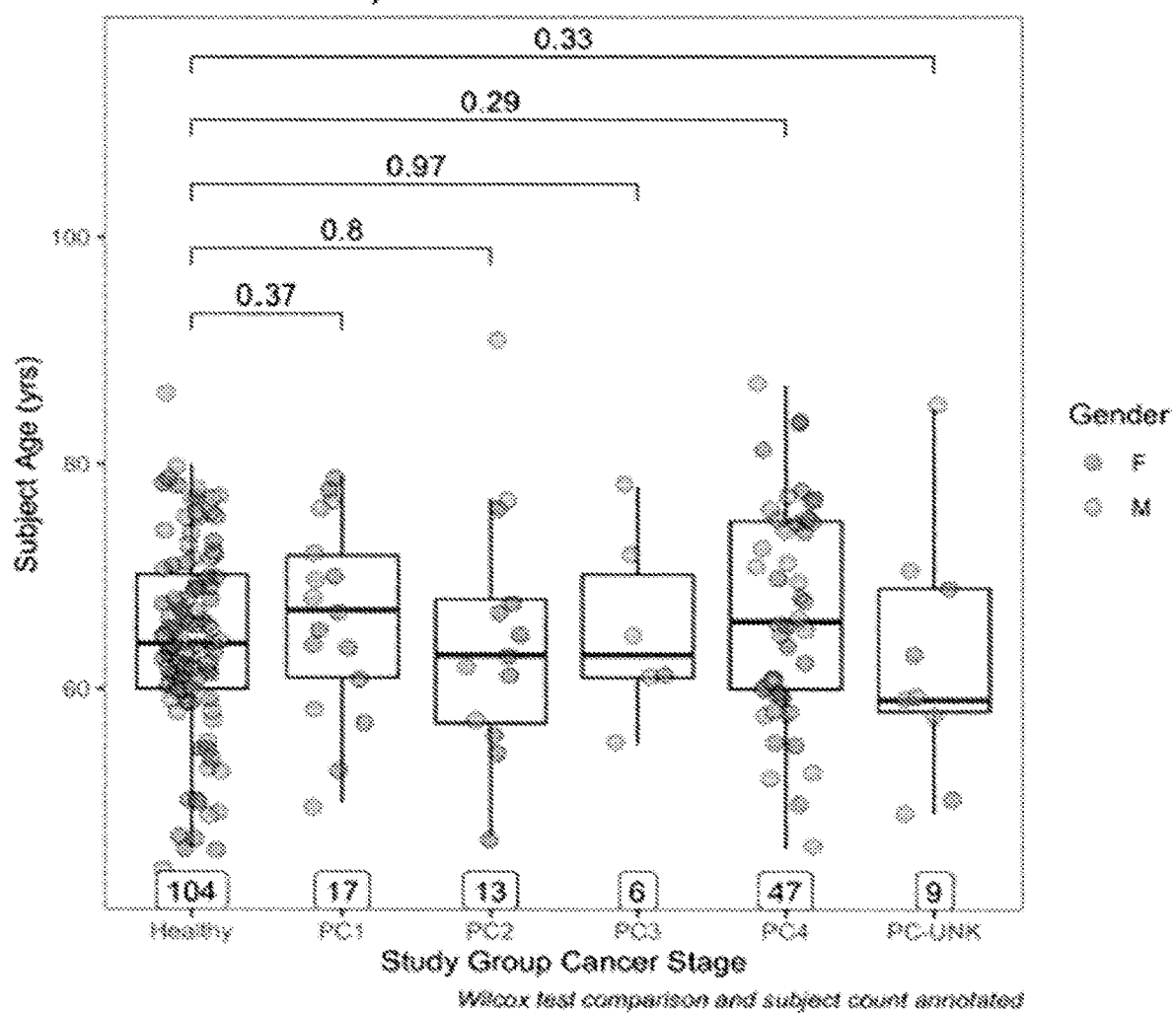
FIG. 28B shows results of a Wilcox test for age comparisons and Fisher's exact test for gender proportionality.

In this case-control study, plasma proteomic, metabolomic, and lipidomic data were collected from 196 human plasma samples. The samples included plasma from 92 patients with pancreatic cancer ("cancer samples" or "PC"), and plasma from 104 healthy subjects without cancer ("healthy controls"). Specifically, the pancreatic cancer included pancreatic adenocarcinoma. The cancer patients were age- and gender-matched with the healthy subjects (Table 9, FIG. 28A-FIG. 28B). In some tables and figures herein, samples from healthy subjects without cancer are referred to as "healthy," and samples from subjects with pancreatic cancer are referred to as "pancreatic." The cancer samples were from patients with a variety of stages of pancreatic cancer, and included 9 samples from subjects with an undefined cancer stage ("unknown"). No bias was observed based on age or gender comparisons between classes.

TABLE 9

196 subjects

| Gender | Healthy | Pancreatic |
|---|---|---|
| F | 53 | 43 |
| M | 51 | 49 |

The data were obtained using liquid chromatography-mass spectrometry (LC-MS). Samples from the subjects with cancer were collected after diagnosis and before treatment of the pancreatic cancer. Data from the cancer samples were compared to the healthy controls. Sample collection and handling was the same for all samples.

Proteins were measured separately by two methods. One protein measurement method (referred to as "Proteograph") included the use of particles, where plasma samples were contacted individually with particles to adsorb proteins from the plasma onto a corona around each particle. Proteins adsorbed to the particles were then assessed by liquid chromatography-mass spectrometry (LC-MS). Proteomic data were obtained from the use of 5 physiochemically distinct particle types (designated "NP1," "NP2," "NP3," "NP4," and "NP5"). Data from the nanoparticles were analyzed separately, as well as a combined panel. These particles were purchased commercially from Seer, Inc. where they were identified as S-003, S-006, S-007, P-039, and P-073, respectively. FIG. 29A-FIG. 29B show total numbers of proteins observed by Proteograph per sample. Here, MAXLFQ processing of DIANN report data was used.

The second protein measurement method included the use of known amounts of isotopically labeled, internal reference proteins (referred to as "PiQuant"). The internal reference proteins were spiked into each plasma sample, then used to identify mass spectra of individual endogenous proteins, and further used as standards for determining amounts of the individual endogenous proteins.

In the analysis, 3,381 proteins were detected in all samples (where a protein was detected in a minimum of 3 samples). Using a Bonferroni correction (FDR=0.05), 124 proteins were measured at statistically significant levels in the cancer samples compared to the healthy controls. The data also included ~200 lipids out of 678 total lipids and 49 of 299 metabolites present in all samples (minimum of 3 samples per class) that were determined to be at statistically significant differential levels (using a Bonferroni correction; FDR=0.05). The detected analytes (proteins, lipids and metabolites) included analytes that were previously unassociated with pancreatic cancer. Additional analyses will be performed to further integrate the multi-omics datasets and determine multivariate statistical performance to detect pancreatic cancer.

Figure 30B:
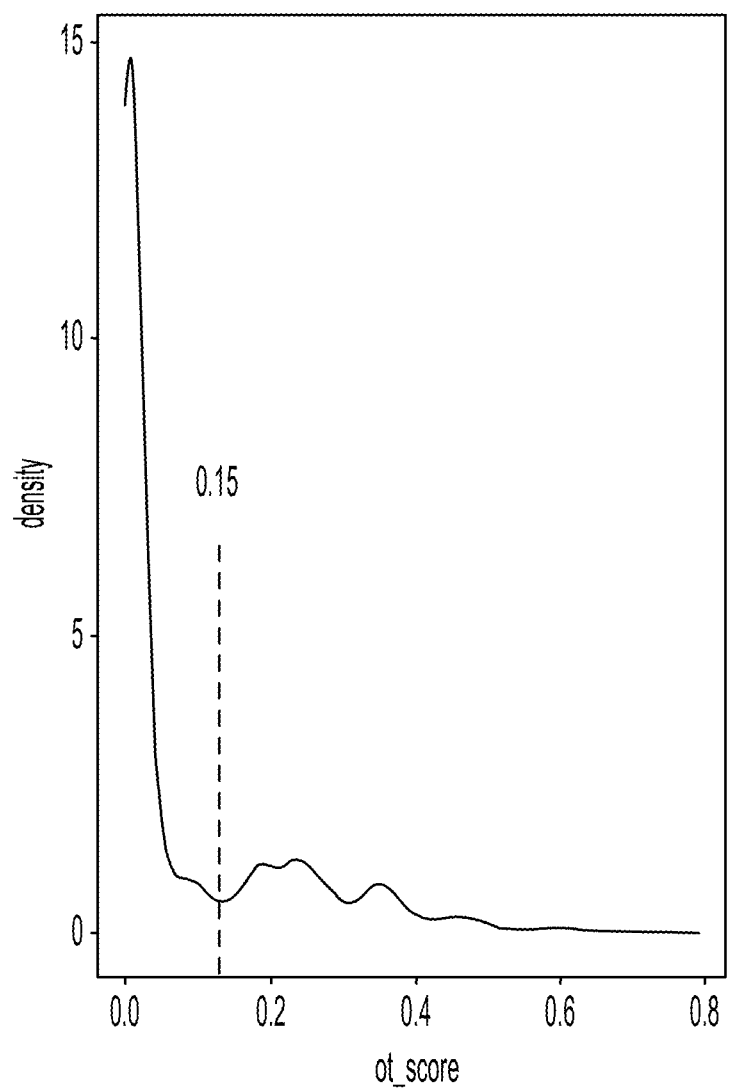
FIG. 30B is a plot showing a distribution of Open Targets (OT) scores. OT scores (from 0 to 0.8) are on the x-axis includes, while the y-axis includes density (0 to 15).

Proteins were detected through a full range of a plasma proteome, including a significant number of high OpenTargets (OT)-scoring proteins for pancreatic carcinoma. Table 10 shows some aspects of 2,933 proteins total, where about 50% mapped to HPPP. Table 11 shows aspects of 10 proteins (out of 213 that had an OT score of 0.15 or greater) that had the highest OT scores. FIG. 30A shows some data that included mapping to 3,486 proteins in the HPPP database, and includes estimated ng per mL concentrations. The proteins in FIG. 30A include MYH9, TUBB1, TUBB, CALR, FLT4, NOTCH2, RHOA, IDH2, CDH1, PRKAR1A, NOTCH1, EXT1, PPP2R1A, SND1, BTK, LPP, MAPK1, FAT1, CDH11, and MAP2K1. FIG. 30B shows a pancreatic carcinoma OT score distribution, where an arbitrary threshold (0.15) for significance is included and was based on inspection of distribution.

TABLE 10

| N | High OT | HPPP |
|---|---|---|
| 1436 | FALSE | FALSE |
| 1337 | FALSE | TRUE |
| 50 | TRUE | FALSE |
| 110 | TRUE | TRUE |

TABLE 11

| Gene ID | OT Score |
|---|---|
| GNAS | 0.67 |
| EGFR | 0.65 |
| TUBB4B | 0.61 |
| RRM1 | 0.60 |

TABLE 11-continued

| Gene ID | OT Score |
|---|---|
| TUBB1 | 0.58 |
| TUBB6 | 0.58 |
| TUBB8 | 0.58 |
| TUBB | 0.58 |
| SMAD3 | 0.55 |
| MAPK1 | 0.52 |

Figure 31A:
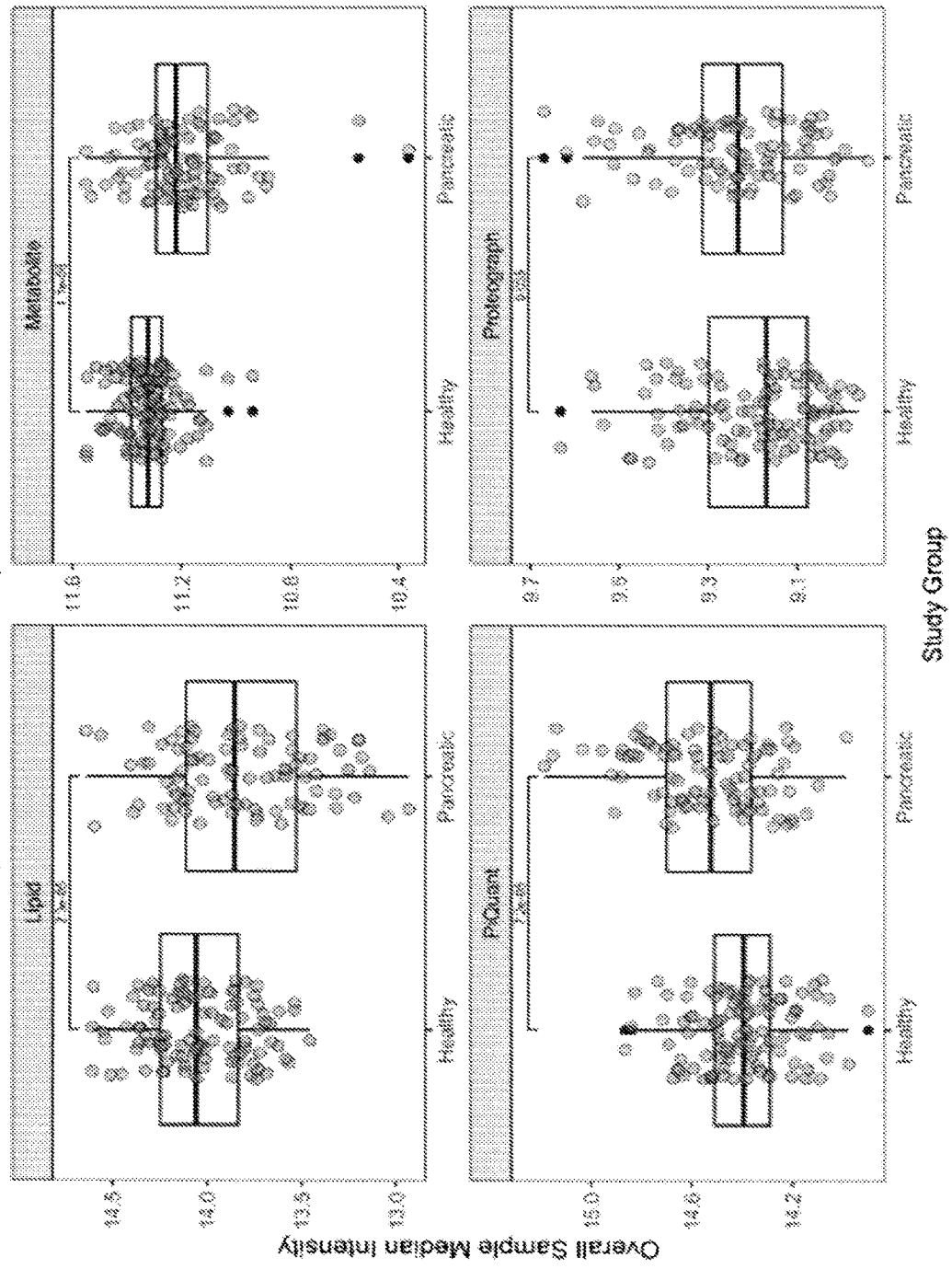
FIG. 31A includes plots showing comparisons of gross signal medians by sample, analyte-type and class.

FIG. 31A shows a comparison of gross signal medians by sample, analyte-type, and class, where large-scale differences may be observed with targeted methods.

Figure 31B:
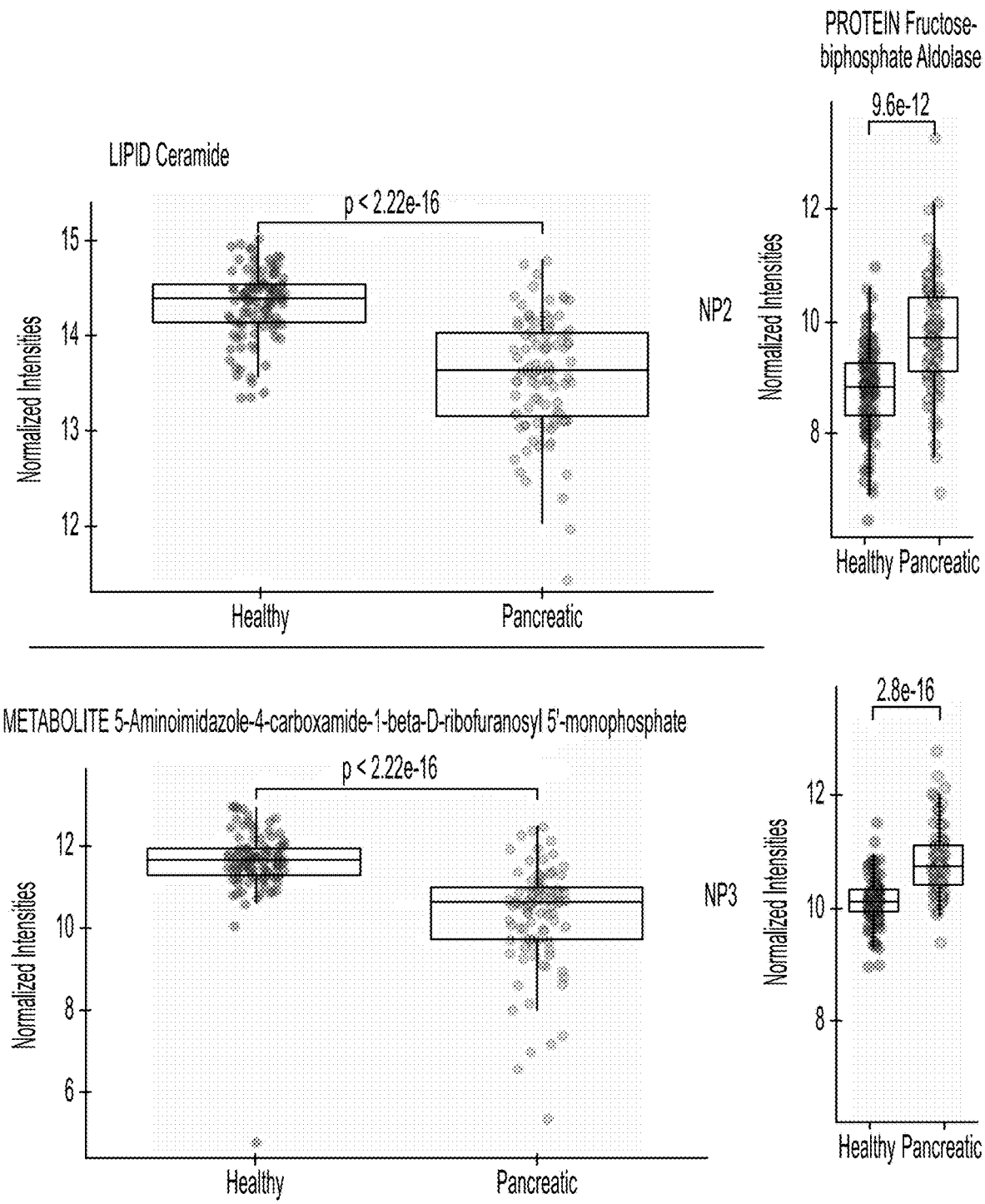
FIG. 31B shows box and whisker plots of most significantly different analytes per omics workflow according to one embodiment; top left: lipid; bottom left: metabolite; and right: proteins).

FIG. 31B shows box and whisker plots of most significantly different analytes per omics workflow (A: lipid; B: metabolite; and C: Protein). Box and whisker plots of the most significantly different analytes in each of the omic classes were investigated. The most significantly different lipid was ceramide. The most significantly different metabolite was 5-aminoimidazole-4-carboxamide-1-beta-D-ribofuranosyl 5'-monophosphate (AICAR). The most significantly different protein, fructose-biphosphate aldolase, was significantly different in two of the five nanoparticle (NP) samples. This highlights the power of the Proteograph assay, which utilized five unique individual NP chemistries that provides complementary protein identifications.

Figure 31C:
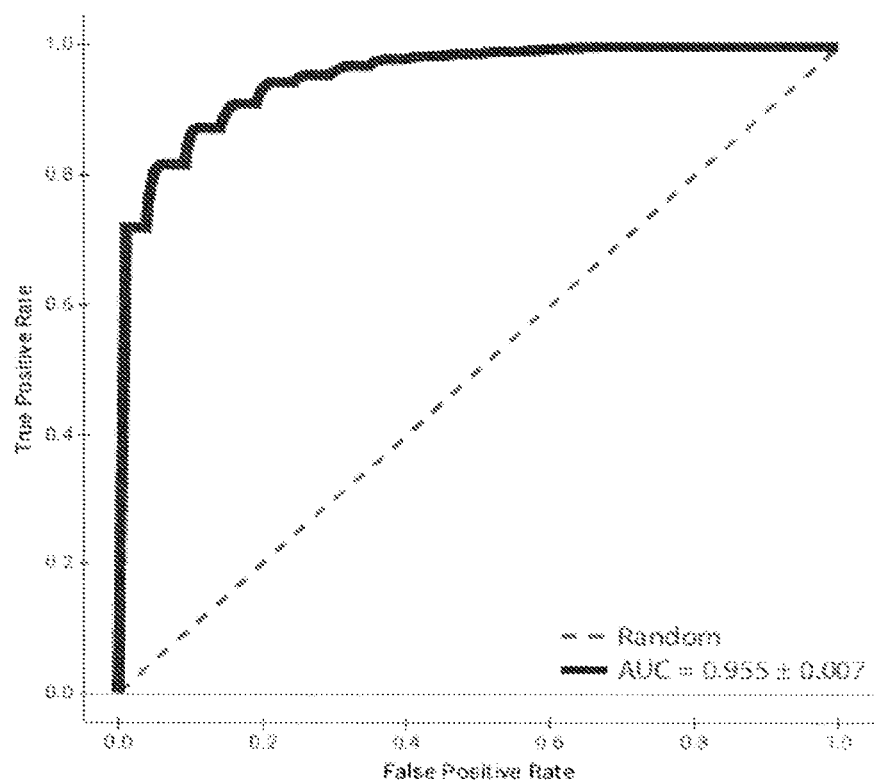
FIG. 31C shows an example multi-omic classifier performance combining proteomic, lipidomic, and metabolomic measurements.

FIG. 31C shows an exemplary multimers classifier performance combining proteomics, lipidomics, and metabolomics measurements. The model was trained with all available samples were cancer stage was known. Then, performance was assessed on each individual or groups of stages. Five-fold cross validation was performed and repeated 30 times. The average AUC was computed across 150 runs. Random forest algorithm was used for proteomics data, and logistic regression was used for metabolomics and lipidomics data.

FIGS. 32A and 32B include results from non-parametric (Wilcox) study group univariate comparisons (EDA) for Proteograph data, using any analyte present in >2 samples per class, and with Bonferroni multiple-testing correction. FIGS. 32C and 32D include results from non-parametric (Wilcox) study group univariate comparisons (EDA) for PiQuant data, using any analyte present in >2 samples per class, and with Bonferroni multiple-testing correction. FIGS. 33A and 33B include results from non-parametric (Wilcox) study group univariate comparisons (EDA) for lipid data, using any analyte present in >2 samples per class, and with Bonferroni multiple-testing correction. FIGS. 34A and 34B include results from non-parametric (Wilcox) study group univariate comparisons (EDA) for metabolite data, using any analyte present in >2 samples per class, and with Bonferroni multiple-testing correction.

Figure 35A:
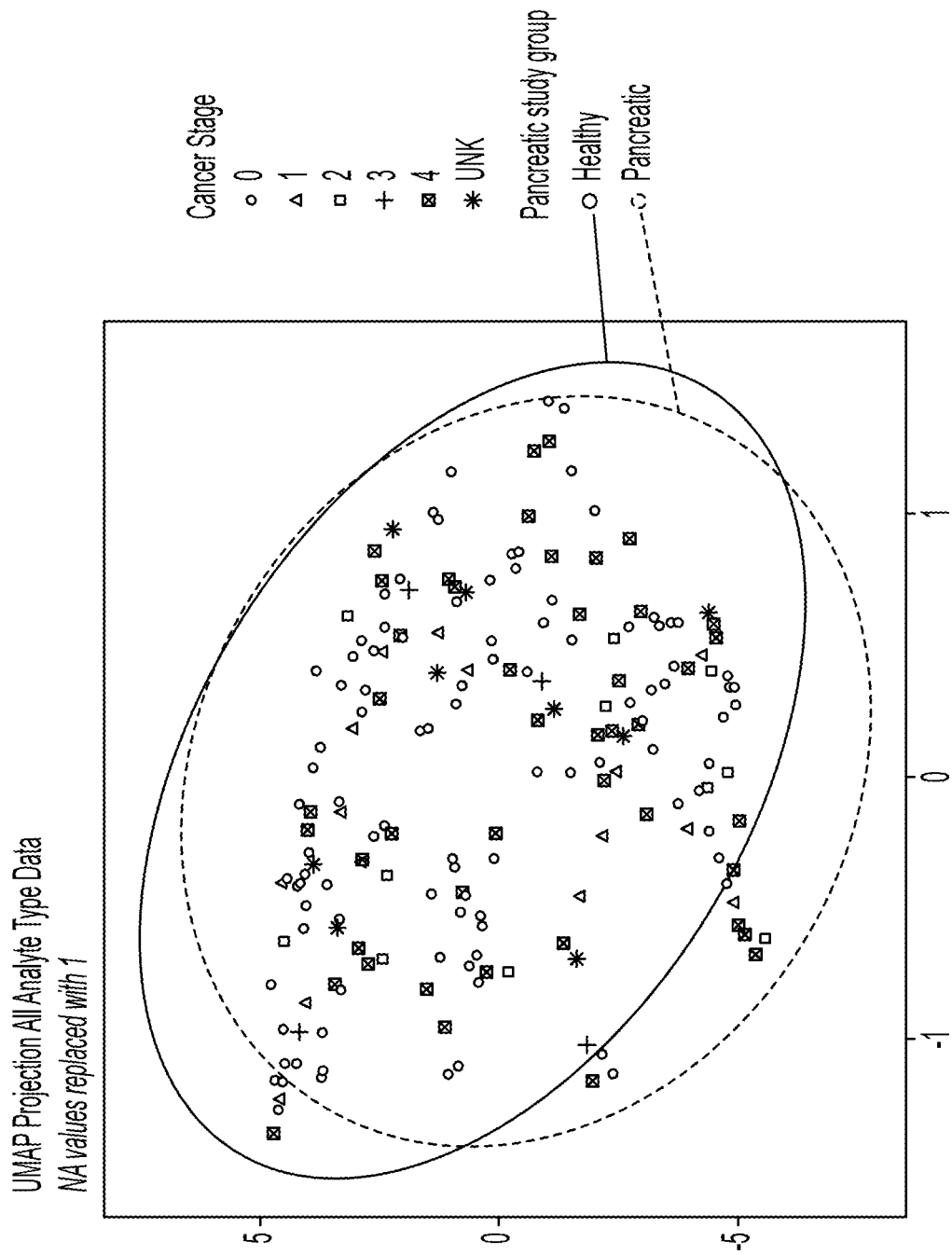
FIG. 35A depicts cancer and healthy sample classification by UMAP projection, based on combined data.
Figure 35B:
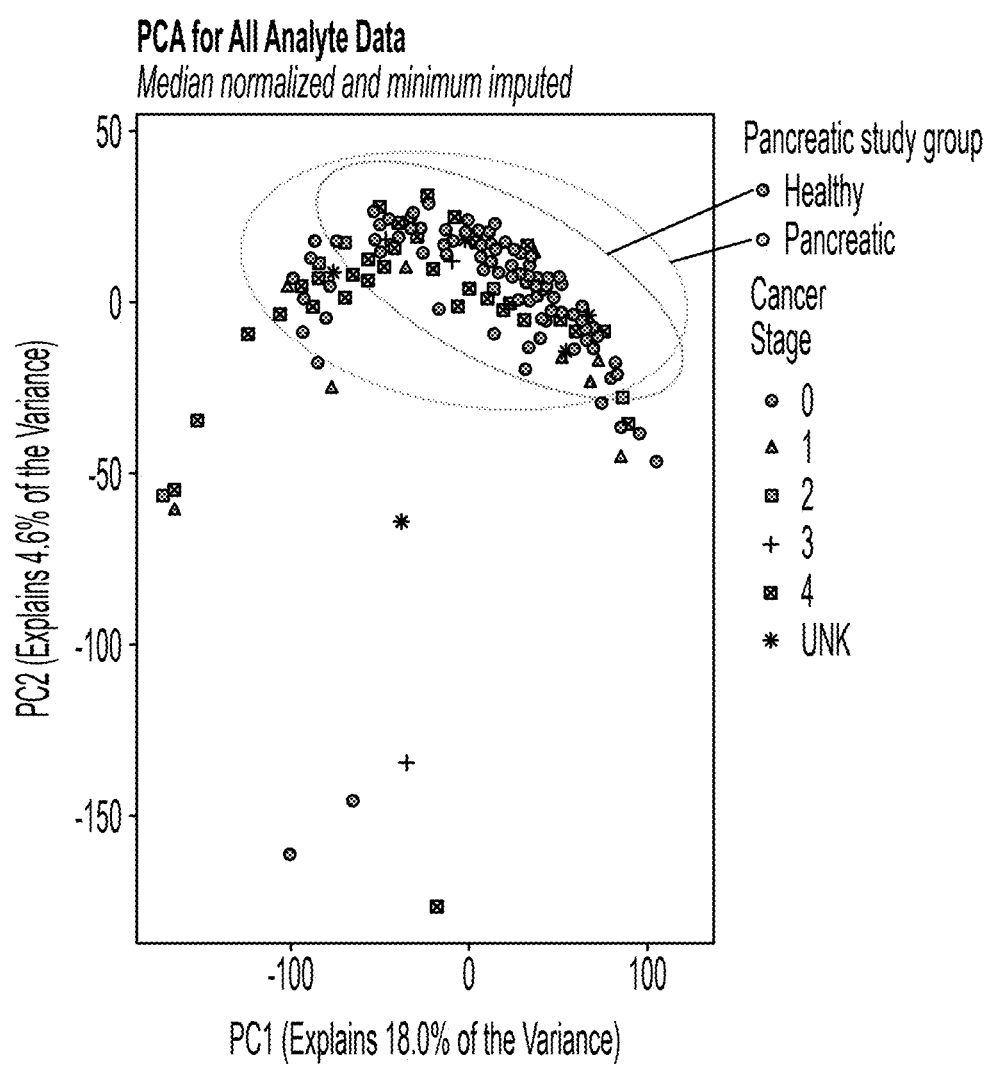
FIG. 35B depicts cancer and healthy sample classification by PCA projection, based on combined data.
Figure 35C:
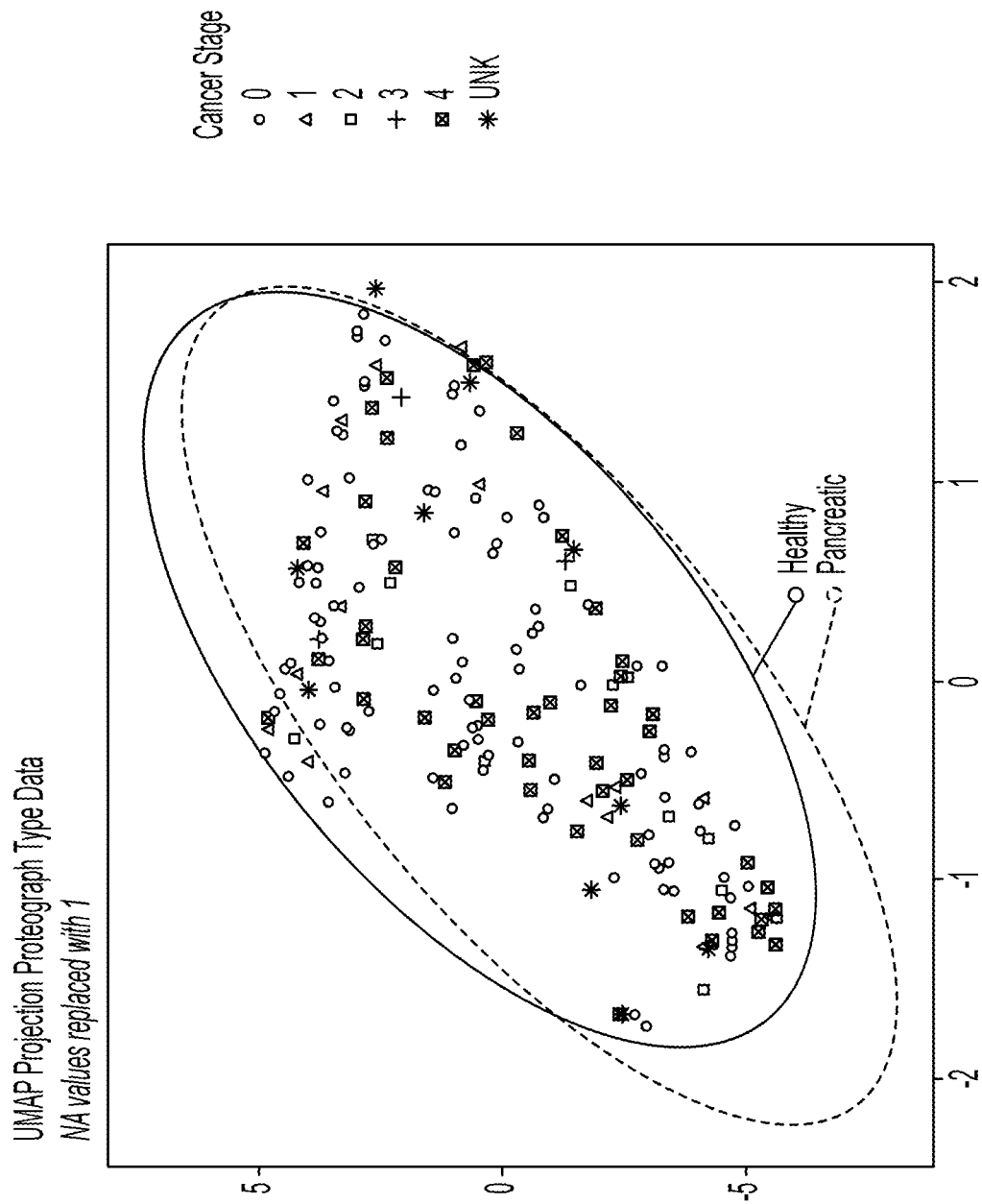
FIG. 35C depicts cancer and healthy sample classification by UMAP projection, based on Proteograph data.
Figure 35D:
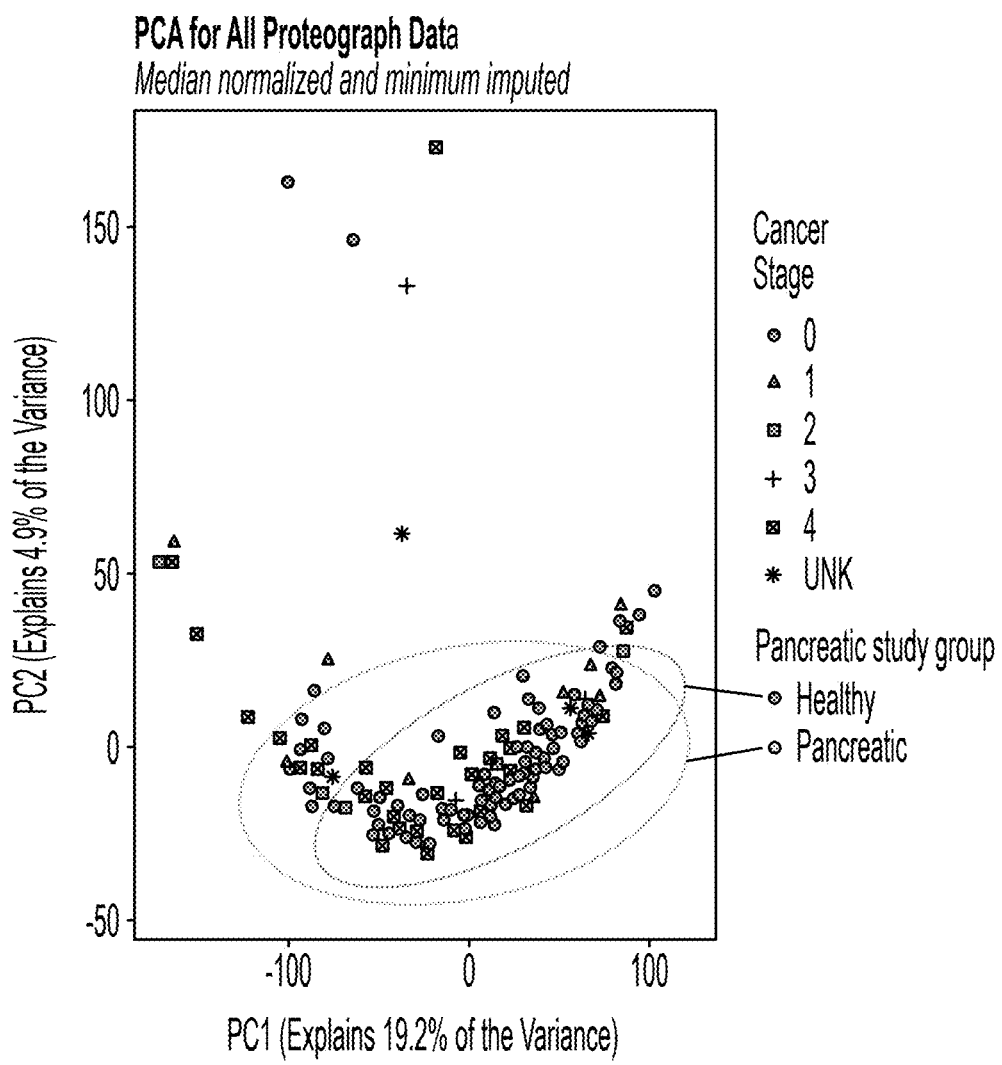
FIG. 35D depicts cancer and healthy sample classification by PCA projection, based on Proteograph data.
Figure 35E:
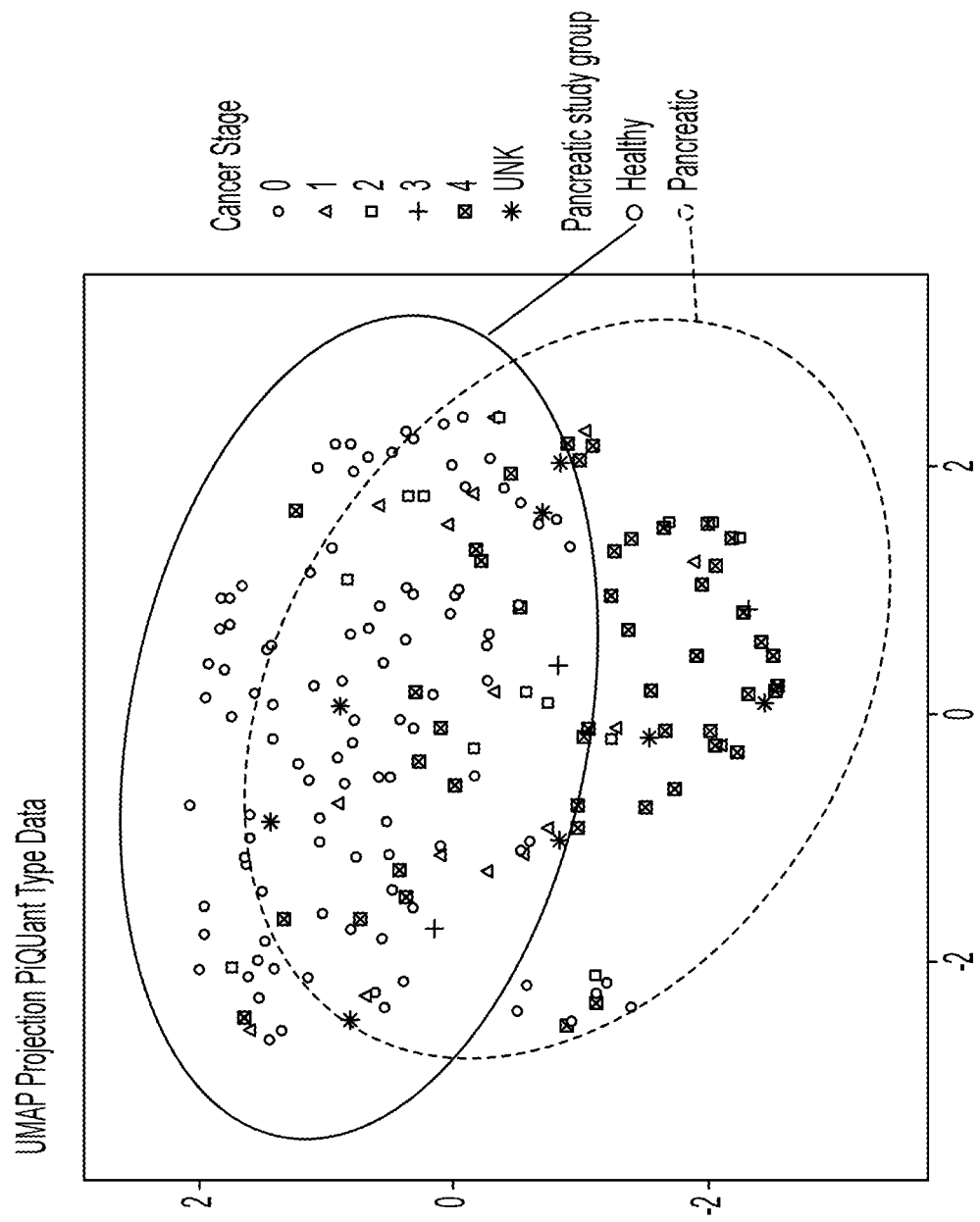
FIG. 35E depicts cancer and healthy sample classification by UMAP projection, based on PiQuant data.
Figure 35F:
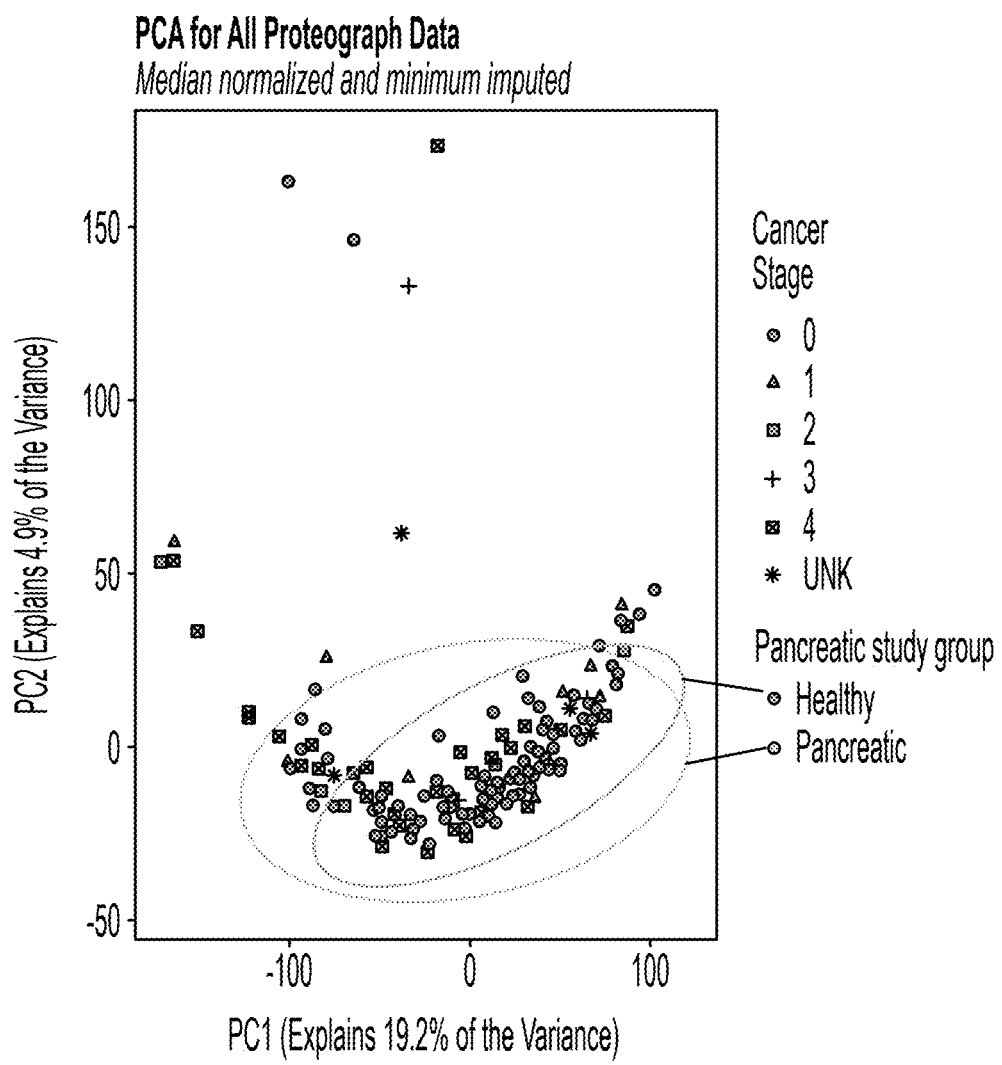
FIG. 35F depicts cancer and healthy sample classification by PCA projection, based on PiQuant data.
Figure 35G:
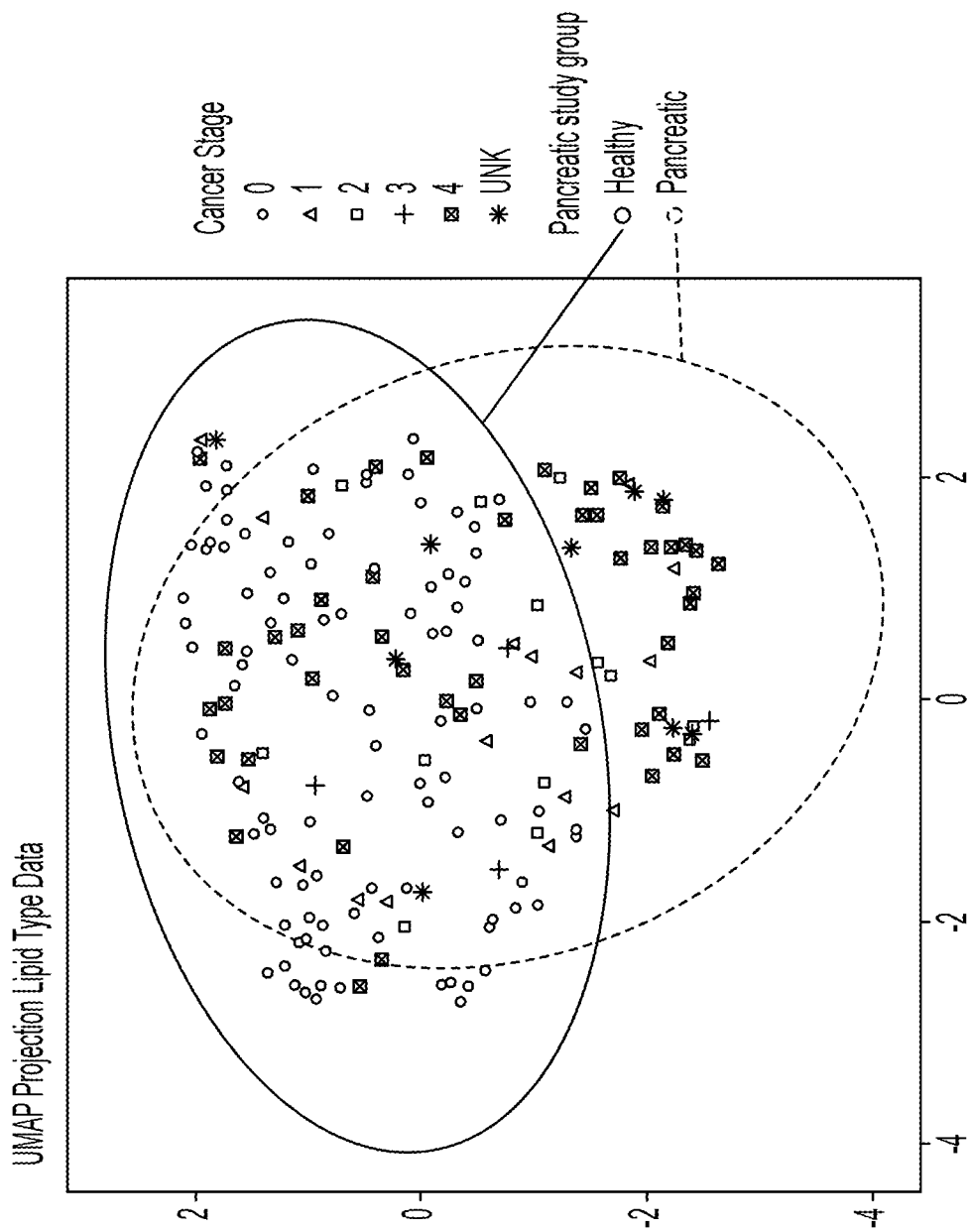
FIG. 35G depicts cancer and healthy sample classification by UMAP projection, based on lipid data.
Figure 35H:
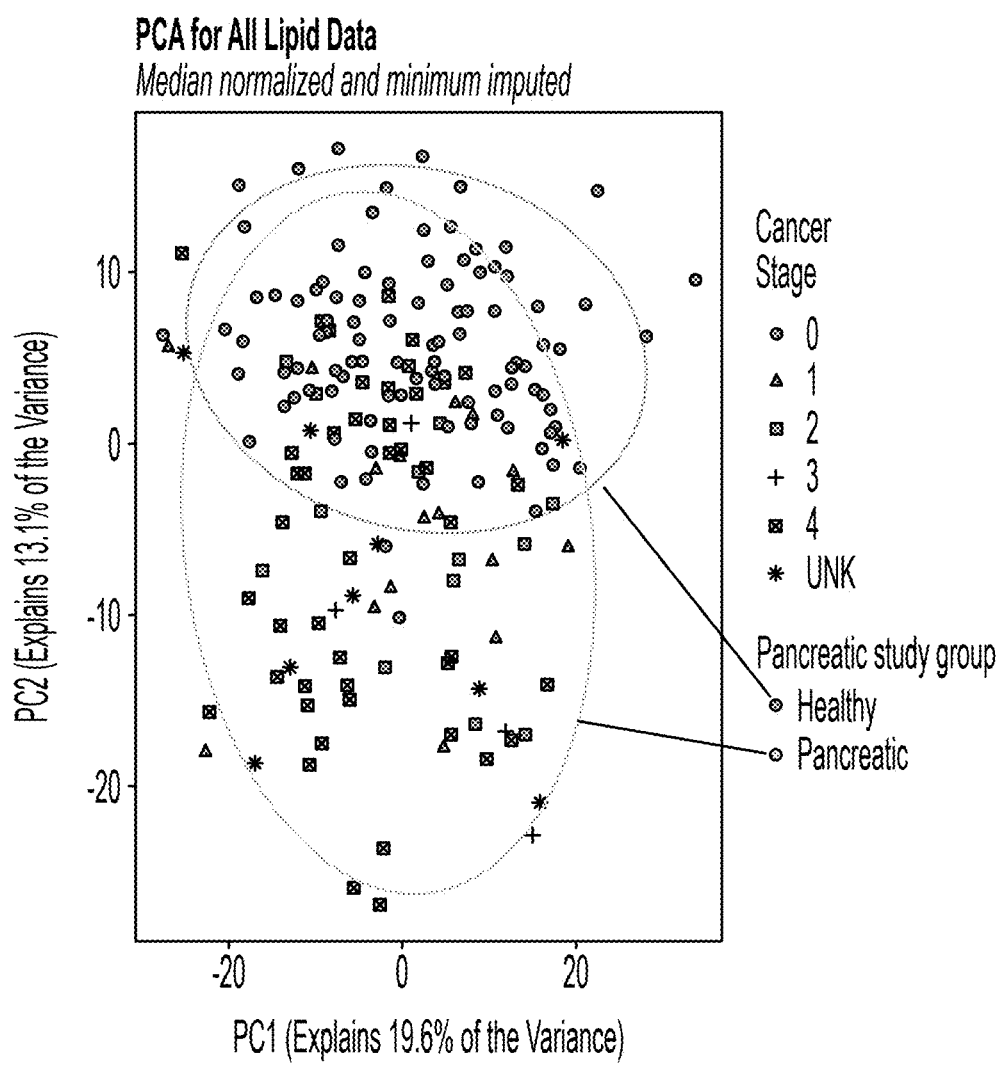
FIG. 35H depicts cancer and healthy sample classification by PCA projection, based on lipid data.
Figure 35I:
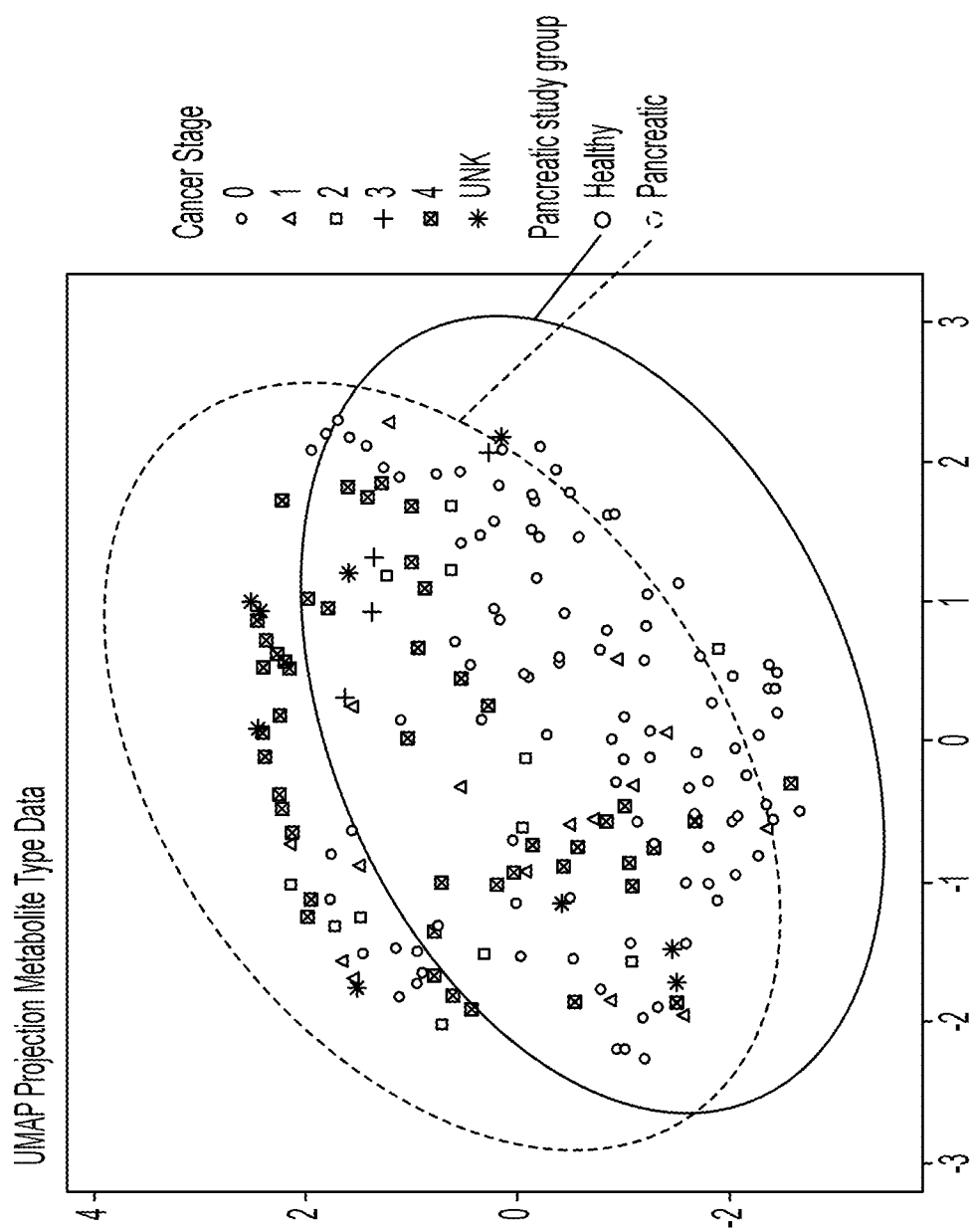
FIG. 35I depicts cancer and healthy sample classification by UMAP projection, based on metabolite data.
Figure 35J:
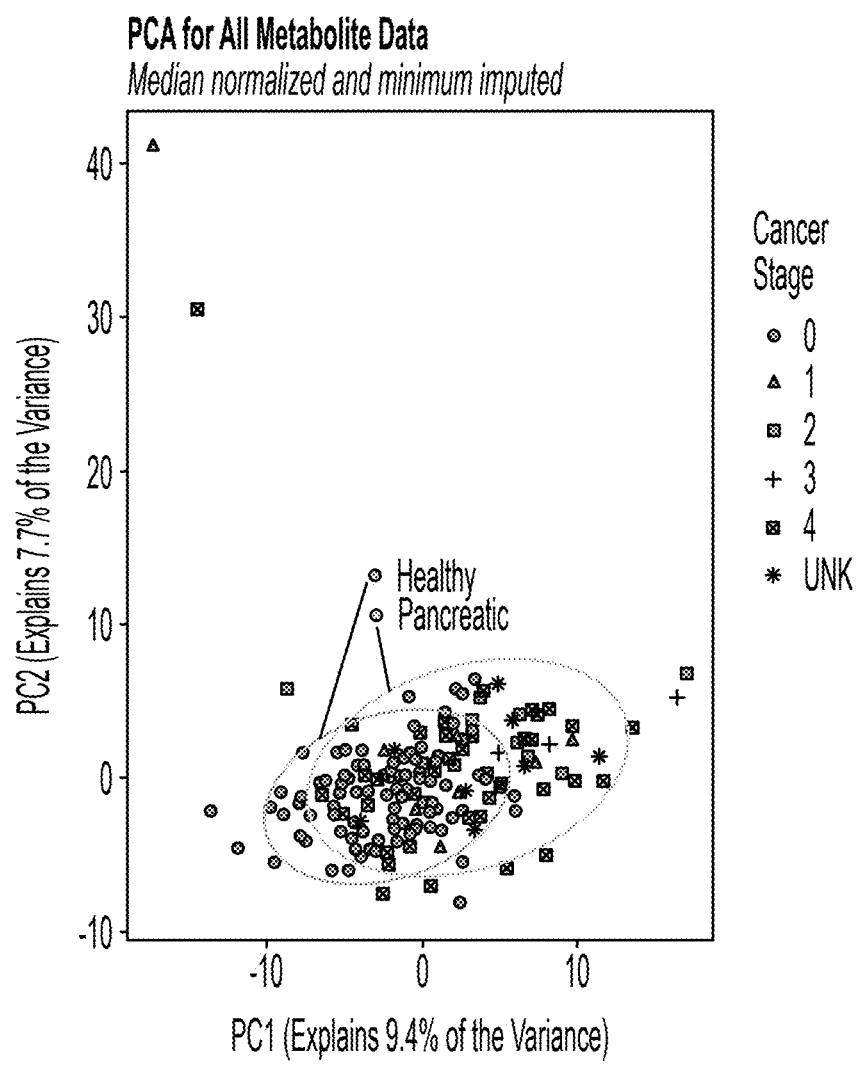
FIG. 35J depicts cancer and healthy sample classification by PCA projection, based on metabolite data.

Initial multi-variate class separations were performed using analyte-complete samples, based on parametric (PCA) and non-parametric (UMAP) projections. Separation data are shown in FIG. 35A-35J. In particular, FIG. 35A-35B are based on combined data (Proteograph, PiQuant, lipid, and metabolite data), FIG. 35C-35D are based on Proteograph data, FIG. 35E-35F are based on PiQuant data, FIG. 35G-35H are based on lipid data, and FIG. 35I-35J are based on metabolite data. In FIG. 35C-35D, missing values were replaced with an arbitrary minimum value.

The intent of this study was to detect a biological signal for pancreatic cancer in non-invasively collected liquid samples. This analysis indicates that there are significant differences between classes in the samples as collected, and that they may be useful in detecting pancreatic cancer.

Further experiments will combine additional features within and across analyte classes to further improve cancer detection. For example, additional proteomic and transcriptomic data will be included in this analysis, including methylation, mRNA, and miRNA data.

Example 12. Multi-Variate Machine Learning Using Gradient Boosted Trees

Figure 37:
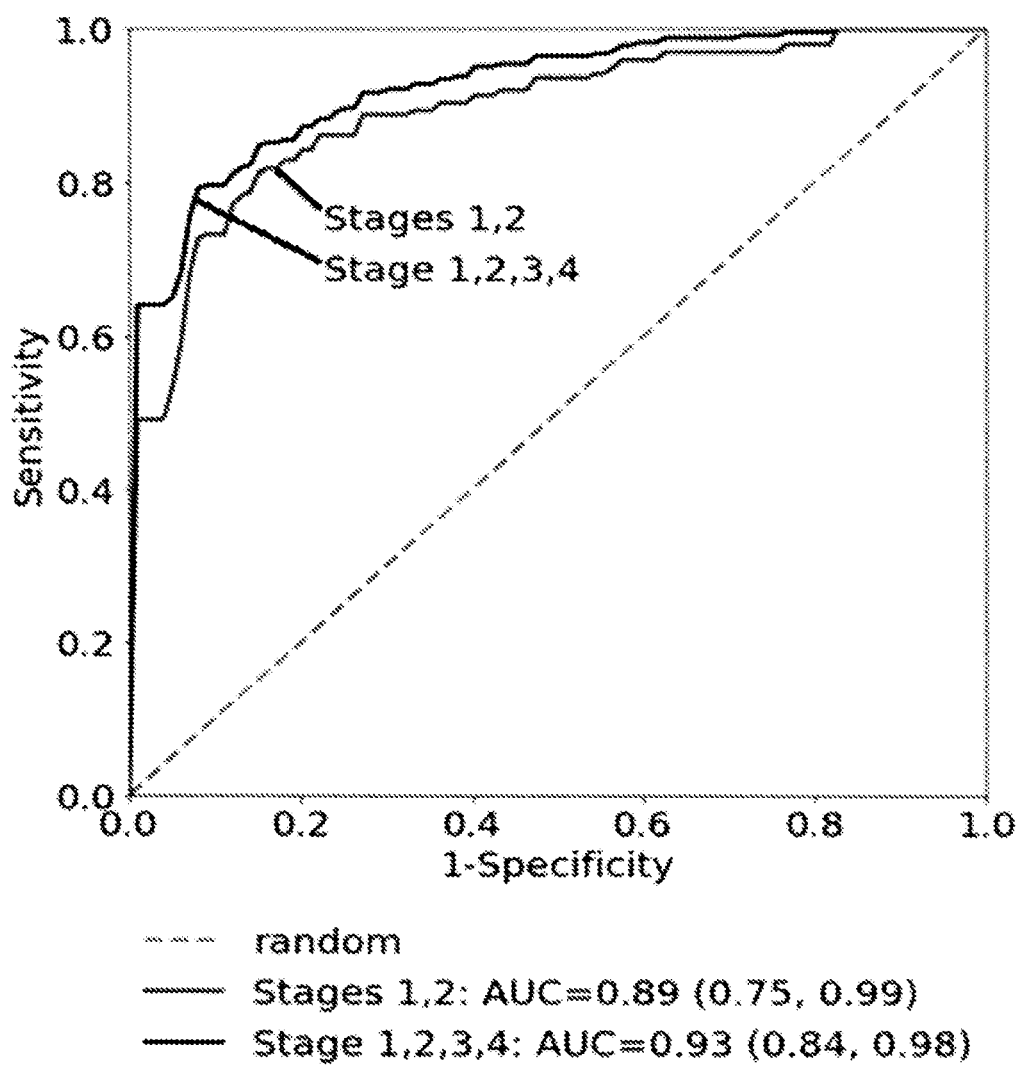
FIG. 37 shows classifier performance in a multi-omic study, and includes receiver operating characteristic (ROC) curves for disease state classification. Area under the curve (AUC) values are also included in the figure with 90% confidence intervals in parentheses.

A training subset of the study was used in initial cross-validation analyses using XGBoost. ln-transformation and median normalization of all intensity data was performed for 189 feature-complete cases from the proteomic, lipidomic, and metabolomic data generated in Example 11. The proteomic data included Proteograph and PiQuant data. Analytes were filtered to those present in at least 25% of the study samples. The 189 complete subjects were split into a training set (n=141) and a held-out validation set (n=48). The training set was used to select hyperparameters for XGBoost-modeling via five rounds of 5-fold cross-validation, with 112-114 for training and 29-27 for testing in each fold. FIG. 36 shows some top features in the training set, where "LPD" refers to a lipid, "MTB" indicates a metabolite, "PQ" refers to protein as assessed by PiQuant methodology, and "PG" refers to protein as assessed by Proteograph methodology. The PQ and PG proteins are included as UniProt reference numbers. Receiver operating characteristic (ROC) curves were generated, and results showed that the combined classifier had an area under the curve (AUC) of 0.924±0.012 (std. err., n=25) when differentiating pancreatic cancer at any stage from non-cancer, or an AUC of 0.89 for identifying early stage pancreatic cancer (here, stage 1 or 2) (FIG. 37). An additional model can be built on the training data with selected parameters and validated on the n=48 validation set.

In this example, a combined classifier was trained on data from mass spectrometry-based assays, including protein, metabolite, and lipid data. The combined classifier may be used to detect pancreatic cancer. Similar classifiers may be trained from samples of subjects having other diseases or cancers, and used to detect the other diseases or cancers.

Example 13. Analyses of Multiple Blood-Based Genomic Assays in Pancreatic Cancer Pancreatic cancer is the third leading cause of cancer-related deaths in the United States. While the 5-year survival rate across all stages is only 10%, in early stages when the disease is localized, the survival rate may reach 40%. Detecting early pancreatic cancer thus helps to reduce mortality; however, most diagnoses are made at stage IV, after onset of clinically detectable symptoms. Hence, there is a need to prioritize between individuals for further testing using minimally invasive procedures, such as liquid biopsies.

A case-control, proof-of-concept study was conducted using 69 subjects: 36 pathology confirmed, treatment naïve cases (5 stage I, 5 stage II, 2 stage III, 22 stage IV, and 2 unknown stages of pancreatic cancer) and 33 demographically matched controls without any pancreatic disease.

For each subject, up to 50 mL of blood was collected in assay-specific tubes. Cell-free DNA as well as mRNA and miRNA from white blood cells were isolated from these samples and assayed following standard NGS protocols. Measurements on CpG methylations, mRNA, and miRNA transcript abundances were then collected. These measurements together may be collectively referred to as genomics assays. Univariate differential analyses of cases versus controls were performed.

The genomic measurements were collected, including CpG methylations and mRNA, and miRNA transcript for cancer and non-cancer subjects. The methylation percentage on CpG sites that covered at least 11 reads was considered. Also, log-transformed counts on canonical mRNA transcripts and miRNA transcripts were used. Then data was split into a training set and a hold-out set. Next, a model on each dataset (omic) was built to differentiate between cancer and non-cancer subjects by training an ensemble classifier on the training data. Each classifier was trained using 30 repeats of 5-fold nested cross-validation with hyperparameter tuning. The domain of the hyperparameters for the classifier was divided into a discrete grid. Then, every combination of the grid values was tried, calculating the performance metrics in the nested cross-validation, and average performance across all runs for each dataset was reported. Eventually, a final performance for all three omics was reported by averaging the predictions of each one. The hyperparameters selected during the search were then used to configure a final model, and the final model was fitted on the entire training dataset for each omic. Then, each model was used to make predictions on the hold-out dataset. A final prediction on the hold-out dataset was computed by averaging the predictions on the hold-out dataset across all omics.

Generally, the final classifier included a random-forest-based classifier trained on the CpG methylations, mRNA, and miRNA data to differentiate between pancreatic cancer cases and noncancer controls. This classifier may be referred to as a genomics classifier.

Figure 38A:
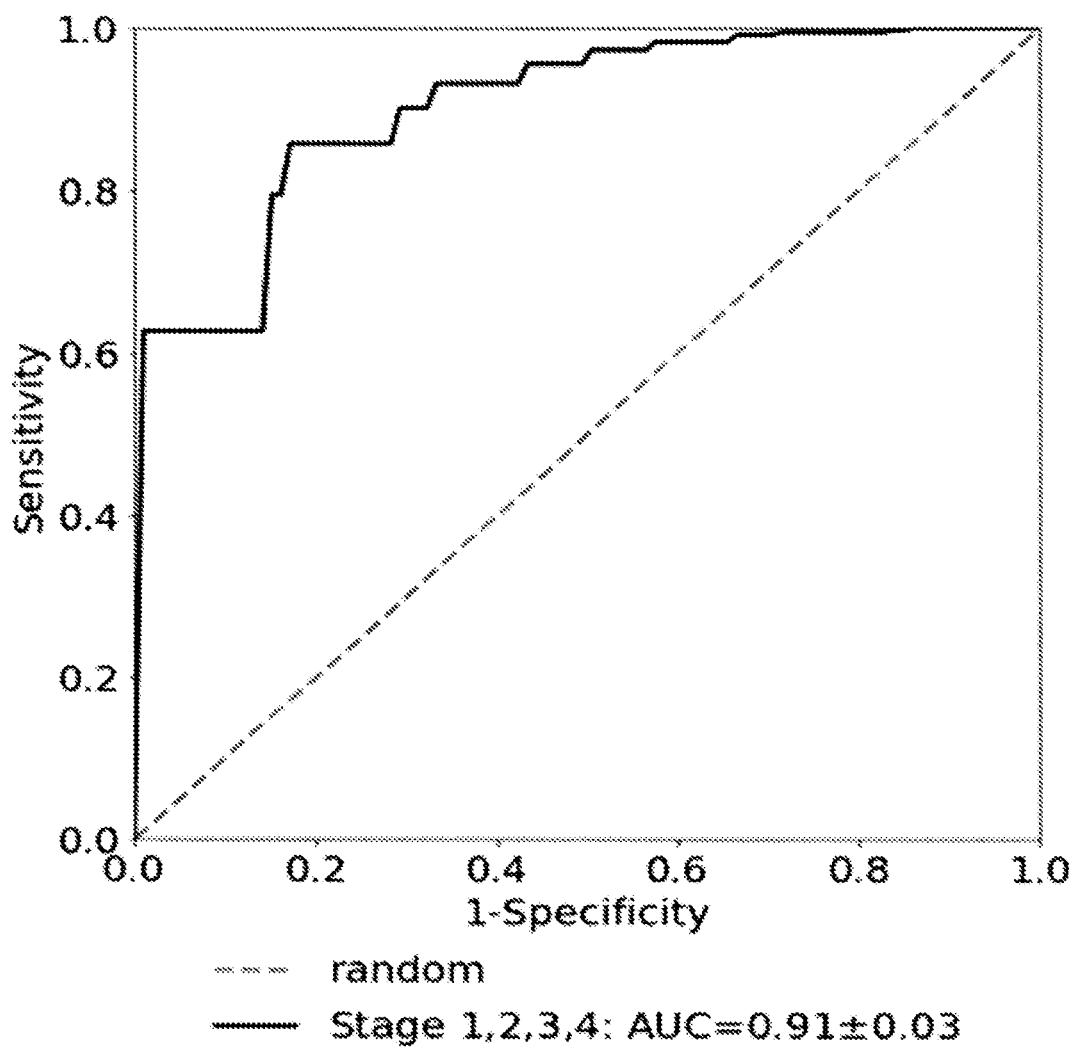
FIG. 38A shows performance of a classifier trained with data from genomics assays, and includes a ROC curve for disease state classification. The AUC value at the bottom of the figure is shown with ±values based on 90% confidence.

Overall, log-transformed counts on 18045 canonical mRNA transcripts and 1035 miRNA transcripts, as well as percentage methylation on 9290 CpG sites (filtered by adequate read coverage) were used. Univariate analyses identified 8769 mRNAs, 204 miRNAs, and 3128 CpG sites that were significantly differentially expressed (or methylated) at a Benjamini-Hochberg FDR<0.05, including both novel and known biomarkers associated with pancreatic cancer. A majority of these mRNAs were less abundant in cases compared to controls while the opposite was true of the miRNAs. CpG site methylations were generally more balanced, but were nonetheless more likely unmethylated in cases compared to controls. The random-forest-based genomics classifier was trained using 30 repeats of 5-fold nested cross-validation with hyperparameter tuning. Across all repeats, mean sensitivities of 46% (95% CI, 20%-72%) were observed for stage 1, 2, 3, 72% (95% CI, 59%-85%) for stage 4, and 64% (95% CI, 52%-76%) for all stages at a specificity of 92%. Data for the genomics classifier are shown in FIG. 38A.

In this initial study on pancreatic cancer using multi-omics readouts from a liquid biopsy, substantial numbers of dysregulated mRNA and miRNA transcripts were observed, which may reflect cancer-associated changes to the immune system. The most discriminative transcripts included novel biomarkers as well as genes under investigation as therapeutic targets in multiple cancers. Machine learning modeling additionally yielded a classifier whose cross-validation performance highlights the potential of multi-omics towards both disease diagnosis as well as novel target discovery.

Example 14. Analyses of Multiple Blood-Based Mass Spectrometry and Genomic Assays in Pancreatic Cancer Plasma samples from the subjects described in Example 13 were also analyzed using mass spectrometry-based omics assays, including protein (Proteograph and PiQuant), lipid, and metabolite assays. A classifier was trained using these mass spectrometry-based omics assays, which may be referred to as a mass spec classifier. A combined classifier was trained using both the mass spectrometry-based omics assays in this example, and the genomics assays in Example 13. The mass spec and combined classifiers were trained and tested similarly to the genomics classifier of Example 13, but using the different or additional data types (including mass spectrometry assays).

Figure 38B:
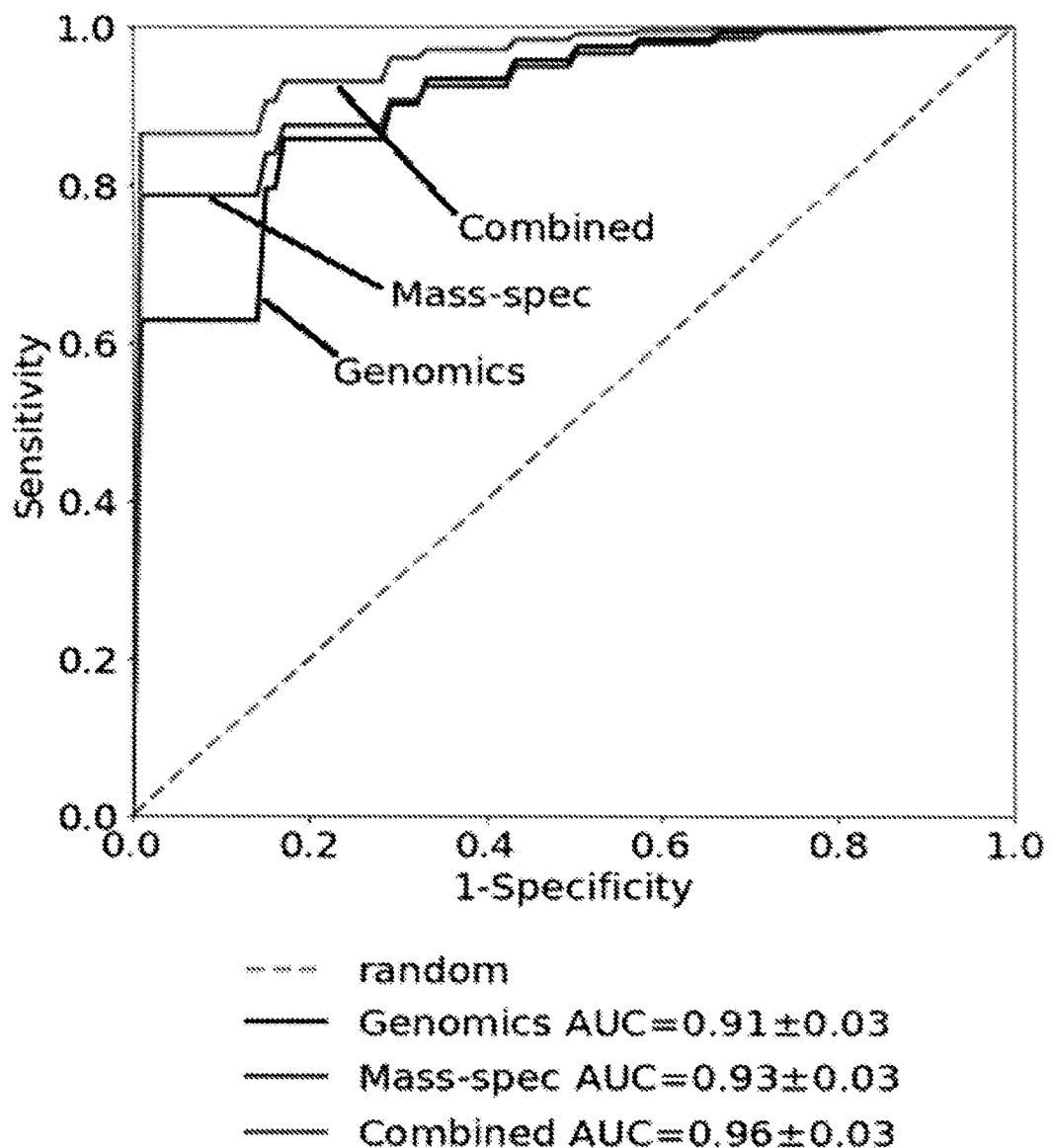
FIG. 38B shows performance of a classifier trained with data from genomics assays ("Genomics"), a classifier trained with data from mass spectrometry assays ("Mass-spec"), and a classifier trained with data from genomics and mass spectrometry assays ("Combined"). The data shown in the figure include ROC curves for disease state classification. The AUC values include ±values based on 90% confidence.

Performance of the mass spec classifier of this example, the genomics classifier of Example 13, and the combined classifier of this example, were all compared. Data are shown in FIG. 38B. Based on classifier performance, the mass spec assays and genomics assays appear to provide complementary information such that the performance of the combined classifier was better than those of the component ones.

Additional data, including ROC curves and AUC values, are shown in FIG. 103, FIG. 104, FIG. 105, and FIG. 106. The data show combined classifiers relative to classifiers with individual data types, and show performance improvements with certain combinations.

The classifiers included the following total numbers of features for any given data type: 9289 for methylation, 18045 for mRNA, 1033 for microRNA (generated with paxgene tubes), 374 for PiQuant, 17975 for Proteograph (split between among separate types of particles), 677 for lipids, or 298 for metabolites.

Example 15. Unbiased Multi-Omics Approach for the Detection of Pancreatic Cancer Biomarkers Utilizing Ion-Mobility Mass Spectrometry and Nano-Particle Based Proteograph Technology Pancreatic cancer is the seventh leading cause of cancer-related death worldwide and the third leading cause of cancer-related death in the USA. Challenges in early detection have led to poor survival rates, highlighting the need for early diagnostic test development. Biomarkers measured in liquid biopsies offer a less invasive and accessible strategy for early cancer detection. Analyte degradation and dilution in complex biological matrix limit high specificity and sensitivity measurements, making biomarker discovery from blood a formidable challenge.

A comprehensive multi-omics platform has been developed that integrates multiple analyte measurements, cutting-edge analytical instrumentation, and novel data-analysis approaches. To demonstrate this platform's power, an unbiased multi-omics study of a pancreatic cancer cohort of 196 subjects was conducted, resulting in the detection of novel biological signals. The study included the same samples and protein data as were used in Example 11. However, this study utilizes a different approach for generating lipid data.

The study cohort comprised 196 human subjects. Out of the 196 subjects, 92 had pancreatic cancer and 104 were healthy. Subject samples were collected post-diagnosis, but pre-treatment for cancer subjects versus healthy controls. Plasma samples were processed for proteomics on the nanoparticle-based Proteograph platform (Seer Inc.). Resulting peptides were analyzed by LC-MS/MS on an Evosep One (60 samples per day) interfacing with a Bruker timsTOF Pro2 mass spectrometer. MS data were acquired in DIA-PASEF mode and analyzed using DIA-NN. Plasma samples were also processed for total lipids utilizing an extraction mixture of 1:1 v/v butanol: methanol. Clean extract from each subject was analyzed by LC-MS/MS on a Bruker timsTOF Pro2 in positive ionization mode utilizing DDA-PASEF. Data was analyzed utilizing Metaboscape to detect, deconvolute, and annotate lipids.

In the initial analysis, 3,381 proteins were detected in all samples (minimum of 3 samples per class). Of these, over 100 proteins were differentially measured with statistical significance in pancreatic cancer subjects following a Bonferroni correction (5% false discovery rate). The initial analysis also annotated >260 lipids in positive ion mode from ~8,000 features following a conservative rules-based annotation approach that incorporated the high resolution, high mass accuracy, ion mobility CCS values, and MS2 spectra of the DDA PASEF data collection. Example lipid classes that were detected included phospholipids, triglycerides, sphingolipids, and cholesteryl esters. Protein and lipid classes measured in the study have previously reported associations with pancreatic cancer, thereby adding confidence to the initial proteomic and lipidomic measurements. The data also comprised protein and lipid classes with no currently known association with pancreatic cancer. Ongoing analysis of the detected proteins and lipids could enable discovery of previously unknown biology and expand the realm of biomarker analytes for early detection of pancreatic cancer.

Preliminary analysis of the cohort study indicated that biological signatures of pancreatic cancer can be inferred using the multi-omics approach evidenced by significant differences between pancreatic cancer and healthy subject across analyte classes. Further analysis of this cohort study will determine if feature integration within and across analyte classes could improve biomarker detection. This is a case-control study, not an intent to test study. This study indicated the detection of pancreatic cancer across a multitude of analyte classes.

This unbiased multi-omics platform leveraging 4D-mass spectrometry will integrate molecular signatures of cancer across multiple analytes to facilitate early biomarker discovery.

Example 16. Combining Proteograph Technology with Zeno SWATH Acquisition Further Improves Deep, Unbiased Discovery of Biomarkers in Blood Recent proteomic advancements have enabled large-scale studies to investigate biomarkers relevant to disease diagnosis and prognosis, while giving insight into the pathogenesis of complex diseases such as cancer. Liquid biopsies have been increasingly investigated for large-scale biomarker studies due to the non-invasive nature of sample collection, compared to invasive techniques such as tissue biopsies, potentially enabling improved prognosis and survival. Despite the challenges of achieving deep proteome coverage in complex biological matrices, innovative sample preparation and liquid chromatography mass spectrometry (LC-MS) technology have facilitated identification and quantification of cancer-specific biomarkers in wide ranges of concentrations in liquid biopsies. This study addresses the unmet need for deep, reproducible identification from the human plasma proteome utilizing advanced sample preparation and LC-MS technology.

From the large multi-omics oncology discovery study, comprised of >1,750 subjects across three different cancers, a retrospective case-control sub-study was performed to survey the plasma proteome profiles of 104 normal and 92 pancreatic cancer subjects (the same plasma samples as in Example 11). The samples were processed utilizing the nanoparticle based Proteograph technology from Seer. The samples were then subjected to data acquisition using a Waters ACQUITY M-class system (LC) with capillary flow rates (5 µL/min) synchronized to the ZenoToF 7600 system from SCIEX (MS). Duplicate injections were made into the mass spectrometer with and without enabling prototype Zeno SWATH acquisition in data independent acquisition (DIA) mode. The data processing and downstream analysis was performed using DIANN.

In this study, the nanoparticle based Proteograph technology was implemented along with prototype Zeno SWATH acquisition methods to yield highly reproducible proteome data while increasing the depth of coverage of low abundant proteins.

An average of >1,500 protein groups and >13,000 peptides were annotated per plasma sample due to the increased sensitivity of Zeno SWATH acquisition methods combined with the additional proteome depth provided by the Proteograph technology. A sub-study of ~200 biological samples and process controls generated robust plasma protein measurements across ~1,000 injections, demonstrating the robustness and reproducibility advantages of a capillary LC combined with Zeno SWATH acquisition. In addition, large differences were observed in reproducible protein identification using Zeno SWATH acquisition versus SWATH acquisition using the same experimental and analytical parameters. These results further demonstrated the feasibility of running larger cohort studies with thousands of clinical samples that address historical technical challenges related to translating proteomics to the clinic.

Furthermore, this study indicated that the Proteograph or Zeno SWATH acquisition workflow may be used to facilitate identifying and quantifying thousands of proteins from human plasma without compromising throughput or reproducibility, creating a unique opportunity to detect robust protein biomarkers that translate into viable clinical tests for complex diseases. Quantification of thousands of plasma proteins was enabled at least in part by combining nanoparticle-assisted sample preparation with reproducible and sensitive MS measurements.

Example 17. A Multi-Omics Study of Liver Cancer

A proteomic and lipidomic study was performed to differentiate plasma samples from subjects with liver cancer relative to healthy subjects. The study was performed using 18 plasma samples from subjects with liver cancer ("liver cancer samples"), and 53 age and gender matched control plasma samples ("healthy samples"). In addition, 9 plasma samples from subjects with ovarian cancer were also assessed (for a total of 80 samples). Some details of the liver cancer samples are included in FIG. 39A, which shows that the liver cancer samples included 1 sample from a subject with stage I liver cancer, 3 samples from subject with stage II liver cancer, 2 samples from subject with stage III liver cancer, 5 samples from subject with stage IV liver cancer, and 6 samples from subjects with an unknown stage of liver cancer. The samples from subjects with ovarian cancer ("ovarian cancer samples") included 4 samples from stage III ovarian cancer and 5 samples from stage IV ovarian cancer.

To generate the proteomic data, the plasma samples were contacted individually with particles to adsorb proteins from the plasma onto a corona around each particle. Proteins adsorbed to the particles were then assessed by liquid chromatography-mass spectrometry (LC-MS). Proteomic data were obtained from the use of 5 physiochemically distinct particle types (designated "NP1," "NP2," "NP3,"

"NP4," and "NP5"). These particles were purchased commercially from Seer, Inc. where they were identified as S-003, S-006, S-007, P-039, and P-073, respectively. The proteomic data were highly reproducible, and included data on the amounts of 2,368 unique protein groups and 22,886 unique peptides. Mean coefficient of variation (CV) values for the peptides and proteins ranged from about 20 to 40 for data generated using the various particles (FIG. 39B).

Figures 1, 39C:
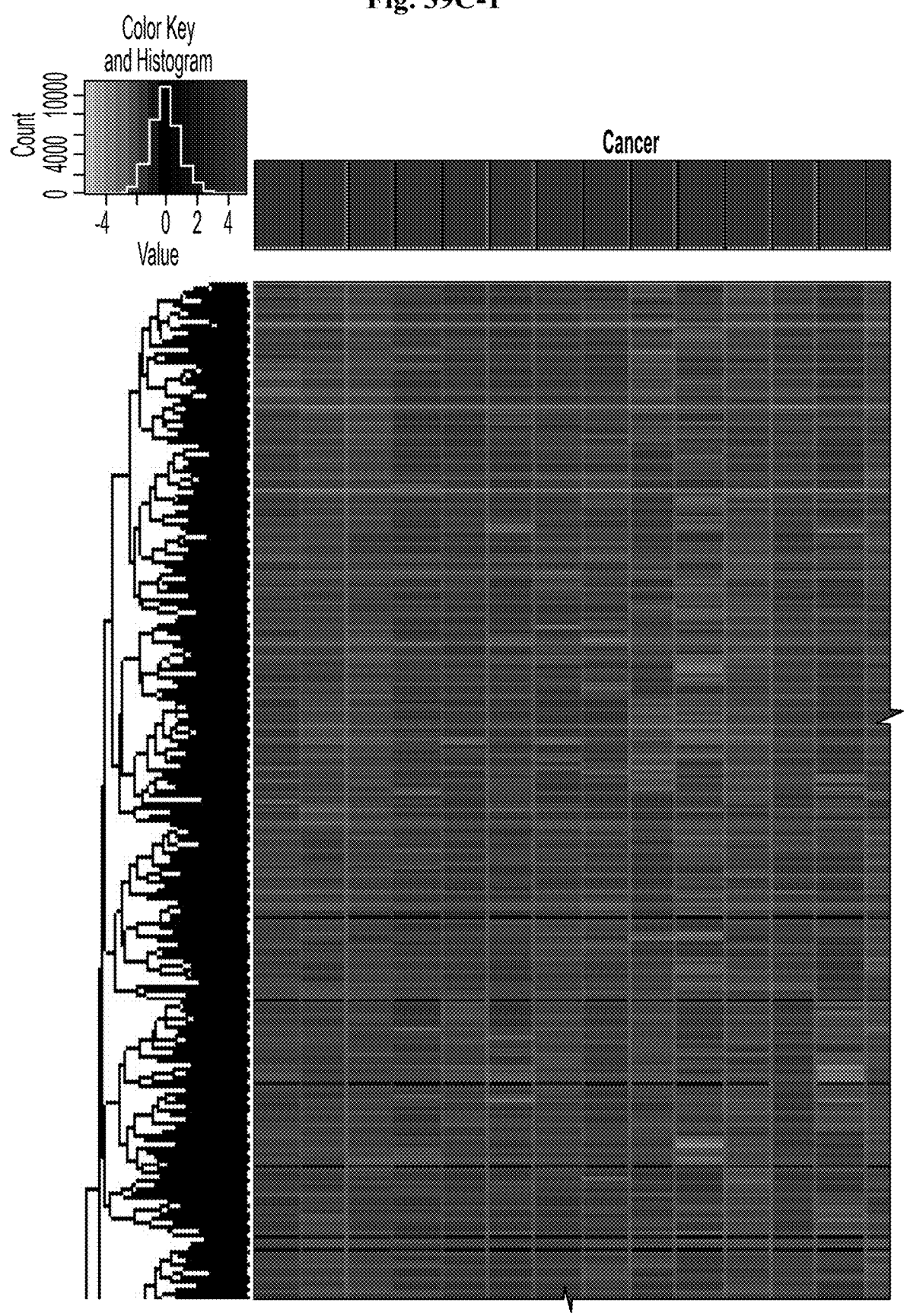
Figures 2, 39C:
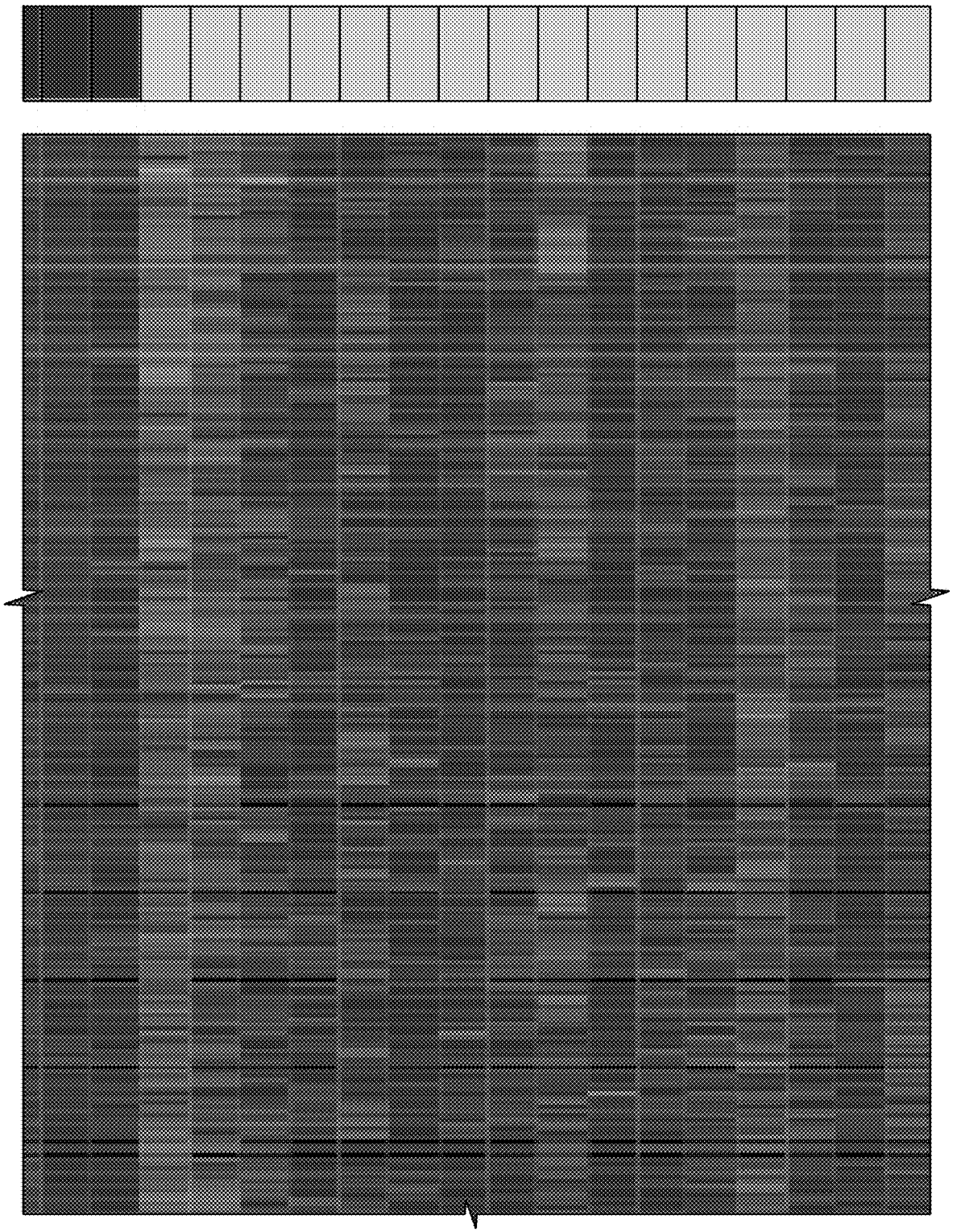
Figures 3, 39C:
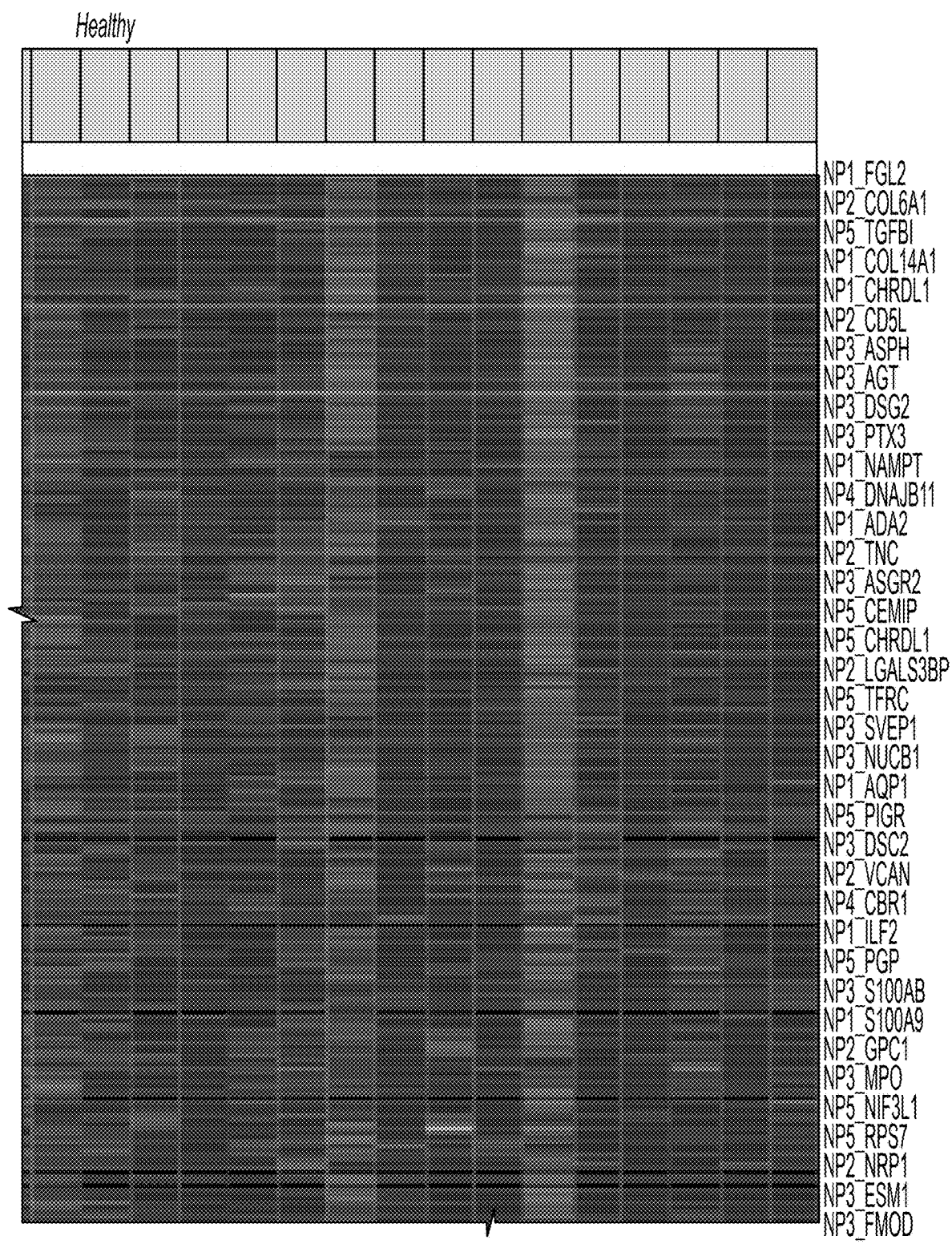
Figures 4, 39C:
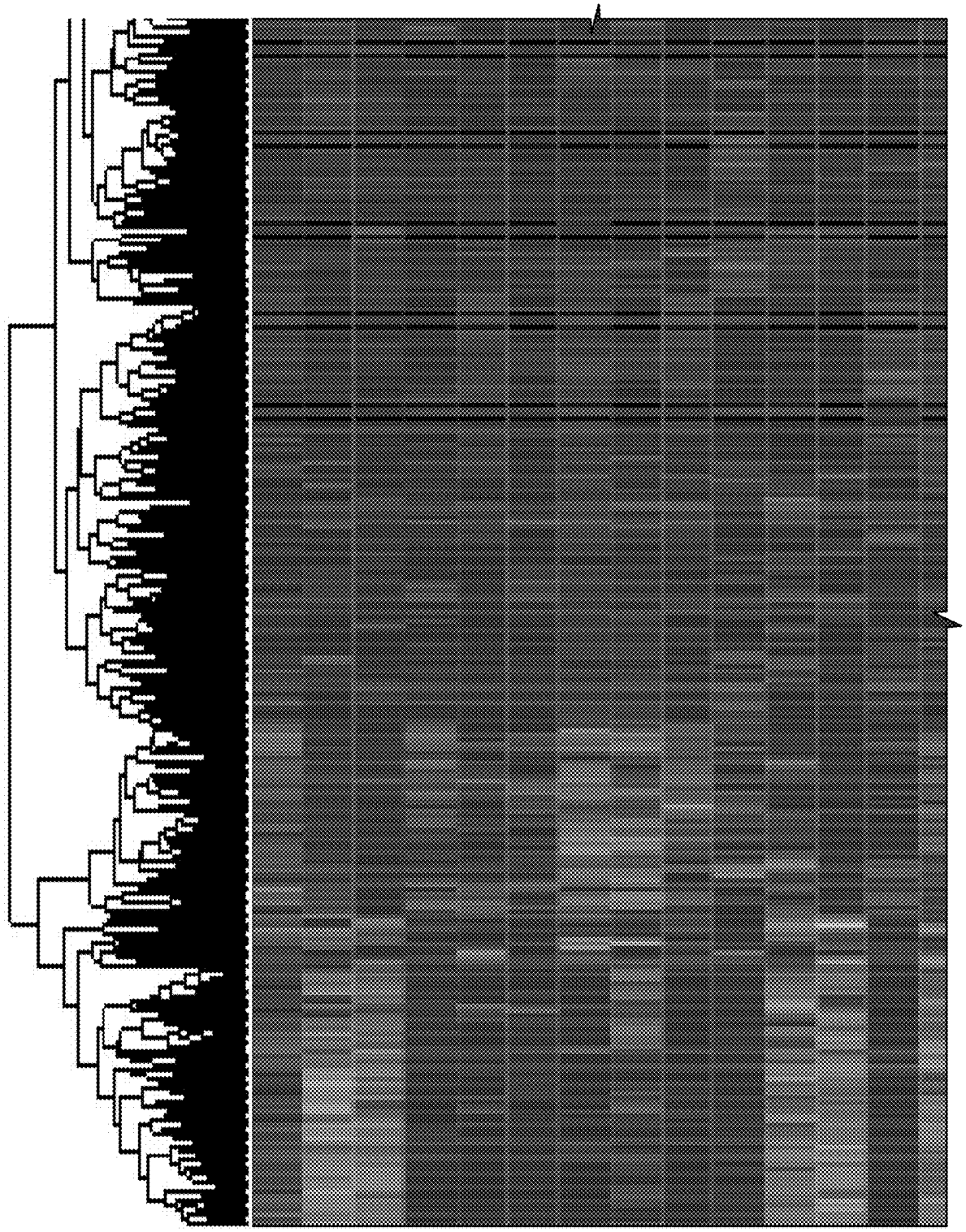
Figures 5, 39C:
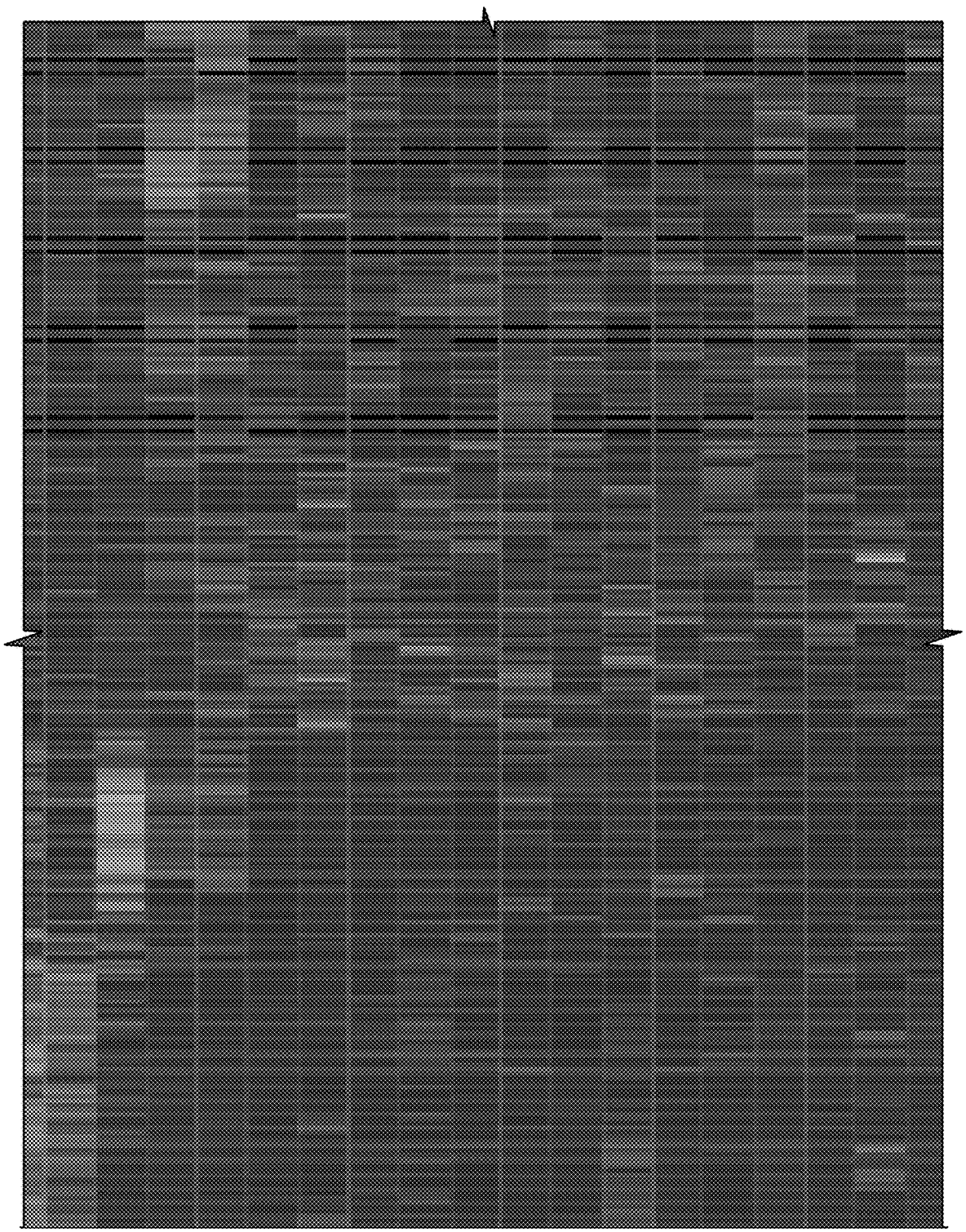
Figures 6, 39C:
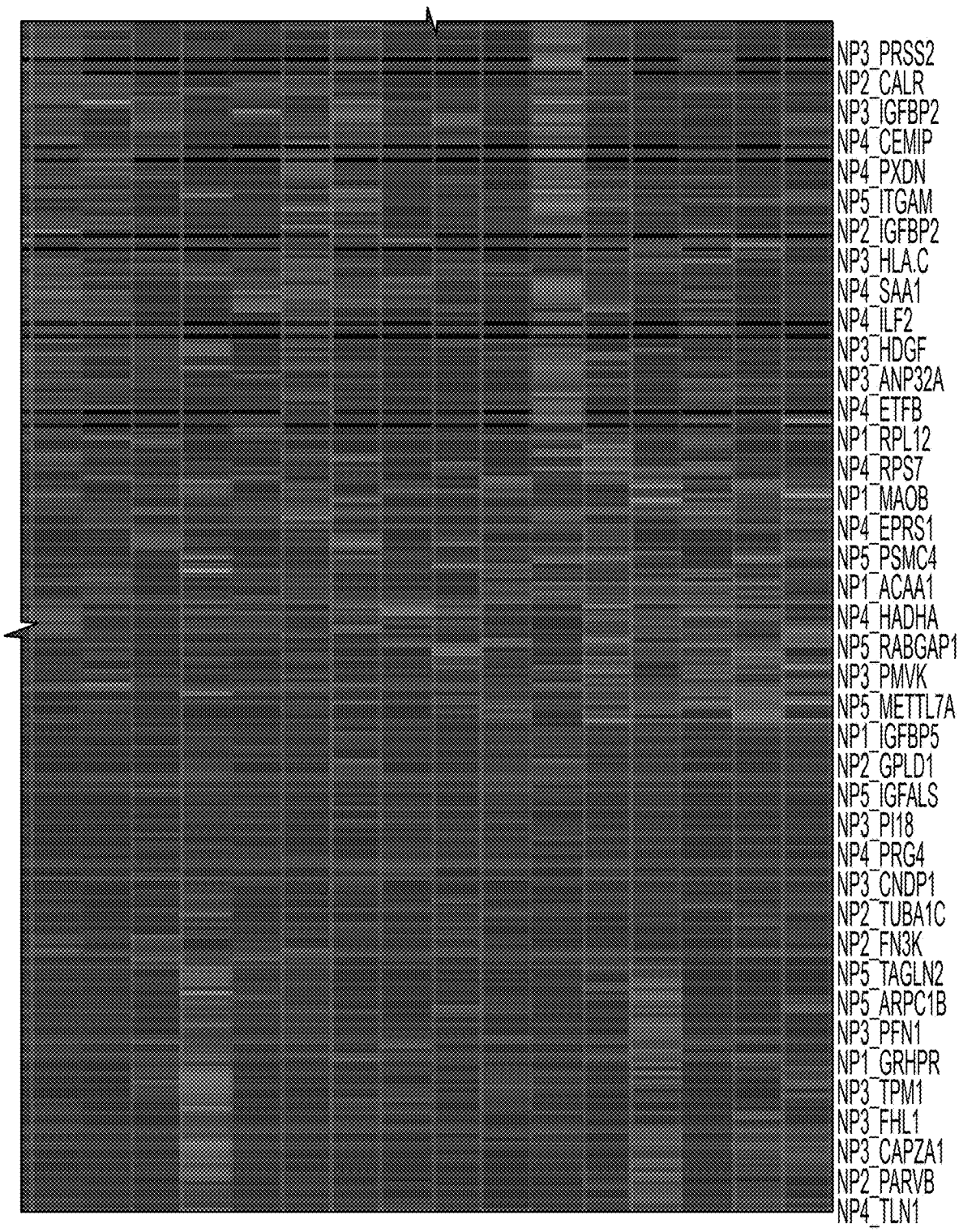

FIG. 39C shows an exemplary protein abundance heatmap of liver cancer samples and healthy samples. A strong difference was seen in expression patterns of liver cancer (especially in late stage liver cancer) and healthy samples. Any of the proteins or particles shown in FIG. 39C may be useful in a method described herein, such as a method of identifying a subject with liver cancer or for ruling out liver cancer. From top to bottom, the proteins listed in FIG. 39C include the following in order: FGL2, COL6A1, TGFB1, COL14A1, CHRDL1, CD5L, ASPH, AGT, DSG2, PTX3, NAMPT, DNAJB11, ADA2, TNC, ASGR2, CEMIP, CHRDL1, LGALS3BP, TFRC, SVEP1, NUCB1, AQP1, PIGR, DSC2, VCAN, CBR1, ILF2, PGP, S100A8, S100A9, GPC1, MPO, NIF3L1, RPS7, NRP1, ESM1, FMOD, PRSS2, CALR, IGFBP2, CEMIP, PXDN, ITGAM, IGFBP2, HLA.C, SAA1, ILF2, HDGF, ANP32A, ETFB, RPL12, RPS7, MAOB, EPRS1, PSMC4, ACAA1, HADHA, RABGAP1, PMVK, METTL7A, IGFBP5, GPLD1, IGFALS, PI16, PRG4, CNDP1, TUBA1C, FN3K, TAGLN2, ARPC1B, PFN1, GRHPR, TPM1, FHL1, CAPZA1, PARVB, and TLN1, in conjunction with various nanoparticles.

Figure 39D:
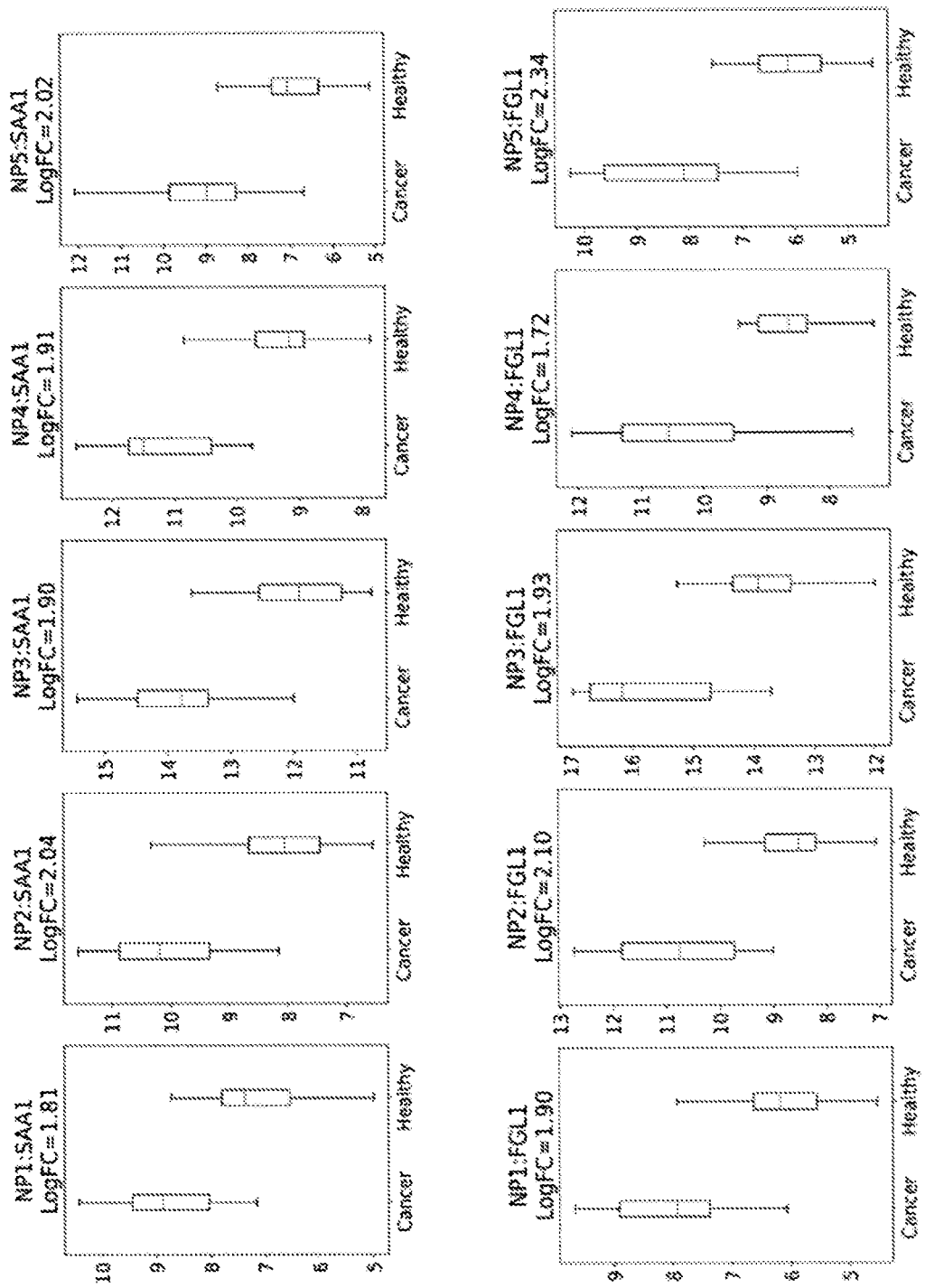
FIG. 39D shows examples of differences in protein abundances identified in samples from subjects with liver cancer or from healthy subjects, after contact of the samples with various particles described herein.

FIG. 39D shows some examples of univariate protein differences for liver cancer from healthy sample. Several differentially abundant proteins (e.g., SAA1 or FGL1) were observed in liver cancer. Abundances for SAA1 and FGL1 varied across separate nanoparticles but log-fold changes between cancer and healthy were consistent among particle types.

Figure 39E:
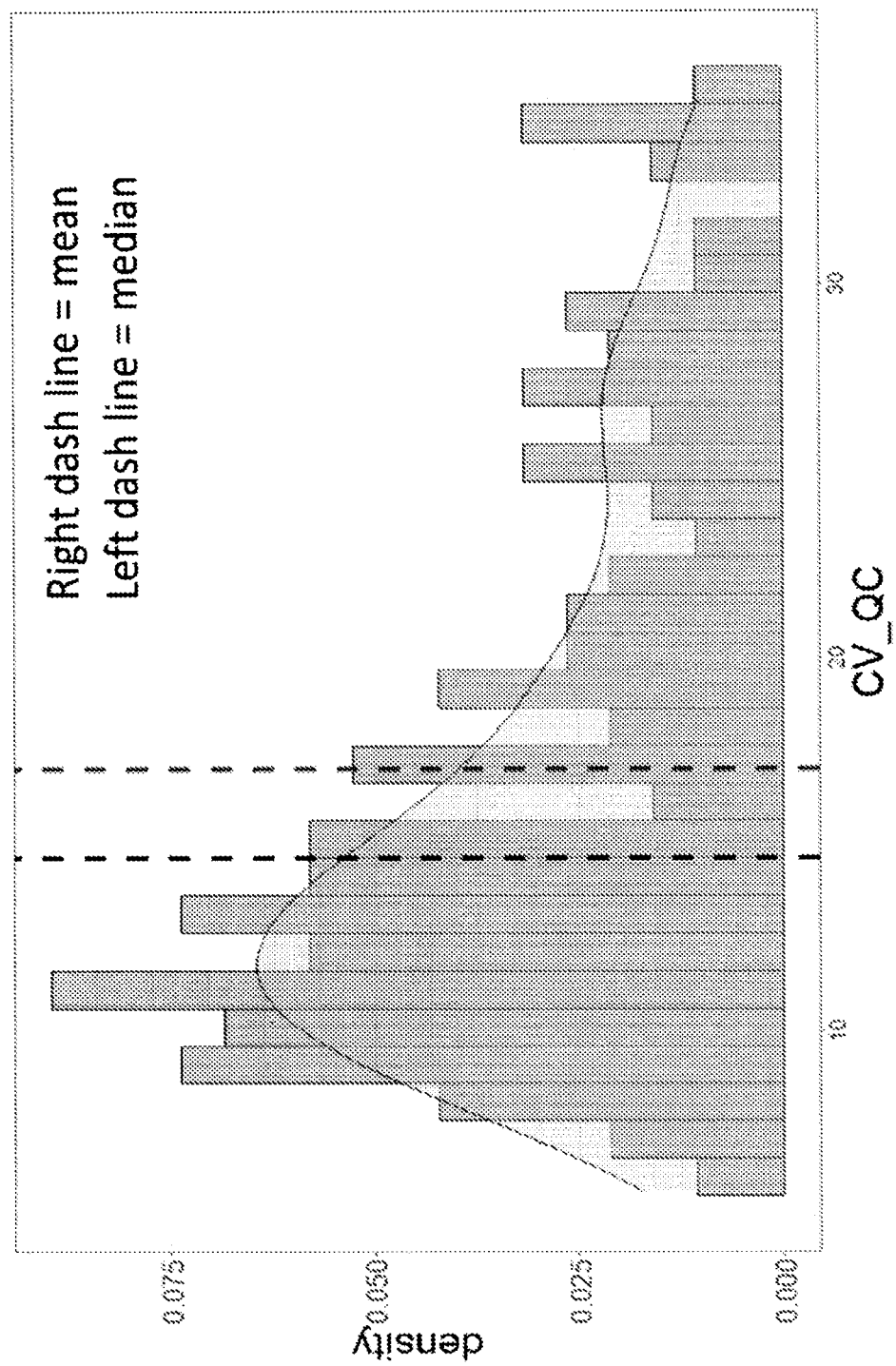
FIG. 39E includes a graph showing that lipidomic data obtained from samples was highly reproducible.

To generate the lipidomic data, the plasma samples were assessed by LC-MS. Lipidomic data for all of the samples showed univariate performance for 75 lipids. FIG. 39E shows that lipidomic data obtained from cancer samples was highly reproducible. Data was analyzed for 188 of 858 lipids for all patient samples. A median coefficient of variation (CV) of 14.6% was observed when calculated across 16 pooled samples. CV was representative of all technical variability (e.g. sample processing, data collection, etc.)

Figures 1, 39F:
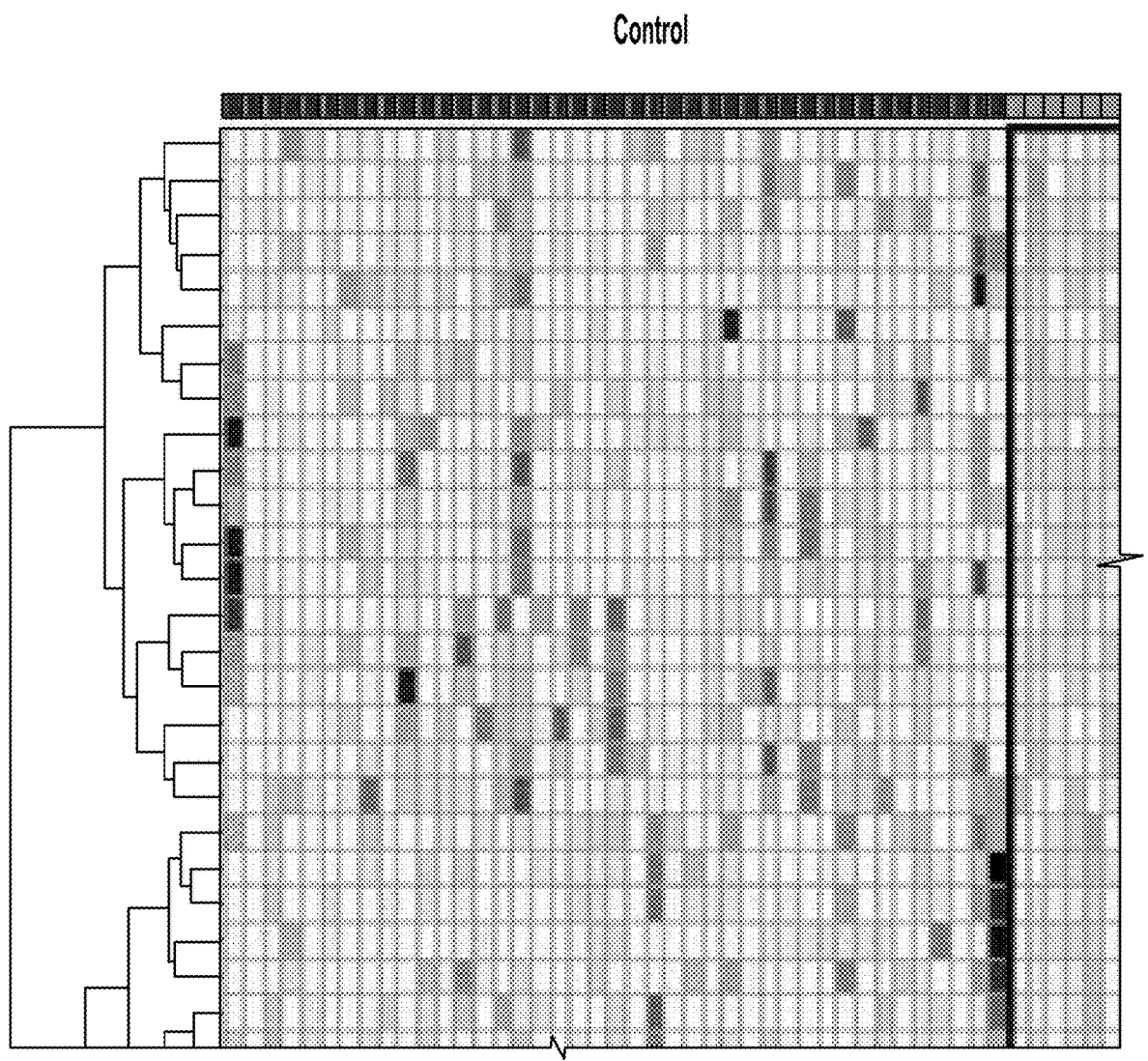
Figures 2, 39F:
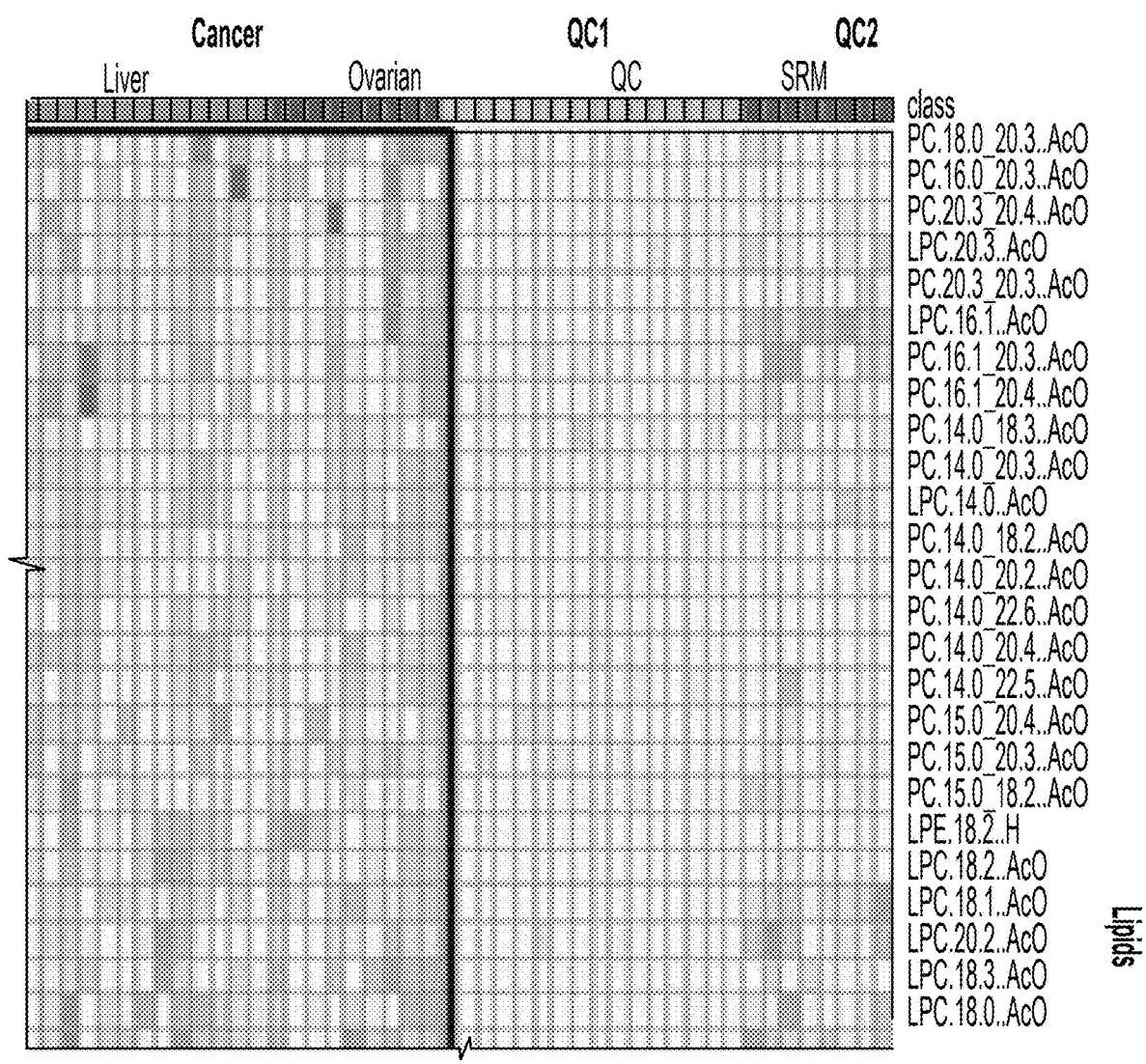
Figures 3, 39F:
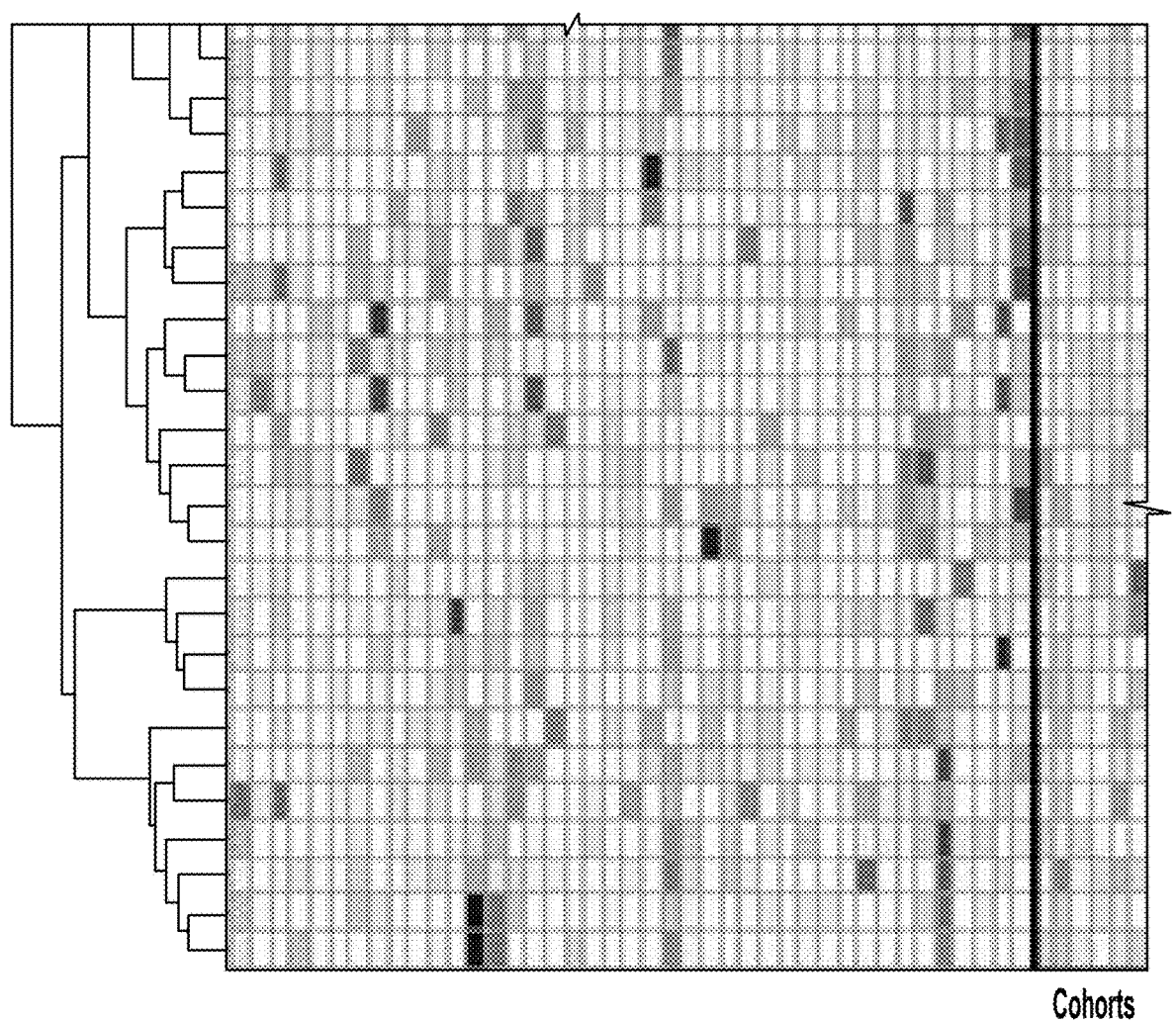
Figures 4, 39F:
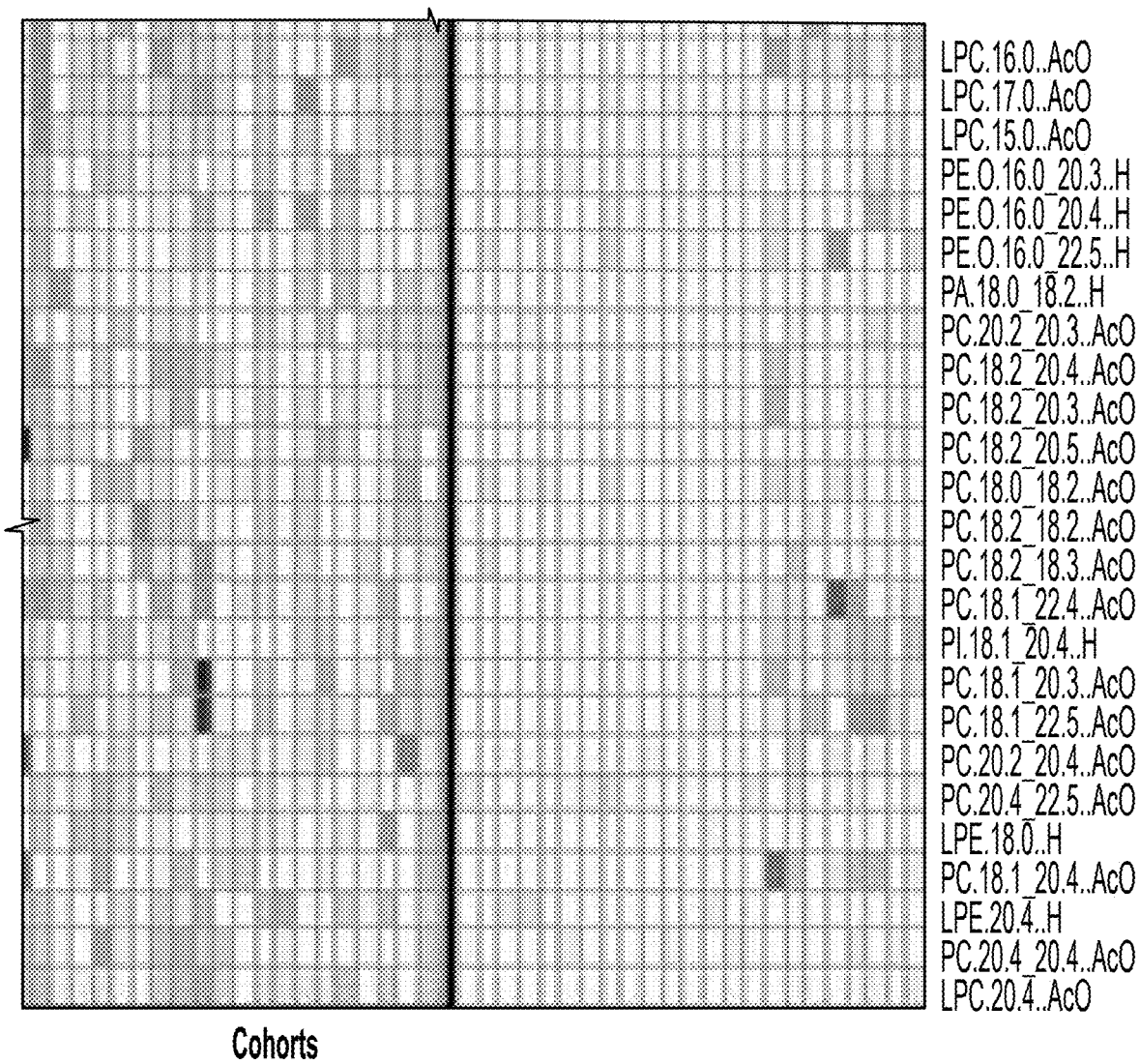

FIG. 39F shows that liver cancer samples exhibited distinct lipid profiles compared to healthy controls. The top 50 lipids based on p-value are shown for all patient samples analyzed, and included phospholipids. The heatmap shows decreased abundances of several phospholipids in cancer samples compared to elevated levels in healthy samples. From top to bottom, the lipids listed in FIG. 39F include the following in order: PC.18.0_20.3 . . . AcO, PC.16.0_20.3 . . . AcO, PC.20.3_20.4 . . . AcO, LPC.20.3 . . . AcO, PC.20.3_20.3 . . . AcO, LPC.16.1 . . . AcO, PC.16.1_20.3 . . . AcO, PC.16.1_20.4 . . . AcO, PC.14.0_18.3 . . . AcO, PC.14.0_20.3 . . . AcO, LPC.14.0 . . . AcO, PC.14.0_18.2 . . . AcO, PC.14.0_20.2 . . . AcO, PC.14.0_22.6 . . . AcO, PC.14.0_20.4 . . . AcO, PC.14.0_22.5 . . . AcO, PC.15.0_20.4 . . . AcO, PC.15.0_20.3 . . . AcO, PC.15.0_18.2 . . . AcO, LPE.18.2 . . . H, LPC.18.2 . . . AcO, LPC.18.1 . . . AcO, LPC.20.2 . . . AcO, LPC.18.3 . . . AcO, LPC.18.0 . . . AcO, PE.O.16.0_22.5 . . . H, PA.18.0_18.2 . . . H, PC.20.2_20.3 . . . AcO, PC.18.2_20.4 . . . AcO, PC.18.2_20.3 . . . AcO, PC.18.2_20.5 . . . AcO, PC.18.0_18.2 . . . AcO, PC.18.2_18.2 . . . AcO, PC.18.2_18.3 . . . AcO, PC.18.1_22.4 . . . AcO, PI.18.1_20.4 . . . H, PC.18.1_20.3 . . . AcO, PC.18.1_22.5 . . . AcO, PC.20.2_20.4 . . . AcO, PC.20.4_22.5 . . . AcO, LPE.18.0 . . . H, PC.18.1_20.4 . . . AcO, LPE.20.4 . . . H, PC.20.4_20.4 . . . AcO, and LPC.20.4 . . . AcO.

Figure 39G:
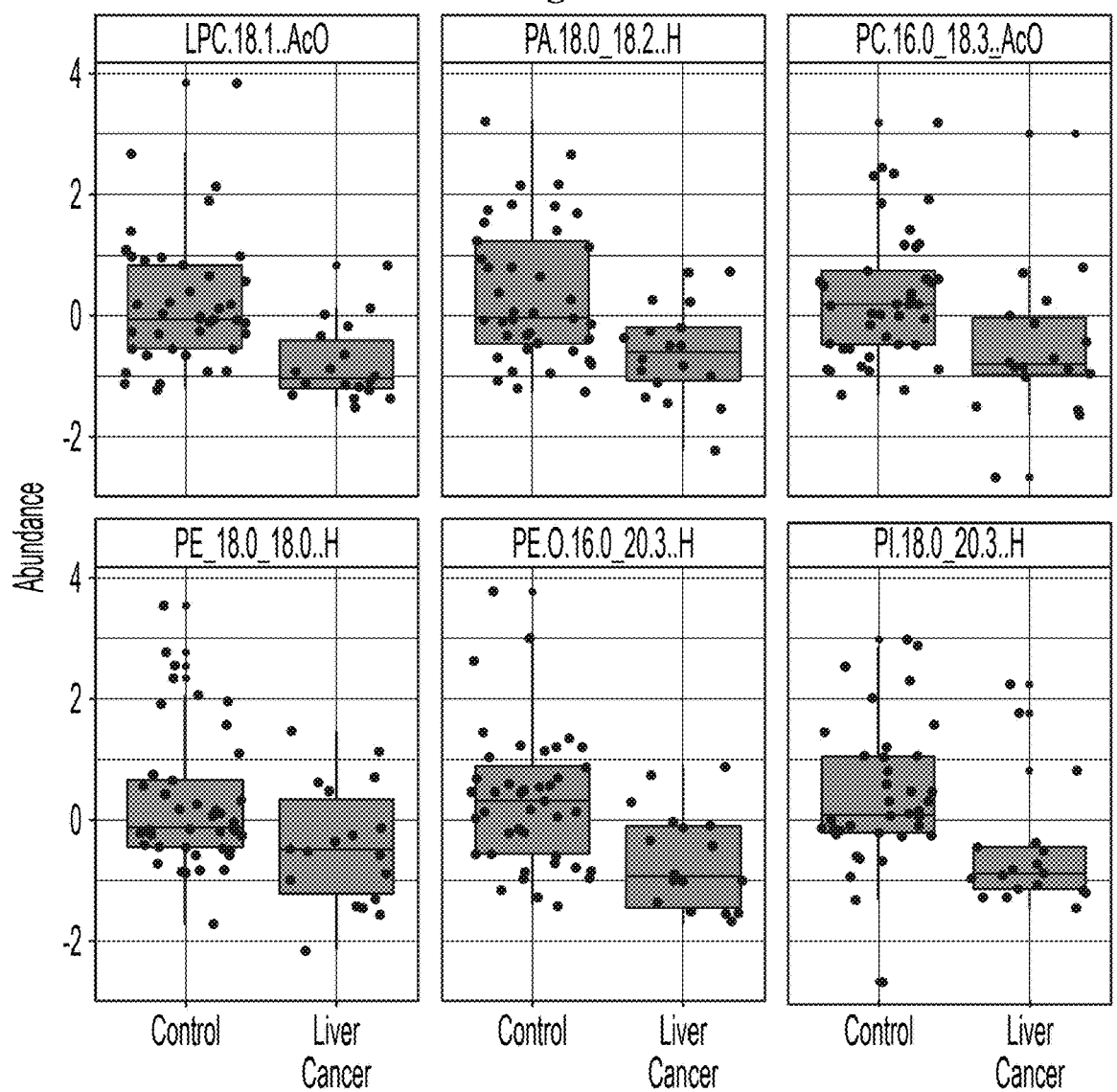
FIG. 39G shows univariate lipid differences for samples from subjects with liver cancer compared to healthy subjects.

FIG. 39G shows univariate lipid differences for liver cancer samples compared to healthy samples. 75/188 lipids were significantly different among healthy and cancer cohorts, as assessed by a one way ANOVA with a Fisher LSD correction at 0.05 (FDR: 7.60e-10-0.048). Several phospholipids were observed to be significantly different among cohorts. For example, lysophosphatidylcholines (LPCs) and lysophosphatidylethanolamines (LPEs) were significantly lower in cancer samples relative to healthy samples. These data indicate that levels of circulating lipids such as phospholipids may be useful as biomarkers for identifying a subject as likely to have a cancer such as liver cancer or as not likely to have the cancer.

Significant differences were also identified in phospholipids between liver cancer samples and ovarian cancer samples, indicating that differences in phospholipid metabolism or circulating levels of phospholipids may be useful for distinguishing between cancer types.

Example 18. Identifying a Likelihood of Liver Cancer in a Subject

A subject comes into a doctor's office due to jaundice and large mass which can be felt in upper, right part of abdomen. The doctor determines that the subject may be at risk of having liver cancer, and performs a non-invasive work-up, including an abdominal ultrasound and a CT scan but nothing of note is detected. A plasma sample is obtained from the patient to be analyzed by the methods described herein. The lab measures the presence and abundance of several proteins. The lab then applies a classifier to generate an output report to the physician for determining whether the subject has liver cancer. The report indicates that the patient likely has a liver cancer. It's possible that the liver cancer is small and developing at an early stage, which explains the why scans did not detect the liver cancer. The physician asks the patient to return for a regular check-up once every 6 months to continue monitoring the liver cancer. During one of the subsequent check-ups, the analysis of the biofluid sample obtained from the subject indicates that the liver cancer has progressed. The physician then prescribes or administers a liver cancer treatment regimen.

Example 19. A Multi-Omics Study of Ovarian Cancer

A proteomic and lipidomic study was performed to differentiate plasma samples from subjects with ovarian cancer relative to healthy subjects. The study was performed using 9 plasma samples from subjects with ovarian cancer ("liver cancer samples"), and 53 age and gender matched control plasma samples ("healthy samples"). In addition, 18 plasma samples from subjects with liver cancer were also assessed (for a total of 80 samples). Some details of the ovarian cancer samples are included in FIG. 39A, which shows that the ovarian cancer samples included 4 samples from subject with stage III ovarian cancer and 5 samples from subject with stage IV ovarian cancer. The samples from subjects with liver cancer ("liver cancer samples") included 1 sample from a subject with stage I liver cancer, 3 samples from subject with stage II liver cancer, 2 samples from subject with stage III liver cancer, 5 samples from subject with stage IV liver cancer, and 6 samples from subjects with an unknown stage of liver cancer.

To generate the proteomic data, the plasma samples were contacted individually with particles to adsorb proteins from the plasma onto a corona around each particle. Proteins adsorbed to the particles were then assessed by liquid chromatography-mass spectrometry (LC-MS). Proteomic data were obtained from the use of 5 physiochemically distinct particle types (designated "NP1," "NP2," "NP3," "NP4," and "NP5"). These particles were purchased commercially from Seer, Inc. where they were identified as S-003, S-006, S-007, P-039, and P-073, respectively. The proteomic data were highly reproducible, and included data on the amounts of 2,368 unique protein groups and 22,886 unique peptides. Mean coefficient of variation (CV) values for the peptides and proteins ranged from about 20 to 40 for data generated using the various particles (FIG. 39B). The data in the FIG. 39B were based on samples of both liver and ovarian cancer.

Figure 40A:
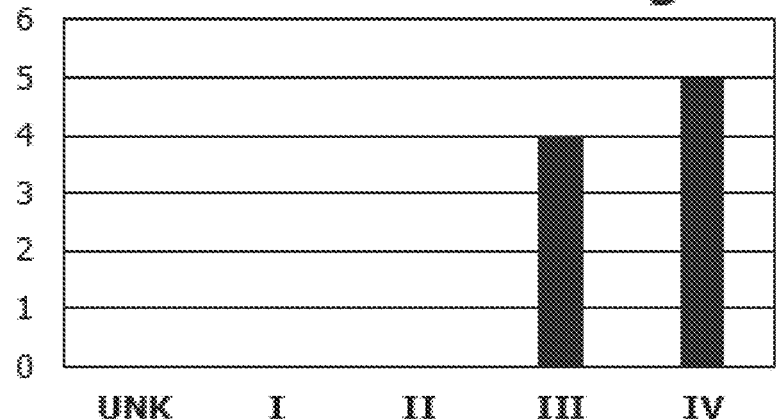
FIG. 40A shows a graphical summary of 9 samples from ovarian cancer subjects used in Example 19.
Figure 40B:
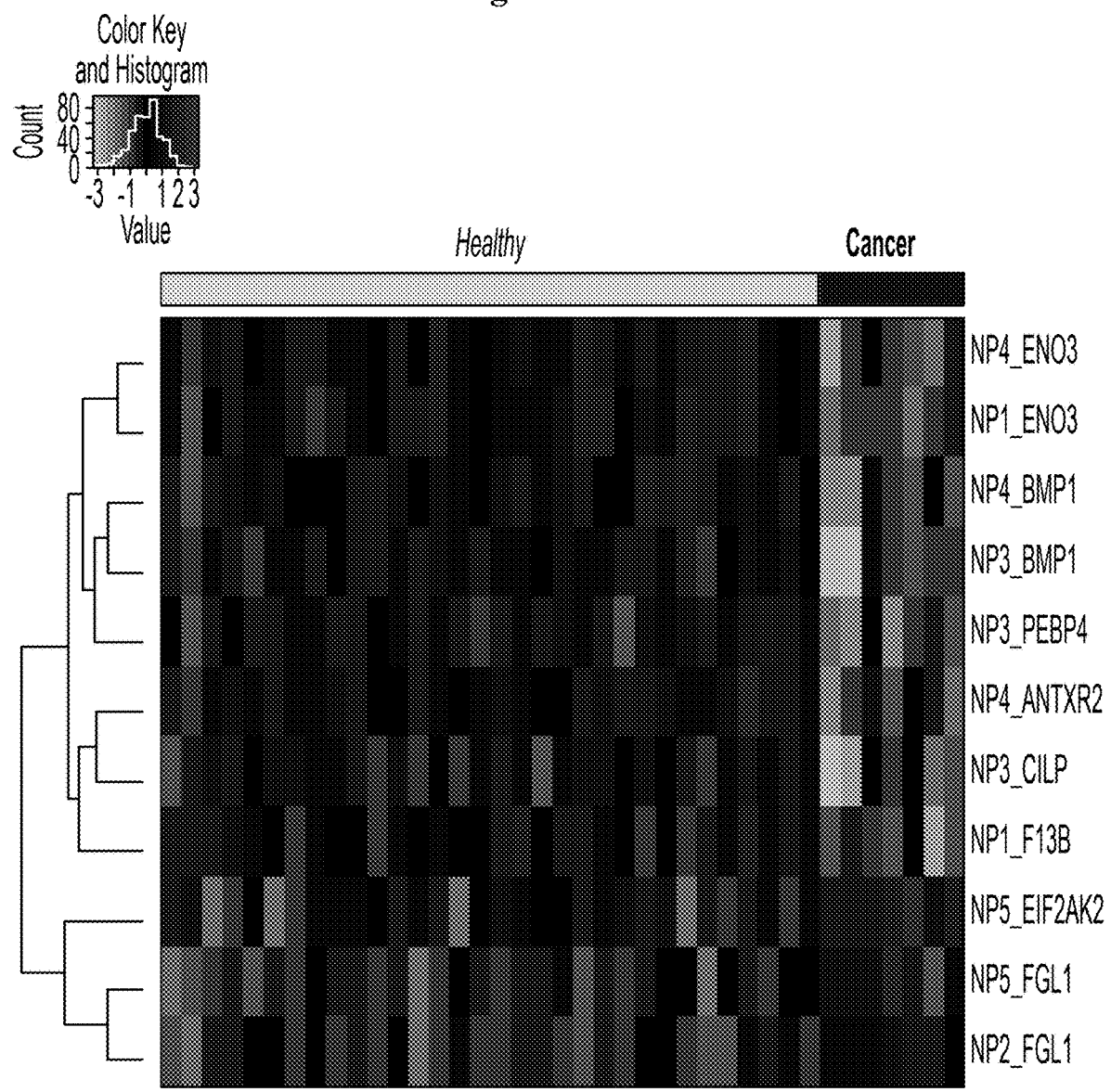
FIG. 40B shows an exemplary protein abundance heatmap of samples from subjects with ovarian cancer and healthy subjects.

FIG. 40B shows an exemplary protein abundance heatmap of ovarian cancer samples and healthy samples. A strong difference was seen in expression patterns of ovarian cancer (particularly in late stage ovarian cancer) and healthy samples. Any of the proteins or particles shown in FIG. 40B may be useful in a method described herein, such as a method of identifying a subject with ovarian cancer or for ruling out ovarian cancer. From top to bottom, the nanoparticles and proteins listed in FIG. 40B include the following in order: NP4_ENO3, NP1_ENO3, NP4_BMP1, NP3_BMP1, NP3_PEBP4, NP4_ANTXR2, NP3_CILP, NP1_F13B, NP5_EIF2AK2, NP5_FGL1, and NP2_FGL1.

To generate the lipidomic data, the plasma samples were assessed by LC-MS. Lipidomic data for all of the samples showed univariate performance for 75 lipids. FIG. 39E shows that lipidomic data obtained from cancer samples was highly reproducible. The data in the FIG. 39E were based on samples of both liver and ovarian cancer. Data was analyzed for 188 of 858 lipids for all patient samples. A median coefficient of variation (CV) of 14.6% was observed when calculated across 16 pooled samples. CV was representative of all technical variability (e.g. sample processing, data collection, etc.)

FIG. 40E shows that ovarian cancer samples exhibited distinct lipid profiles compared to healthy controls. The top 50 lipids based on p-value are shown for all patient samples analyzed, and included phospholipids. The heatmap shows decreased abundances of several phospholipids in cancer samples compared to elevated levels in healthy samples. From top to bottom, the lipids listed in FIG. 40E include the following in order: PC.18.0_20.3 . . . AcO, PC.16.0_20.3 . . . AcO, PC.20.3_20.4 . . . AcO, LPC.20.3 . . . AcO, PC.20.3_20.3 . . . AcO, LPC.16.1 . . . AcO, PC.16.1_20.3 . . . AcO, PC.16.1_20.4 . . . AcO, PC.14.0_18.3 . . . AcO, PC.14.0_20.3 . . . AcO, LPC.14.0 . . . AcO, PC.14.0_18.2 . . . AcO, PC.14.0_20.2 . . . AcO, PC.14.0_22.6 . . . AcO, PC.14.0_20.4 . . . AcO, PC.14.0_22.5 . . . AcO, PC.15.0_20.4 . . . AcO, PC.15.0_20.3 . . . AcO, PC.15.0_18.2 . . . . ACO, LPE.18.2 . . . . H, LPC.18.2 . . . AcO, LPC.18.1 . . . AcO, LPC.20.2 . . . AcO, LPC.18.3 . . . AcO, LPC.18.0 . . . AcO, PE.O.16.0_22.5 . . . . H, PA.18.0_18.2 . . . . H, PC.20.2_20.3 . . . AcO, PC.18.2_20.4 . . . AcO, PC.18.2_20.3 . . . AcO, PC.18.2_20.5 . . . AcO, PC.18.0_18.2 . . . AcO, PC.18.2_18.2 . . . AcO, PC.18.2_18.3 . . . AcO, PC.18.1_22.4 . . . AcO, PI.18.1_20.4 . . . H, PC.18.1_20.3 . . . AcO, PC.18.1_22.5 . . . AcO, PC.20.2_20.4 . . . AcO, PC.20.4_22.5 . . . AcO, LPE.18.0 . . . H, PC.18.1_20.4 . . . AcO, LPE.20.4 . . . . H, PC.20.4_20.4 . . . AcO, and LPC.20.4 . . . AcO.

Figure 40C:
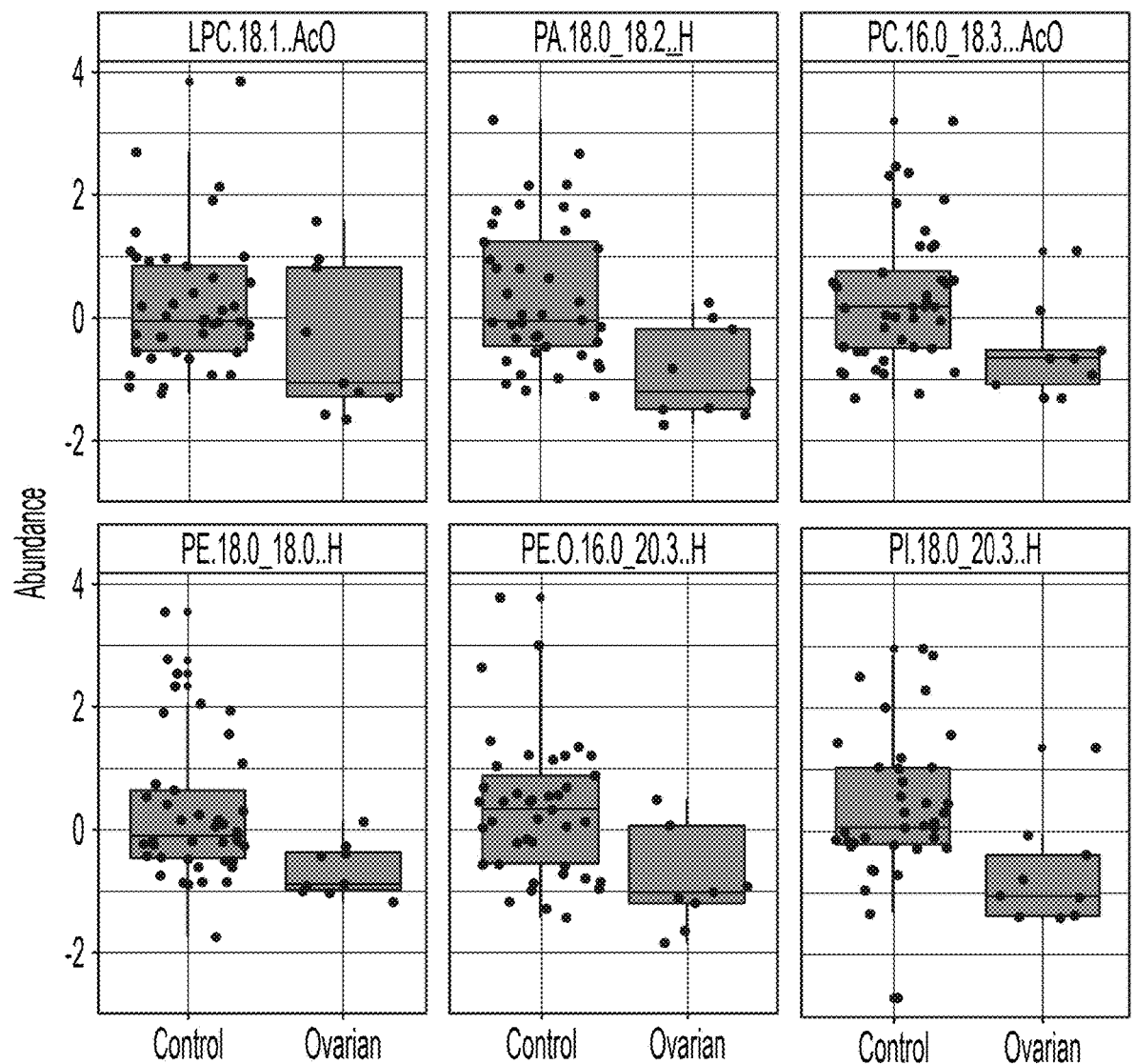
FIG. 40C shows univariate lipid differences for samples from subjects with ovarian cancer compared to healthy subjects.

FIG. 40C shows univariate lipid differences for ovarian cancer samples compared to healthy samples. 75/188 lipids were significantly different among healthy and cancer cohorts, as assessed by a one way ANOVA with a Fisher LSD correction at 0.05 (FDR: 7.60e-10-0.048). Several phospholipids were observed to be significantly different among cohorts. For example, lysophosphatidylcholines (LPCs) and lysophosphatidylethanolamines (LPEs) were significantly lower in cancer samples relative to healthy samples. These data indicate that levels of circulating lipids such as phospholipids may be useful as biomarkers for identifying a subject as likely to have a cancer such as ovarian cancer or as not likely to have the cancer.

Significant differences were also identified in phospholipids between ovarian cancer samples and liver cancer samples, indicating that differences in phospholipid metabolism or circulating levels of phospholipids may be useful for distinguishing between cancer types.

Example 20. Identifying a Likelihood of Ovarian Cancer in a Subject

A subject comes into a doctor's office due to abnormal periods. The doctor determines that the subject may be at risk of having ovarian cancer, and performs a non-invasive work-up such as abdominal and pelvic CT scan but nothing of note is detected. A serum sample is obtained from the patient to be analyzed by the methods described herein. The lab measures the presence and abundance of several proteins. The lab then applies a classifier to generate an output report to the physician for determining whether the subject has ovarian cancer. The report indicates that the patient likely has ovarian cancer. It's possible that the ovarian cancer is small and developing at an early stage, which explains the why scans did not detect the ovarian cancer. The physician asks the patient to return for a regular check-up once every 6 months to continue monitoring the ovarian cancer. During one of the subsequent check-ups, the analysis of the biofluid sample obtained from the subject indicates that the ovarian cancer has progressed. The physician then prescribes or administers an ovarian cancer treatment regimen.

Example 21. Identifying a Likelihood of Colon Cancer in a Subject

A subject comes into a doctor's office due to abdominal discomfort. The doctor determines that the subject may be at risk of having cancer, and performs a non-invasive work-up (e.g., performing a liver function test (LFT), obtaining carcinoembryonic antigen (CEA) measurements, or performing a fecal occult blood test (FOBT)). Nothing of note is detected. A plasma sample is obtained from the patient to be analyzed by the methods described herein. The lab measures the presence and abundance of several proteins. The lab then applies a classifier to generate an output report to the physician for determining whether the subject has colon cancer. The report indicates that a colon cancer is likely present. It's possible that the colon cancer is small and developing at an early stage, which explains the why the initial work-up did not detect the colon cancer. The physician asks the subject to return for a regular check-up once every 6 months to continue monitoring the colon cancer. During one of the subsequent check-ups, the analysis of the biofluid sample obtained from the subject indicates that the colon cancer has progressed. The physician then prescribes or administers a colon cancer treatment regimen.

Example 22. Non-Small Cell Lung Cancer (NSCLC) Study

Design and Collection of Samples, Collection of Results

Results were collected at multiple sites for the following three arms: NSCLC (all stages), pulmonary co-morbidity, and healthy controls. For sample selection, inclusion and exclusion criteria was as follows: 1) Greater than or equal to 18 years if age, informed consent, able to donate 50 mL; 2) No prior history of any cancer; 3) For NSCLC subjects, pathology-confirmed diagnosis and no prior therapy for the newly diagnosed cancer; 4) For pulmonary co-morbidity controls, subjects have one of more of the following: COPD, emphysema, cardiovascular disease, hypertension, pulmonary fibrosis, asthma, any other chronic lung disease; 5) For healthy controls, subjects are non-NSCLC, nonpulmonary call-backs from collection sites (could have other disease). For NSCLC subjects that are post diagnostic procedure and diagnosis aware, the median time from the diagnostic procedure was 26 days and samples were collected either during the post-diagnosis informational visit or immediately pre-treatment. Results collected included: 1) Nanoparticle-panel results: 10 particle types were incubated in depleted plasma ("DP"), samples were randomized across 4 plates per particle type/DP, and results collected included assay process and mass spectrometry (MS) injection controls; 2) Targeted MS results: assays were developed and implemented for 51 peptides from 31 proteins based on established panels; and 3) ELISA results: assays were implemented for 2 candidate proteins including CA-125 and CK19. 288 subjects were included in the study over a 9-week period.

24 sites were used to collect subject samples grouped into NSCLC stages 1, 2, 3 (early), NSCLC stage 4 (late), or healthy and pulmonary co-morbid control arms. Samples included plasma and serum tubes, PAXgene RNA tubes, and Streck blood cell collection tubes. A randomly selected cohort of 288 age- and gender-matched subjects used for NP protein profiling. Peptides from the proteins bound by the NPs were evaluated by data-independent-acquisition mass spectrometry (DIA-MS). Depleted plasma was also prepared for analysis. 268 subject samples gave complete datasets for all 10 particle types in the panel and depleted plasma; (80 healthy, 80 co-morbid control, 61 early NSCLC (Stages 1, 2 and 3) and 47 late NSCLC (Stage 4). MS results acquisition took 7 weeks for all 288 samples. Historically, depleted plasma-only analysis has not been productive. The depth of protein profiling by the particle panel allowed for the in silico removal of all proteins associated with depleted plasma before classifier analysis. This focused analysis on novel proteins not otherwise observable in a study this size. Classification analysis was performed for each pairwise comparison of the study arms using ten rounds of 10-fold cross-validation with random forest models.

Figure 42:
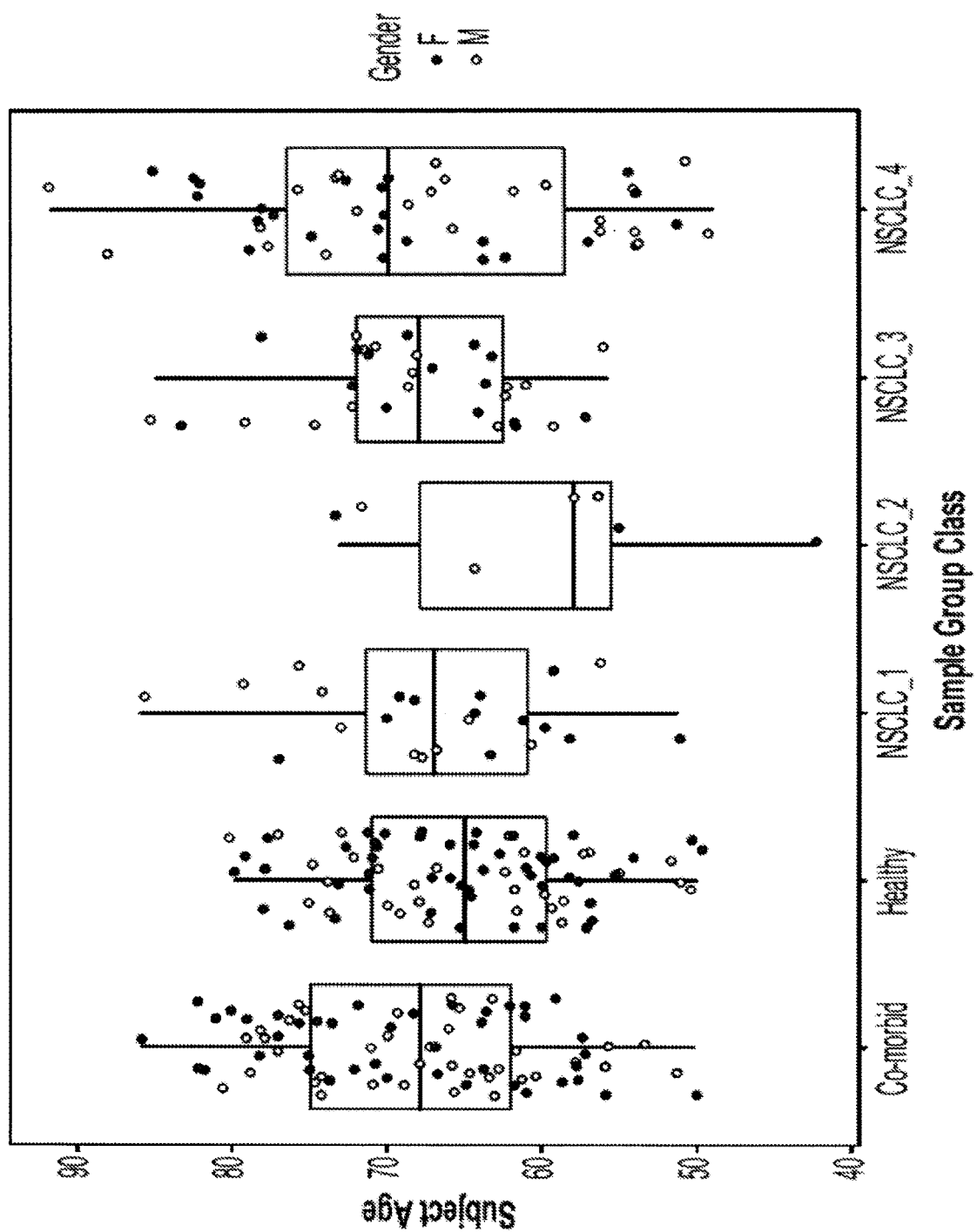
FIG. 42 shows an age and gender breakdown for 268 subjects in a NSCLC biomarker discovery study.

Subjects were age- and gender-matched and results from multiple sites were included within each class (co-morbid, healthy, NSCLC Stage 1 "NSCLC_1," NSCLC Stage 2 "NSCLC_2," NSCLC Stage 3 "NSCLC_3," and NSCLC Stage 4 "NSCLC_4") to avoid bias. FIG. 42 shows the age and gender breakout for the 268 subjects in the NSCLC biomarker discovery study. NSCLC Stages 1, 2, and 3 were combed as "Early NSCLC" to boost power for the creating the classifier. The study had no age or gender bias by class in the 141 subjects used for healthy (80 subjects) versus NSCLC (61 subjects) classification studies, as shown in Table 3.

TABLE 3

Age and Gender Statistical Validation

| Variable | P-value | Test |
| --- | --- | --- |
| Age | 0.26 | T-Test |
| Gender | 0.17 | Fisher Test |

A summary of the particle types in the 10-particle type panel are shown below in TABLE 4, all of which are superparamagnetic.

TABLE 4

10-Particle Type Panel

| Particle Type | Particle Description |
| --- | --- |
| P-033 | Carboxylate, surfactant free; Functional Group: Carboxyl |
| S-010 | Poly(acrylic acid), PAA; Functional Group: Carboxyl |
| P-073 | Dextran based coating, 0.13 µm; Functional Group: Dextran |
| P-039 | Polystyrene carboxyl functionalized; Functional Group: Carboxyl |
| S-007 | Poly(dimethyl aminopropyl methacrylamide) (Dimethylamine); Functional Group: PDMAPMA |
| P-053 | Amino, 0.4-0.6 um; Functional Group: Amine |
| P-047 | Silica, 200 nm; Functional Group: Silanol |
| P-065 | Silica; Functional Group: Silanol |
| S-006 | N-(3-Trimethoxysilylpropyl)diethylenetriamine; Functional Group: Amine |
| S-003 | Silica; Functional Group: Silanol |

Figure 43:
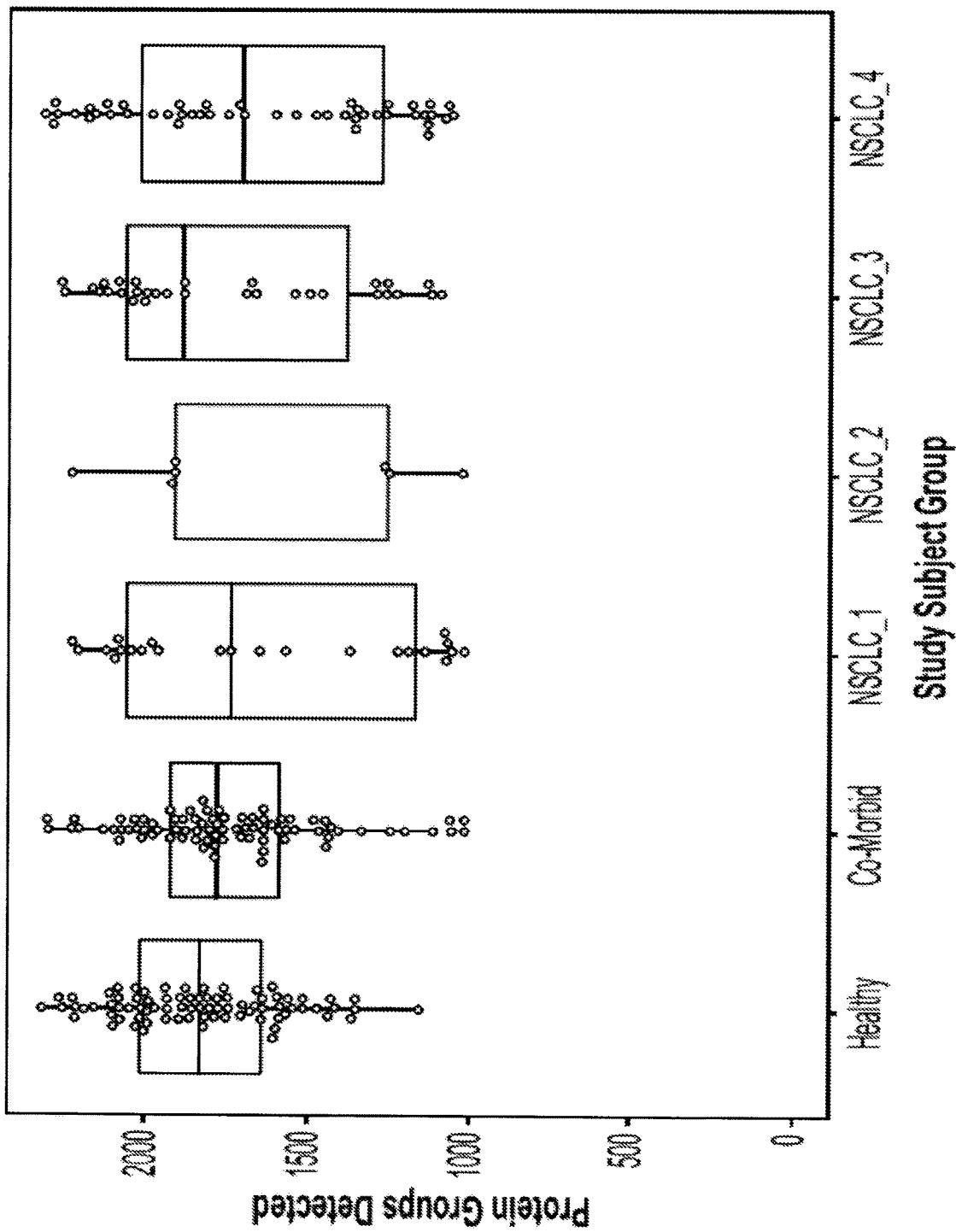
FIG. 43 shows protein counts by study group including healthy, co-morbid, NSCLC Stage 1 "NSCLC_1," NSCLC Stage 2 "NSCLC_2," NSCLC Stage 3 "NSCLC_3," and NSCLC Stage 4 "NSCLC_4".
Figure 44:
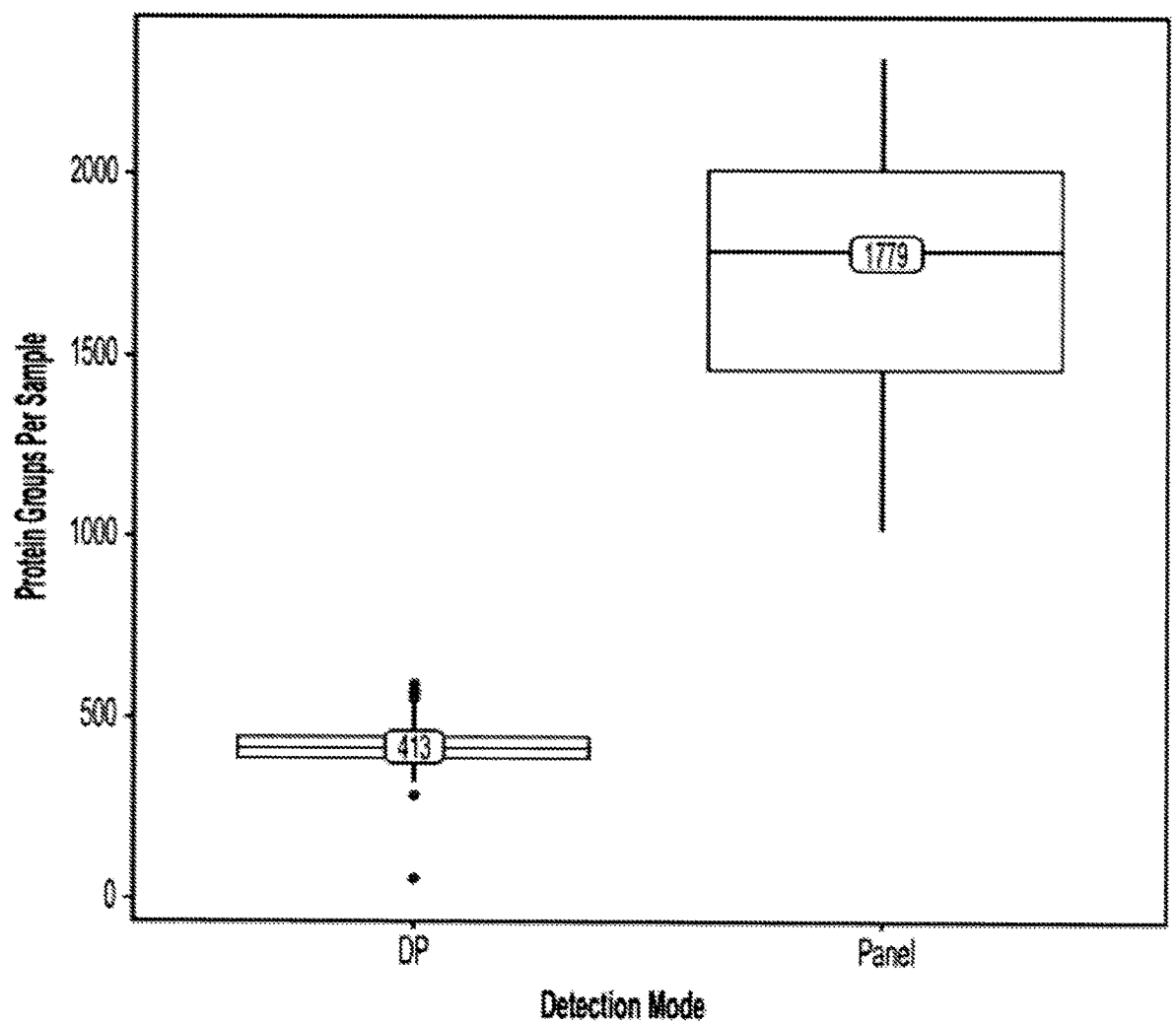
FIG. 44 shows protein counts for depleted plasma DP and a particle panel.

Initial observations from the NSCLC study quantified the number of proteins that were observed using the 10-particle type panel. The average protein count observed using the 10-particle type panel across the samples was 1,797±337. FIG. 43 shows protein counts by each study group including healthy, co-morbid, NSCLC Stage 1 "NSCLC_1," NSCLC Stage 2 "NSCLC_2," NSCLC Stage 3 "NSCLC_3," and NSCLC Stage 4 "NSCLC_4". FIG. 44 shows the protein counts for depleted plasma DP and the particle panel.

Figure 45:
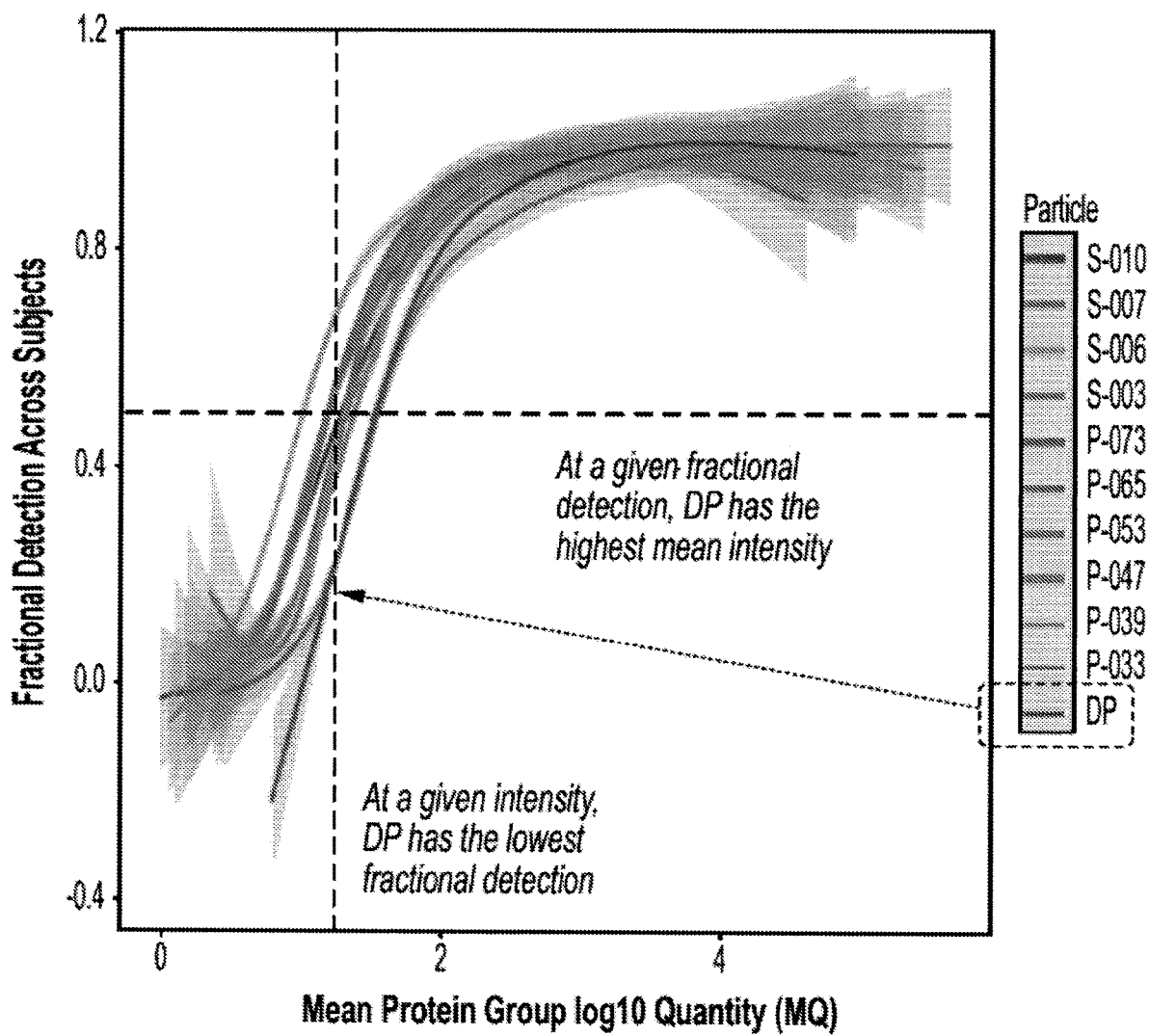
FIG. 45 shows a summary of fractional detection of a protein across subjects versus mean abundance of said protein for 10 particle types in a particle panel and depleted plasma (DP).

It was observed that particles achieved superior protein detection consistency as compared to depleted plasma on a like-intensity basis. The variation in protein group detection as a function of intensity was evaluated. The proteins detected in healthy subjects from the NSCLC study (n=82) were scored by particle type including the number of subjects in which a given protein was detected and the mean signal intensity for that protein. FIG. 45 shows the resulting summary of fractional detection of a protein across subjects versus mean abundance of said protein for all 10 particle types in the particle panel and depleted plasma (DP). Curves included smoothed fits of the results. As shown in FIG. 45 particles outperformed depleted plasma for detection consistency. At a given intensity, depleted plasma exhibited the lowest fractional detection of a protein across samples.

On average 1,779 proteins were detected from each of the 268 subject samples with the multi-particle type panel as compared to only 413 with depleted plasma.

Classification for Healthy Vs. Early NSCLC (Stage 1, 2, 3)

Initial classifier builds showed equivalent, high performance between depleted plasma ("DP") and the 10-particle type panel ("Panel"). Examination of important features for both methods reveals possible acute-phase-response (APR) or stress-related proteins as drivers for initial classification.

Figure 46:
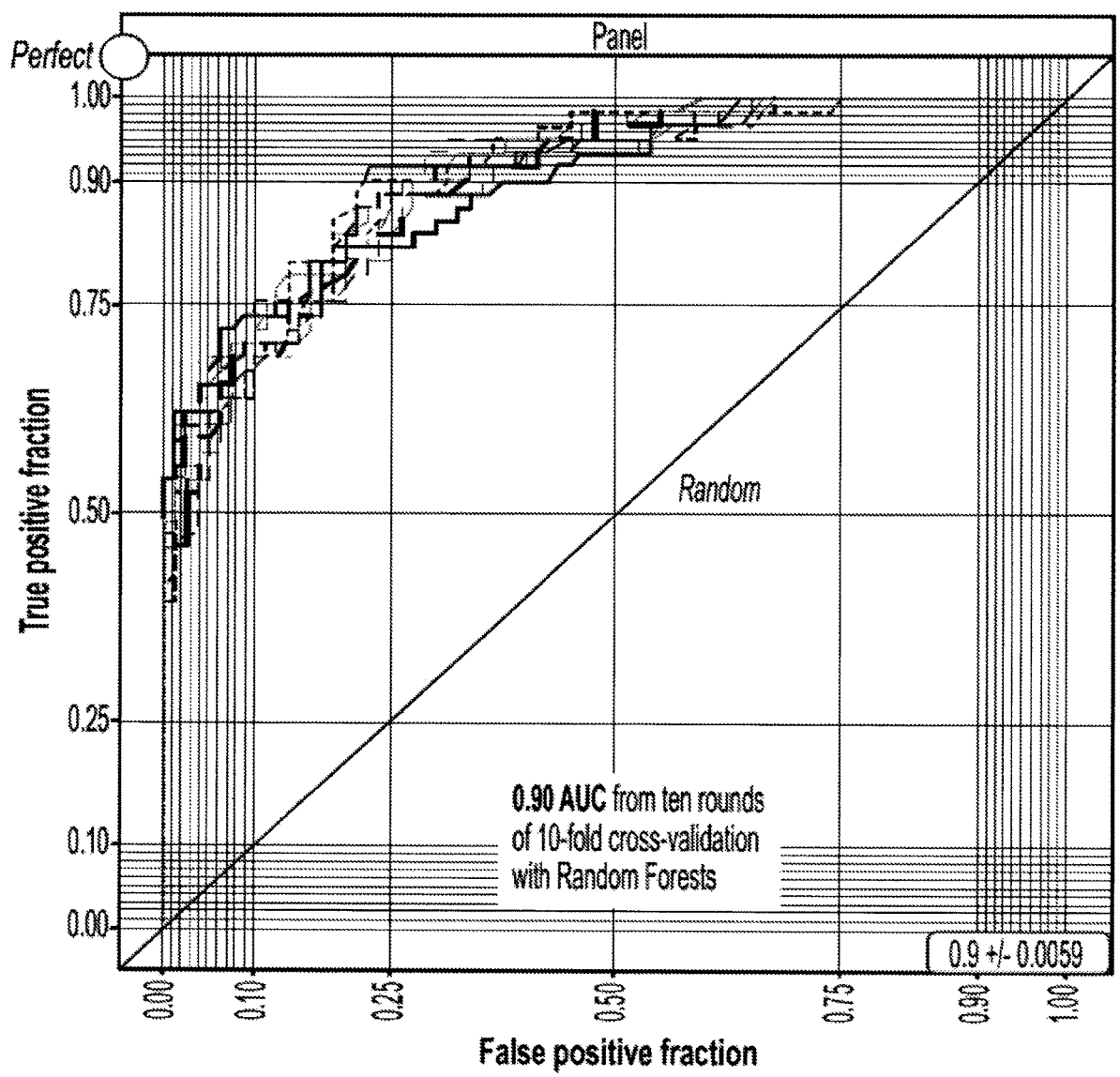
FIG. 46 shows performance of a cross-validated particle panel classifier with the x-axis showing the fraction of classifications that are false positives and the y-axis showing the fraction of classifications that are true positives.
Figure 47:
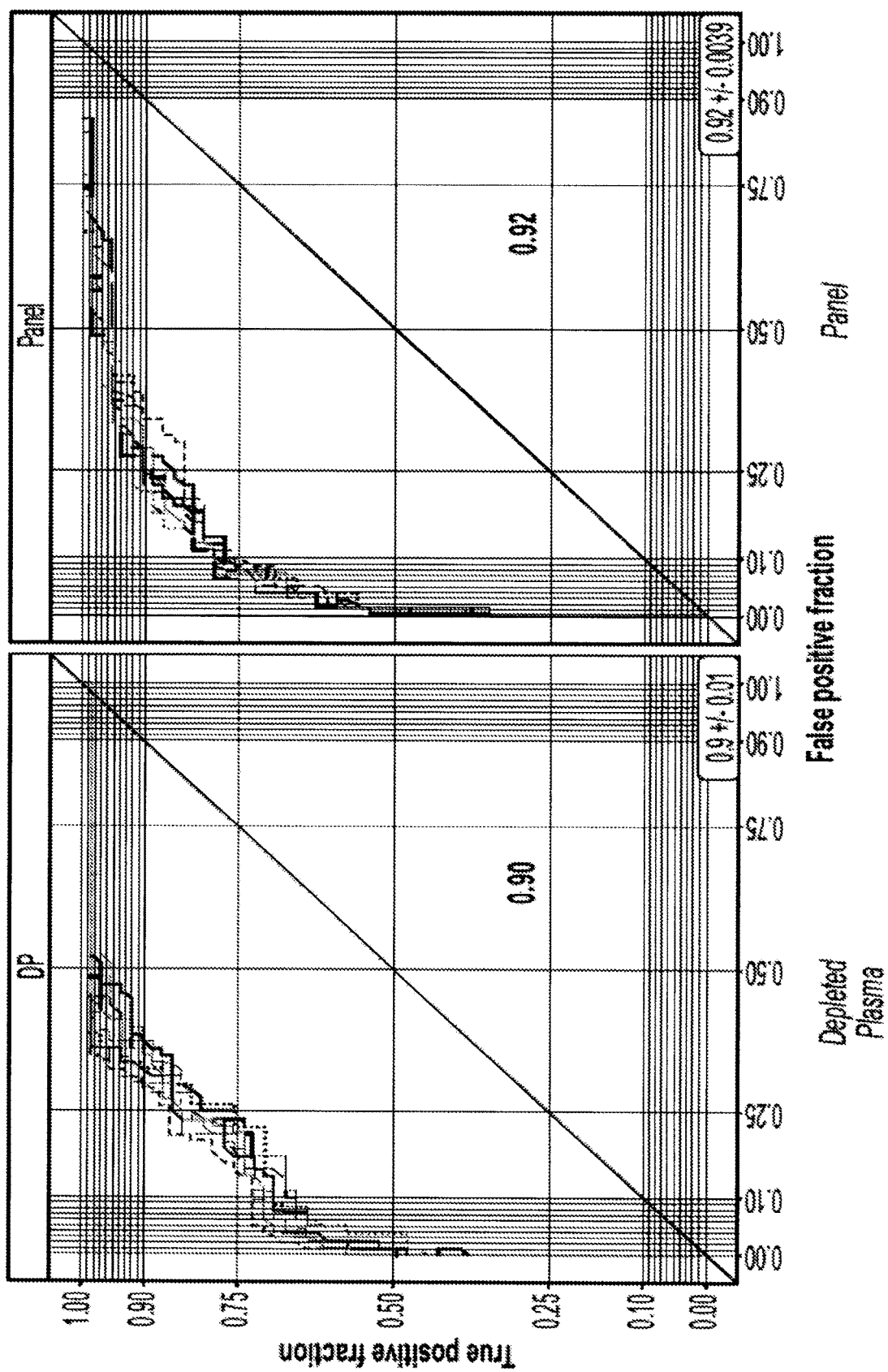
FIG. 47 shows a graph of random forest models for healthy vs NSCLC (Stages 1, 2, and 3) for depleted plasma (on left) and the 10-particle panel (right) and depict the false positive fraction on the x-axis and the true positive fraction on the y-axis.

The diagnostic procedure itself and diagnosis-awareness in subjects may be triggering APR and other stress-related proteins as (artifactual) classifier signals. Removing any particle panel feature related to a protein also found in depleted plasma removed potential bias. This option not available to "shallow" profiling efforts. The final cross-validated classifier leveraged the deep profiling available with the particle panel. FIG. 46 shows the performance of the cross-validated particle panel classifier with the x-axis showing the fraction of classifications that are false positives and the y-axis showing the fraction of classifications that are true positives. APR and stress protein bias was observed in depleted plasma and the 10-particle type panel ("Panel"). As shown below in Table 5 and Table 6, top features were identified as associated with APR and related proteins, which were the prime drivers of initial classification. The importance scores indicate APR proteins, specifically CRP, drove the initial performance of the classifier. FIG. 47 shows a graph of random forest models for healthy vs NSCLC (Stages 1, 2, and 3) for depleted plasma (on left) and the 10-particle type panel (right) and depict the false positive fraction on the x-axis and the true positive fraction on the y-axis.

TABLE 5

Depleted Plasma

| Importance | UniProt | Entry name | Protein names |
|---|---|---|---|
| *100.0 | P02741 | CRP_HUMAN | C-reactive protein |
| ¥14.5 | P00739 | HPTR_HUMAN | Haptoglobin-related protein |
| ¥10.5 | P00738 | HPT_HUMAN | Haptoglobin |
| 7.0 | P03952 | KLKB1_HUMAN | Plasma kallikrein |
| †5.4 | P06702 | S10A9_HUMAN | Protein S100-A9 |
| 4.5 | P13591 | NCAM1_HUMAN | Neural cell adhesion molecule 1 |
| †4.2 | P05109 | S10A8_HUMAN | Protein S100-A8 |
| 4.0 | Q9NTJ3 | SMC4_HUMAN | Structural maintenance of chromosomes protein 4 |
| 3.6 | P69905 | HBA_HUMAN | Hemoglobin subunit alpha |
| 3.3 | P26992 | CNTFR_HUMAN | Ciliary neurotrophic factor receptor subunit alpha |
| 2.8 | P02654 | APOC1_HUMAN | Apolipoprotein C-I |
| 2.7 | O95445 | APOM_HUMAN | Apolipoprotein M |
| 2.6 | P54289 | CA2D1_HUMAN | Voltage-dependent calcium channel subunit alpha-2/delta-1 |
| 2.4 | Q96KN2 | CNDP1_HUMAN | Beta-Ala-His dipeptidase |
| 2.2 | Q9BWP8 | COL11_HUMAN | Collectin-11 |
| 2.1 | P02750 | A2GL_HUMAN | Leucine-rich alpha-2-glycoprotein |
| 2.0 | P60709 | ACTB_HUMAN | Actin, cytoplasmic 1 |
| 2.0 | P63261 | ACTG_HUMAN | Actin, cytoplasmic 2 |
| 1.7 | P29622 | KAIN_HUMAN | Kallistatin |
| 1.7 | P55290 | CAD13_HUMAN | Cadherin-13 |
| 1.7 | P19823 | ITIH2_HUMAN | Inter-alpha-trypsin inhibitor heavy chain H2 |

TABLE 6

10-Particle Type Panel

| Importance | UniProt | Entry name | Protein names |
|---|---|---|---|
| †100.0 | P06702 | S10A9_HUMAN | Protein S100-A9 |
| *84.8 | P02741 | CRP_HUMAN | C-reactive protein |
| 62.1 | P19823 | ITIH2_HUMAN | Inter-alpha-trypsin inhibitor heavy chain H2 |

TABLE 6-continued

10-Particle Type Panel

| Importance | UniProt | Entry name | Protein names |
|---|---|---|---|
| †52.6 | P05109 | S10A8_HUMAN | Protein S100-A8 |
| †49.7 | P05109 | S10A8_HUMAN | Protein S100-A8 |
| †49.7 | P06702 | S10A9_HUMAN | Protein S100-A9 |
| *49.7 | P02741 | CRP_HUMAN | C-reactive protein |
| †46.4 | P06702 | S10A9_HUMAN | Protein S100-A9 |
| *36.7 | P02741 | CRP_HUMAN | C-reactive protein |
| *36.0 | P05109 | S10A8_HUMAN | Protein S100-A8 |
| 26.3 | Q92743 | HTRA1_HUMAN | Serine protease HTRA1 |
| 22.7 | Q8NI99 | ANGL6_HUMAN | Angiopoietin-related protein 6 |
| †18.4 | P05109 | S10A8_HUMAN | Protein S100-A8 |
| ¥16.1 | P00739 | HPTR_HUMAN | Haptoglobin-related protein |
| 15.4 | P55774 | CCL18_HUMAN | C-C motif chemokine 18 |
| 14.1 | P55774 | CCL18_HUMAN | C-C motif chemokine 18 |
| 13.7 | P60709 | ACTB_HUMAN | Actin, cytoplasmic 1 |
| 13.7 | P63261 | ACTG_HUMAN | Actin, cytoplasmic 2 |
| 13.0 | P0DJI8 | SAA1_HUMAN | Serum amyloid A-1 protein |
| *12.7 | P02741 | CRP_HUMAN | C-reactive protein |
| 12.5 | P01834 | IGKC_HUMAN | Immunoglobulin kappa constant |

*CRP,
¥Haptoglobin,
†S10a8/9

The final classifier included features that highlight the importance of unbiased proteomics. This final classifier used proteins know to have high importance and low importance to NSCLC as well as proteins that had no prior importance to NSCLC. Table 7 shows the proteins in the final classifier. The OT Score is the OpenTargets database score for the protein. An OT Score of 0 indicates that there is no entry of that protein in Open Targets for lung cancer. These proteins are newly discovered features from the above described study. Higher OT scores are effective confirmation that the classifier is built on proteins that are associated with lung cancer. For example, TBA1A and SDC1 are drug targets for lung cancer, and were a part of the classifier.

TABLE 7

Top Proteins in Final Classifier

| Importance | UniProt | Entry name | Protein names | OT Score |
|---|---|---|---|---|
| 100.0 | Q8NI99 | ANGL6_HUMAN | Angiopoietin-related protein 6 | 0 |
| 73.8 | Q92743 | HTRA1_HUMAN | Serine protease HTRA1 | 0.012 |
| 51.6 | Q92743 | PXDN_HUMAN | Peroxidasin homolog | 0.017 |
| 49.3 | P55774 | CCL18_HUMAN | C-C motif chemokine 18 | 0.15 |
| 44.6 | P55774 | CCL18_HUMAN | C-C motif chemokine 18 | 0.15 |
| 44.2 | Q92743 | HTRA1_HUMAN | Serine protease HTRA1 | 0.012 |
| 41.4 | Q92743 | HTRA1_HUMAN | Serine protease HTRA1 | 0.012 |
| 36.1 | P58335 | ANTR2_HUMAN | Anthrax toxin receptor 2 | 0.04 |
| 35.2 | Q71U36 | TBA1A_HUMAN | Tubulin alpha-1A chain | 1 |
| 32.5 | P18827 | SDC1_HUMAN | Syndecan-1 | 0.6 |
| 32.3 | P0DJI9 | SAA2_HUMAN | Serum amyloid A-2 protein | 0.016 |
| 30.2 | P13611 | CSPG2_HUMAN | Versican core protein | 0.05 |
| 29.2 | Q9H6X2 | ANTR1_HUMAN | Anthrax toxin receptor 1 | 0.02 |

TABLE 7-continued

Top Proteins in Final Classifier

| Importance | UniProt | Entry name | Protein names | OT Score |
|---|---|---|---|---|
| 25.1 | P18827 | SDC1_HUMAN | Syndecan-1 | 0.6 |
| 24.7 | Q6P988 | NOTUM_HUMAN | Palmitoleoyl-protein carboxylesterase NOTUM | 0 |
| 21.0 | O75339 | CILP1_HUMAN | Cartilage intermediate layer protein 1 | 0 |
| 19.9 | P17655 | CAN2_HUMAN | Calpain-2 catalytic subunit | 0.041 |
| 18.6 | P05387 | RLA2_HUMAN | 60S acidic ribosomal protein P2 | 0 |
| 16.6 | P15907 | SIAT1_HUMAN | Beta-galactoside alpha-2,6-sialyltransferase 1 | 0.43 |
| 16.4 | P13224 | GP1BB_HUMAN | Platelet glycoprotein Ib beta chain | 0 |

TABLE 8

Proteins Detected by Targeted MS and ELISA

| AUC | Uniprot | Mode |
|---|---|---|
| 0.81 | CA125 | ELISA |
| 0.67 | MMP9 | MRM |
| 0.66 | MMP9 | MRM |
| 0.63 | *CEAM5 | MRM |
| 0.60 | *CEAM5 | MRM |
| 0.58 | IL6RA | MRM |
| 0.58 | GSLG1 | MRM |
| 0.57 | CK19 | ELISA |
| 0.55 | SPB4 | MRM |
| 0.55 | FRIL | MRM |
| 0.53 | MIF | MRM |
| 0.52 | ENOG | MRM |
| 0.51 | HS90A | MRM |
| 0.51 | SCF | MRM |
| 0.50 | ENOG | MRM |

*CEA

Comparison of the top features comprising the NSCLC classifiers to the co-morbid classifier indicated significant differences that can enable clinical differentiation. Furthermore, examination of the NSCLC top 20 classifier features highlights proteins that may play a role in NSCLC. The Table includes an Open Targets (OT) annotation for each gene as it may relate to lung cancer.

Figure 48:
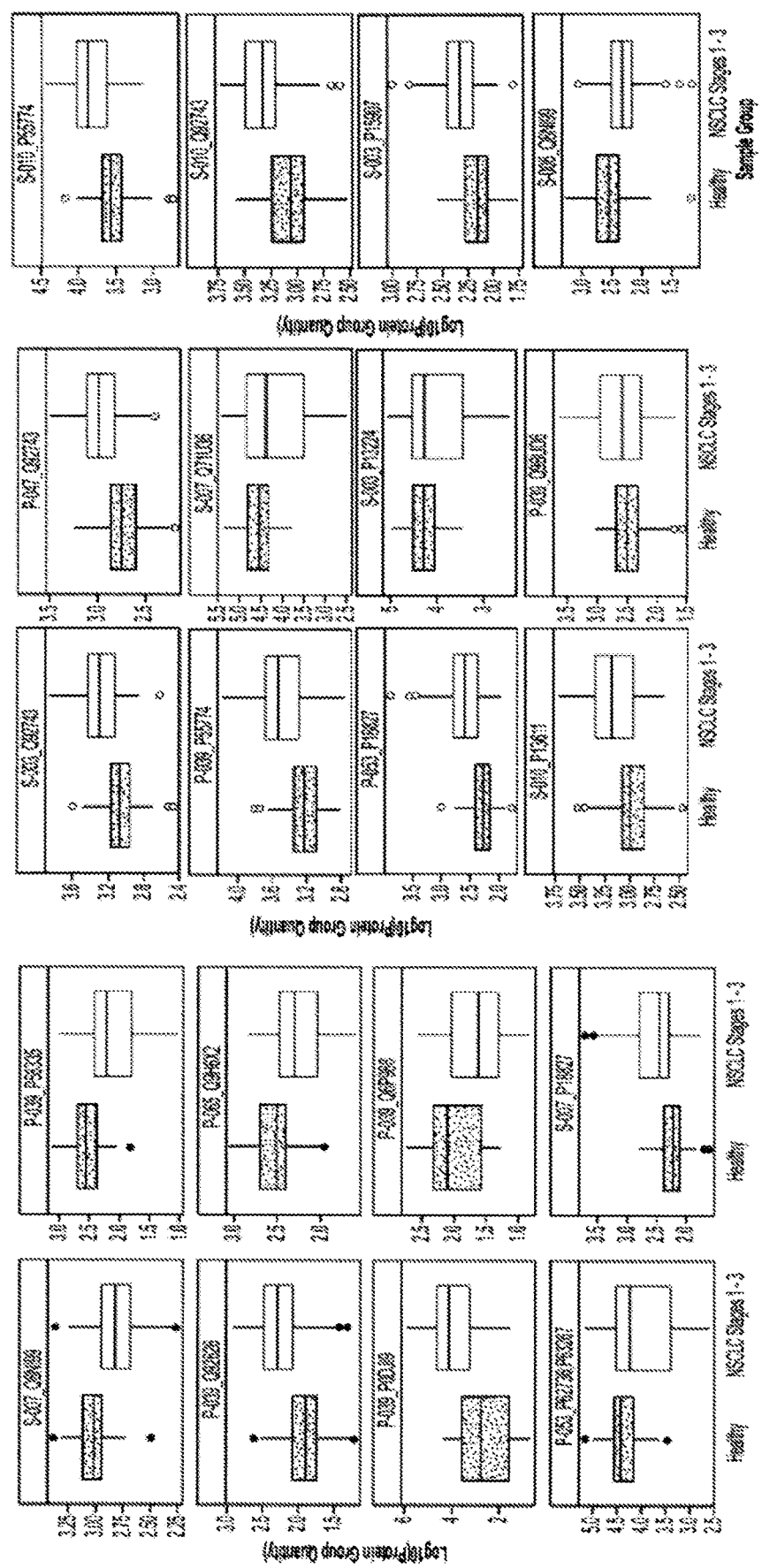
FIG. 48 shows performance of classifier features across study samples.

FIG. 48 shows the performance of classifier features across study samples. In each graph, the differences in protein levels for the top 20 features are shown across all subject results for various particle types. A 0.3 difference on the y-axis represents an approximate 2-fold change in protein levels. Results were suitable for ELISA confirmation.

Figure 49:
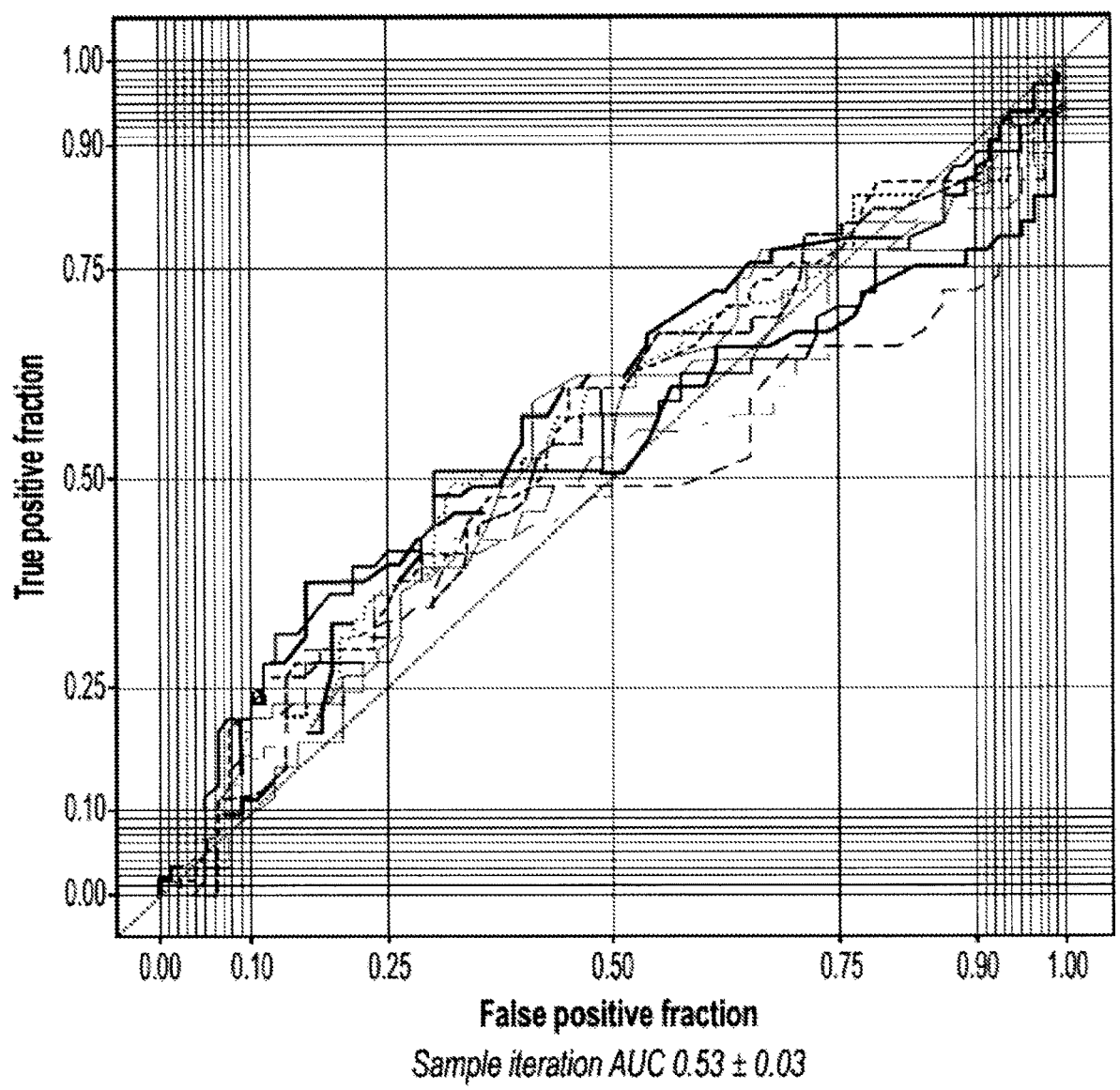
FIG. 49 shows results from 10 iterations of 10 rounds of 10-fold cross-validation with subject class assignments randomized with the false positive fraction on the x-axis and the true positive fraction on the y-axis.

FIG. 49 shows the results from 10 iterations of 10 rounds of 10-fold cross-validation with subject class assignments randomized with the false positive fraction on the x-axis and the true positive fraction on the y-axis. As taking measurements on a few number of samples can lead to over-fitting, in which some features separate two groups by random chance, ten rounds of 10-fold cross validation was carried out to avoid over-fitting. Subject classes ("healthy" or "NSCLC") were randomized 10 times. Each time, a new ten rounds of 10-fold cross-validation was performed. Results shown in FIG. 49 are features present in the 10-particle type panel protein dataset after proteins found in depleted plasma were removed. The average area under the curve (AUC) for the class randomized classifiers was 0.52±0.04 (Max: 0.58). No overfitting was observed in the Random Forest classifier builds.

Figure 50:
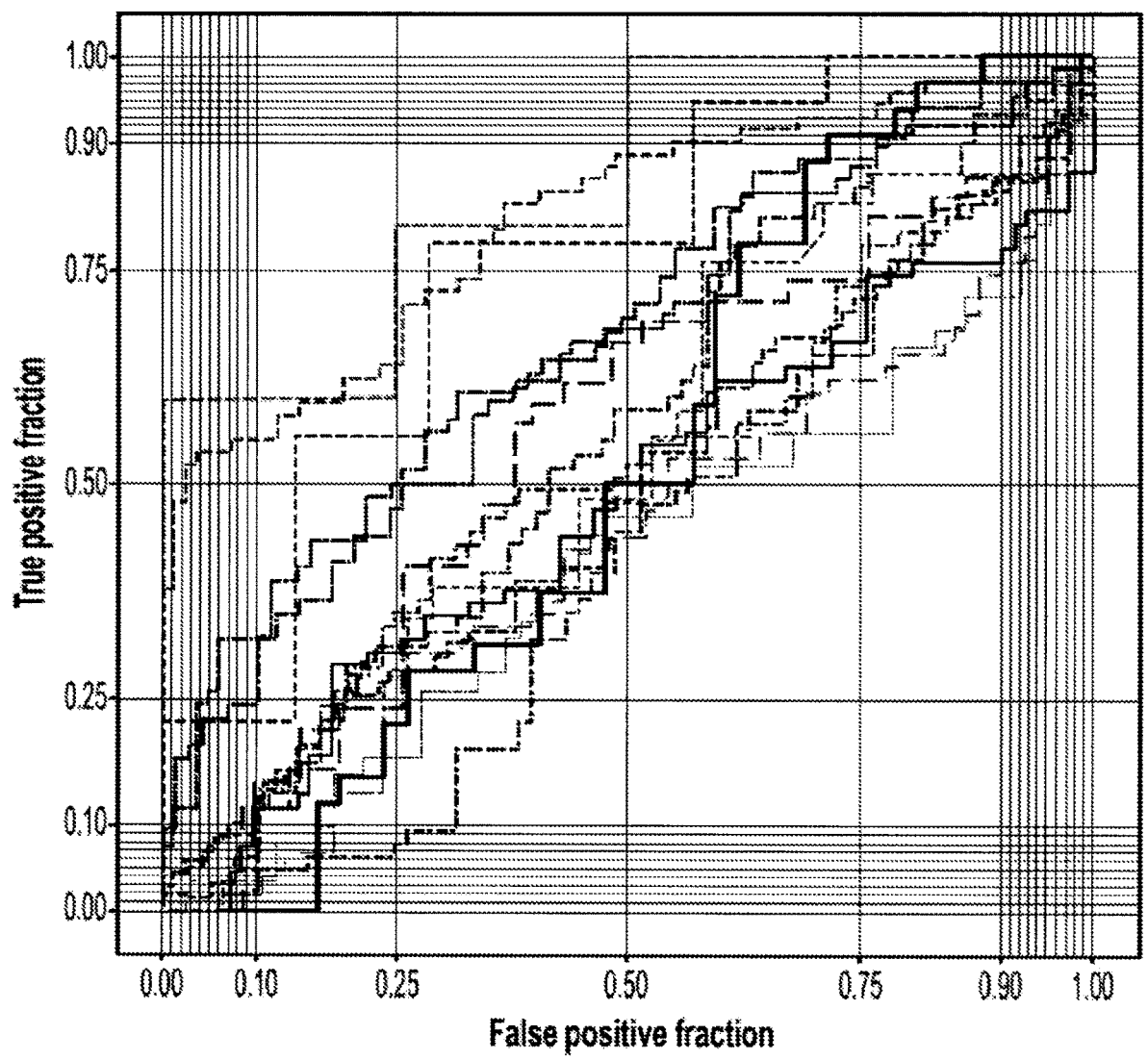
FIG. 50 shows ROC plots for 13 peptides by MRM-MS and 2 proteins by ELISA, after proteins found in depleted plasma had been removed.

The performance of candidate markers via targeted mass spectrometry (MS) and ELISA was assessed. Targeted MS and ELISA were used to evaluate candidate markers identified from published NSCLC classifier panels. 51 peptides were targeted by MS and 2 proteins were detected by ELISA. Proteins detected in depleted plasma were removed from consideration, as for the particle panel results described above. FIG. 50 shows ROC plots for 13 peptides by MRM-MS and 2 proteins by ELISA, after proteins found in depleted plasma had been removed. The x-axis shows the false positive fraction and the y-axis shows the true positive fraction. Table 8 shows proteins detected by targeted MS and ELISA.

Figure 51:
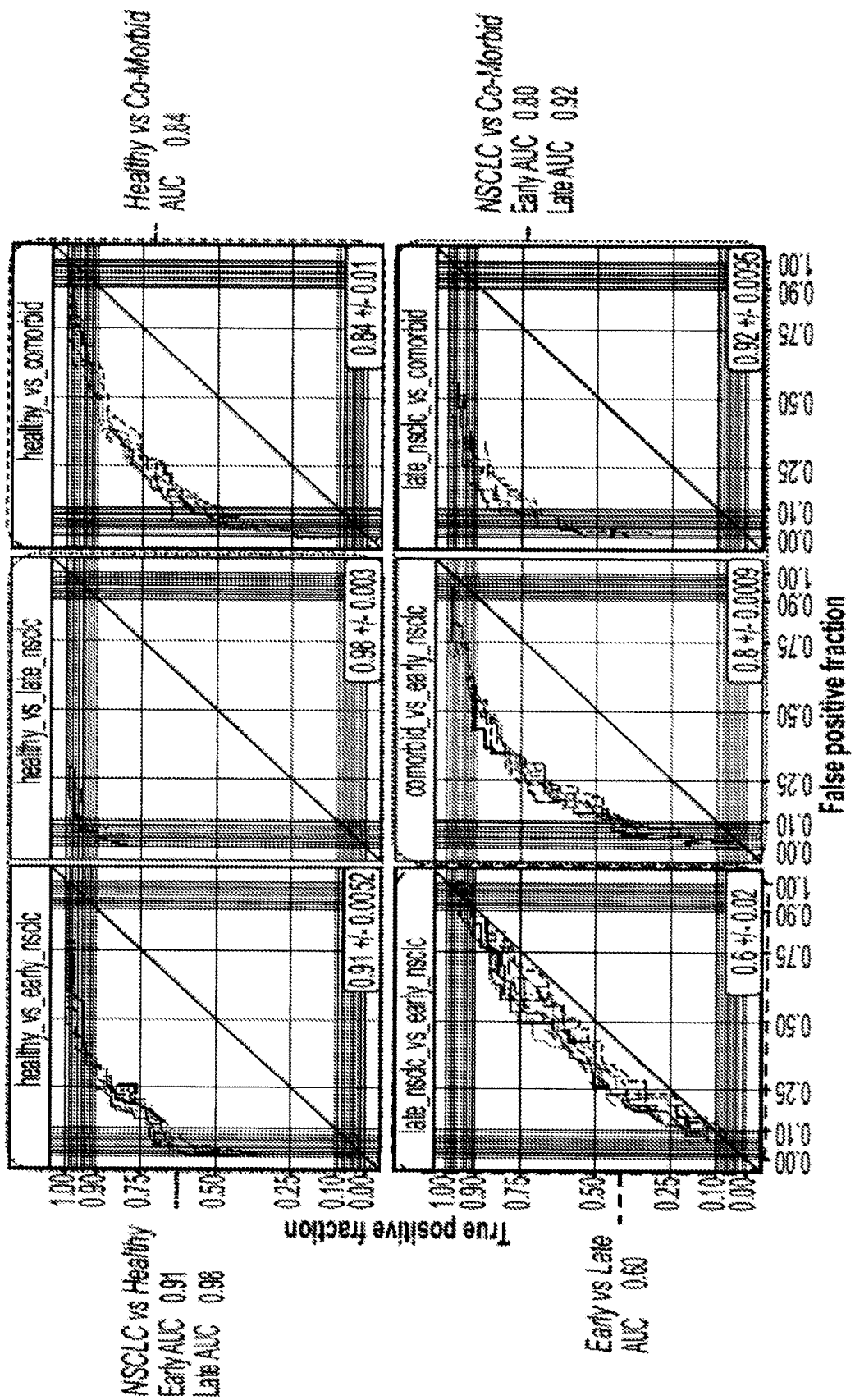
FIG. 51 shows Random Forest models for all study group comparisons.

FIG. 51 shows Random Forest models for all study group comparisons. Classifiers for all study group comparisons included ten rounds of 10-fold cross-validation after removal of depleted plasma-related features in all classifier builds. The healthy versus early NSCLC random classification after depleted plasma-related protein removal achieved an average AUC of 0.90. The comparison of the same healthy subjects to the late NSCLC and co-morbid subjects achieved average AUCs of 0.98 and 0.84, respectively.

FIG. 52 shows the differentiation of important features in study group comparisons. A comparison of proteins related to the top 20 features for each of the 6 pair-wise groupings is depicted.

In one analysis shown in FIG. 6, 13 out of the 17 top proteins in a classifier (76%) were secreted proteins. In that analysis, in plasma, ~28% of the proteins picked up in reference plasma by Proteograph were secreted proteins. Secreted proteins may play important roles in mechanisms of cancer disease and treatment. Some cancer driver mutations are for intracellular (e.g. BRAF, KRAS, PIK3CA, TP53) or receptor proteins (e.g. EGFR). FIG. 54 includes some optional details about some biomarkers.

Example 23. Detection of Lung Cancer

This example illustrates detection of lung cancer with using a classifier trained to distinguish between various biological states using the biomarkers disclosed herein. A drug is engineered to target any one of the biomarkers listed in Table 7, including ANGL6_HUMAN, HTRA1_HUMAN, PXDN_HUMAN, CCL18_HUMAN, ANTR2_HUMAN, TBA1A_HUMAN, SDC1_HUMAN, SAA2_HUMAN, CSPG2_HUMAN, ANTR1_HUMAN, NOTUM_HUMAN, CILP1_HUMAN, CAN2_HUMAN, RLA2_HUMAN, SIAT1_HUMAN, or GP1BB_HUMAN. Optionally, the drug targets more than one of ANGL6_HUMAN, HTRA1_HUMAN, PXDN_HUMAN, CCL18_HUMAN, ANTR2_HUMAN, TBA1A_HUMAN, SDC1_HUMAN, SAA2_HUMAN, CSPG2_HUMAN, ANTR1_HUMAN, NOTUM_HUMAN, CILP1_HUMAN, CAN2_HUMAN, RLA2_HUMAN, SIAT1_HUMAN, or GP1BB_HUMAN.

A sample is obtained from a subject identified as having a lung nodule and is incubated with a particle panel disclosed herein (e.g., the 10-particle panel of Table 4). The particles are separated from the sample to remove unbound protein and the biomolecule coronas on the particles are analyzed by mass spectrometry for one or more of the above described biomarkers. A trained classifier, trained to distinguish between healthy, co-morbid, and NSCLC Stage 1, 2, and 3 biological states based on one or more of the above described biomarkers, is used to determine the biological state of the sample.

Example 24. Treatment of Lung Cancer

This example illustrates treatment of lung cancer with a drug targeting a biomarker disclosed herein. A drug is engineered to target any one of the biomarkers listed in Table 7, including ANGL6_HUMAN, HTRA1_HUMAN, PXDN_HUMAN, CCL18_HUMAN, ANTR2_HUMAN, TBA1A_HUMAN, SDC1_HUMAN, SAA2_HUMAN, CSPG2_HUMAN, ANTR1_HUMAN, NOTUM_HUMAN, CILP1_HUMAN, CAN2_HUMAN, RLA2_HUMAN, SIAT1_HUMAN, or GP1BB_HUMAN. Optionally, the drug targets more than one of ANGL6_HUMAN, HTRA1_HUMAN, PXDN_HUMAN, CCL18_HUMAN, ANTR2_HUMAN, TBA1A_HUMAN, SDC1_HUMAN, SAA2_HUMAN, CSPG2 HUMAN, ANTR1_HUMAN, NOTUM_HUMAN, CILP1_HUMAN, CAN2_HUMAN, RLA2 HUMAN, SIAT1_HUMAN, or GP1BB_HUMAN. The drug is manufactured by chemical synthesis or recombinant expression. The drug is administered to a subject in need thereof. The subject has a cancerous lung nodule. Upon administration to the subject, symptoms of the lung cancer are alleviated and/or lung cancer cells are targeted and eliminated.

Example 25. Identifying a Lung Nodule as Malignant

A subject comes into a doctor's office for check-up. A CT scan is performed and a lung nodule is detected. A serum sample is obtained from the subject to be analyzed by the methods described herein. The lab measures the presence and abundance of at least one of the biomarkers. The lab then applies the classifier to generate an output report to the physician for determining whether the lung nodule is cancerous. The report indicates that the lung nodule is likely benign. Based on the report, the physician refrains from obtaining a biopsy of the lung nodule. The physician asks the subject to return for regular check-up once every 6 months to continue monitoring the lung nodule. During a subsequent check-up, the analysis of the biofluid sample obtained from the subject indicates that the lung nodule has likely become malignant. A biopsy of the nodule is then obtained, and the physician administers or prescribes a lung cancer treatment to the subject.

Example 26. Screening for Malignant Lung Nodule

A subject comes into a doctor's office for check-up. A CT scan is performed but nothing of note is detected. A serum sample is obtained from the subject to be analyzed by the methods described herein. The lab measures the presence and abundance of at least one of the biomarkers. The lab then applies the classifier to generate an output report to the physician for determining whether a lung nodule is present in the subject. The report indicates that a benign lung nodule is likely present. It's possible that the lung nodule is small and developing at an early stage, which explains the why CT scan does not detect the lung nodule. The physician asks the subject to return for regular check-up once every 6 month to continue monitoring the lung nodule. During one of the subsequent check-up, the analysis of the biofluid sample obtained from the subject indicates that the lung nodule has become malignant. The physician, based on the treatment option generated by the methods described herein, prescribes treatments to treat the subject.

Example 27. Use of a Classifier for Determining Whether a Lung Nodule is Malignant or Benign Biofluid samples comprising plasma samples of subjects identified as having a lung nodule were assayed using a proteomic method to generate proteomic results including measurements of protein abundances. The lung nodules were identified in the subjects by subjecting the subjects to a computed tomography (CT) scan. A total of 161 samples were used in this analysis.

FIG. 57 and FIG. 58 illustrate that the protein results were able to accurately distinguish samples from subjects with benign lung nodules versus cancerous lung nodules. Such protein classifiers may more robustly identify the samples as from a subject having a benign or cancerous lung nodule than other classifiers.

FIG. 57 illustrates a lung nodule classifier generated from the methods described herein to determine whether the lung nodule is malignant or benign. FIG. 58 illustrates the feature information and importance for the lung nodule classifier shown in FIG. 57. The weights of the model (e.g., ridge regression) were assigned to each of the features to be used in training. More important features, i.e. features which were better at distinguishing between cancer and benign, have larger absolute weights. The + or − sign in FIG. 58 denotes whether features were overexpressed (+ values) or underexpressed (− values) in malignant versus benign lung nodules.

The biofluid samples in this example were plasma samples, but it is expected that the assay will also work well in other biofluid samples such as serum or whole blood samples. Further, the proteomic method in this example included contacting the biofluid samples with particles followed by a mass spectrometry assay proteins adsorbed to the particles. In particular, the samples were measured using Proteograph methods (which includes the use of particles to adsorb proteins) followed by liquid chromatography-mass spectrometry (LC-MS). However, it is expected that other methods for assaying proteins would work similarly. For example, the use of mass spectrometry without particle-protein adsorption, or the use of an immunoassay would also work. In some cases, an immunoassay using any of the same protein biomarkers as were included in this example, may be used to successfully determine whether a biofluid sample is from a subject having a cancerous lung nodule as opposed to having a non-cancerous lung nodule.

Example 28. Use of a Classifier for Determining Whether a Lung Nodule is Malignant or Benign An additional analysis was performed using samples from more subjects. Biofluid samples comprising plasma samples of human subjects identified as having a lung nodule were assayed using a proteomic method to generate proteomic results including measurements of protein abundances. The lung nodules were identified in the subjects by subjecting the subjects to a computed tomography (CT) scan. A total of 212 samples were used in this analysis.

A goal of the study was to identify protein signatures that differentiate between malignant and benign lung nodules. An additional goal was to integrate the results into a multi-omics signature. FIG. 59 illustrates numbers of samples from various groups used in this study. The experimental design included 212 patient plasma samples randomized across 14 plates at 40 µL per patient. The samples from subjects with malignant nodules mostly included stage 1 cancer. A benefit of using early-stage (e.g. stage 1 cancer) samples is that they may be useful in addressing the unmet need of early cancer detection.

To generate the proteomic results, the plasma samples were contacted individually with particles to adsorb proteins from the plasma onto a corona around each particle. Proteins adsorbed to the particles were then assessed by liquid chromatography-mass spectrometry (LC-MS). Proteomic results were obtained from the use of 5 physiochemically distinct particle types (designated "NP1," "NP2," "NP3," "NP4," and "NP5"). These particles were purchased commercially from Seer, Inc. where they were identified as S-003, S-006, S-007, P-39, and P-73, respectively. Results were collected utilizing Bruker timsTOF, 60-minute gradients, and DDA. Multiple quality controls were conducted on every plate.

Figure 60:
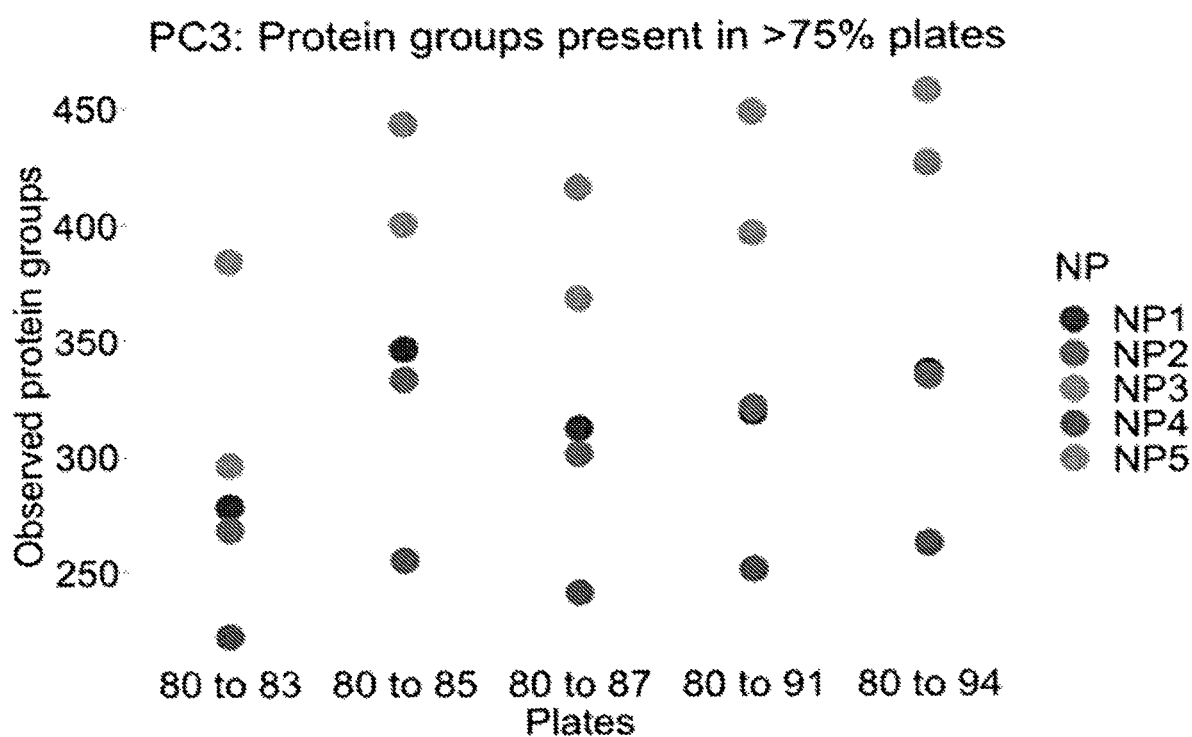
FIG. 60 illustrates numbers of observed protein groups in a process control sample.

FIG. 60 illustrates numbers of observed protein groups in a process control (PC3) sample detected in greater than 75% of plates. There were 972 unique proteins detected across all nanoparticles in PC3 at 75% level. 2083 unique proteins were observed in greater than 25% of the samples.

Figure 61:
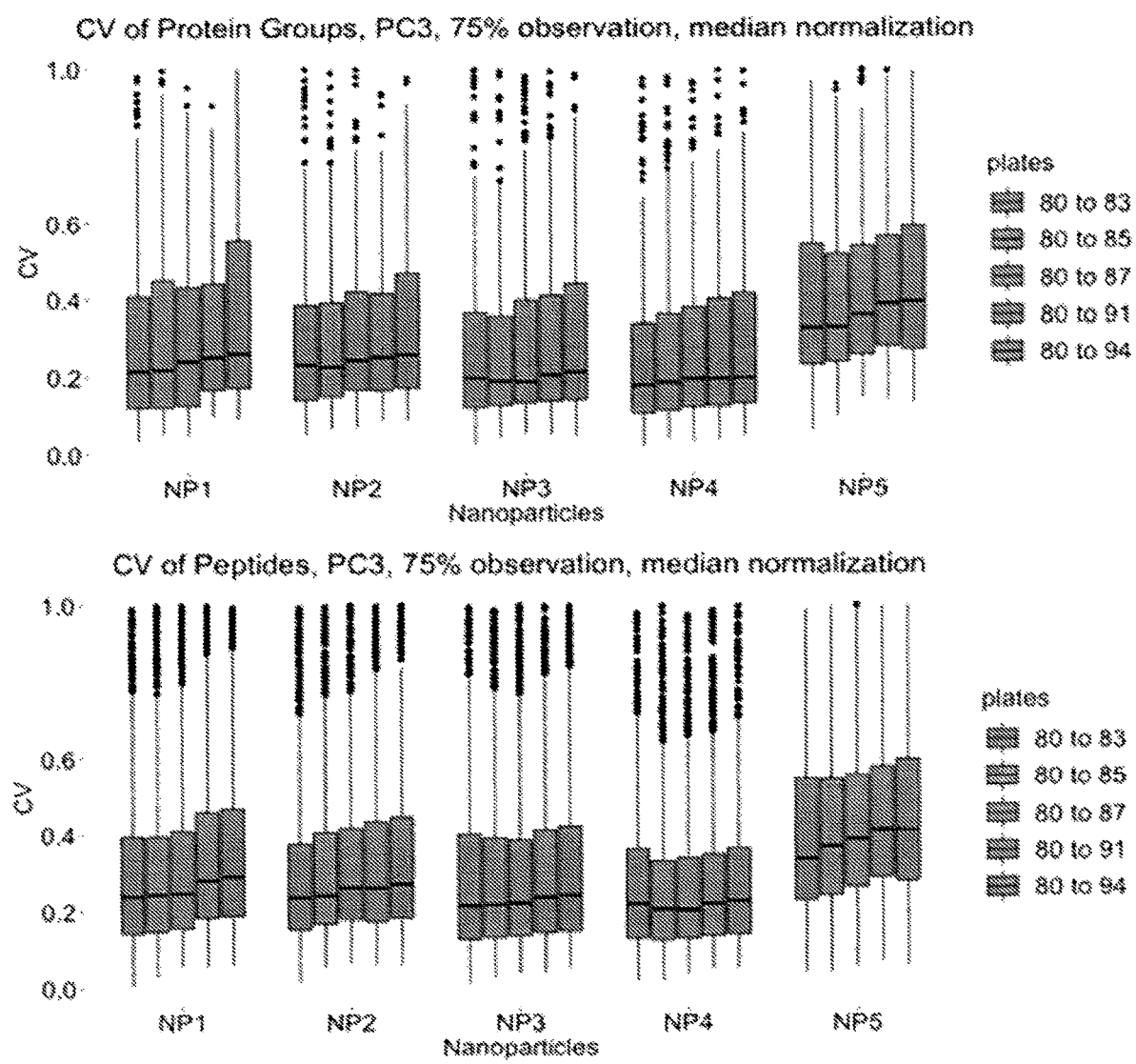
FIG. 61 illustrates some coefficient of variation (CV) values.

FIG. 61 illustrates coefficient of variation (CV) values. The PC3 sample was processed across all 5 nanoparticles on all plates. Total variability across entire study matched expectations.

FIG. 62 includes a protein abundance heatmap of samples from subjects having malignant and benign lung nodules (denoted "malignant samples" or benign samples". The malignant samples and benign samples demonstrated different expression patterns. Furthermore, the same proteins were observed on different nanoparticles clustered together, indicating that the fold changes tracked across nanoparticles, and corroborating the biological signals. From top to bottom, the proteins listed in FIG. 62 include the following in order: PIGR, BPIFB1, IGKC, GSN, IGFBP2, IGFBP2, IGFBP2, IGFBP2, ADAMDEC1, TSKU, CHGA, CHGB, MMP19, COL18A1, SVEP1, IGF2, SERPINA1, SERPINA1, SERPINA1, C6, C8G, LTBP2, CILP, RBP4, PGK1, CTTN, DMTN, SERPINA3, C1QA, C1QB, CNDP1, CNDP1, IGFALS, IGFALS, CETP, DSC3, PAMR1, IGFBP3, COLEC10, ANGPTL2, HABP2, F2, F2, LALBA, F11, and GZMH, in conjunction with various nanoparticles. The proteins listed in FIG. 62 may be useful for differentiating cancerous lung nodules from benign lung nodules.

FIG. 63 includes a volcano diagram plotting log-fold changes in protein abundances against negative log of p-value. Utilizing Benjamini-Hochberg procedure for multiple hypothesis correction, multiple proteins were observed to be statistically significant and differentially abundant. The proteins listed in FIG. 63 may be useful for differentiating cancerous lung nodules from benign lung nodules.

FIG. 64 illustrates some example proteins from an initial univariate analysis. Top up-regulated and down-regulated proteins showed in FIG. 64 had approximately 2-fold changes between malignant and benign samples. The proteins listed in FIG. 64 may be useful for differentiating cancerous lung nodules from benign lung nodules.

Example 29. Use of a Classifier for Determining Whether a Lung Nodule is Malignant or Benign An additional analysis was performed using some samples from Example 28. This analysis was an interim analysis before all of the analysis in Example 28 was complete. Biofluid samples comprising plasma samples of subjects identified as having a lung nodule were assayed using a proteomic method to generate proteomic results including measurements of protein abundances. The lung nodules were identified in the subjects by subjecting the subjects to a computed tomography (CT) scan.

Figure 65A:
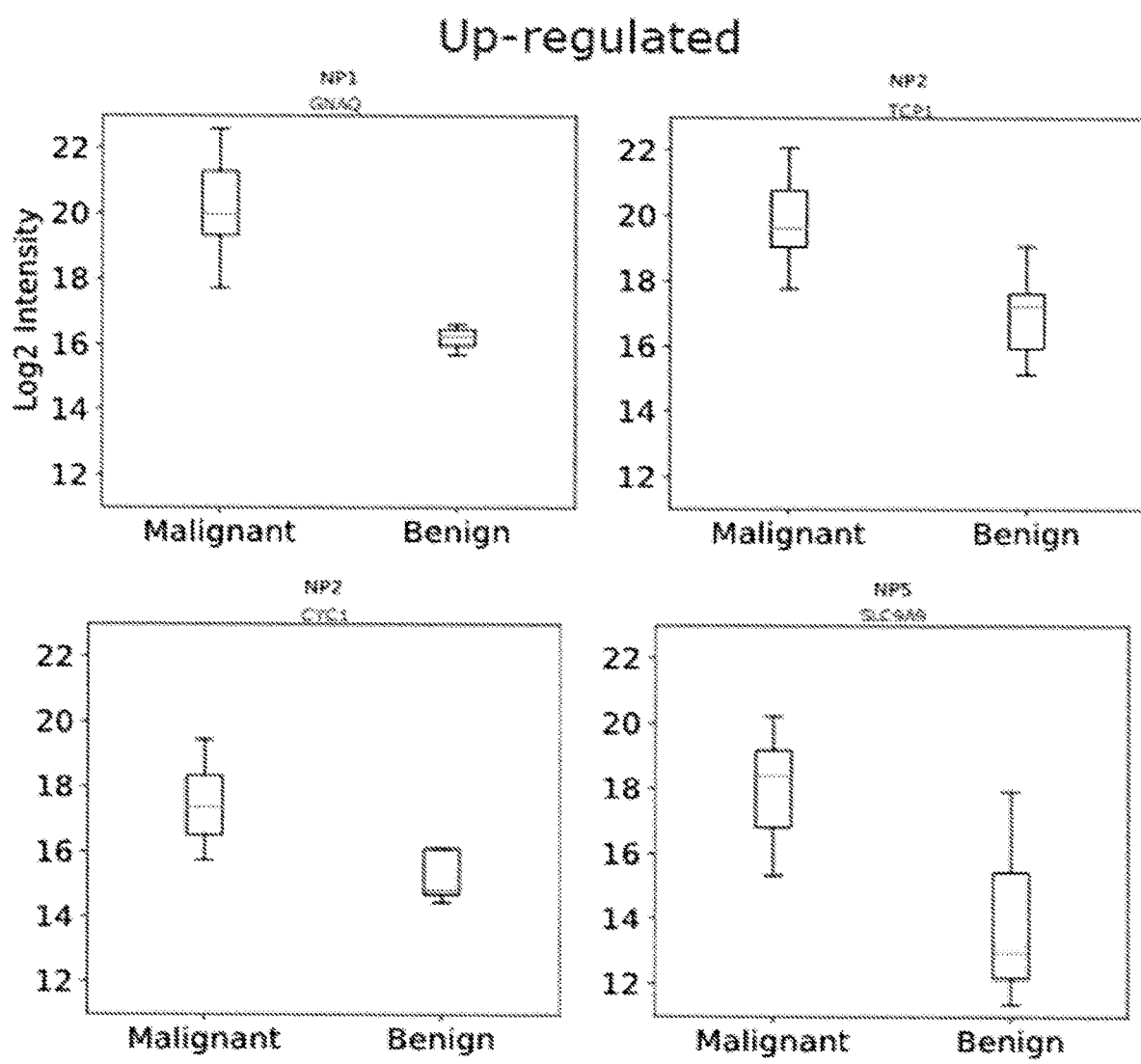
FIG. 65A includes graphs showing some proteins that were upregulated in biofluid samples from subjects with malignant lung nodules.
Figure 65B:
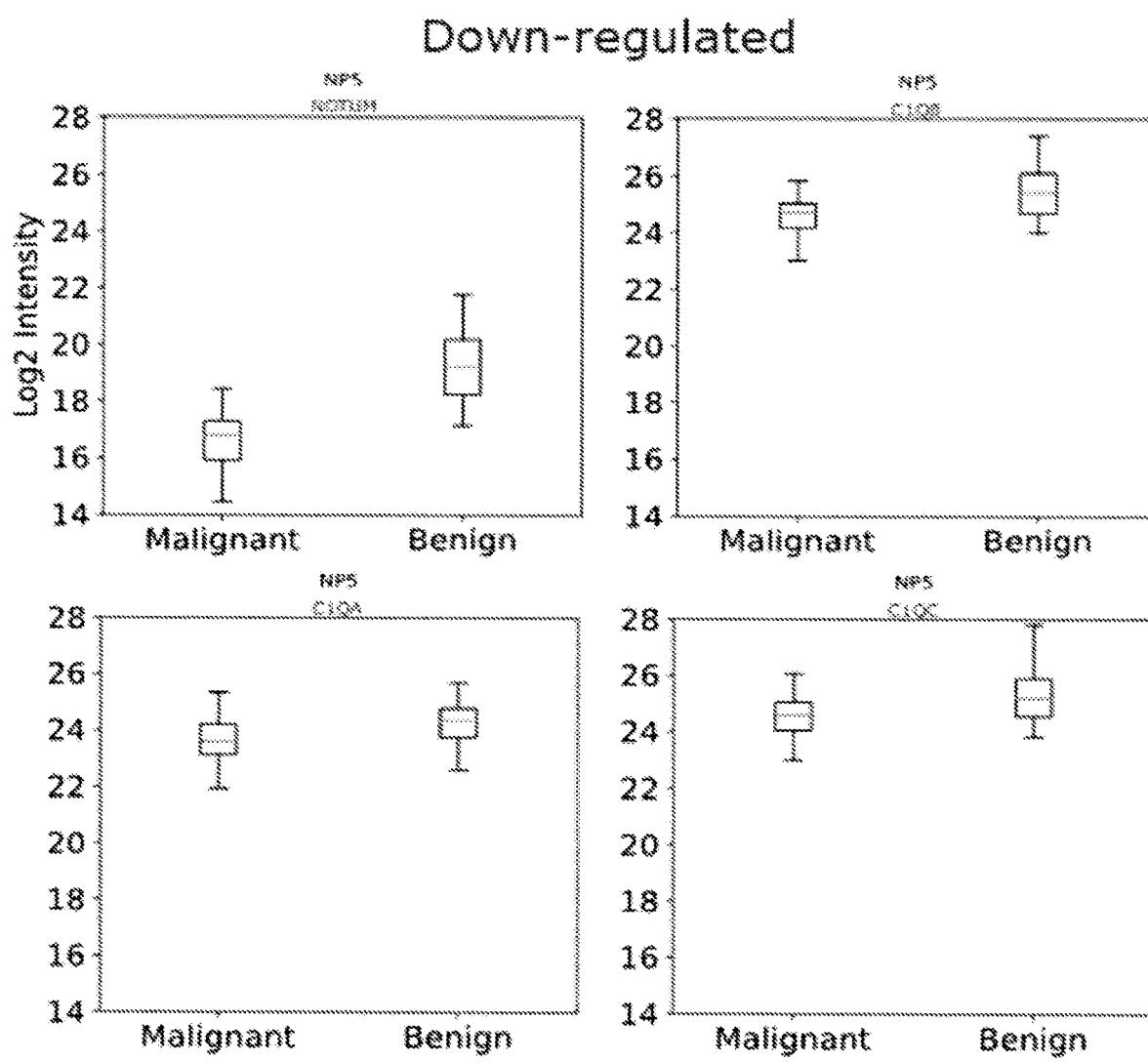
FIG. 65B includes graphs showing some proteins that were downregulated in biofluid samples from subjects with malignant lung nodules.

FIG. 65A and FIG. 65B illustrate some proteins that were found to be upregulated or downregulated in plasma samples from subjects with malignant lung nodules versus non-malignant lung nodules. Upregulated proteins included Guanine nucleotide-binding protein G (q) subunit alpha (GNAQ), T-complex protein 1 subunit alpha (TCP1), cytochrome C1 (CYC1), and Sodium/hydrogen exchanger 9 (SLC9A9). Downregulated proteins included Palmitoleoyl-protein carboxylesterase NOTUM, Complement C1q subcomponent subunit A (C1QA), Complement C1q subcomponent subunit B (C1QB), and Complement C1q subcomponent subunit C (C1QC).

Figure 66:
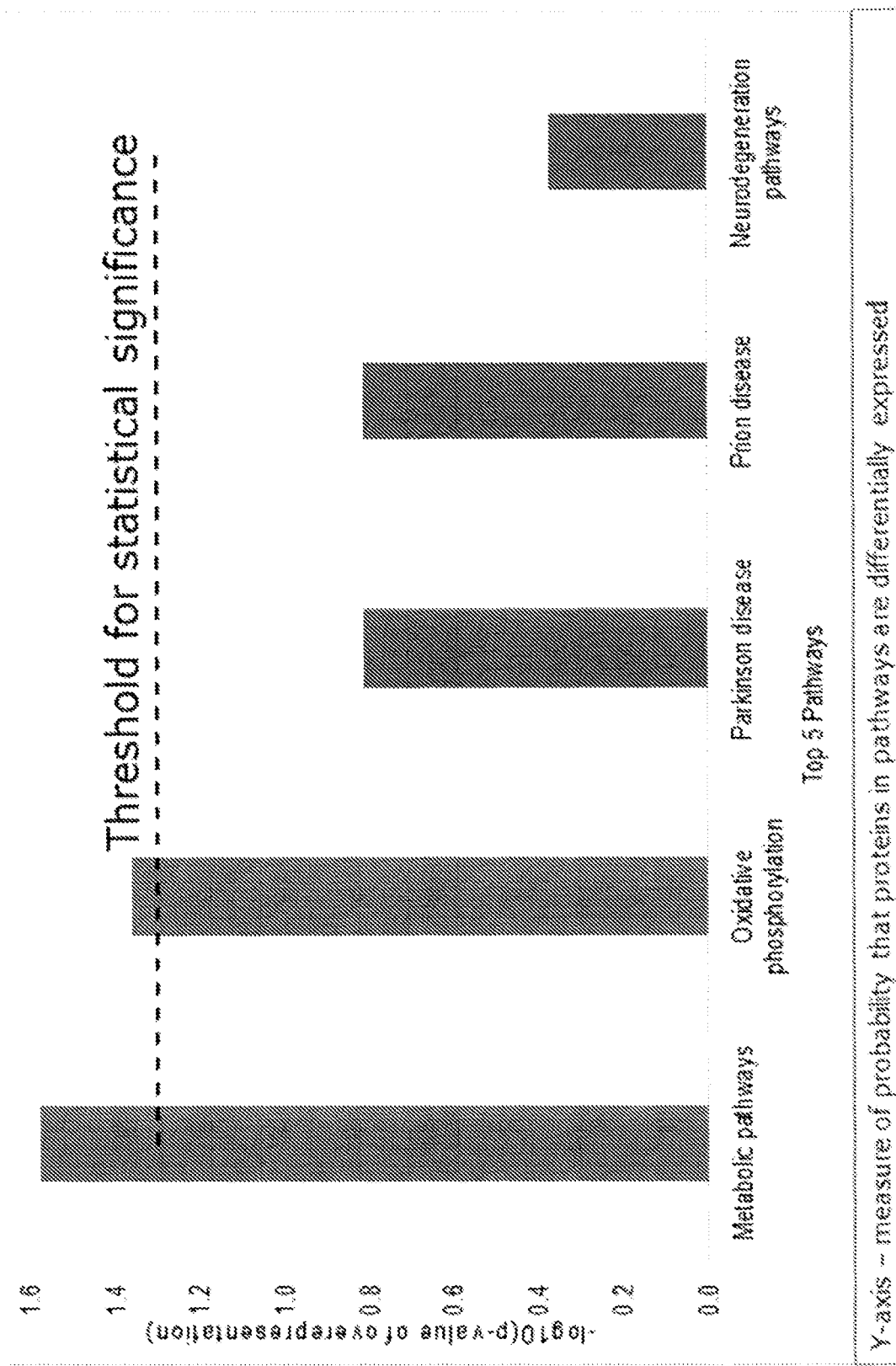
FIG. 66 includes a graph illustrating that differentially expressed proteins were enriched in metabolic and phosphorylation pathways.

FIG. 66 illustrates that differentially expressed proteins were enriched in metabolic and phosphorylation pathways. These pathways may be further addressed using a multi-omic approach.

Figure 67:
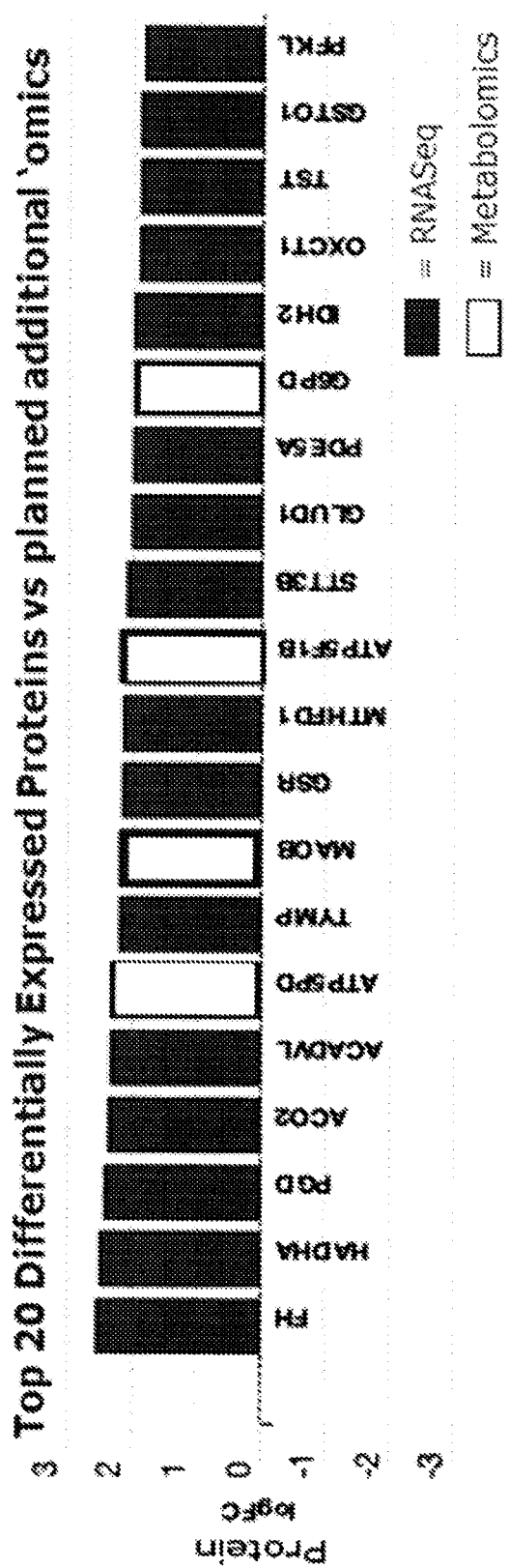
FIG. 67 illustrates some extrapolated mRNA data showing differentially expressed proteins in metabolic pathways.

Dysregulation of metabolic pathways may be enriched in the proteomics results in cancer. FIG. 67 illustrates some extrapolated mRNA results showing 16 of top 20 differentially expressed (DE) proteins in the metabolic pathways measured by RNAseq. Additional metabolomics experiments will measure metabolites associated with the top pathways and DE proteins, e.g., ATP, Glucose-6-phosphate.

Example 30. Use of Particles in Identifying a Lung Nodule as Malignant or Benign In a further analysis, lung nodules were identified by CT scan in human subjects, and proteins of plasma samples adsorbed to commercially available nanoparticles (Seer, Inc.) were analyzed by mass spectrometry. This study included large scale, deep and unbiased plasma proteomics profiling a sub-study of a multi-cancer cohort. At least some samples and sample data of the example overlapped with that of Example 27-Example 29.

Profiling biological responses to cancer has historically been challenging. Multi-omic profiling may unlock possibilities for early cancer detection in biofluids. Innovations in early cancer detection have a significant impact in cancer care, and early detection improves survival rates and may improve treatment options.

Figure 69A:
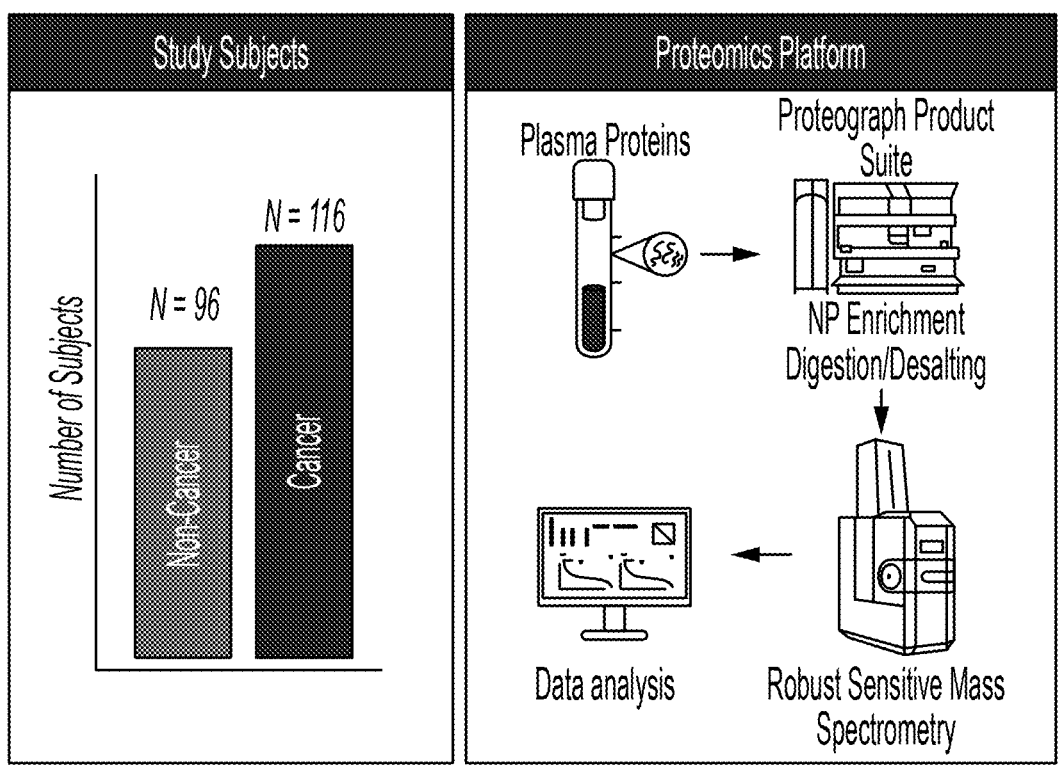
FIG. 69A shows some aspects of study subjects and a proteomics platform that may be used in the methods described herein.
Figure 69B:
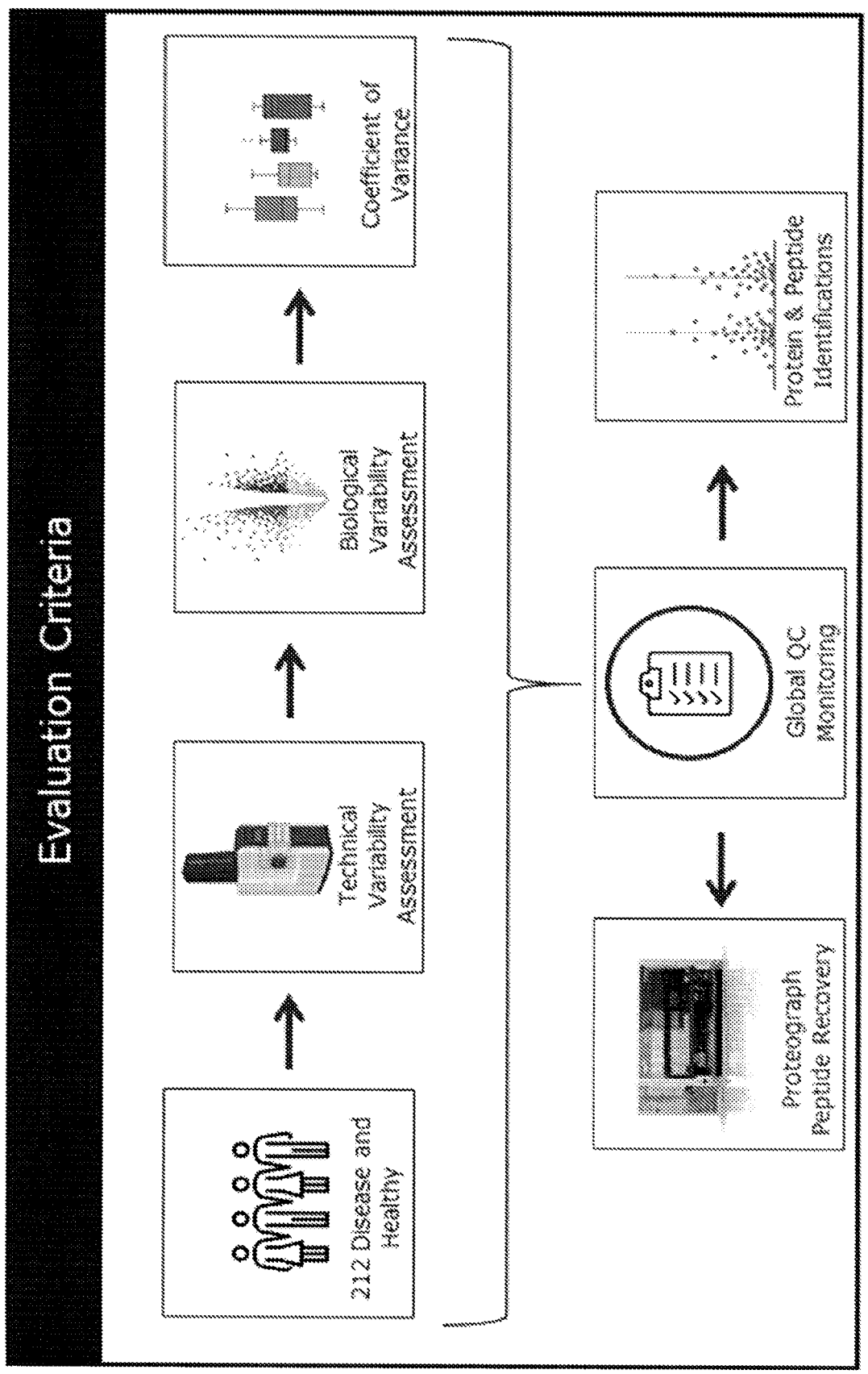
FIG. 69B shows some aspects of a proteomics platform that may be used in the methods described herein.
Figure 69C:
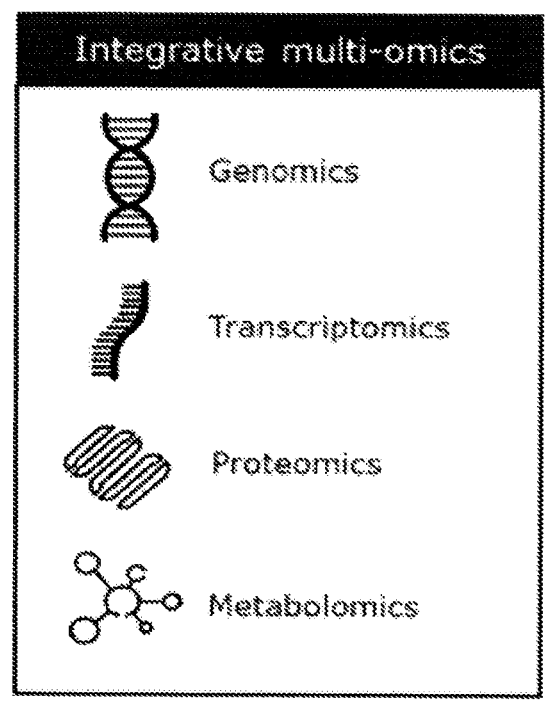
FIG. 69C shows some additional multi-omic aspects.

A goal is to build better tools for physicians treating a multitude of cancers using multi-omics. To address this goal, a multi-cancer sample repository was created that includes 1,000's of samples, >1,000 cancer subjects, and optimal sample types for each 'omic data type. Every 'omics technology in the platform was empirically selected through a series of feasibility studies. Reported here is a proteomics feasibility study of 212 biofluid samples (plasma) performed using PROTEOGRAPH™ Product Suite with a multi-nanoparticle (NPs) enrichment technology and LC-IM-MS/MS analysis. The samples were collected from non-cancerous subjects and subjects with lung cancer. The samples were collected from various sites as described in FIG. 68. FIG. 69A and FIG. 69B describes some aspects of the study. Additional omics data types may be incorporated into a study like this, as shown in FIG. 69C. Results of the study that was performed are shown in FIG. 70 to FIG. 76.

The data show that deep, untargeted, rapid proteomic biomarker studies are feasable and useful for methods such as cancer detection or monitoring in biofluid samples from subjects such as subjects that have a lung nodule. The mass spectrometry, as shown in FIG. 69A and FIG. 69B, included 60 min DDA-PASEF runs. The data analysis included Max-Quant search parameters: 0.1% peptide/protein FDR search, default timsTOF parameters searched against complete Uni-Prot SwissProt human proteome database with contaminants (50% reversed decoys).

Based on FIG. 70, technical variability was lower than detected biological variability. The data included a median coefficient of variation (CV) of 32% across all technical controls with biological variability of 96%. Median normalization was based on features common to all samples for a particle. Intensities were natural log transformed prior to normalization.

Figure 71:
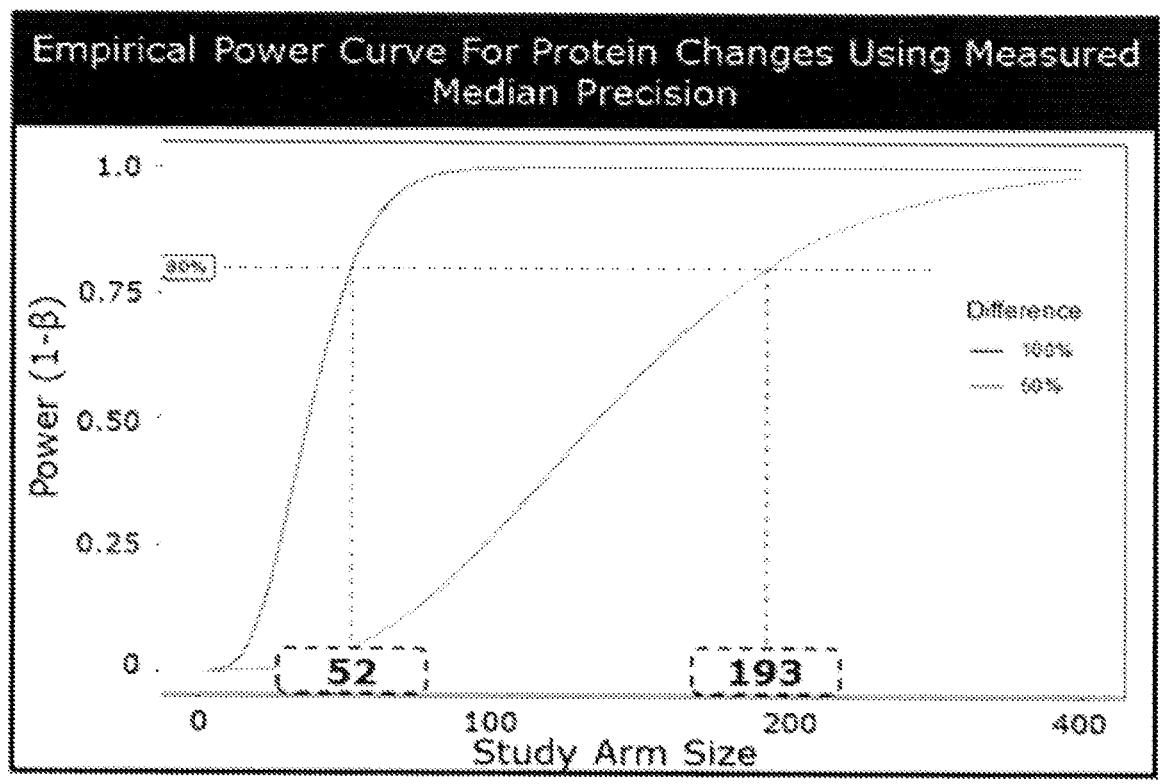
FIG. 71 includes an empirical power curve for protein changes in a study described herein.

Based on FIG. 71, measurement reproducibility enabled detection of expected fold changes, providing desired statistical power for multi-cancer biomarker studies. A median precision of 96% and Bonferroni correction assuming 2000 proteins was used.

Based on FIG. 72, over 5000 proteins were detected among the subjects. A median of 4 peptides per protein were detected for proteins present in over 25% of the samples.

Figure 73:
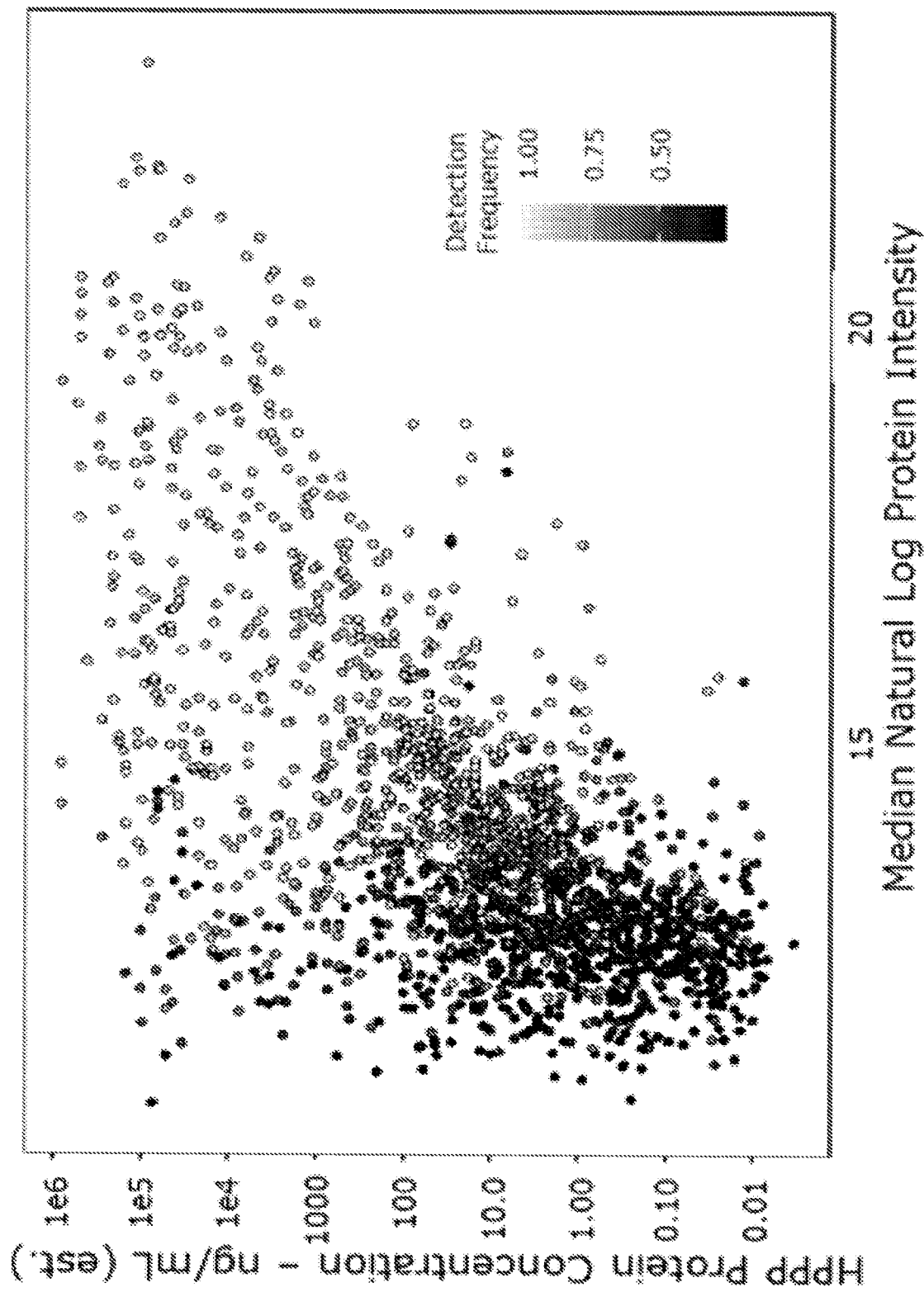
FIG. 73 includes a graphical depiction of protein concentrations relative to natural log protein intensity data obtained in a study described herein.

Based on FIG. 73, detected HPPP proteins covered 8 orders of magnitude in concentration. An increased depth of coverage was highlighted by compression of proteome dynamic range. In FIG. 73, maximum measured intensity and minimum reported concentrations for duplicates are plotted. 201 samples with full data were filtered to ≥25%. About 40% of 3,486 HPPP1 proteins with estimated plasma concentrations were detected at a 25% threshold, and NP-based enrichment compressed effective protein concentrations and provided a rapid measurement of high and low concentration proteins. The data included reproducible detection of low abundance proteins. In particular, 392 proteins with estimated concentrations<10 ng/ml were detected in >50% of the samples.

For the results in FIG. 74, measuring proteins across 8 orders of magnitude enabled detection of HPPP proteins with known correlations in cancer, and about 40% of the top 50 detected GeneCards cancer proteins were known to have plasma concentrations of <10 ng/mL. This study shows the usefulness of detecting novel cancer biomarkers that include low abundance functional proteins. Enhanced proteomic coverage detected cancer related proteins. All detected, matching proteins from samples were plotted on an HPPP curve, as shown in FIG. 74. GeneCards data used a score reported from a matching gene ID and the search term, "cancer." Biomarkers shown in FIG. 74 include ALB, CASP3, CD44, CDH1, CYCS, ENO2, EXT2, FBN1, FH, FN1, GNAQ, GSTP1, HABP2, HSP90AA1, IDH1, IDH2, IGF1, IGF2, IGFBP3, ITGB1, KRAS, MAPK1, MINPP1, MMP1, MMP14, MMP2, MT-CO2, MXRA5, PHB, PLA2G2A, PRKAR1A, PRKCA, PTPN12, PTPRJ, RHOA1, SDHA, SERPINA3, SLC2A1, SLC9A9, SLMAP, SOD2, SPP1, SRC, STAT3, TGFB1, THBS1, TIMP1, TYMP, and VEGFC. Any of these biomarkers may be useful in the methods disclosed herein, such as a method of identifying a lung nodule as cancerous.

Figure 75A:
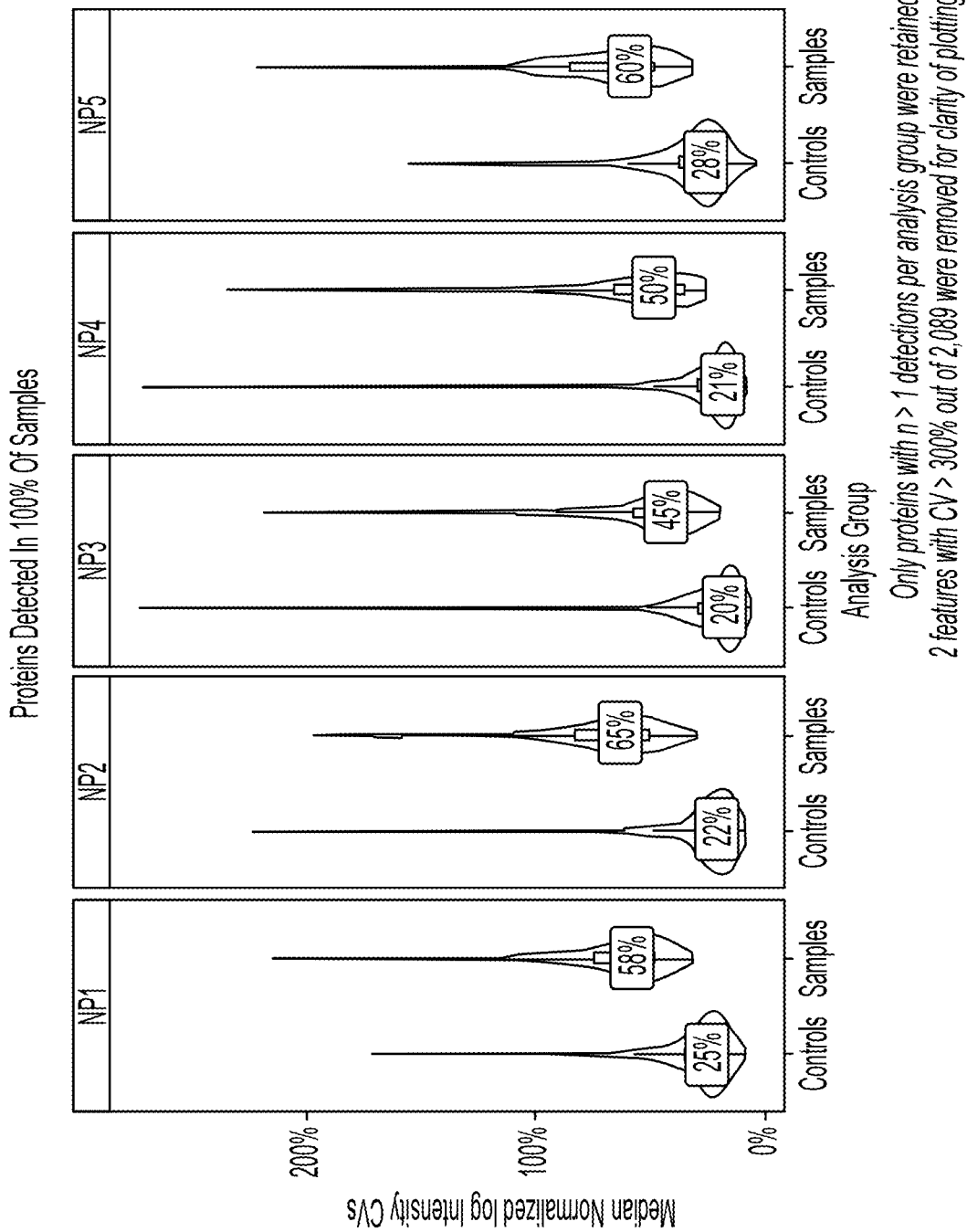
FIG. 75A includes median normalized log intensity CVs for proteins detected in 100% of samples.
Figure 75B:
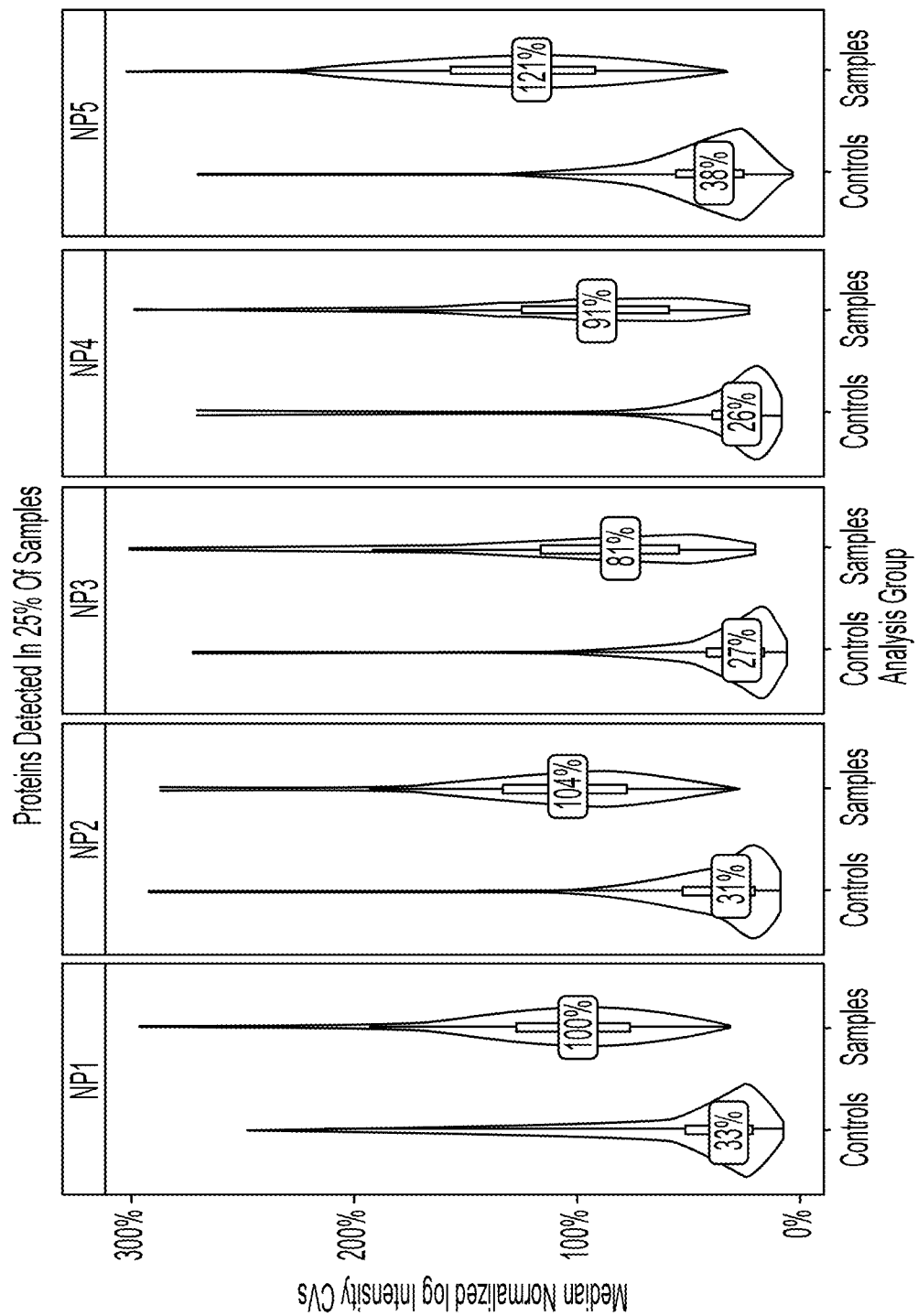
FIG. 75B includes median normalized log intensity CVs for proteins detected in at least 25% of samples.

FIG. 75A and FIG. 75B include proteins detected in 100% or 25% of samples, and show reproducibility of the platform and ability to detect biological signal. The performance was evaluated across 15 plates and 2 months.

FIG. 76 shows that large numbers of proteins were reproducibly detected across samples. Individual nanoparticles yielded both complementary and common protein identifications.

Additional samples were analyzed to further assess some of methods described herein, such as methods that include particle use. FIG. 77A to FIG. 77B show that quantitative performance of Proteograph is suitable for large scale studies. FIG. 78A to FIG. 78B show that protein enrichment by Proteograph at scale is highly reproducible. FIG. 79A to FIG. 7B show an assessment of system robustness across 1000s of injections, and indicate that the robust LC-MS platform described herein may facilitate large cohort studies. FIG. 80A to FIG. 80B show that the Evosep system was both robust and reproducible over >1800 plasma injections. A reproducible LC-MS platform may be useful for large biomarker studies with many samples. FIG. 81A to FIG. 81B show representative data from an ongoing multi-cancer study with 3159 protein groups across 5 nanoparticles.

The data from this study demonstrated, among other things, the usefulness of using particles such as in the Proteograph technology (Seer Inc.) for proteomics biomarker discovery studies. In this analysis, excellent depth of coverage, reproducibility and direct detection of expected cancer relevant proteins across 8 orders of magnitude in concentration were achieved, providing a well-defined use case for large-scale discovery studies. Nanoparticle enrichment of proteins from plasma provided similar depth of coverage (5,099 proteins) as best of class depletion and fractionation strategies, but at a much higher throughput. The combination of Proteograph and Bruker timsTOF Pro dia-PASEF technology has provided a robust, sensitive and high-throughput proteomics platform to support large scale untargeted proteomics biomarker discovery studies. The combination of Proteograph+Evosep+Bruker timsTOF Pro2 technologies generated deep proteome coverage at high throughput with reproducibility at a level useful for large scale proteomics biomarker discoveries.

Example 31. Lung Nodule Discovery Study: Interim Analysis of Proteomics and Metabolomics A univariate analysis was performed to determine the statistical significance between classes for each analyte. The analysis contained 208 total subject samples. 65 peptides and 57 proteins were found to be statistically significant between classes. Over 10% of the evaluated proteins were statistically different between malignant and benign classes. The analysis demonstrated significant biological signals to separate classes. It also improved the probability to build a high performing machine learning ("ML") based classifier and showed an easier path for assay development. The multitude of univariate signals provided a higher probability of success in building multivariate classifiers. A volcano plot of intensity differences and P-values for peptides detected in samples was created (FIG. 82). The analysis was based on an evaluation of individual peptide transitions combined as dependent measures.

The most statistically significant different protein was IGFALS ("Insulin-like growth factor-binding protein complex acid labile subunit"). All measured peptides for IGFALS were highly correlated and under expressed in Malignant subjects. This was the ideal candidate for assay development on LCMS because of its robust, highly abundant signal with strong statistical significance. Graphs were created (FIG. 83) that depict the transitions for peptide ANVFVQLPR from protein P35858.

An Open Target (OT) score quantified the known association between a particular protein and lung cancer on a 0-1 scale. FIG. 84 shows a graph illustrating a comparison of lung cancer OpenTarget scores to peptide difference significance. Statistically significant hits from interim univariate analysis of proteomic data had known (high OT score) as well as unknown (low OT score) associations with lung cancer. The unbiased approach may help discover important classifier features that may not be known from literature.

A univariate analysis was performed on 208 subject samples. After Benjamini-Hochberg multiple hypothesis correction, statistically significant metabolite found: 3-Methyl-3-hydroxyglutaric acid that was overexpressed in malignant versus benign. When combined with proteomics data, this improved the likelihood of a high-performing multi-omics classifier. FIG. 85 shows a volcano plot of intensity differences and P-values for metabolites in lung nodule subjects.

Example 32. Seer-Lung Study

The purpose of this study was to develop and validate the accuracy of a blood-based panel of protein biomarkers for use in patients with lung nodules who were considered for biopsy or radiologically followed. This study was a prospective, multicenter minimal-risk sample collection study. It was a single-visit blood sample collection study with clinical data submission via EDC. The diagnostic accuracy of the PrognomiQ test will be compared to and combined with physician judgment and available risk prediction calculators. The subjects will be followed for up to 24 months until definitive pathology results are available, either via surgical or non-surgical (bronchoscopy, transthoracic needle biopsy) lung biopsy or the subject has a one year and up to 2-year radiology follow up.

As an overview of the study population, the first patient was enrolled in January 2019. There is a current enrollment of around 850, with a goal of around 600 additional patients for 2022. The goal is to have 3,000 subjects in total. The current protocol, which was amended in May 2021, is to (1) have subjects followed by imaging at the 1 and 2 year since identification of nodule, and not only subjects planned for biopsy, and (2) have patients with prior history of cancer >5 year prior to enrollment allowed versus requirement of no prior history of cancer.

Out of 589 eligible subjects, 186 subjects met all criteria. Of the 186 subjects that met all criteria, 143 were cancer cohort and 43 were benign cohort (FIG. 86).

A staged approach to classifier and test development was used. Various versions of classifiers were analyzed from discovery to test development (FIG. 87).

Power curves for analyte classes were created, including curves for proteins, metabolites, and lipids (FIG. 88). The smallest arm was well powered.

A volcano plot of intensity differences and P-values for peptides in lung nodule subjects was created (FIG. 89) to show the peptide changes between groups. The significance was based on Wilcoxon test p-value with BH multiple testing correction.

The IGFALS Gene is the Insulin Like Growth Factor Binding Protein Acid Labile Subunit. FIG. 90 and FIG. 91 show graphs for peptide LEYLLLSR and peptide ANVFVQLPR from protein P35858. The graphs show the transitions for the peptides from protein P35858 in benign and malignant groups.

The IGFBP3 Gene is the Insulin Like Growth Factor Binding Protein 3. FIG. 92 shows a graph showing the transitions for peptide FLNVLSPR from protein P17936 in benign and malignant groups. FIG. 93 depicts StringDB and the known interaction of IGFALS and IGFBP3.

FIG. 94 shows volcano plots of intensity differences and P-values for metabolites in lung nodule subjects. Metabolite changes between groups are shown and the significance was based on Wilcoxon test p-value with BH correction. FIG. 95 shows a graph showing biopterin metabolite quantities in benign and malignant groups.

FIG. 96 shows a volcano plot of intensity differences and P-values for lipids in lung nodule subjects. The plots compare positive and negative samples. Lipid changes between groups are shown and the significance was based on Wilcoxon test p-value with BH correction.

The Lung Nodule Protein Differences were diagramed (FIG. 97), showing the potentially novel combinations of known and unknown analytes-OpenTargets lung cancer. FIG. 98 shows a diagram illustrating the staged approach of version one classifier, version two classifier, and version three classifier discovery through test development.

FIG. 99 shows bar graphs for pre-test probabilities for subjects with benign nodules and pre and post-test probabilities for subjects with benign nodules. Test performance determined post-test probability of malignancy. Based on LDCT results, pre-test probabilities of cancer may be estimated. The pre-test probabilities fell into three risk categories defined by the American Thoracic Society: (1) Very Low risk <5%; (2) Low/Moderate risk 5%-65%; and (3) High risk >65%. A perfect test with 100% sensitivity and 100% specificity will correctly identify all subjects with benign nodules as negative and move their post-test probabilities to the very-low-risk category. A less-than-perfect test will move a fraction of the subjects with benign nodules in the low/moderate-risk category to the very-low-risk category upon testing negative. For different levels of sensitivity and specificity this fraction is indicative of the number of unnecessary biopsies that can be avoided. This fraction may be computationally estimated for a given a pre-test probability distribution.

FIG. 100 shows a graph comparing sensitivity and specificity. Each contour identifies sensitivity, specificity values that reclassify a given fraction of benign nodules. For different levels of sensitivities and specificities, the simulations show the fraction of subjects with benign nodules in low/moderate-risk category that can be reclassified to the very-low-risk category upon testing negative. Probabilistic model simulates 50K subjects with 25% prevalence rate of malignancy. Simulations assume pre-test probabilities in benign and malignant groups follow the distributions reported in Silvestri et al. (CHEST 2018; 154 (3): 491-500).

Example 33. Colorectal Cancer Study

The genomic measurement including mRNA transcript for colorectal cancer ("CRC") and non-cancer subjects were collected. Also, log-transformed counts on canonical mRNA transcripts were used. Data was split into a training set and a hold-out set.

223 total subjects were analyzed. FIG. 101 shows the ROC curve for 223 subjects with mRNA data in the study. Out of the 223 total subjects, 133 had colorectal cancer and 90 were comorbid controls. The cancer subjects were at various stages of colon cancer. Of the cancer subjects, 13 subjects had stage I cancer, 27 subjects had stage II cancer, 32 subjects had stage III cancer, 41 subjects had stage IV cancer, and 20 subjects had an unknown stage of cancer. 60,649 mRNA features were used in the analysis. The study was performed on white blood cells.

Next, a model on the dataset was built to differentiate between cancer and non-cancer subjects by training an ensemble classifier on the training data. The classifier was trained using 10 repeats of 5-fold nested cross-validation with hyperparameter tuning. The domain of the hyperparameters for the classifier was divided into a discrete grid. Then, every combination of the grid values was tried, calculating the performance metrics in the nested cross-validation, and average performance across all runs for each dataset was reported.

For each of the 50 runs, the model was trained on 80% of the data and was tested on the other 20% of the samples. The final ROC AUC was the average of all AUCs.

The hyperparameters selected during the search were then used to configure a final model, and the final model was fitted on the entire training dataset. Then, the model was used to make predictions on the hold-out dataset. A volcano plot illustrating the differential expression of various genes in the study was created (FIG. 102).

Example 34. PiQuant Methods

Plasma samples were generated from whole blood collected in K2EDTA preservation tubes. 1 mL of each of the neat plasma samples was paced in a well on a 96-well plate and digested using PreOmics iST Kit following the manufacturer's instructions. Once digested samples were collected, they were speed evaporated to dryness and stored at −80 C until use. When ready, samples were removed from the freezer and allowed to come to RT for 15 minutes. Samples were then resuspended in 50 mL of Peptide Buffer A (98% Optima LC-MS Grade Water 2% Optima LC-MS Grade Acetonitrile with 0.1% Optima LC-MS Grade Formic Acid), and shaken vigorously for 10 minutes using a Bio-Shake XP (1800 RPM). All peptide amounts were then quantified using the Thermo Fisher Pierce Quantitative Fluorometric Peptide Assay following the manufacturer's instructions. Peptide amounts were then normalized to 133 ng/ml, using Peptide Buffer A. 12 mL of each digested patient sample was then placed into individual positions in a 96-well plate. PQ500 internal standard reference standards were then prepared following the manufacturer's instructions. Briefly, 20 mL, dissolution buffer was added to each vial and sonicated for 5 minutes. After sonication completed, 100 mL, of LC buffer was added to each vial. Vials were then vortexed briefly and centrifuged, resulting in ready to use reagent. 4 mL, of prepared PQ500 reagent was added to each 12 mL, patient sample, resulting in a final endogenous peptide concentration of 100 ng/mL.

Samples were then loaded onto an LC-MS instrumental setup comprised of an Ultimate 3000 liquid chromatography instrument connected to an Thermo Fisher Orbitrap Exploris 480 mass spectrometer.

Analytical separation was performed on a Thermo Fisher column (Acclaim PepMap RSLC 300 mm×15 cm C18, 2 mm, 100A). Peptides were separated on a 36-minute gradient (45-minute total LC runtime). Peptides were electrosprayed into the mass spectrometer though a Thermo Fisher NanosprayFlex ion source equipped with a New Objective Pre-Cut Pico Tip emitter (360 mm OD×20 mm ID, 10 mm tip, 2.5' length) The mass spectrometer was operated in positive mode with a static spray voltage of 1800 V. The instrument was programmed to collect a full MS1 scan of intact peptides at 120K resolution with the RF lens at 40%. Immediately after full MS1 scan, the instrument performed an unscheduled low resolution (7.5K Resolution) MS/MS scan for targeted mass triggers present within the full scan. These masses were of selected internal standard peptide masses arising from all the peptides found within the PQ500 panel. Following fragmentation of the internal standard masses in the low-resolution MS/MS scan, a targeted mass trigger high resolution second MS/MS scan of endogenous peptides was performed on masses that had at least 5 matched ions from the low resolution MS/MS scan of the internal standard scan. The max number of scans between targeted MS/MS mass fragmentation and triggered MS/MS scan was set to 1. In total, 803 standard PQ500 peptides were present in the internal standard mass trigger library. All fragmentation energies were set to 27%. The total max cycle time allowed was 7 seconds.

Once collected, data was processed using Biognosys SpectroDive software (Version 10.4.210316.47784 (Ictineo II)). Searches were set up by beginning a targeted analysis from file and each sample had the PQ500_V1_SureQuant panel (downloaded from Biognosys website) assigned and the workflow was changed to labeled. Use reference normalization was disabled and the condition file was set up following software guidelines. Once the search was completed, the final report was exported with all output selections enabled

Example 35. Methods for Targeted LC-MS Approach to Study the Human Plasma Lipidome and Metabolome Lipidomics Assay:

Lipid Extraction: Total lipid was extracted using single phase organic extraction method. 5 µL of cohort, SRM1950, and human pooled plasmas were placed in 96 well plate and spiked with 20 µL of 1:20v/v Ultimate SPLASH mix (Avanti Polar, Alabaster, AL) working internal standard. To each sample-internal standard mix, 475 µL of 1:1v/v butanol: methanol mixture was added and shaken for 10 min at 500 rpm at 4° C. The mixture was incubated for 15 min at 4° C. and shaken for 10 min at 500 rpm at 4° C. Further the sample was re-incubated for 15 min at 4° C. and centrifuged at 3500 rpm for 10 min. Approximately 300 µL clean extract was transferred into clean collection plate and stored at −20° C. until injecting into LC-MS system.

Liquid Chromatography-Mass Spectrometry: Two chromatographic analytical separation methods were used for the separation of lipid class using binary gradient flow system. Data was collected in multiple reaction monitoring (MRM) mode equipped with electrospray ionization in positive and negative polarity using SCIEX7500 triple quadrupole mass spectrometer. Positive mode lipids were separated using SCIEX LC AD (SCIEX, Redwood City, CA) liquid chromatography system and Waters Acuity UPLC BEH C18 (50×2.1 mm×1.7 µm) (Waters, Waltham, MA) column with gradient elution containing mobile phase A as water: acetonitrile (40:60v/v) and mobile phase B as isopropanol: acetonitrile (90:10v/v), The gradient flow parameters for mobile phase B were as follows: 0.00-0.2 min 40%, 0.20-8.00 min 40-99%, 8.00-8.50 min 99%, 8.50-9.00 99-40%, 9-10 min 40%. The solvent flow rate and column temperature were maintained at 0.5 ml/min and 50° C. respectively. Lipids in negative mode were separated using SCIEX LC AD liquid chromatography system and Luna NH2 (100×2.0 mm×3 µm) (Phenomenex, Torrance, CA) column with gradient elution containing mobile phase A as water: acetonitrile (50:50v/v) and mobile phase B as dichloromethane: acetonitrile (7:93v/v), The gradient flow parameters for mobile phase B were as follows: 0.00-1.00 min 5%, 1.00-7.50 min 5-90%, 7.50-8.00 min 90%, 8.00-9.00 90-5%, 9-10 min 5%. The solvent flow rate and column temperature were maintained at 0.6 ml/min and 40° C. respectively. For both separation methods, the autosampler temperature was maintained at 4° C.

Data Processing: The MRM mode data were processed using SCIEX OS Analytics (SCIEX, Redwood City, CA) software. LC-MS data in positive and negative polarities were processed separately. MQ4 algorithm was selected to build the method for data processing. NIST SRM1950 and pooled quality control samples were utilized for optimizing peak integration parameters such as intensity thresholds, signal noise ratio, and smoothing parameters. Further the method was utilized to process in all the samples. The processed data was manually reviewed and curated to ensure accurate peak integration. The processed data was exported as .txt file and utilized for downstream statistical analysis.

Metabolomics Assay:

Metabolite Extraction: 30 µL human plasma was used to extract polar metabolites utilizing 1:1 v/v water: methanol mixture from cohort, NIST SRM1950, and pooled plasma samples. Briefly, 20 µL of QreSS 1 and 2 (Cambridge, Tewksbury, MA), a working internal standard was spiked to 30 µL plasma sample aliquoted into 96 deep well plate. Further the metabolites were extracted by dispensing 450 µL of 50% methanol into each plasma sample. The sample-solvent mixture was shaken for 5 min at 1000 rpm maintained at 4° C. The mixture was then incubated for 60 min at 4° C. and centrifuged for 15 min at 3000 rpm maintained at 4° C.

Liquid Chromatography-Mass Spectrometry

Data was collected in multiple reaction monitoring (MRM) mode equipped with electrospray ionization in positive and negative polarities using SCIEX7500 (SCIEX, Redwoodcity, CA) triple quadrupole mass spectrometer. The metabolites were separated using SCIEX LC AD liquid chromatography system and Kinetex F5 100 Å (150×2.1 mm×2.6 µm) (Phenomenex, Torrance, CA) column with gradient elution system containing mobile phase A as 2 mM ammonium acetate and 0.1% formic acid in water and mobile phase B as 0.1% formic acid in acetonitrile, The gradient flow parameters for mobile phase B were as follows: 0.00-1.00 min 10%, 1.00-10.00 min 10-95%, 10.00-11.00 min 95%, 11.00-12.00 95-10%, 12.00-14.00 min 10%. The solvent flow rate and column temperature were maintained at 0.2 ml/min and 40° C. respectively. For both separation methods, the autosampler temperature was maintained at 4° C.

Data Processing

The MRM mode data were processed using SCIEX OS Analytics (SCIEX, Redwood City, CA) software. LC-MS data in positive and negative polarities were processed separately. MQ4 algorithm was selected to build the method for data processing. NIST SRM1950 and pooled quality control samples were utilized for optimizing peak integration parameters such as intensity thresholds, signal noise ratio, and smoothing parameters. Further the method was utilized to process all the samples under study. The processed data was manually reviewed and curated to ensure accurate peak integration. Ultimately, the processed data was exported as .txt file and utilized for downstream statistical analysis.

Example 36. Proteograph Evosep Methods

Plasma samples were processed through the Proteograph (Seer, Redwood City, CA) using the standard five nanoparticle panel and three process controls following the manufacturer's protocol. Eluted peptide concentration was measured using a quantitative fluorometric peptide assay kit (Thermo Fisher, Waltham, MA) and dried down in a Centrivap vacuum concentrator (LabConco, Kansas City, MO) at room temperature overnight. Dried peptides were sealed and stored at −80° C. until reconstitution. Prior to reconstitution, peptides were equilibrated at room temperature for 30 min and then reconstituted on the Proteograph in 0.1% formic acid (Thermo Fisher, Waltham, MA) in LCMS-grade water (Honeywell, Charlotte, NC,) spiked with heavy-labeled retention time peptide standards-iRT (Biogynosys, Switzerland) and Pepcal (SciEX, Redwood City, CA) prepared according to manufacturer's instructions. Peptides from Nanoparticles 1-4 were reconstituted to 30 ng/µL while Nanoparticle 5 peptides were reconstituted to 15 ng/µL. Reconstituted peptides were homogenized in solution by shaking for 10 min @ 1000 rpm at room temperature on an orbital shaker (Bioshake, Germany) and spun down briefly (~10 secs) in a centrifuge (Eppendorf, Germany).

Reconstituted peptides were loaded onto Evotips (Evosep, Denmark) packed with C18 resin following the manufacturer's protocol. LCMS-grade water and acetonitrile were purchased from Honeywell (Charlotte, NC), formic acid was purchased from Thermo Fisher (Waltham, MA) and 2-propanol was purchased from EMD Millipore (Burlington, MA). 0.1% Formic acid in water (Solvent A) and 0.1% formic acid in acetonitrile (Solvent B) were prepared for both the preparation of Evotips and for the Evosep One LC system. After each step, tips were centrifuged for 1 min @ 700 g (Eppendorf, Germany). Evotips were first washed with Solvent B, conditioned with 2-propanol for 15 secs and then washed with Solvent A. Evotips were placed in Solvent A while reconstituted peptides were loaded on the Evotips. Evotips now loaded with sample were washed with Solvent A. 200 µL of Solvent A were added to Evotips in addition to placing them in Solvent A to keep the C18 resin wet during LCMS analysis.

Evotips were placed on the Evosep One LC system (Evosep, Denmark) and peptides were separated on a reversed-phase 8 cm×150 µM, 1.5 µM, 100 Å column packed with C18 resin (Pepsep, Denmark) using the 60 samples per day (21 min gradient) Evosep LC method. 600 ng of Nanoparticle 1-4 and 300 ng of Nanoparticle 5 were loaded on the Evotips.

Peptides fractionated on the Evosep system were analyzed on a timsTOF Pro II (Bruker, Germany) using Data Independent Acquisition mode with Parallel accumulation-serial fragmentation (DIA-PASEF) using the following parameters: Source capillary voltage was set to 1700 V and 200° C. Precursors (MS1) across m/z 100-1700 and within an ion mobility window spanning 1/K0 0.84-1.31 V·s/cm$^2$ were fragmented using collision energies following a linear step-function ranging between 20 eV-63 eV. Tims cell accumulation time was set at 100 ms and the ramp time at 85 ms. Resulting MS/MS fragment spectra between m/z 390-1250 were analyzed using a DIA schema with 57 Da windows (15 mass steps) with no mass/mobility overlap resulting in a cycle time of just under 0.8 s.

While the foregoing disclosure has been described in some detail for purposes of clarity and understanding, it will be clear to one skilled in the art from a reading of this disclosure that various changes in form and detail can be made without departing from the true scope of the disclosure. For example, all the techniques and apparatus described above can be used in various combinations. All publications, patents, patent applications, and/or other documents cited in this application are incorporated by reference in their entirety for all purposes to the same extent as if each individual publication, patent, patent application, and/or While preferred embodiments of the present invention have been shown and described herein, it will be obvious to those skilled in the art that such embodiments are provided by way of example. It is not intended that the invention be limited by the specific examples provided within the specification. While the invention has been described with reference to the aforementioned specification, the descriptions and illustrations of the embodiments herein are not meant to be construed in a limiting sense. Numerous variations, changes, and substitutions will now occur to those skilled in the art without departing from the invention. Furthermore, it shall be understood that all aspects of the invention are not limited to the specific depictions, configurations or relative proportions set forth herein which depend upon a variety of conditions and variables. It should be understood that various alternatives to the embodiments of the invention described herein may be employed in practicing the invention. It is therefore contemplated that the invention shall also cover any such alternatives, modifications, variations or equivalents. It is intended that the following claims define the scope of the invention and that methods and structures within the scope of these claims and their equivalents be covered thereby.

The invention claimed is:

1. A multi-omic method, comprising:
   sequencing nucleic acids obtained from a biofluid sample from a subject to obtain nucleic acid sequence information;
   quantifying the nucleic acids to obtain nucleic acid quantification information;
   processing proteins from the biofluid sample from the subject to obtain proteomic data;
   generating a combined dataset comprising at least a portion of the proteomic data, at least a portion of the nucleic acid quantification information, and at least a portion of the nucleic acid sequence information; and
   determining a presence or an absence of cancer at least in part by inputting the combined dataset into a trained machine learning classifier, wherein the trained machine learning classifier has
   a performance characteristic comprising an area under the curve (AUC) of a receiver operating characteristic (ROC) curve of at least 0.83, and wherein the trained machine learning classifier is trained on cancer samples and non-cancer samples.

2. The method of claim 1, further comprising forming biomolecule coronas by contacting the biofluid sample with nanoparticles, wherein the biomolecule coronas comprise the proteins of the biofluid sample adsorbed to the nanoparticles.

3. The method of claim 2, wherein processing the proteins of the biomolecule coronas comprises performing mass spectrometry.

4. The method of claim 2, wherein the nanoparticles comprise physiochemically distinct groups of nanoparticles.

5. The method of claim 4, wherein the physiochemically distinct groups of nanoparticles comprise lipid nanoparticles, metal nanoparticles, silica nanoparticles, or polymer nanoparticles.

6. The method of claim 1, wherein the nucleic acids comprise mRNA and/or miRNA.

7. The method of claim 1, wherein the nucleic acids comprise DNA.

8. The method of claim 1, wherein the trained machine learning classifier distinguishes between the presence and the absence of cancer with at least 4% greater sensitivity, at a given specificity, than a trained machine learning classifier trained using only proteomic data or trained using only nucleic acid sequence information and amounts of nucleic acids, wherein the sensitivity of the trained machine learning classifier is determined in a data set derived from a trial of over 20 subjects having the cancer and over 20 control subjects not having the cancer.

9. The method of claim 1, wherein the AUC is determined by application of the trained machine learning classifier to a dataset derived from a trial of at least 20 subjects having cancer and over 20 control subjects not having cancer.

10. The method of claim 1, wherein the determining comprises:
    generating a first label corresponding to a presence, absence, or likelihood of the cancer based on the proteomic data;
    generating a second label corresponding to a presence, absence, or likelihood of the cancer based on the nucleic acid sequence information and amounts of the sequenced nucleic acids; and
    performing (a), (b) or (c):
    (a) generating a non-weighted average of the first and second labels, wherein the first and second labels comprise probabilities of the presence or absence of the cancer,
    (b) generating a weighted average of the first and second labels, wherein the first and second labels comprise probabilities of the presence or absence of the cancer, or
    (c) generating a majority voting score based on the first and second labels, wherein the first and second labels comprise indications of the likelihood of the cancer.

11. The method of claim 10, further comprising assigning weights to the first and second labels based on an area under a ROC curve, area under a precision-recall curve, accuracy, precision, recall, sensitivity, F1-score, specificity, or a combination thereof.

12. The method of claim 1, wherein the generating further comprises:
    identifying a subset of top features, based on feature importance in a test dataset, from among the proteomic data;
    identifying at least a subset of top features, based on feature importance in a test dataset, from among the nucleic acid sequence information and the nucleic acid quantification information, wherein the feature importance is determined based on at least a portion of a machine learning model; and
    pooling the subset of top features from among the proteomic data and the at least a subset of top features from among the nucleic acid sequence information and the amounts of the sequenced nucleic acids.

13. The method of claim 12, wherein the identifying the subset of top features from among the proteomic data comprises identifying protein features having an improved classification performance in univariate protein data, relative to other protein features in the univariate protein data, or wherein the identifying the at least a subset of top features from among the nucleic acid sequence information and the amounts of the sequenced nucleic acids comprises identifying nucleic acid features having an improved classification performance in univariate nucleic acid data, relative to other nucleic acid features in the univariate nucleic acid data.

14. The method of claim 1, wherein the trained machine learning classifier is trained-using deep learning, a hierarchical cluster analysis, a principal component analysis, a partial least squares discriminant analysis, a random forest classification analysis, a support vector machine analysis, a k-nearest neighbors analysis, a naive Bayes analysis, a K-means clustering analysis, a gradient boosted analysis, a boosted decision tree analysis, or a hidden Markov analysis.

15. The method of claim 1, wherein the cancer is selected from the group consisting of: lung cancer, pancreatic cancer, colon cancer, liver cancer, breast cancer, and ovarian cancer.

16. The method of claim 1, further comprising selecting a cancer therapy based on the determining, via the trained machine learning classifier, the presence or the absence of the cancer.

17. The method of claim 1, further comprising:
identifying, via the trained machine learning classifier, a biological state as indicative of the presence of the cancer; and
based on the identifying the biological state as indicative of the presence of the cancer, administering a chemotherapy, radiation or surgical cancer treatment to the subject.

18. The method of claim 1, wherein identifying, via the classifier, the combined data as indicative of the presence, absence, or likelihood of cancer comprises identifying the combined data as indicative of an absence of cancer in the subject.

19. The method of claim 1, wherein the biofluid sample comprises a blood, serum, or plasma sample.

20. The method of claim 1, wherein the subject is human.

21. The method of claim 1, wherein trained machine learning the classifier comprises a performance characteristic comprising an average AUC of a ROC curve of at least 0.85.

22. The method of claim 12, wherein the feature importance is determined by assessing a change in performance of a machine learning model when a feature of a set of features is not present.

23. A multi-omic method, comprising:
sequencing nucleic acids obtained from a biofluid sample from a subject to obtain nucleic acid sequence information;
quantifying the nucleic acids to obtain nucleic acid quantification information;
combining the biofluid sample with internal standard proteins;
processing the internal standard proteins;
processing endogenous proteins of the biofluid sample based on the internal standard proteins to obtain proteomic data;
generating a combined dataset comprising at least a portion of the proteomic data, at least a portion of the nucleic acid quantification information, and at least a portion of the nucleic acid sequence information;
determining a presence or an absence of cancer by inputting the combined dataset into a classifier; and measuring a performance characteristic comprising an average AUC of a ROC curve of at least 0.83.

24. The method of claim 23, wherein the AUC is determined by application of the classifier when applied to a held-out data set derived from a trial of at least 25 subjects having the cancer, and over 25 control subjects not having the cancer, and wherein the ROC curve comprises a plot of true positive and false positive rates obtained when the classifier is applied to the held-out data set.

25. The method of claim 23, wherein the internal standard proteins comprise an isotopic label.

26. The method of claim 23, wherein the processing the endogenous proteins of the biofluid sample based on the internal standard proteins to obtain proteomic data comprises performing mass spectrometry.

27. The method of claim 23, wherein the biofluid sample comprises a blood, serum, or plasma sample.

28. The method of claim 23, wherein the method further comprises selecting a cancer treatment for the subject or administering the cancer treatment to the subject, wherein the cancer treatment comprises a chemotherapy, radiation or surgical treatment.

29. The method of claim 23, wherein the subject is human.

30. The method of claim 23, further comprising:
determining at least in part, via the classifier, a biological state as indicative of the presence of the cancer: and
based on the determining the biological state as indicative of the presence of the cancer, administering a chemotherapy, radiation or surgical cancer treatment to the subject.

31. The method of claim 23, wherein the classifier comprises a performance characteristic comprising an average AUC of a ROC curve of at least 0.85.

* * * * *